US012758650B2

(12) United States Patent
Malhotra et al.

(10) Patent No.: US 12,758,650 B2
(45) **Date of Patent: *Oct. 13, 2026**

(54) ENPP1 GENE THERAPY FOR THE TREATMENT OF VASCULAR DISEASE

(71) Applicants: The General Hospital Corporation, Boston, MA (US); The Brigham and Women's Hospital, Inc., Boston, MA (US)

(72) Inventors: Rajeev Malhotra, Boston, MA (US); Patricia L. Musolino, Boston, MA (US); Mark Evan Lindsay, Winchester, MA (US); Natalie Artzi, Brookline, MA (US); Eliz Amar-Lewis, Newton, MA (US); Christian Lacks Lino Cardenas, Boston, MA (US)

(73) Assignees: The General Hospital Corporation, Oston, MA (US); The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/171,179

(22) Filed: Apr. 4, 2025

(65) Prior Publication Data

US 2025/0313857 A1 Oct. 9, 2025

Related U.S. Application Data

(60) Provisional application No. 63/719,040, filed on Nov. 11, 2024, provisional application No. 63/719,028, filed on Nov. 11, 2024, provisional application No. 63/574,833, filed on Apr. 4, 2024, provisional application No. 63/574,782, filed on Apr. 4, 2024.

(51) Int. Cl.

| | |
|---|---|
| ***C12N 9/14*** | (2006.01) |
| ***A61K 38/46*** | (2006.01) |
| ***A61K 47/54*** | (2017.01) |
| ***A61K 47/60*** | (2017.01) |
| ***A61K 47/64*** | (2017.01) |
| ***A61K 47/69*** | (2017.01) |
| ***A61K 48/00*** | (2006.01) |
| ***C12N 9/16*** | (2006.01) |
| ***C12N 15/86*** | (2006.01) |
| ***C12N 15/88*** | (2006.01) |

(52) U.S. Cl.

CPC ........ *A61K 48/0033* (2013.01); *A61K 38/465* (2013.01); *A61K 47/543* (2017.08); *A61K 47/60* (2017.08); *A61K 47/64* (2017.08); *A61K 47/6925* (2017.08); *C12N 9/14* (2013.01); *C12N 15/86* (2013.01); *C12N 2750/14143* (2013.01)

(58) Field of Classification Search

None

See application file for complete search history.

(56) References Cited

U.S. PATENT DOCUMENTS

| | | | | |
|---|---|---|---|---|
| 5,399,363 | A | 3/1995 | Liversidge et al. | |
| 5,478,745 | A | 12/1995 | Samulski et al. | |
| 5,543,158 | A | 8/1996 | Gref et al. | |
| 5,552,157 | A | 9/1996 | Yagi et al. | |
| 5,565,213 | A | 10/1996 | Nakamori et al. | |
| 5,567,434 | A | 10/1996 | Szoka, Jr. | |
| 5,641,515 | A | 6/1997 | Ramtoola | |
| 5,738,868 | A | 4/1998 | Shinkarenko | |
| 5,741,516 | A | 4/1998 | Webb et al. | |
| 5,795,587 | A | 8/1998 | Gao et al. | |
| 6,001,650 | A | 12/1999 | Colosi | |
| 6,156,303 | A | 12/2000 | Russell et al. | |
| 7,198,951 | B2 | 4/2007 | Gao et al. | |
| 7,504,490 | B1 | 3/2009 | Weinstock et al. | |
| 8,158,601 | B2 * | 4/2012 | Chen ................. | A61K 31/7088 554/103 |
| 8,802,644 | B2 | 8/2014 | Chen et al. | |
| 8,846,603 | B2 | 9/2014 | Quinn et al. | |
| 9,102,949 | B2 | 8/2015 | Gao et al. | |
| 9,540,621 | B2 | 1/2017 | Quinn et al. | |
| 9,585,971 | B2 | 3/2017 | Deverman et al. | |
| 9,744,219 | B2 | 8/2017 | Braddock et al. | |

(Continued)

FOREIGN PATENT DOCUMENTS

| | | | |
|---|---|---|---|
| CN | 101883859 | A | 11/2010 |
| CN | 109207520 | A | 1/2019 |

(Continued)

OTHER PUBLICATIONS

Ramirez et al. An Engineered Adeno-Associated Virus Capsid Mediates Efficient Transduction of Pericytes and Smooth Muscle Cells of the Brain Vasculature. Hum Gene Ther. 2023;34(15-16):682-696. doi: 10.1089/hum.2022.211. Erratum in: Hum Gene Ther. Dec. 2023;34(23-24):1273. doi: 10.1089/hum.2022.211 (Year: 2023).*

Qiao C, Yuan Z, Li J, He B, Zheng H, Mayer C, Li J, Xiao X. Liver-specific microRNA-122 target sequences incorporated in AAV vectors efficiently inhibits transgene expression in the liver. Gene Ther. Apr. 2011: 18(4):403-10. doi: 10.1038/gt.2010.157. Epub Dec. 9, 2010. PMID: 21150938; PMCID: PMC3686499. (Year: 2010).*

Invitation to Pay Additional Fees and, Where Applicable, Protest Fee in International Appln. No. PCT/US2025/023323, mailed on May 20, 2025, 3 pages.

Albright et al., "ENPP1-Fc prevents mortality and vascular calcifications in rodent model of generalized arterial calcification of infancy," Nature Communications, Dec. 2015, 6:10006, 11 pages.

(Continued)

*Primary Examiner* — Anna Skibinsky

*Assistant Examiner* — Catherine L McCormick

(74) *Attorney, Agent, or Firm* — Fish & Richardson P.C.

(57) ABSTRACT

Provided herein are compositions and methods for gene therapy for disorders of arterial calcification as well as Generalized Arterial Calcification of Infancy (GACI). The methods include a gene addition strategy to deliver a DNA construct to target tissues (such as liver and smooth muscle cells) to express soluble recombinant ENPP1 (srENPP1) or transmembrane full-length recombinant ENPP1 (rENPP1).

20 Claims, 75 Drawing Sheets

Specification includes a Sequence Listing.

(56) References Cited

U.S. PATENT DOCUMENTS

| | | | |
|---|---|---|---|
| 9,913,881 | B2 | 3/2018 | Braddock et al. |
| 9,920,317 | B2 | 3/2018 | Lee et al. |
| 9,956,271 | B2 | 5/2018 | Guild et al. |
| 10,052,367 | B2 | 8/2018 | Braddock et al. |
| 10,493,135 | B2 | 12/2019 | Quinn et al. |
| 10,624,958 | B2 | 4/2020 | Braddock et al. |
| 11,149,256 | B2 | 10/2021 | Gradinaru et al. |
| 11,266,722 | B2 | 3/2022 | Braddock et al. |
| 11,364,284 | B2 | 6/2022 | Yan et al. |
| RE49,529 | E | 5/2023 | Quinn et al. |
| 2003/0138772 | A1 | 7/2003 | Gao et al. |
| 2003/0194721 | A1 | 10/2003 | Mikita et al. |
| 2004/0214272 | A1 | 10/2004 | La Rosa et al. |
| 2007/0020624 | A1 | 1/2007 | Rubenfield et al. |
| 2007/0243526 | A1 | 10/2007 | Kay et al. |
| 2008/0311627 | A1 | 12/2008 | Tetzner et al. |
| 2009/0270480 | A1 | 10/2009 | Amegadzie et al. |
| 2012/0164205 | A1 | 6/2012 | Baum et al. |
| 2013/0273021 | A1 | 10/2013 | Quinn et al. |
| 2014/0336245 | A1 | 11/2014 | Mingozzi et al. |
| 2014/0377859 | A1 | 12/2014 | Quinn et al. |
| 2015/0359858 | A1 | 12/2015 | Braddock et al. |
| 2017/0021038 | A1 | 1/2017 | Pan et al. |
| 2017/0145393 | A1 | 5/2017 | Quinn et al. |
| 2017/0166926 | A1 | 6/2017 | Deverman et al. |
| 2017/0183647 | A1 | 6/2017 | Chavez et al. |
| 2017/0240885 | A1 | 8/2017 | Deverman et al. |
| 2018/0016601 | A1 | 1/2018 | Qi et al. |
| 2018/0187213 | A1 | 7/2018 | High et al. |
| 2018/0282382 | A1 | 10/2018 | Alagramam |
| 2018/0318400 | A1 | 11/2018 | Quinn et al. |
| 2019/0167811 | A1 | 6/2019 | Benenato et al. |
| 2020/0010521 | A1 | 1/2020 | Hirsch et al. |
| 2020/0263153 | A1 | 8/2020 | Khan et al. |
| 2020/0306349 | A1 | 10/2020 | Yan et al. |
| 2021/0079406 | A1 | 3/2021 | Maguire et al. |
| 2021/0187067 | A1 | 6/2021 | Jungles et al. |
| 2021/0261932 | A1 | 8/2021 | Kleinstiver et al. |
| 2021/0301268 | A1 | 9/2021 | Quinn et al. |
| 2021/0355509 | A1 | 11/2021 | Davidson et al. |
| 2022/0119475 | A1 | 4/2022 | Corey et al. |
| 2022/0195458 | A1 | 6/2022 | Maguire et al. |
| 2022/0280427 | A1 | 9/2022 | Su et al. |
| 2022/0354933 | A1 | 11/2022 | Yan et al. |
| 2023/0031809 | A1 | 2/2023 | Jungles et al. |
| 2023/0129977 | A1 | 4/2023 | Quinn et al. |
| 2023/0293429 | A1 | 9/2023 | Hennig et al. |
| 2024/0148666 | A1 | 5/2024 | Cheng et al. |
| 2025/0312482 | A1 | 10/2025 | Artzi et al. |

FOREIGN PATENT DOCUMENTS

| | | | | |
|---|---|---|---|---|
| EP | 2010663 | B1 | 3/2015 | |
| EP | 4157328 | A1 | 4/2023 | |
| EP | 4157329 | A1 | 4/2023 | |
| EP | 4175657 | A2 | 5/2023 | |
| JP | 2008-263851 | A | 11/2008 | |
| RU | 2611202 | C2 | 2/2017 | |
| RU | 2018128780 | A | 12/2018 | |
| WO | WO 1998/000041 | A1 | 1/1998 | |
| WO | WO 1998/010088 | A1 | 3/1998 | |
| WO | WO 2003/097685 | A1 | 11/2003 | |
| WO | WO 2004/112727 | A2 | 12/2004 | |
| WO | WO 2006/119432 | A2 | 11/2006 | |
| WO | WO 2008/073303 | A2 | 6/2008 | |
| WO | WO 2011/119484 | A1 | 9/2011 | |
| WO | WO 2015/013148 | A2 | 1/2015 | |
| WO | WO 2015/038958 | A1 | 3/2015 | |
| WO | WO 2015/130840 | A2 | 9/2015 | |
| WO | WO 2016/112242 | A1 | 7/2016 | |
| WO | WO 2016/134375 | A1 | 8/2016 | |
| WO | WO 2016/141224 | A1 | 9/2016 | |
| WO | WO 2017/100791 | A1 | 6/2017 | |
| WO | WO 2017/136536 | A1 | 8/2017 | |
| WO | WO 2018/022608 | A2 | 2/2018 | |
| WO | WO 2018/189244 | A1 | 10/2018 | |
| WO | WO 2019/028306 | A2 | 2/2019 | |
| WO | WO 2019/046069 | A1 | 3/2019 | |
| WO | WO 2019/169132 | A1 | 9/2019 | |
| WO | WO 2019/200016 | A1 | 10/2019 | |
| WO | WO 2020/014471 | A1 | 1/2020 | |
| WO | WO 2020/028751 | A2 | 2/2020 | |
| WO | WO 2020/077295 | A1 | 4/2020 | |
| WO | WO 2020/097372 | A1 | 5/2020 | |
| WO | WO-2020150716 | A1 * | 7/2020 | ............. A61K 48/00 |
| WO | WO 2020/160337 | A1 | 8/2020 | |
| WO | WO 2020/198737 | A1 | 10/2020 | |
| WO | WO 2020/206302 | A1 | 10/2020 | |
| WO | WO 2020/210655 | A1 | 10/2020 | |
| WO | WO 2021/067448 | A1 | 4/2021 | |
| WO | WO 2021/151065 | A2 | 7/2021 | |
| WO | WO 2021/151073 | A2 | 7/2021 | |
| WO | WO 2021/252549 | A1 | 12/2021 | |
| WO | WO 2022/076848 | A1 | 4/2022 | |
| WO | WO 2022/109344 | A1 | 5/2022 | |
| WO | WO 2022/204043 | A1 | 9/2022 | |
| WO | WO 2022/204043 | A8 | 11/2022 | |
| WO | WO-2022232327 | A2 * | 11/2022 | ............. C12N 15/86 |
| WO | WO 2023/049864 | A1 | 3/2023 | |
| WO | WO 2023/107574 | A2 | 6/2023 | |
| WO | WO 2024/073715 | A2 | 4/2024 | |
| WO | WO 2025/213135 | A1 | 10/2025 | |

OTHER PUBLICATIONS

Barash et al., "Human secretory signal peptide description by hidden Markov model and generation of a strong artificial signal peptide for secreted protein expression," Biochemical and Biophysical Research Communications, Jun. 2002, 294(4), 1 page (abstract only).

Bernhard et al., "A reference range for plasma levels of inorganic pyrophosphate in children using the ATP sulfurylase method," The Journal of Clinical Endocrinology and Metabolism, Jan. 2022, 107(1):109-118.

Bianco et al., "A Protocol for a Novel Human Ex Vivo Model of Aneurysm," STAR Protocols, Dec. 2020, 1(3):100108, 15 pages.

Borza et al., "Structure and function of the ecto-nucleotide pyrophosphatase/phosphodiesterase (ENPP) family: Tidying up diversity," JBC Reviews, Feb. 2022, 298(2):101526, 12 pages.

Bose et al., "Role of nucleolin in human parainfluenza virus type 3 infection of human lung epithelial cells," Journal of Virology, Aug. 2004, 78(15):8146-58.

Cheng et al., "Selective organ targeting (SORT) nanoparticles for tissue-specific mRNA delivery and CRISPR-Cas gene editing," Nature Nanotechnology, Apr. 2020, 15(4):313, 22 pages.

Dai et al., "Identification of synthetic endothelial cell-specific promoters by use of a high-throughput screen," Journal of Virology, Jun. 2004, 78(12):6209-6221.

Dong et al., "Poly(d,1-lactide-co-glycolide)/montmorillonite nanoparticles for oral delivery of anticancer drugs," Biomaterials, Oct. 2005, 26(30):6068-6076.

Geisler et al., "MicroRNA-regulated viral vectors for gene therapy," World J. Exp. Med., May 2016, 6(2):37-54.

Huang et al., "Adenovirus-Mediated ABCC6 Gene Therapy for Heritable Ectopic Mineralization Disorders," Journal of Investigative Dermatology, Jun. 2019, 139(6):1254-1263.

Kavousi et al., "Multi-ancestry genome-wide study identifies effector genes and druggable pathways for coronary artery calcification," Nature Genetics, Oct. 2023, 55(10):1651-1664, 25 pages.

Khan et al., "ENPPI enzyme replacement therapy improves blood pressure and cardiovascular function in a mouse model of generalized arterial calcification of infancy," Disease Models & Mechanisms, Oct. 2018, 11(10):dmm035691, 10 pages.

Langer, "New methods of drug delivery," Science, Sep. 1990, 249(4976):1527-1533.

Li et al., "Mutant Enpp1$^{asj}$ mice as a model for generalized arterial calcification of infancy," Disease Models & Mechanisms, Sep. 2013, 6(5):1227-1235.

(56) References Cited

OTHER PUBLICATIONS

Lipskaia et al., "SERCA2a gene transfer prevents intimal proliferation in an organ culture of human internal mammary artery," Gene Therapy, Apr. 2013, 20(4):396-406.
Löbenberg et al., "Improved Body Distribution of $^{14}C$-labelled AZT bound to Nanoparticles in Rats determined by Radioluminography," Journal of Drug Targeting, 1998, 5(3):171-9.
Lopez-Berestein, "Treatment of Systemic Fungal Infections with Liposomal-Amphotericin B," Liposomes in the Therapy of Infectious Diseases and Cancer: Proceedings of a Ciba-Geigy-Squibb-UCLA Colloquium, Lake Tahoe, CA, Feb. 16-20, 1988, pp. 317-327.
Nitschke et al., "ENPP1-Fc prevents neointima formation in generalized arterial calcification of infancy through the generation of AMP," Experimental & Molecular Medicine, Oct. 2018, 50:139, 12 pages.
Nitschke et al., "Generalized arterial calcification of infancy and pseudoxanthoma elasticum can be caused by mutations in either ENPP1 or ABCC6," The American Journal of Human Genetics, Jan. 2012, 90(1):25-39.
Ralph et al., "ENPP1 variants in patients with GACI and PXE expand the clinical and genetic heterogeneity of heritable disorders of ectopic calcification," PLoS Genetics, Apr. 2022, 18(4):e1010192, 16 pages.
Ramirez et al., "An Engineered Adeno-Associated Virus Capsid Mediates Efficient Transduction of Pericytes and Smooth Muscle Cells of the Brain Vasculature," Human Gene Therapy, Aug. 2023, 34(15-16):682-696.
Robinson et al., "Lipid Nanoparticle-Delivered Chemically Modified mRNA Restores Chloride Secretion in Cystic Fibrosis," Molecular Therapy, Aug. 2018, 26(8):2034-2046.
Rutsch et al., "Hypophosphatemia, hyperphosphaturia, and bisphosphonate treatment are associated with survival beyond infancy in generalized arterial calcification of infancy," Circulation: Cardiovascular Genetics, Dec. 2008, 1(2):133-140.
Saifan et al., "Warfarin-induced calciphylaxis: a case report and review of literature," International Journal of Genetic Medicine, Aug. 2013, 6:665-669.
Sakuma et al., "Mucoadhesion of polystyrene nanoparticles having surface hydrophilic polymeric chains in the gastrointestinal tract," International Journal of Pharmaceutics, Jan. 1999, 177(2):161-72.
Théry et al., "Isolation and characterization of exosomes from cell culture supernatants and biological fluids," Current Protocols Cell Biology, 2006, Chapter 3, 29 pages.
Treat et al., "Liposome Encapsulated Doxorubicin Preliminary Results of Phase I and Phase II Trials," Liposomes in the Therapy of Infectious Diseases and Cancer: Proceedings of a Ciba-Geigy-Squibb-UCLA Colloquium, Lake Tahoe, CA, Feb. 16-20, 1988, pp. 353-365.
Virovic et al., "Novel delivery methods for treatment of viral hepatitis: an update," Expert Opinion on Drug Delivery, Jul. 2005, 2(4):707-717.
Xu et al., "Multifunctional cationic nanosystems for nucleic acid therapy of thoracic aortic dissection," Nature Communications, Jul. 2019, 10:3184, 15 pages.
Ziegler et al., "Generalized Arterial Calcification of Infancy," GeneReviews® [Internet], Nov. 13, 2014, last updated Dec. 30, 2020, retrieved on Apr. 30, 2025, retrieved from URL<https://www.ncbi.nlm.nih.gov/books/NBK253403/>, 25 pages.
Zimmermann et al., "Electrolyte- and pH-stabilities of aqueous solid lipid nanoparticle (SLN) dispersions in artificial gastrointestinal media," European Journal of Pharmaceutics and Biopharmaceutics, Sep. 2001, 52(2):203-10.
Anananuchatkul et al., "Construction of a stapled α-helix peptide library displayed on phage for the screening of galectin-3-binding peptide ligands," ACS omega, Mar. 2020, 5(11):5666-74.
Anzalone et al., "Genome editing with CRISPR-Cas nucleases, base editors, transposases and prime editors," Nature Biotechnology, Jul. 2020, 38(7):824-44.
Anzalone et al., "Search-and-replace genome editing without double-strand breaks or donor DNA," Nature, Dec. 2019, 576(7785), 39 pages (Author Manuscript only).
Arno et al., "Mutations in ACTA2 in a British cohort of TAAD patients," Abstract, Presented at Proceedings of the 12th International Congress of Human Genetics (ICHG) and the 61st American Society of Human Genetics (ASHG) Annual Meeting, Montreal, Canada, Oct. 11-15, 2011, 1 page.
Ash et al., "Functional connectivity with the retrosplenial cortex predicts cognitive aging in rats," Proceedings of the National Academy of Sciences, Oct. 2016, 113(43):12286-91.
Burnett et al., "Examination of the cell cycle dependence of cytosine and adenine base editors," Frontiers in Genome Editing, Jul. 2022, 4:923718, 15 pages.
Cardenas et al., "An HDAC9-MALATI-BRGI complex mediates smooth muscle dysfunction in thoracic aortic aneurysm," Nature Communications, Mar. 2018, 9(1):1009, 14 pages.
Cardenas et al., "HDAC9 complex inhibition improves smooth muscle—dependent stenotic vascular disease," JCI Insight, Jan. 2019, 4(2):e124706, 12 pages.
Chung et al., "Determinants of optogenetic cortical spreading depolarizations," Cerebral Cortex, Mar. 2019, 29(3):1150-61.
Doudna, "The promise and challenge of therapeutic genome editing," Nature, Feb. 2020, 578(7794):229-36 (Author Manuscript only).
Etchevers et al., "The cephalic neural crest provides pericytes and smooth muscle cells to all blood vessels of the face and forebrain," Development, Apr. 2001, 128(7):1059-68.
Foroud et al., "Genome-wide association study of intracranial aneurysm identifies a new association on chromosome 7," Stroke, Nov. 2014, 45(11):3194-9.
Gallo et al., "Angiotensin II-dependent TGF-β signaling contributes to Loeys-Dietz syndrome vascular pathogenesis," The Journal of Clinical Investigation, Jan. 2014, 124(1):448-60.
Gaudelli et al., "Directed evolution of adenine base editors with increased activity and therapeutic application," Nature Biotechnology, Jul. 2020, 38(7):892-900.
Gaudelli et al., "Programmable base editing of A• T to G• C in genomic DNA without DNA cleavage," Nature, Nov. 2017, 551(7681):8 pages (Author Manuscript only).
GenBank Accession No. AC002433, "*Homo sapiens* BAC clone CTA-317M2 from 7, complete sequence," Jul. 26, 2016, 38 pages.
Georgescu et al., "The defining pathology of the new clinical and histopathologic entity ACTA2-related cerebrovascular disease," Acta Neuropathologica Communications, Dec. 2015, 3(1):81, 13 pages.
Grunstein, "Histone acetylation in chromatin structure and transcription," Nature, Sep. 1997, 389(6649):349-52.
Guo et al., "Mutations in smooth muscle alpha-actin (ACTA2) cause coronary artery disease, stroke, and Moyamoya disease, along with thoracic aortic disease," The American Journal of Human Genetics, May 2009, 84(5):617-27.
Guo et al., "Mutations in smooth muscle α-actin (ACTA2) lead to thoracic aortic aneurysms and dissections," Nature Genetics, Dec. 2007, 39(12):1488-93.
Haberland et al., "Regulation of HDAC9 gene expression by MEF2 establishes a negative-feedback loop in the transcriptional circuitry of muscle differentiation," Molecular and Cellular Biology, Jan. 2007, 27(2):518-25.
Haberland et al., "The many roles of histone deacetylases in development and physiology: implications for disease and therapy," Nature Reviews Genetics, Jan. 2009, 10(1):11 pages (Author Manuscript only).
Hattori et al., "A novel mouse model of ischemic carotid artery disease," PloS One, Jun. 2014, 9(6):e100257, 7 pages.
He et al., "Development of a combined lipid-based nanoparticle formulation for enhanced siRNA delivery to vascular endothelial cells," Pharmaceutics, Sep. 2022, 14(10):2086, 16 pages.
International Preliminary Report on Patentability in International Appln. No. PCT/US2023/075589, mailed on Apr. 10, 2025, 10 pages.
International Search Report and Written Opinion in International Appln. No. PCT/US2023/075589, mailed on Apr. 9, 2024, 16 pages.

(56) References Cited

OTHER PUBLICATIONS

International Search Report and Written Opinion in International Appln. No. PCT/US2025/023323, mailed on Aug. 5, 2025, 18 pages.
International Stroke Genetics et al., "Genome-wide association study identifies a variant in HDAC9 associated with large vessel ischemic stroke," National Genetics, Sep. 2012, 44(3):328-333, 20 pages (Author Manuscript only).
Jeong et al., "Adenine base editor engineering reduces editing of bystander cytosines," Nature Biotechnology, Nov. 2021, 39(11):1426-33.
Jiang et al., "MO352: The Effect and Mechanism of Renal Targeted Delivery of MSC Exosomes in the Treatment of AKI," Nephrology Dialysis Transplantation, May 2022, 37(Supplement_3):gfac 135-007, 2 pages.
Jiang et al., "Normal fate and altered function of the cardiac neural crest cell lineage in retinoic acid receptor mutant embryos," Mechanisms of Development, Sep. 2002, 117(1-2):115-22.
Jinek et al., "A programmable dual-RNA—guided DNA endonuclease in adaptive bacterial immunity," Science, Aug. 2012, 337(6096):816-21.
Judge et al., "Evidence for a critical contribution of haploinsufficiency in the complex pathogenesis of Marfan syndrome," The Journal of Clinical Investigation, Jul. 2004, 114(2):172-81.
Kato et al., "Trans-ancestry genome-wide association study identifies 12 genetic loci influencing blood pressure and implicates a role for DNA methylation," Nat Genet, Nov. 2015, 47(11), 34 pages (Author Manuscript only).
Kim et al., "Adenine base editors catalyze cytosine conversions in human cells," Nature Biotechnology, Oct. 2019, 37(10):1145-8.
Kim et al., "Comparison of in vivo targeting ability between cRGD and collagen-targeting peptide conjugated nano-carriers for atherosclerosis," Journal of Controlled Release, Jan. 2018, 269:337-46.
Kitagawa et al., "Cerebral ischemia after bilateral carotid artery occlusion and intraluminal suture occlusion in mice: evaluation of the patency of the posterior communicating artery," Journal of Cerebral Blood Flow & Metabolism, May 1998, 18(5):570-9.
Kleinstiver et al., "Broadening the targeting range of *Staphylococcus aureus* CRISPR-Cas9 by modifying PAM recognition," Nature Biotechnology, Dec. 2015, 33(12):1293-8.
Kleinstiver et al., "Engineered CRISPR-Cas12a variants with increased activities and improved targeting ranges for gene, epigenetic and base editing," Nature Biotechnology, Mar. 2019, 37(3), 22 pages (Author Manuscript only).
Kleinstiver et al., "Engineered CRISPR-Cas9 nucleases with altered PAM specificities," Nature, Jul. 2005, 523(7561), 27 pages (Author Manuscript only).
Kleinstiver et al., "High-fidelity CRISPR-Cas9 nucleases with no detectable genome-wide off-target effects," Nature, Jan. 2016, 529(7587), 24 pages (Author Manuscript only).
Koblan et al., "Improving cytidine and adenine base editors by expression optimization and ancestral reconstruction," Nature Biotechnology, Oct. 2018, 36(9), 11 pages (Author Manuscript only).
Koblan et al., "In vivo base editing rescues Hutchinson—Gilford progeria syndrome in mice," Nature, Jan. 2021, 589(7843), 48 pages.
Komor et al., "Programmable editing of a target base in genomic DNA without double-stranded DNA cleavage," Nature, May 2016, 533(7603), 25 pages (Author Manuscript only).
Lauer et al., "Cerebral Small Vessel Diseases and Sleep Related Strokes," Journal of Stroke and Cerebrovascular Diseases, Apr. 2020, 29(4):104606, 7 pages.
Lauer et al., "Cerebrovascular disease progression in patients with ACTA2 Arg179 pathogenic variants," Neurology, Jan. 2021, 96(4):e538-52.
Levy et al., "Cytosine and adenine base editing of the brain, liver, retina, heart and skeletal muscle of mice via adeno-associated viruses," Nature Biomedical Engineering, Jan. 2020, 4(1), 35 pages (Author Manuscript only).
Li et al., "Docking sites inside Cas9 for adenine base editing diversification and RNA off-target elimination," Nature Communications, Nov. 2020, 11(1):5827, 11 pages.
Li et al., "Intrastriatal transplantation of bone marrow nonhematopoietic cells improves functional recovery after stroke in adult mice," Journal of Cerebral Blood Flow & Metabolism, Sep. 2000, 20(9):1311-9.
Meng et al., "Three-dimensional description and mathematical characterization of the parasellar internal carotid artery in human infants," Journal of Anatomy, May 2008, 212(5):636-44.
Milewicz et al., "De novo ACTA2 mutation causes a novel syndrome of multisystemic smooth muscle dysfunction," American Journal of Medical Genetics Part A, Oct. 2010, 152(10), 14 pages (Author Manuscript only).
Milewicz et al., "Genetic basis of thoracic aortic aneurysms and dissections: focus on smooth muscle cell contractile dysfunction," Annual Review Genomics and Human Genetics, Sep. 2008, 9(1):283-302.
Miller et al., "Continuous evolution of SpCas9 variants compatible with non-G PAMs," Nature Biotechnology, Apr. 2020, 38(4), 32 pages (Author Manuscript only).
Munot et al., "A novel distinctive cerebrovascular phenotype is associated with heterozygous Arg179 ACTA2 mutations," Brain, Aug. 2012, 135(8):2506-14.
Myocardial Infarction Genetics et al., "Genome-wide association of early-onset myocardial infarction with single nucleotide polymorphisms and copy number variants," Nat Genet, Mar. 2009, 41(3), 21 pages (Author Manuscript only).
Papke et al., "Smooth muscle hyperplasia due to loss of smooth muscle α-actin is driven by activation of focal adhesion kinase, altered p53 localization and increased levels of platelet-derived growth factor receptor-β," Human Molecular Genetics, Aug. 2013, 22(15):3123-3137.
Porto et al., "Base editing: advances and therapeutic opportunities," Nature Reviews Drug Discovery, Dec. 2020, 19(12), 60 pages (Author Manuscript only).
Rees et al., "Base editing: precision chemistry on the genome and transcriptome of living cells," Nature Reviews Genetics, Dec. 2018, 19(12), 41 pages (Author Manuscript only).
Regalado et al., "Aortic disease presentation and outcome associated with ACTA2 mutations," Circulation: Cardiovascular Genetics, Jun. 2015, 8(3):457-64.
Regalado et al., "Clinical history and management recommendations of the smooth muscle dysfunction syndrome due to ACTA2 arginine 179 alterations," Genetics in Medicine, Oct. 2018, 20(10):1206-15.
Richter et al., "Phage-assisted evolution of an adenine base editor with improved Cas domain compatibility and activity," Nature Biotechnology, Jul. 2020, 38(7), 30 pages (Author Manuscript only).
Schiffner et al., "Redistribution of cerebral blood flow during severe hypovolemia and reperfusion in a sheep model: critical role of α1-adrenergic signaling," International Journal of Molecular Sciences, May 2017, 18(5):1031, 15 pages.
Schildmeyer et al., "Impaired vascular contractility and blood pressure homeostasis in the smooth muscle α-actin null mouse," The FASEB Journal, Nov. 2000, 14(14):2213-20.
Shen et al., "Aortic aneurysms and dissections series," Arteriosclerosis, Thrombosis, and Vascular Biology, Mar. 2020, 40(3):e37-46.
Silasi et al., "Intact skull chronic windows for mesoscopic wide-field imaging in awake mice," Journal of Neuroscience Methods, Jul. 2016, 267, 19 pages (Author Manuscript only).
Sternberg et al., "DNA interrogation by the CRISPR RNA-guided endonuclease Cas9," Biophysical Journal, Jan. 2014, 106(2):695a.
Stevens et al., "Design of a split intein with exceptional protein splicing activity," Journal of the American Chemical Society, Feb. 2016, 138(7):2162-5.
Sun et al., "Optimization of DOTAP/chol cationic lipid nanoparticles for mRNA, pDNA, and oligonucleotide delivery," AAPS PharmSciTech, May 2022, 23(5):135, 10 pages.
Truong et al., "Development of an intein-mediated split—Cas9 system for gene therapy," Nucleic Acids Research, Jul. 2015, 43(13):6450-8.

(56) References Cited

OTHER PUBLICATIONS

Walton et al., "Unconstrained genome targeting with near-PAMless engineered CRISPR-Cas9 variants," Science, Apr. 2020, 368(6488), 18 pages (Author Manuscript only).
Wang et al., "Antitumoral cascade-targeting ligand for IL-6 receptor-mediated gene delivery to glioma," Molecular Therapy, Jul. 2017, 25(7):1556-66.
Wu et al., "ENPP1 ameliorates vascular calcification via inhibiting the osteogenic transformation of VSMCs and generating Ppi," Open Medicine, Dec. 2023, 18(1):20230861, 11 pages.
Wu et al., "Protein trans-splicing by a split intein encoded in a split DnaE gene of *Synechocystis* sp. PCC6803," Proceedings of the National Academy of Sciences, Aug. 1998, 95(16):9226-31.
Xie et al., "Differential effects of anesthetics on resting state functional connectivity in the mouse," Journal of Cerebral Blood Flow & Metabolism, Apr. 2020, 40(4):875-84.
Yuan et al., "An intein-mediated split—nCas9 system for base editing in plants," ACS Synthetic Biology, Jun. 2022, 11(7):2513-7.
Zettler et al., "The naturally split Npu DnaE intein exhibits an extraordinarily high rate in the protein trans-splicing reaction," FEBS Letters, Mar. 2009, 583(5):909-14.
Ahmad et al., "Mutations of the protocadherin gene PCDH15 cause Usher syndrome type 1F," Am J Hum Genet., Jul. 2001, 69(1):25-34.
Ahmad et al., "PCDH15 is expressed in the neurosensory epithelium of the eye and ear and mutant alleles are responsible for both USHIF and DFNB23," Hum Mol Genet., Dec. 2003, 12(24):3215-23.
Ahmad et al., "Restoration of connexin26 protein level in the cochlea completely rescues hearing in a mouse model of human connexin30-linked deafness," Proc Natl Acad Sci U S A, Jan. 2007, 104(4):1337-41.
Akil et al., "Dual AAV-mediated gene therapy restores hearing in a DFNB9 mouse model," Proc. Natl. Acad. Sci. U S A, Mar. 2019, 116(10):4496-4501.
Akil et al., "Restoration of hearing in the VGLUT3 knockout mouse using virally mediated gene therapy," Neuron, Jul. 2012, 75(2):283-93.
Alagramam et al., "Mutations in protocadherin 15 and cadherin 23 affect tip links and mechanotransduction in mammalian sensory hair cells," PLoS One, Apr. 2011, 6(4):e19183, 16 pages.
Al-Moyed et al., "A dual-AAV approach restores fast exocytosis and partially rescues auditory function in deaf otoferlin knock-out mice," EMBO Mol Med., Jan. 2019, 11(1):e9396, 13 pages.
Al-Zaidy et al., "VXS-101 (Onasemnogene Abeparvovec) for SMA 1 : Comparative Study with a Prospective Natural History Cohort," J. Neuromuscul. Dis., 2019, 6(3):307-317.
Angueyra et al., "Leveraging Zebrafish to Study Retinal Degeneration," Front Cell Dev Biol., Sep. 2018, 6:110, 19 pages.
Araya-Secchi et al., "An elastic element in the protocadherin-15 tip link of the inner ear," Nat Commun., Nov. 2016, 7:13458, 14 pages.
Assad et al., "An active motor model for adaptation by vertebrate hair cells," J Neurosci., Sep. 1992, 12(9):3291-309.
Assad et al., "Tip-link integrity and mechanical transduction in vertebrate hair cells," Neuron, Dec. 1991, 7(6):985-94.
Aurnhammer et al., "Universal real-time PCR for the detection and quantification of adeno-associated virus serotype 2-derived inverted terminal repeat sequences," Hum Gene Ther Methods, Feb. 2012, 23(1):18-28.
Azaiez et al., "Genomic Landscape and Mutational Signatures of Deafness-Associated Genes," Am J Hum Genet., Oct. 2018, 103(4):484-497.
Azaiez et al., "GJB2: the spectrum of deafness-causing allele variants and their phenotype," Hum Mutat., Oct. 2004, 24(4):305-11.
Ben-Yosef et al., "A mutation of PCDH15 among Ashkenazi Jews with the type 1 Usher syndrome," N Engl J Med., Apr. 2003, 348(17):1664-70.
Berry and Asokan, "Cellular transduction mechanisms of adeno-associated viral vectors," Curr Opin Virol, Dec. 2016, 21:54-60.
Boshart et al., "A very strong enhancer is located upstream of an immediate early gene of human cytomegalovirus," Cell, Jun. 1985, 41(2):521-30.
Boulay et al., "Hearing is normal without connexin30," J Neurosci., Jan. 2013, 33(2):430-4.
Brownstein et al., "The R245X mutation of PCDH15 in Ashkenazi Jewish children diagnosed with nonsyndromic hearing loss foreshadows retinitis pigmentosa," Pediatr Res., Jun. 2004, 55(6): 995-1000.
Buenrostro et al., "Transposition of native chromatin for fast and sensitive epigenomic profiling of open chromatin, DNA-binding proteins and nucleosome position," Nat Methods, Dec. 2013, 10(12):1213-8.
Caron et al., "Potent and sustained huntingtin lowering via AAV5 encoding miRNA preserves striatal volume and cognitive function in a humanized mouse model of Huntington disease," Nucleic Acids Res., Jan. 2020, 48(1):36-54.
Cehajic-Kapetanovic et al., "Initial results from a first-in-human gene therapy trial on X-linked retinitis pigmentosa caused by mutations in RPGR," Nat. Med., Mar. 2020, 26(3):354-359, 18 pages.
Chamberlain et al., "Progress toward Gene Therapy for Duchenne Muscular Dystrophy," Mol Ther., 2017, 25:1125-31.
Chan et al., "Engineered AAVs for efficient noninvasive gene delivery to the central and peripheral nervous systems," HHS Public Access Author Manuscript, published online Dec. 26, 2017; published in final edited form as: Nat Neurosci., Aug. 2017, 20(8):1172-1179.
Chang et al., "Functional studies reveal new mechanisms for deafness caused by connexin mutations," Otol Neurotol., Feb. 2009, 30(2):237-40.
Chang et al., "Gap junction mediated intercellular metabolite transfer in the cochlea is compromised in connexin30 null mice," PloS one, 2008, 3(12):e4088, 10 pages.
Chang et al., "Timed conditional null of connexin26 in mice reveals temporary requirements of connexin26 in key cochlear developmental events before the onset of hearing," Neurobiol Dis., Jan. 2015, 73:418-27.
Chen et al., "Characterization of a knock-in mouse model of the homozygous p. V37I variant in Gjb2," Sci Rep., Sep. 2016, 6:33279, 7 pages.
Chen et al., "Developmental abnormalities in supporting cell phalangeal processes and cytoskeleton in the Gjb2 knockdown mouse model," Dis Model Mech., Feb. 2018, 11(2):dmm033019, 11 pages.
Chen et al., "Down regulated connexin26 at different postnatal stage displayed different types of cellular degeneration and formation of organ of Corti," Biochem Biophys Res Commun., Feb. 2014, 445(1):71-7.
Chen et al., "Molecular signatures of disease brain endothelia provide new sites for CNS-directed enzyme therapy," Nat Med, Oct. 2009, 15(10):1215-1218.
Cheung et al., "$Ca^{2+}$changes the force sensitivity of the hair-cell transduction channel," Biophys J., Jan. 2006, 90(1):124-39.
Chow et al., "Inducible Cre Recombinase Activity in Mouse Cerebellar Granule Cell Precursors and Inner Ear Hair Cells," Dev Dyn., Nov. 2006, 235(11):2991-8.
Christensen et al., "TRP channels in mechanosensation: Direct or indirect activation?," Nat Rev Neurosci., Jul. 2007, 8(7):510-21.
Christine et al., "Magnetic resonance imaging-guided phase 1 trial of putaminal AADC gene therapy for Parkinson's disease," Ann. Neural., May 2019, 85(5):704-714.
Chu et al., "SV40 DNA transfection of cells in suspension: analysis of efficiency of transcription and translation of T-antigen," Gene, Mar. 1981, 13(2):197-202.
Cohen-Salmon et al., "Targeted ablation of connexin26 in the inner ear epithelial gap junction network causes hearing impairment and cell death," Curr Biol., Jul. 2002, 12(13):1106-11.
Corey et al., "Kinetics of the receptor current in bullfrog saccular hair cells," J Neurosci., May 1983, 3(5):962-76.
Corey et al., "TRPA1 is a candidate for the mechanosensitive transduction channel of vertebrate hair cells," Nature, Dec. 2004, 432(7018):723-30.

(56) References Cited

OTHER PUBLICATIONS

Creyghton et al., "Histone H3K27ac separates active from poised enhancers and predicts developmental state," Proc Natl Acad Sci U S A, Dec. 2010, 107(50):21931-6.
Crispino et al., "BAAV mediated GJB2 gene transfer restores gap junction coupling in cochlear organotypic cultures from deaf Cx26Sox10Cre mice," PloS one, 2011, 6(8):e23279, 11 pages.
Crispino et al., "In vivo genetic manipulation of inner ear connexin expression by bovine adeno-associated viral vectors," Sci Rep., Aug. 2017, 7(1):6567, 13 pages.
Dai et al., "Rhesus Cochlear and Vestibular Functions Are Preserved After Inner Ear Injection of Saline Volume Sufficient for Gene Therapy Delivery," J Assoc Res Otolaryngol., Aug. 2017, 18(4):601-617.
Darcy et al., "Abstract 691: Dual adeno-associated viral Anc80 vector efficiently transduces inner ear cells in non-human primates," Abstract, Presented at the 43rd Annual MidWinter Meeting, San Jose, CA, Jan. 25-29, 2020, 43:447-48, 3 pages.
Dashkoff et al., "Tailored transgene expression to specific cell types in the central nervous system after peripheral injection with AAV9," Mol Ther Methods Clin Dev, 2016, 3:16081, 9 pages.
D'Costa et al., "Practical utilization of recombinant AAV vector reference standards: focus on vector genomes titration by free ITR qPCR," Mol Ther Methods Clin Dev, 2016. 5:16019, 9 pages.
De Felipe et al., "Tricistronic and tetracistronic retroviral vectors for gene transfer," Hum Gene Ther., Sep. 2000, 11(13):1921-31.
De Felipe et al., "Use of the 2A sequence from foot-and-mouth disease virus in the generation of retroviral vectors for gene therapy," Gene Ther., Feb. 1999, 6(2):198-208.
Degen et al., "Connexin32 can restore hearing in connexin26 deficient mice," Eur J Cell Biol., Oct. 2011, 90(10):817-24.
del Castillo et al., "A novel deletion involving the connexin-30 gene, del(GJB6-d13s1854), found in trans with mutations in the GJB2 gene (connexin-26) in subjects with DFNB1 non-syndromic hearing impairment," J Med Genet., Jul. 2005, 42(7):588-94.
del Castillo et al., "DFNB1 Non-syndromic Hearing Impairment: Diversity of Mutations and Associated Phenotypes," Front Mol Neurosci., Dec. 2017, 10:428.
Delmaghani et al., "Inner ear gene therapies take off: current promises and future challenges," J Clin Med., Jul. 2020, 9(7):2309.
Derby et al., "Gene transfer into the mammalian inner ear using HSV-1 and vaccinia virus vectors," Hear Res., Aug. 1999, 134(1-2):1-8.
Deverman et al., "Cre-dependent selection yields AAV variants for widespread gene transfer to the adult brain," Nat Biotechnol, Feb. 2016, 34(2):204-9, 8 pages.
Dinculescu et al., "AAV-Mediated Clarin-1 Expression in the Mouse Retina: Implications for USH3A Gene Therapy," PLoS One, Feb. 2016, 11(2):e0148874.
Dinh et al., "Diverse deafness mechanisms of connexin mutations revealed by studies using in vitro approaches and mouse models," Brain Res., Jun. 2009, 1277:52-69.
Doane et al., "Regulatory elements in molecular networks," Wiley Interdiscip Rev Syst Biol Med., May 2017, 9(3):10.1002/wsbm.1374, 13 pages.
Doucette et al., "Profound, prelingual nonsyndromic deafness maps to chromosome 10q21 and is caused by a novel missense mutation in the Usher syndrome type IF gene PCDH15," Eur J Hum Genet., May 2009, 17(5):554-64.
Duan, "Systemic AAV Micro-dystrophin Gene Therapy for Duchenne Muscular Dystrophy" Mol. Ther., Oct. 2018, 26(10):2337-2356.
Dulon et al., "Clarin-1 gene transfer rescues auditory synaptopathy in model of Usher syndrome," J Clin Invest., Aug. 2018, 128(8):3382-3401.
Dyka et al., "Dual adeno-associated virus vectors result in efficient in vitro and in vivo expression of an oversized gene, MYO7A," Hum Gene Ther Methods, Apr. 2014, 25(2):166-77.
Eichler et al., "Hematopoietic stem-cell gene therapy for cerebral adrenoleukodystrophy," N. Engl. J. Med., Oct. 2017, 377(17):1630-1638, 9 pages.
Ellis et al., "A survey of ex vivo/in vitro transduction efficiency of mammalian primary cells and cell lines with Nine natural adeno-associated virus (AAV1-9) and one engineered adeno-associated virus serotype," Virol J., Mar. 2013, 10:74.
Feigenspan et al., "Expression of connexin36 in cone pedicles and OFF-cone bipolar cells of the mouse retina," J Neurosci., Mar. 2004, 24(13):3325-34.
Fetoni et al., "Cx26 partial loss causes accelerated presbycusis by redox imbalance and dysregulation of Nfr2 pathway," Redox Biol., Oct. 2018, 19:301-317.
Fields et al., "Usher syndrome type III: revised genomic structure of the USH3 gene and identification of novel mutations," Am J Hum Genet., Sep. 2002, 71(3):607-17.
Fisher et al., "Transduction with recombinant adeno-associated virus for gene therapy is limited by leading-strand synthesis," J Virol., Jan. 1996, 70(1):520-32.
Forge et al., "Gap junctions and connexin expression in the inner ear," Novartis Found Symp., 1999, 219:134-50.
Forge et al., "Gap junctions in the inner ear: comparison of distribution patterns in different vertebrates and assessment of connexin composition in mammals," J Comp Neurol., Dec. 2003, 467(2):207-31.
Furler et al., "Recombinant AAV vectors containing the foot and mouth disease virus 2A sequence confer efficient bicistronic gene expression in cultured cells and rat substantia nigra neurons," Gene Ther., Jun. 2001, 8(11):864-73.
Garcia et al., "Localization of myosin-Iβ near both ends of tip links in frog saccular hair cells," J Neurosci., Nov. 1998, 18(21):8637-47.
Gaudelli et al., "Programmable base editing of A•T to G•C in genomic DNA without DNA cleavage," Nature, Nov. 2017, 551(7681):464-471.
Ge et al., "Structure of mouse protocadherin 15 of the stereocilia tip link in complex with LHFPL5," eLife, Aug. 2018, 7:e38770, 24 pages.
GenBank Accession No. AAM88774.1., "clarin-1 [*Homo sapiens*]," mailed on Aug. 5, 2002, 1 page.
GenBank Accession No. KAA0147029.1, "hypothetical protein FNF29_07656 [Cafeteria roenbergensis]," mailed on Sep. 9, 2019, 2 pages.
Genbank Accession No. NM_004004.6., "*Homo sapiens* gap junction protein beta 2 (GJB2), mRNA," mailed on Dec. 20, 2021, 4 pages.
Genbank Accession No. NP_001182723.1, "clarin-1 isoform d [*Homo sapiens*]," mailed on Oct. 11, 2020, 3 pages.
Genbank Accession No. NP_001243748.1, clarin-1 isoform e [*Homo sapiens*], mailed on Dec. 13, 2020, 3 pages.
Genbank Accession No. NP_443721.1, clarin-1 isoform c [*Homo sapiens*], mailed on Oct. 10, 2020, 3 pages.
Genbank Accession No. NP_700433.1, clarin-1 isoform 1 [Mus musculus], mailed on Oct. 7, 2020, 3 pages.
Genbank Accession No. NP_700434.1, "clarin-1 isoform 2 [Mus musculus]," mailed on Oct. 9, 2020, 4 pages.
Genbank Accession No. NP_700435.1, "clarin-1 isoform 3 [Mus musculus]," mailed on Oct. 10, 2020, 3 pages.
Genbank Accession No. NP_777367.1, "clarin-1 isoform a [*Homo sapiens*]," mailed on Dec. 14, 2020, 3 pages.
GenBank Accession No. CDJ33539, "hypothetical protein EMH_0016460 [Eimeria mitis]," Nov. 5, 2013, 1 page.
Geng et al., "Modeling and Preventing Progressive Hearing Loss in Usher Syndrome III," Sci Rep., Oct. 2017, 7(1):13480, 15 pages.
Gong et al., "Adenoassociated virus serotype 9-mediated gene therapy for X-linked adrenoleukodystrophy," Mol. Ther., May 2015, 23(5):824-834.
Gossen et al., "Tight control of gene expression in mammalian cells by tetracycline-responsive promoters," Proc Natl Acad Sci U S A, Jun. 1992, 89(12):5547-51.
Gossen et al., "Transcriptional activation by tetracyclines in mammalian cells," Science, Jun. 1995, 268(5218):1766-9.
Graham et al., "A new technique for the assay of infectivity of human adenovirus 5 DNA," Virology, Apr. 1973, 52(2):456-67.
Gray and Samulski, "Vector design and considerations for CNS applications," Gene Vector Design and Application to Treat Nervous System Disorders, 2011, 9 pages.

(56) References Cited

OTHER PUBLICATIONS

Gray et al., "Directed evolution of a novel adeno-associated virus (AAV) vector that crosses the seizure-compromised blood-brain barrier (BBB)," Mol Ther, Mar. 2010, 18(3):570-8.
Gregorevic et al., "rAAV6-microdystrophin preserves muscle function and extends lifespan in severely dystrophic mice," Nat Med., Jul. 2006, 12(7):787-9.
Griciuc et al., "Alzheimer's disease risk gene CD33 inhibits microglial uptake of amyloid beta," Neuron, May 2013, 78(4):631-43.
Grimm et al., "In vitro and in vivo gene therapy vector evolution via multispecies interbreeding and retargeting of adeno-associated viruses," J Virol., Jun. 2008, 82(12):5887-911.
György et al., "Allele-specific gene editing prevents deafness in a model of dominant progressive hearing loss," Nat Med., Jul. 2019, 25(7):1123-1130.
György et al., "An AAV9 capsid variant efficiently transduces inner ear hair cells in mice and non-human primates and rescues hearing in a mouse model of human deafness," Mol Ther Methods Clin Dev., Nov. 2018, 13:1-13.
György et al., "Gene Transfer with AAV9-PHP.B Rescues Hearing in a Mouse Model of Usher Syndrome 3A and Transduces Hair Cells in a Non-human Primate," Mol Ther Methods Clin Dev, Jun. 2019, 13:1-13.
György et al., "Rescue of Hearing by Gene Delivery to Inner-Ear Hair Cells Using Exosome-Associated AAV," Mol Ther., Feb. 2017, 25(2):379-391.
Halpin et al., "Self-processing 2A-polyproteins—a system for coordinate expression of multiple proteins in transgenic plants," Plant J., Feb. 1999, 17(4):453-9.
Hanlon et al., "151: AAV-S: A Novel AAV Vector Selected in Brain Transduces the Cochlea with High Efficiency," Abstract, Presented at Proceedings of the 2020 American Society of Gene and Cell Therapy Annual Meeting, Virtual, May 12-15, 2020; Molecular Therapy, Apr. 2020, 28(4S1):76-77, 2 pages.
Hanlon et al., "AAV-S: A novel AAV vector selected in brain transduces the inner ear with high efficiency," Poster, Presented at Proceedings of the ASGCT, Harvard Medical School, Boston, MA, Apr. 28, 2020, 1 page.
Hanlon et al., "Selection of an Efficient AAV Vector for Robust CNS Transgene Expression," Molecular Therapy: Methods and Clinical Development, Dec. 2019, 15:320-332.
Harvey et al., "Inducible control of gene expression: prospects for gene therapy," Curr Opin Chem Biol., Aug. 1998, 2(4):512-8.
Hasson et al., "Unconventional myosins in inner-ear sensory epithelia," J Cell Biol., Jun. 1997, 137(6):1287-307.
Hinderer et al., "Severe Toxicity in Nonhuman Primates and Piglets Following High-Dose Intravenous Administration of an Adeno-Associated Virus Vector Expressing Human SMN," Hum Gene Ther, Mar. 2018, 29(3):285-298.
Hirsch et al., "Delivering Transgenic DNA Exceeding the Carrying Capacity of AAV Vectors," Methods Mol Biol., 2016, 1382:21-39.
Holt et al., "A chemical-genetic strategy demonstrates myosin 1c mediates sensory adaptation in hair cells," Cell, Feb. 2002, 108(3):371-81.
Holt et al., "Functional expression of exogenous proteins in mammalian sensory hair cells infected with adenoviral vectors," J Neurophysiol., Apr. 1999, 81(4):1881-8.
Hordeaux et al., "The GPI-Linked Protein LY6A Drives AAV-PHP.B Transport across the Blood-Brain Barrier," Mol Ther, May 2019, 27(5):912-921.
Hordeaux et al., "The Neurotropic Properties of AAV-PHP.B Are Limited to C57BL/6J Mice," Mol Ther, Mar. 2018, 26(3):664-668.
Hrvatin et al., "Single-cell analysis of experience-dependent transcriptomic states in the mouse visual cortex," Nat Neurosci., Jan. 2018, 21(1):120-129.
Huang et al., "Role of the hepatitis B virus posttranscriptional regulatory element in export of intronless transcripts," Mol Cell Biol., 1995, 15(7):3864-3869.
Hudry et al., "Exosome-associated AAV vector as a robust and convenient neuroscience tool," Gene Ther, 2016, 23(4):380-92.
Hughes et al., "AAV9 intracerebroventricular gene therapy improves lifespan, locomotor function and pathology in a mouse model of Niemann-Pick type C1 disease," Hum. Mol. Genet., Sep. 2018, 27(17):3079-3098.
Iizuka et al., "Perinatal Gjb2 gene transfer rescues hearing in a mouse model of hereditary deafness," Hum Mol Genet., Jul. 2015, 24(13):3651-61.
Indzhykulian et al., "Molecular remodeling of tip links underlies mechanosensory regeneration in auditory hair cells," PLoS Biol., 2013, 11(6):e1001583, 15 pages.
International Search Report and Written Opinion in International Appln. No. PCT/US2025/023316, mailed on Sep. 8, 2025, 17 pages.
Iossa et al., "GJB2 Gene Mutations in Syndromic Skin Diseases with Sensorineural Hearing Loss," Curr Genomics, Nov. 2011, 12(7):475-785.
Isgrig et al., "AAV2.7m8 is a powerful viral vector for inner ear gene therapy," Nat Commun., Jan. 2019, 10(1):427, 8 pages.
Isgrig et al., "Gene Therapy Restores Balance and Auditory Functions in a Mouse Model of Usher Syndrome," Mol. Ther., Mar. 2017, 25(3):780-791.
Ivanchenko et al., "4: Preclinical testing of AAV9-PHP.B for transgene expression in the non-human primate cochlea," Abstract, Presented at Proceedings of the 2020 American Society of Gene and Cell Therapy Annual Meeting, Virtual, May 12-15, 2020; Molecular Therapy, Apr. 2020, 28(4S1):2, 1 page.
Ivanchenko et al., "AAV-S: A versatile capsid variant for transduction of mouse and primate inner ear," Mol Ther Methods Clin Dev., Mar. 2021, 21:382-398.
Ivanchenko et al., "Preclinical testing of AAV9-PHP.B for transgene expression in the non-human primate cochlea," Hear Res., Sep. 2020, 394:107930, 11 pages.
Johnson et al., "Connexin-Mediated Signaling in Nonsensory Cells Is Crucial for the Development of Sensory Inner Hair Cells in the Mouse Cochlea," J Neurosci., Jan. 2017, 37(2):258-268.
Jovičić et al., "Comprehensive Expression Analyses of Neural Cell-Type-Specific miRNAs Identify New Determinants of the Specification and Maintenance of Neuronal Phenotypes," J Neurosci., Mar. 2013, 33(12):5127-37.
Kamiya et al., "Assembly of the cochlear gap junction macromolecular complex requires connexin 26," J Clin Invest., Apr. 2014, 124(4):1598-607.
Kazmierczak et al., "Cadherin 23 and protocadherin 15 interact to form tip-link filaments in sensory hair cells," Nature, Sep. 2007, 449(7158):87-91.
Kelsell et al., "Connexin 26 mutations in hereditary non-syndromic sensorineural deafness," Nature, May 1997, 387(6628):80-3.
Kenna et al., "Audiologic phenotype and progression in GJB2 (Connexin 26) hearing loss," Arch Otolaryngol Head Neck Surg., Jan. 2010, 136(1):81-7.
Keppeler et al., "Ultrafast optogenetic stimulation of the auditory pathway by targeting-optimized Chronos," EMBO J, Dec. 2018, 37(24):e99649, 15 pages.
Keskin et al., "AAV5-miHTT Lowers Huntingtin mRNA and Protein without Off-Target Effects in Patient-Derived Neuronal Cultures and Astrocytes," Mol. Ther. Methods Clin. Dev., Dec. 2019, 15:275-284.
Kiang et al., "Upstream genomic sequence of the human connexin26 gene," Gene, Oct. 1997, 199(1-2):165-71.
Kikuchi et al., "Gap junction systems in the mammalian cochlea," Brain Res Brain Res Rev., Apr. 2000, 32(1):163-6.
Kikuchi et al., "Gap junctions in the rat cochlea: immunohistochemical and ultrastructural analysis," Anat Embryol (Berl)., Feb. 1995, 191(2):101-18.
Klump et al., "Retroviral vector-mediated expression of HoxB4 in hematopoietic cells using a novel coexpression strategy," Gene Ther., May 2001, 8(10):811-7.
Kodippili et al., "Dual AAV Gene Therapy for Duchenne Muscular Dystrophy with a 7-kb Mini-Dystrophin Gene in the Canine Model," Hum Gene Ther., Mar. 2018, 29(3):299-311.
Koehler et al., "Generation of inner ear organoids containing functional hair cells from human pluripotent stem cells," Nat Biotechnol., Jun. 2017, 35(6):583-589.

(56) References Cited

OTHER PUBLICATIONS

Koerber et al., "Construction of diverse adeno-associated viral libraries for directed evolution of enhanced gene delivery vehicles," Nat Protoc, Jul. 2006, 1(2):701-6.
Kohrman et al., "Gene therapy for deafness," Gene Ther., Dec. 2013, 20(12):1119-23.
Körbelin et al., "A brain microvasculature endothelial cell-specific viral vector with the potential to treat neurovascular and neurological diseases," EMBO Mol Med., Jun. 2016, 8(6):609-25.
Körbelin et al., "Pulmonary Targeting of Adeno-associated Viral Vectors by Next-generation Sequencing-guided Screening of Random Capsid Displayed Peptide Libraries," Mol Ther, Jun. 2016, 24(6):1050-1061.
Kwan et al., "TRPA1 contributes to cold, mechanical, and chemical nociception but is not essential for hair-cell transduction," Neuron, Apr. 2006, 50(2):277-89.
Landegger et al., "A synthetic AAV vector enables safe and efficient gene transfer to the mammalian inner ear," Nat Biotechnol., Mar. 2017, 35(3):280-284.
Lang et al., "Effects of chronic furosemide treatment and age on cell division in the adult gerbil inner ear," J Assoc Res Otolaryngol., Jun. 2003, 4(2):164-75.
Lang et al., "Standard screening methods underreport AAV-mediated transduction and gene editing," Nat Commun., Jul. 2019, 10(1):3415, 10 pages.
Lee et al., "Efficient viral transduction in mouse inner ear hair cells with utricle injection and AAV9-PHP.B," Hear Res., Sep. 2020, 394:107882, 11 pages.
Lee et al., "Mice with conditional deletion of Cx26 exhibit no vestibular phenotype despite secondary loss of Cx30 in the vestibular end organs," Hearing Res., Oct. 2015, 328:102-12.
Leone et al., "Long-term follow-up after gene therapy for canavan disease," Sci. Transl. Med., 2012, 4(165):165ra163, 14 pages.
Levy et al., "Cytosine and adenine base editing of the brain, liver, retina, heart and skeletal muscle of mice via adeno-associated viruses," Nat Biomed Eng., Jan. 2020, 4(1):97-110.
Li et al., "Characterization of slow-cycling cells in the mouse cochlear lateral wall," PloS one, Jun. 2017, 12(6):e0179293.
Li et al., "Engineering adeno-associated virus vectors for gene therapy," Nature Reviews Genetics, Apr. 2020, 21(4):255-272, 18 pages.
Li et al., "MicroRNAs in hair cell development and deafness," Curr Opin Otolaryngol Head Neck Surg., Oct. 2010, 18(5):459-65.
Li et al., "Notch inhibition induces mitotically generated hair cells in mammalian cochleae via activating the Wnt pathway," Proc Natl Acad Sci U S A, Jan. 2015, 112(1):166-71.
Lin et al., "Hearing loss and incident dementia," Arch Neurol., Feb. 2011, 68(2):214-20.
Lin et al., "Hearing loss prevalence in the United States," Arch Intern Med., Nov. 2011, 171(20):1851-2.
Lopes et al., "Gene therapy for the retinal degeneration of usher syndrome caused by mutations in MYO7A," Cold Spring Harb. Perspect. Med., Jun. 2015, 5(6):a017319, 10 pages.
Lukashkina et al., "Amplification mode differs along the length of the mouse cochlea as revealed by connexin 26 deletion from specific gap junctions," Sci Rep., Jul. 2017, 7(1);5185, 11 pages.
Lustig et al., "Cochlear Gene Therapy," Cold Spring Harb Perspect Med., Sep. 2019, 9(9):a033191, 15 pages.
Ma et al., "Abstract 404: Connexin 26 in mature ears influences survival of hair cells and neurons," Abstract, Presented at Proceedings of the 43rd Annual MidWinter Meeting, San Jose, CA, Jan. 25-29, 2020, 43:258-9, 3 pages.
Magari et al., "Pharmacologic control of a humanized gene therapy system implanted into nude mice," J Clin Invest., Dec. 1997, 100(11):2865-72.
Maguire et al., "Efficacy, Safety, and Durability of Voretigene Neparvovec-rzyl in RPE65 Mutation-Associated Inherited Retinal Dystrophy: Results of Phase 1 and 3 Trials," Ophthalmology, 2019, 126(9):1273-1285.
Maguire et al., Microvesicle-associated AAV vector as a novel gene delivery system. Mol Ther, 2012, 20(5):960-71.
Mahendrasingam et al., "Subcellular distribution and relative expression of fibrocyte markers in the CD/1 mouse cochlea assessed by semiquantitative immunogold electron microscopy," J Histochem Cytochem., Nov. 2011, 59(11):984-1000.
Mammano et al., "Inner Ear Connexin Channels: Roles in Development and Maintenance of Cochlear Function," Cold Spring Harb Perspect Med., Jul. 2019, 9(7):a033233, 26 pages.
Manno et al., "Successful transduction of liver in hemophilia by AAV-Factor IX and limitations imposed by the host immune response," Nat Med, 2006, 12(3):342-7.
Mason et al., "Universal infant hearing screening by automated auditory brainstem response measurement," Pediatrics, Feb. 1998, 101(2):221-8.
Matsuzaki et al., "Intravenous administration of the adeno-associated virus-PHP.B capsid fails to upregulate transduction efficiency in the marmoset brain," Neurosci Lett., Feb. 2018, 665:182-188.
Matsuzaki et al., "Neurotropic Properties of AAV-PHP.B Are Shared among Diverse Inbred Strains of Mice," Mol Ther, 2019, 27(4):700-704.
Mattion et al., "Foot-and-mouth disease virus 2A protease mediates cleavage in attenuated Sabin 3 poliovirus vectors engineered for delivery of foreign antigens," J Virol., Nov. 1996, 70(11):8124-7.
McCarthy, "Self-complementary AAV vectors; advances and applications," Mol Ther., Oct. 2008, 16(10):1648-56.
McLean et al., "Great improves functional interpretation of cis-regulatory regions," Nat Biotechnol., May 2010, 28(5):495-501.
Mei et al., "A deafness mechanism of digenic Cx26 (GJB2) and Cx30 (GJB6) mutations: Reduction of endocochlear potential by impairment of heterogeneous gap junctional function in the cochlear lateral wall," Neurobiol Dis., Dec. 2017, 108:195-203.
Mendell et al., "Single-Dose Gene-Replacement Therapy for Spinal Muscular Atrophy," N Engl J Med, Nov. 2017, 377(18):1713-1722.
Millington-Ward et al., "Suppression and Replacement Gene Therapy for Autosomal Dominant Disease in a Murine Model of Dominant Retinitis Pigmentosa," Mol. Ther., Apr. 2011, 19(4):642-649.
Mookherjee et al., "Long-term rescue of cone photoreceptor degeneration in retinitis pigmentosa 2 (RP2)-knockout mice by gene replacement therapy," Hum. Mol. Genet., Nov. 2015, 24(22):6446-58.
Mutai et al., "Mitotic activity and specification of fibrocyte subtypes in the developing rat cochlear lateral wall," Neuroscience, Nov. 2009, 163(4):1255-63.
Narui et al., "Tuning Inner-Ear Tip-Link Affinity Through Alternatively Spliced Variants of Protocadherin-15," Biochemistry, Mar. 2018, 57(11):1702-1710.
Naso et al., "Adeno-associated virus (AAV) as a vector for gene therapy," BioDrugs, Aug. 2017, 31(4):317-34.
Nathwani, "Gene therapy for hemophilia," Hematol. Am Soc Hematol Educ Program, Dec. 2019, 2019(1):1-8.
Nickel et al., "Gap junctions and connexins in the inner ear: their roles in homeostasis and deafness," Curr Opin Otolaryngol Head Neck Surg., Oct. 2008, 16(5):452-7.
Nist-Lund et al., "Improved TMC1 gene therapy restores hearing and balance in mice with genetic inner ear disorders," Nat. Commun., 2019, 10(1):236, 14 pages.
Niwa et al., "In vitro polyadenylation is stimulated by the presence of an upstream intron," Genes Dev., Sep. 1990, 4(9):1552-9.
No et al., "Ecdysone-inducible gene expression in mammalian cells and transgenic mice," Proc Natl Acad Sci U S A, Apr. 1996, 93(8):3346-3351.
Nonnenmacher et al., "High capsid-genome correlation facilitates creation of AAV libraries for directed evolution," Mol Ther, Apr. 2015, 23(4):675-82.
Olson et al., "Post-translational tools expand the scope of synthetic biology," Curr Opin Chem Biol., Aug. 2012, 16(3-4):300-6.
Pan et al., "Gene therapy restores auditory and vestibular function in a mouse model of Usher syndrome type 1c," Nat Biotechnol., Mar. 2017, 35(3):264-272.

(56) References Cited

OTHER PUBLICATIONS

Park et al., "Generation of transgenic marmosets expressing genetically encoded calcium indicators," Sci Rep, Oct. 2016, 6:34931, 12 pages.
Paulk et al., "Bioengineered AAV Capsids with Combined High Human Liver Transduction in Vivo and Unique Humoral Seroreactivity," Mol Ther, Jan. 2018, 26(1):289-303.
Paulk et al., "Bioengineered Viral Platform for Intramuscular Passive Vaccine Delivery to Human Skeletal Muscle," Mol Ther Methods Clin Dev, Jul. 2018, 10:144-155.
Pepermans et al., "The CD2 isoform of protocadherin-15 is an essential component of the tip-link complex in mature auditory hair cells," EMBO Mol Med., Jul. 2014, 6(7):984-92.
Powers et al., "A Partial Calcium-Free Linker Confers Flexibility to Inner-Ear Protocadherin-15," Structure, Mar. 2017, 25(3):482-495.
Prabhakar et al., "AAV9 transduction mediated by systemic delivery of vector via retro-orbital injection in newborn, neonatal and juvenile mice," Exp Anim., Nov. 2021, 70(4):450-458.
Pulicherla et al., "Engineering liver-detargeted AAV9 vectors for cardiac and musculoskeletal gene transfer," Mol Ther, Jun. 2011, 19(6):1070-1078.
Rada-Iglesias et al., "A unique chromatin signature uncovers early developmental enhancers in humans," Nature, Feb. 2011, 470(7333):279-83.
Ravindra Kumar et al., "Multiplexed Cre-dependent selection yields systemic AAVs for targeting distinct brain cell types," Nat Methods, May 2020, 17(5):541-550.
Rees et al., "Base editing: precision chemistry on the genome and transcriptome of living cells," Nat Rev Genet., Dec. 2018, 19(12):770-788.
Remes et al., "AAV-mediated TIMP-1 overexpression in aortic tissue reduces the severity of allograft vasculopathy in mice," J. Hear. Lung Transplant, Apr. 2020, 39(4):389-398, 10 pages.
Rodriguez-Paris et al., "Comparative functional characterization of novel non-syndromic GJB2 gene variant p.Gly45Arg and lethal syndromic variant p.Gly45Glu," PeerJ, Oct. 2016, 4:e2494, 18 pages.
Ross, "Comments on the article "Persistent confusion of total entropy and chemical system entropy in chemical thermodynamics" [(1996) Proc. Natl. Acad. Sci. USA 93, 7452-7453]," Proc. Natl Acad Sci USA, Dec. 1996, 93(25):14314.
Ryan et al., "Foot-and-mouth disease virus 2A oligopeptide mediated cleavage of an artificial polyprotein," EMBO J., Feb. 1994, 13(4):928-33.
Sacheli et al., "Gene transfer in inner ear cells: a challenging race," Gene Ther., Mar. 2013, 20(3):237-47.
Sallach et al., "Tropism-modified AAV vectors overcome barriers to successful cutaneous therapy," Mol Ther, May 2014, 22(5):929-39.
Sasaki et al., "Generation of transgenic non-human primates with germline transmission," Nature, May 2009, 459(7246):523-7.
Scheffer et al., "Gene expression profiling identifies Hes6 as a transcriptional target of ATOHI in cochlear hair cells," FEBS Lett., Oct. 2007, 581(24):4651-6.
Scheffer et al., "The $\alpha$1 subunit of nicotinic acetylcholine receptors in the inner ear: transcriptional regulation by ATOH1 and co-expression with the $\gamma$ subunit in hair cells," J Neurochem., Dec. 2007, 103(6):2651-64.
Scheffer et al., "XIRP2, an actin-binding protein essential for inner ear hair-cell stereocilia," Cell Rep., Mar. 2015, 10(11):1811-8.
Senís et al., "CRISPR/Cas9-mediated genome engineering: an adeno-associated viral (AAV) vector toolbox," Biotechnol J., Nov. 2014, 9(11):1402-12.
Shepherd et al., "The extent of adaptation in bullfrog saccular hair cells," J Neurosci., Oct. 1994, 14(10):6217-29.
Shu et al., "Identification of Adeno-Associated Viral Vectors That Target Neonatal and Adult Mammalian Inner Ear Cell Subtypes," Hum Gene Ther., Sep. 2016, 27(9):687-99.
Solc et al., "Molecular cloning of myosins from the bullfrog saccular macula: A candidate for the adaptation motor," Auditory Neurosci., 1994, 1:63-75.
Sotomayor et al., "In search of the hair-cell gating spring: Elastic properties of ankyrin and cadherin repeats," Structure, Apr. 2005, 13(4):669-82.
Sotomayor et al., "Structural determinants of cadherin-23 function in hearing and deafness," Neuron, Apr. 2010, 66(1):85-100.
Sotomayor et al., "Structure of a force-conveying cadherin bond essential for inner-ear mechanotransduction," Nature, Dec. 2012, 492(7427):128-32.
Srinivas et al., "Human diseases associated with connexin mutations," Biochim Biophys Acta Biomembr., Jan. 2018, 1860(1):192-201.
Sun et al., "Connexin30 null and conditional connexin26 null mice display distinct pattern and time course of cellular degeneration in the cochlea," J Comp Neurol., Oct. 2009, 516(6):569-79.
Suzuki et al., "Cochlear gene therapy with ancestral AAV in adult mice: complete transduction of inner hair cells without cochlear dysfunction," Sci Rep., Apr. 2017, 7:45524, 11 pages.
Takada et al., "Connexin 26 null mice exhibit spiral ganglion degeneration that can be blocked by BDNF gene therapy," Hearing Res., Mar. 2014, 309:124-35.
Tan et al., "AAV-ie enables safe and efficient gene transfer to inner ear cells," Nat. Commun., Aug. 2019, 10(1):3733, 10 pages.
Tao et al., "Delivery of adeno-associated virus vectors in adult mammalian inner-ear cell subtypes without auditory dysfunction," Hum Gene Ther., Apr. 2018, 29(4):492-506.
Trapani et al., "Effective delivery of large genes to the retina by dual AAV vectors," EMBO Mol Med., Feb. 2014, 6(2):194-211.
Trapani et al., "Seeing the Light after 25 Years of Retinal Gene Therapy," Trends Mol Med., Aug. 2018, 24(8):669-681.
Trapani, "Dual AAV Vectors for Stargardt Disease," Methods Mol Biol., 2018, 1715:153-175.
Truong et al., "Development of an intein-mediated split-Cas9 system for gene therapy," Nucleic Acids Res., Jul. 2015, 43(13):6450-8.
Tse et al., "Structure-guided evolution of antigenically distinct adeno-associated virus variants for immune evasion," Proc Natl Acad Sci U S A, May 2017, 114(24):E4812-E4821.
Tu et al., "Mapping and characterization of the basal promoter of the human connexin26 gene," Biochim Biophys Acta., Nov. 1998, 1443(1-2):169-81.
Västinsalo et al., "Alternative splice variants of the USH3A gene Clarin 1 (CLRN1)," Eur J Hum Genet., Jan. 2011, 19(1):30-5.
Vogl et al., "Tryptophan-rich basic protein (WRB) mediates insertion of the tail-anchored protein otoferlin and is required for hair cell exocytosis and hearing," EMBO J., Dec. 2016, 35(23):2536-2552.
Wan et al., "Efficacy and Safety of rAAV2-ND4 Treatment for Leber's Hereditary Optic Neuropathy," Sci. Rep., Feb. 2016, 6:21587, 10 pages.
Wan et al., "Inner ear supporting cells: Rethinking the silent majority," Semin Cell Dev Biol., May 2013, 24(5):448-59.
Wang et al., "A Rationally Engineered Capsid Variant of AAV9 for Systemic CNS-Directed and Peripheral Tissue-Detargeted Gene Delivery in Neonates," Mol Ther Methods Clin Dev., Mar. 2018, 9:234-246.
Wang et al., "Ligand-inducible and liver-specific target gene expression in transgenic mice," Nat Biotechnol., Mar. 1997, 15(3):239-43.
Wang et al., "Positive and negative regulation of gene expression in eukaryotic cells with an inducible transcriptional regulator," Gene Ther., May 1997, 4(5):432-41.
Wang et al., "Targeted connexin26 ablation arrests postnatal development of the organ of Corti," Biochem Biophys Res Commun., Jul. 2009, 385(1):33-7.
Wassmer et al., "Exosome-associated AAV2 vector mediates robust gene delivery into the murine retina upon intravitreal injection," Sci Rep., Mar. 2017, 7:45329, 10 pages.
Watanabe et al., "Expression of the Sox10 gene during mouse inner ear development," Brain Res Mol Brain Res., Dec. 2000, 84(1-2):141-5.
Watters et al., "Identification and dynamic regulation of tight junction protein expression in human neural stem cells," Stem Cells Dev, Jun. 2015, 24(12):1377-89.

(56) References Cited

OTHER PUBLICATIONS

Wilch et al., "A novel DFNB 1 deletion allele supports the existence of a distant cis-regulatory region that controls GJB2 and GJB6 expression," Clin Genet., Sep. 2010, 78(3):267-74.
Wingard et al., "Cellular and Deafness Mechanisms Underlying Connexin Mutation-Induced Hearing Loss—A Common Hereditary Deafness," Front Cell Neurosci., May 2015, 9:202, 13 pages.
Wise et al., "The effect of deafness duration on neurotrophin gene therapy for spiral ganglion neuron protection," Hearing Res., Aug. 2011, 278(1-2):69-76.
Wright et al., "Identification of factors that contribute to recombinant AAV2 particle aggregation and methods to prevent its occurrence during vector purification and formulation," Mol Ther., Jul. 2005, 12(1):171-8.
Wu et al., "Hair-cell mechanotransduction persists in TRP channel knockout mice," PloS One, May 2016, 11(5):e0155577, 22 pages.
Xia et al., "Expression of connexin 26 and Na,K-ATPase in the developing mouse cochlear lateral wall: functional implications," Brain Res., Oct. 1999, 846(1):106-11.
Xie et al., "MicroRNA-regulated, systemically delivered rAAV9: a step closer to CNS-restricted transgene expression," Mol Ther., Mar. 2011, 19(3):526-35.
Xu et al., "A combination of mutations enhances the neurotropism of AAV-2," Virology, 2005, 341:203-214.
Yang et al., "Gfi1-Cre knock-in mouse line: A tool for inner ear hair cell-specific gene deletion," Genesis, Jun. 2010, 48(6):400-6.
Yang et al., "Long-term outcomes of gene therapy for the treatment of Leber's hereditary optic neuropathy," EBioMedicine, Aug. 2016, 10:258-268.
Yeh et al., "Abstract PS 172: In vivo base editing rescues hearing in a mouse model of recessive deafness," Abstract, Presented at Proceedings of the 43rd Annual MidWinter Meeting, San Jose, CA, Jan. 25-29, 2020, 43:96-7; 3 pages.
Yeh et al., "In vivo base editing of post-mitotic sensory cells," Nature Commun., Jun. 2018, 9(1):2184, 10 pages.
Yu et al., "Nrl knockdown by AAV-delivered CRISPR/Cas9 prevents retinal degeneration in mice," Nat. Commun., Mar. 2017, 8:14716, 15 pages.
Yu et al., "Supplementary Figure 2 to: Virally expressed connexin26 restores gap junction function in the cochlea of conditional Gjb2 knockout mice," Gene Ther., Nov. 2013, 1 page.
Yu et al., "Virally expressed connexin26 restores gap junction function in the cochlea of conditional Gjb2 knockout mice," Gene Ther., Jan. 2014, 21(1):71-80.
Zallocchi et al., "Localization and expression of clarin-1, the Clrn1 gene product, in auditory hair cells and photoreceptors," Hear Res., Sep. 2009, 255(1-2):109-20.
Zelante et al., "Connexin26 mutations associated with the most common form of non-syndromic neurosensory autosomal recessive deafness (DFNB1) in Mediterraneans," Hum Mol Genet., Sep. 1997, 6(9):1605-9.
Zhang et al., "Cochlear Gene Therapy for Sensorineural Hearing Loss: Current Status and Major Remaining Hurdles for Translational Success," Front. Mol. Neurosci., Jun. 2018, 11:221, 15 pages.
Zhu et al., "Active cochlear amplification is dependent on supporting cell gap junctions," Nature Commun., 2013, 4:1786, 8 pages.
Ciani et al., "DOTAP/DOPE and DC-Chol/DOPE lipoplexes for gene delivery: zeta potential measurements and electron spin resonance spectra," Biochimica et Biophysica Acta (BBA)-Biomembranes, Jul. 2004, 1664(1):70-9.
Lomashvili et al., "Vascular calcification is dependent on plasma levels of pyrophosphate Vascular calcification is dependent on plasma levels of pyrophosphate," Kidney International, Jun. 2014, 85(6):1351-1356.
Murshed et al., "Extracellular matrix mineralization is regulated locally; different roles of two gla-containing proteins," The Journal of Cell Biology, Jun. 7, 2004, 165(5):625-630.
Office Action in European Appln. No. 23874010.4, mailed on May 16, 2025, 3 pages.
Ralph et al., "Weighing the Evidence for the Roles of Plasma Versus Local Pyrophosphate in Ectopic Calcification Disorders," Journal of Bone and Mineral Research, Apr. 2023, 38(4):457-463.
Saul et al., "A dual-ligand approach for enhancing targeting selectivity of therapeutic nanocarriers," Journal of Controlled Release, Sep. 2006, 114(3):277-87.

* cited by examiner

FIGs. 17A-C

LIVER

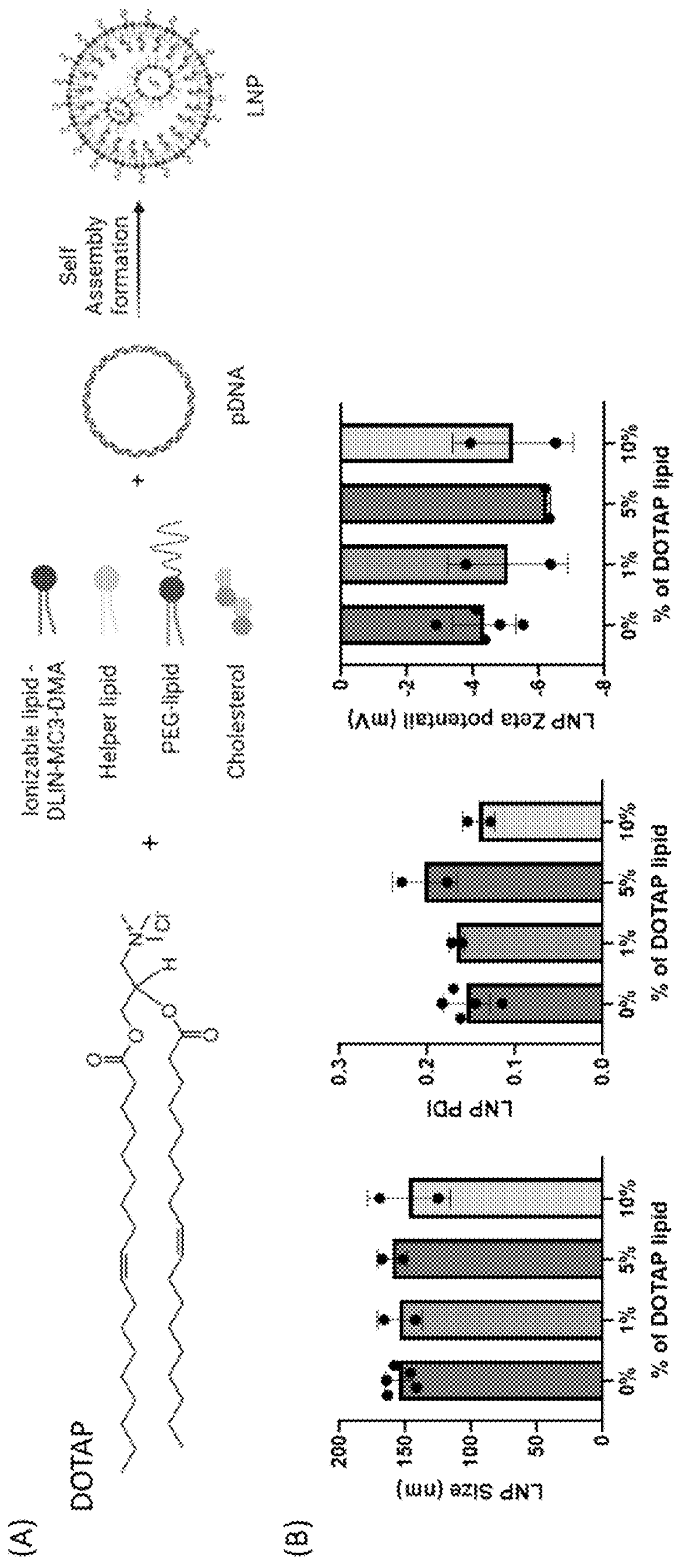
FIGs. 20A-B

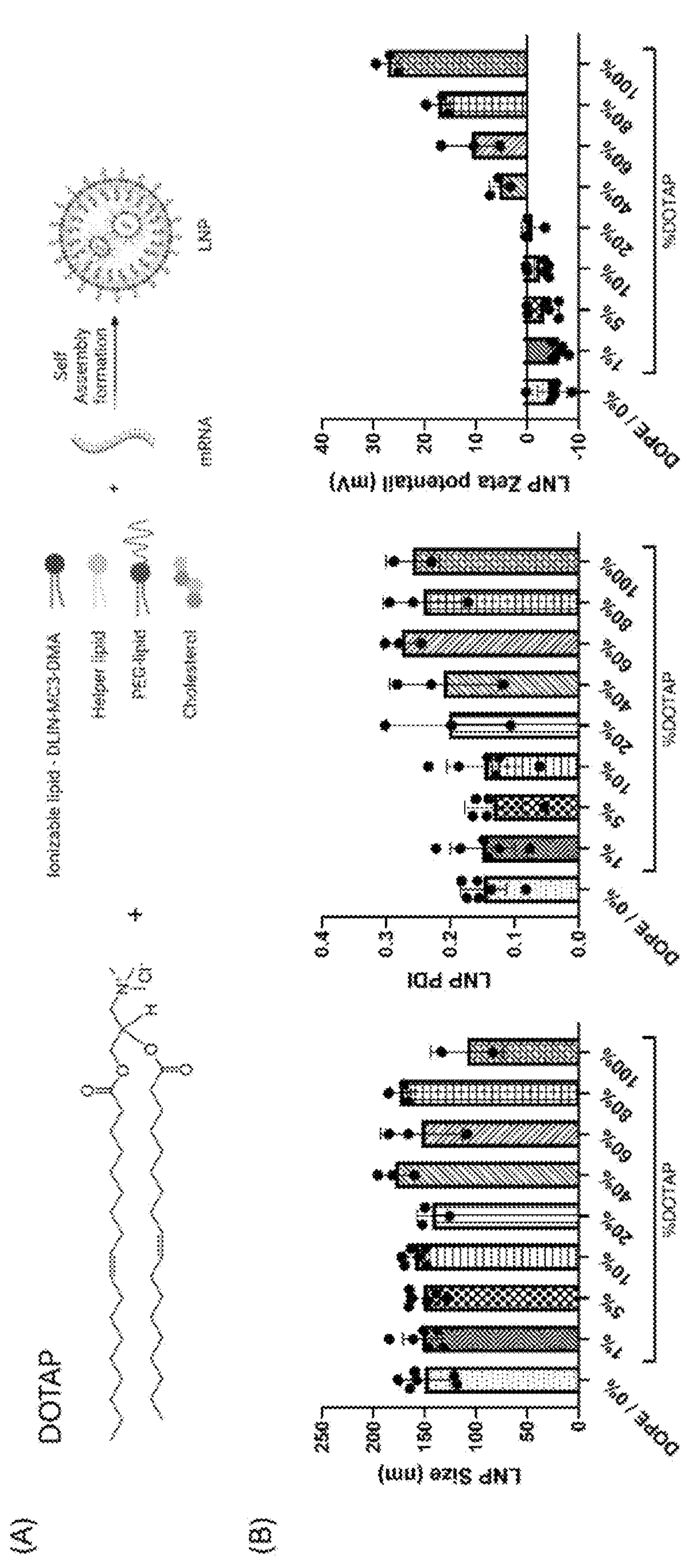
FIGs. 23A-B

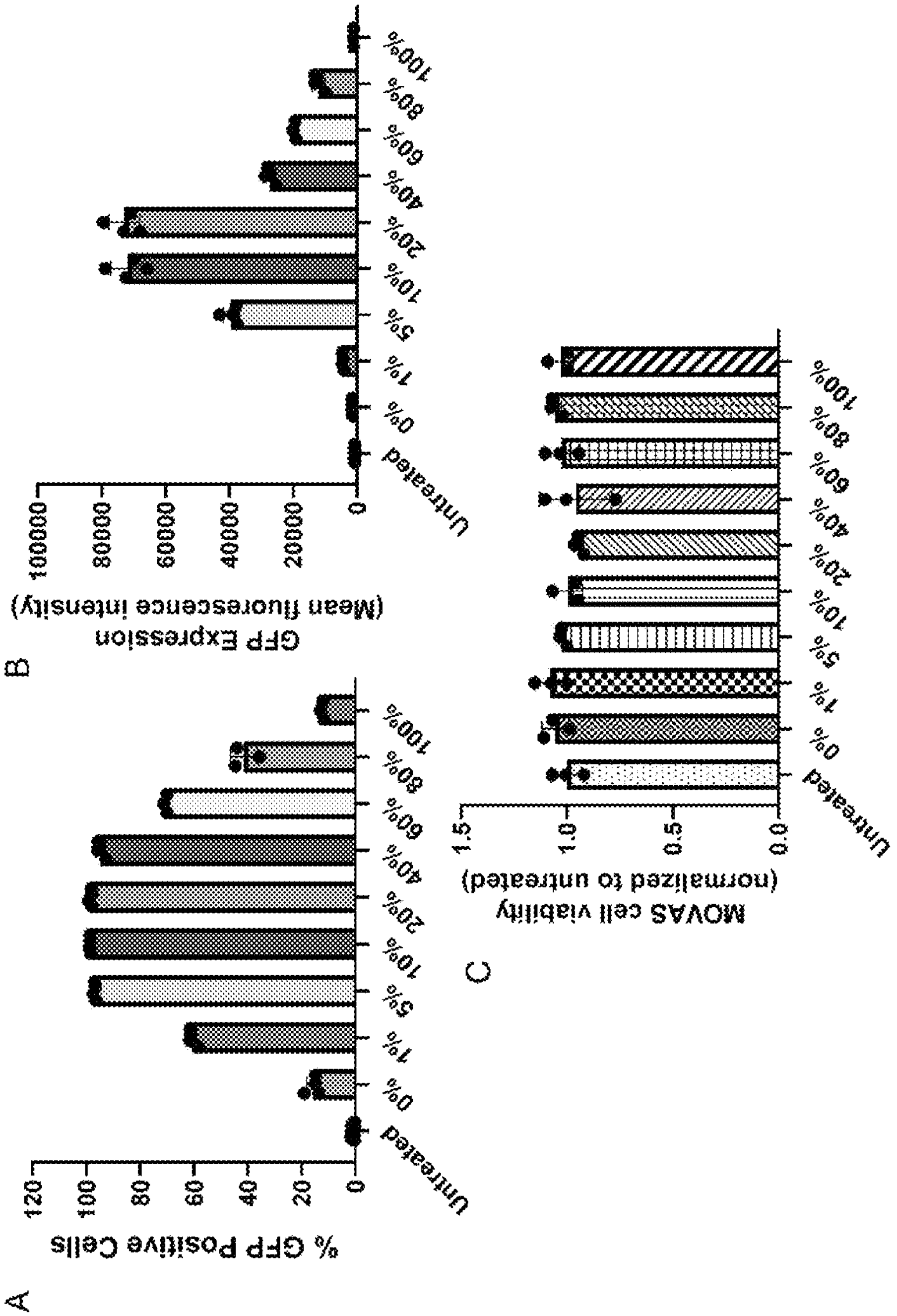
FIGs. 24A-C

Surgical Specimens

ENPP1 GENE THERAPY FOR THE TREATMENT OF VASCULAR DISEASE

CLAIM OF PRIORITY

This application claims the benefit of U.S. Provisional Patent Application Ser, Nos. 63/574,782, filed on Apr. 4, 2024, 63/574,833, filed on Apr. 4, 2024, 63/719,028, filed on Nov. 11, 2024, and 63/719,040, filed on Nov. 11, 2024. The entire contents of the foregoing are hereby incorporated by reference herein.

SEQUENCE LISTING

This application contains a Sequence Listing that has been submitted electronically as an XML file named 29539-0765001_SL_ST26.xml. The XML file, created on Apr. 4, 2025, is 321,155 bytes in size. The material in the XML file is hereby incorporated by reference in its entirety.

TECHNICAL FIELD

Provided herein are compositions and methods for gene therapy for disorders of arterial calcification as well as generalized arterial calcification of infancy (GACI). The methods include a gene addition strategy to deliver a DNA construct to target tissues (such as liver and smooth muscle cells) to express soluble recombinant ENPP1 (srENPP1) or transmembrane domain-containing (e.g., full-length) recombinant ENPP1 (rENPP1).

BACKGROUND

Generalized arterial calcification of infancy (GACI) is a rare genetic disorder that affects the circulatory system in general, and the large and medium sized arteries in particular, throughout the body. GACI is caused by autosomal recessive mutations in the ectonucleotide pyrophosphatase/phosphodiesterase 1 (ENPP1) or ABCC6 genes (Nitschke et al., Am J Hum Genet. 2012 Jan. 13; 90(1):25-39; Ziegler et al., *Generalized Arterial Calcification of Infancy*. In: GeneReviews® [Internet]. Seattle (WA): University of Washington, Seattle; 1993. 2014 Nov. 13 [updated 2020 Dec. 30]). The disease affects children and young adults, and diagnosis can be made in utero or the first months of life. Infants present with heart disease (e.g., myocardial infarction, heart failure, valvular disease, and/or ischemic cardiomyopathy), and the highest mortality rates occur in the first 6 months of life, with about 55% of affected infants dying. During the course of the disease, the arteries mineralize (calcification) and narrow (intima proliferation) causing myocardial infarction, heart failure, kidney failure, severe hypertension, and strokes. Patients who survive to later childhood and adult life typically have phosphate wasting leading to hearing loss, rickets/ostemalacia (e.g., autosomal recessive hypophosphatemic rickets Type 2 (ARHR2), skin findings, and vision loss; see, e.g., Rutsch et al., Circ Cardiovasc Genet. 2008 December; 1(2):133-40).

Although GACI is an extreme example, other conditions are associated with similar vascular calcification pathology, including pseudoxanthoma elasticum (PXE), calciphylaxis, and cardiovascular diseases including diabetic vascular calcification, end-stage renal disease (ESRD)-associated vascular disease, calcific aortic valve disease (CAVD), coronary atherosclerosis, coronary artery bypass graft (CABG) stenosis, in-stent stenosis, peripheral vascular disease, and cerebral atherosclerosis.

SUMMARY

Provided herein are constructs for expression of ectonucleotide pyrophosphatase/phosphodiesterase 1 (ENPP1), comprising a sequence encoding an ENPP1 transgene, wherein the ENPP1 is (i) full-length human ENPP1 (also referred to herein as rENPP1) or (ii) a truncated version thereof comprising the extracellular soluble domain of human ENPP1 (srENPP1) linked to a stabilizing protein, and a promoter that drives expression of the ENPP1 transgene. In some embodiments, the sequence encoding the ENPP1 transgene is codon optimized for expression in human cells. In some embodiments, the constructs comprise (from 5' to 3') a promoter, an optional spacer sequence of about 10-100 or 30-100 nts, a kozak sequence, a secretion signal sequence, a sequence encoding an srENPP1 transgene, a stabilizing protein, optionally with a linker (optionally 10-20 nt long, e.g., comprising CTGATCGTTAAC (SEQ ID NO:104)) between the ENPP1 protein and stabilizing protein, a polyadenylation sequence, and optionally one or more copies of one or more miRNA target sequences, e.g., three copies of a mir155 and/or miR122 target sequence (e.g., comprising one or more repeats of the sequence CAATTACGATTAGCACTATC (SEQ ID NO:2), optionally comprising the sequence CAATTACGATTAGCACTATC-CAATTACGATTAGCACTATCCAATTACGATTAGCAC TATC (SEQ ID NO:3), or comprising one or more repeats, e.g., three repeats, of the sequence ACAAACACCATTGT-CACACTCCA (SEQ ID NO:106)).

Additionally provided herein are constructs for expression of ectonucleotide pyrophosphatase/phosphodiesterase 1 (ENPP1) comprising a sequence encoding an ENPP1 transgene, wherein the ENPP1 is (i) full-length human ENPP1 or (ii) a truncated version thereof comprising the extracellular domain of human ENPP1 (srENPP1) linked to a stabilizing protein, and a promoter that drives expression of the ENPP1 transgene, wherein the construct is packaged in an adeno-associated virus (AAV), preferably wherein the AAV is AAV9 comprising a modified capsid, preferably wherein a VP1 protein of the modified capsid comprises the sequence PRPPSTH (SEQ ID NO:44), MAEPGAR (SEQ ID NO:45), MLYADNT (SEQ ID NO:46), or SQDPSTL (SEQ ID NO:47) inserted into the VP1 protein in a position corresponding to between amino acids 588 and 589.

Also provided herein are nucleic acid constructs for expression of an ENPP1 enzyme, comprising: a nucleic acid sequence encoding an AAV genome comprising: a first inverted terminal repeats (ITR); a nucleic acid encoding a replication (rep) sequence; a nucleic acid encoding a capsid (cap) sequence, the nucleic acid encoding the cap sequence comprising a sequence encoding the peptide PRPPSTH inserted therein (SEQ ID NO:44); a promoter; and a nucleic acid encoding an ectonucleotide pyrophosphatase/phosphodiesterase 1 (ENPP1) enzyme comprising a transmembrane domain; and a second ITR.

In some embodiments, the constructs further comprise one or more sequences that promote expression of the ENPP1 transgene, optionally one or more enhancer sequences (e.g., 5' untranslated region (UTR) or a 3' UTR) and/or insulator sequences.

In some embodiments, the constructs comprise one or more regulatory sequences, e.g., tandem repeats of one or more microRNA (miRNA) target sites incorporated into 3' UTR, optionally wherein the one or more miRNA target sites are selected from miRNA 155 (miR155), miR21, miR122, miR210, miR30b, miR103, and/or miR82 target sites. In some embodiments, the constructs comprise at least two or three tandem repeats of a miR155 target site comprising the sequence CAATTACGATTAGCACTATC (SEQ ID NO:2) or at least two or three tandem repeats of a miR122 target site comprising the sequence ACAAACACCATTGTCACACTCCA (SEQ ID NO:106).

In some embodiments, the constructs further comprise a woodchuck hepatitis virus posttranscriptional response element (WPRE).

In some embodiments, the promoter is CMV immediate/early gene enhancer/CBA promoter (CAG); cytomegalovirus (CMV) promoter, chicken beta-actin (CBA) promoter, Rous sarcoma virus (RSV) LTR promoter, SV40 promoter, dihydrofolate reductase promoter, phosphoglycerol kinase promoter, phosphoglycerol kinase (PGK) promoter, EF1alpha promoter, Ubiquitin C (UBC), B-glucuronidase (GUSB), hAlb, hMGP, or HDAC9_prom2 HDAC9 promoter, Hepcidin promoter, Myh11 promoter, ENPP1 promoter, ENPP2 promoter, or ENPP3 promoter.

In some embodiments, the stabilizing protein is human albumin, transthyretin, transferrin, or IgG Fc; in some embodiments, the stabilizing protein is not IgG Fc.

In some embodiments, the constructs comprise srENPP1 linked to human albumin, optionally wherein srENPP1 is codon-optimized and human albumin is not.

In some embodiments, the constructs comprise a viral vector, e.g., an adeno-associated virus (AAV), optionally AAVPR.

In some embodiments, the constructs comprise a sequence that is at least 80%, 85%, 90%, 95%, 97%, 98%, or 99% identical to a construct shown herein, preferably omitting any tag sequences or plasmid sequences.

In some embodiments, the constructs comprise a construct as described herein, e.g., listed in Table B, or having a sequence provided herein, optionally omitting any tag.

Also provided herein are pharmaceutically acceptable compositions comprising the constructs described herein.

Additionally provided herein are methods of treating a subject who has a condition associated with vascular calcification, the method comprising administering to the subject a therapeutically effective amount of a construct or composition as described herein. In some embodiments, the condition is generalized arterial calcification of infancy (GACI), pseudoxanthoma elasticum (PXE), calciphylaxis, and cardiovascular disease including diabetic vascular calcification, end-stage renal disease (ESRD)-associated vascular disease, calcific aortic valve disease (CAVD), coronary atherosclerosis, coronary artery bypass graft (CABG) stenosis, in-stent stenosis, peripheral vascular disease, or cerebral atherosclerosis.

In some embodiments, the construct is administered intravenously.

Also provided herein are particles comprising:

a) an amount of an ionizable lipid;
   an amount of neutral lipid;
   an amount of cholesterol;
   an amount of one or more PEG-lipids; and
   an amount of a DOTAP molecule;
b) a peptide conjugated to a linker in the particle; and
c) a construct for expression of ectonucleotide pyrophosphatase/phosphodiesterase 1 (ENPP1), comprising a sequence encoding an ENPP1 transgene, wherein the ENPP1 is (i) full-length human ENPP1 or (ii) a truncated version thereof comprising the extracellular domain of human ENPP1 (srENPP1) linked to a stabilizing protein, and a promoter that drives expression of the ENPP1 transgene.

In some embodiments, the linker is a maleimide group at a PEG lipid of the one or more PEG-lipids in the particle.

In some embodiments, at least one of the one or more PEG-lipids is a maleimide-terminally modified PEG lipid.

In some embodiments, the one or more PEG-lipids comprise DMG-PEG and/or DSPE-PEG-maleimide.

In some embodiments, the peptide is a peptide targeting collagen IV (Col-IV), IL-6R, CD63, GAL-3, or any combination thereof.

In some embodiments, the ionizable lipid, the neutral lipid, the cholesterol, the one or more PEG-lipids, and DOTAP are present at a molar ratio of 10:2.1:7.6:1.5:78.8.

In some embodiments, the phosphatidylcholine lipid or the phosphatidylethanolamine lipid is selected from the group consisting of DOPE, DOPC, DSPC, DPPC, POPC, and SOPC.

In some embodiments, the ionizable lipid is selected from the group consisting of DLin-MC2-DMA, DLin-MC3-DMA, DSDMA, DODMA, DLinDMA, DLenDMA, 7-DLenDMA, DLin-K-DMA, DLin-C2K-DMA, DLin-K-C3-DM A, DLin-K-C4-DMA, DLen-C2K-DMA, γ-DLen-C2K-DMA, or DLin-MP-DMA.

In some embodiments, the particles comprise: about 75-85% of DOTAP; about 10% of an MC3 ionizable lipid; about 2-2.5% of a DOPE neutral lipid; about 7-8% of cholesterol; and about 1-2% of one or more PEG-lipids. In some embodiments, the particles comprise: about 78.8% of DOTAP; about 10% of an MC3 ionizable lipid; about 2.1% of a DOPE neutral lipid; about 7.6% of cholesterol; and about 1.5% of one or more PEG-lipids.

Further, provided herein are particles comprising:

from 0.1% to 10% of a molecule of formula I

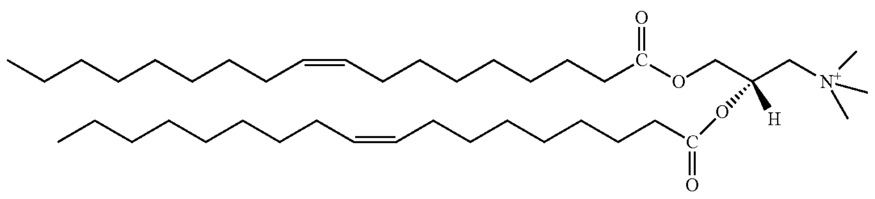 [SMILES: CCCCCCCC/C=C\CCCCCCCC(=O)OC[C@H](C[N+](C)(C)C)OC(=O)CCCCCCC/C=C\CCCCCCCC]

;

(DOTAP)

and a construct as described herein.

In some embodiments, the particles further comprise:

an amount of an ionizable lipid;

an amount of neutral lipid;

an amount of cholesterol;

an amount of a PEG-lipid;

wherein the ionizable lipid, the neutral lipid, the cholesterol, and the PEG-lipid are present at a molar ratio of 50/10/38.5/1.5 of the remaining weight of the particle.

In some embodiments, the particles comprise:

from 45% up to 52% of an ionizable lipid;

from 9% up to 11% of a neutral lipid;

from 34% up to 40% of cholesterol;

from 1% up to 2% of PEG-lipid.

In some embodiments, the PEG-lipid is a maleimide-terminally modified PEG lipid.

In some embodiments, the particles further comprise a peptide conjugated to the particle via the maleimide-terminally modified PEG lipid. In some embodiments, the particles comprise one or more peptides targeting collagen IV (Col-IV), IL-6R, CD63, GAL-3, or any combination thereof.

In some embodiments, the neutral lipid is a phosphatidylcholine lipid or a phosphatidylethanolamine lipid. In some embodiments, the phosphatidylcholine lipid or the phosphatidylethanolamine lipid is selected from the group consisting of DSPC, DPPC, and POPC.

In some embodiments, the ionizable lipid is selected from the group consisting of DLin-MC2-DMA, DLin-MC3-DMA, DSDMA, DODMA, DLinDMA, DLenDMA, γ-DLenDMA, DLin-K-DMA, DLin-C2K-DMA, DLin-K-C3-DM A, DLin-K-C4-DMA, DLen-C2K-DMA, γ-DLen-C2K-DMA, or DLin-MP-DMA.

In some embodiments, the particle comprises:

about 7% of DOTAP;

about 46% of an MC3 ionizable lipid;

about 9.8% of a DOPE neutral lipid;

about 35.3% of cholesterol; and about 1.4% a PEG-lipid.

Also provided herein are pharmaceutically acceptable compositions or therapeutic formulations comprising particles as described herein.

Additionally, provide herein are methods of delivering an ENPP1 nucleic acid therapeutic cargo to a smooth muscle cell; the methods comprise administering to or contacting the smooth muscle cell with a construct, composition, particle, or formulation as described herein.

Further, provided herein are methods of treating a subject who has a condition associated with vascular calcification, comprising administering to the subject a therapeutically effective amount of a particle, composition, or therapeutic formulation as described herein. Also provided are the constructs, particles, compositions, or therapeutic formulations for use in a method of treating a subject who has a condition associated with vascular calcification. In some embodiments, the condition is generalized arterial calcification of infancy (GACI), pseudoxanthoma elasticum (PXE), calciphylaxis, and cardiovascular disease including diabetic vascular calcification, ESRD-associated vascular disease, calcific aortic valve disease (CAVD), coronary atherosclerosis, coronary artery bypass graft (CABG) stenosis, in-stent stenosis, peripheral vascular disease, or cerebral atherosclerosis.

As used herein, "about" means plus or minus 10%, unless otherwise indicated. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

CBA_srENPP1_Albumin—contains (1) albumin secretory signal (hAlb sig) to signal the protein for secretion from the cell and (2) hAlbumin to stabilize the protein and increase its half-life;

CBA_srENPP1—contains the albumin secretory signal but not a stabilizing fusion protein;

CBA_srENPP1_Fc—contains ENPP1 cytosolic domain (CD, amino acids 1-76), ENPP2 signal sequence (SS, amino acids 12-30), with the extracellular ENPP1 domain fused with the IgG Fc domain for stabilization;

CMV_srENPP1_Albumin—contains (1) albumin secretory signal (hAlb sig) to signal the protein for secretion from the cell and (2) hAlbumin to stabilize the protein and increase its half-life.

Most of the constructs also included Kozak sequences and spacer sequences from the pcDNA3.1 plasmid between the Kozak sequences and the promoter. The promoter can be swapped, e.g., CMV replaced with CBA and vice-versa.

Figure 3:
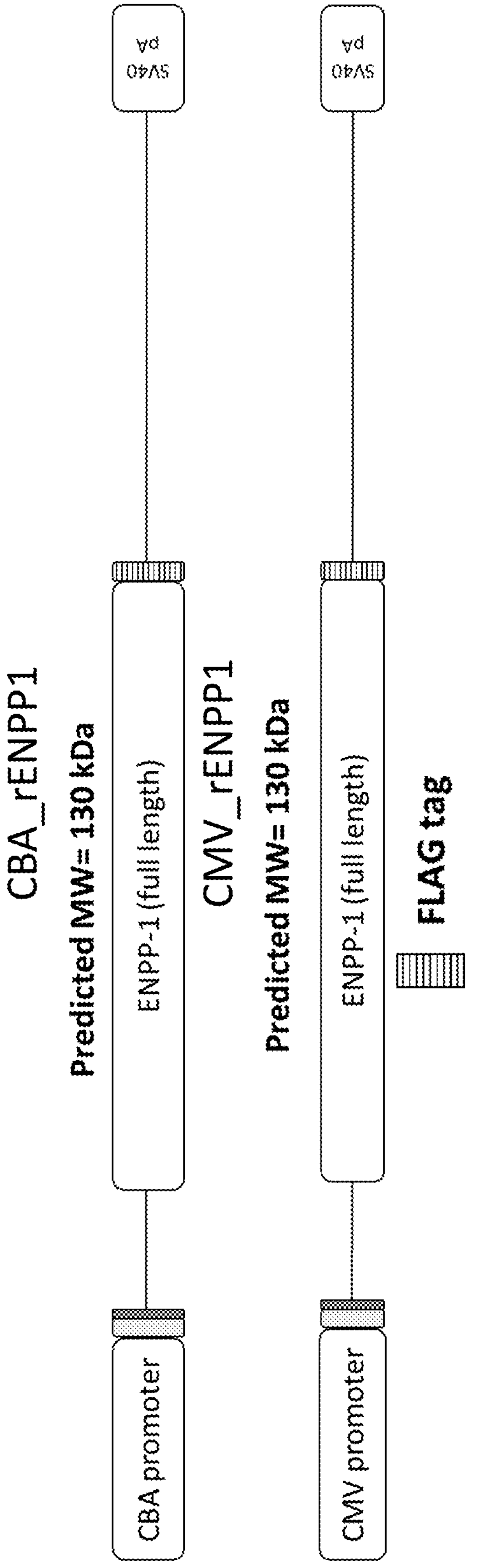

FIG. 3. Schematic illustration of DNA constructs with the CBA (top) or CMV (bottom) promoter driving expression of a FLAG-tagged human recombinant transmembrane full-length ENPP1 (rENPP1).

Figure 4:
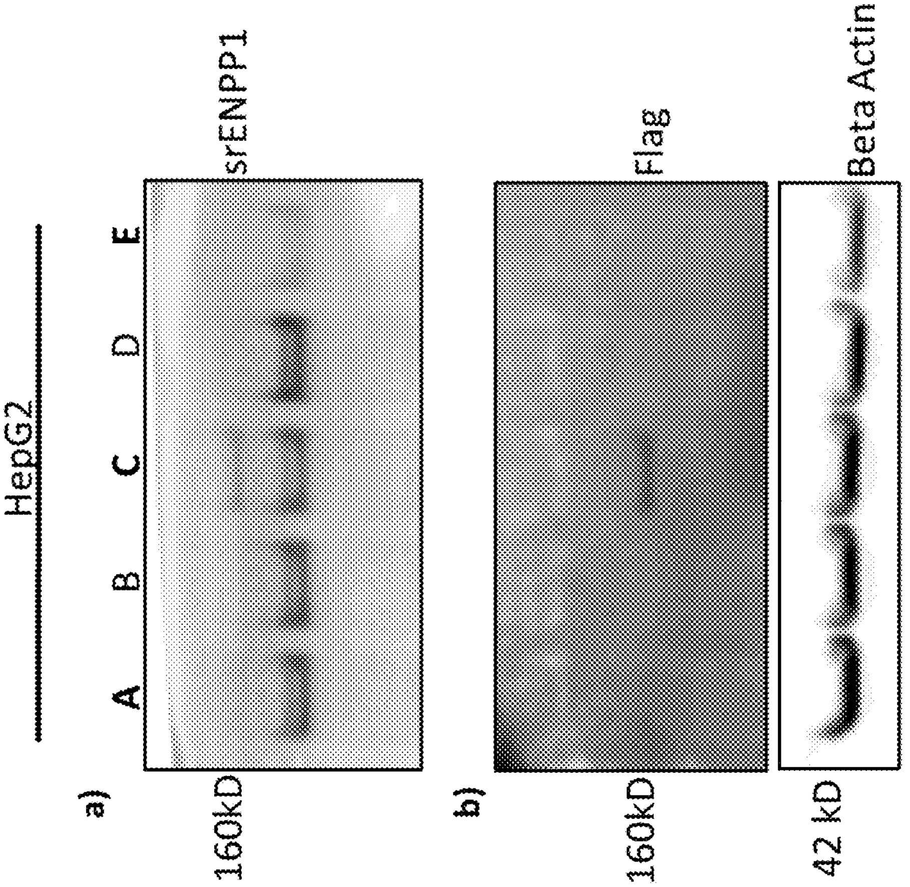

FIG. 4. Western blot analysis of ENPP1 constructs under the CBA or CMV promoters from total lysates of human liver cells (HepG2). In lanes A and C, results showed superior expression of the srENPP1 transgene (160 kD) in cells transfected with the CMV_srENPP1_albumin vs CBA_srENPP1_albumin as assessed by ENPP1 (top blot) or Flag-tag (middle blot) antibody immunoblot. In lanes B and D, results showed superior expression of the transmembrane rENPP1 transgene (130 kD) in cells transfected with the CMV_rENPP1 vs CBA_rENPP1.

Lanes:

A. CBA_srENPP1_Albumin

B. CBA_rENPP1

C. CMV_srENPP1_Albumin

D. CMV_rENPP1

Ctrl. Untransfected

Expected molecular weights: Soluble srENPP1=160 kD; Transmembrane rENPP1=130 kD

Figure 5:
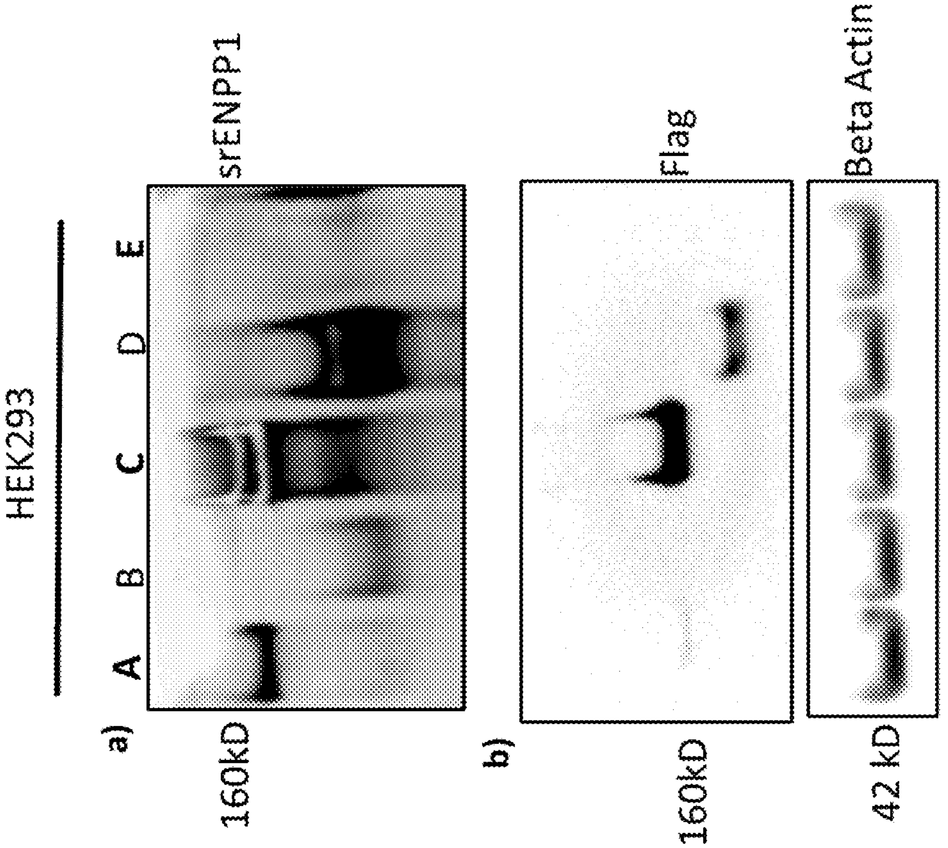

FIG. 5. Western blot analysis of rENPP1 constructs under the CBA or CMV promoters from total lysates of human cells HEK293T. In lanes A and C, results showed superior expression of the srENPP1 transgene (160 kD) in cells transfected with the CMV_srENPP1_albumin vs CBA_srENPP1_albumin as assessed by ENPP1 (top blot) or Flag-tag (middle blot) antibody immunoblot. In lanes B and D, results showed superior expression of the transmembrane rENPP1 transgene (130 kD) in cells transfected with the CMV_rENPP1 vs CBA_rENPP1.

Lanes:

A. CBA_srENPP1_Albumin
B. CBA_rENPP1
C. CMV_srENPP1_Albumin
D. CMV_rENPP1
Ctrl. Untransfected Expected molecular weights: Soluble srENPP1=160 kD; Transmembrane rENPP1=130 kD FIG. 6. HepG2 cells (left) and HEK293T cells (right) were co-transfected with the CMV_srENPP1_Albumin plasmid and a control plasmid (pcDNA3-mRFP) and cultured in minimal essential media with FBS. RFP expression was confirmed under microscope 3 days after transfection. Cell supernatants were harvested for western blot analysis at 72 h post transfection. Supernatant protein was pulled down with anti-FLAG antibody and probed for either ENPP1 or FLAG. Recombinant Human ENPP1/PC1 protein (ab167943) was used as a positive control. These results indicate good cellular secretion of srENPP1 into the supernatant of human cells transfected with CMV_srENPP1_Albumin.

Figure 7A:
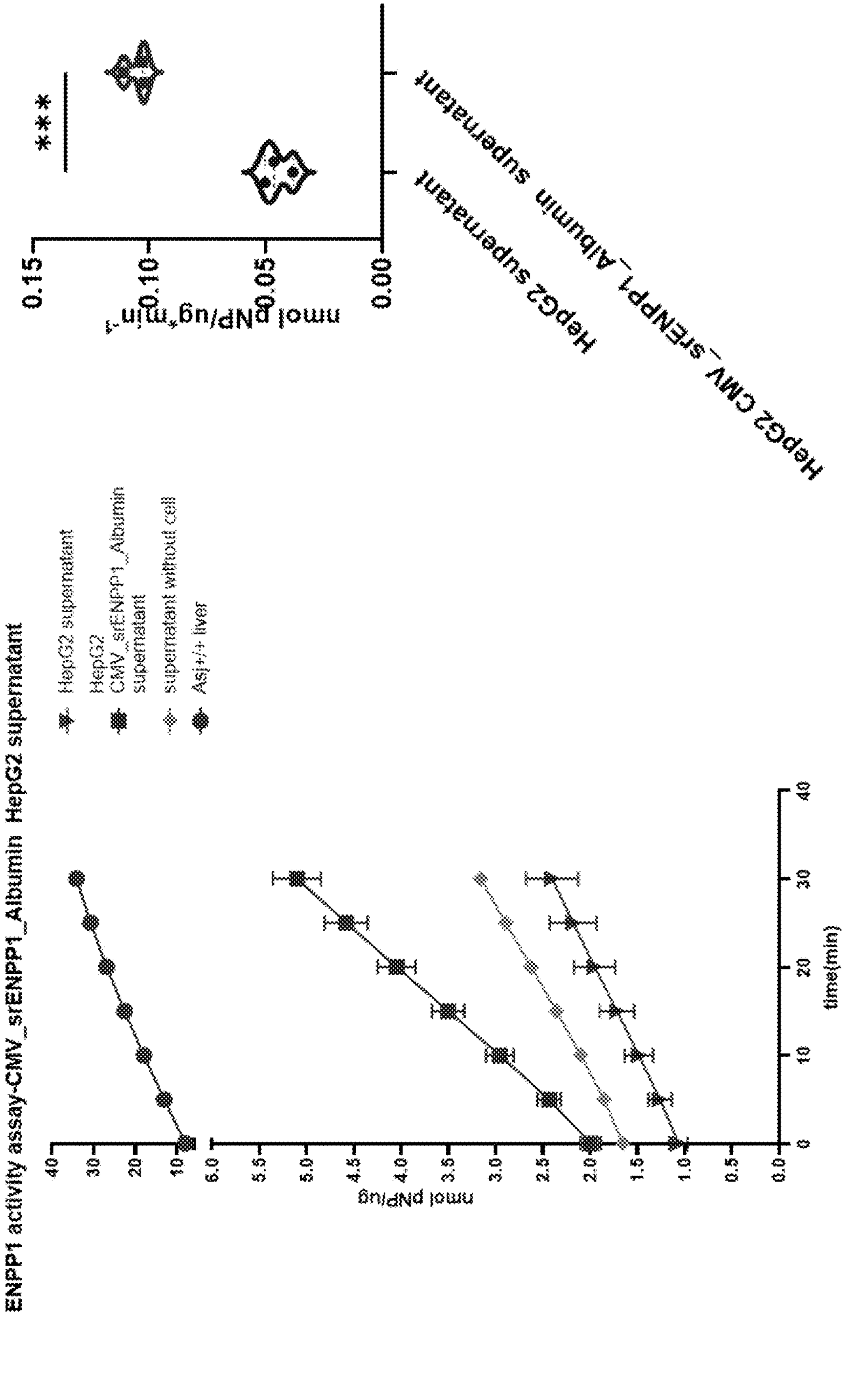
Figure 7B:
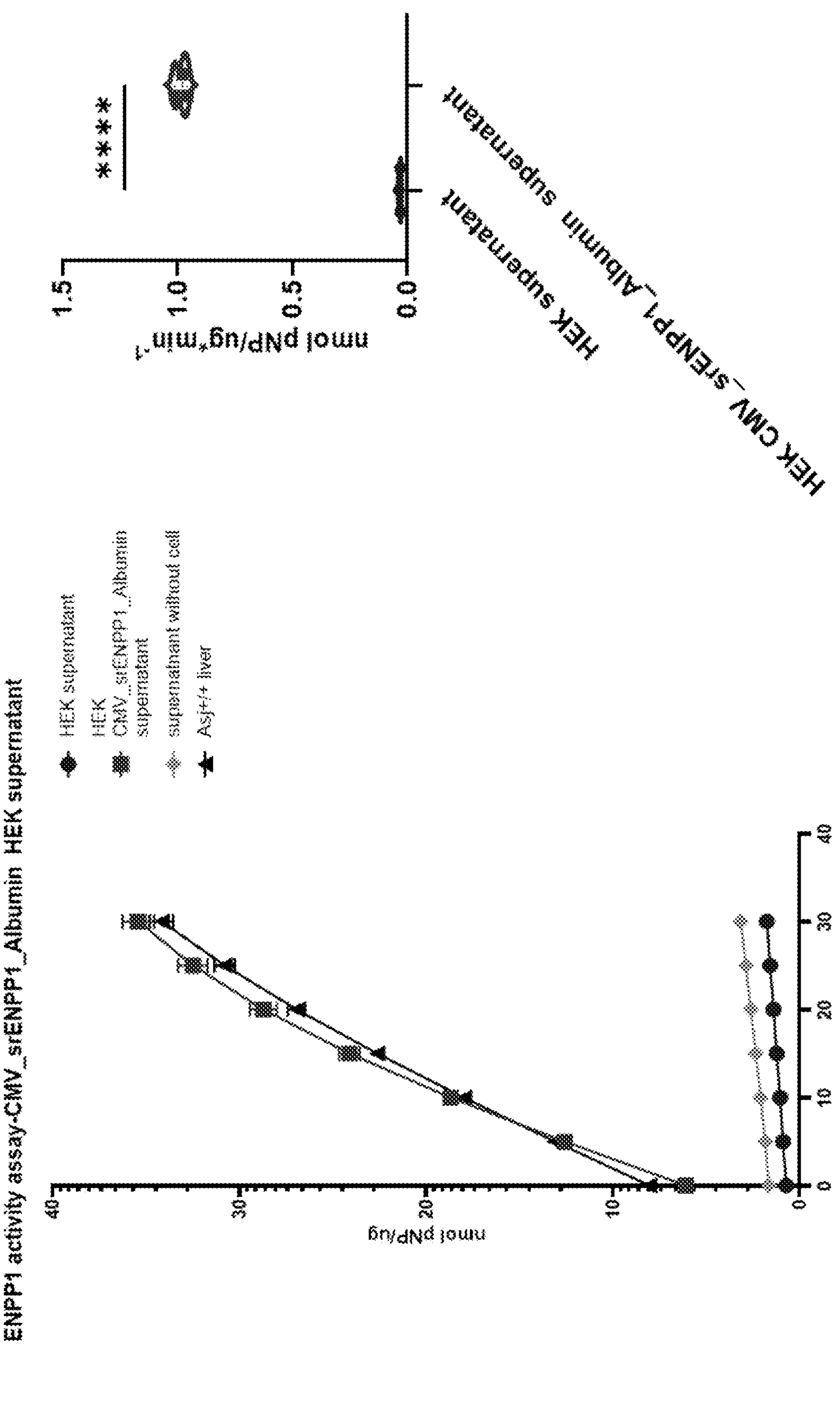

FIGS. 7A-B. srENPP1 was enzymatically active in the HepG2/HEK293T cell supernatants. Enzymatic phosphodiesterase activity of srENPP1 was measured from the supernatants of HepG2 cells (7A) and HEK293T cells (7B) transfected with plasmid expressing srENPP1 or control cells. A significant increase in the ENPP1 activity (right panels in both the figures) was observed compared to supernatants from untransfected cells. Wild-type mouse liver ("Asj+/+ liver") was used as a positive control and cell media without cells was used as a negative control.

Figure 8A:
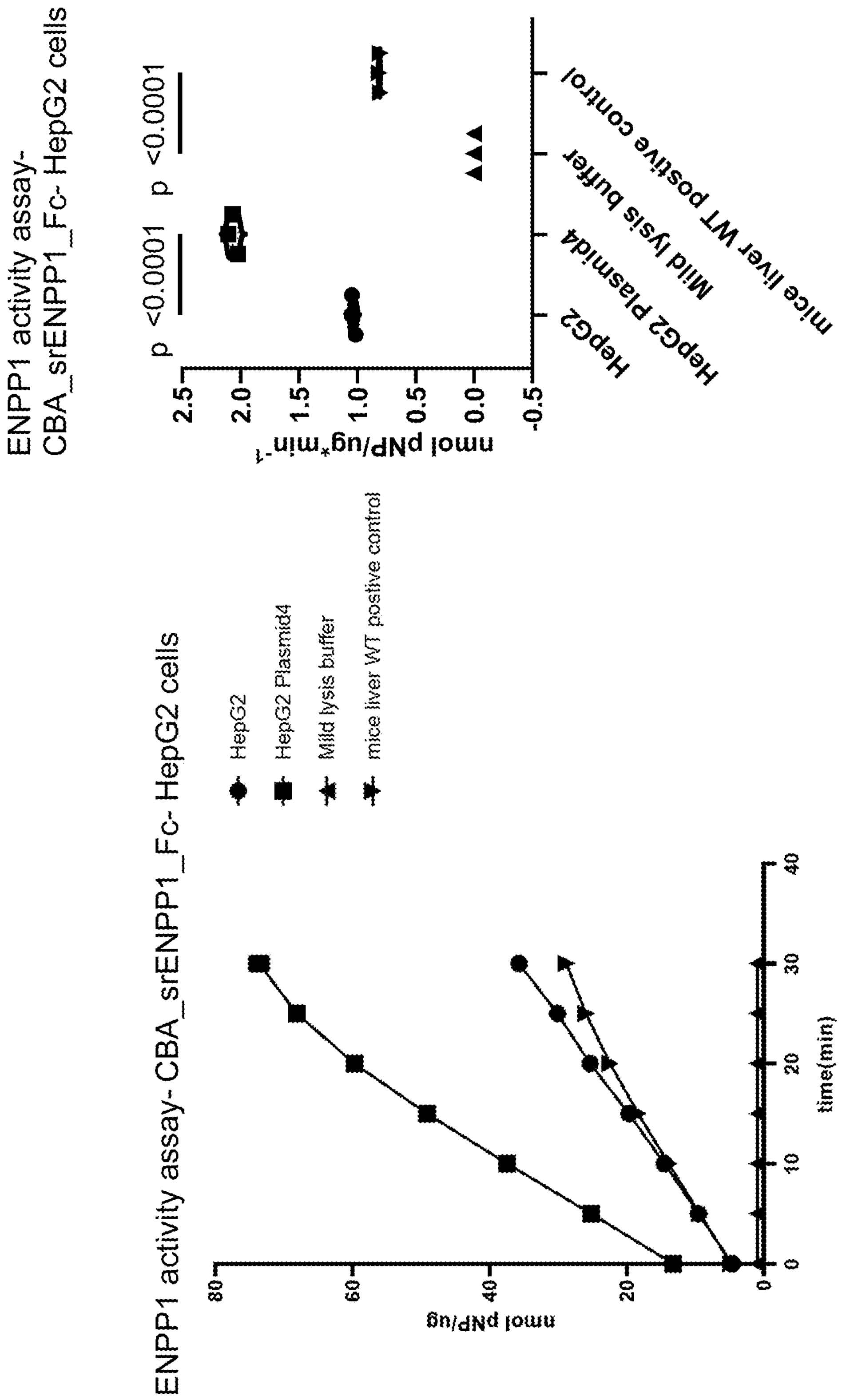
Figure 8B:
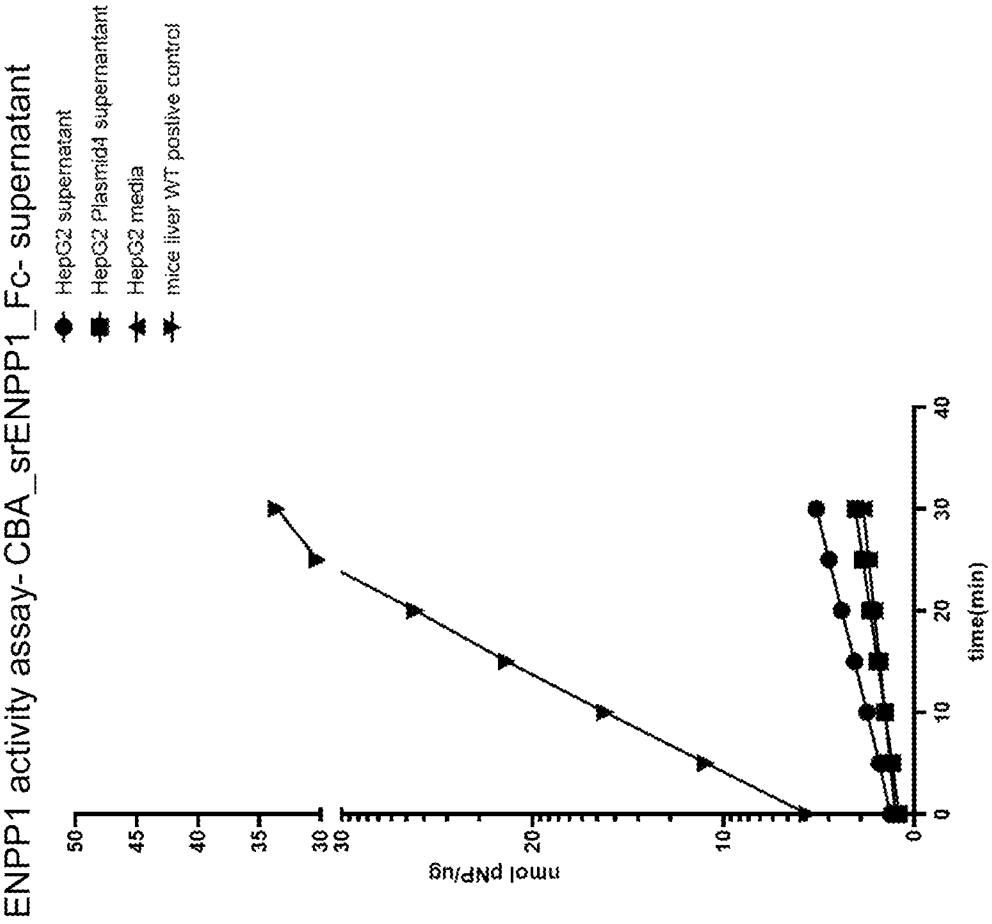

FIGS. 8A-B. Construct for soluble recombinant ENPP1 linked to Fc (srENPP1-Fc) was enzymatically active in HepG2 cell lysates but not the supernatants. Enzymatic phosphodiesterase activity of srENPP1-Fc ("plasmid #4") was measured from the cell lysates (8A) and supernatants (8B) of HepG2 cells transfected with plasmid #4. A significant increase in the ENPP1 activity was observed compared to cell lysates from untransfected cells but no increase in activity was observed in the supernatant of transfected cells, indicating that this soluble version of the ENPP1 is not appropriately secreted from cells.

Figure 9B:
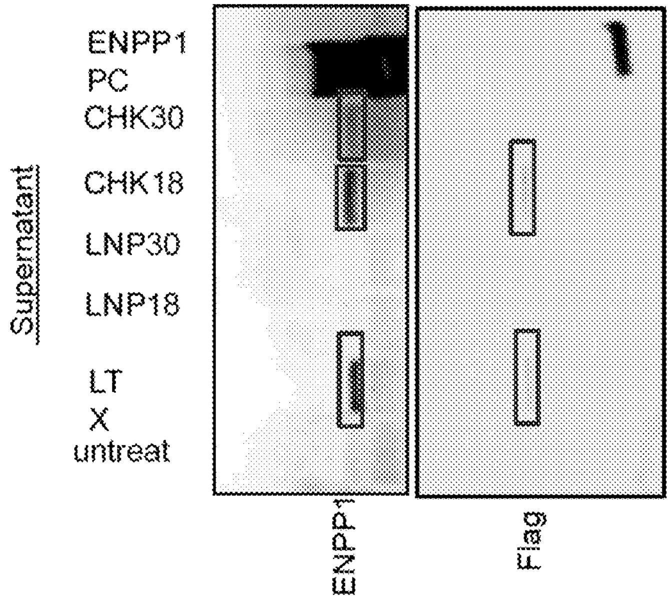
Figure 9A:
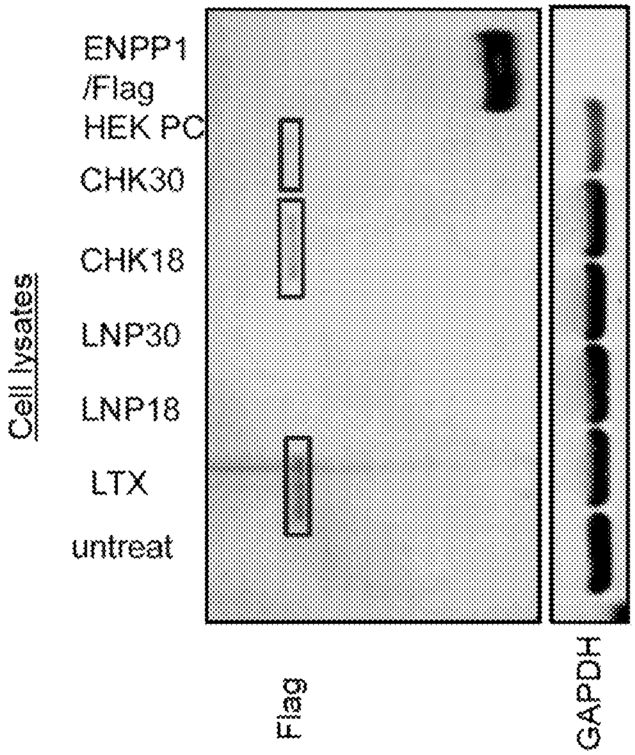

FIGS. 9A-B. CMV_srENPP1_hAlbumin gene delivery using LTX lipofectamine and 4 versions of nanoparticles to assess srENPP1 expression in cell lysates (9A) or supernatant (9B) from human HepG2 cells. Expression was detected in cell lysates using a Flag-directed antibody (9A) and in supernatants using an ENPP1 antibody and Flag antibody (9B). Results demonstrated srENPP1 transgene expression levels for CHK18 and CHK30 nanoparticles comparable to commercial LTX lipofectamine reagent using either a Flag-directed antibody or an ENPP1-directed antibody.

Figure 10:
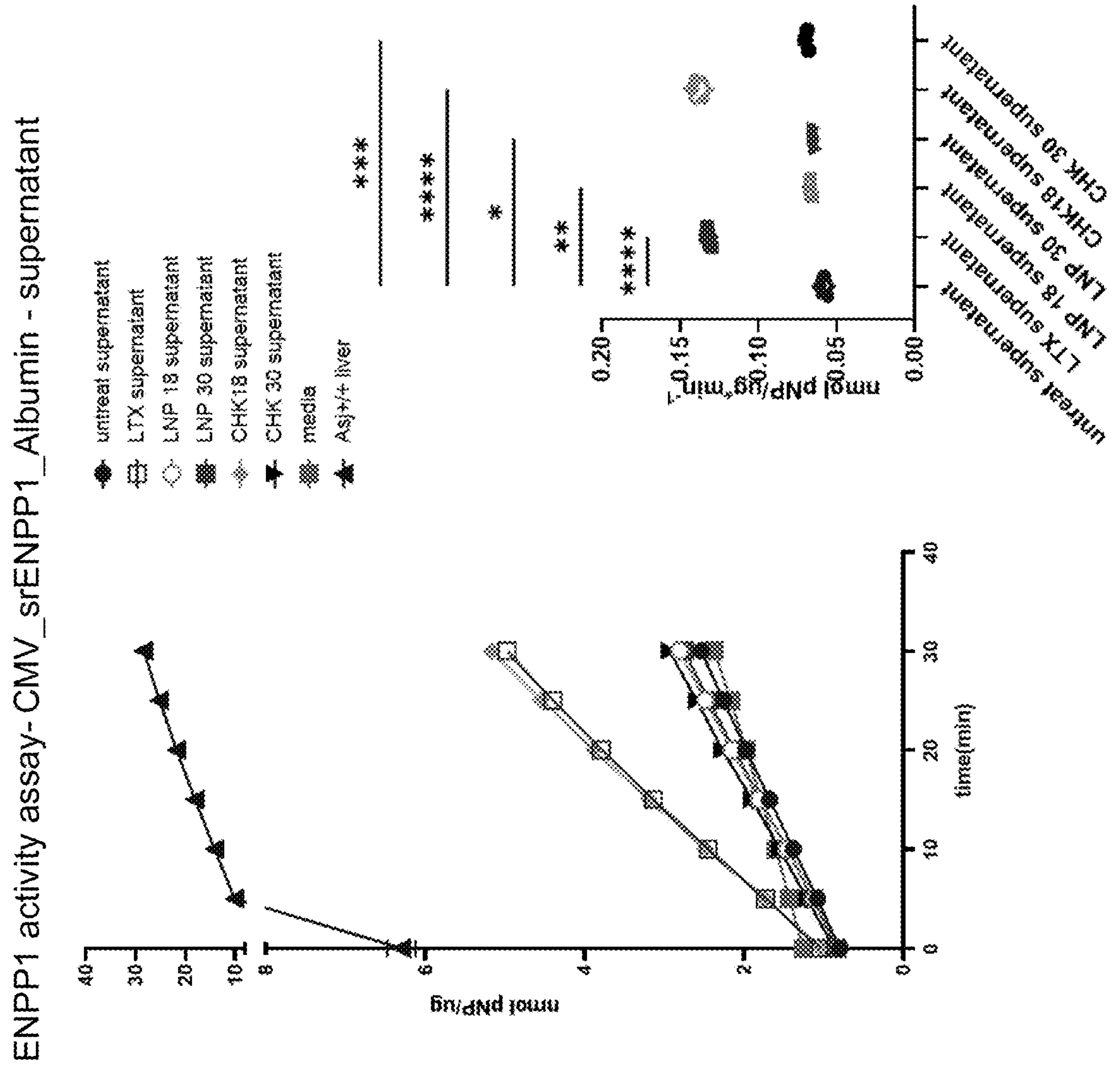

FIG. 10. ENPP1 enzymatic activity assay from the supernatant of human HepG2 cells transfected with CMV_srENPP1_albumin using nanoparticles. Right panel indicates absolute values of increased ENPP1 activity of cells transfected with CMV_srENPP1_albumin compared with untransfected cells. Results show transgene delivery and activity in CHK18 nanoparticles comparable with LTX lipofectamine.

Figure 11:
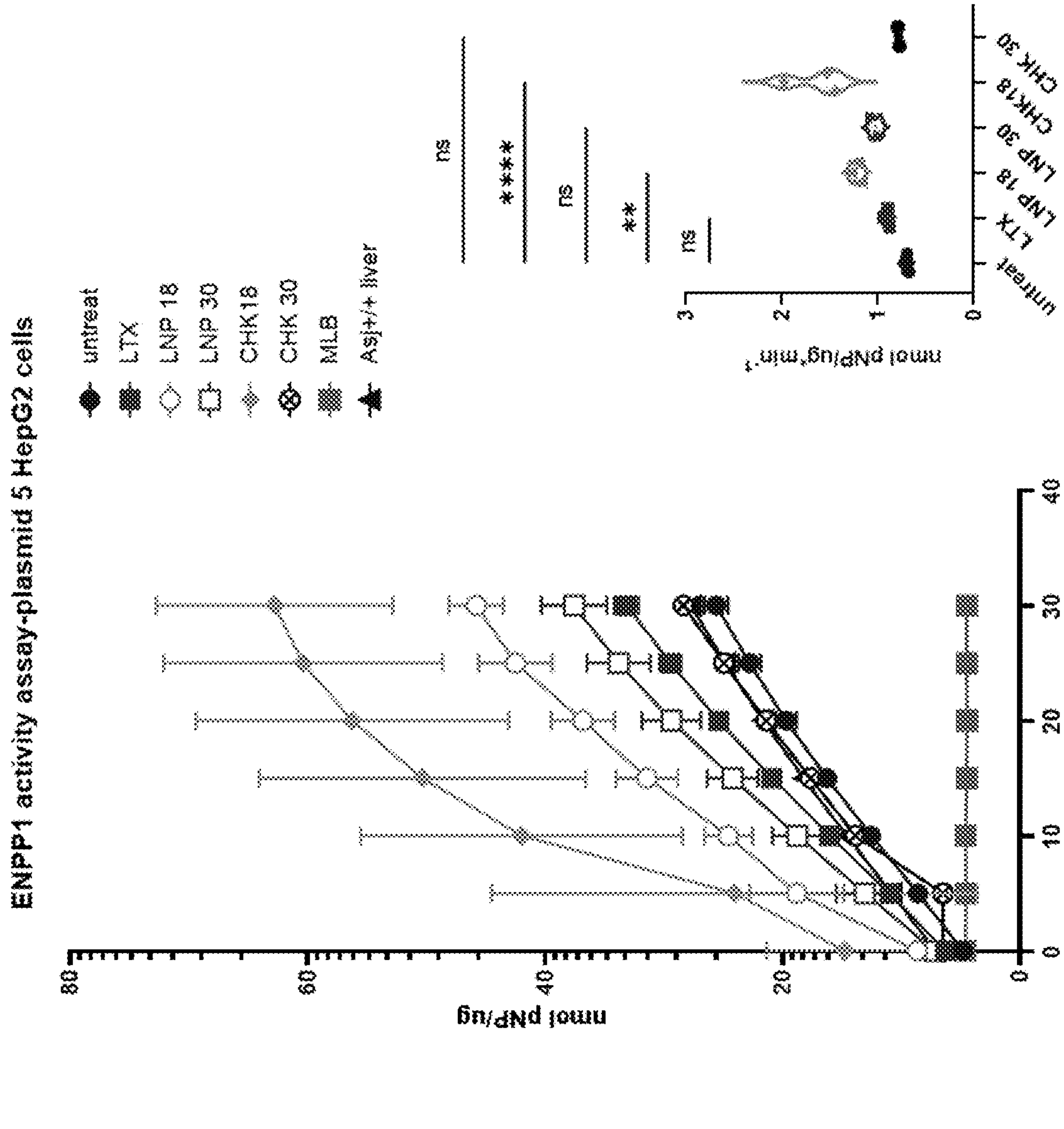

FIG. 11. ENPP1 enzymatic activity assay from total lysates of human HepG2 cells transfected with CMV_srENPP1_albumin using nanoparticles. Right panel indicates absolute values of increased ENPP1 activity of cells transfected with CMV_srENPP1_albumin compared with untransfected cells. Results show transgene delivery and activity with CHK18 nanoparticles that was even higher than with LTX lipofectamine.

Figure 12A:
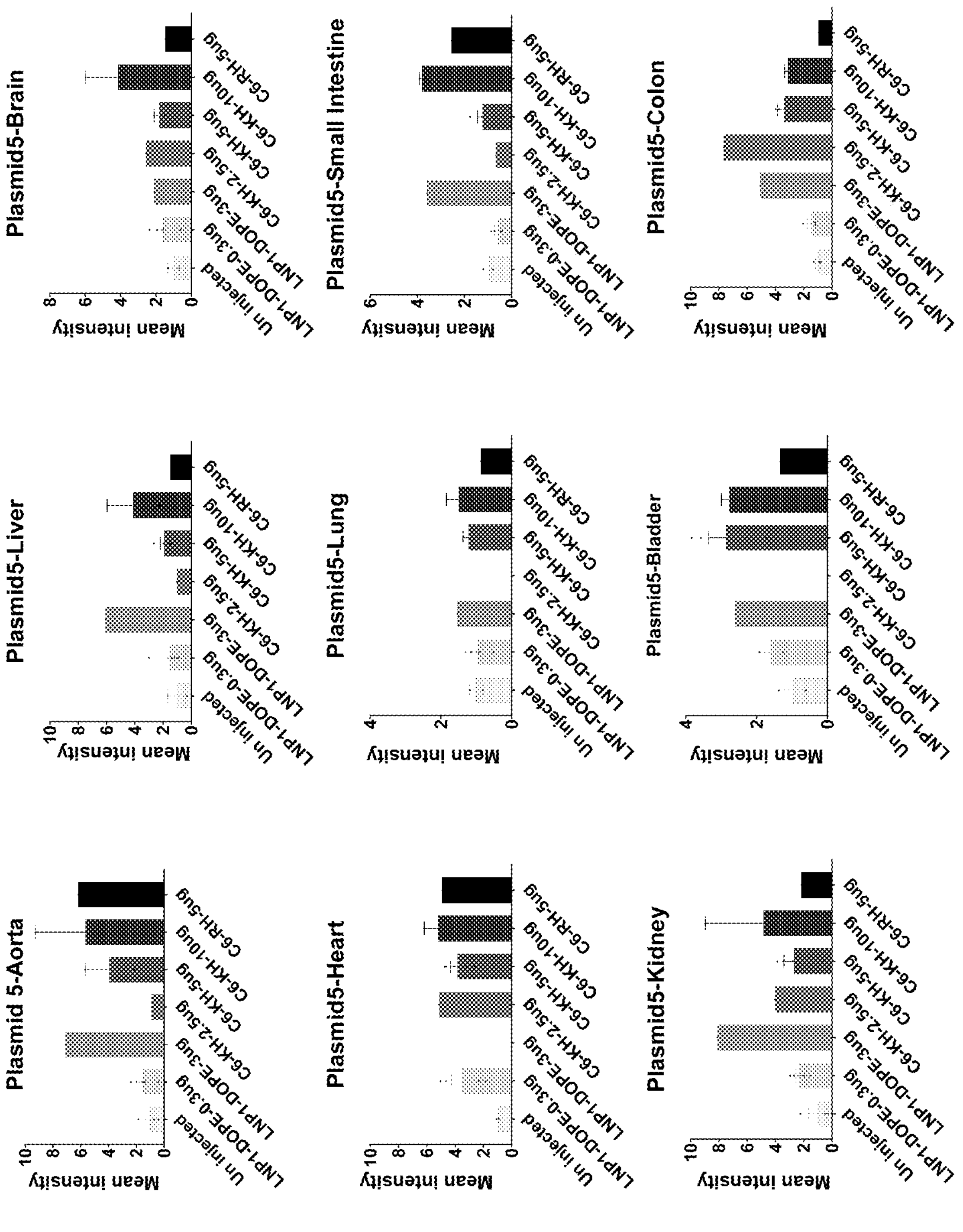
Figure 12B:
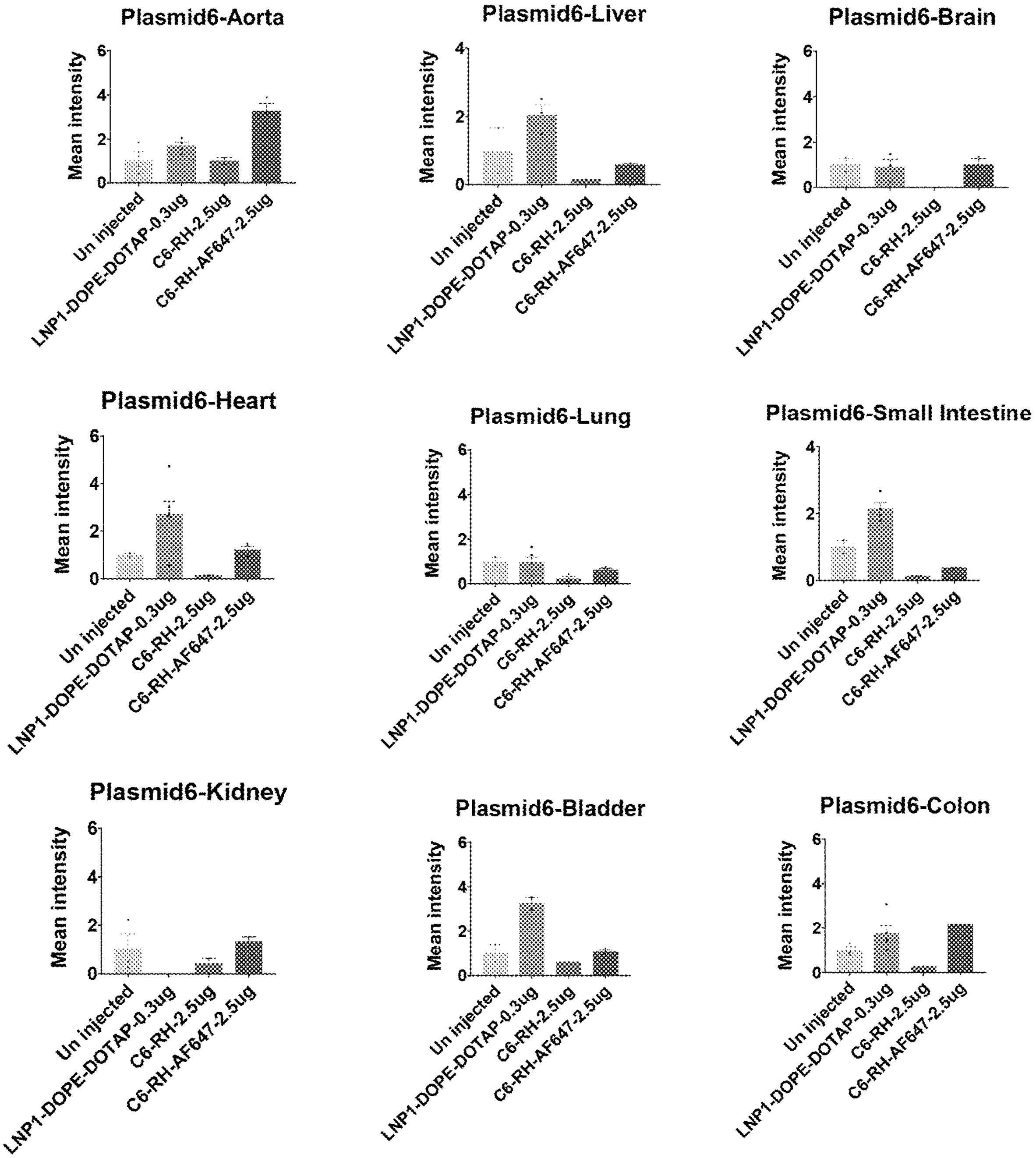

FIGS. 12A-B. Graphs representing the fold increase in expression of srENPP1 (12A) and rENPP1 (12B) in different tissues of mice injected with different CMV_srENPP1_Albumin (12A, "plasmid 5") or CMV_rENPP1 (12B, "plasmid 6") plasmid concentrations and nanoparticle preparations compared to control un-injected. Newborn pups were injected on day 3 with CMV_srENPP1_Albumin expression plasmid packed in various nanoparticle preparations through retroorbital route. Tissue/organs were harvested on day 6 post injection and placed on fresh OCT blocks followed by cryosectioning and immunohistochemistry to study the expression profile of srENPP1 or rENPP1 in various tissues and organs. Depicted are the quantification of the immunohistochemistry signals from anti-FLAG antibody representing transgene expression.

FIGS. 13A-F. In vitro assessment of AAVPR rENPP1 expression, activity, and inhibition of osteogenic VSMC phenotypic change. (A) AAVPR-GFP transduces human VSMCs more robustly than AAV9-GFP. (B) Human aortic VSMCs treated with AAVPR rENPP1 at low and high doses demonstrated dose-dependent overexpression of ENPP1 at the protein level. (C) Increased rENPP1 activity was detected in human VSMCs treated with AAVPR rENNP1 compared to untreated cells. AAVPR rENPP1 treatment decreased VSMC osteogenic phenotype switch: (D) AAVPR rENPP1 treated cells demonstrated decreased calcification on Alizarin red staining compared to untreated cells after 21 days of culture in osteogenic media, (E) AAVPR treatment decreased migration of VSMCs compared to control-treated cells after 12 hours in osteogenic media. (F) These phenotypic changes correlated with a reduction in RUNX2 protein levels with AAVPR rENPP1 treatment.

Figure 13A:
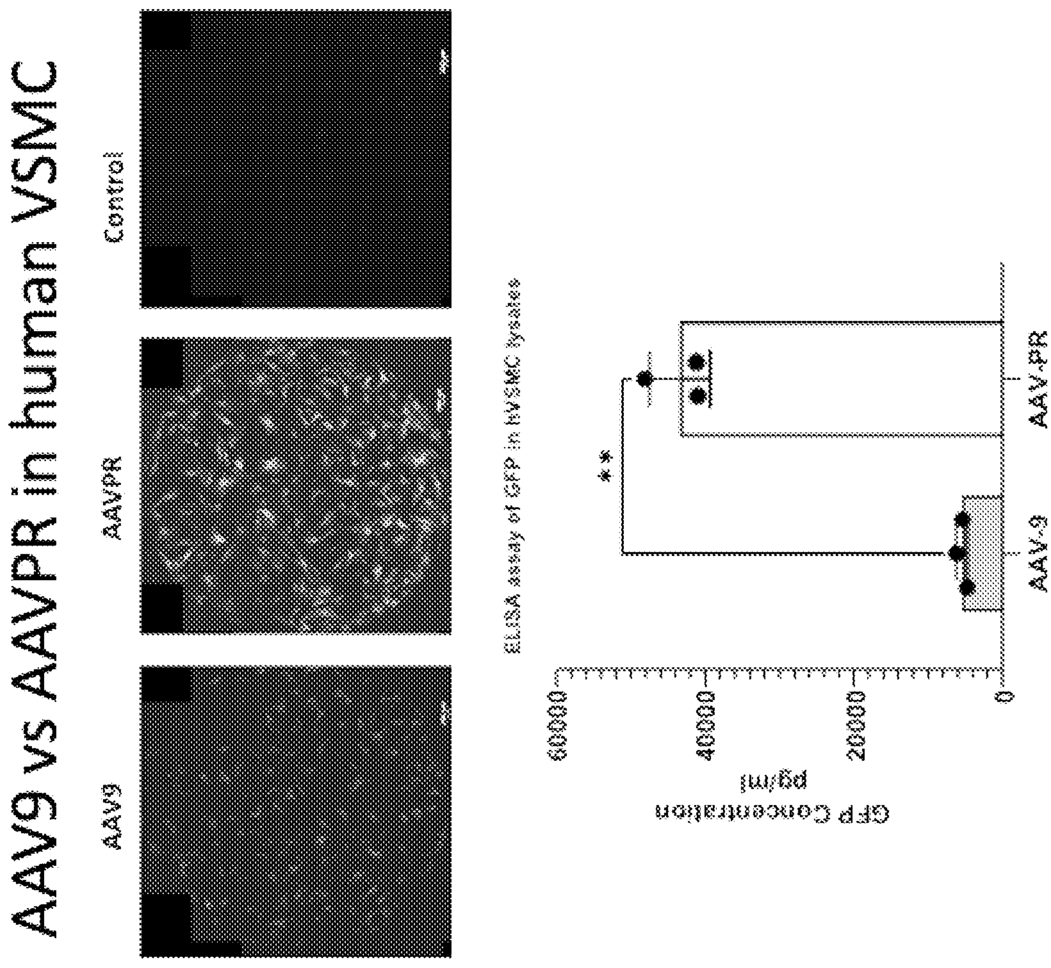
Figure 13B:
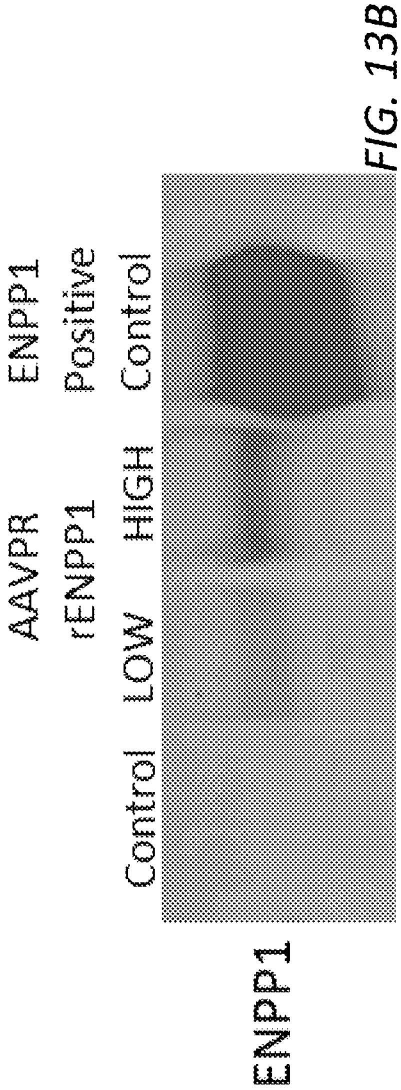
Figure 13C:
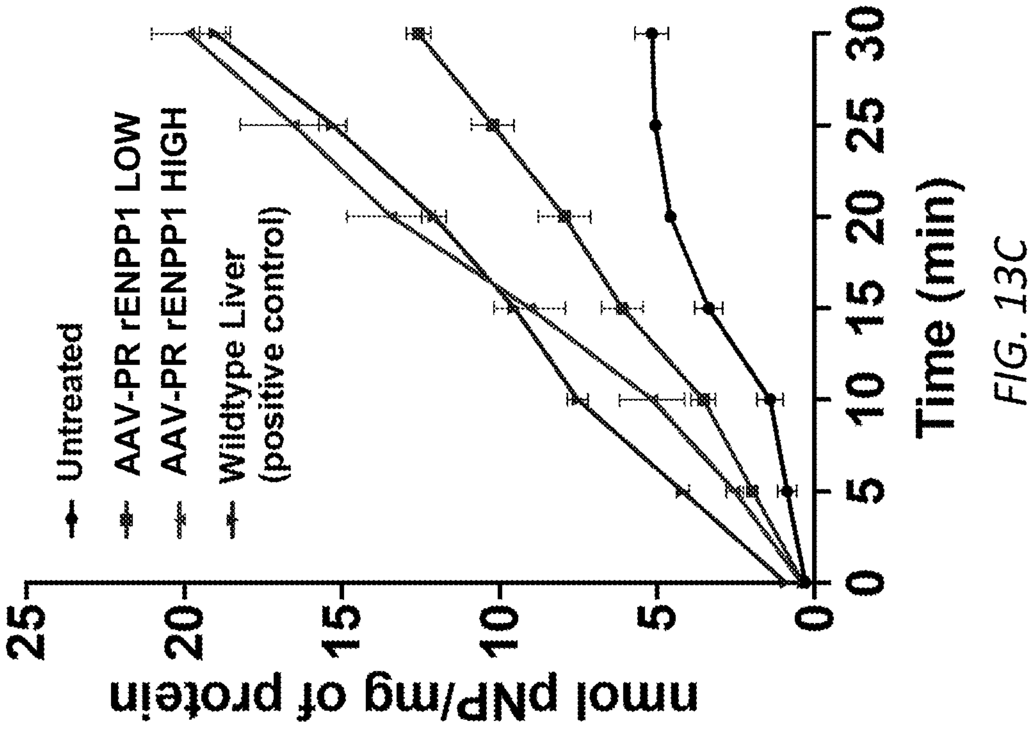
Figure 13D:
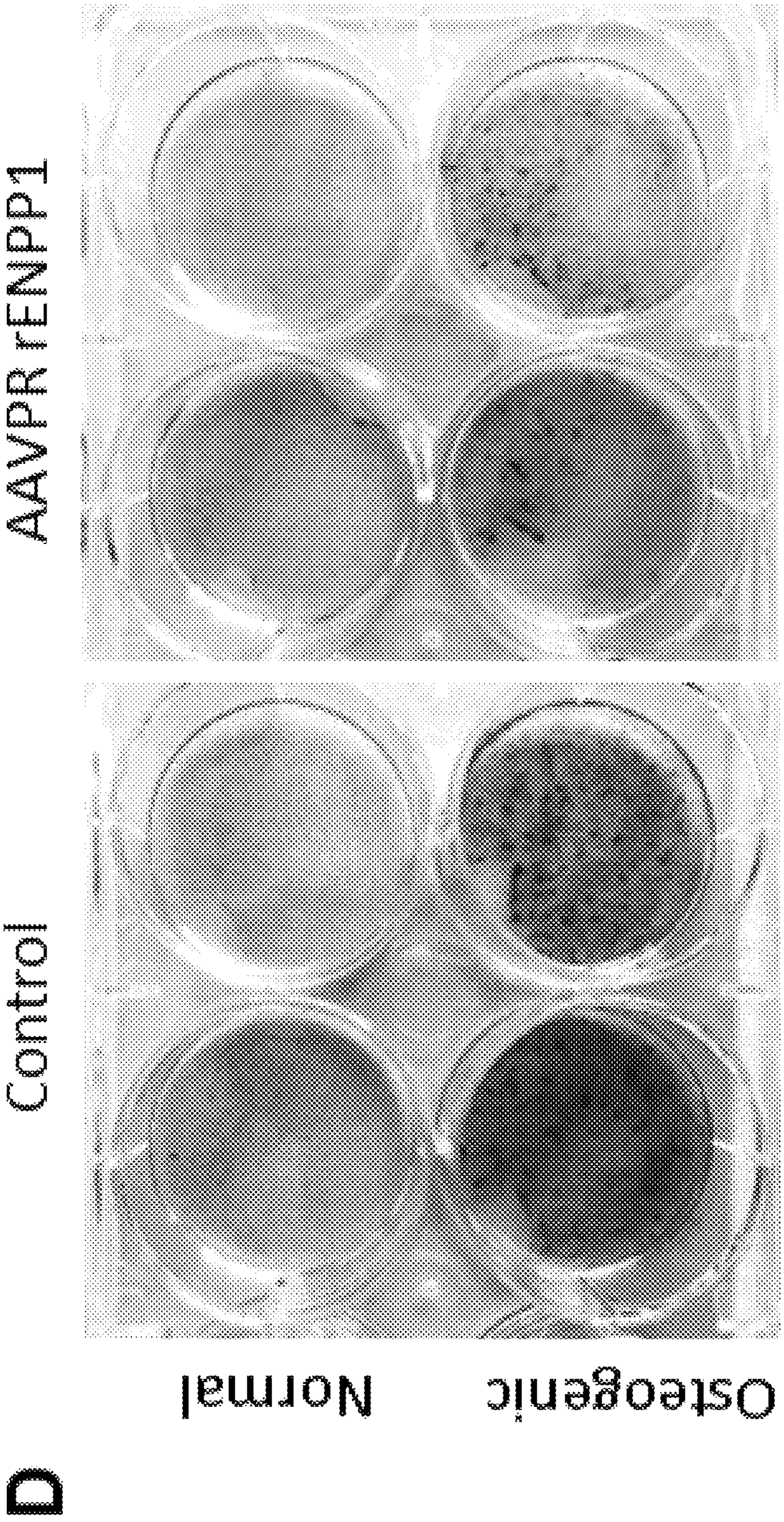
Figure 13E:
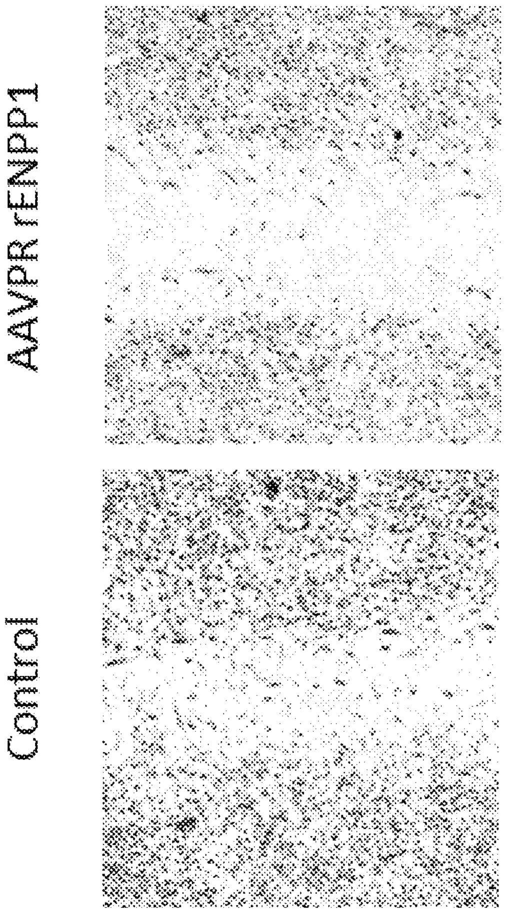
Figure 13F:
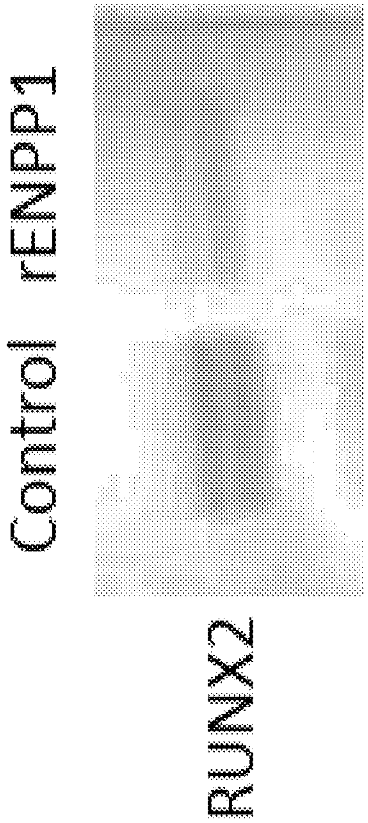
Figure 13G:
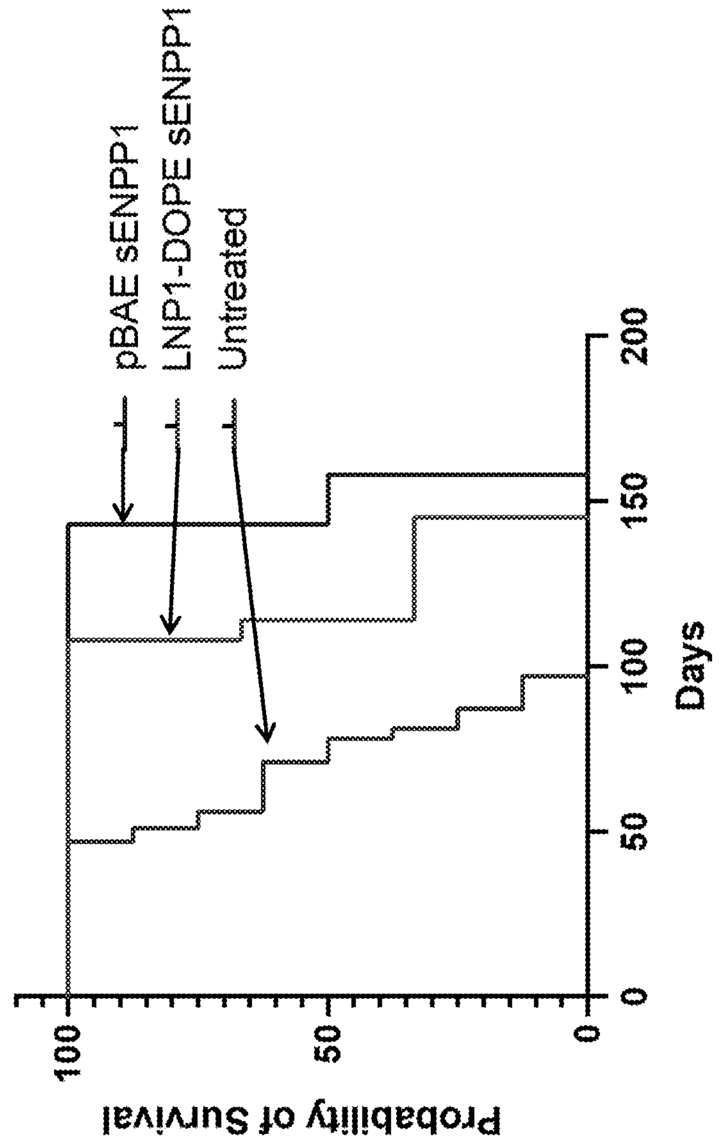

FIG. 13G. ENPP1 gene therapy using LNP delivery in GACI Mice (Asj−/− mice). Compared to vehicle-treated GACI mice, GACI mice treated with poly-beta amino ester (pBAE) srENPP1 or LNP1-DOPE srENPP1 showed improved survival with log rank p=0.03 and p=0.008, respectively.

Figure 14A:
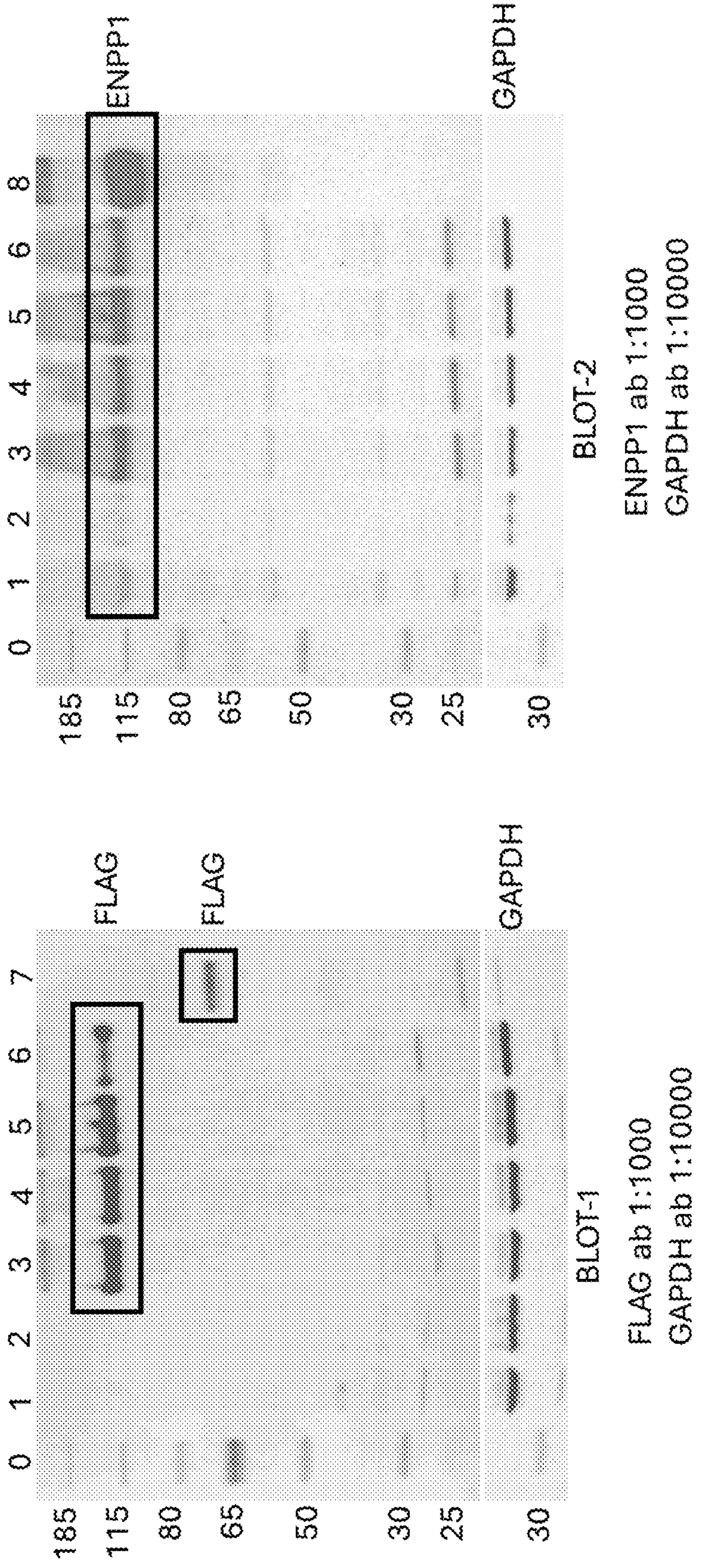
Figure 14B:
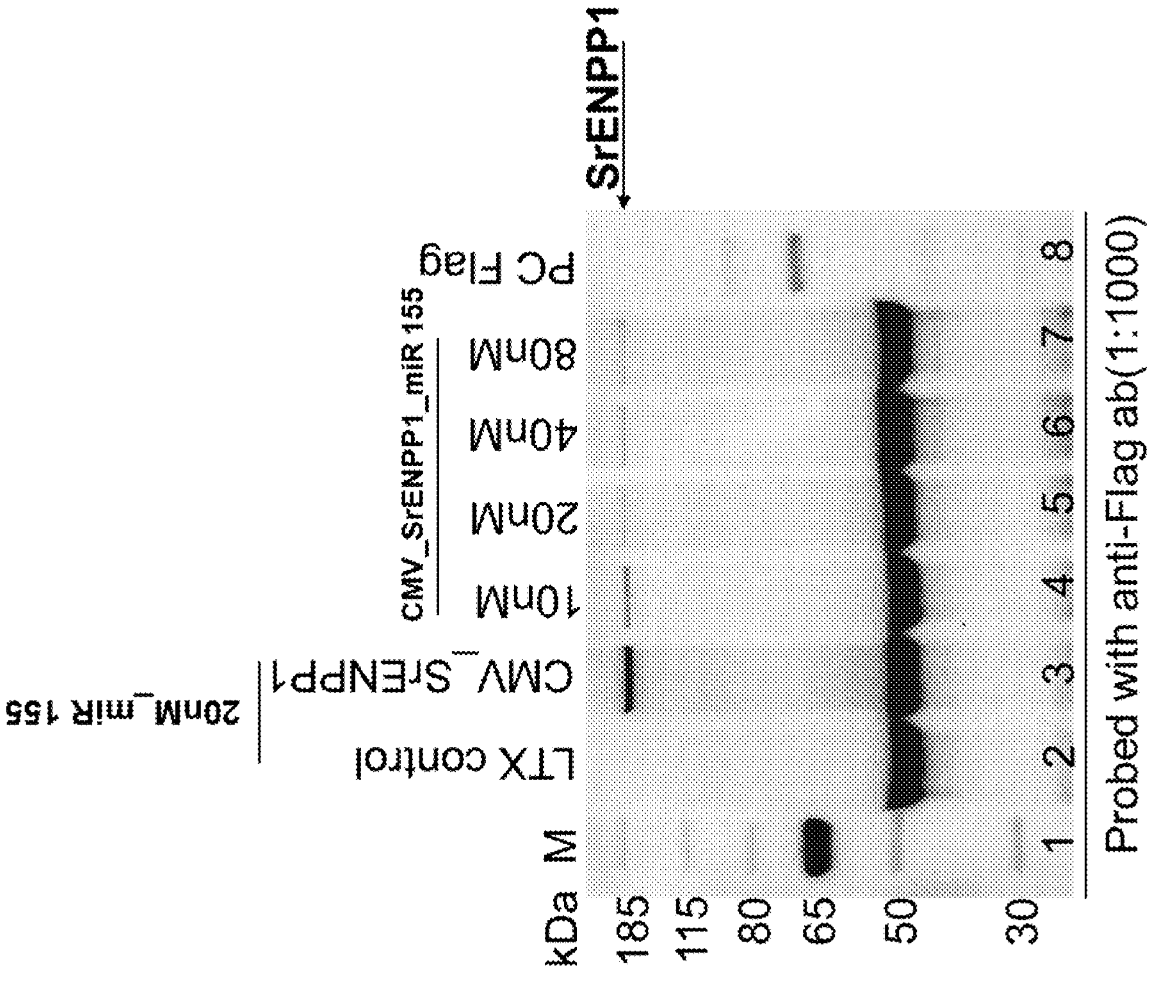

FIGS. 14A-B. (A) Expression of rENPP1 from CAG-rENPP1-FLAG-miR 122 AND CAG-rENPP1-FLAG-miR 155 plasmids. Flag-tagged rENPP1 was expressed from plasmid with constructs consisting of a CAG promoter upstream of rENPP1-FLAG. One plasmid had miR122 target sequences at the 3' UTR of the construct (#3-4) and the other plasmid (#5-6) had miR155 target sequences at the 3' UTR of the construct. Human aortic SMCs were transfected with these plasmids with lipofectamine (LTX). The Western blots, probing for either FLAG expression (on the left) or ENPP1 expression (on the right), demonstrated cellular rENPP1 protein overexpression with these plasmid transfections, highlighting the feasibility of adding 3' miR regulatory elements to therapeutic constructs.

Lanes:

0. Ladder
1. Untreated
2. Only LTX treated
3. LTX+rENPP1-miR122-1 ug/well
4. LTX+rENPP1-miR122-2 ug/well
5. LTX+rENPP1-miR155-1 ug/well 6. LTX+rENPP1-miR155-2 ug/well
7. Positive control for FLAG
8. Positive control for ENPP1

(B) Western blot analysis of expression of srENPP1 in constructs with or without miR155 target sequences in the presence of varying concentrations of miR155. Expression of srENPP1 was reduced with miR155 in a dose-dependent manner. HEK 293T Cells (lanes 4-7) transfected with CMV_srENPP1_Albumin plasmid containing miR155 target sequence showed a reduction in expression of srENPP1 with miR155 in a dose dependent manner compared to cells transfected with CMV_srENPP1_Albumin plasmid without miR155 target sequence (lane3).

Lanes:

1: Molecular weight marker
2: LTX control with 20 nM miR 155
3: CMV_SrENPP1_Albumin without target sequence–with 20 nM miR 155
4: CMV_SrENPP1_Albumin with miR155 target sequence+10 nM miR 155
5: CMV_SrENPP1_Albumin with miR155 target sequence+20 nM miR 155
6: CMV_SrENPP1_Albumin with miR155 target sequence+40 nM miR 155
7: CMV_SrENPP1_Albumin with miR155 target sequence+80 nM miR 155
8: Flag positive control FIG. 15. ENPP1 activity was reduced with miR155 in a dose-dependent manner. A decrease in ENPP1 activity was observed with miR155 in a dose dependent manner in supernatant isolated from HEK293T cells transfected with plasmid expressing srENPP1_Albumin with miR155 target sequence and treated with miR155 at a range of concentrations (0, 10, 20, 40, and 80 nM).

Figure 16:
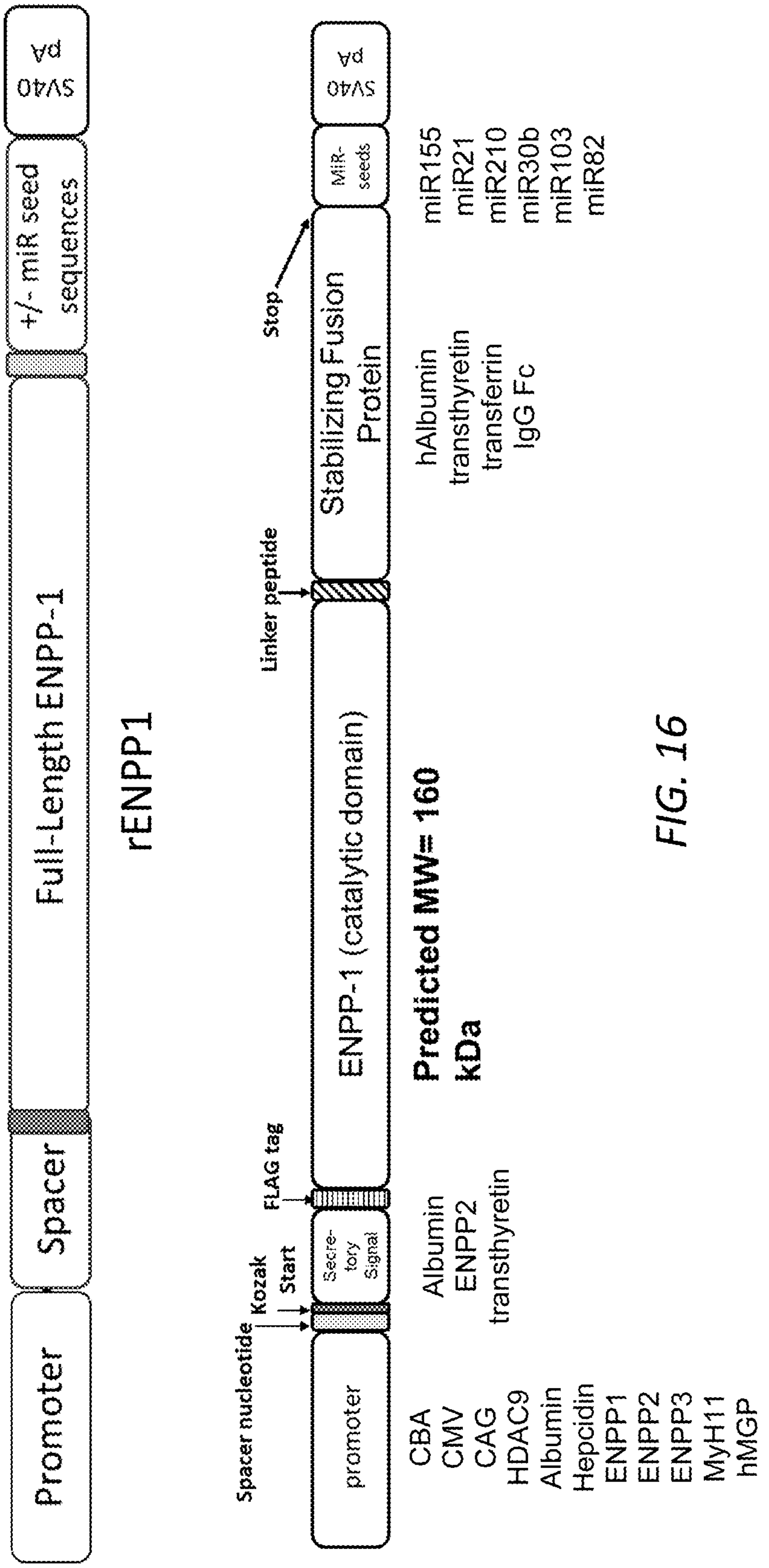

FIG. 16. Schematic illustration of exemplary constructs encoding full length ENPP1 (rENPP1, top), or soluble ENPP1 (srENPP1, bottom) with a stabilizing protein, optionally including miRNA target sequences in the 3' UTR, with exemplary non-limiting promoters, secretory sequences, stabilizing proteins, and miRNAs listed below. Other polyA sequences can also be used, e.g., BGH polyA and variants there.

Figure 17:
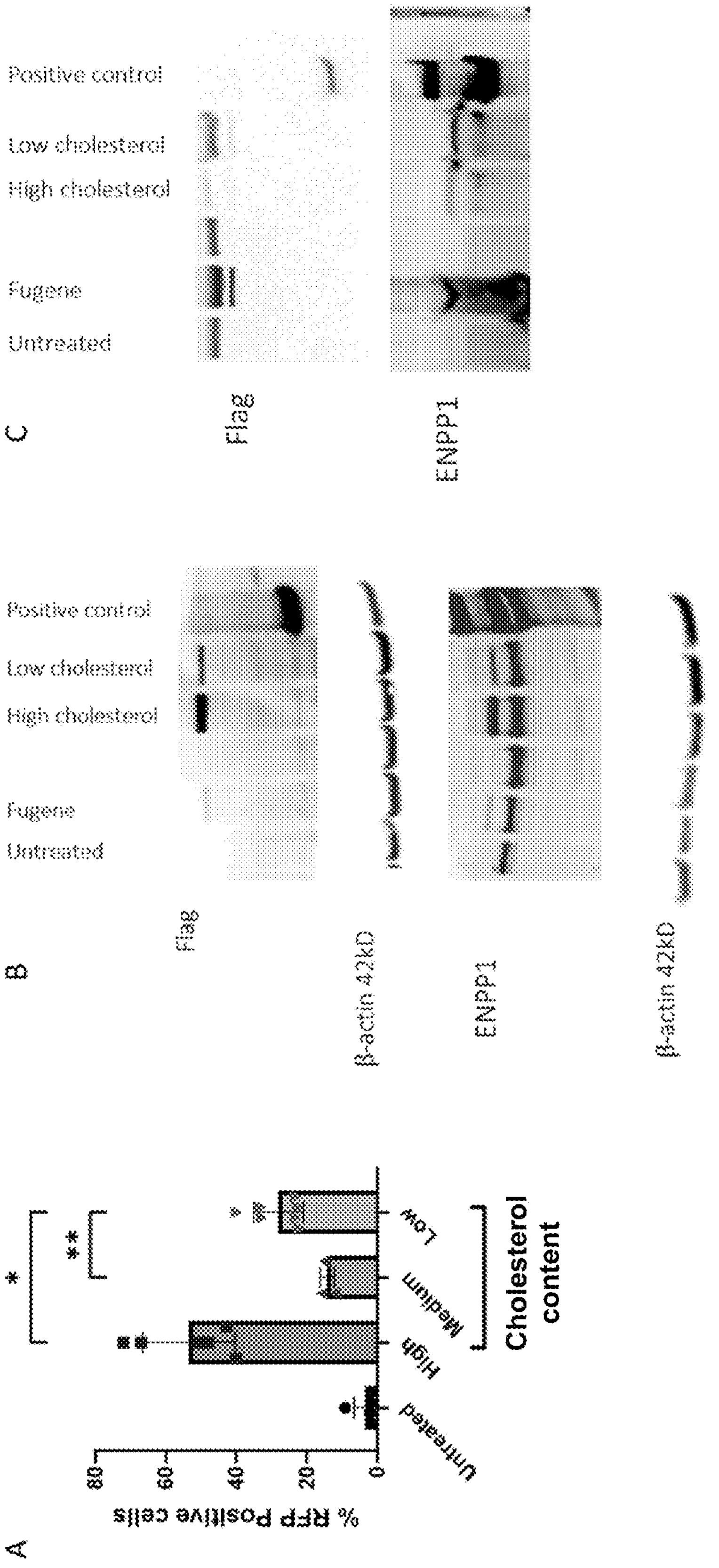

FIGS. 17A-C: LNPs in vitro screening in human liver hepatocytes (HepG2 cell line) based on formulation composition varying in cholesterol and DOPE content (high, medium, low). (A) is a graph showing the delivery of plasmid expressing RFP, measured by flow cytometry. (B-C) are gel electrophoresis images showing the delivery of plasmid construct expressing soluble ENPP1 (srENPP1) and detection in (B) cell lysates and (C) cell supernatant.

Figure 18:
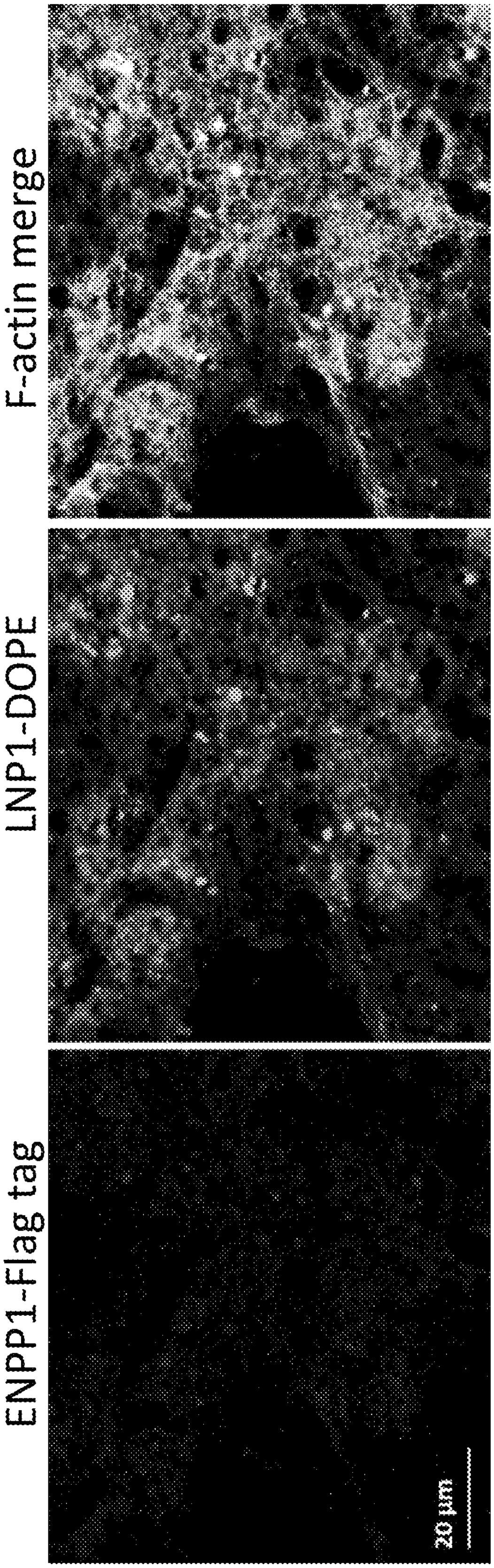

FIG. 18: Microscopy images illustrating efficient soluble ENPP1 expression in the liver among other organs 6 days post injection with a particle of the disclosure in an Asj mouse model for generalized arterial calcification of infancy (GACI). Asj mice injected with soluble srENPP1 plasmid (0.3 mg/kg) at day 3 (P3) express high levels of the enzyme in the liver, 6 days post injection.

FIGS. 19A-D: Efficacy study of LNP delivery using plasmids expressing soluble srENPP1. (A) is a schematic illustration presenting the injection regimen at day 3, 10, and 17 days of age. (B) are survival curves of treated animals, (C) a graph showing animal body weight, and (D) MicroCT scans to detect early development of calcification in treated (LNPs encapsulating soluble ENPP1, 0.3 mg/kg) and untreated animals.

FIGS. 20A-B: (A) is a schematic illustration presenting the LNP four-component system encapsulating plasmid DNA and the addition of a fifth lipid. (B) are graphs showing LNPs' hydrodynamic size, PDI, and zeta potential as a function of % of DOTAP in the formulation.

Figure 21:
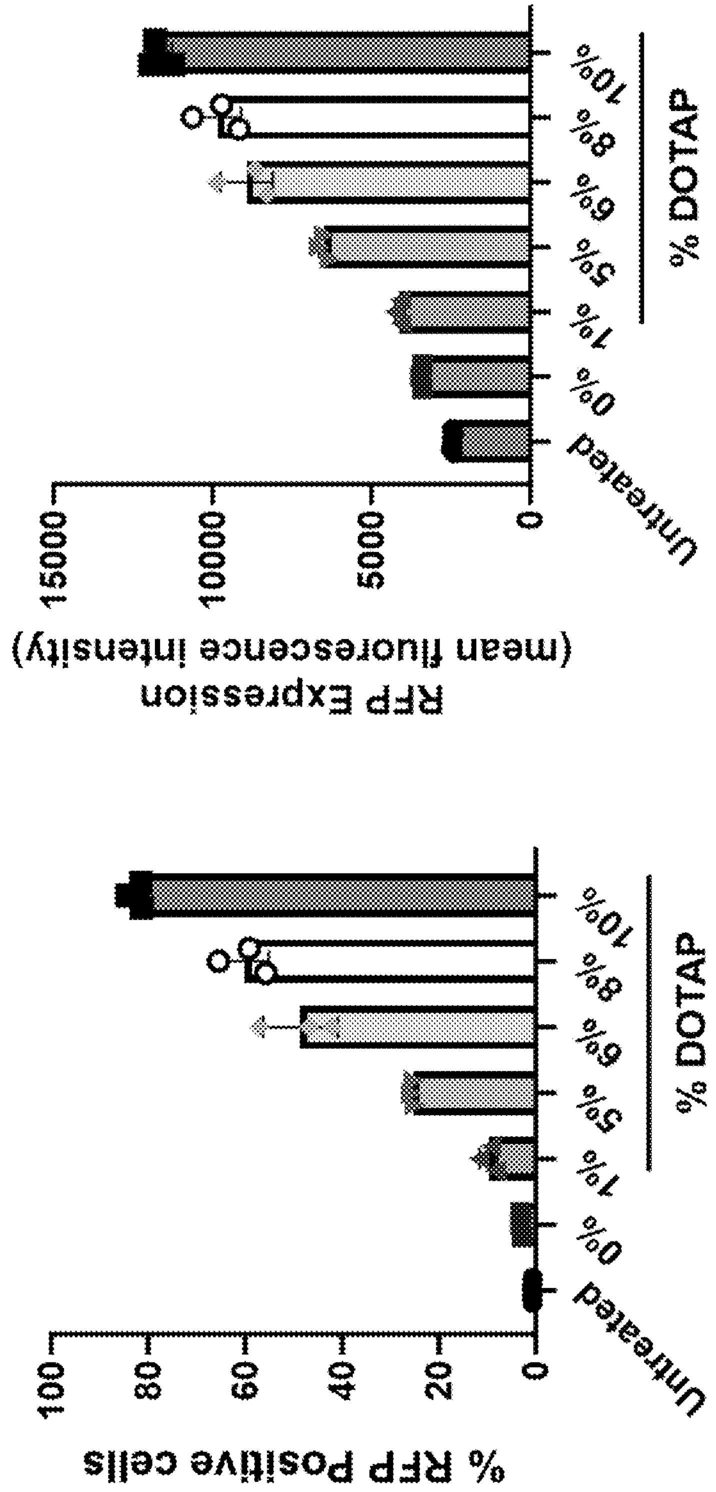

FIG. 21 is a pair of bar graphs illustrating that introduction of DOTAP lipid into a 4-component formulation enables the delivery of plasmid encoding red fluorescent protein (RFP) to MOVAS (mouse smooth muscle) cell line. MOVAS cells incubated for 48 h with plasmid (2 ug/48 well plate) encoding RFP. Cellular expression was identified and measured using flow cytometry. Left, a graph depicting the % of RFP positive cells as a function of % of DOTAP. Right, a graph depicting the mean fluorescence intensity of RFP expression as a function of % of DOTAP.

Figure 22:
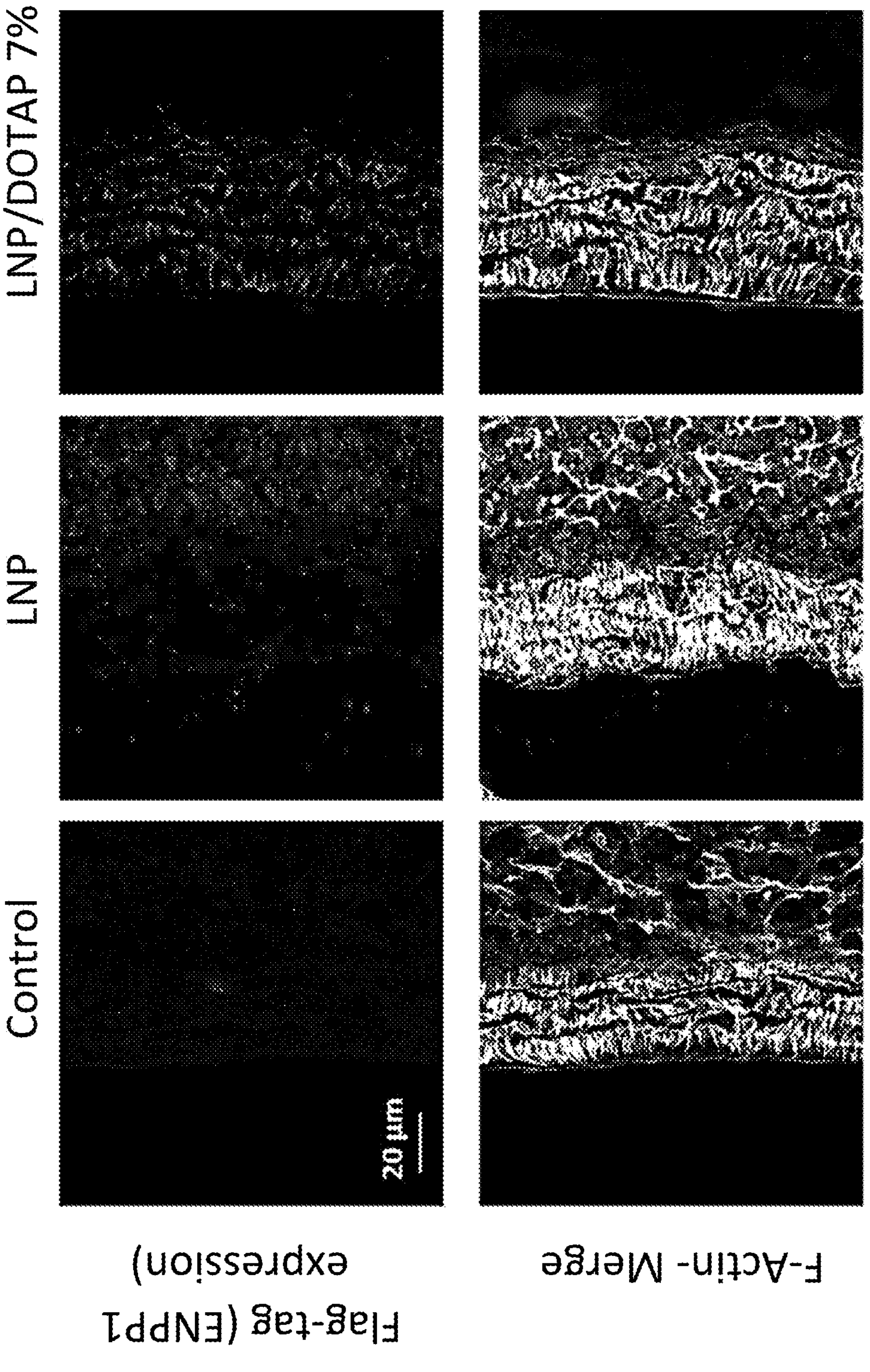

FIG. 22: are histological images illustrating that the introduction of DOTAP LNPs enabled the in vivo delivery of plasmid DNA to smooth muscle cells (SMCs) in the aorta. In vivo transduction of transmembrane rENPP1 in SMCs of the aorta using DOTAP LNPs. Asj mouse model at P3 injected systemically with PBS (control)(left column), LNPs (conventional four-component formulation)(middle column) and DOTAP LNPs formulation (7% DOTAP)(right column) at 0.3 mg/kg plasmid dose. Histological images of the aorta in which SMCs (F-actin)(bottom row) colocalize with ENPP1 expression (Flag-tag)(top row).

FIGS. 23A-B: (A) is a schematic illustration presenting the LNP four-component system encapsulating mRNA and the addition of a fifth lipid; (B) are charts showing the LNPs' hydrodynamic size, PDI, and zeta potential as a function of % of DOTAP in the formulation.

FIGS. 24A-D: are graphs illustrating that introduction of DOTAP into the formulation enables the in vitro delivery of mRNA encoding GFP to MOVAS cell line and primary human aortic cells cultured from an ACTA2 patient. (A-B) MOVAS cells incubated for 24 h with DOTAP/LNPs encapsulating mRNA (0.1 ug/48 well plate) encoding GFP. Cellular expression was identified and measured using flow cytometry presenting (A) percentage of cells expressing GFP and (B) GFP fluorescent intensity. (C) MOVAS cell viability, assessed to confirm the treatment toxicity. (D) 10% DOTAP LNPs provided robust delivery to primary human aortic.

FIGS. 25A-E: Cellular uptake study (A) of 10% DOTAP LNPs in comparison to 0% and 100% determined by (B) fluorescent microscopy and (C) flow cytometry. LNPs encapsulated mRNA labeled by Cy5. (D) LNPs utilize Caveolin and Macropinocytosis-mediated uptake into SMCs. SMCs were used in an optimized (10% DOTAP) LNP cellular internalization study and the uptake mechanism was investigated using Cy5-fluorescently labeled LNPs (mRNA Cy5). Uptake was quantified using flow cytometry. (E) LNPs with 10% or more DOTAP also provided excellent delivery of plasmid DNA encoding RFP to MOVAS cells.

FIGS. 26A-D: are experimental results depicting in vivo delivery of Cre-mRNA utilizing LNP and DOTAP LNP and expression of tdTom in a Marfan disease mouse model. Mice at P3 injected with 1 mg/kg mRNA encapsulated in LNPs or DOTAP LNPs. (A) is a chart depicting expression of tdTom in different organs 6 days post injection as a fold-change relative to untreated mice. (B) Histological images of the aorta in which tdTom is expressed in SMCs from DOTAP LNP-injected mice. (C) tdTom expression was identified 7 days post injection by fluorescent imaging in the aorta and demonstrated strong SMC cell-specific signal by immunofluorescent microscopy. (D) Histological images of Cre-mRNA delivery utilizing LNPs with increasing DOTAP content and expression of tdTom in a Marfan disease mouse model. Increasing the % of DOTAP in LNP formulation increases SMC tdTom expression in vivo. Mice at P3 were injected with 1 mg/kg mRNA encapsulated in LNPs formulated with 0, 10, 50 and 80% DOTAP lipid. tdTom expression was identified using immunofluorescence in histological sections of the aorta and localized to SMCs (indicated by α-SMA expression).

Figure 27:
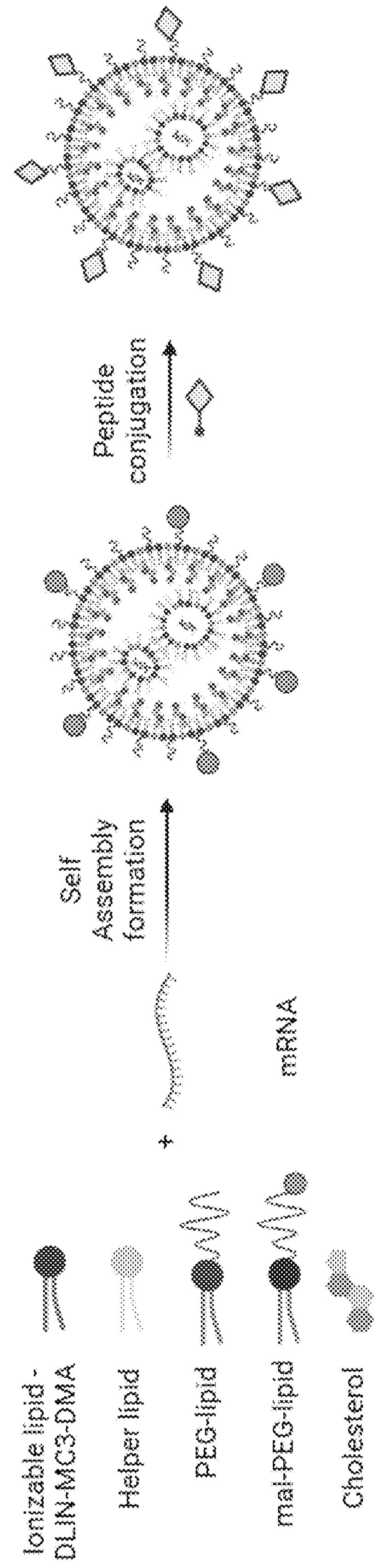

FIG. 27: is a schematic illustration presenting the LNPs' conjugation scheme. LNPs are conjugated with the desired peptide following the assembly of the nanoparticle. Peptide conjugation was done in different densities controlled by the percentage of the linker lipid in the LNP formulation that was 0.15-1.2%.

Figure 28:
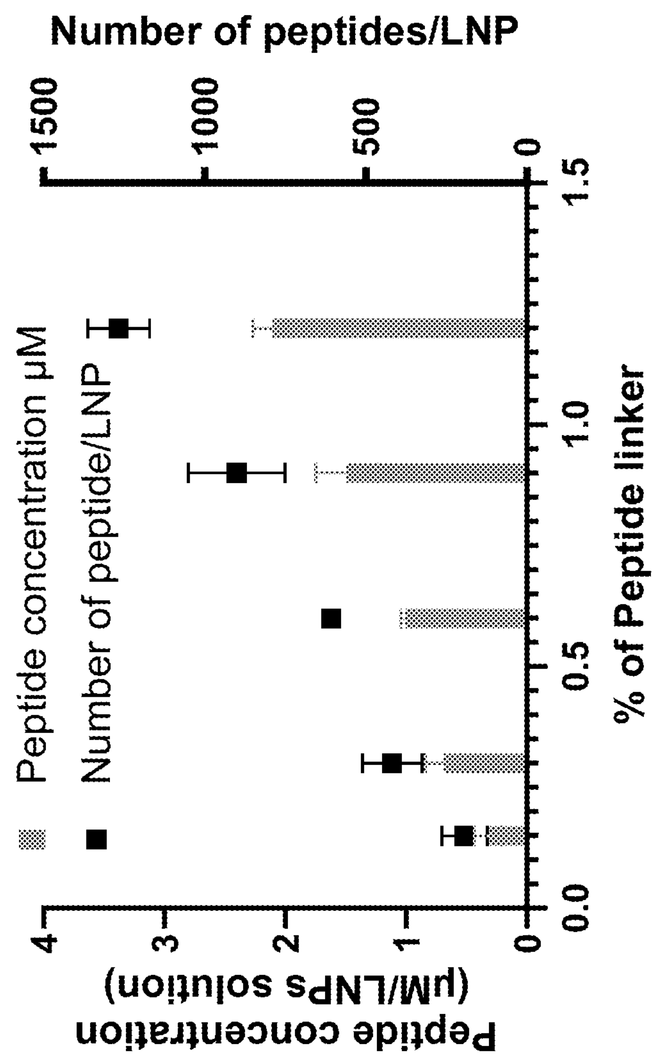

FIG. 28: is a chart depicting the correlation between percentage of linker lipid within peptide-conjugated LNPs, their measured peptide concentration and the resulting calculated number of peptides per LNP.

Figure 29:
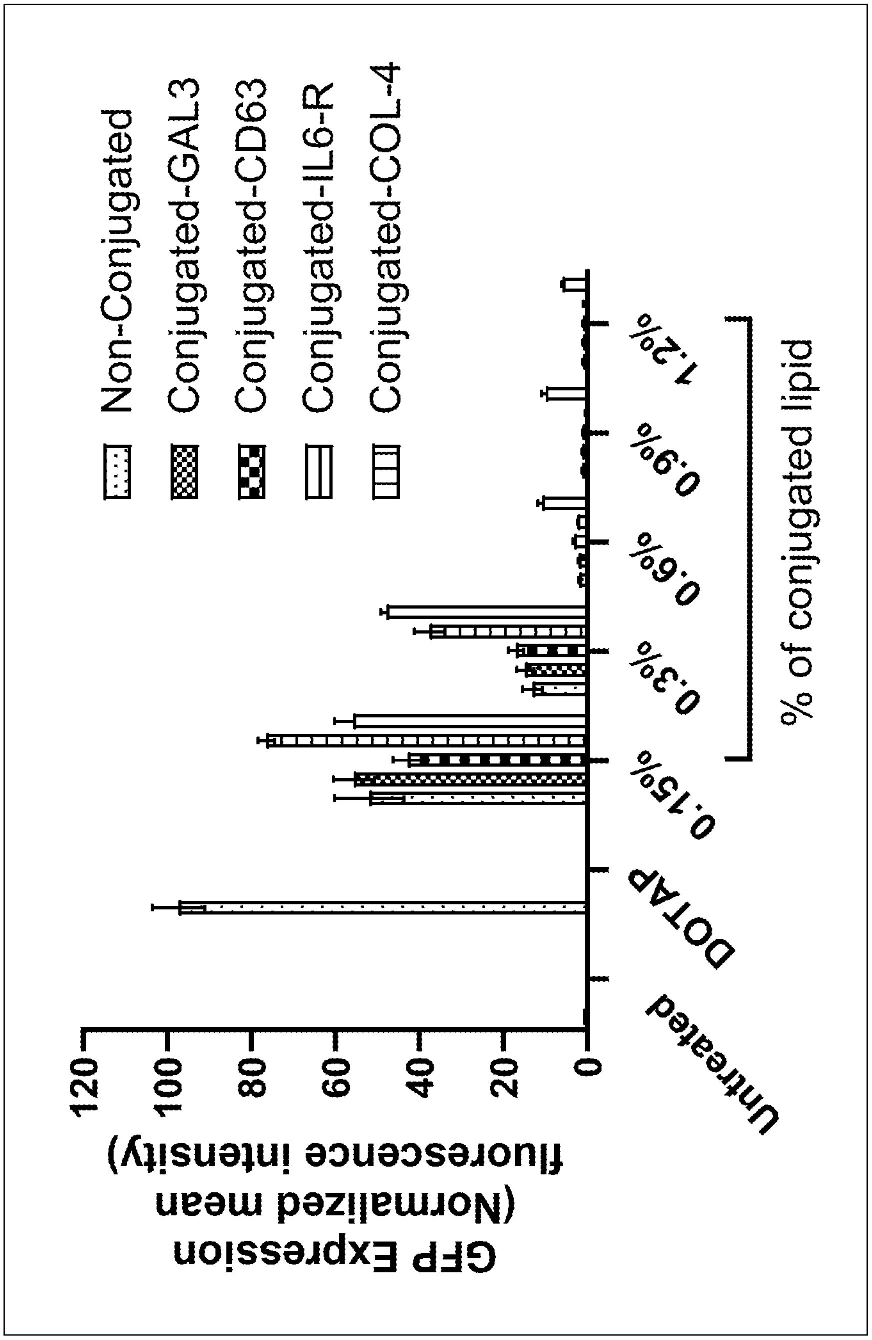

FIG. 29: is a chart depicting the functional activity of peptide-conjugated LNPs in vitro. MOVAS cells treated (24 h) with LNPs conjugated with Col-IV/IL6R/CD63/Gal3 targeting peptides encapsulating mRNA encoding GFP. Cellular expression was measured using flow cytometry.

Figure 30A:
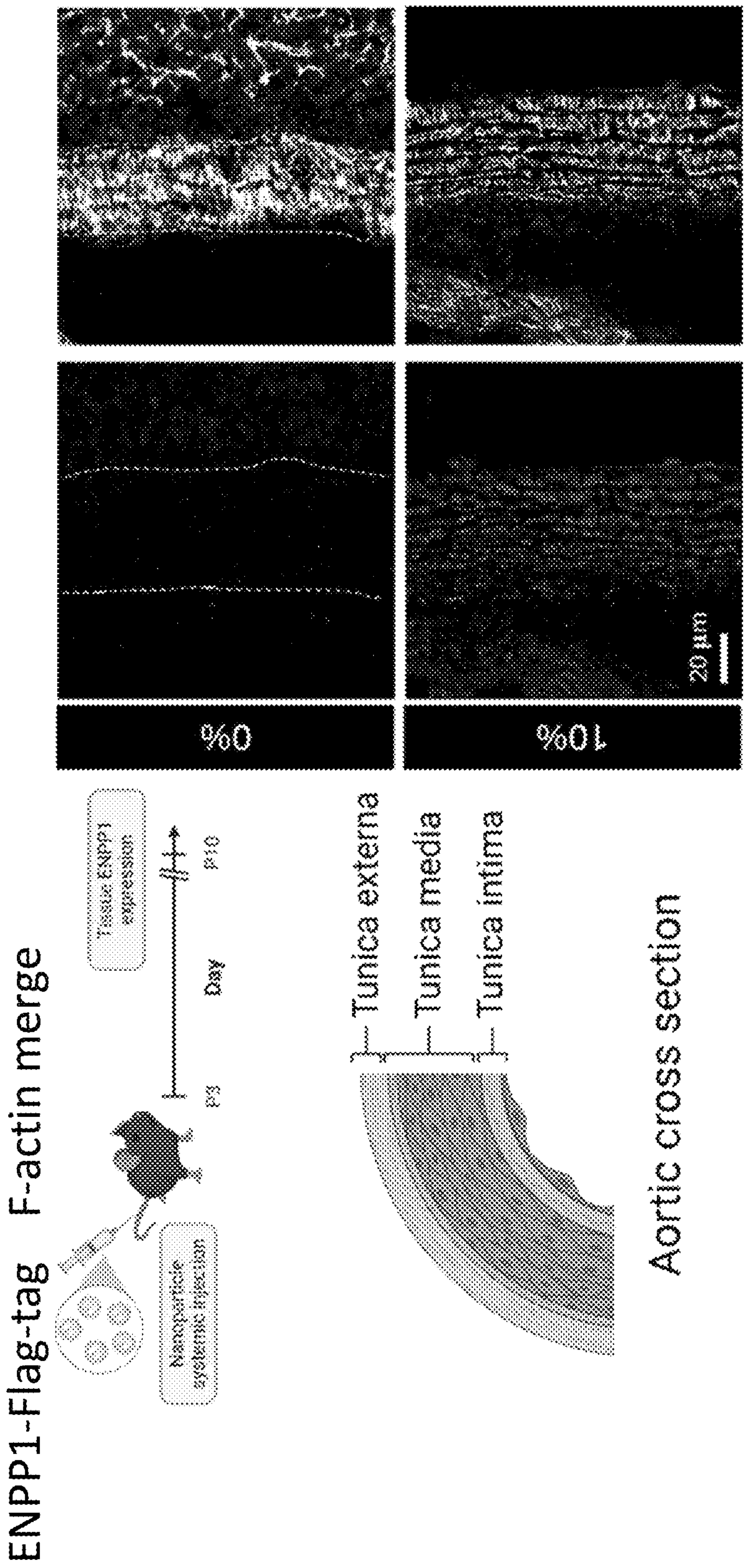
Figure 30B:
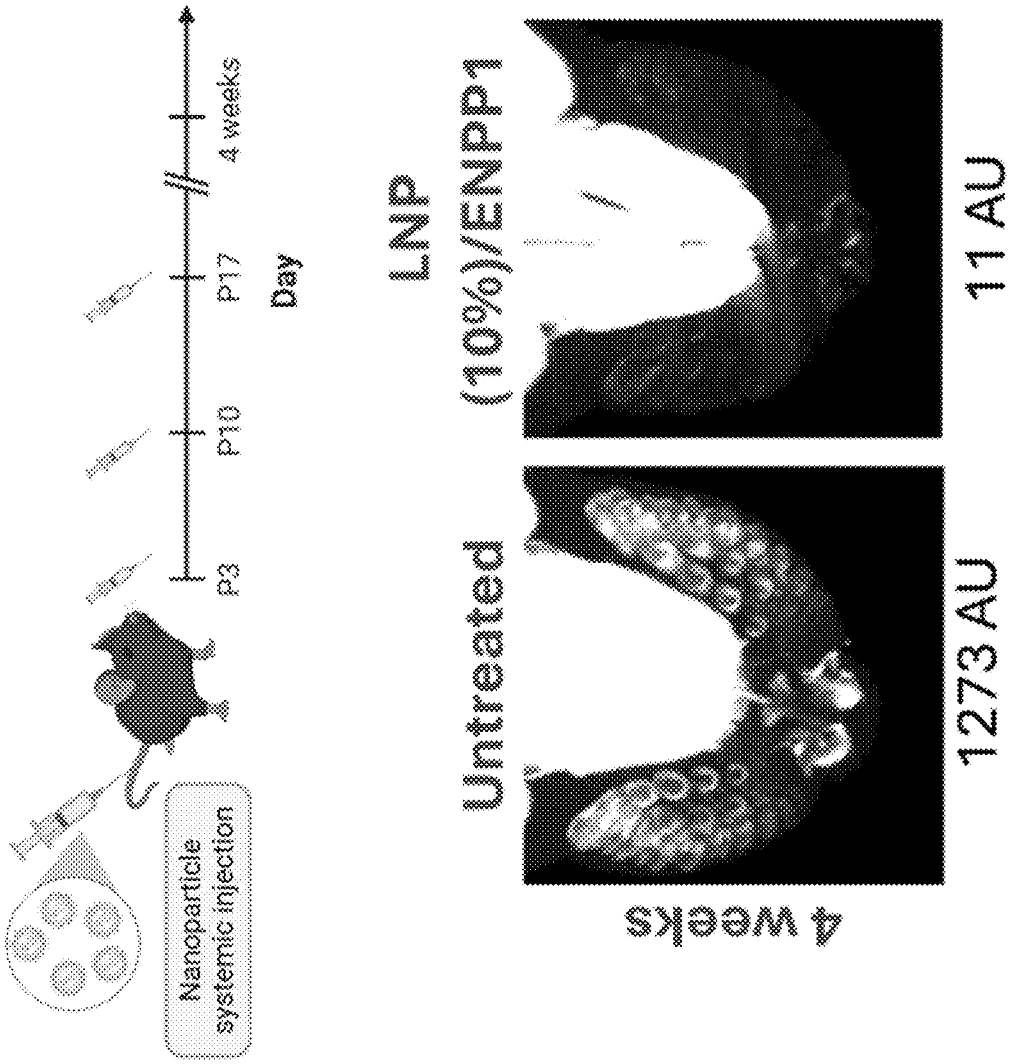

FIGS. 30A-B: (A) In vivo ENPP1 aortic SMC expression (with immunofluorescence (IF) using antibody specific for the FLAG-tag) in ENPP1$^{asj/asj}$ mice injected at P3 by SMC-optimized LNPs (10% DOTAP). Aortic SMC expression was identified using IF, 7 days post injection. (B) ENPP1 gene therapy in ENPP1$^{asj/asj}$ mice administered with three doses of SMC optimized LNPs (10% DOTAP) encapsulating plasmid expressing ENPP1. Efficacy was identified by vibrissae calcification imaged by microCT.

Figure 31:
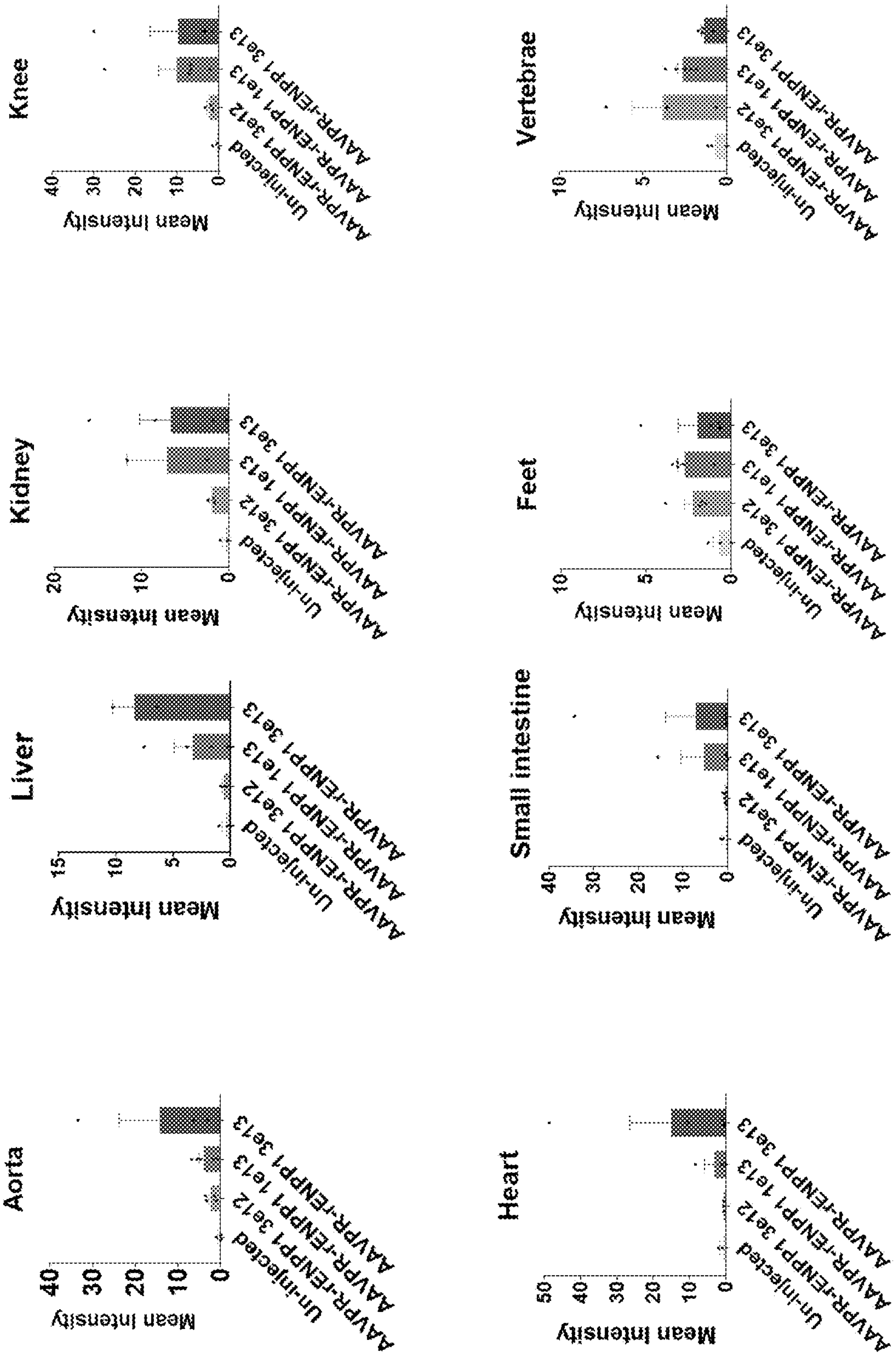

FIG. 31. Graphs representing the fold increase in expression of rENPP1 in different tissues from mice injected with a CAG_rENPP1 expression construct packaged in AAVPR. Newborn pups were injected on day 3 with rENPP1 expression construct packaged in AAVPR through retroorbital route. Tissue/organs were harvested on day 7 post injection and placed on fresh OCT blocks followed by cryosectioning and immunohistochemistry to study the expression profile of rENPP1 in various tissues and organs.

FIGS. 32A-E: (A) ENPP1 gene therapy with either NP delivery of srENPP1 or AAVPR delivery of rENPP1 reduced vibrissae calcification on micro-CT. (B-C) Micro-CT images of male Asj−/− mice demonstrated decreased vibrissae calcification with different doses of AAVPR-CAG-rENPP1 (B) and graphs quantifying calcification at 6 and 8 weeks are shown (C). (D-E) Micro-CT images of female Asj$^{-/-}$ mice demonstrated decreased vibrissae calcification with different doses of AAVPR-CAG-rENPP1 (D) and graphs quantifying calcification at 6 and 8 weeks are shown (E).

Figure 33A:
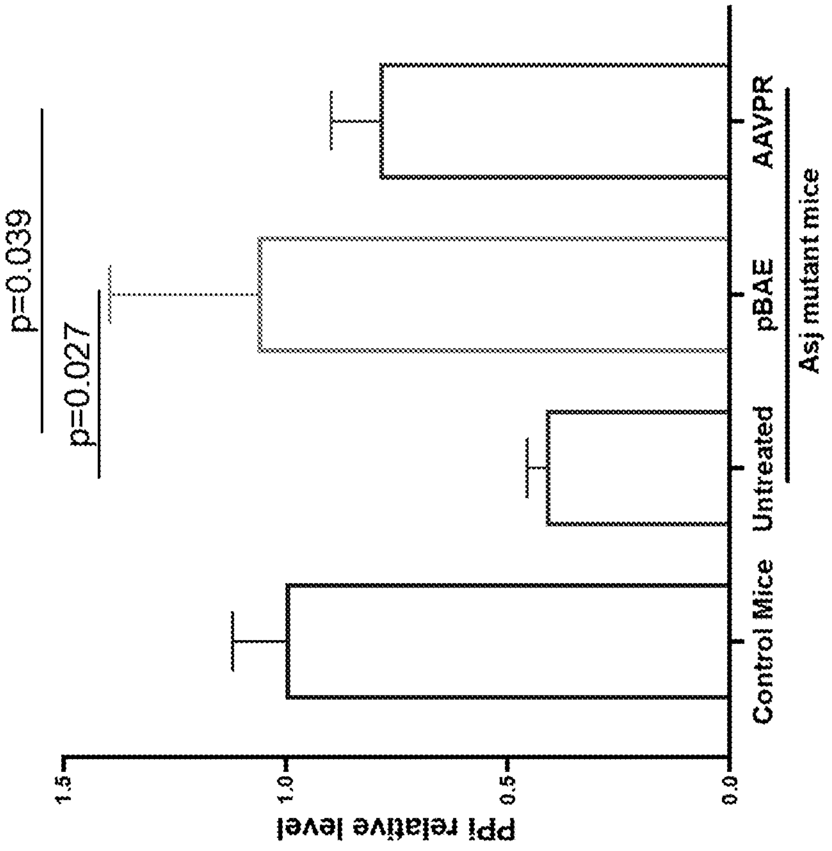
Figure 33B:
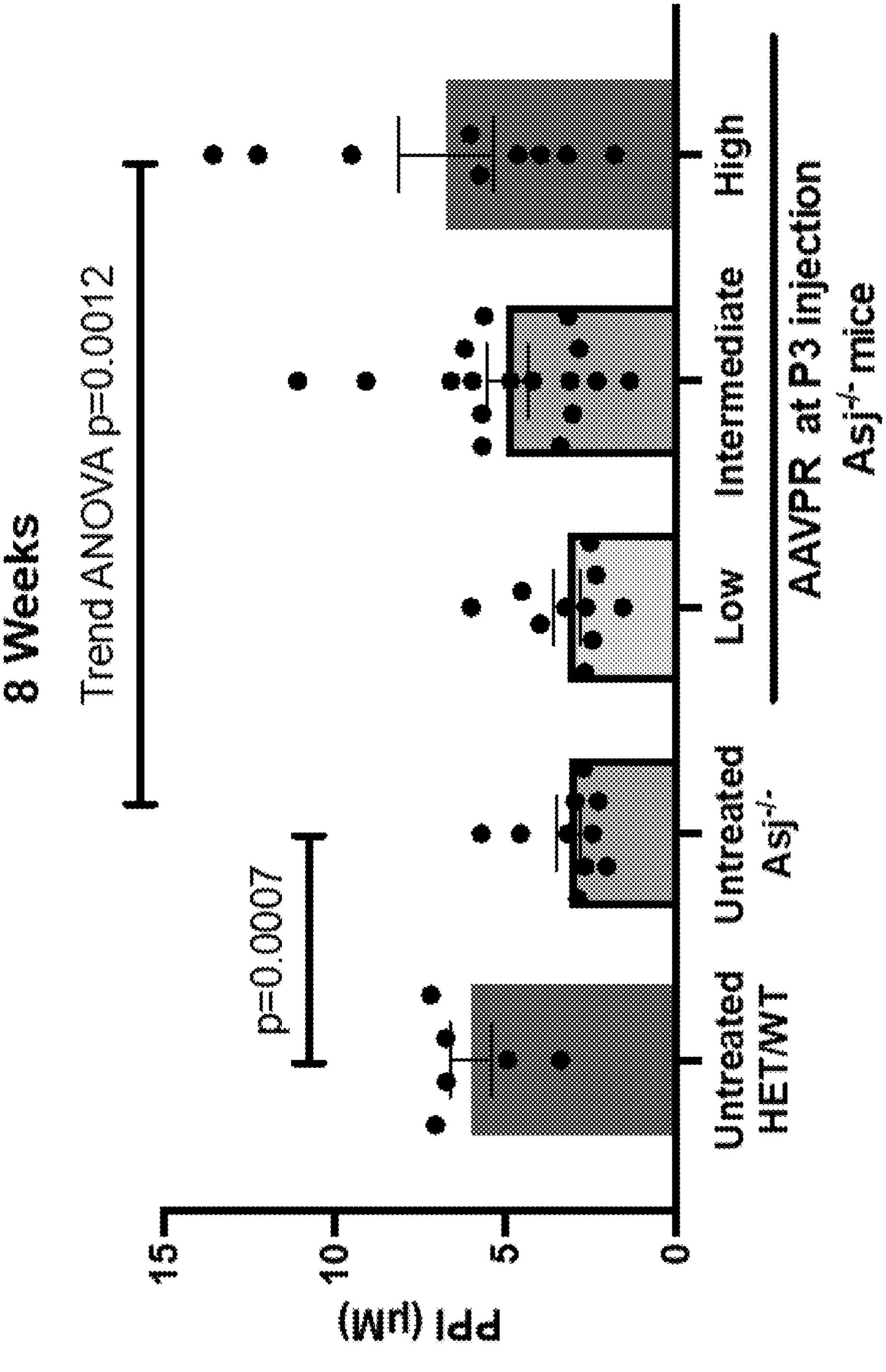

FIGS. 33A-B: (A) Pyrophosphate is the chemical product of ENPP1 enzymatic activity and is significantly reduced in calcification disorders such as GACI. Serum pyrophosphate (PPi) levels were normalized in GACI mice treated with pBAE srENPP1 or AAVPR rENPP1. (B) Plasma pyrophosphate (PPI) was increased in a dose-dependent manner in ASJ$^{-/-}$ GACI mice that received 3 different doses of AAVPR-CAG-rENPP1 (low=3e12 vg/kg, intermediate=1e13 vg/kg, high=3e13 vg/kg).

Figure 34A:
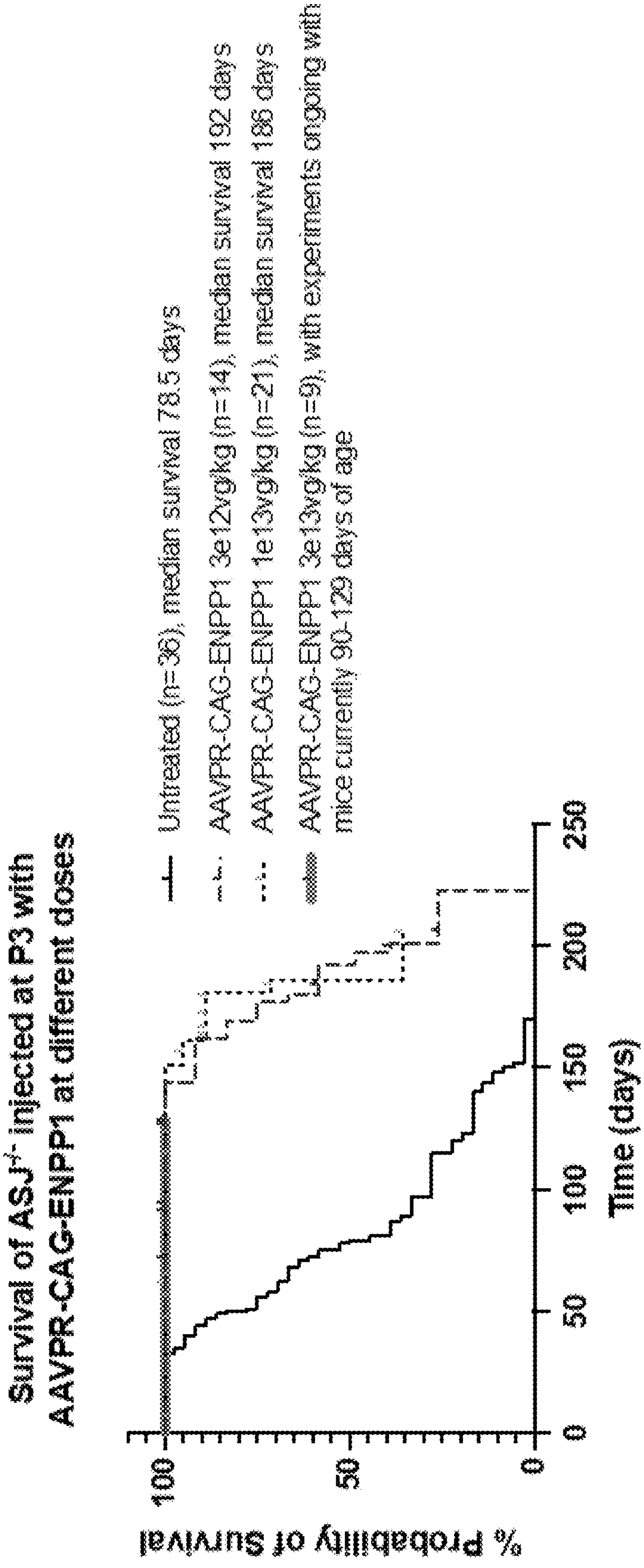
Figure 34B:
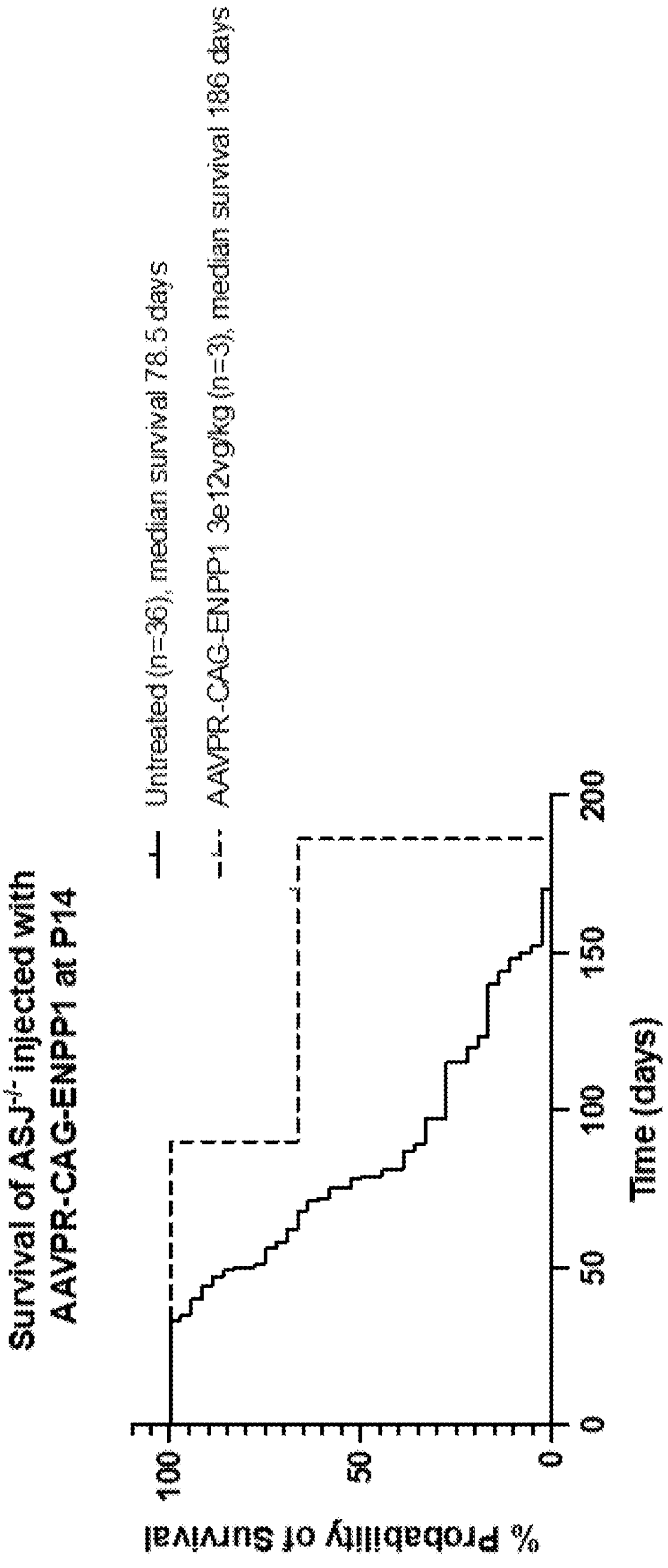

FIGS. 34A-B: (A) Kaplan-Meier survival curves of ASJ$^{-/-}$ GACI mice injected with AAVPR-CAG-rENPP1 at different doses at P3 of age (low=3e12 vg/kg, intermediate=1e13 vg/kg, high=3e13 vg/kg). (B) Kaplan-Meier survival curves of ASJ$^{-/-}$ mice injected with AAVPR-CAG-rENPP1 at a low dose (3e12 vg/kg) at P14 of age.

Figure 35:
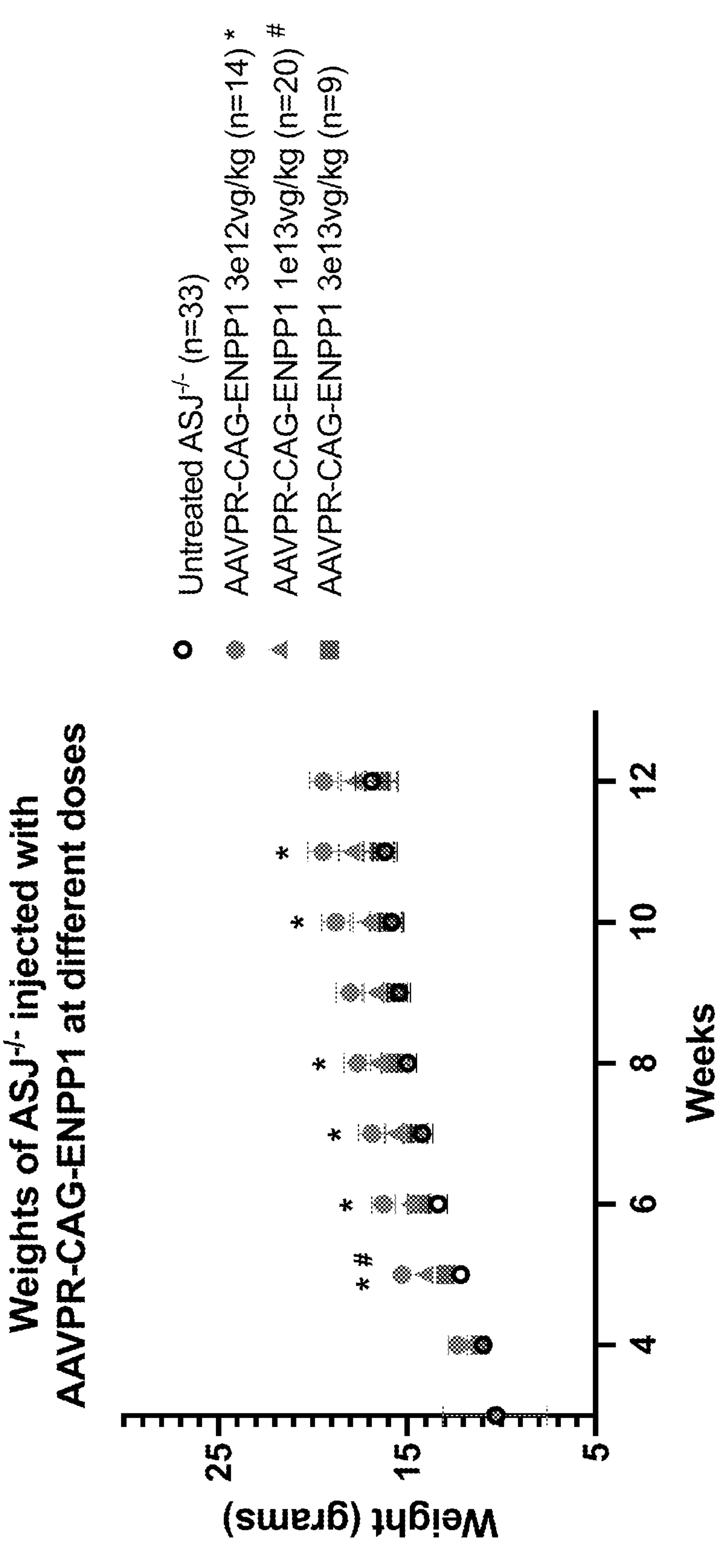

FIG. 35: depicts weights of ASJ$^{-/-}$ mice injected retroorbitally with 3 different doses of AAVPR-CAG-rENPP1 (low=3e12 vg/kg, intermediate=1e13 vg/kg, high=3e13 vg/kg). * indicates $p<0.05$ comparing untreated vs low dose treated Asj$^{-/-}$ mice. # indicates $p<0.05$ comparing untreated vs intermediate dose treated Asj$^{-/-}$ mice. Generally, body weights of GACI ASJ$^{-/-}$ mice improved with AAVPR-CAG-rENPP1 therapy.

Figure 36A:
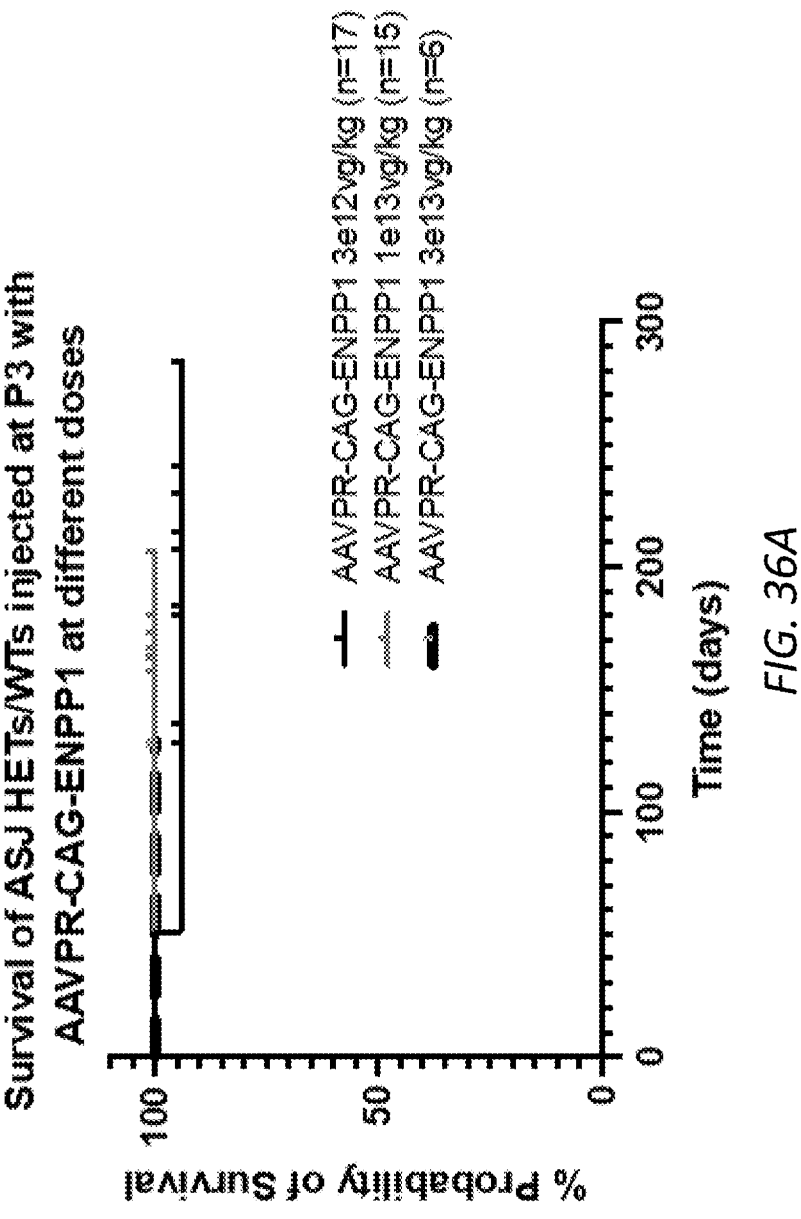
Figure 36B:
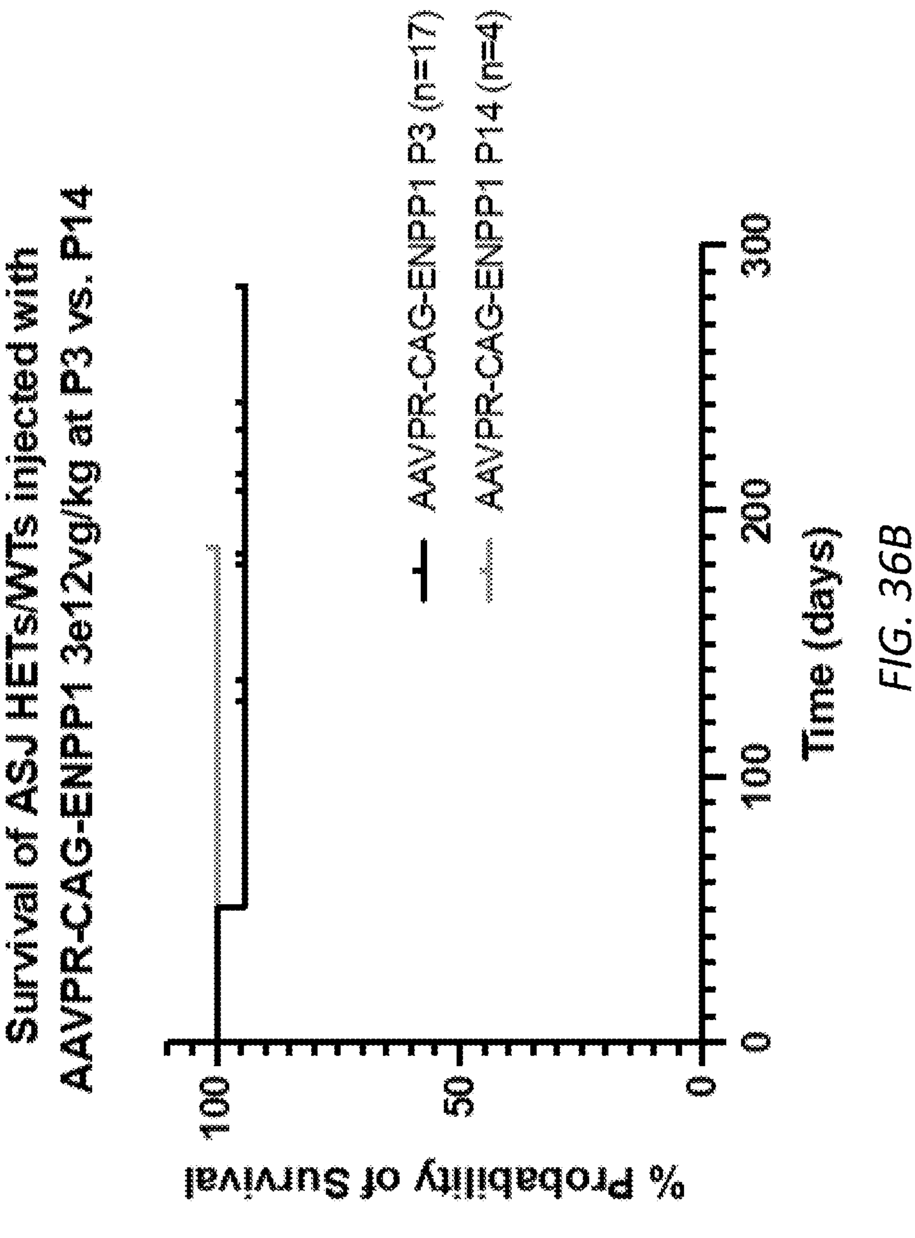

FIGS. 36A-B: (A) Wild-type (WT) and ASJ$^{+/-}$ (HETs or heterozygotes) were injected retro-orbitally with 3 different doses of AAVPR-CAG-ENPP1 (low=3e12 vg/kg, intermediate=1e13 vg/kg, high=3e13 vg/kg). Survival was similar to what would be expected of untreated WT and HET mice. (B) WT and ASJ HETs were injected retro-orbitally at postnatal day 3 (P3) versus postnatal day 14 (P14) with the low dose of AAVPR-CAG-ENPP1. Survival was similar to what would be expected of untreated WT and HET mice.

FIGS. 37A-E: collectively depict treatment of human vascular smooth muscle cells (VSMCs) with AAVPR-CAG-rENPP1. (A) AAVPR-CAG-rENPP1 treatment at low (8e9 vg/mL) and high (1.6e10 vg/mL) doses resulted in dose-dependent increase in ENPP1-Flag expression as measured on western blot. (B) Similarly, AAVPR-CAG-rENPP1 treatment at low and high dose resulted in dose-dependent increase in ENPP1 activity compared to untreated cells. (C) AAVPR-CAG-rENPP1 treatment of human VSMCs grown in osteogenic media for 21 days resulted in reduced calcification on alizarin red stain, and (D) RUNX2 protein levels. RUNX2 is a master transcriptional regulator of the osteogenic phenotype switch of VSMCs that results in calcification across a whole host of disorders, including calciphylaxis, atherosclerosis, calcification related to chronic kidney disease and diabetes mellitus. (E) The osteogenic phenotype switch of VSMCs is associated with increased migration, which was reduced after treatment with AAVPR-CAG-rENPP1.

Figure 38A:
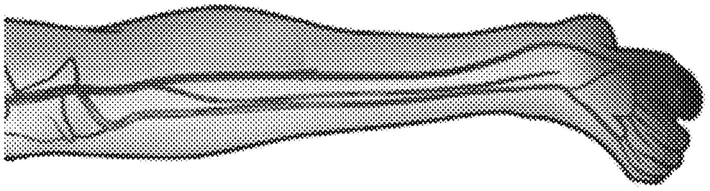
Figure 38B:
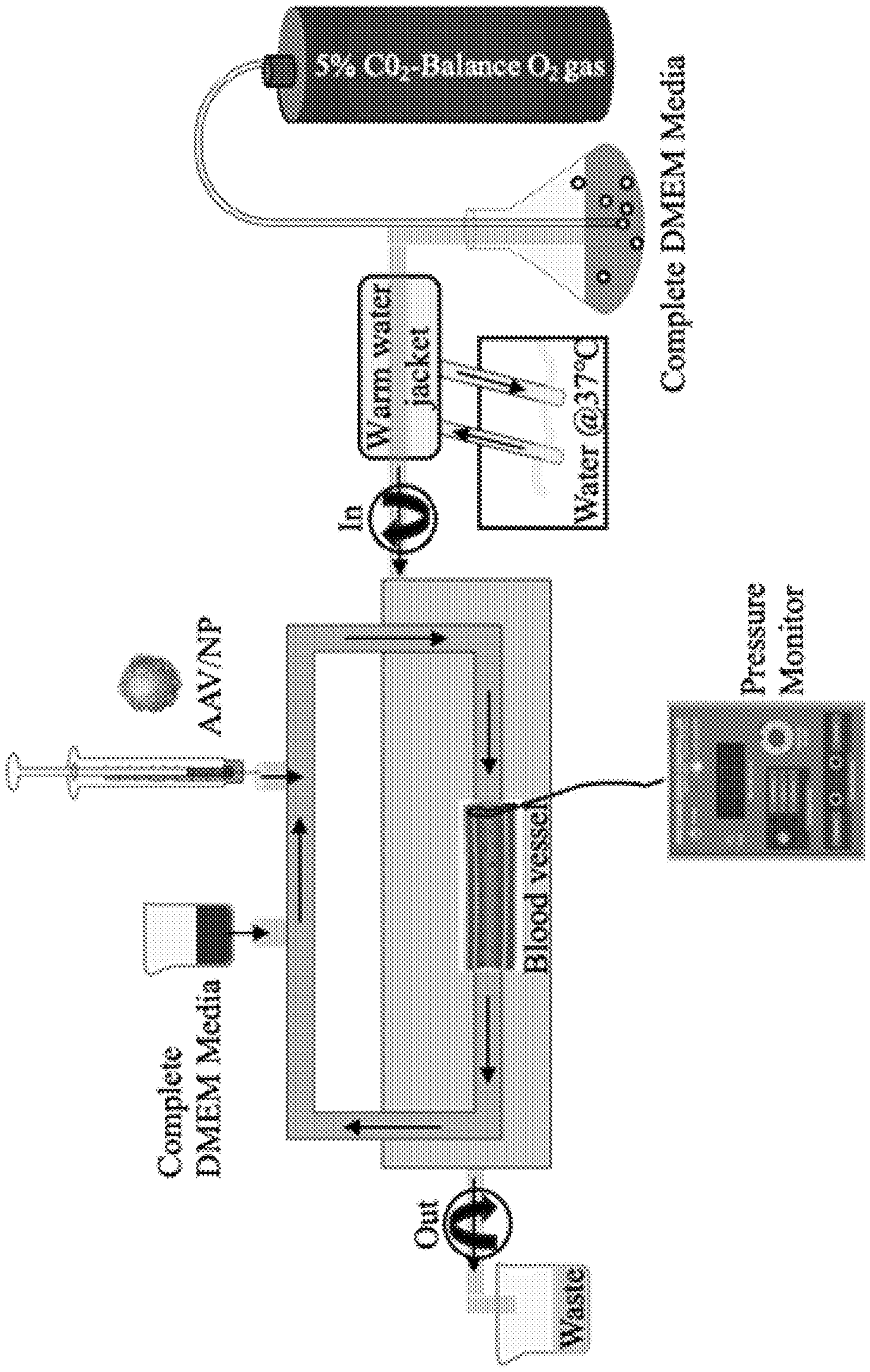

FIGS. 38A-B. Testing performance of AAVPR in human vessels ex vivo. (A) Surgical Specimens isolated were vessels from patients undergoing lower limb amputation under an IRB-approved protocol. (B) Schematic illustrating perfusion bioreactor, the experimental setup in which human vessels harvested from the operating room were attached to a perfusion pump for AAVPR or AAV9 treatment.

Figure 39A:
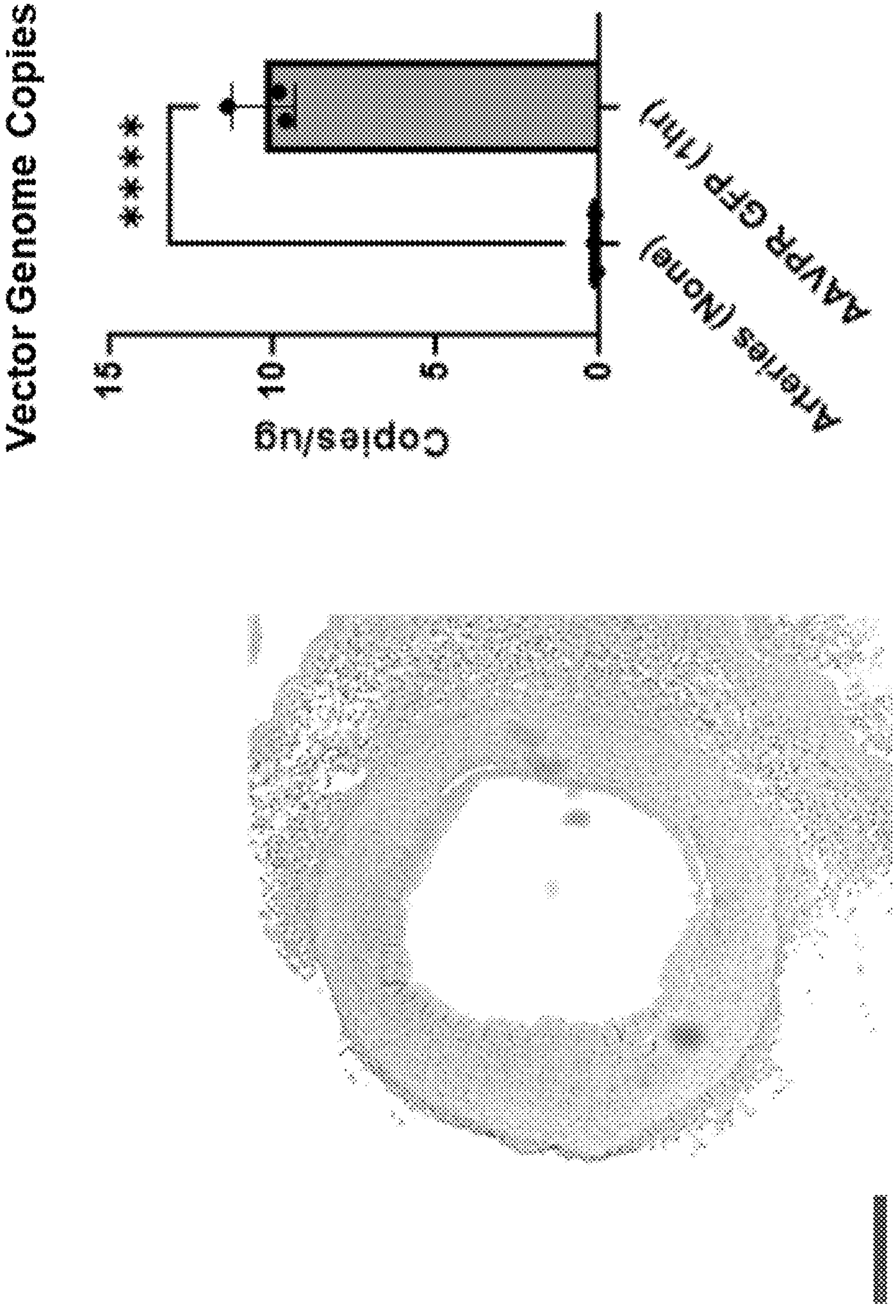
Figure 39B:
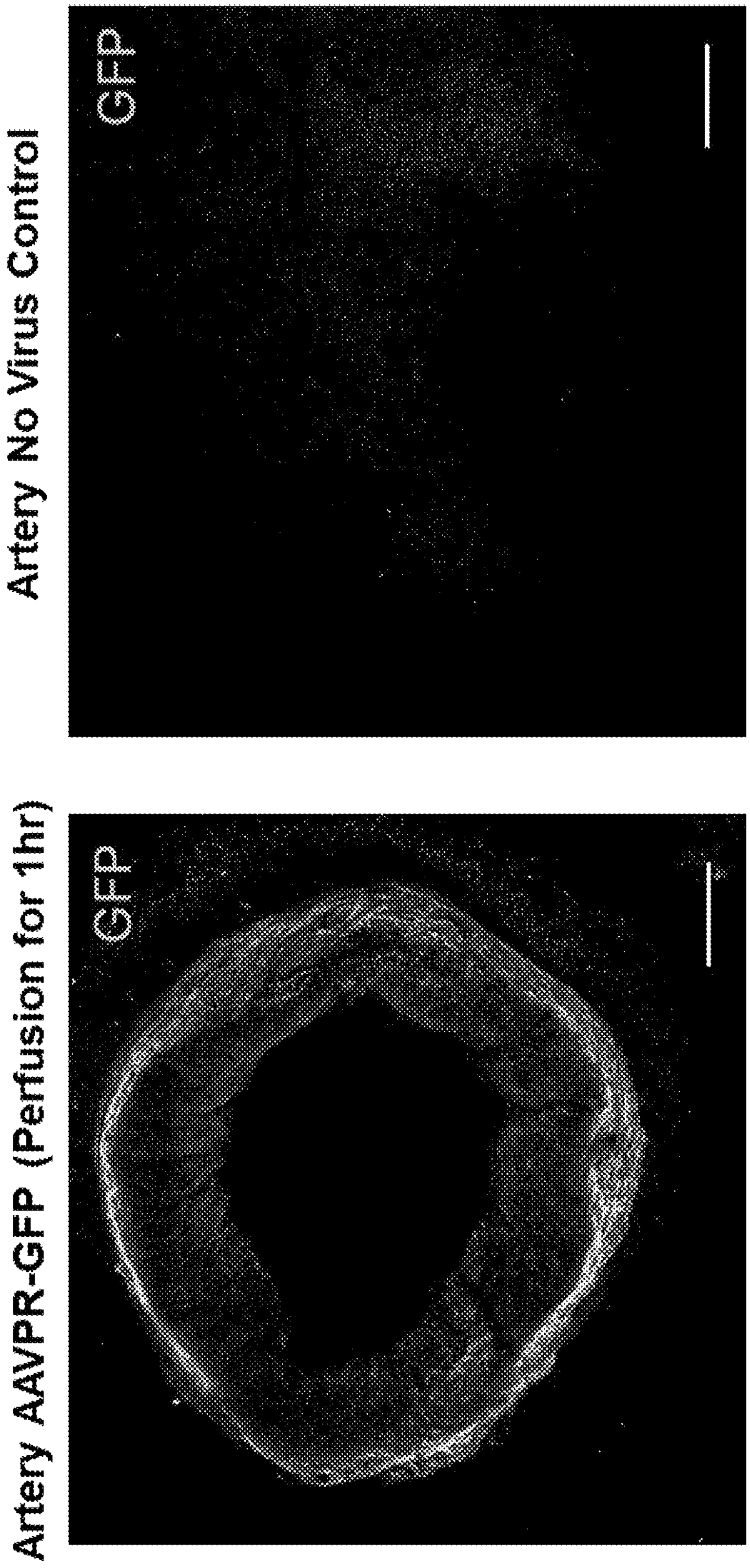

FIGS. 39A-B. AAV-PR has High Transduction Efficiency in Healthy Human Vessels. (A) Illustrative image of a cross-section of a human vessel (A) upon which copies of vector genomes were quantified (right). (B) Fluorescence images of GFP expression after perfusion with AAVPR-GFP construct for one hour demonstrates strong AAVPR transduction of human arteries.

Figure 40A:
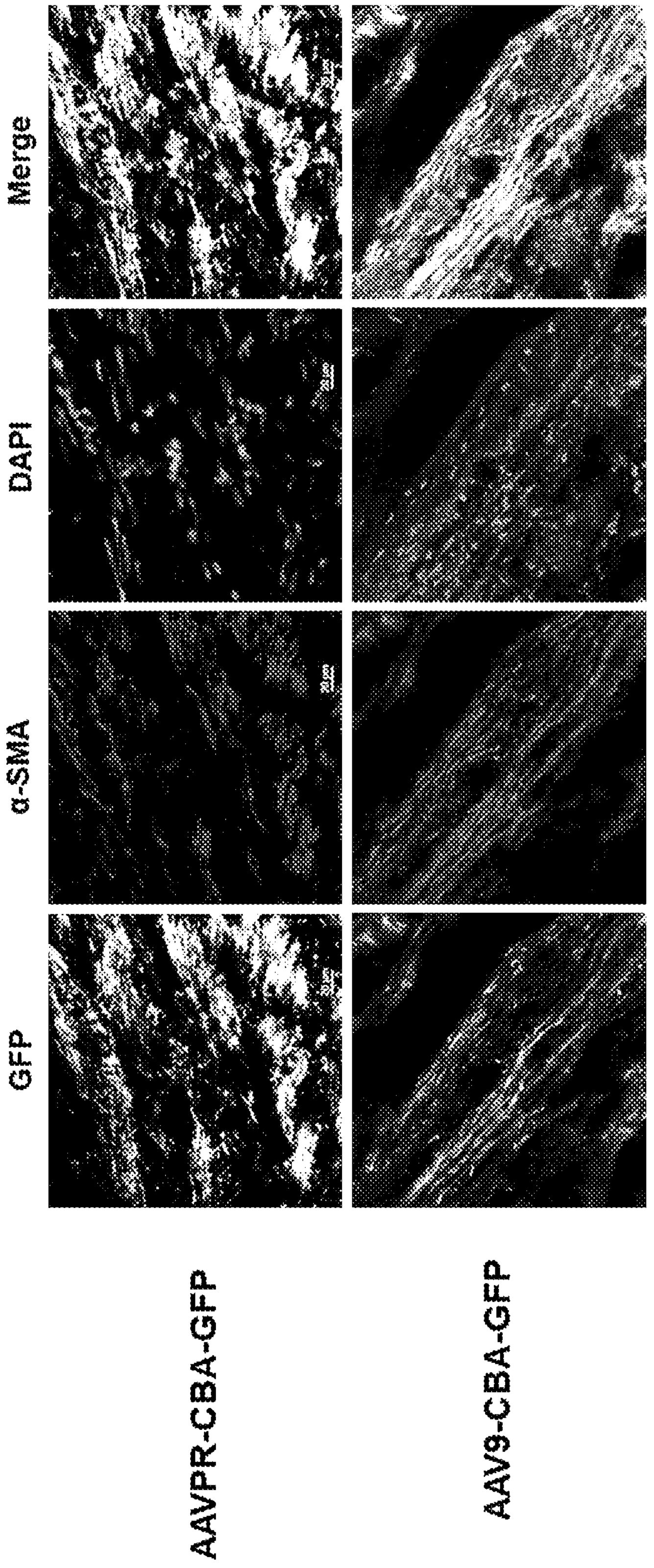
Figure 40B:
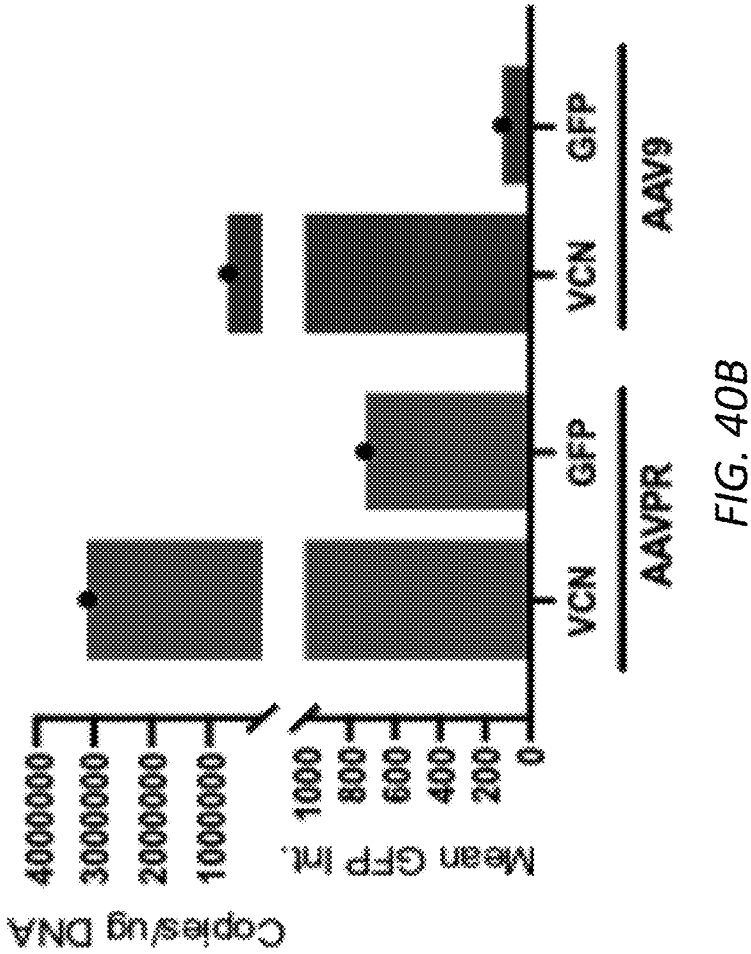

FIGS. 40A-B. Ex vivo Perfused Human Vessels—Comparison of AAVPR-GFP and AAV9-GFP transduction efficiency. (A) The AAVPR-transduced vessels exhibited significant GFP signal in the medial layer with co-localization with α-SMA indicating strong transduction of vascular smooth muscle cells. (B) Ex vivo perfusion of diseased human vessels with AAVPR-CBA-GFP resulted in significantly higher viral copy numbers and GFP expression compared to AAV9-CBA-GFP indicating a great vascular tropism with AAVPR than AAV9.

DETAILED DESCRIPTION

Generalized arterial calcification of infancy (GACI) is characterized by widespread arterial calcification and/or stenoses of large and medium-sized vessels resulting in a range of clinical manifestations including myocardial infarction, respiratory distress, hypertension, cardiomegaly, and stroke. GACI is estimated to affect one in 200,000 pregnancies. Mortality is particularly high in early infancy; approximately 55% of patients die within the first 6 months of life despite intensive care and supportive measures. After 6 months of life, the mortality rate is markedly reduced and patients tend to survive, though many still have sequalae from their initial hypoxic insults, and a majority eventually develop hearing loss and hypophosphatemic rickets. GACI typically results from biallelic loss-of-function mutations in ENPP1, which encodes an ectonucleotide pyrophosphatase/phosphodiesterase that converts ATP into AMP and pyrophosphate (PPi), a potent inhibitor of calcification. Loss of ENPP1 activity results in decreased quantity of PPi both locally and systemically, and GACI patients have low plasma and urinary PPi concentrations. AMP inhibits vascular smooth muscle cell proliferation, so loss of ENPP1 directly impact vascular function. Nitschke et al., Exp Mol Med. 2018 October; 50(10): 139. Endogenous ENPP1 is integrated into the plasma membrane with a single transmembrane domain and an active extracellular domain. Borza et al., J Biol Chem. 2022 February; 298(2):101526.

An ENPP1-deficient mouse model (the 'ages with stiffened joints' (asj) mouse) has been developed that recapitulates calcification and clinical presentation found in GACI patients, see, e.g., Li et al., Dis Model Mech. 2013 September; 6(5): 1227-1235. The mice typically die between ages of 35-71 days, with a median survival of 58 days. Postmortem histological examination of heart, aorta, and kidneys showed calcification, and about 40-60% of mice exhibit calcification of these organs on microCT. 100% of the Asj mice develop vibrissae vascular calcification and this is considered the most consistent phenotype of the model. See, e.g., Li et al., supra; Khan et al., Dis Model Mech. 2018 Oct. 8; 11(10):dmm03569; Albright et al., Nat Commun. 2015 Dec. 1:6:10006.

Provided herein are compositions and methods for gene therapy for disorders of arterial calcification as well as Generalized Arterial Calcification of Infancy (GACI) and other disorders as described herein. The methods include a gene addition strategy to deliver a DNA construct to target tissues (such as liver and smooth muscle cells) to express soluble recombinant ENPP1 (srENPP1) or recombinant full length transmembrane ENPP1 (rENPP1), e.g., under the CBA, CMV, CAG or other promoters as described herein. The DNA constructs can include 3' miRNA target sites to allow for regulation of ENPP1 mRNA levels and therefore ENPP1 protein expression. Also described herein are methods of delivering recombinant ENPP1, e.g., intravenously, to a subject who is deficient in ENPP1 to restore enzyme activity and reverse or reduce risk of disease progression, e.g., using a viral vector such as an adeno-associated virus (AAV) or a nanoparticle (NP) carrying an ENPP1 gene construct, optionally including a CBA, CMV, CAG, or other promoter, e.g., as described herein; or using lipid nanoparticles as described herein. Such methods can be used for treatment of GACI and other conditions associated with similar vascular calcification pathology, including pseudoxanthoma elasticum (PXE), calciphylaxis, and cardiovascular diseases including diabetic vascular calcification, end-stage renal disease (ESRD)-associated vascular disease, calcific aortic valve disease (CAVD), coronary atherosclerosis, coronary artery bypass graft (CABG) stenosis, in-stent stenosis, peripheral vascular disease, and cerebral atherosclerosis.

Gene Therapy Constructs

Provided herein are gene therapy constructs for expression of ENPP1, e.g., recombinant transmembrane ENPP1 (rENPP1) or secreted recombinant ENPP1 (srENPP1), in cells of a subject. The constructs can thus include sequences encoding full-length human ENPP1 or a truncated version thereof comprising the extracellular domain of human ENPP1 (srENPP1). The constructs can optionally be codon optimized. Exemplary sequences of human ENPP1 protein is provided in GenBank at RefSeq ID NM_006208.3 (nucleic acid) and NP_006199.2 (protein), e.g., as follows:

(SEQ ID NO: 1)

1 merdgcaggg srggeggrap regpagngrd rgrshaaeap gdpqaaasll apmdvgeepl 61 ekaarartak dpntykvlsl vlsvcvltti lgcifglkps cakevksckg rcfertfgnc

121 rcdaacvelg nccldyqetc iepehiwtcn kfrcgekrlt rslcacsddc kdkgdcciny

181 ssvcqgeksw veepcesine pqcpagfetp ptllfsldgf raeylhtwgg llpvisklkk

241 cgtytknmrp vyptktfpnh ysivtglype shgiidnkmy dpkmnasfsl kskekfnpew

301 ykgepiwvta kyqglksgtf fwpgsdvein gifpdiykmy ngsvpfeeri lavlqwlqlp

361 kderphfytl yleepdssgh sygpvssevi kalqrvdgmv gmlmdglkel nlhrclnlil

421 isdhgmeqgs ckkyiylnky lgdvknikvi ygpaarlrps dvpdkyysfn yegiarnlsc

481 repnqhfkpy lkhflpkrlh faksdriepl tfyldpqwql alnpserkyc gsgfhgsdnv

541 fsnmqalfvg ygpgfkhgie adtfenievy nlmcdllnlt papnngthgs lnhllknpvy

601 tpkhpkevhp lvqcpftrnp rdnlgcscnp silpiedfqt qfnltvaeek iikhetlpyg

661 rprvlqkent icllsqhqfm sgysqdilmp lwtsytvdrn dsfstedfsn clyqdfripl

721 spvhkcsfyk nntkvsygfl sppqlnknss giysealltt nivpmyqsfq viwryfhdtl

781 lrkyaeerng vnvvsgpvfd fdydgrcdsl enlrqkrrvi rnqeilipth ffivltsckd

841 tsqtplhcen ldtlafilph rtdnsescvh gkhdsswvee llmlhrarit dvehitglsf

901 yqqrkepvsd ilklkthlpt fsqed

Amino acids 103-925 are bolded above; in some embodiments, the srENPP1 sequence comprises amino acids 103-925, and preferably amino acids 96-925 or 97-925 of SEQ ID NO:1.

The constructs (examples of which are shown in FIGS. 1A-B, 2, and 3) preferably comprise (from 5' to 3') a promoter, an optional spacer sequence (e.g., comprising one or more restriction cut sites to replace promoter or secretory signal-FLAG tag or a sequence, e.g., of about 10-100 or 30-100 nts, from the pcDNA3.1 plasmid providing space between the promoter and Kozak sequence), a kozak sequence, secretion signal sequences for soluble proteins, a transgene sequence comprising ENPP1 sequence (e.g., srENPP1 or rENPP1) and optionally a linker (e.g., between the srENPP1 protein and stabilizing protein) and a stabilizing protein, and a polyadenylation sequence. The construct can also include one or more sequences that promote expression of a transgene, e.g., one or more enhancer sequences, e.g., 5' untranslated region (UTR) or a 3' UTR; and/or insulator sequences (see, e.g., Haberman and McCrown, Methods. 2002 October; 28(2):219-26; Suoranta et al., Front Mol Med. 2022 Nov. 1:2:1054069). The woodchuck hepatitis virus posttranscriptional response element (WPRE) can also be used. An exemplary construct can include a Kozak sequence, a human albumin (hAlb) signal sequence, and a sequence encoding a soluble ENPP1-human albumin fusion protein, with a CBA, CMV, CAG, hAlb, hepcidin, ENPP1, ENPP2, ENPP3, myH11, hMGP, or HDAC9 (e.g., HDAC9_prom2 promoter, optionally HDAC9-P2.1 as described herein), and optionally one or more copies of one or more miRNA target sequences, e.g., mir155×3 (e.g., comprising one or more repeats of CAATTACGATTAGCACTATC (SEQ ID NO:2), e.g., comprising the sequence CAATTACGATTAGCACTATCCAATTACGATTAGCACTATCCAATTACGATTAGC ACTATC (SEQ ID NO:3), or another miRNA, e.g., as described herein. Optionally, the sequence encoding the ENPP1 is codon optimized, but the human albumin is wild type (not codon optimized). Another exemplary construct includes a Kozak sequence and a sequence encoding a full length ENPP1, with a CBA, CMV, CAG, hAlb, hepcidin, ENPP1, ENPP2, ENPP3, MYH11, hMGP, or HDAC9 (e.g., HDAC9_prom2 promoter, optionally HDAC9-P2.1 as described herein) promoter. An exemplary spacer sequence is CTCTGGCTAACTAGAGAACCCACTGCTTACTGGCTTATCGAAATTAATACGACT CACTATAGGGAGACCCAAGCTGGCTAGC (SEQ ID NO:4). See, e.g., FIG. 16.

The constructs used in the methods and compositions described herein can include the examples shown in Table B, optionally omitting the tag sequence. Exemplary sequences for the constructs listed in Table B are provided below. The constructs comprising srENPP1 can also include a bone targeting sequence, e.g., at the N- or C-terminus of the protein product, preferably at the C-terminus.

TABLE B

Exemplary constructs and applications

Soluble ENPP1

| Promoter | Kozak | Sig Seq | Tag* | ENPP1 | Fusion | 3' UTR | Disease Condition |
|---|---|---|---|---|---|---|---|
| CMV | Kozak | hAlb-ss | FLAG | opt-srENPP1 | hAlb | | GACI, calciphylaxis, PXE |
| CAG | Kozak | hAlb-ss | FLAG | opt-srENPP1 | hAlb | | GACI, calciphylaxis, PXE, CKD, diabetic calcification, atherocalcific disease, aortic valve calcification |
| hAlb | Kozak | hAlb-ss | FLAG | opt-srENPP1 | hAlb | | GACI, calciphylaxis, PXE, CKD, diabetic calcification, atherocalcific disease, aortic valve calcification |
| HDAC9_prom2 | Kozak | hAlb-ss | FLAG | opt-srENPP1 | hAlb | | calciphylaxis, CKD, diabetic calcification, atherocalcific disease |
| CMV | Kozak | hAlb-ss | FLAG | opt-srENPP1 | hAlb | mir155x3 | GACI, calciphylaxis, PXE |
| hMGP | Kozak | hAlb-ss | FLAG | opt-srENPP1 | hAlb | | GACI, calciphylaxis, PXE, CKD, diabetic calcification, atherocalcific disease, aortic valve calcification |
| hMGP | Kozak | hMGP-ss | FLAG | opt-srENPP1 | hAlb | | GACI, calciphylaxis, PXE, CKD, diabetic calcification, atherocalcific disease, aortic valve calcification |
| CAG | Kozak | hAlb-ss | FLAG | opt-srENPP1 | hAlb | mir155x3 | GACI, calciphylaxis, PXE, CKD, diabetic calcification, atherocalcific disease, aortic valve calcification |
| CMV | Kozak | hAlb-ss | FLAG | opt-srENPP1 | hAlb | mir122x3 | GACI, calciphylaxis, PXE |
| CAG | Kozak | hAlb-ss | FLAG | opt-srENPP1 | hAlb | mir122x3 | GACI, calciphylaxis, PXE, CKD, diabetic calcification, atherocalcific disease, aortic valve calcification |

Transmembrane ENPP1:

| Promoter | Kozak | ENPP1 | Tag* | 3' UTR | Disease Condition |
|---|---|---|---|---|---|
| CMV | Kozak | rENPP1 | FLAG | | GACI, calciphylaxis, PXE |
| CAG | Kozak | rENPP1 | FLAG | | GACI, calciphylaxis, PXE, CKD, diabetic calcification, atherocalcific disease, aortic valve calcification |
| CMV | Kozak | rENPP1 | FLAG | mir155x3 | GACI, calciphylaxis, PXE, CKD, diabetic calcification, atherocalcific disease, aortic valve calcification |

TABLE B-continued

| Exemplary constructs and applications | | | | | |
|---|---|---|---|---|---|
| CAG | Kozak | rENPP1 | FLAG | mir155x3 | GACI, calciphylaxis, PXE, CKD, diabetic calcification, atherocalcific disease, aortic valve calcification |
| CMV | Kozak | rENPP1 | FLAG | mir122x3 | GACI, calciphylaxis, PXE |
| CAG | Kozak | rENPP1 | FLAG | mir122x3 | GACI, calciphylaxis, PXE, CKD, diabetic calcification, atherocalcific disease, aortic valve calcification |
| HDAC9_prom2 | Kozak | rENPP1 | FLAG | | calciphylaxis, CKD, diabetic calcification, atherocalcific disease |
| HDAC9_prom2 | Kozak | rENPP1 | FLAG | miR-155 | GACI, calciphylaxis, CKD, diabetic calcification, atherocalcific disease |
| Myh11 | Kozak | rENPP1 | FLAG | | GACI, calciphylaxis, PXE, CKD, diabetic calcification, atherocalcific disease |
| Myh11 | Kozak | rENPP1 | FLAG | miR-122 | GACI, calciphylaxis, PXE, CKD, diabetic calcification, atherocalcific disease |
| hMGP | Kozak | rENPP1 | FLAG | | GACI, calciphylaxis, PXE, CKD, diabetic calcification, atherocalcific disease, aortic valve calcification |

*optionally omitted in final constructs

In some embodiments, the constructs comprise a sequence provided herein, or are at least 80%, 85%, 90%, 95%, 97%, 98%, or 99% identical to a construct sequence set forth herein, optionally omitting any FLAG or other tag sequences, or any plasmid sequences, included in the sequences herein.

Promoters

The constructs can include a promoter that drives expression of the ENPP1 sequence. As shown herein, the CMV promoter was able to drive expression of srENPP1 and rENPP1 proteins that showed catalytic activity in an assay.

In some embodiments, the promoter is a vascular endothelial cell-specific promoter, e.g., VE-cadherin promoter, fins-like tyrosine kinase-1 (FLT-1), intercellular adhesion molecule-2 (JCAM-2), a Claudin 5 (CLDN-5), a von Willebrand factor (vWF) promoter, a TIE2 promoter, or a synthetic EC-specific promoter (see, e.g., Dai et al., J Virol. 2004 June; 78(12): 6209-6221) or SMC-specific promoter as described herein, e.g., HDAC9 or SM22 or MYH11 or MGP, or promoters from albumin or hepcidin, ENPP1, ENPP2, and ENPP3. In some embodiments, the promoter is a pan-cell type promoter, e.g., a "ubiquitous" promoter that drives expression in most cell types, e.g., cytomegalovirus (CMV) promoter (optionally with the CMV enhancer), chicken beta-actin (CBA) promoter, Rous sarcoma virus (RSV) LTR promoter (optionally with the RSV enhancer), SV40 promoter, dihydrofolate reductase promoter, phosphoglycerol kinase promoter, phosphoglycerol kinase (PGK) promoter, EF1alpha promoter, Ubiquitin C (UBC), B-glucuronidase (GUSB), and CMV immediate/early gene enhancer/CBA promoter (CAG); or a steroid promoter or metallothionein promoter. Other promoters may be used, including smooth-muscle specific promoters from HDAC9 or SM22 or MYH11 or MGP, or promoters from albumin or hepcidin, ENPP1, ENPP2, and ENPP3. Exemplary sequences for these promoters are provided herein.

Linkers

The constructs can also include linkers between the ENPP1 proteins and stabilizing proteins, which can include any sequence that does not interfere with the function of the ENPP1 proteins. In preferred embodiments, the linkers are short, e.g., 2-40 amino acids, and are typically flexible (i.e., comprising amino acids with a high degree of freedom such as glycine, alanine, and serine). In some embodiments, the linker comprises one or more units consisting of GGGS (SEQ ID NO:5) or GGGGS (SEQ ID NO:6), e.g., two, three, four, or more repeats of the GGGS (SEQ ID NO:5) or GGGGS (SEQ ID NO:6) unit. In some embodiments, the linker comprises an XTEN linker (e.g., a 32 amino acid modified XTEN linker (flanked with extended GlySer linkers on both sides)). Other linker sequences can also be used.

Kozak Sequence

The constructs typically include a Kozak sequence at the 5' end of the construct; a consensus Kozak sequence is generally considered as GCCGCCACCATGG (SEQ ID NO:7), where ATG is the start codon.

Secretory Signal Sequence

A number of secretory signal peptide sequences are known in the art, including human signal sequences, examples of which are shown in Table A (Table adapted from novoprolabs.com/support/articles/commonly-used-leader-peptide-sequences-forefficient-secretion-of-a-recombinant-protein-expressed-in-mammalian-cells-201804211337.html).

TABLE A

Exemplary Human Secretory Signal Peptide Sequences

| Human Signal sequence | Sequence | SEQ ID NO: |
|---|---|---|
| Oncostatin M | MGVLLTQRTLLSLVLALLFPSMASM | 8. |
| IgG2 H | MGWSCIILFLVATATGVHS | 9. |
| Secrecon* | MWWRLWWLLLLLLLLWPMVWA | 10. |
| IgK VIII | MDMRVPAQLLGLLLLWLRGARC | 11. |
| CD33 | MPLLLLLPLLWAGALA | 12. |

TABLE A-continued

| Exemplary Human Secretory Signal Peptide Sequences | | |
|---|---|---|
| Human Signal sequence | Sequence | SEQ ID NO: |
| tPA | MDAMKRGLCCVLLLCGAVFVSPS | 13. |
| Chymotrypsinogen | MAFLWLLSCWALLGTTFG | 14. |
| trypsinogen-2 | MNLLLILTFVAAAVA | 15. |
| Interleukin 2 (IL-2) | MYRMQLLSCIALSLALVINS | 16. |
| Albumin (HSA) | MKWVTFISLLFSSAYS | 17. |
| Transthyretin | MASHRLLLLCLAGLVFVSEA | 18. |
| ENPP2 | MARRSSFQSCQIISLFTFAVGVNICLG | 19. |
| insulin | MALWMRLLPLLALLALWGPDPAAA | 20. |
| alpha 1-antitrypsin | MPSSVSWGILLLAGLCCLVPVSLA | 21. |

*Barash et al., Biochem Biophys Res Commun. 2002 Jun. 21;294(4): 835-42.

In some embodiments, another signal sequence that promotes secretion is used, e.g., as described in Table 5 of U.S. Ser. No. 10/993,967, von Heijne, J Mol Biol. 1985 Jul. 5; 184(1):99-105; Kober et al., Biotechnol. Bioeng. 2013; 110: 1164-1173; Tsuchiya et al., Nucleic Acids Research Supplement No. 3 261-262 (2003). In some embodiments, the signal sequence is not an azuricidin signal sequence.

Bone Targeting Peptide Sequences

The present constructs can also include one or more bone targeting sequences, e.g., (SEQ ID NO: 22)
AAGAATTTCCAGAGCAGAAGCCAC;

(SEQ ID NO: 23)
AAGAGAAGAACCCCTGTGCGGGAG;

(SEQ ID NO: 24)
AAGACCTACGCCTCTATGCAGTGG;
or (SEQ ID NO: 25)
GATGATGACGACGACGATGACTGC.

See, e.g., Bang et al., Sci Rep. 2020; 10: 10576; Kim et al., Adv Sci (Weinh). 2023 October; 10(28): 2301570. In some embodiments, the bone targeting peptide is not $Asp_{10}$, or does not contain a consecutive stretch of 4 or more acidic amino acids, for example, glutamic acids or aspartic acids.

In some embodiments, the construct does not include an azuricidin peptide.

microRNA Target Sequences microRNA (miRNA)-dependent post-transcriptional suppression of transgene expression can be used to increase specificity of vector-mediated transgene expression. MicroRNAs typically regulate gene expression by binding to sequences in the 3' untranslated region (UTR) of the mRNA. To control exogenous transgene expression, tandem repeats (e.g., 1, 2, 3, 4, or 5, but preferably 3 repeats) of artificial microRNA target sites (also referred to as targets) can be incorporated into the 3' UTR of the ENPP1 transgene expression cassette, leading to subsequent degradation of transgene mRNA in cells expressing the corresponding microRNA, thereby decreasing expression, e.g., as shown in FIG. 16 as well as FIG. 14B and FIG. 15. See, e.g., Geisler and Fechner, World J Exp Med. 2016 May 20; 6(2):37-54. Artificial miR-target for miRs useful in the present constructs can include those that have altered expression in T2D/CKD/CAD (21-3p, 155-5p, 126-5p) or are conserved for binding to the endogenous ENPP1 3'UTR (873-5p, 653-5p, 151-3p). In some embodiments, miRNA 155, miR21, miR122, miR210, miR30b, miR103, and/or miR82 binding sites can be incorporated into the 3' UTR. In some embodiments, the miR target is for miR155, as it is decreased in coronary artery disease (CAD) and chronic kidney disease (CKD) but not in type 2 diabetes (T2D).

| Target Sequences | | | |
|---|---|---|---|
| Micro RNA | Sequence | Target sequence | NCBI ref |
| miR155 | TTAATGCTAATCGTGATAGGGGTT (SEQ ID NO: 26) | AATTACGATTAGCACTATCCCCAA (SEQ ID NO: 27) | NR_ 030784.1 |
| miR-21 | TAGCTTATCAGACTGATGTTGA (SEQ ID NO: 28) | ATCGAATAGTCTGACTACAACT (SEQ ID NO: 29) | NR_ 029493.1 |
| miR-210 | AGCCCCTGCCCACCGCACACTG (SEQ ID NO: 30) | TCGGGGACGGGTGGCGTGTGAC (SEQ ID NO: 31) | NR_ 029623.1 |
| miR-30B | TGTAAACATCCTACACTCAGCT (SEQ ID NO: 32) | ACATTTGTAGGATGTGAGTCGA (SEQ ID NO: 33) | NR_ 029666.1 |

-continued

| Target Sequences | | | |
|---|---|---|---|
| Micro RNA | Sequence | Target sequence | NCBI ref |
| miR-103B1 | TCATAGCCCTGTACAATGCTGCT (SEQ ID NO: 34) | AGTATCGGGACATGTTACGACGA (SEQ ID NO: 35) | NR_031721.1 |
| miR-873-5p | GCAGGAACTTGTGAGTCTCCT (SEQ ID NO: 36) | CGTCCTTGAACACTCAGAGGA (SEQ ID NO: 37) | NR_030618.1 |
| miR-653-5P | GTGTTGAAACAATCTCTACTG (SEQ ID NO: 38) | CACAACTTTGTTAGAGATGAC (SEQ ID NO: 39) | NR_030388.1 |
| miR-151b | TCGAGGAGCTCACAGTCT (SEQ ID NO: 40) | AGCTCCTCGAGTGTCAGA (SEQ ID NO: 41) | NR_039601.1 |
| miR-122 | TGTTTGTGGTAACAGTGTGAGGT (SEQ ID NO: 105) | ACAAACACCATTGTCACACTCCA (SEQ ID NO: 106) | NR_029667.1 |
| miR-126-5p | CATTATTACTTTTGGTACGCG (SEQ ID NO: 42) | GTAATAATGAAAACCATGCGC (SEQ ID NO: 43) | NR_029695.1 |

Stabilizing Protein

The constructs can preferably include a stabilizing protein that is linked to and increases the half-life of the ENPP1 protein. Exemplary stabilizing proteins include human albumin, transthyretin, transferrin, and IgG Fc.

Delivery Methods

The present methods and compositions can include the delivery of the gene therapy constructs described herein, e.g., via viral vectors or nanoparticles.

Viral Vectors

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid. Viral vectors for use in the present methods and compositions include recombinant retroviruses, adenovirus, adeno-associated virus, alphavirus, and lentivirus, comprising the targeting peptides described herein and optionally a transgene for expression in a target tissue.

A preferred viral vector system useful for delivery of nucleic acids in the present methods is the adeno-associated virus (AAV). AAV is a tiny non-enveloped virus having a 25 nm capsid. No disease is known or has been shown to be associated with the wild-type virus. AAV has a single-stranded DNA (ssDNA) genome. AAV has been shown to exhibit long-term episomal transgene expression. Space for exogenous DNA in AAV is generally limited to an amount of nucleic acid that can physically fit inside the particle. For example, AAV types 1-5 can package up to 6 kb DNA, and in some reports AAV5 has been shown to package up to 8.9 kb DNA. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993). There are numerous alternative AAV variants (over 100 have been cloned), and AAV variants have been identified based on desirable characteristics. The present disclosure contemplates uses of peptides that can be incorporated into an AAV capsid-thus providing capsid modified AAVs, e.g., AAVPR for selectively transfecting endothelium, pericytes and SMC after delivery to a subject. Such AAV's can also be used for delivery of a nucleic acid comprising an HDAC9-derived promoter as described herein. In some embodiments, an AAV suitable for use with a nucleic acid or a targeting peptide of the disclosure is AAV1, AAV2, AAV3, AAV4, AAV5, AAV6, AV6.2, AAV7, AAV8, rh.8, AAV9, rh.10, rh.39, rh.43 or CSp3; for CNS use, in some embodiments the AAV is AAV1, AAV2, AAV4, AAV5, AAV6, AAV8, or AAV9.

In some embodiments, the present methods use vessel-specific viral vectors that have been shown to transduce cerebral vasculature in large mammals and humans, including AAV such as AAV2 or 9, as well as capsid-modified AAVs that have improved specificity, transient expression, and/or higher transduction efficiency for SMCs including AAV9-PR, a modified version of AAV9 described herein and in WO2022232327 (which is incorporated by reference herein in its entirety). AAVPR comprises the sequence PRPPSTH (SEQ ID NO:44) in the capsid (i.e., inserted into the VP1 protein in a position corresponding to amino acids 588 and 589, see WO2022232327; alternatively, AAV-MA (comprising the sequence MAEPGAR (SEQ ID NO:45)), AAV-ML (comprising the sequence MLYADNT (SEQ ID NO:46), or AAV-SQ (comprising the sequence SQDPSTL (SEQ ID NO:47) inserted into the VP1 protein in a position corresponding to amino acids 588 and 589. AAVPR has been shown to have highly efficient transduction of endothelium and pericytes. AAVPR transduced the intima of capillaries, perforating arterioles and subarachnoid cerebral arteries (GFP) and vascular smooth muscle cells of cerebral arteries (SMCs). See Ramirez et al., Hum Gene Ther. 2023 August; 34(15-16):682-696. In cases where an AAV vector is used, the gene therapy construct can also include components such as inverted terminal repeats (ITRs) and Rep.cl Nanoparticles In some embodiments, the ENPP1 polynucleotides as disclosed herein for delivery to a target tissue in vivo are encapsulated or associated with in a nanoparticle. Methods for nanoparticle packaging are well known in the art, and are described, for example, in Bose S, et al (Role of Nucleolin in Human Parainfluenza Virus Type 3 Infection of Human Lung Epithelial Cells. J. Virol. 78:8146. 2004); Dong Y et al. Poly(d,l-lactide-co-glycolide)/montmorillonite nanoparticles for oral delivery of anticancer drugs. Biomaterials 26:6068. 2005); Lobenberg R. et al (Improved body distribution of 14C-labelled AZT bound to nanoparticles in rats determined by radioluminography. J Drug Target 5:171.1998); Sakuma S R et al (Mucoadhesion of polystyrene nanoparticles having surface hydrophilic polymeric chains in the gastrointestinal tract. Int J Pharm 177:161. 1999); Virovic L et al. Novel delivery methods for treatment of viral hepatitis: an update. Expert Opin Drug Deliv 2:707.2005); and Zimmermann E et al, Electrolyte- and pH-stabilities of aqueous solid lipid nanoparticle (SLN) dispersions in artificial gastrointestinal media. Eur J Pharm Biopharm 52:203. 2001). In some embodiments, one or more polynucleotides is delivered to a target tissue in vivo in a vesicle, e.g., a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid). In some embodiments, lipid-based nanoparticles (LNP) are used; see, e.g., Robinson et al., Mol Ther. 2018 Aug. 1; 26(8):2034-2046; U.S. Pat. No. 9,956,271B2.

The present methods and compositions can include microvesicles or a preparation thereof that contains one or more therapeutic molecules, e.g., polynucleotides or RNA, as described herein. "Microvesicles", as the term is used herein, refers to membrane-derived microvesicles, which includes a range of extracellular vesicles, including exosomes, microparticles and shed microvesicles secreted by many cell types under both normal physiological and pathological conditions. See, e.g., EP2010663B1. The methods and compositions described herein can be applied to microvesicles of all sizes. In some embodiments, 30 to 200 nm. In some embodiments, 30 to 800 nm. In some embodiments, up to 2 μm. The methods and compositions described herein can also be more broadly applied to all extracellular vesicles, a term which encompasses exosomes, shed microvesicles, oncosomes, ectosomes, and retroviral-like particles. Such a microvesicle or preparation is produced by the herein described methods. As the term is used herein, a microvesicle preparation refers to a population of microvesicles obtained/prepared from the same cellular source. Such a preparation is generated, for example, in vitro, by culturing cells expressing the nucleic acid molecule of the instant invention and isolating microvesicles produced by the cells. Methods of isolating such microvesicles are known in the art (Thery et al., Isolation and characterization of exosomes from cell culture supernatants and biological fluids, in Current Protocols Cell Biology, Chapter 3, 322, (John Wiley, 2006); Palmisano et al., (Mol Cell Proteomics. 2012 August; 11(8):230-43) and Waldenstrom et al., ((2012) PLoS ONE 7(4): e34653)), some examples of which are described herein. Such techniques for isolating microvesicles from cells in culture include, without limitation, sucrose gradient purification/separation and differential centrifugation, and can be adapted for use in a method or composition described herein. See, e.g., EP2010663B1.

In some embodiments, the microvesicles are isolated by gentle centrifugation (e.g., at about 300 g) of the culture medium of the donor cells for a period of time adequate to separate cells from the medium (e.g., about 15 minutes). This leaves the microvesicles in the supernatant, to thereby yield the microvesicle preparation. In some embodiments, the culture medium or the supernatant from the gentle centrifugation, is more strongly centrifuged (e.g., at about 16,000 g) for a period of time adequate to precipitate cellular debris (e.g., about 30 minutes). This leaves the microvesicles in the supernatant, to thereby yield the microvesicle preparation. In some embodiments, the culture medium, the gentle centrifuged preparation, or the strongly centrifuged preparation is subjected to filtration (e.g., through a 0.22 um filter or a 0.8 um filter, whereby the microvesicles pass through the filter. In some embodiments, the filtrate is subjected to a final ultracentrifugation (e.g., at about 110,000 g) for a period of time that will adequately precipitate the microvesicles (e.g. for about 80 minutes). The resulting pellet contains the microvesicles and can be resuspended in a volume of buffer that yields a useful concentration for further use, to thereby yield the microvesicle preparation. In some embodiments, the microvesicle preparation is produced by sucrose density gradient purification. In some embodiments, the microvesicles are further treated with DNAse (e.g., DNAse I) and/or RNAse and/or proteinase to eliminate any contaminating DNA, RNA, or protein, respectively, from the exterior. In some embodiments, the microvesicle preparation contains one or more RNAse inhibitors.

The molecules contained within the microvesicle preparation will comprise the therapeutic molecule. Typically the microvesicles in a preparation will be a heterogeneous population, and each microvesicle will contain a complement of molecule that may or may not differ from that of other microvesicles in the preparation. The content of the therapeutic molecules in a microvesicle preparation can be expressed either quantitatively or qualitatively. One such method is to express the content as the percentage of total molecules within the microvesicle preparation. By way of example, if the therapeutic molecule is an mRNA, the content can be expressed as the percentage of total RNA content, or alternatively as the percentage of total mRNA content, of the microvesicle preparation. Similarly, if the therapeutic molecule is a protein, the content can be expressed as the percentage of total protein within the microvesicles. In some embodiments, therapeutic microvesicles, or a preparation thereof, produced by the method described herein contain a detectable, statistically significantly increased amount of the therapeutic molecule as compared to microvesicles obtained from control cells (cells obtained from the same source which have not undergone scientific manipulation to increase expression of the therapeutic molecule). In some embodiments, the therapeutic molecule is present in an amount that is at least about 10%, 20%, 30% 40%, 50%, 60%, 70% 80% or 90%, more than in microvesicles obtained from control cells. Higher levels of enrichment may also be achieved. In some embodiments, the therapeutic molecule is present in the microvesicle or preparation thereof, at least 2 fold more than control cell microvesicles. Higher fold enrichment may also be obtained (e.g., 3, 4, 5, 6, 7, 8, 9 or 10 fold).

In some embodiments, a relatively high percentage of the microvesicle content is the therapeutic molecule (e.g., achieved through overexpression or specific targeting of the molecule to microvesicles). In some embodiments, the microvesicle content of the therapeutic molecule is at least about 10%, 20%, 30% 40%, 50%, 60%, 70% 80% or 90%, of the total (like) molecule content (e.g., the therapeutic molecule is an mRNA and is about 10% of the total mRNA content of the microvesicle). Higher levels of enrichment may also be achieved. In some embodiments, the therapeutic molecule is present in the microvesicle or preparation thereof, at least 2 fold more than all other such (like) molecules. Higher fold enrichment may also be obtained (e.g., 3, 4, 5, 6, 7, 8, 9 or 10 fold).

Lipid Nanoparticles (LNPs)

The present methods and compositions can include the use of lipid nanoparticles (LNPs) for active delivery of target nucleic acids to smooth muscle cells (SMCs), in particular to vascular smooth muscle cells (vSMCs). Passive targeting of LNPs in the body is believed to be governed primarily by the size and charge of the LNP, which is acquired through changes in the molar compositions of the four types of lipids used in the formulation. In some aspects, the instant disclosure provides for lipid nanoparticles that comprise a permanently cationic lipid, in addition to having cholesterol, helper lipid(s), PEGylated lipid(s), and ionizable amine-containing lipid(s). The present disclosure demonstrates that certain ranges of permanently cationic lipids in formulations provide for particles and formulations with preferred tropism toward SMCs, in particular vSMCs. In some instances, such particles and formulations comprise from 0.1% to 85%, or 50% to 85%, or about 80% (molar percentage) of 1,2-Dioleoyl-3-trimethylammonium propane (often abbreviated DOTAP or 18:1TAP), a di-chain, or gemini, cationic surfactant molecule of formula I.

0.9%, about 0.15% to about 1.2%, about 0.15% to about 1.4%, about 0.15% to about 2%, about 0.3% to about 0.6%, about 0.3% to about 0.9%, about 0.3% to about 1.2%, about 0.3% to about 1.4%, about 0.3% to about 2%, about 0.6% to about 0.9%, about 0.6% to about 1.2%, about 0.6% to about 1.4%, about 0.6% to about 2%, about 0.9% to about 1.2%, about 0.9% to about 1.4%, about 0.9% to about 2%, about 1.2% to about 1.4%, about 1.2% to about 2%, about 0.10% to about 1.5%, about 0.2% to about 1.5%, about 0.3% to about 1.5%, about 0.4% to about 1.5%, about 0.5% to about 1.5%, about 0.6% to about 1.5%, about 0.7% to about 1.5%, about 0.8% to about 1.5%, about 0.9% to about 1.5%, about 1% to about 1.5%, about 1.1% to about 1.5%, about 1.2% to about 1.5%, about 1.3% to about 1.5%, about 1.4% to about 1.5%, 1.5% to about 1.6%, 1.5% to about 1.7%, 1.5% to about 1.8%, 1.5% to about 1.9%, or 1.5% to about 2%) of the total amounts of lipids (% of total lipids) in the particle.

In some embodiments, the LNPs include about 80% (molar percentage) of DOTAP. In some embodiments, the LNPs include about 78.8% of DOTAP. In some embodiments, the LNPs include about 75% to about 85% (e.g.,

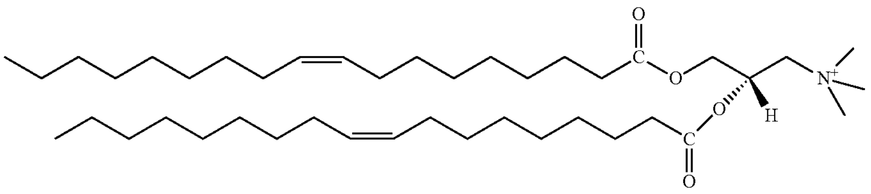 [SMILES: CCCCCCCC/C=C\CCCCCCCC(=O)OC[C@H](C[N+](C)(C)C)OC(=O)CCCCCCC/C=C\CCCCCCCC]

In some aspects, provided herein are lipid nanoparticles comprising certain amounts of DOTAP, an ionizable lipid, a neutral lipid, cholesterol, and one or more PEG-lipids, with demonstrable tropism towards smooth muscle cells. In some instances, the particles comprise an ionizable lipid, a neutral lipid, cholesterol, and one or more PEG-lipids at a molar ratio of about 50/10/38.5/1.5. In some instances, the particles comprise an ionizable lipid, a neutral lipid, cholesterol, and one or more PEG-lipids at a molar ratio of about 10/2.1/7.6/1.5. In many instances, the percentage of the ionizable lipid, the neutral lipid (e.g., phospholipid), the cholesterol, and the one or more PEG-lipids in a particle is selected to accommodate the incorporation of DOTAP into the particle. Specifically, in instances where the amounts of DOTAP in a particle are selected to range from 0.1% to 85% (molar percentage) (e.g., about 10% to about 80%, about 40% to about 85%, about 50% to about 85%, about 75% to about 85%, or about 0.1 to about 10%) of the total amounts of lipids in the particles. The amounts of the other lipids in the particle can be adjusted to conform to the amounts of DOTAP. For example, the amounts of ionizable lipid can be adjusted to range from 5%, 6%, 7%, 8%, 9%, 10%, 11%, 12%, 13%, 14%, 15%, 45%, 46%, 47%, 48%, 49%, 50%, 51%, up to 52% (molar percentage); amounts of a neutral lipid can be adjusted to range from 1%, 2%, 3%, 9%, 10%, 11% (molar percentage), amounts of cholesterol can be adjusted to range from 5%, 6%, 7%, 8%, 9%, 10%, 11%, 30%, 31%, 32%, 33%, 34%, 35%, 36%, 37%, 38%, 39%, up to 40% (molar percentage); and amounts of the one or more PEG-lipids can be adjusted from 0.1%, 1%, 1.5%, up to 2% (molar percentage) (e.g., about 0.1% to about 0.15%, about 0.1% to about 0.3%, about 0.1% to about 0.6%, about 0.1% to about 0.9%, about 0.1% to about 1.2%, about 0.1% to about 1.4%, about 0.1% to about 2%, about 0.15% to about 0.3%, about 0.15% to about 0.6%, about 0.15% to about about 75% to about 78.8%, about 75% to about 79%, about 75% to about 80%, about 75% to about 81%, about 75% to about 82%, about 75% to about 83%, about 75% to about 84%, about 75% to about 85%, about 76% to about 78.8%, about 76% to about 79%, about 76% to about 80%, about 76% to about 81%, about 76% to about 82%, about 76% to about 83%, about 76% to about 84%, about 76% to about 85%, about 77% to about 78.8%, about 77% to about 79%, about 77% to about 80%, about 77% to about 81%, about 77% to about 82%, about 77% to about 83%, about 77% to about 84%, about 77% to about 85%, about 78% to about 78.8%, about 78% to about 79%, about 78% to about 80%, about 78% to about 81%, about 78% to about 82%, about 78% to about 83%, about 78% to about 84%, about 78% to about 85%, about 79% to about 80%, about 79% to about 81%, about 79% to about 82%, about 79% to about 83%, about 79% to about 84%, about 79% to about 85%, about 80% to about 81%, about 80% to about 82%, about 80% to about 83%, about 80% to about 84%, or about 80% to about 85%) of DOTAP. In some embodiments, the LNPs include about 0.1% to about 10% DOTAP.

In some embodiments, the LNPs include about 10% of an ionizable lipid. In some embodiments, the LNPs include about 5% to about 15% (e.g., about 6% to about 10%, about 7% to about 10%, about 8% to about 10%, about 9% to about 10%, about 10% to about 11%, about 10% to about 12%, about 10% to about 13%, about 10% to about 14%, or about 10% to about 15%) of an ionizable lipid.

In some embodiments, the LNPs include about 2.1% of a neutral lipid. In some embodiments, the LNPs include about 2% of a neutral lipid. In some embodiments, the LNPs include about 0.5% to about 3.5% (e.g., about 0.5% to about 2.1%, about 0.6% to about 2.1%, about 0.7% to about 2.1%, about 0.8% to about 2.1%, about 0.9% to about 2.1%, about 1% to about 2.1%, about 1.1% to about 2.1%, about 1.2% to about 2.1%, about 1.3% to about 2.1%, about 1.4% to about 2.1%, about 1.5% to about 2.1%, about 1.6% to about 2.1%, about 1.7% to about 2.1%, about 1.8% to about 2.1%, about 1.9% to about 2.1%, about 2% to about 2.1%, about 2.1% to about 2.2%, about 2.1% to about 2.3%, about 2.1% to about 2.4%, about 2.1% to about 2.5%, about 2.1% to about 2.6%, about 2.1% to about 2.7%, about 2.1% to about 2.8%, about 2.1% to about 2.9%, about 2.1% to about 3.0%, about 2.1% to about 3.1%, about 2.1% to about 3.2%, about 2.1% to about 3.3%, about 2.1% to about 3.4%, or about 2.1% to about 3.5%) of a neutral lipid.

In some embodiments, the LNPs include about 7.6% of cholesterol. In some embodiments, the LNPs include about 7% to about 8% of a neutral lipid. In some embodiments, the LNPs include about 5% to about 10% (e.g., about 5% to about 7.6%, about 6% to about 7.6%, about 7% to about 7.6%, about 7% to about 8%, about 7% to about 9%, about 7% to about 10%, about 7.6% to about 8%, about 7.6% to about 9%, about 7.6% to about 10%) of a neutral lipid.

In some embodiments, the LNPs include one or more PEG-lipids comprising DMG-PEG and DSPE-PEG-maleimide (DSPE-PEG-mal). In some embodiments, the LNPs include about 1.2% DMG-PEG and about 0.3% DSPE-PEG-mal. In some embodiments, the LNPs include about 0.3% to about 1.2% of DMG-PEG and about 0% to about 0.6% DSPE-PEG-mal. In some embodiments, the LNPs include about 0% to about 1.5% (e.g., about 0% to about 0.3%, about 0.3% to about 0.75%, about 0.3% to about 1%, about 0.3% to about 1.05%, about 0.3% to about 1.2%, about 0.3% to about 1.5%) of DMG-PEG. In some embodiments, the LNPs include about 0% to about 1% (e.g., about 0% to about 0.3%, about 0% to about 0.4%, about 0% to about 0.5%, about 0% to about 0.6%, about 0.1% to about 0.3%, about 0.1% to about 0.4%, about 0.1% to about 0.5%, about 0.1% to about 0.6%, about 0.2% to about 0.3%, about 0.2% to about 0.4%, about 0.2% to about 0.5%, about 0.2% to about 0.6%, about 0.3% to about 0.4%, about 0.3% to about 0.5%, about 0.3% to about 0.6%, about 0.3% to about 1%, or about 0.6% to about 1%) of DSPE-PEG-mal.

Specifically, amounts of DOTAP in a particle of the disclosure can be specified in terms of total lipid percentage. Specifically, in instances where the percentage of DOTAP in a particle is selected to range from about 0.1% to about 80% of the total percentage of lipids in the particles, the amounts of the other lipids in the particle can be adjusted based on the remaining lipid percentage as follows: amounts of ionizable lipid can be adjusted to range from 10% up to 52% of the remaining lipid percentage; amounts of a neutral lipid can be adjusted to range from 2% up to 11% of the remaining lipid percentage, amounts of cholesterol can be adjusted to range from 7% up to 40% of the remaining lipid percentage; and amounts of one or more PEG-lipids can be adjusted from 0% up to 2% of the remaining lipid percentage.

For example, when up to 10% DOTAP is added, the remaining 90% of the total lipid amount is distributed accordingly among the remaining lipids. For example, in some embodiments, if the percentage of DOTAP in a particle is 10%, the amounts of the other lipids in the particle can be adjusted based on the remaining 90% as follows: amounts of ionizable lipid can be adjusted to range from 45% up to 52% of the remaining 90%; amounts of a neutral lipid can be adjusted to range from 9% up to 11% of the remaining 90%, amounts of cholesterol can be adjusted to range from 34% up to 40% of the remaining 90%; and amounts of a PEG-lipid can be adjusted from 0.1% up to 2% of the remaining 90% of the total lipids in the composition.

In another example, when up to 80% DOTAP is added, the remaining 20% of the total lipid amount is distributed accordingly among the remaining lipids. For example, in some embodiments, if the percentage of DOTAP in a particle is 80%, the amounts of the other lipids in the particle can be adjusted based on the remaining 10% as follows: amount of ionizable lipid can be adjusted to range from 7% up to 13% of the remaining 10%; amount of a neutral lipid can be adjusted to range from 1% up to 3% of the remaining 10%, amount of cholesterol can be adjusted to range from 6% up to 8% of the remaining 10%; and amounts of the one or more PEG-lipids can be adjusted from 0.1% up to 2% of the remaining 10% of the total lipids in the composition.

In some embodiments, the LNPs provided herein can be spherical or ellipsoidal, or can have an amorphous shape. In some embodiments, the LNPs provided herein (e.g., conjugated or non-conjugated LNPs) can have a diameter (between any two points on the exterior surface of the LNP) of between about 100 nanometers (nm) to about 250 nm (e.g., between about 100 nm to about 150 nm, between about 100 nm to about 200 nm, between about 100 nm to about 250 nm, between about 125 nm to about 150 nm, between about 150 nm to about 175 nm, between about 150 nm to about 200 nm, between about 150 nm to about 250 nm). In some embodiments, LNPs having a diameter of between about 100 nm to about 250 nm localize to the diseased vasculature in a subject. In some embodiments, LNPs having a diameter of between about 100 nm to about 150 nm localize to the smooth muscle cells of a subject.

Lipid Nanoparticles (LNPs)

The LNP compositions can be prepared by various techniques which are presently known in the art. Multilamellar vesicles (MHLVs) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULVs), such as the LNPs of the disclosure, can then be formed by homogenization, sonication, or extrusion of the multi-lamellar vesicles. In addition, unilamellar vesicles can be formed by detergent removal techniques.

In many instances, the particles, formulations, and compositions of the disclosure comprise at least the following five lipid components:

Permanently Cationic Lipids

Structurally, synthetic and/or natural lipids usually contain three parts: (i) cationic or ionizable head groups, (ii) linker groups, and (iii) hydrophobic tails. The chemical diversity of each part results in a number of structurally distinct ionizable lipids that can be produced by combinatorial chemistry. Conventional permanently charged cationic lipids previously used for nucleic acid delivery (e.g., DOTAP) are believed to readily interact with negatively charged serum proteins and aggregate in the bloodstream, which was believed to lead to rapid clearance of LNP by mononuclear phagocytes. Thus, the relatively high hemolytic activity of cationic lipids was believed to increase the risk of toxic side effects, such as hemoglobin release due to red cell membrane damage.

The disclosure demonstrates that the presence of certain ratios or amounts of permanently cationic lipids (e.g., DOTAP) in a particle can preferably target the particle to vascular smooth blood cells (vSMCs), in vitro and in vivo. In some embodiments, the particles of the disclosure include DOTAP. In some embodiments, the particles of the disclosure include DOTAP, 1,2-di-O-octadecenyl-3-trimethylammonium propane (chloride salt) (DOTMA), dimethyldioctadecylammonium (DDAB), 1,2-dimyristoyl-sn-glycero-3-ethylphosphocholine (EPC), or any combination thereof.

Ionizable Cationic Lipids

Ionizable cationic lipids are traditional components in many existing LNP formulation(s). Their acid dissociation constants (pKa) determine the ionization and surface charge of the LNP, further affecting its stability and toxicity. To avoid these problems, ionizable cationic lipids with pKa values typically ranging from 6.0 to 7.0 have been developed and deployed, most notably in vaccine formulations. This ionizable lipid-based LNP (iLNP) ensures efficient encapsulation of nucleic acids under acidic conditions and reduces toxicity during recycling under physiological conditions. After entering endosomes/lysosomes (which have a pH below surface pKa), LNPs can be positively charged again to facilitate endosome escape and release mRNA into the cytoplasm. It has been reported that LNPs with pKa values of 6.2-6.5 and 6.6-6.9 favored hepatic delivery of siRNA in vivo and intramuscular administration of mRNA vaccines, respectively.

Depending on the number of amino heads, ionizable cationic lipids can be classified as either monoamino or polyamino lipids. Non-limiting examples of monoamino acid ionizable cationic lipids contemplated in particles of the disclosure include DLin-MC3-DMA (MC3), SM-102, and ALC-0315. Non-limiting examples of monoamino acid ionizable cationic lipids contemplated in particles of the disclosure include $3060_{i10}$, cKK-E12, C12-200, 5A2-SC8, TT3, and FTT5. In many instances, the ionizable lipid is selected from the group consisting of DLin-MC2-DMA, DLin-MC3-DMA, DSDMA, DODMA, DLinDMA, DLenDMA, γ-DLenDMA, DLin-K-DMA, DLin-C2K-DMA, DLin-K-C3-DM A, DLin-K-C4-DMA, DLen-C2K-DMA, γ-DLen-C2K-DMA, or DLin-MP-DMA.

PEG-Lipids

Although PEG-lipids generally constitute the smallest molar percentage of the lipid components in LNPs (typically about 0.5 mol % and up to about 2.0 mol %), they have several effects on the properties of lipid nanoparticles, including influencing particle size and zeta potential. A variety of PEG lipids are contemplated for use with the LNPs of the disclosure, including terminally modified PEG lipids. The LNPs can include one, two, or more different species of PEG lipids.

PEG lipids for use in the present disclosure can be, for example, maleimide terminally modified PEG lipids that can be conjugated with cell targeting peptides. PEG lipids for use with the instant LNPs can have the general structure $-(CH_2CH_2O)n$- or $-(CH_2CH_2O)nCH_2CH_2$. This general structure can further be modified with heterobifunctional maleimide linker. The disclosure contemplates that a variety of PEG molecules can be incorporated into its LNPs, including poly(ethylene glycol) (PEG) maleimide (e.g., PEG-2000 maleimide), polyalkylene glycols, polypropylene or polybutylene glycols, methoxy poly (ethylene glycol), or methoxy poly (ethylene glycol) propionic acid (mPEG-acid) where n can be from about 1 to about 400. An LNP comprising a thiol reactive motive conjugated to a PEG molecule (e.g., heterobifunctional maleimide PEG) can be decorated with various types of peptides that are displayed on the surface of the LNP molecule.

In some instances, a PEG molecule is linked to a thiol reactive group for further conjugation to a peptide. In some instances the PEG molecule is a maleimide conjugated PEG molecule. Reactive PEGs can be used for amine pegylation, thiol pegylation, or N-terminal pegylation. The amine in the N-terminus and/or the carboxyl group in the C-terminus can react with a targeting peptide.

In some instances, the PEG-lipid that is suitable for use in the particles of the disclosure is 1,2-dimyristoyl-rac-glycero-3-methoxypolyethylene glycol (DMG-PEG) and/or DSPE-PEG (1,2-distearoyl-sn-glycero-3-phosphoethanolamine-N-[maleimide(polyethylene glycol). In some embodiments, the PEG-lipid that is suitable for use in the particles of the disclosure is DMG-PEG 2000 and/or DSPE-PEG 2000 (1,2-distearoyl-sn-glycero-3-phosphoethanolamine-N-[maleimide(polyethylene glycol)-2000]. In some instances, the PEG molecule is methoxy poly (ethylene glycol) succinimidyl proprionate (mPEG-SPA). In some instances, a PEG molecule is a methoxy poly (ethylene glycol) propionic acid (mPEG-acid). In some cases, the polyethylene glycol molecule weighs from about 1,000 kilodaltons to about 5,000 kilodaltons. The covalent attachment of a targeting peptide to an LNP via a thiol reactive linkage can change the physicochemical characteristics of the LNP. Examples of physicochemical characteristics that can be altered by binding to a PEG include its zeta potential, its PDI, and the overall hydrodynamic size of the LNP.

Non-limiting examples of commercially available PEGs suitable for use in the particles of the disclosure include, but are not limited to those available from Nektar Therapeutics, San Carlos, CA, such as $mPEG-NH_2$ (Mw about 10 kDa, about 20 kDa), methoxy PEG Succinimidyl α-Methylbutanoate (SMB), SMB-PEG-SMB, methoxy PEG Succinimidyl Propionate (mPEG-SPA), Branched PEG N-Hydroxysuccinimide (mPEG2-NHS), mPEG-CM-HBA-NHS, NHS-HBA-CM-PEG-CM-HBA-NHS, mPEG-ButyrALD, ButyrALD-PEG-ButyrALD, Branched PEG ButyrALD (mPEG2-ButyrALD), Ortho-pyridylthioester (mPEG-OPTE), mPEG Maleimide (MAL), MAL-PEG-MAL, Branched PEG Maleimide (mPEG2-MAL), Forked Maleimide (mPEG-MAL2 and mPEG2-MAL2), mPEG-Ortho-pyridyldisulfide (mPEG-OPSS), OPSS-PEG-OPSS, mPEG-SH, SH-PEG-SH, Amine-PEG-Acid, Boc-PEG-NHS, Fmoc-PEG-NHS, MAL-PEG-NHS, Vinylsulfone-PEG-NHS, Acrylate-PEG-NHS Ester. In some embodiments, the LNPs comprise DMG-PEG and/or DSPE-PEG-maleimide.

Non-limiting examples of PEGs that can be used in amine pegylation include, for example, PEGs manufactured by Jenken Technology USA such as: Y-shape PEG NHS Esters, Y-shape PEG Carboxyl, Glucose PEG NHS Ester, Galactose PEG NHS Ester, Methoxy PEG Succinimidyl Carboxymethyl Ester, Methoxy PEG Carboxyl, Methoxy PEG Succinimidyl Butanoate, Methoxy PEG Succinimidyl Hexanoate, Methoxy PEG Hexanoic Acid, Methoxy PEG Succinimidyl Succinamide, Methoxy PEG Succinimidyl Glutaramide, Methoxy PEG Succinimidyl Carbonate, Methoxy PEG Nitrophenyl Carbonate, Methoxy PEG Succinimidyl Succinate, Methoxy PEG Succinimidyl Glutarate. Non-limiting examples of PEGs that can be used in thiol pegylation include Y-shape PEG Maleimide, Methoxy PEG Maleimide, Methoxy PEG Vinylsulfone, Methoxy PEG Thiol. Non-limiting examples of PEGs that can be used in N-terminal pegylation include, for example, PEGs manufactured by Jenken Technology USA such as: Y-shape PEG Aldehyde, Y-shape PEG Acetaldehyde, Y-shape PEG Propionaldehyde, Methoxy PEG Propionaldehyde.

In many instances, a targeting peptide can have a molecular weight that is small compared to the PEG molecule to which it is attached. The molecular weight of a PEG molecule used in an LNP of the disclosure can be, for example, no greater than 5 kilodaltons (kDa), no greater than 4.5 kilodaltons, no greater than 4 kilodaltons, no greater 3.5 than kilodaltons (kDa), no greater than 3 kilodaltons (kDa), no greater than 2.5 kilodaltons (kDa), no greater than 2 kilodaltons (kDa), no greater than 1.5 kilodaltons (kDa), or no greater than 1 kilodaltons (kDa).

In some cases, the molecular weight of a PEG molecule can be greater than 1 kilodalton (kDa), greater than 1.5 kilodaltons (kDa), greater than 2 kilodaltons (kDa), greater than 2.5 kilodaltons (kDa), greater than 3 kilodaltons (kDa), greater than 3.5 kilodaltons (kDa), greater than 4 kilodaltons (kDa), or greater than 4.5 kilodaltons (kDa).

In some cases the molecular weight of a PEG oligomer can be from about 1 kilodalton (kDa) to about 5 kilodaltons (kDa), from about 1 kilodalton (kDa) to about 2 kilodaltons (kDa), from about 1 kilodaltons (kDa) to about 3 kilodaltons (kDa), from about 1 kilodaltons (kDa) to about 4 kilodaltons (kDa), from about 1 kilodaltons (kDa) to about 5 kilodaltons (kDa), from about 1.5 kilodaltons (kDa) to about 2 kilodaltons (kDa), from about 1.5 kilodaltons (kDa) to about 3 kilodaltons (kDa), from about 1.5 kilodaltons (kDa) to about 3.5 kilodaltons (kDa), from about 1.5 kilodaltons (kDa) to about 4 kilodaltons (kDa), from about 1.5 kilodaltons (kDa) to about 4.5 kilodaltons (kDa), from about 1.5 kilodaltons (kDa) to about 5 kilodaltons (kDa), from about 2 kilodaltons (kDa) to about 3 kilodaltons (kDa), from about 2 kilodaltons (kDa) to about 3.5 kilodaltons (kDa), from about 2 kilodaltons (kDa) to about 4 kilodaltons (kDa), from about 2 kilodaltons (kDa) to about 4.5 kilodaltons (kDa), from about 2 kilodaltons (kDa) to about 5 kilodaltons (kDa).

In some embodiments, the molecular weight of a maleimide-terminally modified PEG lipid is about 2 kilodaltons (kDa). In some embodiments, the molecular weight of a PEG molecule is from about 1 kilodaltons (kDa) to about 5 kilodaltons (kDa).

Neutral-Lipids Helper Lipids—Phospholipids

Phospholipids are neutral "helper" lipids that contribute to the formation of lipid nanoparticles and the escape of endosomes. In many instances, a particle of the disclosure comprises a neutral lipid that is a phosphatidylcholine lipid or a phosphatidylethanolamine lipid. The phosphatidylcholine lipid or the phosphatidylethanolamine lipid can be selected from the group comprising 1,2-dioleoyl-sn-glycero-3-phosphoethanolamine (DOPE), 1,2-dioleoyl-sn-glycero-3-phosphocholine (DOPC), 1,2-distearoyl-sn-glycero-3-phosphocholine (DSPC), 1,2-dipalmitoyl-sn-glycero-3-phosphocholine (DPPC), 1-palmitoyl-2-oleoyl-glycero-3-phosphocholine (POPC), and 1-stearoyl-2-oleoyl-sn-glycero-3-phosphocholine (SOPC).

Cholesterol

The inclusion of cholesterol in nucleic acid-containing LNP formulations is based primarily on two major findings obtained with liposomal formulations of small molecule therapeutics: 1) cholesterol is an exchangeable molecule that can accumulate within liposomes during circulation, 2) cholesterol dramatically reduces the amount of surface-bound proteins and improves the circulating half-life.

Particles Comprising Cell Targeting Peptides

In some aspects, the disclosure provides "decorated" with peptides on their exterior surface. In order to enhance the targeting of the nanoparticles to specific tissue or cells, the disclosure further conjugated the aforementioned particles with peptides that can target tissue or cell surface receptors. In some embodiments, the LNPs described herein can contain at least one type (e.g., two, three, or four) of targeting peptides covalently-linked to the LNP. Targeting peptides often contain an amino acid sequence that is recognized by a molecule present on the surface of a cell (e.g., a cell type present in a target tissue). For example, a targeting peptide comprising a collagen IV-targeting peptide specifically binds to collagen IV receptors in the extracellular matrix of diseased vasculature. Additional non-limiting targeting peptides that can be covalently-linked to any of the therapeutic nanoparticles described herein include: an interleukin 6 receptor (IL-6R)-targeting peptide, a CD63-targeting peptide, a contiguous sequence of amino acids (e.g., at least 10, 15, or 20) present within a contiguous sequence of CD63, a galectin-3 (GAL-3)-targeting peptide, amino acids (e.g., at least 10, 15, or 20) present within Col-4 KLWVLPK-GGG-C(SEQ ID NO:48), TL6-R C-GGG-LSLITRL (SEQ ID NO:49), CD63 CRHSQMTVTSRL-GGG (SEQ ID NO:50), and/or Gal-3 C-GGG-ANTPCGPYTHDCPVKR (SEQ ID NO:51). Additional examples of targeting peptides are known in the art.

In some embodiments, the targeting peptide is covalently conjugated to the LNP by using a maleimide-terminally modified PEG lipid. Such conjugation includes the reaction of maleimides with thiol groups of the peptides to form thioether bonds. In some embodiments, peptide conjugation can be done in different densities controlled by the percentage of the maleimide-terminally modified PEG lipid in the LNP formulation (see, e.g., Example 4). In some embodiments, the amount of maleimide-terminally modified PEG lipid in the LNP formulation ranges from about 0.15% to about 1.2%. In some embodiments, the number of targeting peptide molecules that can decorate an outer surface of the particles of the disclosure ranges from about 192 targeting peptides per LNP to about 1270 targeting peptides per LNP (e.g., from about 192 to about 420 targeting peptides per LNP, from about 192 to about 609 targeting peptides per LNP, from about 192 to about 901 targeting peptides per LNP, from about 192 to about 1270 targeting peptides per LNP, from about 420 to about 609 targeting peptides per LNP, from about 420 to about 901 targeting peptides per LNP, from about 420 to about 1270 targeting peptides per LNP, from about 609 to about 901 targeting peptides per LNP, from about 609 to about 1270 targeting peptides per LNP, from about 901 to about 1270 targeting peptides per LNP).

In some embodiments, the targeting peptide can be covalently linked to the LNP at its N-terminus or at its C-terminus. In some embodiments, the targeting peptide can be covalently linked to the LNP through an amino acid side chain. Targeting peptides can be covalently-linked to any of the LNPs described herein through a chemical moiety containing a disulfide bond, an amide bond, or a thioether bond. Additional chemical moieties that can be used to covalently link a targeting peptide to a therapeutic nanoparticle are known in the art.

A variety of different methods can be used to covalently link a targeting peptide to a therapeutic nanoparticle. In some embodiments, the LNPs can be activated for attachment with a targeting peptide, for example in non-limiting embodiments, the LNPs can be epoxy-activated, carboxyl-activated, iodoacetyl-activated, aldehyde-terminated, amine-terminated, or thiol-activated. Additional methods for covalently linking a targeting peptide to a therapeutic nanoparticle are known in the art.

Preferably, the particles are conjugated with peptides (e.g., collagen IV peptides) that target receptors highly expressed in diseased vasculature extracellular matrix (collagen IV) in order to increase the accumulation and the retention of the nanoparticles in diseased tissues. For example, the particles can be conjugated with peptides that target receptors highly expressed on the surface of vascular SMCs (e.g., IL-6R, CD63, and/or GAL-3), thereby increasing the uptake into these cells. In some aspects, the disclosure further comprises particles comprising encapsulating a nucleic acid therapeutic cargo encoding a gene (e.g., ENPP1) for rescuing gene expression in a smooth muscle cell. The disclosure demonstrates that a combination of any of these three approaches can potentially increase accumulation and retention at the SMC target site and cell specificity.

In some aspects, the disclosure comprises a particle comprising: a) a molecule of formula I about 34% to about 40%. In some embodiments, the amount of the one or more PEG-lipids range from about 0.1% to about 2%.

In some aspects, the linker molecule is a molecule that is used to covalently link the peptide to the LNP. In some embodiments, the linker molecule is a maleimide group at a PEG lipid in the particle as discussed supra. The peptide can be a collagen IV (Col-IV) peptide, an TL-6R peptide, a CD63, a GAL-3, and/or a functional fragment thereof sufficient for increasing an accumulation and the retention of the nanoparticles in target tissues. The neutral lipid can be a phosphatidylcholine lipid or a phosphatidylethanolamine

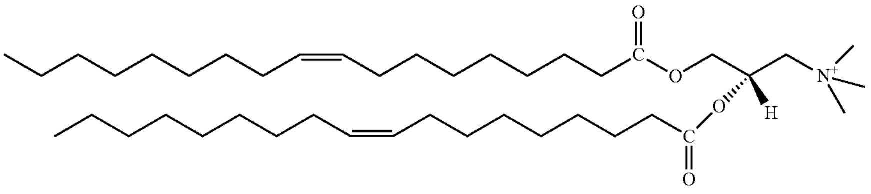 [SMILES: CCCCCCCC/C=C\CCCCCCCC(=O)OC[C@H](C[N+](C)(C)C)OC(=O)CCCCCCC/C=C\CCCCCCCC]

(DOTAP) (e.g., from 0.1% to 85% DOTAP); and a peptide conjugated to a linker molecule in the particle, wherein the peptide has an affinity for a vasculature extracellular matrix molecule. The particles can also comprise: a) from 0.1% to 85% of a molecule of formula I lipid, such as the ones selected from the group consisting of DOPE, DOPC, DSPC, DPPC, POPC, and SOPC. The ionizable lipid can be selected from the group consisting of DLin-MC2-DMA, DLin-MC3-DMA, DSDMA, DODMA, DLinDMA, DLenDMA, γ-DLenDMA, DLin-K-DMA,

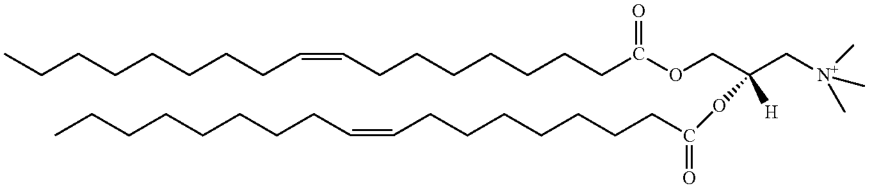

(DOTAP); and a nucleic acid therapeutic cargo encoding a gene for rescuing gene expression in a smooth muscle cell. In many instances, the composition also comprises an amount of an ionizable lipid; an amount of neutral lipid; an amount of cholesterol; and an amount of a PEG-lipid. In many instances, the concentration of DOTAP ranges from 0.1% to 85%, and the molar ratios of the ionizable lipid, the neutral lipid, the cholesterol, and the PEG-lipid are adjusted to a molar ratio of approximately 50/10/38.5/1.5. In some instances, the particles comprise an ionizable lipid, a neutral lipid, cholesterol, and one or more PEG-lipids at a molar ratio of about 10/2.1/7.6/1.5. In some embodiments, the amount of the ionizable lipid ranges from about 45% to about 52% or about 5% to about 15%. In some embodiments, the amount of the neutral lipid ranges from about 1% to about 3% or 9% to about 11%. In some embodiments, the amount of cholesterol ranges from about 5% to about 9% or DLin-C2K-DMA, DLin-K-C3-DM A, DLin-K-C4-DMA, DLen-C2K-DMA, γ-DLen-C2K-DMA, or DLin-MP-DMA.

Such particles can encapsulate any one of the aforementioned nucleic acid therapeutic cargo(s). In some embodiments, the therapeutic cargo is an mRNA molecule encoding a gene for rescuing gene expression in the smooth muscle cell. In some embodiments, the therapeutic cargo is a plasmid encoding a gene for rescuing gene expression in the smooth muscle cell. In some embodiments, the therapeutic cargo is a nucleic acid molecule encoding an ENPP1 therapeutic cargo. In some embodiments, the ENPP1 therapeutic cargo encodes a transmembrane ENPP1 molecule. In some embodiments, the ENPP1 therapeutic cargo encodes a soluble ENPP1 molecule. In some embodiments, the transmembrane ENPP1 molecule is or comprises a sequence at least 80% identical to SEQ ID NO: 1.

Further, provided are therapeutic formulations comprising: from 75% to 85% of a molecule of formula I

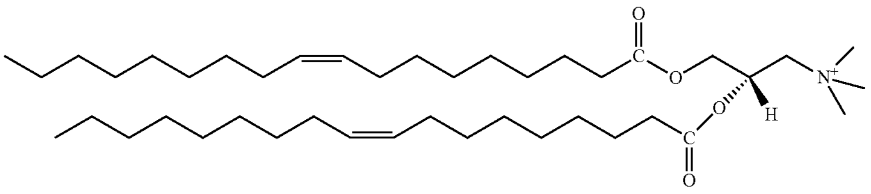 [SMILES: CCCCCCCC/C=C\CCCCCCCC(=O)OC[C@H](C[N+](C)(C)C)OC(=O)CCCCCCC/C=C\CCCCCCCC]

(DOTAP); an amount of an ionizable lipid; an amount of neutral lipid; an amount of cholesterol; an amount of a PEG-lipid; comprising amounts of the ionizable lipid, the neutral lipid, the cholesterol, and the PEG-lipid at a molar ratio of 50/10/38.5/1.5 or at a molar ratio of about 10/2.1/7.6/1.5; and a nucleic acid construct encoding an ectonucleotide pyrophosphatase/phosphodiesterase 1 (ENPP1) therapeutic cargo as described herein. The ENPP1 therapeutic cargo can be a transmembrane ENPP1 molecule or a soluble ENPP1 molecule. In some instances, the disclosure provides a therapeutic formulation comprising: about 10% of DOTAP; about 6% of an MC3 ionizable lipid; about 9.8% of a DOPE neutral lipid; about 35.3% of cholesterol; about 1.4% of one or more PEG-lipids; and a nucleic acid construct encoding an ectonucleotide pyrophosphatase/phosphodiesterase 1 (ENPP1) therapeutic cargo. In some instances, the disclosure provides a therapeutic formulation comprising: about 80% of DOTAP; about 10% of an MC3 ionizable lipid; about 2.1% of a DOPE neutral lipid; about 7.6% of cholesterol; about 1.5% of one or more PEG-lipids; and a nucleic acid construct encoding an ectonucleotide pyrophosphatase/phosphodiesterase 1 (ENPP1) therapeutic cargo. Exemplary formulations can comprise: about 75-85% of DOTAP; about 10% of an MC3 ionizable lipid; about 2-2.5% of a DOPE neutral lipid; about 7-8% of cholesterol; and about 1-2% of one or more PEG-lipids. For example, a preferred formulation can comprise about 78.8% of DOTAP; about 10% of an MC3 ionizable lipid; about 2.1% of a DOPE neutral lipid; about 7.6% of cholesterol; and about 1.5% of one or more PEG-lipids.

In some aspects, the disclosure comprises a therapeutic formulation comprising: a) from 75% to 85% of a molecule of formula I

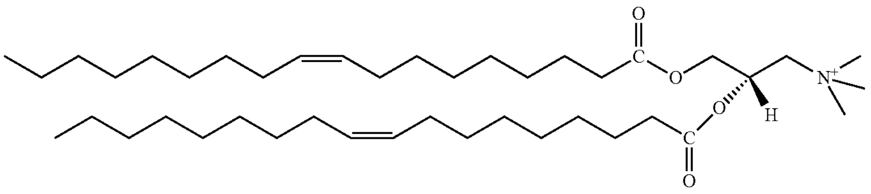 [SMILES: CCCCCCCC/C=C\CCCCCCCC(=O)OC[C@H](C[N+](C)(C)C)OC(=O)CCCCCCC/C=C\CCCCCCCC]

(DOTAP); and an amount of an ionizable lipid; an amount of neutral lipid; an amount of cholesterol; an amount of a PEG-lipid; comprising amounts of the ionizable lipid, the neutral lipid, the cholesterol, and the PEG-lipid at a molar ratio of 10/2.1/7.6/1.5; and a nucleic acid construct encoding a smooth muscle alpha (α)-2 actin (ACTA2) therapeutic cargo.

Exemplary formulations can comprise: about 75-85% of DOTAP; about 10% of an MC3 ionizable lipid; about 2-2.5% of a DOPE neutral lipid; about 7-8% of cholesterol; and about 1-2% of one or more PEG-lipids. For example, a preferred formulation can comprise about 78.8% of DOTAP; about 10% of an MC3 ionizable lipid; about 2.1% of a DOPE neutral lipid; about 7.6% of cholesterol; and about 1.5% of one or more PEG-lipids.

Methods of Treatment

Provided herein are methods of treating a subject who has a condition associated with vascular calcification. Diseases that can be treated using the methods and compositions described herein include GACI, pseudoxanthoma elasticum (PXE), calciphylaxis, in-stent restenosis (which is due to proliferation of SMCs), graft stenosis (e.g., coronary artery bypass graft stenosis), and cardiovascular disease including diabetic vascular calcification, ESRD-associated vascular disease, calcific aortic valve disease (CAVD), coronary atherosclerosis, peripheral vascular disease, and cerebral atherosclerosis. In general, the methods include administering a therapeutically effective amount of an ENPP1 gene construct, e.g., using a viral vector such as an adeno-associated virus (AAV) or a lipid nanoparticle (LNP) carrying the ENPP1 gene construct, optionally including a CBA, CMV, CAG, or other promoter. The ENPP1 gene constructs are preferably administered intravenously, but can also be administered by other routes such as subcutaneous injection. Exemplary constructs are described herein and include those in Table B, optionally with additional components such as bone targeting peptide sequences.

In clinical settings, viral- or LNP-based ENPP1 gene therapy constructs can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

A pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

An "effective amount" is an amount sufficient to effect beneficial or desired results. For example, a therapeutic amount is one that achieves a desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic constructs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Constructs that exhibit high therapeutic indices are preferred. While constructs that exhibit toxic side effects may be used, care should be taken to design a delivery system that targets such constructs to the site of affected tissue in order to minimize potential damage to unaffected cells and, thereby, reduce side effects.

Data obtained from cell culture assays and animal studies can be used in formulating a range of dosage for use in humans. The dosage of such constructs lies preferably within a range of circulating concentrations that include the ED50 with little or no toxicity. The dosage may vary within this range depending upon the dosage form employed and the route of administration utilized. For any construct used in a method described herein, a therapeutically effective dose can be estimated initially from animal models or based on other constructs. Such information can be used to more accurately determine useful doses in humans.

Conditions Treatable Using the Present Methods and Compositions Include the Following:

Generalized arterial calcification of infancy (GACI): GACI is characterized by widespread arterial calcification and/or stenoses of large and medium-sized vessels resulting in a range of clinical manifestations including myocardial infarction, respiratory distress, hypertension, cardiomegaly, and stroke. GACI is estimated to affect one in 200,000 pregnancies. Mortality is particularly high in early infancy; approximately 55% of patients die within the first 6 months of life despite intensive care and supportive measures. After 6 months of life, the mortality rate is markedly reduced and patients tend to survive, though many still have sequalae from their initial hypoxic insults, and a majority eventually develop hearing loss and hypophosphatemic rickets. GACI typically results from biallelic loss-of-function mutations in ENPP1, which encodes an ectonucleotide pyrophosphatase/phosphodiesterase that converts ATP into AMP and pyrophosphate (PPi), a potent inhibitor of calcification. Loss of ENPP1 activity results in decreased quantity of PPi both locally and systemically, and GACI patients have low plasma and urinary PPi concentrations. A treatment as described herein can result in reduced arterial calcification and/or stenoses of large and medium-sized vessels, and increased plasma and/or urinary PPi concentrations (approaching, near, or within normal; normal plasma PPi is about 2.4-4.4 uM in humans, see Bernhard et al., J Clin Endocrinol Metab. 2022 January; 107(1): 109-118).

Pseudoxanthoma elasticum (PXE): PXE is caused by defects in the presumptive ATP-dependent exporter ABCC6, disrupts extracellular ATP metabolism resulting in calcification of elastic fibers in the skin, eyes, and arterial wall. Furthermore, mutations in ENPP1 have been described in patients with PXE. Null mice (Abcc6−/−) recapitulate the genetic, histopathologic and ultrastructural features of PXE, and they demonstrate early and progressive mineralization of vibrissae dermal sheath, which serves as a biomarker of the overall mineralization process. A treatment as described herein can result in reduced calcification of elastic fibers in the skin, eyes, and arterial wall, and/or reduced mineralization of vibrissae dermal sheath.

Calciphylaxis: Calciphylaxis is a rare, life-threatening disease of rapidly progressive vascular calcification characterized by microvascular occlusion in the dermis and subcutaneous tissue. Patients with calciphylaxis have limited survival of typically less than one year. They also have significant morbidity from cutaneous pain and soft tissue infections, often requiring surgical debridement and amputation. Traditionally observed in patients with end-stage kidney disease (ESKD; e.g., ~1% of hemodialysis patients have calciphylaxis), calciphylaxis is also associated with diabetes, hyperphosphatemia, and warfarin use.[4] However, the molecular mechanisms of calciphylaxis are incompletely understood, which has precluded the development of approved therapies. Recent investigations have demonstrated that the process of small vessel arteriolar calcification in calciphylaxis exhibits similarities to that of large artery calcification. Coronary and aortic calcification are characterized by the phenotypic switch of vascular smooth muscle cells (VSMCs) from contractile to osteogenic cells, which is induced by Runt-related transcription factor 2 (Runx2) and vitamin K-dependent modulation of matrix Gla protein (MGP) and the bone morphogenetic protein (BMP) signaling pathway. Similarly, in calciphylaxis, there is increased expression of osteogenic markers as well as proteins associated with altered remodeling of the extracellular matrix. Vitamin K deficiency-mediated reduction in carboxylated MGP (a known inhibitor of BMP signaling) is associated with increased risk of calciphylaxis in patients on hemodialysis. Patients with calciphylaxis have reduced pyrophosphate levels compared to matched ESKD patients (unpublished data), implicating ENPP1 in the pathogenesis of calciphylaxis. A treatment as described herein can result in reduced vascular calcification.

Cardiovascular disease: Vascular calcification plays an important role in human arterial disease (e.g., in atherosclerosis and diabetes). Cardiovascular disease is the leading cause of morbidity and mortality in the world. In the United States alone, cardiovascular disease accounts for over 780,000 deaths annually. Vascular calcification is a hallmark of atherosclerotic disease and serves as strong predictor and risk factor for cardiovascular events. Two primary types of vascular calcification have been reported in adults: intimal calcification, associated with atherosclerosis, and medial calcification, associated with chronic kidney disease and diabetes. Intimal calcification occurs in the setting of lipid accumulation and macrophage infiltration into the vessel wall. Medial wall calcification localizes to elastin fibers or smooth muscle cells and is not associated with lipid deposition or macrophage infiltration. Intimal calcification of the atherosclerotic vessel wall is thought to contribute to plaque destabilization and predicts increased risk in cardiovascular disease. Calcification of the medial vessel layer also predicts cardiovascular events and is associated with increased wall stress, pulse pressure, and risk of rupture in aortic aneurysms. Vascular calcification is a tightly regulated process and overlap exists in the molecular underpinnings of atherosclerotic intimal calcification and medial calcification. More recently, common variants (single nucleotide polymorphisms, SNPs) in the ENPP1 locus have been associated with coronary artery calcification at a genomewide level of significance (Kavousi et al., Nat Genet. 2023 October; 55(10):1651-1664). These SNPs that are associated with increased risk of coronary calcification are also associated with lower expression of ENPP1. These findings implicate relative ENPP1 deficiency in the development of calcification and cardiovascular disease in the general population. A treatment as described herein can result in reduced vascular calcification, and reduced risk of cardiovascular disease. Subjects at risk can be identified, e.g., by family history, early stage disease, and/or the presence of SNPs associated with coronary artery calcification.

Calcific Aortic Valve Disease (CAVD): CAVD is the most prevalent cardiac valvular disease among elderly individuals and the prevalence of CAVD is increasing with ~5% of all individuals above the age of 75 affected. A 3.5-fold increased annual incidence now compared to 30 years ago has been reported.41 CAVD progresses from mild calcification of the valve leaflets to severe calcification and narrowing of the aortic valve orifice, resulting in an obstruction to forward blood flow from the left ventricle and left ventricular hypertrophy. No medical treatment exists for CAVD and treatments are surgical including surgical aortic valve replacement (SAVR) or transcatheter aortic valve implantation (TAVI). An ex vivo study of aortic valve leaflets demonstrated an important role for endogenous pyrophosphate in the inhibition of valvular calcification. Furthermore, a combined proteomic-metabolomic analysis of CAVD vs control aortic valve tissue identified ENPP1 as a hub protein in the metabolite-protein-pathway network. This evidence points towards ENPP1 as a potential therapeutic in aortic valve calcification. Multiple animal models for CAVD exist that overlap with models of atherosclerosis and vascular calcification. A treatment as described herein can result in reduced aortic valve calcification.

Vascular conditions associated with proliferation of SMCs can also be treated using the methods described herein, including in-stent restenosis and graft stenosis (e.g., coronary artery bypass graft stenosis), both of which are due to proliferation of SMCs.

Pharmaceutical Compositions

Also provided herein are pharmaceutically acceptable compositions that contain a gene therapy construct, e.g., in a viral or non-viral delivery vector, e.g., in an LNP, as described herein, e.g., in a physiologically acceptable carrier. The pharmaceutical compositions can be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile carrier such as a diluent (e.g., sterile water or saline), a fixed oil, polyethylene glycol, glycerin, propylene glycol or other synthetic solvents, antibacterial or antifungal agents such as benzyl alcohol or methyl parabens, chlorobutanol, phenol, ascorbic acid, thimerosal, and the like, antioxidants such as ascorbic acid or sodium bisulfite, chelating agents such as ethylenediaminetetraacetic acid, buffers such as acetates, citrates, or phosphates, and isotonic agents such as sugars (e.g., dextrose), polyalcohols (e.g., mannitol or sorbitol), or salts (e.g., sodium chloride), or any combination thereof. Preparations of the compositions can be formulated and enclosed in ampules, disposable syringes, or multiple dose vials. Where required (as in, for example, injectable formulations), proper fluidity can be maintained by, for example, the use of a coating such as lecithin, or a surfactant. Absorption of the therapeutic nanoparticles can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid.

Any of the compositions described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Dosage, toxicity and therapeutic efficacy of the therapeutic constructs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Constructs that exhibit high therapeutic indices are preferred. While constructs that exhibit toxic side effects may be used, care should be taken to design a delivery system that targets such constructs to the site of affected tissue in order to minimize potential damage to unaffected cells and, thereby, reduce side effects.

Data obtained from cell culture assays and animal studies can be used in formulating a range of dosage for use in humans. The dosage of such constructs lies preferably within a range of circulating concentrations that include the ED50 with little or no toxicity. The dosage may vary within this range depending upon the dosage form employed and the route of administration utilized. For any construct used in a method described herein, a therapeutically effective dose can be estimated initially from animal models or based on other constructs. Such information can be used to more accurately determine useful doses in humans.

An "effective amount" is an amount sufficient to effect beneficial or desired results. For example, a therapeutic amount is one that achieves a desired therapeutic effect. This amount can be the same or different from a prophylactically effective amount, which is an amount necessary to prevent onset of disease or disease symptoms. An effective amount can be administered in one or more administrations, applications, or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

The pharmaceutical compositions can be included in a container, pack, or dispenser together with instructions for administration.

Exemplary Sequences and Constructs

In some embodiments, the sequence of a protein or nucleic acid used in a composition or method described herein is at least 80%, 85%, 90%, 95%, 97%, 98%, or 99% identical to a reference sequence set forth herein. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) *J. Mol. Biol.* 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

SECRETORY SEQUENCES

| | Sequence | Amino Acid Sequence |
|---|---|---|
| Albumin Secretory Sequence used in exemplary constructs | ATGAAGTGGGTAACCTTTATTTCCCTTCTTTTT CTCTTTAGCTCGGCTTATTCCAGGGGTGTGTT TCGTCGA (SEQ ID NO: 52) | MKWVTFISLLFLF SSAYSRGVFRR (SEQ ID NO: 53) |
| Albumin secretory sequence | ATGAAGTGGGTAACCTTTATTTCCCTTCTTTTT CTCTTTAGCTCGGCTTATTCC (SEQ ID NO: 54) | MKWVTFISLLFLF SSAYS (SEQ ID NO: 55) |
| ENPP2 Secretory Sequence | ATGGCAAGGAGGAGCTCGTTCCAGTCGTGTC AGATAATATCCCTGTTCACTTTTGCCGTTGGAG TCAATATCTGCTTAGGA (SEQ ID NO: 56) | MARRSSFQSCQII SLFTFAVGVNICL G (SEQ ID NO: 57) |
| Transthyretin Secretory Sequence | ATGGCTTCTCATCGTCTGCTCCTCCTCTGCCT TGCTGGACTGGTATTTGTGTCTGAGGCT (SEQ ID NO: 58) | MASHRLLLLCLAG LVFVSEA (SEQ ID NO: 59) |

PROMOTERS

HDAC9-P1 (full length)

ataaatgttttgtagaataaaaaaaaaaaaagttcttcaaaagaaatctcaaatctccaaatggaaacaggta
aaagtggagctcccctggttccacggagaacctttttttgaggaaacttaggcaactcgcaggtaccttatgtc
atgagacagagtttgaaaactacaattgactatctctaaatttcctcccaggtctaaaatgtgatgatagtta
ctacttcagtacatcatccttaaggaaaattattaggtccacactgtttctatcctttgaattttacacataa
attttgtaatcaaaagtttatttgtaatatcagatggaatcagataattgctttttgtttttccactgacag
gaacataagatttttgttgtgtagcttaagtcaaacgcagtttggaatatatattttttaaaaattgtaactta
catatccaaatacaatttttcaagaagtagagtattcagtagaaattaatctgtgaaagaagaggaattcagc
agtggcctatttgatgaatgatttaacgtgcttatttcttccctttcatcaaaactctgtgtccccttgtttg
ccccctctgacttcatactctggagttgaccaagatccctcttccatcggattgttctgggaattttgaaata
atctgctttttcctctctttccccctgttgcttctgatgccttagaattacattttcctcgctgatttagttta
gaaaagagaaaagagcttccatgactagtagattatcacttttgggtttgctcttggaagtgacaagatgcta
ggatccctctttggaatgtaaaatttatctcttatatagaaaggatataaatgtagcaccagagactataaaa
ctctgatactatctactgtactgtatagctgaacgccacaatgtgtctggtaatctattgactatcataaatg
ctatttctacagaaaagttaggaggtccatatttcgggcaaccaatgtatagctgaatgcagaacagtcatag
ttgggtactaaccatatatatgatttatccatcaacaggtgcatatgctcagaaattctgtatccataagaaa
tcagactactttcttttccttttgcaagtaaattgaatttagcctgagaggctgaggggaaattttcacatat
aagccacggttttgtgttttgtgttttgttttgtttatagatatagtactaactggatggatgcgataaaatt
cataggtggtactaagatacaataggatttgtgaaatggacaattgtcttgcataaatagcaagtaaaaaatc
aagcctgtccttcataaaaattttattctggggtgtgcttgttttccaaaagtacctctgctaaatctcctgt
tagtcctgaaactagaaggcagaaaagcttctagtgctacagccaactgcagtgtagcctgagaaacaggcaa
caaaaatagaacaccaggattgctgtgcgtgggtgaggcagaaaccacattatgagcaaaagcttccagtatt
attttagaaccaatacagagctctgtacttctctcctctctcttccaaaaacacatactacaaaaataaaatg -continued

| PROMOTERS |
| --- |

aaatgaaatgtatgtgcatttgccctcttagaattatgattcttaattttttttcttgccttcctttctttgg
aagcgaatcgccagtatggaaacacagtgtgtaaagcaagcttcgagagaggaaagagttaattggttttaag
gccctgcgatagagaattatggttggaaagatagaggctggacagctgggtttgctggggtatttttaaatgc
attaatgcaggctccaatcactcggccatgcttgacctattttggctcaggccgaccattgttctatttctg
tgcctgtgggccatgctgttgttgattcatatgcaaatggattatcactcgctttagccaacttgagctgaga
gagactgagaaaggggaagagaggcacagacacagataggagaagggcaccggctggagccacttgcaggac
tgagggtttttgcaacaaaaccctagcagcctgaagaactctaagccaggtttaattggtttctttttctcgt
gggtagacttaataattttctacgtattctgacaaagaaataaccccgaagcacgttcctatttcccacctgc
ttgtagtttccgggataacctaaactccagagagctatagcatccactctgtcctttctgctttgcacacagg
ttggtaacatgggaaaagtgtccaggtctttttaaaagtggatgcccatttgagcagaaaggaaatcattgtc
gaagttgatcctctgctgcttctcctcagggaggagggagaaccagcgagggtagctcctggggccggtgcac
tgagcagtgatgaatgtttcatgtagctgaagtaagagtgactggaatatgctgcagacaatttacgagagtg
actcctgtttttcctcagATGGGGTGGCTGGACGAGAGCAGCTCTTGGCTCAGCAAAGA (SEQ ID
NO: 60)

HDAC9-P2
ataaatgttttgtagaataaaaaaaaaaaaagttcttcaaaagaaatctcaaatctccaaatggaaacaggta
aaagtggagctcccctggttccacggagaacctttttttgaggaaacttaggcaactcgcaggtaccttatgtc
atgagacagagtttgaaaactacaattgactatctctaaatttcctcccaggtctaaaatgtgatgatagtta
ctacttcagtacatcatccttaaggaaaattattaggtccacactgtttctatcctttgaattttacacataa
attttgtaatcaaaagtttatttgtaatatcagatggaatcagataattgctttttgtttttttccactgacag
gaacataagatttttgttgtgtagcttaagtcaaacgcagtttggaatatatattttttaaaaattgtaactta
catatccaaatacaattttttcaagaagtagagtattcagtagaaattaatctgtgaaagaagaggaattcagc
agtggcctatttgatgaatgatttaacgtgcttatttcttccctttcatcaaaactctgtgtccccttgtttg
cccccctctgacttcatactctggagttgaccaagatccctcttccatcggattgttctgggaattttgaaata
atctgctttttcctctctttcccctgttgcttctgatgccttagaattacattttcctcgctgatttagttta
gaaaagagaaaagagcttccatgactagtagattatcacttttgggtttgctcttggaagtgacaagatgcta
ggatccctctttggaatgtaaaatttatctcttatatagaaaggatataaatgtagcaccagagactataaaa
ctctgatactatctactgtactgtatagctgaacgccacaatgtgtctggtaatctattgactatcataaatg
ctatttctacagaaaagttaggaggtccatatttcgggcaaccaatgtatagctgaatgcagaacagtcatag
ttgggtactaaccatatatatgatttatccatcaacaggtgcatatgctcagaaattctgtatccataagaaa
tcagactactttcttttccttttgcaagtaaattgaatttagcctgagaggctgaggggaaattttcacatat
aagccacggttttgtgttttgtgttttgttttgtttatagatatagtactaactggatggatgcgataaaatt
cataggtggtactaagatacaataggatttgtgaaatggacaattgtcttgcataaatagcaagtaaaaaatc
aagcctgtccttcataaaaaattttattctggggtgt (SEQ ID NO: 61)

HDAC9-P3
gcttgttttccaaaagtacctctgctaaatctcctgttagtcctgaaactagaaggcagaaaagcttctagtg
ctacagccaactgcagtgtagcctgagaaacaggcaacaaaaatagaacaccaggattgctgtgcgtgggtga
ggcagaaaccacattatgagcaaaagcttccagtattatttagaaccaatacagagctctgtacttctctcc
tctctcttccaaaaacacatactacaaaaataaaatgaaatgaaatgtatgtgcatttgccctcttagaatta
tgattcttaattttttttcttgccttcctttctttggaagcgaatcgccagtatggaaacacagtgtgtaaag
caagcttcgagagaggaaagagttaattggttttaaggccctgcgatagagaattatggttggaaagatagag
gctggacagctgggtttgctggggtatttttaaatgcattaatgcaggctccaatcactcggccatgcttgac
ctattttggctcaggccgaccattgttctatttctgtgcctgtgggccatgctgttgttgattcatatgcaa
atggattatcactcgctttagccaacttgagctgagagagactgagaaaggggaagagaggcacagacacag
ataggagaagggcaccggctggagccacttgcaggactgagggtttttgcaacaaaaccctagcagcctgaag
aactctaagccaggtttaattggtttctttttctcgtgggtagacttaataattttctacgtattctgacaaa
gaaataaccccgaagcacgttcctatttcccacctgcttgtagtttccgggataacctaaactccagagagct
atagcatccactctgtcctttctgctttgcacacaggttggtaacatgggaaaagtgtccaggtctttttaaa
agtggatgcccatttgagcagaaaggaaatcattgtcgaagttgatcctctgctgcttctcctcagggaggag
ggagaaccagcgagggtagctcctggggccggtgcactgagcagtgatgaatgtttcatgtagctgaagtaag
agtgactggaatatgctgcagacaatttacgagagtgactcctgtttttcctcagATGGGGTGGCTGGACGAG
AGCAGCTCTTGGCTCAGCAAAGA (SEQ ID NO: 62)

HDAC9-P2.1_RFP
Ataaatgttttgtagaataaaaaaaaaaaaagttcttcaaaagaaatctcaaatctccaaatggaaacaggta
aaagtggagctcccctggttccacggagaacctttttttgaggaaacttaggcaactcgcaggtaccttatgtc
atgagacagagtttgaaaactacaattgactatctctaaatttcctcccaggtctaaaatgtgatgatagtta
ctacttcagtacatcatccttaaggaaaattattaggtccacactgtttctatcctttgaattttacacataa
attttgtaatcaaaagtttatttgtaatatcagatggaatcagataattgctttttgtttttttccactgacag
gaacataagatttttgttgtgtagcttaagtcaaacgcagtttggaatatatattttttaaaaattgtaa
(SEQ ID NO: 63)

HDAC9-P2.2_RFP
Cttacatatccaaatacaattttttcaagaagtagagtattcagtagaaattaatctgtgaaagaagaggaatt
cagcagtggcctatttgatgaatgatttaacgtgcttatttcttccctttcatcaaaactctgtgtccccttg
tttgcccccctctgacttcatactctggagttgaccaagatccctcttccatcggattgttctgggaattttga
aataatctgctttttcctctctttcccctgttgcttctgatgccttagaattacattttcctcgctgatttag
tttagaaaagagaaaagagcttccatgactagtagattatcacttttgggtttgctcttggaagtgacaagat
gctaggatccctctttggaatgtaaaatttatctcttatatagaaaggatataaatgtagcaccagagactat
aaaactctgatactatctactgtactgtatagctgaacgccaca (SEQ ID NO: 64)

HDAC9P2.3_RFP
Atgtgtctggtaatctattgactatcataaatgctatttctacagaaaagttaggaggtccatatttcgggca
accaatgtatagctgaatgcagaacagtcatagttgggtactaaccatatatatgatttatccatcaacaggt
gcatatgctcagaaattctgtatccataagaaatcagactactttcttttccttttgcaagtaaattgaattt -continued

PROMOTERS agcctgagaggctgaggggaaattttcacatataagccacggttttgtgttttgtgttttgttttgtttatag
atatagtactaactggatggatgcgataaaattcataggtggtactaagatacaataggatttgtgaaatgga
caattgtcttgcataaatagcaagtaaaaaatcaagcctgtccttcataaaaattttattctggggtgt
(SEQ ID NO: 65)

MiniHDAC9
Gaaaactacaattgactatctctaaattttaaaatgtgatgatagttactacttcagtggtccacactgtttc
tatcctttggaacataagattttgttgtgtagcttaaggaagaggaattcagcagttgactatctcgattgtt
ctgggaattttggaggctgaggggaaattttcacatataagcgctgggtttgctggggtattgagagtgac
(SEQ ID NO: 66)

human matrix Gla protein (hMGP)
aagattatagttgtcatttgaacttggggataaaggagacatctatgacttggctggaaaagacagagctaat
gtacattgcaaagcacatatttatagcaggaaaatgggaagatttctctttaattctggagatggagtgggga
tggggagagtagactactcattttaagggtgaaacattggaattcaacttgtttgatgttatattaattggtg
gttaattactaagctaagtacgtataaaacttttatctatggctagcttgtcccccaaagtcatgcaatata
gtgaactggctttcgcactttaaattattcattgatcatgtaatgattcagatgattcatcttccaagatgga
cactgaaactaacactcatagtaggttgtggtttaaagagtggaacaaccgccagtctcattagtggaaattg
tgatggttgaatttatcaaggatgaacatacacggtcttctttctgagattttctttaagattttcgcacaga
taatctatttcttaggttttggagagaaaacttgaattttattgatccctcagaactcaatctttcagatttc
aaaggagctatttcttttaatggggactctgttaatatttataaaagctcttcacaggatggagggtgggagg
gaaactccatcccaacaagacaaaaagaatgaagcatgaggctccacctagttcatcactgctccttgaaata
catcagtattgaaagacacatccaccccacccccaacccagccctattgctgttccagctcaagagtcagagg
tcccgaagctgtagctcttctacaatctgctgctctgtgacttcaagtctgttgtctgcaaagaaaactattg
ggttcccaagcaagagaggcacatctggtaggacagattttgtgattgcaaaagaaggggaaaaaaagaaag
aaagaaaagacctctctatacaagataaccagaggcatcaaactgaaatcctcctgtggaaaataagctagta
cttctgggcctgatggtgtagtgaaaacctgtgcttgaggatacattacagtgaaagagcaaagtgaatagta
agtagctattacttacctccttagggaggtgtgttgtttgtctgtacatcccccacagcacctagcacagtac
cttgcatctcacctgccactcactaaaaagtctatcaagttagttaattatcgagacaacgccctcagaaatg
agagaacagtaccctcttatccttgctgcactttccagcactgatacgctgcctaaaagaggactagggcaca
ggtttgaattaatgtcacaaaactggatgggcaagttacaacggtgttgattaaggaaacagaactcatggtg
caccggatatctccatcctgatgaacccttggaaaaatgccaaagatgcatatccccaggcaaatgcctgatt
agtctgggattgatagattggtctaggattcagccctactgggaagatgtctaaattataatcagtgtagaaa
gcgaagttctcctagaagaagaggcaaaggttaaaaagaagaaaagaaaagaaagtgaagtcctttctccccc
aaaacctctcatcaatcaatcagggtaacaaacagaacactagggctctgtctgtggaccaaacccaaaagcc
ctgcggtcagggccaggagggtagatcatgtgtttgtggcaacttcctctgtgggcttttgcccaggtctgtc
cccaagcatacgatggccaaaacttctgcaccagagcagcatcctgtgtaacacagtcaggtccagcagttag
ggaaaactgcccactcagagtagataatatctggaaggaatgactgtttgggaaaagttccaatgctagttca
gtgccaacccttccccaccttctccagctctctcccactggttcctcccctctcaactgctctggttcttata
aaaacctcacagccttccactaacatcccGTAGGAGCCTCTCTCCCTACTGCTGCTACACAAGACCCTGAGAC
TGACCTGCAGGACGAAACC (SEQ ID NO: 67)

hMyh11
CGCCGGGGAGCAGGAAGGCCACTCGGCACCATATTTAGTCAGGGGGAGCCGGCAGCCCAGAGCTGGTATGCGG
CGCTGGGAATTCCTGCAGGAAGGAGTCCGCGCCTGCCCTTTTTGGGTTGTCTCCCGCCCGCCGCTCCCGCCGC
TCCCGGGGAGGGGGACCGGCCCGGCCCGGCCCGGCCCGGGAACCTCGGAGGAGCTGGTGCCGCGCGGGGAGCG
GAGCGCCCGGGCTGCCCGCGGGTCCCCGGCCTGGCGCGGGGCCAGCCCACCGCCTCGACTTCCTTTTATGGCC
TGTGTGTGCGTGCGTGGACAGGAGCGGGGAGGGAGGGACGGGGAGAAGACGGAGAGCCTGGGGAAGAGAGAGA
GAGAAAGCGCAGAGATAGGAGTGAGACACGCGGGAGAGATGGAGAGCAAGAGACACAGAGACCAGAGACAAAG
TGAGACAGGAGGGAGAGACAGATACATCGACAGATCTAGAGAAGCGAGAGGGACAGAGACAAAAGATAGAGCG
AGAGACAGCAATGATCAGAGTGACAGACATGCAGAGACAGTGGCAGAGACAGAGCGAGAGAGCCTGTGATGGA
GAGAGACAGGGAATGCAATTTTAGGCGAGGAATCCTTGGGGAAGGGAAGTTGTTGAAGGGAACTCGCAGACTC
TGGGGGCACACCCACTTTCTCCTTGGATCTTGACACTTGCATCTTGTAAATAACGTAATTATCACCGCCACCG
CCTTCCCCCATTTTGTAGCTATGGACACCAAGTCTCAGAGAAGTGAAGTGACTTGCCCAAGGTCACGCAGCTG
GCGAGTGGCGCACAGGGGAGGGGGACAGCTGAAATAATCACAGTGGGCTTATTTTTAATTTTTATTTGTATTT
TGGTCGTGGTGATGTGGGTGGAGGTGGAGATGGCAAGTTGGGAAAAGTAAAAACTTCCCCTTCCTGCACGGTT
CCCAGCAAGGGTGGGGGCCTCCTGTCTTGCACTTTGCAAAGTTCAAGAAATCCCCTTTCCCTACCCTTCACGC
TGCACAGCCGGCCCTCTTTCCAGACAGTGCGATGCCAATAAAATGGGAAGTGGGGTGGGAGATGTCAAGTCAG
ATCCACCACAGCCCCGACACGGGGAGGAAGAGGTTAAAGCCTTTGCGGCCGGAACCGACTCAGGGAAGACGTT
CTCAAGCATCCCGCACAGACACTGCCTGCTCGACCCCCTTTCTCTAGGGATCCGGAGCGTCTGCGACCGCCTG
GGGCCGGGGCTGAGACTCCCGTCCCTGTGCGCACCTGTTCCGTGCGCCCTTGTGCGGTGCGCACCTGTTCCGT
GCACCCTTGTCCCGAGCGCCCCAGCTCCTTGCGCTCCCGCCGGGGGTGCGCCCTGCAGGGGGCGCGGCGAGGG
GGCCGCGAGGGACCCTCCCCAACTCCACCCCTTCGGCCTCCTCCCCTTTCCCAGCCGCGGGCAGCTCCGGGTC
TATAAAGAGAGGCGTCCGAGGACGCGCAGGGAGATTTGGACGCTCCGGCCTGGGAGGTGCGTCAGATCCGAGC
TCGCCATCCAGTTTCCTCTCCACTAGTCCCCCCAGTTGGAGATCTGTAAGTAGTAGTTGTCATTCTGGGGGCA
GATTGCAGGGCAGGGGGGTGTTAAAAGTCCTATAGGGTATTCTATAGGGGCTGGGGTGCACTTAGGGGT
(SEQ ID NO: 68)

ENPP1
ctctcataatattgaagtagctttgttgtctatggtgacatccgaggttcttggtctcacggccacaaagatc
aaatatgtggacacacacaaagggtgaggtttggagcagaattttttaataggcaaaaggaggagaatagctct
gctacagagaggggtcccaaaaaatgggttgcaatacgtggtgaaatgcaggggtttttatagatgagctagt
ggggaggcggtgtctgatctacataaggagggaaaacccggtttcgtgcatatggcatgaaaacccggttagg
accaggtgtgtcatctgcatagggcttaagtgtctggcagccccggccccaatcttctactatataggcaggt
agctactccgtgttgcttatttccttcttactgtgcatgtggtaaaaaagaggggaggtggaacccccatggt
ggacatgcctggccccagtagccccttctgtctgtgccgctgccggcatctcccgtgcaagcttccagtttcc
ttacctatgtttgcagcccaatcttccaggttgctctttgttagaaaggaagtgatttcttgggctgcttttt -continued

| PROMOTERS |
|---|
| gttagaaggtaagttctgccgagggctcttttgctcatactatctgcctaaataatttctatctcctgtatca<br>atatcctatgtgtgactctattctgcatatatgacttaggttttaattattttgtttacgagttggtcctacc<br>cccccacccccgcttccaccacacttaaggaaagatacatttttaattcatttttttatatggtatgcatagttg<br>gaggccaaaagattgagttgaaggattcattacttgatgaataaatggatgggtggatggatgagtcagtata<br>aatgaagagcatcccaagttgactattttaaagggataacatgcattttatatttgttaaacattcattctca<br>tttgtaaacacttgtatatattcatgtattcaaaatgtattgaaaattaattgttttccttggtacctgaagt<br>cagtcctgggtattgcaaagtagttcgaagtcactggtttccctctgtctcacttcactacacactggtgatt<br>ttgctaagtgatgagccagaaaatgtacaagttccagaatcaaaggtaaaacaaaacccaccaagaatcagct<br>cactgttagcgtcctagttgaaaaataaggcttatcaaagtatttcagattgcattaacacttttgatatagc<br>taggtatcagtgtcaacctcaggagagggcaacgccaactcctgaaaccttcaatacagaaagtctagaaaaa<br>taagcaaatatacatacaaacaatagcgagaagactccagaaaccacataaaaccgtgggaatcgaaatatcc<br>cttacgtgtgttcagtacatgtgaacccacgtattttaagtggacgatttctctctcagagtaccgtaggtag<br>tgggggacggggcgcagagggggagaaacagaaagtcgccttcctccatggttcatttgcatttccatccaga<br>aactcacaggtcgaccccaagactccactctctcccgcctttgagaagccggaccggcatcggcggctgcatc<br>cttctcctcctccccgctctatttggggccccatgatctcatgccctctgcagaccacacgctgcaattcca<br>gcccagcccgcgccgcgaggccacgcagggcgattcctgcaagtgtcgggagggtggccggggcgcggggagg<br>ggacggcttggggggaagtttaagacacgcccacgtaagggacccaaaataaccgacacacagagtgcccgaa<br>atcagacaggaagccaaataatccggggcgttgagtcgctttgccctgactgcgagagccgggtgtagggcgg<br>ggagccaaggatctgaccgcgaggggcgggcgcggcggggaggggcggggcggggcgggcggcgcggggccta<br>ttaaaggcgcggccgggcagcggggccggAGCGGCCGGGGCCACG (SEQ ID NO: 69)<br><br>ENPP2<br>gaggtggaggctgcagtgagccgagatcgagccattgcactccagcctgggcaacaagagtgaaactccatct<br>caaaataaacaaataaacaaacaaaaacaaaaaaacaaagaaatagtggctgaggtcaactcttttggatatt<br>gggtaacaagcagatcaacttggctattacagcttttccccctgcccagctagtctgcatataagagaaaaat<br>aaatggatgatgttcagctcctgaaccctaactttttttccaagggaaccctcattgtcttctagctaggttt<br>atacaatcaaatatcagacaaagtcaaaagttgttagactctggcaaggcaaaagaagaggctgtttttgttt<br>ttagaacatttagagcactgtggcatataatgaaataacaggattgccttgatatttttctttggggtttatt<br>gttttcctctatcatgtctggcttgtatcttgaaatttaacataaattataggaaaatctttcatggagttaa<br>catcttttataagccttgctaaataccctactccaaatttgttcagtatggcatacagacaaaagcaagaggc<br>ttacatataaaaatgtataagcctgtcctctttgcaacagtgcaaaactaaaaggattttagaaaggcaatta<br>acagtttggcagtatgtgtatttttctttttttcaattagatattactagattctaagaatctgtaatgaaacc<br>caggcctactgtacaaccccctataaacaagtttttgcttttgtgctatcatgttttatttgagcagagccac<br>tactctgttactaatttgttgcatggtaagtctcgtatttgtttacgcacgaacacatgtgctgcggaagaaa<br>agatggtcactggacctgctgaggaagaggccaaaaacaaatctttttccctcatttgaatcctgaaggcatg<br>taatatttaaacaactttcagatttagagcccttgatttttttcttttgaaagtgtgctggttgccaaattgct<br>tagtaaagaaactttagtacccacaatagcctcaaaggacacagtatttggtggctacatttaaccaagaaat<br>aactagggaaacaattcttgacatttcaattcttgctgccattgagatttccttcctaaattcaattgctaat<br>aaagcttcccatgccatccccttcccccacccatctgcctctcaaaaaccgcccccctcctccgccccgcccga<br>aacaagctgacagtctttacgggaagaagaggcagagactgaagttattttgtccgtcctcccagggcagaag<br>gactttatgctgcgtggctggcatttccagtattttgataaaagttacttctctaaacttgaaccacagcatg<br>gggaaaataatgttatcttttatgttagttacaattttgcgaaatttcatcatgagaaactttcaaggaggca<br>gaagtagctgagaatgtgatactagggacagggtcgctcaaactgccagcaaaataaatagatgggaaagaca<br>ggaacgttattaggtttataaatgataaaactttccttgcttaaaaaaataaagtggtgaggttgacgccatt<br>gaatgactgcattgtaaaccttaaaagcttaaagctggtggaaagcccttgcacagccctgttttcattttta<br>tcggatgaaatgcatttggtttctttttgacaaaccatgtttttgtgaggaaaggaaaatgaacatgcactgt<br>tatgggccacggcaatgtaacaaaccctcctgttgccagaggataccacatgaaagtgtctgtgggttagggg<br>agggacctgtaagggggcggggataagggggatgatagcttaagcctcttaggctcagagctgcgatttgtga<br>acaccctgtgatgtaatcaagctctggacaaatcagaggagtctgtcaacctcccaggtgggattgcttatag<br>ttaatagactaaacccagagcctcaaagcAGTGCACTCCGTGAAGGCAAAGAGAACACGCTGCAAAAGGCTTT<br>CCAAGAATCCTCGAC (SEQ ID NO: 70)<br><br>ENPP3<br>gggaattacctgtagattattattaggagaaaaaaagtgctaattaatgaacagtgtacatggtatatgatca<br>tgctataaaagtgtttctatatgcataaaatacttctagaagaaaacataacctgaggatattggctacagac<br>agaaaaaataacaggtaagagaagagaaagagactagttattggatccaccctttttatacctgtgcattttga<br>accatataaatgtattacctattagaaaacaactaaacaaaaaggttaaaacatgactgtattggcattatat<br>gatccatgtctgagtggcaaatcttatcaccagtggctgacacgcaaacagttctcatttccctacctatagt<br>gtaccatgagaaggtaaggcactactgcaatgtgagctcttcgaggatgacacatttttgtctttttcacgga<br>tacattttctggtagctgttctttgttacttttacagtttgtctcctcatttttactataatattttcctatc<br>cttattatagaatcttggtattcctattgtagcatctttgtatcaatgctgtgccaattcctttatttagcag<br>aaaaatggaatttgtatccttgacaagtaaagcttaacatatctgttttcaagtgtaccaaataaatccgaat<br>aggatgaaaatgatctcaattaatctaacataggggaggttttttttttttaaacatctcacactgtgcagtat<br>caacttgacttctcaacacaggttttccactgaaatatacaaattaaaacaaatggaagccagaataaaaaat<br>gataacaattttatttctcccttctcaggaagatcttaagagcagcatgaaagtaaatgttaaaagaaaaaaa<br>aaaaaaaaaagaagaggccaaaaatcatcagctgaatgtattaaaaatgaagcgctcacctgagaaagaccac<br>cccaaaactgtctgaaggcccccaaacagctaattagttttgttttctcatcttcaggagtatccataaacat<br>gctaaaaaaataaaaattacattatttgtcattcgttttaaaaaggtaattacacacaatcagaatagtggat<br>cttataaccttccaacacgaaactaagtaaaatctgacagacacaatcacataaaaacacaaaactctgccac<br>gcatacactcacccaggaaaagcctcttctataacttccgttttctgtaaaaaaaaaaaaaacaaaatgtaaa<br>caatgttaattttaaaaaggcgcctcccttagccaagtattacaatgtaacacagggcaagtcaccttaatca<br>gctctgaaactatcaatacctgtctggcctgtcactgtatcgatttcaaaggatacaatgaacttgacagcag<br>tttgagaatcactaaacttccccgcatacaacctcggtgtcaaaacaagggaataaaaagggaggcgtgagag<br>gaggttgcccaggccagtttccttggtcggctgcccccgcgtctccccgtccccaagccgtagtcctggatgg<br>ccggcagctgcactcaccaccacctcttcgaaaatgctctgcagttgcgtctccatctgtactatcacccccg<br>cctttccagggtgcccggcaaggcccggatcagactcgagctctgggaatataggggcagaggggcggagacc<br>tctggaggaaaccgtagctcctcggcgtcgcttcctcccccagcgctttacctggagcgttccctcccgagcc |

-continued

PROMOTERS cagccaacagcaggaacctgtacggaagacgggaagggcccggtacgcgccgtttgcaaaccccgcagaaacc
agcggcgccaccagaaggttccgtctgtggagaagggcggcccgcaagccggacgagagcgcccccaaacgga
accttgagcccaaggaccccggaggcatcgtcgaccgcaggccgccacctcccggctggagaaggagttgctt
cctgttcggggctaacccgcttgcagactGAGAAATGAAAAGTTTGGAACCCAGAAGCTGCAGCCTGCGGAAA
ATGCTGGAGCCGCAGCCGACACCAAGTTGATGTCTGTGAGCAGCTGACCTTCTGGACCTCCATCAGCGGCCTG
CAGCCAGGAGCTGAAGCCACAGAGACGGTGTCTTCTCAGCTATGATAACCTCAGTGCAAATATTGCCCAATCA
CTGAAGAGCTGTGATCTTCCTAAACAGTTAAAAGTCAGGCACAGCTATGTAACTCATACAGTTTCTCTTTGCC
AGACTAGACTAAAGAAGGAGCACTAATTTATTCTGATAAAACAGGTCTATGCAGCTACCAGGACA (SEQ
ID NO: 71)

CBA
TCGAGGTGAGCCCCACGTTCTGCTTCACTCTCCCCATCTCCCCCCCCTCCCCACCCCCAATTTTGTATTTATT
TATTTTTTAATTATTTTGTGCAGCGATGGGGGCGGGGGGGGGGGGGGGGGGCGCGCCAGGCGGGGCGGGGCG
GGGCGAGGGGCGGGGCGGGGCGAGGCGGAGAGGTGCGGCGGCAGCCAATCAGAGCGGCGCGCTCCGAAAGTTT
CCTTTTATGGCGAGGCGGCGGCGGCGGCGGCCCTATAAAAAGCGAAGCGCGCGGCGGGCG (SEQ ID
NO: 72)

CMV
GACATTGATTATTGACTAGTTATTAATAGTAATCAATTACGGGGTCATTAGTTCATAGCCCATATATGGAGTT
CCGCGTTACATAACTTACGGTAAATGGCCCGCCTGGCTGACCGCCCAACGACCCCCGCCCATTGACGTCAATA
ATGACGTATGTTCCCATAGTAACGCCAATAGGGACTTTCCATTGACGTCAATGGGTGGAGTATTTACGGTAAA
CTGCCCACTTGGCAGTACATCAAGTGTATCATATGCCAAGTACGCCCCCTATTGACGTCAATGACGGTAAATG
GCCCGCCTGGCATTATGCCCAGTACATGACCTTATGGGACTTTCCTACTTGGCAGTACATCTACGTATTAGTC
ATCGCTATTACCATG (SEQ ID NO: 73)

hALB
AGTTCCAGATGGTAAATATACACAAGGGATTTAGTCAAACAATTTTTTGGCAAGAATATTATGAATTTTGTAA
TCGGTTGGCAGCCAATGAAATACAAAGATGAGTCTAGTTAATAATCTACAATTATTGGTTAAAGAAGTATATT
AGTGCTAATTTCCCTCCGTTTGTCCTAGCTTTTCTCTTCTGTCAACCCCACACGCCTTTGGCAC (SEQ ID
NO: 74)

CAG
GCGTTACATAACTTACGGTAAATGGCCCGCCTGGCTGACCGCCCAACGACCCCCGCCCATTGACGTCAATAAT
GACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTCAATGACGGTAAATGGC
CCGCCTGGCATTATGCCCAGTACATGACCTTATGGGACTTTCCTACTTGGCAGTACATCTACGTATTAGTCAT
CGCTATTACCATGGTCGAGGTGAGCCCCACGTTCTGCTTCACTCTCCCCATCTCCCCCCCCTCCCCACCCCCA
ATTTTGTATTTATTTATTTTTTAATTATTTTGTGCAGCGATGGGGGCGGGGGGGGGGGGGGGGCGCGCGCCAG
GCGGGGCGGGGCGGGGCGAGGGGCGGGGCGGGGCGAGGCGGAGAGGTGCGGCGGCAGCCAATCAGAGCGGCGC
GCTCCGAAAGTTTCCTTTTATGGCGAGGCGGCGGCGGCGGCGGCCCTATAAAAAGCGAAGCGCGCGGCGGGCG
(SEQ ID NO: 75)

hHAMP
tgtgtgtgtgtgttttaattttctttatggaaaaattgacaaaaaaaaaatagagagagaggtatttaactgc
aataaactggccccatgtggcccccgccttgtctgcttgtgtgtttgtccatctcaggagtggggagggggcc
tggggtctgcagagctccacgaggcatggttctgctgttgtgcacatggctgtgcatggtccctgccagctgc
accacccattacccagtggttggttggatggatggaggaattaaggaatgaatgtcccctttgaggccctaga
cgtgcatgagggtgtggggagctggggtcaaggacatgtcccatgttggaggagaggcaggggtctccgtgtc
aacagttcctgaaaacacaaccagcccctggccctgccctgctgggccaaagccctcccctctgcaccagcca
atagtggggcctggccttgagcccctcacccccagggagggcagatggccagggcgccaagcttggcccgtca
gcctgtcgccttgcaccaaggctctggcgcctgtgctgtgacccctgcccctgctgatgatgaaacctgtcct
cagctgagatgcagcgatgcctggtagggctgggggctgctcctgtgtctccccaggtgagcacacccctatt
cactgggccctgcttcagcctgcagcacccttcaactcccaggagctgggcttgccactctgctcaccttgtg
gagctccatctgcctttcctccccaattcccccactccctgcactcgtctcttcccacaagagccctgtctcc
ttttcctagctattcccatctgaggccatctttattcatttagtttttagagacagggtttcactctcaccca
ggctggggtgcagtggcacacaatcacggctcactgcagccttgaccaactacaggtgcgtagcaccacagcc
aagtttttgtatagatggggtctcgctttgttacccaggctgtgacaagag (SEQ ID NO: 76)

hTAGLN
agagcgtctccatgctatggttgcatttccgttttctatgaatgaatttgcattcaataaacaaccagactca
gttcttggggcccttgtttgcactccctctgggtggagctgttgaggatgaggggagaggcggaggtcttcca
tttccccattcttcaagccatggccctactgggaactgcaattccttgattctcccgtttttcctgtccctcc
agcaacagcattaattcagtaaacatttaccggggcactgtgctggacagaggccagttcctggaaaagcctt
tcccacgccatcccactgcagacatccctccttacctccccaggaacagcagtctctgcccacctggccccgc
ccaccagactgaggctcacttcacctctgacctgagcggcccccagctcaccaagccacaggcccaagcagtg
ctccctgatgcggcgtttataatccgctcagcgtgcaggccgaggcaggagggtgatgaaagctgggcaggct
ccaagaggagggagttttgatatgtccctgaaagattcatttagacttcagtcggctaaggaggacatgattt
gggggccaaggaatctgttgaattcagaacacaaccagaggtctgcagggtcagggatggaggagtgggcttt
cccctcgccagggcccactcctcttcctgcttttcctgcaggcgccactgggaggtgctatggctgtgcctcc
cctgggctctggagcatgtccagttgcagtgggcagaactgcggaggcgggcccctcctctgccaggcctggc
agcccccctcctagggccttgtttggctaggggtggtgccgggtgtggcagtgtgtgtgtagtggagagtgtta
ggtcttccctaccagatgcccttgcaggggagtgccacagcagtcagtccagggatcccactgttagtctcac
ctttttttaacctcttatctctccccaagatccctgaagccaggtacgagcaagatgagagtgggttatctctg
gagtgacagaggctggtctgttttccaggctggtagggactgttcctaaagggaggaagggatgataccagcc
tcctgagcctccttctcctgcgttagtgtctcaggccctgccaggccttatagaccctcttattgacactgcc
cactggatggggaccggagttggactcagcttctgccgaaccctcaaatcccagccccaactaaagcatataa
ctcaagacctacctgcactgaaagctcttctcaacctgagcagggtggtccaattgaaagggtgggtctgacc -continued

| PROMOTERS |
|---|
| acctctcctgcacccatgcgggttggcagaggtgtgcaggatctgccacttaccattcaccatgtggccttga ggaagacgcactcggggcctcagtttcctcatctataaaatggggatgtaattacaccctcacactgtagctg tgagtattcaatgagagcactgcaaagggcctggtgtggagtaggtcctcaggaaaggttggatcccatgtcc catcagagctaaaagccccaggaggagagggtggctggtttgtccccacaaacccctgggattcccggctccc cagccccttgcccctctctccagccagactctattgaactcccccctcttctcaaactcggggccagagaacag tgaagtaggagcagccgtaagtccgggcagggtcctgtccataaaaggcttttcccgggccggctccccgccg gcagcgtgccccgccccggcccgctccatctccaaagcatgcagagaatgtctcggcagccccggtagactgc tccaacttggtgtctttccccaaatatggagcctgtgtggagtcactggggagccgggggtggggagcggag ccggcttcctctagcagggagggggccgaggagcgagccagtgggggaggctgacatcaccacggcggcagcc ctttaaacccctcacccagccagcgccccATCCTGTCTGTCCGAACCCAGACACAAGTCTTCACTCCTTCCTG CGAGCCCTGAGGAAGCCTTCTTTCCCCAGAC (SEQ ID NO: 77) |

| Bone targeting sequences | | | |
|---|---|---|---|
| Nucleic Acid | SEQ ID NO: | Amino acid | SEQ ID NO: |
| AAGAATTTCCAGAGCAGAAGCCAC | 22 | KNFQSRSH | 78 |
| AAGAGAAGAACCCCTGTGCGGGAG | 23 | KRRTPVRE | 79 |
| AAGACCTACGCCTCTATGCAGTGG | 24 | KTYASMQW | 80 |
| GATGATGACGACGACGATGACTGC | 25 | DDDDDDDC | 81 |

Plasmid Sequences Comprising ENPP1 Gene Therapy Constructs Full Length Recombinant ENPP1 Constructs CMV_Kozak_ENPP1 Full Length_FLAG_pcDNA3.1(+)

pcDNA3.1+, CMV enhancer, CMV promoter, Kozak seq, ENPP1 full length seq, Flag tag, Stop codon

(SEQ ID NO: 82)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGACATTGATTATTGACTAGTTATTAATAGTAATCAATTACGGGGTCATTAGTTCATAG

CCCATATATGGAGTTCCGCGTTACATAACTTACGGTAAATGGCCCGCCTGGCTGACCGCCCAACGACCCCCGC

CCATTGACGTCAATAATGACGTATGTTCCCATAGTAACGCCAATAGGGACTTTCCATTGACGTCAATGGGTGG

AGTATTTACGGTAAACTGCCCACTTGGCAGTACATCAAGTGTATCATATGCCAAGTACGCCCCCTATTGACGT

CAATGACGGTAAATGGCCCGCCTGGCATTATGCCCAGTACATGACCTTATGGGACTTTCCTACTTGGCAGTAC

ATCTACGTATTAGTCATCGCTATTACCATGGTGATGCGGTTTTGGCAGTACATCAATGGGCGTGGATAGCGGT

TTGACTCACGGGGATTTCCAAGTCTCCACCCCATTGACGTCAATGGGAGTTTGTTTTGGCACCAAAATCAACG

GGACTTTCCAAAATGTCGTAACAACTCCGCCCCATTGACGCAAATGGGCGGTAGGCGTGTACGGTGGGAGGTC

TATATAAGCAGAGCTCTCTGGCTAACTAGAGAACCCACTGCTTACTGGCTTATCGAAATTAATACGACTCACT

ATAGGGAGACCCAAGCTGGCTAGCGCCACCATGGAGCGCGACGGCTGCGCGGGGGGCGGGAGCCGCGGCGGCG

AGGGCGGGCGCGCTCCCCGGGAGGGCCCGGCGGGGAACGGCCGCGATCGGGGCCGCAGCCACGCTGCCGAGGC

-continued

GCCCGGGGACCCGCAGGCCGCGGCGTCCTTGCTGGCCCCTATGGACGTGGGGGAGGAGCCGCTGGAGAAGGCG

GCGCGCGCCCGCACTGCCAAGGACCCCAACACCTATAAAGTACTCTCGCTGGTATTGTCAGTATGTGTGTTAA

CAACAATACTTGGTTGTATATTTGGGTTGAAACCAAGCTGTGCCAAAGAAGTTAAAAGTTGCAAAGGTCGCTG

TTTCGAGAGAACATTTGGGAACTGTCGCTGTGATGCTGCCTGTGTTGAGCTTGGAAACTGCTGTTTAGATTAC

CAGGAGACGTGCATAGAACCAGAACATATATGGACTTGCAACAAATTCAGGTGTGGTGAGAAAAGGTTGACCA

GAAGCCTCTGTGCCTGTTCAGATGACTGCAAGGACAAGGGCGACTGCTGCATCAACTACAGTTCTGTGTGTCA

AGGTGAGAAAAGTTGGGTAGAAGAACCATGTGAGAGCATTAATGAGCCACAGTGCCCAGCAGGGTTTGAAACG

CCTCCTACCCTCTTATTTTCTTTGGATGGATTCAGGGCAGAATATTTACACACTTGGGGTGGACTTCTTCCTG

TTATTAGCAAACTAAAAAAATGTGGAACATATACTAAAAACATGAGACCGGTATATCCAACAAAAACTTTCCC

CAATCACTACAGCATTGTCACCGGATTGTATCCAGAATCTCATGGCATAATCGACAATAAAATGTATGATCCC

AAAATGAATGCTTCCTTTTCACTTAAAAGTAAAGAGAAATTTAATCCTGAGTGGTACAAAGGAGAACCAATTT

GGGTCACAGCTAAGTATCAAGGCCTCAAGTCTGGCACATTTTTCTGGCCAGGATCAGATGTGGAAATTAACGG

AATTTTCCCAGACATCTATAAAATGTATAATGGTTCAGTACCATTTGAAGAAAGGATTTTAGCTGTTCTTCAG

TGGCTACAGCTTCCTAAAGATGAAAGACCACACTTTTACACTCTGTATTTAGAAGAACCAGATTCTTCAGGTC

ATTCATATGGACCAGTCAGCAGTGAAGTCATCAAAGCCTTGCAGAGGGTTGATGGTATGGTTGGTATGCTGAT

GGATGGTCTGAAAGAGCTGAACTTGCACAGATGCCTGAACCTCATCCTTATTTCAGATCATGGCATGGAACAA

GGCAGTTGTAAGAAATACATATATCTGAATAAATATTTGGGGGATGTTAAAAATATTAAAGTTATCTATGGAC

CTGCAGCTCGATTGAGACCCTCTGATGTCCCAGATAAATACTATTCATTTAACTATGAAGGCATTGCCCGAAA

TCTTTCTTGCCGGGAACCAAACCAGCACTTCAAACCTTACCTGAAACATTTCTTACCTAAGCGTTTGCACTTT

GCTAAGAGTGATAGAATTGAGCCCTTGACATTCTATTTGGACCCTCAGTGGCAACTTGCATTGAATCCCTCAG

AAAGGAAATATTGTGGAAGTGGATTTCATGGCTCTGACAATGTATTTTCAAATATGCAAGCCCTCTTTGTTGG

CTATGGACCTGGATTCAAGCATGGCATTGAGGCTGACACCTTTGAAAACATTGAAGTCTATAACTTAATGTGT

GATTTACTGAATTTGACACCGGCTCCTAATAACGGAACTCATGGAAGTCTTAACCACCTTCTAAAGAATCCTG

TTTATACGCCAAAGCATCCCAAAGAAGTGCACCCCCTGGTACAGTGCCCCTTCACAAGAAACCCCAGAGATAA

CCTTGGCTGCTCATGTAACCCTTCGATTTTGCCGATTGAGGATTTTCAAACACAGTTCAATCTGACTGTGGCA

GAAGAGAAGATTATTAAGCATGAAACTTTACCCTATGGAAGACCTAGAGTTCTCCAGAAGGAAAACACCATCT

GTCTTCTTTCCCAGCACCAGTTTATGAGTGGATACAGCCAAGACATCTTAATGCCCCTTTGGACATCCTATAC

CGTGGACAGAAATGACAGTTTCTCTACGGAAGACTTCTCCAACTGTCTGTACCAGGACTTTAGAATTCCTCTT

AGTCCTGTCCATAAATGTTCATTTTATAAAAATAACACCAAAGTGAGTTACGGGTTCCTCTCCCCACCACAAC

TAAATAAAAATTCAAGTGGAATATATTCTGAAGCTTTGCTTACTACAAATATAGTGCCAATGTACCAGAGTTT

TCAAGTTATATGGCGCTACTTTCATGACACCCTACTGCGAAAGTATGCTGAAGAAAGAAATGGTGTCAATGTC

GTCAGTGGTCCTGTGTTTGACTTTGATTATGATGGACGTTGTGATTCCTTAGAGAATCTGAGGCAAAAAAGAA

GAGTCATCCGTAACCAAGAAATTTTGATTCCAACTCACTTCTTTATTGTGCTAACAAGCTGTAAAGATACATC

TCAGACGCCTTTGCACTGTGAAAACCTAGACACCTTAGCTTTCATTTTGCCTCACAGGACTGATAACAGCGAG

AGCTGTGTGCATGGGAAGCATGACTCCTCATGGGTTGAAGAATTGTTAATGTTACACAGAGCACGGATCACAG

ATGTTGAGCACATCACTGGACTCAGCTTCTATCAACAAAGAAAAGAGCCAGTTTCAGACATTTTAAAGTTGAA

AACACATTTGCCAACCTTTAGCCAAGAAGACGACTACAAAGACGATGACGACAAGTGAGGTACCGAGCTCGGA

TCCACTAGTCCAGTGTGGTGGAATTCTGCAGATATCCAGCACAGTGGCGGCCGCTCGAGTCTAGAGGGCCCGT

TTAAACCCGCTGATCAGCCTCGACTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGAGGAAATTGCATCGCATTGTCTGA

-continued

GTAGGTGTCATTCTATTCTGGGGGGTGGGGTGGGGCAGGACAGCAAGGGGGAGGATTGGGAAGACAATAGCAG

GCATGCTGGGGATGCGGTGGGCTCTATGGCTTCTGAGGCGGAAAGAACCAGCTGGGGCTCTAGGGGGTATCCC

CACGCGCCCTGTAGCGGCGCATTAAGCGCGGCGGGTGTGGTGGTTACGCGCAGCGTGACCGCTACACTTGCCA

GCGCCCTAGCGCCCGCTCCTTTCGCTTTCTTCCCTTCCTTTCTCGCCACGTTCGCCGGCTTTCCCCGTCAAGC

TCTAAATCGGGGGCTCCCTTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGCGAATTAATTCTGT

GGAATGTGTGTCAGTTAGGGTGTGGAAAGTCCCCAGGCTCCCCAGCAGGCAGAAGTATGCAAAGCATGCATCT

CAATTAGTCAGCAACCAGGTGTGGAAAGTCCCCAGGCTCCCCAGCAGGCAGAAGTATGCAAAGCATGCATCTC

AATTAGTCAGCAACCATAGTCCCGCCCCTAACTCCGCCCATCCCGCCCCTAACTCCGCCCAGTTCCGCCCATT

CTCCGCCCCATGGCTGACTAATTTTTTTTATTTATGCAGAGGCCGAGGCCGCCTCTGCCTCTGAGCTATTCCA

GAAGTAGTGAGGAGGCTTTTTTGGAGGCCTAGGCTTTTGCAAAAAGCTCCCGGGAGCTTGTATATCCATTTTC

GGATCTGATCAAGAGACAGGATGAGGATCGTTTCGCATGATTGAACAAGATGGATTGCACGCAGGTTCTCCGG

CCGCTTGGGTGGAGAGGCTATTCGGCTATGACTGGGCACAACAGACAATCGGCTGCTCTGATGCCGCCGTGTT

CCGGCTGTCAGCGCAGGGGCGCCCGGTTCTTTTTGTCAAGACCGACCTGTCCGGTGCCCTGAATGAACTGCAG

GACGAGGCAGCGCGGCTATCGTGGCTGGCCACGACGGGCGTTCCTTGCGCAGCTGTGCTCGACGTTGTCACTG

AAGCGGGAAGGGACTGGCTGCTATTGGGCGAAGTGCCGGGGCAGGATCTCCTGTCATCTCACCTTGCTCCTGC

CGAGAAAGTATCCATCATGGCTGATGCAATGCGGCGGCTGCATACGCTTGATCCGGCTACCTGCCCATTCGAC

CACCAAGCGAAACATCGCATCGAGCGAGCACGTACTCGGATGGAAGCCGGTCTTGTCGATCAGGATGATCTGG

ACGAAGAGCATCAGGGGCTCGCGCCAGCCGAACTGTTCGCCAGGCTCAAGGCGCGCATGCCCGACGGCGAGGA

TCTCGTCGTGACCCATGGCGATGCCTGCTTGCCGAATATCATGGTGGAAAATGGCCGCTTTTCTGGATTCATC

GACTGTGGCCGGCTGGGTGTGGCGGACCGCTATCAGGACATAGCGTTGGCTACCCGTGATATTGCTGAAGAGC

TTGGCGGCGAATGGGCTGACCGCTTCCTCGTGCTTTACGGTATCGCCGCTCCCGATTCGCAGCGCATCGCCTT

CTATCGCCTTCTTGACGAGTTCTTCTGAGCGGGACTCTGGGGTTCGAAATGACCGACCAAGCGACGCCCAACC

TGCCATCACGAGATTTCGATTCCACCGCCGCCTTCTATGAAAGGTTGGGCTTCGGAATCGTTTTCCGGGACGC

CGGCTGGATGATCCTCCAGCGCGGGGATCTCATGCTGGAGTTCTTCGCCCACCCCAACTTGTTTATTGCAGCT

TATAATGGTTACAAATAAAGCAATAGCATCACAAATTTCACAAATAAAGCATTTTTTTCACTGCATTCTAGTT

GTGGTTTGTCCAAACTCATCAATGTATCTTATCATGTCTGTATACCGTCGACCTCTAGCTAGAGCTTGGCGTA

ATCATGGTCATAGCTGTTTCCTGTGTGAAATTGTTATCCGCTCACAATTCCACACAACATACGAGCCGGAAGC

ATAAAGTGTAAAGCCTGGGGTGCCTAATGAGTGAGCTAACTCACATTAATTGCGTTGCGCTCACTGCCCGCTT

TCCAGTCGGGAAACCTGTCGTGCCAGCTGCATTAATGAATCGGCCAACGCGCGGGGAGAGGCGGTTTGCGTAT

TGGGCGCTCTTCCGCTTCCTCGCTCACTGACTCGCTGCGCTCGGTCGTTCGGCTGCGGCGAGCGGTATCAGCT

CACTCAAAGGCGGTAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCCCCCCTGACGAGCA

TCACAAAAATCGACGCTCAAGTCAGAGGTGGCGAAACCCGACAGGACTATAAAGATACCAGGCGTTTCCCCCT

GGAAGCTCCCTCGTGCGCTCTCCTGTTCCGACCCTGCCGCTTACCGGATACCTGTCCGCCTTTCTCCCTTCGG

GAAGCGTGGCGCTTTCTCATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTATCGTCTTGAGTCCAACCCG

-continued

GTAAGACACGACTTATCGCCACTGGCAGCAGCCACTGGTAACAGGATTAGCAGAGCGAGGTATGTAGGCGGTG

CTACAGAGTTCTTGAAGTGGTGGCCTAACTACGGCTACACTAGAAGAACAGTATTTGGTATCTGCGCTCTGCT

GAAGCCAGTTACCTTCGGAAAAAGAGTTGGTAGCTCTTGATCCGGCAAACAAACCACCGCTGGTAGCGGTGGT

TTTTTTGTTTGCAAGCAGCAGATTACGCGCAGAAAAAAAGGATCTCAAGAAGATCCTTTGATCTTTTCTACGG

GGTCTGACGCTCAGTGGAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTAAACTTGGTCTGACAGT

TACCAATGCTTAATCAGTGAGGCACCTATCTCAGCGATCTGTCTATTTCGTTCATCCATAGTTGCCTGACTCC

CCGTCGTGTAGATAACTACGATACGGGAGGGCTTACCATCTGGCCCCAGTGCTGCAATGATACCGCGAGACCC

ACGCTCACCGGCTCCAGATTTATCAGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAGTAAGTAGTTCGCCAGTTAATAGTT

TGCGCAACGTTGTTGCCATTGCTACAGGCATCGTGGTGTCACGCTCGTCGTTTGGTATGGCTTCATTCAGCTC

CGGTTCCCAACGATCAAGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCACTGCATAATTCTCTTA

CTGTCATGCCATCCGTAAGATGCTTTTCTGTGACTGGTGAGTACTCAACCAAGTCATTCTGAGAATAGTGTAT

GCGGCGACCGAGTTGCTCTTGCCCGGCGTCAATACGGGATAATACCGCGCCACATAGCAGAACTTTAAAAGTG

CTCATCATTGGAAAACGTTCTTCGGGGCGAAAACTCTCAAGGATCTTACCGCTGTTGAGATCCAGTTCGATGT

AACCCACTCGTGCACCCAACTGATCTTCAGCATCTTTTACTTTCACCAGCGTTTCTGGGTGAGCAAAAACAGG

AAGGCAAAATGCCGCAAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTATTTAGAAAAATAAAC

AAATAGGGGTTCCGCGCACATTTCCCCGAAAAGTGCCACCTGACGTC

CAG_Kozak_ENPP1 Full Length_FLAG_pcDNA3.1 (+)

pcDNA3.1+, CAG promoter, Kozak seq, ENPP1 full length seq, Flag tag, Stop codon

(SEQ ID NO: 83)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGCGTTACATAACTTACGGTAAATGGCCCGCCTGGCTGACCGCCCAACGACCCCCGCCC

ATTGACGTCAATAATGACGTATGTTCCCATAGTAACGCCAATAGGGACTTTCCATTGACGTCAATGGGTGGAG

TATTTACGGTAAACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTTGGCAGTACAT

CTACGTATTAGTCATCGCTATTACCATGGTCGAGGTGAGCCCCACGTTCTGCTTCACTCTCCCCATCTCCCCC

CCCTCCCCACCCCCAATTTTGTATTTATTTATTTTTTAATTATTTTGTGCAGCGATGGGGGCGGGGGGGGGGG

GGGGGCGCGCGCCAGGCGGGGCGGGGCGGGGCGAGGGGCGGGGCGGGGCGAGGCGGAGAGGTGCGGCGGCAGC

CAATCAGAGCGGCGCGCTCCGAAAGTTTCCTTTTATGGCGAGGCGGCGGCGGCGGCGGCCCTATAAAAAGCGA

AGCGCGCGGCGGGCGCTCTGGCTAACTAGAGAACCCACTGCTTACTGGCTTATCGAAATTTAATACGACTCACT

ATAGGGAGACCCAAGCTGGCTAGCGCCACCATGGAGCGCGACGGCTGCGCGGGGGGCGGGAGCCGCGGCGGCG

AGGGCGGGCGCGCTCCCCGGGAGGGCCCGGCGGGGAACGGCCGCGATCGGGGCCGCAGCCACGCTGCCGAGGC

GCCCGGGGACCCGCAGGCCGCGGCGTCCTTGCTGGCCCCTATGGACGTGGGGGAGGAGCCGCTGGAGAAGGCG

GCGCGCGCCCGCACTGCCAAGGACCCCAACACCTATAAAGTACTCTCGCTGGTATTGTCAGTATGTGTGTTAA

-continued

CAACAATACTTGGTTGTATATTTGGGTTGAAACCAAGCTGTGCCAAAGAAGTTAAAAGTTGCAAAGGTCGCTG

TTTCGAGAGAACATTTGGGAACTGTCGCTGTGATGCTGCCTGTGTTGAGCTTGGAAACTGCTGTTTAGATTAC

CAGGAGACGTGCATAGAACCAGAACATATATGGACTTGCAACAAATTCAGGTGTGGTGAGAAAAGGTTGACCA

GAAGCCTCTGTGCCTGTTCAGATGACTGCAAGGACAAGGGCGACTGCTGCATCAACTACAGTTCTGTGTGTCA

AGGTGAGAAAAGTTGGGTAGAAGAACCATGTGAGAGCATTAATGAGCCACAGTGCCCAGCAGGGTTTGAAACG

CCTCCTACCCTCTTATTTTCTTTGGATGGATTCAGGGCAGAATATTTACACACTTGGGGTGGACTTCTTCCTG

TTATTAGCAAACTAAAAAAATGTGGAACATATACTAAAAACATGAGACCGGTATATCCAACAAAAACTTTCCC

CAATCACTACAGCATTGTCACCGGATTGTATCCAGAATCTCATGGCATAATCGACAATAAAATGTATGATCCC

AAAATGAATGCTTCCTTTTCACTTAAAAGTAAAGAGAAATTTAATCCTGAGTGGTACAAAGGAGAACCAATTT

GGGTCACAGCTAAGTATCAAGGCCTCAAGTCTGGCACATTTTTCTGGCCAGGATCAGATGTGGAAATTAACGG

AATTTTCCCAGACATCTATAAAATGTATAATGGTTCAGTACCATTTGAAGAAAGGATTTTAGCTGTTCTTCAG

TGGCTACAGCTTCCTAAAGATGAAAGACCACACTTTTACACTCTGTATTTAGAAGAACCAGATTCTTCAGGTC

ATTCATATGGACCAGTCAGCAGTGAAGTCATCAAAGCCTTGCAGAGGGTTGATGGTATGGTTGGTATGCTGAT

GGATGGTCTGAAAGAGCTGAACTTGCACAGATGCCTGAACCTCATCCTTATTTCAGATCATGGCATGGAACAA

GGCAGTTGTAAGAAATACATATATCTGAATAAATATTTGGGGGATGTTAAAAATATTAAAGTTATCTATGGAC

CTGCAGCTCGATTGAGACCCTCTGATGTCCCAGATAAATACTATTCATTTAACTATGAAGGCATTGCCCGAAA

TCTTTCTTGCCGGGAACCAAACCAGCACTTCAAACCTTACCTGAAACATTTCTTACCTAAGCGTTTGCACTTT

GCTAAGAGTGATAGAATTGAGCCCTTGACATTCTATTTGGACCCTCAGTGGCAACTTGCATTGAATCCCTCAG

AAAGGAAATATTGTGGAAGTGGATTTCATGGCTCTGACAATGTATTTTCAAATATGCAAGCCCTCTTTGTTGG

CTATGGACCTGGATTCAAGCATGGCATTGAGGCTGACACCTTTGAAAACATTGAAGTCTATAACTTAATGTGT

GATTTACTGAATTTGACACCGGCTCCTAATAACGGAACTCATGGAAGTCTTAACCACCTTCTAAAGAATCCTG

TTTATACGCCAAAGCATCCCAAAGAAGTGCACCCCCTGGTACAGTGCCCCTTCACAAGAAACCCCAGAGATAA

CCTTGGCTGCTCATGTAACCCTTCGATTTTGCCGATTGAGGATTTTCAAACACAGTTCAATCTGACTGTGGCA

GAAGAGAAGATTATTAAGCATGAAACTTTACCCTATGGAAGACCTAGAGTTCTCCAGAAGGAAAACACCATCT

GTCTTCTTTCCCAGCACCAGTTTATGAGTGGATACAGCCAAGACATCTTAATGCCCCTTTGGACATCCTATAC

CGTGGACAGAAATGACAGTTTCTCTACGGAAGACTTCTCCAACTGTCTGTACCAGGACTTTAGAATTCCTCTT

AGTCCTGTCCATAAATGTTCATTTTATAAAAATAACACCAAAGTGAGTTACGGGTTCCTCTCCCCACCACAAC

TAAATAAAAATTCAAGTGGAATATATTCTGAAGCTTTGCTTACTACAAATATAGTGCCAATGTACCAGAGTTT

AGCTGTGTGCATGGGAAGCATGACTCCTCATGGGTTGAAGAATTGTTAATGTTACACAGAGCACGGATCACAG

ATGTTGAGCACATCACTGGACTCAGCTTCTATCAACAAAGAAAAGAGCCAGTTTCAGACATTTTAAAGTTGAA

AACACATTTGCCAACCTTTAGCCAAGAAGACGACTACAAAGACGATGACGACAAGTGAGGTACCGAGCTCGGA

TCCACTAGTCCAGTGTGGTGGAATTCTGCAGATATCCAGCACAGTGGCGGCCGCTCGAGTCTAGAGGGCCCGT

TTAAACCCGCTGATCAGCCTCGACTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGAGGAAATTGCATCGCATTGTCTGA

GTAGGTGTCATTCTATTCTGGGGGGTGGGGTGGGGCAGGACAGCAAGGGGGAGGATTGGGAAGACAATAGCAG

GCATGCTGGGGATGCGGTGGGCTCTATGGCTTCTGAGGCGGAAAGAACCAGCTGGGGCTCTAGGGGGTATCCC

CACGCGCCCTGTAGCGGCGCATTAAGCGCGGCGGGTGTGGTGGTTACGCGCAGCGTGACCGCTACACTTGCCA

GCGCCCTAGCGCCCGCTCCTTTCGCTTTCTTCCCTTCCTTTCTCGCCACGTTCGCCGGCTTTCCCCGTCAAGC

TCTAAATCGGGGGCTCCCTTTAGGGTTCCGATTTAGTGCTTTACGGCACCTCGACCCCAAAAAACTTGATTAG

-continued

GGTGATGGTTCACGTAGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGCGAATTAATTCTGT

GGAATGTGTGTCAGTTAGGGTGTGGAAAGTCCCCAGGCTCCCCAGCAGGCAGAAGTATGCAAAGCATGCATCT

CAATTAGTCAGCAACCAGGTGTGGAAAGTCCCCAGGCTCCCCAGCAGGCAGAAGTATGCAAAGCATGCATCTC

AATTAGTCAGCAACCATAGTCCCGCCCCTAACTCCGCCCATCCCGCCCCTAACTCCGCCCAGTTCCGCCCATT

CTCCGCCCCATGGCTGACTAATTTTTTTTATTTATGCAGAGGCCGAGGCCGCCTCTGCCTCTGAGCTATTCCA

GAAGTAGTGAGGAGGCTTTTTTGGAGGCCTAGGCTTTTGCAAAAAGCTCCCGGGAGCTTGTATATCCATTTTC

GGATCTGATCAAGAGACAGGATGAGGATCGTTTCGCATGATTGAACAAGATGGATTGCACGCAGGTTCTCCGG

CCGCTTGGGTGGAGAGGCTATTCGGCTATGACTGGGCACAACAGACAATCGGCTGCTCTGATGCCGCCGTGTT

CCGGCTGTCAGCGCAGGGGCGCCCGGTTCTTTTTGTCAAGACCGACCTGTCCGGTGCCCTGAATGAACTGCAG

GACGAGGCAGCGCGGCTATCGTGGCTGGCCACGACGGGCGTTCCTTGCGCAGCTGTGCTCGACGTTGTCACTG

AAGCGGGAAGGGACTGGCTGCTATTGGGCGAAGTGCCGGGGCAGGATCTCCTGTCATCTCACCTTGCTCCTGC

CGAGAAAGTATCCATCATGGCTGATGCAATGCGGCGGCTGCATACGCTTGATCCGGCTACCTGCCCATTCGAC

CACCAAGCGAAACATCGCATCGAGCGAGCACGTACTCGGATGGAAGCCGGTCTTGTCGATCAGGATGATCTGG

ACGAAGAGCATCAGGGGCTCGCGCCAGCCGAACTGTTCGCCAGGCTCAAGGCGCGCATGCCCGACGGCGAGGA

TCTCGTCGTGACCCATGGCGATGCCTGCTTGCCGAATATCATGGTGGAAAATGGCCGCTTTTCTGGATTCATC

GACTGTGGCCGGCTGGGTGTGGCGGACCGCTATCAGGACATAGCGTTGGCTACCCGTGATATTGCTGAAGAGC

TTGGCGGCGAATGGGCTGACCGCTTCCTCGTGCTTTACGGTATCGCCGCTCCCGATTCGCAGCGCATCGCCTT

CTATCGCCTTCTTGACGAGTTCTTCTGAGCGGGACTCTGGGGTTCGAAATGACCGACCAAGCGACGCCCAACC

TGCCATCACGAGATTTCGATTCCACCGCCGCCTTCTATGAAAGGTTGGGCTTCGGAATCGTTTTCCGGGACGC

CGGCTGGATGATCCTCCAGCGCGGGGATCTCATGCTGGAGTTCTTCGCCCACCCCAACTTGTTTATTGCAGCT

TATAATGGTTACAAATAAAGCAATAGCATCACAAATTTCACAAATAAAGCATTTTTTTCACTGCATTCTAGTT

GTGGTTTGTCCAAACTCATCAATGTATCTTATCATGTCTGTATACCGTCGACCTCTAGCTAGAGCTTGGCGTA

ATCATGGTCATAGCTGTTTCCTGTGTGAAATTGTTATCCGCTCACAATTCCACACAACATACGAGCCGGAAGC

ATAAAGTGTAAAGCCTGGGGTGCCTAATGAGTGAGCTAACTCACATTAATTGCGTTGCGCTCACTGCCCGCTT

TCCAGTCGGGAAACCTGTCGTGCCAGCTGCATTAATGAATCGGCCAACGCGCGGGGAGAGGCGGTTTGCGTAT

TGGGCGCTCTTCCGCTTCCTCGCTCACTGACTCGCTGCGCTCGGTCGTTCGGCTGCGGCGAGCGGTATCAGCT

CACTCAAAGGCGGTAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCCCCCCTGACGAGCA

TCACAAAAATCGACGCTCAAGTCAGAGGTGGCGAAACCCGACAGGACTATAAAGATACCAGGCGTTTCCCCCT

GGAAGCTCCCTCGTGCGCTCTCCTGTTCCGACCCTGCCGCTTACCGGATACCTGTCCGCCTTTCTCCCTTCGG

GAAGCGTGGCGCTTTCTCATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGCGAGGTATGTAGGCGGTG

CTACAGAGTTCTTGAAGTGGTGGCCTAACTACGGCTACACTAGAAGAACAGTATTTGGTATCTGCGCTCTGCT

GAAGCCAGTTACCTTCGGAAAAAGAGTTGGTAGCTCTTGATCCGGCAAACAAACCACCGCTGGTAGCGGTGGT

TTTTTTGTTTGCAAGCAGCAGATTACGCGCAGAAAAAAAGGATCTCAAGAAGATCCTTTGATCTTTTCTACGG

GGTCTGACGCTCAGTGGAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTAAACTTGGTCTGACAGT

-continued

TACCAATGCTTAATCAGTGAGGCACCTATCTCAGCGATCTGTCTATTTCGTTCATCCATAGTTGCCTGACTCC

CCGTCGTGTAGATAACTACGATACGGGAGGGCTTACCATCTGGCCCCAGTGCTGCAATGATACCGCGAGACCC

ACGCTCACCGGCTCCAGATTTATCAGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAGTAAGTAGTTCGCCAGTTAATAGTT

TGCGCAACGTTGTTGCCATTGCTACAGGCATCGTGGTGTCACGCTCGTCGTTTGGTATGGCTTCATTCAGCTC

CGGTTCCCAACGATCAAGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCACTGCATAATTCTCTTA

CTGTCATGCCATCCGTAAGATGCTTTTCTGTGACTGGTGAGTACTCAACCAAGTCATTCTGAGAATAGTGTAT

GCGGCGACCGAGTTGCTCTTGCCCGGCGTCAATACGGGATAATACCGCGCCACATAGCAGAACTTTAAAAGTG

CTCATCATTGGAAAACGTTCTTCGGGGCGAAAACTCTCAAGGATCTTACCGCTGTTGAGATCCAGTTCGATGT

AACCCACTCGTGCACCCAACTGATCTTCAGCATCTTTTACTTTCACCAGCGTTTCTGGGTGAGCAAAAACAGG

AAGGCAAAATGCCGCAAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTATTTAGAAAAATAAAC

AAATAGGGGTTCCGCGCACATTTCCCCGAAAAGTGCCACCTGACGTC hMyh11_Kozak_ENPP1 Full Length_FLAG_pcDNA3.1 (+)

pcDNA3.1+, Myh11 promoter, Kozak seq, ENPP1 full length seg, Flag tag,

Stop codon

(SEQ ID NO: 84)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTCGCCGGGGAGCAGGAAGGCCACTCGGCACCATATTTAGTCAGGGGGAGCCGGCAGCCC

AGAGCTGGTATGCGGCGCTGGGAATTCCTGCAGGAAGGAGTCCGCGCCTGCCCTTTTTGGGTTGTCTCCCGCC

CGCCGCTCCCGCCGCTCCCGGGGAGGGGGACCGGCCCGGCCCGGCCCGGCCCGGGAACCTCGGAGGAGCTGGT

GCCGCGCGGGGAGCGGAGCGCCCGGGCTGCCCGCGGGTCCCCGGCCTGGCGCGGGGCCAGCCCACCGCCTCGA

CTTCCTTTTATGGCCTGTGTGTGCGTGCGTGGACAGGAGCGGGGAGGGAGGGACGGGGAGAAGACGGAGAGCC

TGGGGAAGAGAGAGAGAGAAAGCGCAGAGATAGGAGTGAGACACGCGGGAGAGATGGAGAGCAAGAGACACAG

AGACCAGAGACAAAGTGAGACAGGAGGGAGAGACAGATACATCGACAGATCTAGAGAAGCGAGAGGGACAGAG

ACAAAAGATAGAGCGAGAGACAGCAATGATCAGAGTGACAGACATGCAGAGACAGTGGCAGAGACAGAGCGAG

AGAGCCTGTGATGGAGAGAGACAGGGAATGCAATTTTAGGCGAGGAATCCTTGGGGAAGGGAAGTTGTTGAAG

GGAACTCGCAGACTCTGGGGGCACACCCACTTTCTCCTTGGATCTTGACACTTGCATCTTGTAAATAACGTAA

TTATCACCGCCACCGCCTTCCCCCATTTTGTAGCTATGGACACCAAGTCTCAGAGAAGTGAAGTGACTTGCCC

AAGGTCACGCAGCTGGCGAGTGGCGCACAGGGGAGGGGGACAGCTGAAATAATCACAGTGGGCTTATTTTTAA

TTTTTATTTGTATTTTGGTCGTGGTGATGTGGGTGGAGGTGGAGATGGCAAGTTGGGAAAAGTAAAAACTTCC

CCTTCCTGCACGGTTCCCAGCAAGGGTGGGGGCCTCCTGTCTTGCACTTTGCAAAGTTCAAGAAATCCCCTTT

CCCTACCCTTCACGCTGCACAGCCGGCCCTCTTTCCAGACAGTGCGATGCCAATAAAATGGGAAGTGGGGTGG

GAGATGTCAAGTCAGATCCACCACAGCCCCGACACGGGGAGGAAGAGGTTAAAGCCTTTGCGGCCGGAACCGA

CTCAGGGAAGACGTTCTCAAGCATCCCGCACAGACACTGCCTGCTCGACCCCCTTTCTCTAGGGATCCGGAGC

GTCTGCGACCGCCTGGGGCCGGGGCTGAGACTCCCGTCCCTGTGCGCACCTGTTCCGTGCGCCCTTGTGCGGT

-continued

GCGCACCTGTTCCGTGCACCCTTGTCCCGAGCGCCCCAGCTCCTTGCGCTCCCGCCGGGGGTGCGCCCTGCAG

GGGGCGCGGCGAGGGGGCCGCGAGGGACCCTCCCCAACTCCACCCCTTCGGCCTCCTCCCCTTTCCCAGCCGC

GGGCAGCTCCGGGTCTATAAAGAGAGGCGTCCGAGGACGCGCAGGGAGATTTGGACGCTCCGGCCTGGGAGGT

GCGTCAGATCCGAGCTCGCCATCCAGTTTCCTCTCCACTAGTCCCCCCAGTTGGAGATCTGTAAGTAGTAGTT

GTCATTCTGGGGGCAGATTGCAGGGCAGGGGGGTGTTAAAAGTCCTATAGGGTATTCTATAGGGGCTGGGGTG

CACTTAGGGGTCTCTGGCTAACTAGAGAACCCACTGCTTACTGGCTTATCGAAATTAATACGACTCACTATAG

GGAGACCCAAGCTGGCTAGCGCCACCATGGAGCGCGACGGCTGCGCGGGGGGCGGGAGCCGCGGCGGCGAGGG

CGGGCGCGCTCCCCGGGAGGGCCCGGCGGGGAACGGCCGCGATCGGGGCCGCAGCCACGCTGCCGAGGCGCCC

GGGGACCCGCAGGCCGCGGCGTCCTTGCTGGCCCCTATGGACGTGGGGGAGGAGCCGCTGGAGAAGGCGGCGC

GCGCCCGCACTGCCAAGGACCCCAACACCTATAAAGTACTCTCGCTGGTATTGTCAGTATGTGTGTTAACAAC

AATACTTGGTTGTATATTTGGGTTGAAACCAAGCTGTGCCAAAGAAGTTAAAAGTTGCAAAGGTCGCTGTTTC

GAGAGAACATTTGGGAACTGTCGCTGTGATGCTGCCTGTGTTGAGCTTGGAAACTGCTGTTTAGATTACCAGG

AGACGTGCATAGAACCAGAACATATATGGACTTGCAACAAATTCAGGTGTGGTGAGAAAAGGTTGACCAGAAG

CCTCTGTGCCTGTTCAGATGACTGCAAGGACAAGGGCGACTGCTGCATCAACTACAGTTCTGTGTGTCAAGGT

GAGAAAAGTTGGGTAGAAGAACCATGTGAGAGCATTAATGAGCCACAGTGCCCAGCAGGGTTTGAAACGCCTC

CTACCCTCTTATTTTCTTTGGATGGATTCAGGGCAGAATATTTACACACTTGGGGTGGACTTCTTCCTGTTAT

TAGCAAACTAAAAAAATGTGGAACATATACTAAAAACATGAGACCGGTATATCCAACAAAAACTTTCCCCAAT

CACTACAGCATTGTCACCGGATTGTATCCAGAATCTCATGGCATAATCGACAATAAAATGTATGATCCCAAAA

TGAATGCTTCCTTTTCACTTAAAAGTAAAGAGAAATTTAATCCTGAGTGGTACAAAGGAGAACCAATTTGGGT

CACAGCTAAGTATCAAGGCCTCAAGTCTGGCACATTTTTCTGGCCAGGATCAGATGTGGAAATTAACGGAATT

TTCCCAGACATCTATAAAATGTATAATGGTTCAGTACCATTTGAAGAAAGGATTTTAGCTGTTCTTCAGTGGC

TACAGCTTCCTAAAGATGAAAGACCACACTTTTACACTCTGTATTTAGAAGAACCAGATTCTTCAGGTCATTC

ATATGGACCAGTCAGCAGTGAAGTCATCAAAGCCTTGCAGAGGGTTGATGGTATGGTTGGTATGCTGATGGAT

GGTCTGAAAGAGCTGAACTTGCACAGATGCCTGAACCTCATCCTTATTTCAGATCATGGCATGGAACAAGGCA

GTTGTAAGAAATACATATATCTGAATAAATATTTGGGGGATGTTAAAAATATTAAAGTTATCTATGGACCTGC

AGCTCGATTGAGACCCTCTGATGTCCCAGATAAATACTATTCATTTAACTATGAAGGCATTGCCCGAAATCTT

TCTTGCCGGGAACCAAACCAGCACTTCAAACCTTACCTGAAACATTTCTTACCTAAGCGTTTGCACTTTGCTA

AGAGTGATAGAATTGAGCCCTTGACATTCTATTTGGACCCTCAGTGGCAACTTGCATTGAATCCCTCAGAAAG

GAAATATTGTGGAAGTGGATTTCATGGCTCTGACAATGTATTTTCAAATATGCAAGCCCTCTTTGTTGGCTAT

GGACCTGGATTCAAGCATGGCATTGAGGCTGACACCTTTGAAAACATTGAAGTCTATAACTTAATGTGTGATT

TACTGAATTTGACACCGGCTCCTAATAACGGAACTCATGGAAGTCTTAACCACCTTCTAAAGAATCCTGTTTA

TACGCCAAAGCATCCCAAAGAAGTGCACCCCCTGGTACAGTGCCCCTTCACAAGAAACCCCAGAGATAACCTT

GGCTGCTCATGTAACCCTTCGATTTTGCCGATTGAGGATTTTCAAACACAGTTCAATCTGACTGTGGCAGAAG

AGAAGATTATTAAGCATGAAACTTTACCCTATGGAAGACCTAGAGTTCTCCAGAAGGAAAACACCATCTGTCT

TCTTTCCCAGCACCAGTTTATGAGTGGATACAGCCAAGACATCTTAATGCCCCTTTGGACATCCTATACCGTG

GACAGAAATGACAGTTTCTCTACGGAAGACTTCTCCAACTGTCTGTACCAGGACTTTAGAATTCCTCTTAGTC

CTGTCCATAAATGTTCATTTTATAAAAATAACACCAAAGTGAGTTACGGGTTCCTCTCCCCACCACAACTAAA

TAAAAATTCAAGTGGAATATATTCTGAAGCTTTGCTTACTACAAATATAGTGCCAATGTACCAGAGTTTTCAA

GTTATATGGCGCTACTTTCATGACACCCTACTGCGAAAGTATGCTGAAGAAAGAAATGGTGTCAATGTCGTCA

GTGGTCCTGTGTTTGACTTTGATTATGATGGACGTTGTGATTCCTTAGAGAATCTGAGGCAAAAAAGAAGAGT

-continued

CATCCGTAACCAAGAAATTTTGATTCCAACTCACTTCTTTATTGTGCTAACAAGCTGTAAAGATACATCTCAG

ACGCCTTTGCACTGTGAAAACCTAGACACCTTAGCTTTCATTTTGCCTCACAGGACTGATAACAGCGAGAGCT

GTGTGCATGGGAAGCATGACTCCTCATGGGTTGAAGAATTGTTAATGTTACACAGAGCACGGATCACAGATGT

TGAGCACATCACTGGACTCAGCTTCTATCAACAAAGAAAAGAGCCAGTTTCAGACATTTTAAAGTTGAAAACA

CATTTGCCAACCTTTAGCCAAGAAGACGACTACAAAGACGATGACGACAAGTGAGGTACCGAGCTCGGATCCA

CTAGTCCAGTGTGGTGGAATTCTGCAGATATCCAGCACAGTGGCGGCCGCTCGAGTCTAGAGGGCCCGTTTAA

ACCCGCTGATCAGCCTCGACTGTGCCTTCTAGTTGCCAGCCATCTGTTGTTTGCCCCTCCCCCGTGCCTTCCT

TGACCCTGGAAGGTGCCACTCCCACTGTCCTTTCCTAATAAAATGAGGAAATTGCATCGCATTGTCTGAGTAG

GTGTCATTCTATTCTGGGGGGTGGGGTGGGGCAGGACAGCAAGGGGGAGGATTGGGAAGACAATAGCAGGCAT

GCTGGGGATGCGGTGGGCTCTATGGCTTCTGAGGCGGAAAGAACCAGCTGGGGCTCTAGGGGGTATCCCCACG

CGCCCTGTAGCGGCGCATTAAGCGCGGCGGGTGTGGTGGTTACGCGCAGCGTGACCGCTACACTTGCCAGCGC

CCTAGCGCCCGCTCCTTTCGCTTTCTTCCCTTCCTTTCTCGCCACGTTCGCCGGCTTTCCCCGTCAAGCTCTA

AATCGGGGGCTCCCTTTAGGGTTCCGATTTAGTGCTTTACGGCACCTCGACCCCAAAAAACTTGATTAGGGTG

ATGGTTCACGTAGTGGGCCATCGCCCTGATAGACGGTTTTTCGCCCTTTGACGTTGGAGTCCACGTTCTTTAA

TAGTGGACTCTTGTTCCAAACTGGAACAACACTCAACCCTATCTCGGTCTATTCTTTTGATTTATAAGGGATT

TTGCCGATTTCGGCCTATTGGTTAAAAAATGAGCTGATTTAACAAAAATTTAACGCGAATTAATTCTGTGGAA

TGTGTGTCAGTTAGGGTGTGGAAAGTCCCCAGGCTCCCCAGCAGGCAGAAGTATGCAAAGCATGCATCTCAAT

TAGTCAGCAACCAGGTGTGGAAAGTCCCCAGGCTCCCCAGCAGGCAGAAGTATGCAAAGCATGCATCTCAATT

AGTCAGCAACCATAGTCCCGCCCCTAACTCCGCCCATCCCGCCCCTAACTCCGCCCAGTTCCGCCCATTCTCC

GCCCCATGGCTGACTAATTTTTTTTATTTATGCAGAGGCCGAGGCCGCCTCTGCCTCTGAGCTATTCCAGAAG

TAGTGAGGAGGCTTTTTTGGAGGCCTAGGCTTTTGCAAAAAGCTCCCGGGAGCTTGTATATCCATTTTCGGAT

CTGATCAAGAGACAGGATGAGGATCGTTTCGCATGATTGAACAAGATGGATTGCACGCAGGTTCTCCGGCCGC

TTGGGTGGAGAGGCTATTCGGCTATGACTGGGCACAACAGACAATCGGCTGCTCTGATGCCGCCGTGTTCCGG

CTGTCAGCGCAGGGGCGCCCGGTTCTTTTTGTCAAGACCGACCTGTCCGGTGCCCTGAATGAACTGCAGGACG

AGGCAGCGCGGCTATCGTGGCTGGCCACGACGGGCGTTCCTTGCGCAGCTGTGCTCGACGTTGTCACTGAAGC

GGGAAGGGACTGGCTGCTATTGGGCGAAGTGCCGGGGCAGGATCTCCTGTCATCTCACCTTGCTCCTGCCGAG

AAAGTATCCATCATGGCTGATGCAATGCGGCGGCTGCATACGCTTGATCCGGCTACCTGCCCATTCGACCACC

AAGCGAAACATCGCATCGAGCGAGCACGTACTCGGATGGAAGCCGGTCTTGTCGATCAGGATGATCTGGACGA

AGAGCATCAGGGGCTCGCGCCAGCCGAACTGTTCGCCAGGCTCAAGGCGCGCATGCCCGACGGCGAGGATCTC

GTCGTGACCCATGGCGATGCCTGCTTGCCGAATATCATGGTGGAAAATGGCCGCTTTTCTGGATTCATCGACT

GTGGCCGGCTGGGTGTGGCGGACCGCTATCAGGACATAGCGTTGGCTACCCGTGATATTGCTGAAGAGCTTGG

CGGCGAATGGGCTGACCGCTTCCTCGTGCTTTACGGTATCGCCGCTCCCGATTCGCAGCGCATCGCCTTCTAT

CGCCTTCTTGACGAGTTCTTCTGAGCGGGACTCTGGGGTTCGAAATGACCGACCAAGCGACGCCCAACCTGCC

ATCACGAGATTTCGATTCCACCGCCGCCTTCTATGAAAGGTTGGGCTTCGGAATCGTTTTCCGGGACGCCGGC

TGGATGATCCTCCAGCGCGGGGATCTCATGCTGGAGTTCTTCGCCCACCCCAACTTGTTTATTGCAGCTTATA

ATGGTTACAAATAAAGCAATAGCATCACAAATTTCACAAATAAAGCATTTTTTTCACTGCATTCTAGTTGTGG

TTTGTCCAAACTCATCAATGTATCTTATCATGTCTGTATACCGTCGACCTCTAGCTAGAGCTTGGCGTAATCA

TGGTCATAGCTGTTTCCTGTGTGAAATTGTTATCCGCTCACAATTCCACACAACATACGAGCCGGAAGCATAA

AGTGTAAAGCCTGGGGTGCCTAATGAGTGAGCTAACTCACATTAATTGCGTTGCGCTCACTGCCCGCTTTCCA

-continued

GTCGGGAAACCTGTCGTGCCAGCTGCATTAATGAATCGGCCAACGCGCGGGGAGAGGCGGTTTGCGTATTGGG

CGCTCTTCCGCTTCCTCGCTCACTGACTCGCTGCGCTCGGTCGTTCGGCTGCGGCGAGCGGTATCAGCTCACT

CAAAGGCGGTAATACGGTTATCCACAGAATCAGGGGATAACGCAGGAAAGAACATGTGAGCAAAAGGCCAGCA

AAAGGCCAGGAACCGTAAAAAGGCCGCGTTGCTGGCGTTTTTCCATAGGCTCCGCCCCCCTGACGAGCATCAC

AAAAATCGACGCTCAAGTCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTTTCTCCCTTCGGGAAG

CGTGGCGCTTTCTCATAGCTCACGCTGTAGGTATCTCAGTTCGGTGTAGGTCGTTCGCTCCAAGCTGGGCTGT

GTGCACGAACCCCCCGTTCAGCCCGACCGCTGCGCCTTATCCGGTAACTATCGTCTTGAGTCCAACCCGGTAA

GACACGACTTATCGCCACTGGCAGCAGCCACTGGTAACAGGATTAGCAGAGCGAGGTATGTAGGCGGTGCTAC

AGAGTTCTTGAAGTGGTGGCCTAACTACGGCTACACTAGAAGAACAGTATTTGGTATCTGCGCTCTGCTGAAG

CCAGTTACCTTCGGAAAAAGAGTTGGTAGCTCTTGATCCGGCAAACAAACCACCGCTGGTAGCGGTGGTTTTT

TTGTTTGCAAGCAGCAGATTACGCGCAGAAAAAAAGGATCTCAAGAAGATCCTTTGATCTTTTCTACGGGGTC

TGACGCTCAGTGGAACGAAAACTCACGTTAAGGGATTTTGGTCATGAGATTATCAAAAAGGATCTTCACCTAG

ATCCTTTTAAATTAAAAATGAAGTTTTAAATCAATCTAAAGTATATATGAGTAAACTTGGTCTGACAGTTACC

AATGCTTAATCAGTGAGGCACCTATCTCAGCGATCTGTCTATTTCGTTCATCCATAGTTGCCTGACTCCCCGT

CGTGTAGATAACTACGATACGGGAGGGCTTACCATCTGGCCCCAGTGCTGCAATGATACCGCGAGACCCACGC

TCACCGGCTCCAGATTTATCAGCAATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGTAGTTCGCCAGTTAATAGTTTGCG

CAACGTTGTTGCCATTGCTACAGGCATCGTGGTGTCACGCTCGTCGTTTGGTATGGCTTCATTCAGCTCCGGT

TCCCAACGATCAAGGCGAGTTACATGATCCCCCATGTTGTGCAAAAAAGCGGTTAGCTCCTTCGGTCCTCCGA

TCGTTGTCAGAAGTAAGTTGGCCGCAGTGTTATCACTCATGGTTATGGCAGCACTGCATAATTCTCTTACTGT

CATGCCATCCGTAAGATGCTTTTCTGTGACTGGTGAGTACTCAACCAAGTCATTCTGAGAATAGTGTATGCGG

CGACCGAGTTGCTCTTGCCCGGCGTCAATACGGGATAATACCGCGCCACATAGCAGAACTTTAAAAGTGCTCA

TCATTGGAAAACGTTCTTCGGGGCGAAAACTCTCAAGGATCTTACCGCTGTTGAGATCCAGTTCGATGTAACC

CACTCGTGCACCCAACTGATCTTCAGCATCTTTTACTTTCACCAGCGTTTCTGGGTGAGCAAAAACAGGAAGG

CAAAATGCCGCAAAAAAGGGAATAAGGGCGACACGGAAATGTTGAATACTCATACTCTTCCTTTTTCAATATT

ATTGAAGCATTTATCAGGGTTATTGTCTCATGAGCGGATACATATTTGAATGTATTTAGAAAAATAAACAAAT

AGGGGTTCCGCGCACATTTCCCCGAAAAGTGCCACCTGACGTC

MGP_Kozak_ENPP1 Full Length_FLAG_pcDNA3.1 (+)

pcDNA3.1+, MGP promoter, Kozak seq, ENPP1 full length seg, Flag tag, Stop codon

(SEQ ID NO: 85)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTAAGATTATAGTTGTCATTTGAACTTGGGGATAAAGGAGACATCTATGACTTGGCTGGA

AAAGACAGAGCTAATGTACATTGCAAAGCACATATTTATAGCAGGAAAATGGGAAGATTTCTCTTTAATTCTG

GAGATGGAGTGGGGATGGGGAGAGTAGACTACTCATTTTAAGGGTGAAACATTGGAATTCAACTTGTTTGATG

TTATATTAATTGGTGGTTAATTACTAAGCTAAGTACGTATAAAACTTTTATCTATGGCTAGCTTGTCCCCCCA

AAGTCATGCAATATAGTGAACTGGCTTTCGCACTTTAAATTATTCATTGATCATGTAATGATTCAGATGATTC

-continued

ATCTTCCAAGATGGACACTGAAACTAACACTCATAGTAGGTTGTGGTTTAAAGAGTGGAACAACCGCCAGTCT

CATTAGTGGAAATTGTGATGGTTGAATTTATCAAGGATGAACATACACGGTCTTCTTTCTGAGATTTTCTTTA

AGATTTTCGCACAGATAATCTATTTCTTAGGTTTTGGAGAGAAAACTTGAATTTTATTGATCCCTCAGAACTC

AATCTTTCAGATTTCAAAGGAGCTATTTCTTTTAATGGGGACTCTGTTAATATTTATAAAAGCTCTTCACAGG

ATGGAGGGTGGGAGGGAAACTCCATCCCAACAAGACAAAAAGAATGAAGCATGAGGCTCCACCTAGTTCATCA

CTGCTCCTTGAAATACATCAGTATTGAAAGACACATCCACCCCACCCCCAACCCAGCCCTATTGCTGTTCCAG

CTCAAGAGTCAGAGGTCCCGAAGCTGTAGCTCTTCTACAATCTGCTGCTCTGTGACTTCAAGTCTGTTGTCTG

CAAAGAAAACTATTGGGTTCCCAAGCAAGAGAGGCACATCTGGTAGGACAGATTTTGTGATTGCAAAAGAAGG

GGGAAAAAAAGAAAGAAAGAAAAGACCTCTCTATACAAGATAACCAGAGGCATCAAACTGAAATCCTCCTGTG

GAAAATAAGCTAGTACTTCTGGGCCTGATGGTGTAGTGAAAACCTGTGCTTGAGGATACATTACAGTGAAAGA

GCAAAGTGAATAGTAAGTAGCTATTACTTACCTCCTTAGGGAGGTGTGTTGTTTGTCTGTACATCCCCCACAG

CACCTAGCACAGTACCTTGCATCTCACCTGCCACTCACTAAAAAGTCTATCAAGTTAGTTAATTATCGAGACA

ACGCCCTCAGAAATGAGAGAACAGTACCCTCTTATCCTTGCTGCACTTTCCAGCACTGATACGCTGCCTAAAA

GAGGACTAGGGCACAGGTTTGAATTAATGTCACAAAACTGGATGGGCAAGTTACAACGGTGTTGATTAAGGAA

ACAGAACTCATGGTGCACCGGATATCTCCATCCTGATGAACCCTTGGAAAAATGCCAAAGATGCATATCCCCA

GGCAAATGCCTGATTAGTCTGGGATTGATAGATTGGTCTAGGATTCAGCCCTACTGGGAAGATGTCTAAATTA

TAATCAGTGTAGAAAGCGAAGTTCTCCTAGAAGAAGAGGCAAAGGTTAAAAAGAAGAAAAGAAAAGAAAGTGA

AGTCCTTTCTCCCCCAAAACCTCTCATCAATCAATCAGGGTAACAAACAGAACACTAGGGCTCTGTCTGTGGA

CCAAACCCAAAAGCCCTGCGGTCAGGGCCAGGAGGGTAGATCATGTGTTTGTGGCAACTTCCTCTGTGGGCTT

TTGCCCAGGTCTGTCCCCAAGCATACGATGGCCAAAACTTCTGCACCAGAGCAGCATCCTGTGTAACACAGTC

AGGTCCAGCAGTTAGGGAAAACTGCCCACTCAGAGTAGATAATATCTGGAAGGAATGACTGTTTGGGAAAAGT

TCCAATGCTAGTTCAGTGCCAACCCTTCCCCACCTTCTCCAGCTCTCTCCCACTGGTTCCTCCCCTCTCAACT

GCTCTGGTTCTTATAAAAACCTCACAGCCTTCCACTAACATCCCGTAGGAGCCTCTCTCCCTACTGCTGCTAC

ACAAGACCCTGAGACTGACCTGCAGGACGAAACCCTCTGGCTAACTAGAGAACCCACTGCTTACTGGCTTATC

GAAATTAATACGACTCACTATAGGGAGACCCAAGCTGGCTAGCGCCACCATGGAGCGCGACGGCTGCGCGGGG

GGCGGGAGCCGCGGCGGCGAGGGCGGGCGCGCTCCCCGGGAGGGCCCGGCGGGGAACGGCCGCGATCGGGGCC

GCAGCCACGCTGCCGAGGCGCCCGGGGACCCGCAGGCCGCGGCGTCCTTGCTGGCCCCTATGGACGTGGGGGA

GGAGCCGCTGGAGAAGGCGGCGCGCGCCCGCACTGCCAAGGACCCCAACACCTATAAAGTACTCTCGCTGGTA

TTGTCAGTATGTGTGTTAACAACAATACTTGGTTGTATATTTGGGTTGAAACCAAGCTGTGCCAAAGAAGTTA

AAAGTTGCAAAGGTCGCTGTTTCGAGAGAACATTTGGGAACTGTCGCTGTGATGCTGCCTGTGTTGAGCTTGG

AAACTGCTGTTTAGATTACCAGGAGACGTGCATAGAACCAGAACATATATGGACTTGCAACAAATTCAGGTGT

GGTGAGAAAAGGTTGACCAGAAGCCTCTGTGCCTGTTCAGATGACTGCAAGGACAAGGGCGACTGCTGCATCA

ACTACAGTTCTGTGTGTCAAGGTGAGAAAAGTTGGGTAGAAGAACCATGTGAGAGCATTAATGAGCCACAGTG

CCCAGCAGGGTTTGAAACGCCTCCTACCCTCTTATTTTCTTTGGATGGATTCAGGGCAGAATATTTACACACT

TGGGGTGGACTTCTTCCTGTTATTAGCAAACTAAAAAAATGTGGAACATATACTAAAAACATGAGACCGGTAT

ATCCAACAAAAACTTTCCCCAATCACTACAGCATTGTCACCGGATTGTATCCAGAATCTCATGGCATAATCGA

CAATAAAATGTATGATCCCAAAATGAATGCTTCCTTTTCACTTAAAAGTAAAGAGAAATTTAATCCTGAGTGG

TACAAAGGAGAACCAATTTGGGTCACAGCTAAGTATCAAGGCCTCAAGTCTGGCACATTTTTCTGGCCAGGAT

CAGATGTGGAAATTAACGGAATTTTCCCAGACATCTATAAAATGTATAATGGTTCAGTACCATTTGAAGAAAG

-continued

GATTTTAGCTGTTCTTCAGTGGCTACAGCTTCCTAAAGATGAAAGACCACACTTTTACACTCTGTATTTAGAA

GAACCAGATTCTTCAGGTCATTCATATGGACCAGTCAGCAGTGAAGTCATCAAAGCCTTGCAGAGGGTTGATG

GTATGGTTGGTATGCTGATGGATGGTCTGAAAGAGCTGAACTTGCACAGATGCCTGAACCTCATCCTTATTTC

AGATCATGGCATGGAACAAGGCAGTTGTAAGAAATACATATATCTGAATAAATATTTGGGGGATGTTAAAAAT

ATTAAAGTTATCTATGGACCTGCAGCTCGATTGAGACCCTCTGATGTCCCAGATAAATACTATTCATTTAACT

ATGAAGGCATTGCCCGAAATCTTTCTTGCCGGGAACCAAACCAGCACTTCAAACCTTACCTGAAACATTTCTT

ACCTAAGCGTTTGCACTTTGCTAAGAGTGATAGAATTGAGCCCTTGACATTCTATTTGGACCCTCAGTGGCAA

CTTGCATTGAATCCCTCAGAAAGGAAATATTGTGGAAGTGGATTTCATGGCTCTGACAATGTATTTTCAAATA

TGCAAGCCCTCTTTGTTGGCTATGGACCTGGATTCAAGCATGGCATTGAGGCTGACACCTTTGAAAACATTGA

AGTCTATAACTTAATGTGTGATTTACTGAATTTGACACCGGCTCCTAATAACGGAACTCATGGAAGTCTTAAC

CACCTTCTAAAGAATCCTGTTTATACGCCAAAGCATCCCAAAGAAGTGCACCCCCTGGTACAGTGCCCCTTCA

CAAGAAACCCCAGAGATAACCTTGGCTGCTCATGTAACCCTTCGATTTTGCCGATTGAGGATTTTCAAACACA

GTTCAATCTGACTGTGGCAGAAGAGAAGATTATTAAGCATGAAACTTTACCCTATGGAAGACCTAGAGTTCTC

CAGAAGGAAAACACCATCTGTCTTCTTTCCCAGCACCAGTTTATGAGTGGATACAGCCAAGACATCTTAATGC

CCCTTTGGACATCCTATACCGTGGACAGAAATGACAGTTTCTCTACGGAAGACTTCTCCAACTGTCTGTACCA

GGACTTTAGAATTCCTCTTAGTCCTGTCCATAAATGTTCATTTTATAAAAATAACACCAAAGTGAGTTACGGG

TTCCTCTCCCCACCACAACTAAATAAAAATTCAAGTGGAATATATTCTGAAGCTTTGCTTACTACAAATATAG

TGCCAATGTACCAGAGTTTTCAAGTTATATGGCGCTACTTTCATGACACCCTACTGCGAAAGTATGCTGAAGA

AAGAAATGGTGTCAATGTCGTCAGTGGTCCTGTGTTTGACTTTGATTATGATGGACGTTGTGATTCCTTAGAG

AATCTGAGGCAAAAAAGAAGAGTCATCCGTAACCAAGAAATTTTGATTCCAACTCACTTCTTTATTGTGCTAA

CAAGCTGTAAAGATACATCTCAGACGCCTTTGCACTGTGAAAACCTAGACACCTTAGCTTTCATTTTGCCTCA

CAGGACTGATAACAGCGAGAGCTGTGTGCATGGGAAGCATGACTCCTCATGGGTTGAAGAATTGTTAATGTTA

CACAGAGCACGGATCACAGATGTTGAGCACATCACTGGACTCAGCTTCTATCAACAAAGAAAAGAGCCAGTTT

CAGACATTTTAAAGTTGAAAACACATTTGCCAACCTTTAGCCAAGAAGACGACTACAAAGACGATGACGACAA

GTGAGGTACCGAGCTCGGATCCACTAGTCCAGTGTGGTGGAATTCTGCAGATATCCAGCACAGTGGCGGCCGC

TCGAGTCTAGAGGGCCCGTTTAAACCCGCTGATCAGCCTCGACTGTGCCTTCTAGTTGCCAGCCATCTGTTGT

TTGCCCCTCCCCCGTGCCTTCCTTGACCCTGGAAGGTGCCACTCCCACTGTCCTTTCCTAATAAAATGAGGAA

ATTGCATCGCATTGTCTGAGTAGGTGTCATTCTATTCTGGGGGGTGGGGTGGGGCAGGACAGCAAGGGGGAGG

ATTGGGAAGACAATAGCAGGCATGCTGGGGATGCGGTGGGCTCTATGGCTTCTGAGGCGGAAAGAACCAGCTG

GGGCTCTAGGGGGTATCCCCACGCGCCCTGTAGCGGCGCATTAAGCGCGGCGGGTGTGGTGGTTACGCGCAGC

GTGACCGCTACACTTGCCAGCGCCCTAGCGCCCGCTCCTTTCGCTTTCTTCCCTTCCTTTCTCGCCACGTTCG

CCGGCTTTCCCCGTCAAGCTCTAAATCGGGGGCTCCCTTTAGGGTTCCGATTTAGTGCTTTACGGCACCTCGA

CCCCAAAAAACTTGATTAGGGTGATGGTTCACGTAGTGGGCCATCGCCCTGATAGACGGTTTTTCGCCCTTTG

ACGTTGGAGTCCACGTTCTTTAATAGTGGACTCTTGTTCCAAACTGGAACAACACTCAACCCTATCTCGGTCT

ATTCTTTTGATTTATAAGGGATTTTGCCGATTTCGGCCTATTGGTTAAAAAATGAGCTGATTTAACAAAAATT

TAACGCGAATTAATTCTGTGGAATGTGTGTCAGTTAGGGTGTGGAAAGTCCCCAGGCTCCCCAGCAGGCAGAA

GTATGCAAAGCATGCATCTCAATTAGTCAGCAACCAGGTGTGGAAAGTCCCCAGGCTCCCCAGCAGGCAGAAG

TATGCAAAGCATGCATCTCAATTAGTCAGCAACCATAGTCCCGCCCCTAACTCCGCCCATCCCGCCCCTAACT

CCGCCCAGTTCCGCCCATTCTCCGCCCCATGGCTGACTAATTTTTTTTATTTATGCAGAGGCCGAGGCCGCCT

-continued

CTGCCTCTGAGCTATTCCAGAAGTAGTGAGGAGGCTTTTTTGGAGGCCTAGGCTTTTGCAAAAAGCTCCCGGG

AGCTTGTATATCCATTTTCGGATCTGATCAAGAGACAGGATGAGGATCGTTTCGCATGATTGAACAAGATGGA

TTGCACGCAGGTTCTCCGGCCGCTTGGGTGGAGAGGCTATTCGGCTATGACTGGGCACAACAGACAATCGGCT

GCTCTGATGCCGCCGTGTTCCGGCTGTCAGCGCAGGGGCGCCCGGTTCTTTTTGTCAAGACCGACCTGTCCGG

TGCCCTGAATGAACTGCAGGACGAGGCAGCGCGGCTATCGTGGCTGGCCACGACGGGCGTTCCTTGCGCAGCT

GTGCTCGACGTTGTCACTGAAGCGGGAAGGGACTGGCTGCTATTGGGCGAAGTGCCGGGGCAGGATCTCCTGT

CATCTCACCTTGCTCCTGCCGAGAAAGTATCCATCATGGCTGATGCAATGCGGCGGCTGCATACGCTTGATCC

GGCTACCTGCCCATTCGACCACCAAGCGAAACATCGCATCGAGCGAGCACGTACTCGGATGGAAGCCGGTCTT

GTCGATCAGGATGATCTGGACGAAGAGCATCAGGGGCTCGCGCCAGCCGAACTGTTCGCCAGGCTCAAGGCGC

GCATGCCCGACGGCGAGGATCTCGTCGTGACCCATGGCGATGCCTGCTTGCCGAATATCATGGTGGAAAATGG

CCGCTTTTCTGGATTCATCGACTGTGGCCGGCTGGGTGTGGCGGACCGCTATCAGGACATAGCGTTGGCTACC

CGTGATATTGCTGAAGAGCTTGGCGGCGAATGGGCTGACCGCTTCCTCGTGCTTTACGGTATCGCCGCTCCCG

ATTCGCAGCGCATCGCCTTCTATCGCCTTCTTGACGAGTTCTTCTGAGCGGGACTCTGGGGTTCGAAATGACC

GACCAAGCGACGCCCAACCTGCCATCACGAGATTTCGATTCCACCGCCGCCTTCTATGAAAGGTTGGGCTTCG

GAATCGTTTTCCGGGACGCCGGCTGGATGATCCTCCAGCGCGGGGATCTCATGCTGGAGTTCTTCGCCCACCC

CAACTTGTTTATTGCAGCTTATAATGGTTACAAATAAAGCAATAGCATCACAAATTTCACAAATAAAGCATTT

TTTTCACTGCATTCTAGTTGTGGTTTGTCCAAACTCATCAATGTATCTTATCATGTCTGTATACCGTCGACCT

CTAGCTAGAGCTTGGCGTAATCATGGTCATAGCTGTTTCCTGTGTGAAATTGTTATCCGCTCACAATTCCACA

CAACATACGAGCCGGAAGCATAAAGTGTAAAGCCTGGGGTGCCTAATGAGTGAGCTAACTCACATTAATTGCG

TTGCGCTCACTGCCCGCTTTCCAGTCGGGAAACCTGTCGTGCCAGCTGCATTAATGAATCGGCCAACGCGCGG

GGAGAGGCGGTTTGCGTATTGGGCGCTCTTCCGCTTCCTCGCTCACTGACTCGCTGCGCTCGGTCGTTCGGCT

GCGGCGAGCGGTATCAGCTCACTCAAAGGCGGTAATACGGTTATCCACAGAATCAGGGGATAACGCAGGAAAG

AACATGTGAGCAAAAGGCCAGCAAAAGGCCAGGAACCGTAAAAAGGCCGCGTTGCTGGCGTTTTTCCATAGGC

TCCGCCCCCCTGACGAGCATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCATAGCTCACGCTGTAGGTATCTCAGTTCGGTGTAGG

TCGTTCGCTCCAAGCTGGGCTGTGTGCACGAACCCCCCGTTCAGCCCGACCGCTGCGCCTTATCCGGTAACTA

TCGTCTTGAGTCCAACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACTAGAAGAACAGTAT

TTGGTATCTGCGCTCTGCTGAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACGTTAAGGGATTTTGGTCATGAGAT

TATCAAAAAGGATCTTCACCTAGATCCTTTTAAATTAAAAATGAAGTTTTAAATCAATCTAAAGTATATATGA

GTAAACTTGGTCTGACAGTTACCAATGCTTAATCAGTGAGGCACCTATCTCAGCGATCTGTCTATTTCGTTCA

TCCATAGTTGCCTGACTCCCCGTCGTGTAGATAACTACGATACGGGAGGGCTTACCATCTGGCCCCAGTGCTG

CAATGATACCGCGAGACCCACGCTCACCGGCTCCAGATTTATCAGCAATAAACCAGCCAGCCGGAAGGGCCGA

GCGCAGAAGTGGTCCTGCAACTTTATCCGCCTCCATCCAGTCTATTAATTGTTGCCGGGAAGCTAGAGTAAGT

AGTTCGCCAGTTAATAGTTTGCGCAACGTTGTTGCCATTGCTACAGGCATCGTGGTGTCACGCTCGTCGTTTG

GTATGGCTTCATTCAGCTCCGGTTCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAGTGTTATCACTCATGGTTATGGCA

-continued

GCACTGCATAATTCTCTTACTGTCATGCCATCCGTAAGATGCTTTTCTGTGACTGGTGAGTACTCAACCAAGT

CATTCTGAGAATAGTGTATGCGGCGACCGAGTTGCTCTTGCCCGGCGTCAATACGGGATAATACCGCGCCACA

TAGCAGAACTTTAAAAGTGCTCATCATTGGAAAACGTTCTTCGGGGCGAAAACTCTCAAGGATCTTACCGCTG

TTGAGATCCAGTTCGATGTAACCCACTCGTGCACCCAACTGATCTTCAGCATCTTTTACTTTCACCAGCGTTT

CTGGGTGAGCAAAAACAGGAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGAGCGGATACATATTTGAA

TGTATTTAGAAAAATAAACAAATAGGGGTTCCGCGCACATTTCCCCGAAAAGTGCCACCTGACGTC

MiniH9Prom_Kozak_ENPP1 Full Length_FLAG_pcDNA3.1 (+)

(SEQ ID NO: 86)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGAAAACTACAATTGACTATCTCTAAATTTTAAAATGTGATGATAGTTACTACTTCAGT

GGTCCACACTGTTTCTATCCTTTGGAACATAAGATTTTGTTGTGTAGCTTAAGGAAGAGGAATTCAGCAGTTG

ACTATCTCGATTGTTCTGGGAATTTTGGAGGCTGAGGGGAAATTTTCACATATAAGCGCTGGGTTTGCTGGGG

TATTGAGAGTGACCTCTGGCTAACTAGAGAACCCACTGCTTACTGGCTTATCGAAATTAATACGACTCACTAT

AGGGAGACCCAAGCTGGCTAGCGCCACCATGGAGCGCGACGGCTGCGCGGGGGGCGGGAGCCGCGGCGGCGAG

GGCGGGCGCGCTCCCCGGGAGGGCCCGGCGGGGAACGGCCGCGATCGGGGCCGCAGCCACGCTGCCGAGGCGC

CCGGGGACCCGCAGGCCGCGGCGTCCTTGCTGGCCCCTATGGACGTGGGGGAGGAGCCGCTGGAGAAGGCGGC

GCGCGCCCGCACTGCCAAGGACCCCAACACCTATAAAGTACTCTCGCTGGTATTGTCAGTATGTGTGTTAACA

ACAATACTTGGTTGTATATTTGGGTTGAAACCAAGCTGTGCCAAAGAAGTTAAAAGTTGCAAAGGTCGCTGTT

TCGAGAGAACATTTGGGAACTGTCGCTGTGATGCTGCCTGTGTTGAGCTTGGAAACTGCTGTTTAGATTACCA

GGAGACGTGCATAGAACCAGAACATATATGGACTTGCAACAAATTCAGGTGTGGTGAGAAAAGGTTGACCAGA

AGCCTCTGTGCCTGTTCAGATGACTGCAAGGACAAGGGCGACTGCTGCATCAACTACAGTTCTGTGTGTCAAG

GTGAGAAAAGTTGGGTAGAAGAACCATGTGAGAGCATTAATGAGCCACAGTGCCCAGCAGGGTTTGAAACGCC

TCCTACCCTCTTATTTTCTTTGGATGGATTCAGGGCAGAATATTTACACACTTGGGGTGGACTTCTTCCTGTT

ATTAGCAAACTAAAAAAATGTGGAACATATACTAAAAACATGAGACCGGTATATCCAACAAAAACTTTCCCCA

ATCACTACAGCATTGTCACCGGATTGTATCCAGAATCTCATGGCATAATCGACAATAAAATGTATGATCCCAA

AATGAATGCTTCCTTTTCACTTAAAAGTAAAGAGAAATTTAATCCTGAGTGGTACAAAGGAGAACCAATTTGG

GTCACAGCTAAGTATCAAGGCCTCAAGTCTGGCACATTTTTCTGGCCAGGATCAGATGTGGAAATTAACGGAA

TTTTCCCAGACATCTATAAAATGTATAATGGTTCAGTACCATTTGAAGAAAGGATTTTAGCTGTTCTTCAGTG

GCTACAGCTTCCTAAAGATGAAAGACCACACTTTTACACTCTGTATTTAGAAGAACCAGATTCTTCAGGTCAT

TCATATGGACCAGTCAGCAGTGAAGTCATCAAAGCCTTGCAGAGGGTTGATGGTATGGTTGGTATGCTGATGG

ATGGTCTGAAAGAGCTGAACTTGCACAGATGCCTGAACCTCATCCTTATTTCAGATCATGGCATGGAACAAGG

CAGTTGTAAGAAATACATATATCTGAATAAATATTTGGGGGATGTTAAAAATATTAAAGTTATCTATGGACCT

GCAGCTCGATTGAGACCCTCTGATGTCCCAGATAAATACTATTCATTTAACTATGAAGGCATTGCCCGAAATC

TTTCTTGCCGGGAACCAAACCAGCACTTCAAACCTTACCTGAAACATTTCTTACCTAAGCGTTTGCACTTTGC

TAAGAGTGATAGAATTGAGCCCTTGACATTCTATTTGGACCCTCAGTGGCAACTTGCATTGAATCCCTCAGAA

AGGAAATATTGTGGAAGTGGATTTCATGGCTCTGACAATGTATTTTCAAATATGCAAGCCCTCTTTGTTGGCT

ATGGACCTGGATTCAAGCATGGCATTGAGGCTGACACCTTTGAAAACATTGAAGTCTATAACTTAATGTGTGA

-continued

TTTACTGAATTTGACACCGGCTCCTAATAACGGAACTCATGGAAGTCTTAACCACCTTCTAAAGAATCCTGTT

TATACGCCAAAGCATCCCAAAGAAGTGCACCCCCTGGTACAGTGCCCCTTCACAAGAAACCCCAGAGATAACC

TTGGCTGCTCATGTAACCCTTCGATTTTGCCGATTGAGGATTTTCAAACACAGTTCAATCTGACTGTGGCAGA

AGAGAAGATTATTAAGCATGAAACTTTACCCTATGGAAGACCTAGAGTTCTCCAGAAGGAAAACACCATCTGT

CTTCTTTCCCAGCACCAGTTTATGAGTGGATACAGCCAAGACATCTTAATGCCCCTTTGGACATCCTATACCG

TGGACAGAAATGACAGTTTCTCTACGGAAGACTTCTCCAACTGTCTGTACCAGGACTTTAGAATTCCTCTTAG

TCCTGTCCATAAATGTTCATTTTATAAAAATAACACCAAAGTGAGTTACGGGTTCCTCTCCCCACCACAACTA

AATAAAAATTCAAGTGGAATATATTCTGAAGCTTTGCTTACTACAAATATAGTGCCAATGTACCAGAGTTTTC

AAGTTATATGGCGCTACTTTCATGACACCCTACTGCGAAAGTATGCTGAAGAAAGAAATGGTGTCAATGTCGT

CAGTGGTCCTGTGTTTGACTTTGATTATGATGGACGTTGTGATTCCTTAGAGAATCTGAGGCAAAAAAGAAGA

GTCATCCGTAACCAAGAAATTTTGATTCCAACTCACTTCTTTATTGTGCTAACAAGCTGTAAAGATACATCTC

AGACGCCTTTGCACTGTGAAAACCTAGACACCTTAGCTTTCATTTTGCCTCACAGGACTGATAACAGCGAGAG

CTGTGTGCATGGGAAGCATGACTCCTCATGGGTTGAAGAATTGTTAATGTTACACAGAGCACGGATCACAGAT

GTTGAGCACATCACTGGACTCAGCTTCTATCAACAAAGAAAAGAGCCAGTTTCAGACATTTTAAAGTTGAAAA

CACATTTGCCAACCTTTAGCCAAGAAGACGACTACAAAGACGATGACGACAAGTGAGGTACCGAGCTCGGATC

CACTAGTCCAGTGTGGTGGAATTCTGCAGATATCCAGCACAGTGGCGGCCGCTCGAGTCTAGAGGGCCCGTTT

AAACCCGCTGATCAGCCTCGACTGTGCCTTCTAGTTGCCAGCCATCTGTTGTTTGCCCCTCCCCCGTGCCTTC

CTTGACCCTGGAAGGTGCCACTCCCACTGTCCTTTCCTAATAAAATGAGGAAATTGCATCGCATTGTCTGAGT

AGGTGTCATTCTATTCTGGGGGGTGGGGTGGGGCAGGACAGCAAGGGGGAGGATTGGGAAGACAATAGCAGGC

ATGCTGGGGATGCGGTGGGCTCTATGGCTTCTGAGGCGGAAAGAACCAGCTGGGGCTCTAGGGGGTATCCCCA

CGCGCCCTGTAGCGGCGCATTAAGCGCGGCGGGTGTGGTGGTTACGCGCAGCGTGACCGCTACACTTGCCAGC

GCCCTAGCGCCCGCTCCTTTCGCTTTCTTCCCTTCCTTTCTCGCCACGTTCGCCGGCTTTCCCCGTCAAGCTC

TAAATCGGGGGCTCCCTTTAGGGTTCCGATTTAGTGCTTTACGGCACCTCGACCCCAAAAAACTTGATTAGGG

TGATGGTTCACGTAGTGGGCCATCGCCCTGATAGACGGTTTTTCGCCCTTTGACGTTGGAGTCCACGTTCTTT

AATAGTGGACTCTTGTTCCAAACTGGAACAACACTCAACCCTATCTCGGTCTATTCTTTTGATTTATAAGGGA

TTTTGCCGATTTCGGCCTATTGGTTAAAAAATGAGCTGATTTAACAAAAATTTAACGCGAATTAATTCTGTGG

AATGTGTGTCAGTTAGGGTGTGGAAAGTCCCCAGGCTCCCCAGCAGGCAGAAGTATGCAAAGCATGCATCTCA

ATTAGTCAGCAACCAGGTGTGGAAAGTCCCCAGGCTCCCCAGCAGGCAGAAGTATGCAAAGCATGCATCTCAA

TTAGTCAGCAACCATAGTCCCGCCCCTAACTCCGCCCATCCCGCCCCTAACTCCGCCCAGTTCCGCCCATTCT

CCGCCCCATGGCTGACTAATTTTTTTTATTTATGCAGAGGCCGAGGCCGCCTCTGCCTCTGAGCTATTCCAGA

AGTAGTGAGGAGGCTTTTTTGGAGGCCTAGGCTTTTGCAAAAAGCTCCCGGGAGCTTGTATATCCATTTTCGG

ATCTGATCAAGAGACAGGATGAGGATCGTTTCGCATGATTGAACAAGATGGATTGCACGCAGGTTCTCCGGCC

GCTTGGGTGGAGAGGCTATTCGGCTATGACTGGGCACAACAGACAATCGGCTGCTCTGATGCCGCCGTGTTCC

GGCTGTCAGCGCAGGGGCGCCCGGTTCTTTTTGTCAAGACCGACCTGTCCGGTGCCCTGAATGAACTGCAGGA

CGAGGCAGCGCGGCTATCGTGGCTGGCCACGACGGGCGTTCCTTGCGCAGCTGTGCTCGACGTTGTCACTGAA

GCGGGAAGGGACTGGCTGCTATTGGGCGAAGTGCCGGGGCAGGATCTCCTGTCATCTCACCTTGCTCCTGCCG

AGAAAGTATCCATCATGGCTGATGCAATGCGGCGGCTGCATACGCTTGATCCGGCTACCTGCCCATTCGACCA

CCAAGCGAAACATCGCATCGAGCGAGCACGTACTCGGATGGAAGCCGGTCTTGTCGATCAGGATGATCTGGAC

GAAGAGCATCAGGGGCTCGCGCCAGCCGAACTGTTCGCCAGGCTCAAGGCGCGCATGCCCGACGGCGAGGATC

TCGTCGTGACCCATGGCGATGCCTGCTTGCCGAATATCATGGTGGAAAATGGCCGCTTTTCTGGATTCATCGA

-continued

CTGTGGCCGGCTGGGTGTGGCGGACCGCTATCAGGACATAGCGTTGGCTACCCGTGATATTGCTGAAGAGCTT

GGCGGCGAATGGGCTGACCGCTTCCTCGTGCTTTACGGTATCGCCGCTCCCGATTCGCAGCGCATCGCCTTCT

ATCGCCTTCTTGACGAGTTCTTCTGAGCGGGACTCTGGGGTTCGAAATGACCGACCAAGCGACGCCCAACCTG

CCATCACGAGATTTCGATTCCACCGCCGCCTTCTATGAAAGGTTGGGCTTCGGAATCGTTTTCCGGGACGCCG

GCTGGATGATCCTCCAGCGCGGGGATCTCATGCTGGAGTTCTTCGCCCACCCCAACTTGTTTATTGCAGCTTA

TAATGGTTACAAATAAAGCAATAGCATCACAAATTTCACAAATAAAGCATTTTTTTCACTGCATTCTAGTTGT

GGTTTGTCCAAACTCATCAATGTATCTTATCATGTCTGTATACCGTCGACCTCTAGCTAGAGCTTGGCGTAAT

CATGGTCATAGCTGTTTCCTGTGTGAAATTGTTATCCGCTCACAATTCCACACAACATACGAGCCGGAAGCAT

AAAGTGTAAAGCCTGGGGTGCCTAATGAGTGAGCTAACTCACATTAATTGCGTTGCGCTCACTGCCCGCTTTC

CAGTCGGGAAACCTGTCGTGCCAGCTGCATTAATGAATCGGCCAACGCGCGGGGAGAGGCGGTTTGCGTATTG

GGCGCTCTTCCGCTTCCTCGCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAACATGTGAGCAAAAGGCCAG

CAAAAGGCCAGGAACCGTAAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGATACCAGGCGTTTCCCCCTGG

AAGCTCCCTCGTGCGCTCTCCTGTTCCGACCCTGCCGCTTACCGGATACCTGTCCGCCTTTCTCCCTTCGGGA

AGCGTGGCGCTTTCTCATAGCTCACGCTGTAGGTATCTCAGTTCGGTGTAGGTCGTTCGCTCCAAGCTGGGCT

GTGTGCACGAACCCCCCGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGAGGTATGTAGGCGGTGCT

ACAGAGTTCTTGAAGTGGTGGCCTAACTACGGCTACACTAGAAGAACAGTATTTGGTATCTGCGCTCTGCTGA

AGCCAGTTACCTTCGGAAAAAGAGTTGGTAGCTCTTGATCCGGCAAACAAACCACCGCTGGTAGCGGTGGTTT

TTTTGTTTGCAAGCAGCAGATTACGCGCAGAAAAAAAGGATCTCAAGAAGATCCTTTGATCTTTTCTACGGGG

TCTGACGCTCAGTGGAACGAAAACTCACGTTAAGGGATTTTGGTCATGAGATTATCAAAAAGGATCTTCACCT

AGATCCTTTTAAATTAAAAATGAAGTTTTAAATCAATCTAAAGTATATATGAGTAAACTTGGTCTGACAGTTA

CCAATGCTTAATCAGTGAGGCACCTATCTCAGCGATCTGTCTATTTCGTTCATCCATAGTTGCCTGACTCCCC

GTCGTGTAGATAACTACGATACGGGAGGGCTTACCATCTGGCCCCAGTGCTGCAATGATACCGCGAGACCCAC

GCTCACCGGCTCCAGATTTATCAGCAATAAACCAGCCAGCCGGAAGGGCCGAGCGCAGAAGTGGTCCTGCAAC

TTTATCCGCCTCCATCCAGTCTATTAATTGTTGCCGGGAAGCTAGAGTAAGTAGTTCGCCAGTTAATAGTTTG

CGCAACGTTGTTGCCATTGCTACAGGCATCGTGGTGTCACGCTCGTCGTTTGGTATGGCTTCATTCAGCTCCG

GTTCCCAACGATCAAGGCGAGTTACATGATCCCCCATGTTGTGCAAAAAAGCGGTTAGCTCCTTCGGTCCTCC

GATCGTTGTCAGAAGTAAGTTGGCCGCAGTGTTATCACTCATGGTTATGGCAGCACTGCATAATTCTCTTACT

GTCATGCCATCCGTAAGATGCTTTTCTGTGACTGGTGAGTACTCAACCAAGTCATTCTGAGAATAGTGTATGC

GGCGACCGAGTTGCTCTTGCCCGGCGTCAATACGGGATAATACCGCGCCACATAGCAGAACTTTAAAAGTGCT

CATCATTGGAAAACGTTCTTCGGGGCGAAAACTCTCAAGGATCTTACCGCTGTTGAGATCCAGTTCGATGTAA

CCCACTCGTGCACCCAACTGATCTTCAGCATCTTTTACTTTCACCAGCGTTTCTGGGTGAGCAAAAACAGGAA

GGCAAAATGCCGCAAAAAAGGGAATAAGGGCGACACGGAAATGTTGAATACTCATACTCTTCCTTTTTCAATA

-continued

TTATTGAAGCATTTATCAGGGTTATTGTCTCATGAGCGGATACATATTTGAATGTATTTAGAAAAATAAACAA

ATAGGGGTTCCGCGCACATTTCCCCGAAAAGTGCCACCTGACGTC)

HDAC9 Prom2 (1350bp)_Kozak_ENPP1 Full Length_FLAG_pcDNA3.1 (+)

pcDNA3.1+, HDAC9 promoter, Kozak seq, ENPP1 full length seg, Flag tag,

Stop codon

(SEQ ID NO: 87)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTATAAATGTTTTGTAGAATAAAAAAAAAAAAAAGTTCTTCAAAAGAAATCTCAAATCTCC

AAATGGAAACAGGTAAAAGTGGAGCTCCCCTGGTTCCACGGAGAACCTTTTTTGAGGAAACTTAGGCAACTCG

CAGGTACCTTATGTCATGAGACAGAGTTTGAAAACTACAATTGACTATCTCTAAATTTCCTCCCAGGTCTAAA

ATGTGATGATAGTTACTACTTCAGTACATCATCCTTAAGGAAAATTATTAGGTCCACACTGTTTCTATCCTTT

GAATTTTACACATAAATTTTGTAATCAAAAGTTTATTTGTAATATCAGATGGAATCAGATAATTGCTTTTTGT

TTTTTCCACTGACAGGAACATAAGATTTTGTTGTGTAGCTTAAGTCAAACGCAGTTTGGAATATATATTTTTT

AAAAATTGTAACTTACATATCCAAATACAATTTTTCAAGAAGTAGAGTATTCAGTAGAAATTAATCTGTGAAA

GAAGAGGAATTCAGCAGTGGCCTATTTGATGAATGATTTAACGTGCTTATTTCTTCCCTTTCATCAAAACTCT

GTGTCCCCTTGTTTGCCCCCTCTGACTTCATACTCTGGAGTTGACCAAGATCCCTCTTCCATCGGATTGTTCT

GGGAATTTTGAAATAATCTGCTTTTTCCTCTCTTTCCCCTGTTGCTTCTGATGCCTTAGAATTACATTTTCCT

CGCTGATTTAGTTTAGAAAAGAGAAAAGAGCTTCCATGACTAGTAGATTATCACTTTTGGGTTTGCTCTTGGA

AGTGACAAGATGCTAGGATCCCTCTTTGGAATGTAAAATTTATCTCTTATATAGAAAGGATATAAATGTAGCA

CCAGAGACTATAAAACTCTGATACTATCTACTGTACTGTATAGCTGAACGCCACAATGTGTCTGGTAATCTAT

TGACTATCATAAATGCTATTTCTACAGAAAAGTTAGGAGGTCCATATTTCGGGCAACCAATGTATAGCTGAAT

GCAGAACAGTCATAGTTGGGTACTAACCATATATATGATTTATCCATCAACAGGTGCATATGCTCAGAAATTC

TGTATCCATAAGAAATCAGACTACTTTCTTTTCCTTTTGCAAGTAAATTGAATTTAGCCTGAGAGGCTGAGGG

GAAATTTTCACATATAAGCCACGGTTTTGTGTTTTGTGTTTTGTTTTGTTTATAGATATAGTACTAACTGGAT

GGATGCGATAAAATTCATAGGTGGTACTAAGATACAATAGGATTTGTGAAATGGACAATTGTCTTGCATAAAT

AGCAAGTAAAAAATCAAGCCTGTCCTTCATAAAAATTTTATTCTGGGGTGTCTCTGGCTAACTAGAGAACCCA

CTGCTTACTGGCTTATCGAAATTAATACGACTCACTATAGGGAGACCCAAGCTGGCTAGCGCCACCATGGAGC

GCGACGGCTGCGCGGGGGGCGGGAGCCGCGGCGGCGAGGGCGGGCGCGCTCCCCGGGAGGGCCCGGCGGGGAA

CGGCCGCGATCGGGGCCGCAGCCACGCTGCCGAGGCGCCCGGGGACCCGCAGGCCGCGGCGTCCTTGCTGGCC

CCTATGGACGTGGGGGAGGAGCCGCTGGAGAAGGCGGCGCGCGCCCGCACTGCCAAGGACCCCAACACCTATA

AAGTACTCTCGCTGGTATTGTCAGTATGTGTGTTAACAACAATACTTGGTTGTATATTTGGGTTGAAACCAAG

CTGTGCCAAAGAAGTTAAAAGTTGCAAAGGTCGCTGTTTCGAGAGAACATTTGGGAACTGTCGCTGTGATGCT

GCCTGTGTTGAGCTTGGAAACTGCTGTTTAGATTACCAGGAGACGTGCATAGAACCAGAACATATATGGACTT

GCAACAAATTCAGGTGTGGTGAGAAAAGGTTGACCAGAAGCCTCTGTGCCTGTTCAGATGACTGCAAGGACAA

GGGCGACTGCTGCATCAACTACAGTTCTGTGTGTCAAGGTGAGAAAAGTTGGGTAGAAGAACCATGTGAGAGC

ATTAATGAGCCACAGTGCCCAGCAGGGTTTGAAACGCCTCCTACCCTCTTATTTTCTTTGGATGGATTCAGGG

CAGAATATTTACACACTTGGGGTGGACTTCTTCCTGTTATTAGCAAACTAAAAAAATGTGGAACATATACTAA

AAACATGAGACCGGTATATCCAACAAAAACTTTCCCCAATCACTACAGCATTGTCACCGGATTGTATCCAGAA

-continued

TCTCATGGCATAATCGACAATAAAATGTATGATCCCAAAATGAATGCTTCCTTTTCACTTAAAAGTAAAGAGA

AATTTAATCCTGAGTGGTACAAAGGAGAACCAATTTGGGTCACAGCTAAGTATCAAGGCCTCAAGTCTGGCAC

ATTTTTCTGGCCAGGATCAGATGTGGAAATTAACGGAATTTTCCCAGACATCTATAAAATGTATAATGGTTCA

GTACCATTTGAAGAAAGGATTTTAGCTGTTCTTCAGTGGCTACAGCTTCCTAAAGATGAAAGACCACACTTTT

ACACTCTGTATTTAGAAGAACCAGATTCTTCAGGTCATTCATATGGACCAGTCAGCAGTGAAGTCATCAAAGC

CTTGCAGAGGGTTGATGGTATGGTTGGTATGCTGATGGATGGTCTGAAAGAGCTGAACTTGCACAGATGCCTG

AACCTCATCCTTATTTCAGATCATGGCATGGAACAAGGCAGTTGTAAGAAATACATATATCTGAATAAATATT

TGGGGGATGTTAAAAATATTAAAGTTATCTATGGACCTGCAGCTCGATTGAGACCCTCTGATGTCCCAGATAA

ATACTATTCATTTAACTATGAAGGCATTGCCCGAAATCTTTCTTGCCGGGAACCAAACCAGCACTTCAAACCT

TACCTGAAACATTTCTTACCTAAGCGTTTGCACTTTGCTAAGAGTGATAGAATTGAGCCCTTGACATTCTATT

TGGACCCTCAGTGGCAACTTGCATTGAATCCCTCAGAAAGGAAATATTGTGGAAGTGGATTTCATGGCTCTGA

CAATGTATTTTCAAATATGCAAGCCCTCTTTGTTGGCTATGGACCTGGATTCAAGCATGGCATTGAGGCTGAC

ACCTTTGAAAACATTGAAGTCTATAACTTAATGTGTGATTTACTGAATTTGACACCGGCTCCTAATAACGGAA

CTCATGGAAGTCTTAACCACCTTCTAAAGAATCCTGTTTATACGCCAAAGCATCCCAAAGAAGTGCACCCCCT

GGTACAGTGCCCCTTCACAAGAAACCCCAGAGATAACCTTGGCTGCTCATGTAACCCTTCGATTTTGCCGATT

GAGGATTTTCAAACACAGTTCAATCTGACTGTGGCAGAAGAGAAGATTATTAAGCATGAAACTTTACCCTATG

GAAGACCTAGAGTTCTCCAGAAGGAAAACACCATCTGTCTTCTTTCCCAGCACCAGTTTATGAGTGGATACAG

CCAAGACATCTTAATGCCCCTTTGGACATCCTATACCGTGGACAGAAATGACAGTTTCTCTACGGAAGACTTC

TCCAACTGTCTGTACCAGGACTTTAGAATTCCTCTTAGTCCTGTCCATAAATGTTCATTTTATAAAAATAACA

CCAAAGTGAGTTACGGGTTCCTCTCCCCACCACAACTAAATAAAAATTCAAGTGGAATATATTCTGAAGCTTT

GCTTACTACAAATATAGTGCCAATGTACCAGAGTTTTCAAGTTATATGGCGCTACTTTCATGACACCCTACTG

CGAAAGTATGCTGAAGAAAGAAATGGTGTCAATGTCGTCAGTGGTCCTGTGTTTGACTTTGATTATGATGGAC

GTTGTGATTCCTTAGAGAATCTGAGGCAAAAAAGAAGAGTCATCCGTAACCAAGAAATTTTGATTCCAACTCA

CTTCTTTATTGTGCTAACAAGCTGTAAAGATACATCTCAGACGCCTTTGCACTGTGAAAACCTAGACACCTTA

GCTTTCATTTTGCCTCACAGGACTGATAACAGCGAGAGCTGTGTGCATGGGAAGCATGACTCCTCATGGGTTG

AAGAATTGTTAATGTTACACAGAGCACGGATCACAGATGTTGAGCACATCACTGGACTCAGCTTCTATCAACA

AAGAAAAGAGCCAGTTTCAGACATTTTAAAGTTGAAAACACATTTGCCAACCTTTAGCCAAGAAGACGACTAC

AAAGACGATGACGACAAGTGAGGTACCGAGCTCGGATCCACTAGTCCAGTGTGGTGGAATTCTGCAGATATCC

AGCACAGTGGCGGCCGCTCGAGTCTAGAGGGCCCGTTTAAACCCGCTGATCAGCCTCGACTGTGCCTTCTAGT

TGCCAGCCATCTGTTGTTTGCCCCTCCCCCGTGCCTTCCTTGACCCTGGAAGGTGCCACTCCCACTGTCCTTT

CCTAATAAAATGAGGAAATTGCATCGCATTGTCTGAGTAGGTGTCATTCTATTCTGGGGGGTGGGGTGGGGCA

GGACAGCAAGGGGGAGGATTGGGAAGACAATAGCAGGCATGCTGGGGATGCGGTGGGCTCTATGGCTTCTGAG

GCGGAAAGAACCAGCTGGGGCTCTAGGGGGTATCCCCACGCGCCCTGTAGCGGCGCATTAAGCGCGGCGGGTG

TGGTGGTTACGCGCAGCGTGACCGCTACACTTGCCAGCGCCCTAGCGCCCGCTCCTTTCGCTTTCTTCCCTTC

CTTTCTCGCCACGTTCGCCGGCTTTCCCCGTCAAGCTCTAAATCGGGGGCTCCCTTTAGGGTTCCGATTTAGT

GCTTTACGGCACCTCGACCCCAAAAAACTTGATTAGGGTGATGGTTCACGTAGTGGGCCATCGCCCTGATAGA

CGGTTTTTCGCCCTTTGACGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCTATTGGTTAAAAAATGAG

CTGATTTAACAAAAATTTAACGCGAATTAATTCTGTGGAATGTGTGTCAGTTAGGGTGTGGAAAGTCCCCAGG

-continued

CTCCCCAGCAGGCAGAAGTATGCAAAGCATGCATCTCAATTAGTCAGCAACCAGGTGTGGAAAGTCCCCAGGC
TCCCCAGCAGGCAGAAGTATGCAAAGCATGCATCTCAATTAGTCAGCAACCATAGTCCCGCCCCTAACTCCGC
CCATCCCGCCCCTAACTCCGCCCAGTTCCGCCCATTCTCCGCCCCATGGCTGACTAATTTTTTTTATTTATGC
AGAGGCCGAGGCCGCCTCTGCCTCTGAGCTATTCCAGAAGTAGTGAGGAGGCTTTTTTGGAGGCCTAGGCTTT
TGCAAAAAGCTCCCGGGAGCTTGTATATCCATTTTCGGATCTGATCAAGAGACAGGATGAGGATCGTTTCGCA
TGATTGAACAAGATGGATTGCACGCAGGTTCTCCGGCCGCTTGGGTGGAGAGGCTATTCGGCTATGACTGGGC
ACAACAGACAATCGGCTGCTCTGATGCCGCCGTGTTCCGGCTGTCAGCGCAGGGGCGCCCGGTTCTTTTTGTC
AAGACCGACCTGTCCGGTGCCCTGAATGAACTGCAGGACGAGGCAGCGCGGCTATCGTGGCTGGCCACGACGG
GCGTTCCTTGCGCAGCTGTGCTCGACGTTGTCACTGAAGCGGGAAGGGACTGGCTGCTATTGGGCGAAGTGCC
GGGGCAGGATCTCCTGTCATCTCACCTTGCTCCTGCCGAGAAAGTATCCATCATGGCTGATGCAATGCGGCGG
CTGCATACGCTTGATCCGGCTACCTGCCCATTCGACCACCAAGCGAAACATCGCATCGAGCGAGCACGTACTC
GGATGGAAGCCGGTCTTGTCGATCAGGATGATCTGGACGAAGAGCATCAGGGGCTCGCGCCAGCCGAACTGTT
CGCCAGGCTCAAGGCGCGCATGCCCGACGGCGAGGATCTCGTCGTGACCCATGGCGATGCCTGCTTGCCGAAT
ATCATGGTGGAAAATGGCCGCTTTTCTGGATTCATCGACTGTGGCCGGCTGGGTGTGGCGGACCGCTATCAGG
ACATAGCGTTGGCTACCCGTGATATTGCTGAAGAGCTTGGCGGCGAATGGGCTGACCGCTTCCTCGTGCTTTA
CGGTATCGCCGCTCCCGATTCGCAGCGCATCGCCTTCTATCGCCTTCTTGACGAGTTCTTCTGAGCGGGACTC
TGGGGTTCGAAATGACCGACCAAGCGACGCCCAACCTGCCATCACGAGATTTCGATTCCACCGCCGCCTTCTA
TGAAAGGTTGGGCTTCGGAATCGTTTTCCGGGACGCCGGCTGGATGATCCTCCAGCGCGGGGATCTCATGCTG
GAGTTCTTCGCCCACCCCAACTTGTTTATTGCAGCTTATAATGGTTACAAATAAAGCAATAGCATCACAAATT
TCACAAATAAAGCATTTTTTTCACTGCATTCTAGTTGTGGTTTGTCCAAACTCATCAATGTATCTTATCATGT
CTGTATACCGTCGACCTCTAGCTAGAGCTTGGCGTAATCATGGTCATAGCTGTTTCCTGTGTGAAATTGTTAT
CCGCTCACAATTCCACACAACATACGAGCCGGAAGCATAAAGTGTAAAGCCTGGGGTGCCTAATGAGTGAGCT
AACTCACATTAATTGCGTTGCGCTCACTGCCCGCTTTCCAGTCGGGAAACCTGTCGTGCCAGCTGCATTAATG
AATCGGCCAACGCGCGGGGAGAGGCGGTTTGCGTATTGGGCGCTCTTCCGCTTCCTCGCTCACTGACTCGCTG
CGCTCGGTCGTTCGGCTGCGGCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTCTCATAGCTCACGCTGTAGGTA
TCTCAGTTCGGTGTAGGTCGTTCGCTCCAAGCTGGGCTGTGTGCACGAACCCCCCGTTCAGCCCGACCGCTGC
GCCTTATCCGGTAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCCTAACTACGGCTA
CACTAGAAGAACAGTATTTGGTATCTGCGCTCTGCTGAAGCCAGTTACCTTCGGAAAAAGAGTTGGTAGCTCT
TGATCCGGCAAACAAACCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACGAAAACTCACGTTAAGG
GATTTTGGTCATGAGATTATCAAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGATTTATCAGCAATAAACCAG

-continued

CCAGCCGGAAGGGCCGAGCGCAGAAGTGGTCCTGCAACTTTATCCGCCTCCATCCAGTCTATTAATTGTTGCC

GGGAAGCTAGAGTAAGTAGTTCGCCAGTTAATAGTTTGCGCAACGTTGTTGCCATTGCTACAGGCATCGTGGT

GTCACGCTCGTCGTTTGGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAGTTGGCCGCAGTGTTAT

CACTCATGGTTATGGCAGCACTGCATAATTCTCTTACTGTCATGCCATCCGTAAGATGCTTTTCTGTGACTGG

TGAGTACTCAACCAAGTCATTCTGAGAATAGTGTATGCGGCGACCGAGTTGCTCTTGCCCGGCGTCAATACGG

GATAATACCGCGCCACATAGCAGAACTTTAAAAGTGCTCATCATTGGAAAACGTTCTTCGGGGCGAAAACTCT

CAAGGATCTTACCGCTGTTGAGATCCAGTTCGATGTAACCCACTCGTGCACCCAACTGATCTTCAGCATCTTT

TACTTTCACCAGCGTTTCTGGGTGAGCAAAAACAGGAAGGCAAAATGCCGCAAAAAAGGGAATAAGGGCGACA

CGGAAATGTTGAATACTCATACTCTTCCTTTTTCAATATTATTGAAGCATTTATCAGGGTTATTGTCTCATGA

GCGGATACATATTTGAATGTATTTAGAAAAATAAACAAATAGGGGTTCCGCGCACATTTCCCCGAAAAGTGCC

ACCTGACGTC

Soluble recombinant ENPP1 (srENPP1) constructs
(ENPP1opt is a codon optimized version of srENPP1)
CMV_kozak_hAlb sig_FLAG_ENPP1opt_halb_STOP_pcDNA3.1 (+)
(SEQ ID NO: 88)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTAGTTCCAGATGGTAAATATACACAAGGGATTTAGTCAAACAATTTTTTGGCAAGAATA

TTATGAATTTTGTAATCGGTTGGCAGCCAATGAAATACAAAGATGAGTCTAGTTAATAATCTACAATTATTGG

TTAAAGAAGTATATTAGTGCTAATTTCCCTCCGTTTGTCCTAGCTTTTCTCTTCTGTCAACCCCACACGCCTT

TGGCACCTCTGGCTAACTAGAGAACCCACTGCTTACTGGCTTATCGAAATTAATACGACTCACTATAGGGAGA

CCCAAGCTGGCTAGCGCCACCATGAAGTGGGTAACCTTTATTTCCCTTCTTTTTCTCTTTAGCTCGGCTTATT

CCAGGGGTGTGTTTCGTCGAGACTACAAAGACGATGACGACAAGAGCGCTGGCCTGAAGCCAAGCTGCGCCAA

GGAGGTGAAGAGCTGCAAGGGCAGATGTTTCGAACGGACCTTCGGCAACTGCAGATGCGACGCCGCCTGCGTG

GAACTGGGAAACTGTTGTCTGGACTACCAGGAGACATGTATCGAGCCTGAGCACATCTGGACATGCAACAAGT

TCAGATGTGGCGAGAAAAGACTGACTCGGAGTCTGTGCGCCTGTTCTGACGACTGCAAGGACAAGGGCGATTG

CTGCATCAACTACAGCAGCGTGTGCCAGGGCGAAAAGAGCTGGGTCGAGGAACCCTGCGAGAGCATCAACGAG

CCCCAGTGCCCTGCCGGATTTGAGACACCTCCTACCCTGCTCTTCTCCCTGGATGGCTTCAGAGCTGAGTACC

TGCATACATGGGGAGGACTGCTGCCTGTGATCAGCAAGCTGAAGAAGTGCGGCACCTACACAAAGAACATGCG

GCCTGTCTACCCTACCAAGACCTTCCCCAACCACTACAGCATCGTGACCGGCCTGTACCCCGAGAGCCACGGC

ATCATCGACAACAAGATGTACGACCCCAAAATGAACGCCAGCTTCAGCCTGAAATCTAAGGAAAAGTTCAACC

CTGAGTGGTATAAGGGCGAGCCAATCTGGGTGACAGCCAAGTACCAGGGCCTGAAGAGCGGCACCTTCTTCTG

GCCTGGCAGCGACGTGGAGATCAACGGAATCTTCCCTGATATCTACAAGATGTATAACGGCTCCGTGCCTTTC

GAGGAGCGGATCTTGGCTGTTCTTCAGTGGCTGCAGCTGCCCAAGGACGAGAGACCCCACTTCTACACCCTGT

ACCTGGAAGAACCTGACAGCAGCGGCCACAGCTACGGCCCTGTGTCTAGCGAGGTGATCAAGGCCCTGCAAAG

AGTGGATGGCATGGTGGGCATGCTGATGGATGGACTGAAGGAACTGAACCTCCATCGTTGCCTGAACCTGATC

CTGATCTCCGACCACGGCATGGAACAGGGCAGCTGTAAAAAGTACATCTACCTGAACAAGTACCTGGGCGACG

TGAAGAATATCAAGGTGATCTACGGGCCGGCCGCCAGGCTGCGGCCTAGCGACGTGCCCGACAAGTATTACAG

CTTCAACTACGAGGGCATCGCCAGAAACCTGTCTTGCAGAGAACCCAATCAACACTTCAAGCCTTACCTGAAG

CACTTTCTGCCTAAGAGACTGCACTTCGCCAAAAGCGACAGAATTGAACCCCTGACATTCTATCTGGACCCTC

-continued

AGTGGCAGCTGGCCCTCAATCCTTCTGAACGCAAATACTGCGGTAGCGGATTTCACGGCTCTGATAACGTGTT

TTCTAACATGCAGGCCCTGTTTGTGGGCTACGGCCCTGGCTTCAAGCACGGAATCGAGGCTGACACCTTCGAG

AACATCGAAGTTTACAATCTGATGTGCGACCTGCTGAATCTGACCCCAGCCCCTAACAACGGCACACACGGCT

CTCTGAATCACCTGCTCAAGAACCCCGTGTATACCCCCAAACACCCTAAAGAGGTCCATCCACTGGTGCAGTG

CCCATTCACCAGAAACCCTCGGGACAACCTTGGCTGCAGCTGCAACCCTAGCATCCTCCCTATCGAAGATTTC

CAGACCCAGTTTAACCTGACTGTCGCCGAAGAGAAGATCATCAAGCACGAAACCCTGCCCTACGGGAGGCCCA

GAGTGCTGCAGAAAGAAAACACAATCTGTCTGCTGAGCCAGCACCAGTTTATGAGCGGCTACAGTCAGGACAT

CCTGATGCCTCTGTGGACCAGCTACACCGTGGACCGGAATGACAGCTTCAGCACCGAGGACTTCAGCAACTGC

CTGTATCAGGACTTCCGCATCCCTCTGTCCCCTGTGCATAAGTGCAGCTTTTACAAGAACAACACCAAGGTGA

GCTACGGGTTTCTGAGCCCACCACAACTGAACAAAAATAGCTCTGGCATCTACTCTGAGGCGCTGCTGACCAC

CAACATCGTGCCAATGTACCAGAGCTTCCAGGTGATCTGGCGGTACTTCCATGATACCCTGCTTCGGAAGTAC

GCCGAAGAACGGAACGGCGTGAACGTGGTGTCCGGCCCAGTGTTCGACTTCGACTACGACGGCAGATGTGATT

CCCTTGAGAATCTGAGACAGAAGCGGCGGGTTATCAGAAACCAGGAGATCCTGATTCCTACCCACTTCTTCAT

CGTGCTGACATCTTGCAAGGATACCAGCCAAACACCTCTGCACTGCGAGAACCTGGACACCCTGGCCTTCATC

CTGCCTCACCGGACCGATAATAGCGAATCCTGTGTGCACGGCAAACACGACTCTAGCTGGGTGGAAGAGCTGC

TGATGCTGCACAGAGCCCGGATCACAGATGTGGAACACATCACCGGCCTGTCCTTCTACCAACAGAGAAAGGA

ACCCGTGTCTGATATCCTGAAGCTGAAAACCCACCTGCCTACCTTCAGCCAGGAGGACCTGATCGTTAACGAT

GCACACAAGAGTGAGGTTGCTCATCGGTTTAAAGATTTGGGAGAAGAAAATTTCAAAGCCTTGGTGTTGATTG

CCTTTGCTCAGTATCTTCAGCAGTGTCCATTTGAAGATCATGTAAAATTAGTGAATGAAGTAACTGAATTTGC

AAAAACATGTGTTGCTGATGAGTCAGCTGAAAATTGTGACAAATCACTTCATACCCTTTTTGGAGACAAATTA

TGCACAGTTGCAACTCTTCGTGAAACCTATGGTGAAATGGCTGACTGCTGTGCAAAACAAGAACCTGAGAGAA

ATGAATGCTTCTTGCAACACAAAGATGACAACCCAAACCTCCCCCGATTGGTGAGACCAGAGGTTGATGTGAT

GTGCACTGCTTTTCATGACAATGAAGAGACATTTTTGAAAAAATACTTATATGAAATTGCCAGAAGACATCCT

TACTTTTATGCCCCGGAACTCCTTTTCTTTGCTAAAAGGTATAAAGCTGCTTTTACAGAATGTTGCCAAGCTG

CTGATAAAGCTGCCTGCCTGTTGCCAAAGCTCGATGAACTTCGGGATGAAGGGAAGGCTTCGTCTGCCAAACA

GAGACTCAAGTGTGCCAGTCTCCAAAAATTTGGAGAAAGAGCTTTCAAAGCATGGGCAGTAGCTCGCCTGAGC

CAGAGATTTCCCAAAGCTGAGTTTGCAGAAGTTTCCAAGTTAGTGACAGATCTTACCAAAGTCCACACGGAAT

GCTGCCATGGAGATCTGCTTGAATGTGCTGATGACAGGGCGGACCTTGCCAAGTATATCTGTGAAAATCAAGA

TTCGATCTCCAGTAAACTGAAGGAATGCTGTGAAAAACCTCTGTTGGAAAAATCCCACTGCATTGCCGAAGTG

GAAAATGATGAGATGCCTGCTGACTTGCCTTCATTAGCTGCTGATTTTGTTGAAAGTAAGGATGTTTGCAAAA

ACTATGCTGAGGCAAAGGATGTCTTCCTGGGCATGTTTTTGTATGAATATGCAAGAAGGCATCCTGATTACTC

TGTCGTGCTGCTGCTGAGACTTGCCAAGACATATGAAACCACACTCGAGAAGTGCTGTGCCGCTGCAGATCCT

CATGAATGCTATGCCAAAGTGTTCGATGAATTTAAACCTCTTGTGGAAGAGCCTCAGAATTTAATCAAACAAA

ATTGTGAGCTTTTTGAGCAGCTTGGAGAGTACAAATTCCAGAATGCGCTATTAGTTCGTTACACCAAGAAAGT

ACCCCAAGTGTCAACTCCAACTCTTGTAGAGGTCTCAAGAAACCTAGGAAAAGTGGGCAGCAAATGTTGTAAA

CATCCTGAAGCAAAAAGAATGCCCTGTGCAGAAGACTATCTATCCGTGGTCCTGAACCAGTTATGTGTGTTGC

ATGAGAAAACGCCAGTAAGTGACAGAGTCACCAAATGCTGCACAGAATCCTTGGTGAACAGGCGACCATGCTT

TTCAGCTCTGGAAGTCGATGAAACATACGTTCCCAAAGAGTTTAATGCTGAAACATTCACCTTCCATGCAGAT

ATATGCACACTTTCTGAGAAGGAGAGACAAATCAAGAAACAAACTGCACTTGTTGAGCTCGTGAAACACAAGC

CCAAGGCAACAAAAGAGCAACTGAAAGCTGTTATGGATGATTTCGCAGCTTTTGTAGAGAAGTGCTGCAAGGC

-continued

TGACGATAAGGAGACCTGCTTTGCCGAGGAGGGTAAAAAACTTGTTGCTGCAAGTCAAGCTGCCTTAGGCTTA

TGAGGTACCGAGCTCGGATCCACTAGTCCAGTGTGGTGGAATTCTGCAGATATCCAGCACAGTGGCGGCCGCT

CGAGTCTAGAGGGCCCGTTTAAACCCGCTGATCAGCCTCGACTGTGCCTTCTAGTTGCCAGCCATCTGTTGTT

TGCCCCTCCCCCGTGCCTTCCTTGACCCTGGAAGGTGCCACTCCCACTGTCCTTTCCTAATAAAATGAGGAAA

TTGCATCGCATTGTCTGAGTAGGTGTCATTCTATTCTGGGGGGTGGGGTGGGGCAGGACAGCAAGGGGGAGGA

TTGGGAAGACAATAGCAGGCATGCTGGGGATGCGGTGGGCTCTATGGCTTCTGAGGCGGAAAGAACCAGCTGG

GGCTCTAGGGGGTATCCCCACGCGCCCTGTAGCGGCGCATTAAGCGCGGCGGGTGTGGTGGTTACGCGCAGCG

TGACCGCTACACTTGCCAGCGCCCTAGCGCCCGCTCCTTTCGCTTTCTTCCCTTCCTTTCTCGCCACGTTCGC

CGGCTTTCCCCGTCAAGCTCTAAATCGGGGGCTCCCTTTAGGGTTCCGATTTAGTGCTTTACGGCACCTCGAC

CCCAAAAAACTTGATTAGGGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACTCAACCCTATCTCGGTCTA

TTCTTTTGATTTATAAGGGATTTTGCCGATTTCGGCCTATTGGTTAAAAAATGAGCTGATTTAACAAAAATTT

AACGCGAATTAATTCTGTGGAATGTGTGTCAGTTAGGGTGTGGAAAGTCCCCAGGCTCCCCAGCAGGCAGAAG

TATGCAAAGCATGCATCTCAATTAGTCAGCAACCAGGTGTGGAAAGTCCCCAGGCTCCCCAGCAGGCAGAAGT

ATGCAAAGCATGCATCTCAATTAGTCAGCAACCATAGTCCCGCCCCTAACTCCGCCCATCCCGCCCCTAACTC

CGCCCAGTTCCGCCCATTCTCCGCCCCATGGCTGACTAATTTTTTTTATTTATGCAGAGGCCGAGGCCGCCTC

TGCCTCTGAGCTATTCCAGAAGTAGTGAGGAGGCTTTTTTGGAGGCCTAGGCTTTTGCAAAAAGCTCCCGGGA

GCTTGTATATCCATTTTCGGATCTGATCAAGAGACAGGATGAGGATCGTTTCGCATGATTGAACAAGATGGAT

TGCACGCAGGTTCTCCGGCCGCTTGGGTGGAGAGGCTATTCGGCTATGACTGGGCACAACAGACAATCGGCTG

CTCTGATGCCGCCGTGTTCCGGCTGTCAGCGCAGGGGCGCCCGGTTCTTTTTGTCAAGACCGACCTGTCCGGT

GCCCTGAATGAACTGCAGGACGAGGCAGCGCGGCTATCGTGGCTGGCCACGACGGGCGTTCCTTGCGCAGCTG

TGCTCGACGTTGTCACTGAAGCGGGAAGGGACTGGCTGCTATTGGGCGAAGTGCCGGGGCAGGATCTCCTGTC

ATCTCACCTTGCTCCTGCCGAGAAAGTATCCATCATGGCTGATGCAATGCGGCGGCTGCATACGCTTGATCCG

GCTACCTGCCCATTCGACCACCAAGCGAAACATCGCATCGAGCGAGCACGTACTCGGATGGAAGCCGGTCTTG

TCGATCAGGATGATCTGGACGAAGAGCATCAGGGGCTCGCGCCAGCCGAACTGTTCGCCAGGCTCAAGGCGCG

CATGCCCGACGGCGAGGATCTCGTCGTGACCCATGGCGATGCCTGCTTGCCGAATATCATGGTGGAAAATGGC

CGCTTTTCTGGATTCATCGACTGTGGCCGGCTGGGTGTGGCGGACCGCTATCAGGACATAGCGTTGGCTACCC

GTGATATTGCTGAAGAGCTTGGCGGCGAATGGGCTGACCGCTTCCTCGTGCTTTACGGTATCGCCGCTCCCGA

TTCGCAGCGCATCGCCTTCTATCGCCTTCTTGACGAGTTCTTCTGAGCGGGACTCTGGGGTTCGAAATGACCG

ACCAAGCGACGCCCAACCTGCCATCACGAGATTTCGATTCCACCGCCGCCTTCTATGAAAGGTTGGGCTTCGG

AATCGTTTTCCGGGACGCCGGCTGGATGATCCTCCAGCGCGGGGATCTCATGCTGGAGTTCTTCGCCCACCCC

AACTTGTTTATTGCAGCTTATAATGGTTACAAATAAAGCAATAGCATCACAAATTTCACAAATAAAGCATTTT

TTTCACTGCATTCTAGTTGTGGTTTGTCCAAACTCATCAATGTATCTTATCATGTCTGTATACCGTCGACCTC

TAGCTAGAGCTTGGCGTAATCATGGTCATAGCTGTTTCCTGTGTGAAATTGTTATCCGCTCACAATTCCACAC

AACATACGAGCCGGAAGCATAAAGTGTAAAGCCTGGGGTGCCTAATGAGTGAGCTAACTCACATTAATTGCGT

TGCGCTCACTGCCCGCTTTCCAGTCGGGAAACCTGTCGTGCCAGCTGCATTAATGAATCGGCCAACGCGCGGG

GAGAGGCGGTTTGCGTATTGGGCGCTCTTCCGCTTCCTCGCTCACTGACTCGCTGCGCTCGGTCGTTCGGCTG

CGGCGAGCGGTATCAGCTCACTCAAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCGTTGCTGGCGTTTTTCCATAGGCT

-continued

CCGCCCCCCTGACGAGCATCACAAAAATCGACGCTCAAGTCAGAGGTGGCGAAACCCGACAGGACTATAAAGA

TACCAGGCGTTTCCCCCTGGAAGCTCCCTCGTGCGCTCTCCTGTTCCGACCCTGCCGCTTACCGGATACCTGT

CCGCCTTTCTCCCTTCGGGAAGCGTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACACTAGAAGAACAGTATT

TGGTATCTGCGCTCTGCTGAAGCCAGTTACCTTCGGAAAAAGAGTTGGTAGCTCTTGATCCGGCAAACAAACC

ACCGCTGGTAGCGGTGGTTTTTTTGTTTGCAAGCAGCAGATTACGCGCAGAAAAAAAGGATCTCAAGAAGATC

CTTTGATCTTTTCTACGGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATCTGTCTATTTCGTTCAT

CCATAGTTGCCTGACTCCCCGTCGTGTAGATAACTACGATACGGGAGGGCTTACCATCTGGCCCCAGTGCTGC

AATGATACCGCGAGACCCACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGGGAAGCTAGAGTAAGTA

GTTCGCCAGTTAATAGTTTGCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCCCATGTTGTGCAAAAAAGCG

GTTAGCTCCTTCGGTCCTCCGATCGTTGTCAGAAGTAAGTTGGCCGCAGTGTTATCACTCATGGTTATGGCAG

CACTGCATAATTCTCTTACTGTCATGCCATCCGTAAGATGCTTTTCTGTGACTGGTGAGTACTCAACCAAGTC

ATTCTGAGAATAGTGTATGCGGCGACCGAGTTGCTCTTGCCCGGCGTCAATACGGGATAATACCGCGCCACAT

AGCAGAACTTTAAAAGTGCTCATCATTGGAAAACGTTCTTCGGGGCGAAAACTCTCAAGGATCTTACCGCTGT

TGAGATCCAGTTCGATGTAACCCACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGGCGACACGGAAATGTTGAATACTC

ATACTCTTCCTTTTTCAATATTATTGAAGCATTTATCAGGGTTATTGTCTCATGAGCGGATACATATTTGAAT

GTATTTAGAAAAATAAACAAATAGGGGTTCCGCGCACATTTCCCCGAAAAGTGCCACCTGACGTC

CMV_kozak_hAlb sig_FLAG_ENPPlopt_halb_STOP_MIR155_pcDNA3.1 (+)

(SEQ ID NO: 89)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGACATTGATTATTGACTAGTTATTAATAGTAATCAATTACGGGGTCATTAGTTCATAG

CCCATATATGGAGTTCCGCGTTACATAACTTACGGTAAATGGCCCGCCTGGCTGACCGCCCAACGACCCCCGC

CCATTGACGTCAATAATGACGTATGTTCCCATAGTAACGCCAATAGGGACTTTCCATTGACGTCAATGGGTGG

AGTATTTACGGTAAACTGCCCACTTGGCAGTACATCAAGTGTATCATATGCCAAGTACGCCCCCTATTGACGT

CAATGACGGTAAATGGCCCGCCTGGCATTATGCCCAGTACATGACCTTATGGGACTTTCCTACTTGGCAGTAC

ATCTACGTATTAGTCATCGCTATTACCATGGTGATGCGGTTTTGGCAGTACATCAATGGGCGTGGATAGCGGT

TTGACTCACGGGGATTTCCAAGTCTCCACCCCATTGACGTCAATGGGAGTTTGTTTTGGCACCAAAATCAACG

GGACTTTCCAAAATGTCGTAACAACTCCGCCCCATTGACGCAAATGGGCGGTAGGCGTGTACGGTGGGAGGTC

TATATAAGCAGAGCTCTCTGGCTAACTAGAGAACCCACTGCTTACTGGCTTATCGAAATTAATACGACTCACT

ATAGGGAGACCCAAGCTGGCTAGCGCCACCATGAAGTGGGTAACCTTTATTTCCCTTCTTTTTCTCTTTAGCT

CGGCTTATTCCAGGGGTGTGTTTCGTCGAGACTACAAAGACGATGACGACAAGAGCGCTGGCCTGAAGCCAAG

CTGCGCCAAGGAGGTGAAGAGCTGCAAGGGCAGATGTTTCGAACGGACCTTCGGCAACTGCAGATGCGACGCC

-continued

GCCTGCGTGGAACTGGGAAACTGTTGTCTGGACTACCAGGAGACATGTATCGAGCCTGAGCACATCTGGACAT

GCAACAAGTTCAGATGTGGCGAGAAAAGACTGACTCGGAGTCTGTGCGCCTGTTCTGACGACTGCAAGGACAA

GGGCGATTGCTGCATCAACTACAGCAGCGTGTGCCAGGGCGAAAAGAGCTGGGTCGAGGAACCCTGCGAGAGC

ATCAACGAGCCCCAGTGCCCTGCCGGATTTGAGACACCTCCTACCCTGCTCTTCTCCCTGGATGGCTTCAGAG

CTGAGTACCTGCATACATGGGGAGGACTGCTGCCTGTGATCAGCAAGCTGAAGAAGTGCGGCACCTACACAAA

GAACATGCGGCCTGTCTACCCTACCAAGACCTTCCCCAACCACTACAGCATCGTGACCGGCCTGTACCCCGAG

AGCCACGGCATCATCGACAACAAGATGTACGACCCCAAAATGAACGCCAGCTTCAGCCTGAAATCTAAGGAAA

AGTTCAACCCTGAGTGGTATAAGGGCGAGCCAATCTGGGTGACAGCCAAGTACCAGGGCCTGAAGAGCGGCAC

CTTCTTCTGGCCTGGCAGCGACGTGGAGATCAACGGAATCTTCCCTGATATCTACAAGATGTATAACGGCTCC

GTGCCTTTCGAGGAGCGGATCTTGGCTGTTCTTCAGTGGCTGCAGCTGCCCAAGGACGAGAGACCCCACTTCT

ACACCCTGTACCTGGAAGAACCTGACAGCAGCGGCCACAGCTACGGCCCTGTGTCTAGCGAGGTGATCAAGGC

CCTGCAAAGAGTGGATGGCATGGTGGGCATGCTGATGGATGGACTGAAGGAACTGAACCTCCATCGTTGCCTG

AACCTGATCCTGATCTCCGACCACGGCATGGAACAGGGCAGCTGTAAAAAGTACATCTACCTGAACAAGTACC

TGGGCGACGTGAAGAATATCAAGGTGATCTACGGGCCGGCCGCCAGGCTGCGGCCTAGCGACGTGCCCGACAA

GTATTACAGCTTCAACTACGAGGGCATCGCCAGAAACCTGTCTTGCAGAGAACCCAATCAACACTTCAAGCCT

TACCTGAAGCACTTTCTGCCTAAGAGACTGCACTTCGCCAAAAGCGACAGAATTGAACCCCTGACATTCTATC

TGGACCCTCAGTGGCAGCTGGCCCTCAATCCTTCTGAACGCAAATACTGCGGTAGCGGATTTCACGGCTCTGA

TAACGTGTTTTCTAACATGCAGGCCCTGTTTGTGGGCTACGGCCCTGGCTTCAAGCACGGAATCGAGGCTGAC

ACCTTCGAGAACATCGAAGTTTACAATCTGATGTGCGACCTGCTGAATCTGACCCCAGCCCCTAACAACGGCA

CACACGGCTCTCTGAATCACCTGCTCAAGAACCCCGTGTATACCCCCAAACACCCTAAAGAGGTCCATCCACT

GGTGCAGTGCCCATTCACCAGAAACCCTCGGGACAACCTTGGCTGCAGCTGCAACCCTAGCATCCTCCCTATC

GAAGATTTCCAGACCCAGTTTAACCTGACTGTCGCCGAAGAGAAGATCATCAAGCACGAAACCCTGCCCTACG

GGAGGCCCAGAGTGCTGCAGAAAGAAAACACAATCTGTCTGCTGAGCCAGCACCAGTTTATGAGCGGCTACAG

TCAGGACATCCTGATGCCTCTGTGGACCAGCTACACCGTGGACCGGAATGACAGCTTCAGCACCGAGGACTTC

AGCAACTGCCTGTATCAGGACTTCCGCATCCCTCTGTCCCCTGTGCATAAGTGCAGCTTTTACAAGAACAACA

CCAAGGTGAGCTACGGGTTTCTGAGCCCACCACAACTGAACAAAAATAGCTCTGGCATCTACTCTGAGGCGCT

GCTGACCACCAACATCGTGCCAATGTACCAGAGCTTCCAGGTGATCTGGCGGTACTTCCATGATACCCTGCTT

CGGAAGTACGCCGAAGAACGGAACGGCGTGAACGTGGTGTCCGGCCCAGTGTTCGACTTCGACTACGACGGCA

GATGTGATTCCCTTGAGAATCTGAGACAGAAGCGGCGGGTTATCAGAAACCAGGAGATCCTGATTCCTACCCA

CTTCTTCATCGTGCTGACATCTTGCAAGGATACCAGCCAAACACCTCTGCACTGCGAGAACCTGGACACCCTG

GCCTTCATCCTGCCTCACCGGACCGATAATAGCGAATCCTGTGTGCACGGCAAACACGACTCTAGCTGGGTGG

AAGAGCTGCTGATGCTGCACAGAGCCCGGATCACAGATGTGGAACACATCACCGGCCTGTCCTTCTACCAACA

GAGAAAGGAACCCGTGTCTGATATCCTGAAGCTGAAAACCCACCTGCCTACCTTCAGCCAGGAGGACCTGATC

GTTAACGATGCACACAAGAGTGAGGTTGCTCATCGGTTTAAAGATTTGGGAGAAGAAAATTTCAAAGCCTTGG

TGTTGATTGCCTTTGCTCAGTATCTTCAGCAGTGTCCATTTGAAGATCATGTAAAATTAGTGAATGAAGTAAC

TGAATTTGCAAAAACATGTGTTGCTGATGAGTCAGCTGAAAATTGTGACAAATCACTTCATACCCTTTTTGGA

GACAAATTATGCACAGTTGCAACTCTTCGTGAAACCTATGGTGAAATGGCTGACTGCTGTGCAAAACAAGAAC

CTGAGAGAAATGAATGCTTCTTGCAACACAAAGATGACAACCCAAACCTCCCCCGATTGGTGAGACCAGAGGT

TGATGTGATGTGCACTGCTTTTCATGACAATGAAGAGACATTTTTGAAAAAATACTTATATGAAATTGCCAGA

AGACATCCTTACTTTTATGCCCCGGAACTCCTTTTCTTTGCTAAAAGGTATAAAGCTGCTTTTACAGAATGTT

-continued

GCCAAGCTGCTGATAAAGCTGCCTGCCTGTTGCCAAAGCTCGATGAACTTCGGGATGAAGGGAAGGCTTCGTC

TGCCAAACAGAGACTCAAGTGTGCCAGTCTCCAAAAATTTGGAGAAAGAGCTTTCAAAGCATGGGCAGTAGCT

CGCCTGAGCCAGAGATTTCCCAAAGCTGAGTTTGCAGAAGTTTCCAAGTTAGTGACAGATCTTACCAAAGTCC

ACACGGAATGCTGCCATGGAGATCTGCTTGAATGTGCTGATGACAGGGCGGACCTTGCCAAGTATATCTGTGA

AAATCAAGATTCGATCTCCAGTAAACTGAAGGAATGCTGTGAAAAACCTCTGTTGGAAAAATCCCACTGCATT

GCCGAAGTGGAAAATGATGAGATGCCTGCTGACTTGCCTTCATTAGCTGCTGATTTTGTTGAAAGTAAGGATG

TTTGCAAAAACTATGCTGAGGCAAAGGATGTCTTCCTGGGCATGTTTTTGTATGAATATGCAAGAAGGCATCC

TGATTACTCTGTCGTGCTGCTGCTGAGACTTGCCAAGACATATGAAACCACACTCGAGAAGTGCTGTGCCGCT

GCAGATCCTCATGAATGCTATGCCAAAGTGTTCGATGAATTTAAACCTCTTGTGGAAGAGCCTCAGAATTTAA

TCAAACAAAATTGTGAGCTTTTTGAGCAGCTTGGAGAGTACAAATTCCAGAATGCGCTATTAGTTCGTTACAC

CAAGAAAGTACCCCAAGTGTCAACTCCAACTCTTGTAGAGGTCTCAAGAAACCTAGGAAAAGTGGGCAGCAAA

TGTTGTAAACATCCTGAAGCAAAAAGAATGCCCTGTGCAGAAGACTATCTATCCGTGGTCCTGAACCAGTTAT

GTGTGTTGCATGAGAAAACGCCAGTAAGTGACAGAGTCACCAAATGCTGCACAGAATCCTTGGTGAACAGGCG

ACCATGCTTTTCAGCTCTGGAAGTCGATGAAACATACGTTCCCAAAGAGTTTAATGCTGAAACATTCACCTTC

CATGCAGATATATGCACACTTTCTGAGAAGGAGAGACAAATCAAGAAACAAACTGCACTTGTTGAGCTCGTGA

AACACAAGCCCAAGGCAACAAAAGAGCAACTGAAAGCTGTTATGGATGATTTCGCAGCTTTTGTAGAGAAGTG

CTGCAAGGCTGACGATAAGGAGACCTGCTTTGCCGAGGAGGGTAAAAAACTTGTTGCTGCAAGTCAAGCTGCC

TTAGGCTTATGACAATTACGATTAGCACTATCCAATTACGATTAGCACTATCCAATTACGATTAGCACTATCG

GTACCGAGCTCGGATCCACTAGTCCAGTGTGGTGGAATTCTGCAGATATCCAGCACAGTGGCGGCCGCTCGAG

TCTAGAGGGCCCGTTTAAACCCGCTGATCAGCCTCGACTGTGCCTTCTAGTTGCCAGCCATCTGTTGTTTGCC

CCTCCCCCGTGCCTTCCTTGACCCTGGAAGGTGCCACTCCCACTGTCCTTTCCTAATAAAATGAGGAAATTGC

ATCGCATTGTCTGAGTAGGTGTCATTCTATTCTGGGGGGTGGGGTGGGGCAGGACAGCAAGGGGGAGGATTGG

GAAGACAATAGCAGGCATGCTGGGGATGCGGTGGGCTCTATGGCTTCTGAGGCGGAAAGAACCAGCTGGGGCT

CTAGGGGGTATCCCCACGCGCCCTGTAGCGGCGCATTAAGCGCGGCGGGTGTGGTGGTTACGCGCAGCGTGAC

CGCTACACTTGCCAGCGCCCTAGCGCCCGCTCCTTTCGCTTTCTTCCCTTCCTTTCTCGCCACGTTCGCCGGC

TTTCCCCGTCAAGCTCTAAATCGGGGGCTCCCTTTAGGGTTCCGATTTAGTGCTTTACGGCACCTCGACCCCA

AAAAACTTGATTAGGGTGATGGTTCACGTAGTGGGCCATCGCCCTGATAGACGGTTTTTCGCCCTTTGACGTT

GGAGTCCACGTTCTTTAATAGTGGACTCTTGTTCCAAACTGGAACAACACTCAACCCTATCTCGGTCTATTCT

TTTGATTTATAAGGGATTTTGCCGATTTCGGCCTATTGGTTAAAAAATGAGCTGATTTAACAAAAATTTAACG

CGAATTAATTCTGTGGAATGTGTGTCAGTTAGGGTGTGGAAAGTCCCCAGGCTCCCCAGCAGGCAGAAGTATG

CAAAGCATGCATCTCAATTAGTCAGCAACCAGGTGTGGAAAGTCCCCAGGCTCCCCAGCAGGCAGAAGTATGC

AAAGCATGCATCTCAATTAGTCAGCAACCATAGTCCCGCCCCTAACTCCGCCCATCCCGCCCCTAACTCCGCC

CAGTTCCGCCCATTCTCCGCCCCATGGCTGACTAATTTTTTTTATTTATGCAGAGGCCGAGGCCGCCTCTGCC

TCTGAGCTATTCCAGAAGTAGTGAGGAGGCTTTTTTGGAGGCCTAGGCTTTTGCAAAAAGCTCCCGGGAGCTT

GTATATCCATTTTCGGATCTGATCAAGAGACAGGATGAGGATCGTTTCGCATGATTGAACAAGATGGATTGCA

CGCAGGTTCTCCGGCCGCTTGGGTGGAGAGGCTATTCGGCTATGACTGGGCACAACAGACAATCGGCTGCTCT

GATGCCGCCGTGTTCCGGCTGTCAGCGCAGGGGCGCCCGGTTCTTTTTGTCAAGACCGACCTGTCCGGTGCCC

TGAATGAACTGCAGGACGAGGCAGCGCGGCTATCGTGGCTGGCCACGACGGGCGTTCCTTGCGCAGCTGTGCT

CGACGTTGTCACTGAAGCGGGAAGGGACTGGCTGCTATTGGGCGAAGTGCCGGGGCAGGATCTCCTGTCATCT

-continued

CACCTTGCTCCTGCCGAGAAAGTATCCATCATGGCTGATGCAATGCGGCGGCTGCATACGCTTGATCCGGCTA

CCTGCCCATTCGACCACCAAGCGAAACATCGCATCGAGCGAGCACGTACTCGGATGGAAGCCGGTCTTGTCGA

TCAGGATGATCTGGACGAAGAGCATCAGGGGCTCGCGCCAGCCGAACTGTTCGCCAGGCTCAAGGCGCGCATG

CCCGACGGCGAGGATCTCGTCGTGACCCATGGCGATGCCTGCTTGCCGAATATCATGGTGGAAAATGGCCGCT

TTTCTGGATTCATCGACTGTGGCCGGCTGGGTGTGGCGGACCGCTATCAGGACATAGCGTTGGCTACCCGTGA

TATTGCTGAAGAGCTTGGCGGCGAATGGGCTGACCGCTTCCTCGTGCTTTACGGTATCGCCGCTCCCGATTCG

CAGCGCATCGCCTTCTATCGCCTTCTTGACGAGTTCTTCTGAGCGGGACTCTGGGGTTCGAAATGACCGACCA

AGCGACGCCCAACCTGCCATCACGAGATTTCGATTCCACCGCCGCCTTCTATGAAAGGTTGGGCTTCGGAATC

GTTTTCCGGGACGCCGGCTGGATGATCCTCCAGCGCGGGGATCTCATGCTGGAGTTCTTCGCCCACCCCAACT

TGTTTATTGCAGCTTATAATGGTTACAAATAAAGCAATAGCATCACAAATTTCACAAATAAAGCATTTTTTTC

ACTGCATTCTAGTTGTGGTTTGTCCAAACTCATCAATGTATCTTATCATGTCTGTATACCGTCGACCTCTAGC

TAGAGCTTGGCGTAATCATGGTCATAGCTGTTTCCTGTGTGAAATTGTTATCCGCTCACAATTCCACACAACA

TACGAGCCGGAAGCATAAAGTGTAAAGCCTGGGGTGCCTAATGAGTGAGCTAACTCACATTAATTGCGTTGCG

CTCACTGCCCGCTTTCCAGTCGGGAAACCTGTCGTGCCAGCTGCATTAATGAATCGGCCAACGCGCGGGGAGA

GGCGGTTTGCGTATTGGGCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGGATAACGCAGGAAAGAACAT

GTGAGCAAAAGGCCAGCAAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGACAGGACTATAAAGATACC

AGGCGTTTCCCCCTGGAAGCTCCCTCGTGCGCTCTCCTGTTCCGACCCTGCCGCTTACCGGATACCTGTCCGC

CTTTCTCCCTTCGGGAAGCGTGGCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGCGCCTTATCCGGTAACTATCGTC

TTGAGTCCAACCCGGTAAGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAGAAGAACAGTATTTGGT

ATCTGCGCTCTGCTGAAGCCAGTTACCTTCGGAAAAAGAGTTGGTAGCTCTTGATCCGGCAAACAAACCACCG

CTGGTAGCGGTGGTTTTTTTGTTTGCAAGCAGCAGATTACGCGCAGAAAAAAAGGATCTCAAGAAGATCCTTT

GATCTTTTCTACGGGGTCTGACGCTCAGTGGAACGAAAACTCACGTTAAGGGATTTTGGTCATGAGATTATCA

AAAAGGATCTTCACCTAGATCCTTTTAAATTAAAAATGAAGTTTTAAATCAATCTAAAGTATATATGAGTAAA

CTTGGTCTGACAGTTACCAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCTGGCCCCAGTGCTGCAATG

ATACCGCGAGACCCACGCTCACCGGCTCCAGATTTATCAGCAATAAACCAGCCAGCCGGAAGGGCCGAGCGCA

GAAGTGGTCCTGCAACTTTATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGTTGTGCAAAAAAGCGGTTA

GCTCCTTCGGTCCTCCGATCGTTGTCAGAAGTAAGTTGGCCGCAGTGTTATCACTCATGGTTATGGCAGCACT

GCATAATTCTCTTACTGTCATGCCATCCGTAAGATGCTTTTCTGTGACTGGTGAGTACTCAACCAAGTCATTC

TGAGAATAGTGTATGCGGCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGATCTTACCGCTGTTGAG

ATCCAGTTCGATGTAACCCACTCGTGCACCCAACTGATCTTCAGCATCTTTTACTTTCACCAGCGTTTCTGGG

-continued

TGAGCAAAAACAGGAAGGCAAAATGCCGCAAAAAAGGGAATAAGGGCGACACGGAAATGTTGAATACTCATAC

TCTTCCTTTTTCAATATTATTGAAGCATTTATCAGGGTTATTGTCTCATGAGCGGATACATATTTGAATGTAT

TTAGAAAAATAAACAAATAGGGGTTCCGCGCACATTTCCCCGAAAAGTGCCACCTGACGTC

P2Hdac9_FLAG_ENPPlopt_LINK_hAlb_pcDNA3.1 (+)

(SEQ ID NO: 90)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTATAAATGTTTTGTAGAATAAAAAAAAAAAAAGTTCTTCAAAAGAAATCTCAAATCTCC

AAATGGAAACAGGTAAAAGTGGAGCTCCCCTGGTTCCACGGAGAACCTTTTTTGAGGAAACTTAGGCAACTCG

CAGGTACCTTATGTCATGAGACAGAGTTTGAAAACTACAATTGACTATCTCTAAATTTCCTCCCAGGTCTAAA

ATGTGATGATAGTTACTACTTCAGTACATCATCCTTAAGGAAAATTATTAGGTCCACACTGTTTCTATCCTTT

GAATTTTACACATAAATTTTGTAATCAAAAGTTTATTTGTAATATCAGATGGAATCAGATAATTGCTTTTTGT

TTTTTCCACTGACAGGAACATAAGATTTTGTTGTGTAGCTTAAGTCAAACGCAGTTTGGAATATATATTTTTT

AAAAATTGTAACTTACATATCCAAATACAATTTTTCAAGAAGTAGAGTATTCAGTAGAAATTAATCTGTGAAA

GAAGAGGAATTCAGCAGTGGCCTATTTGATGAATGATTTAACGTGCTTATTTCTTCCCTTTCATCAAAACTCT

GTGTCCCCTTGTTTGCCCCCTCTGACTTCATACTCTGGAGTTGACCAAGATCCCTCTTCCATCGGATTGTTCT

GGGAATTTTGAAATAATCTGCTTTTTCCTCTCTTTCCCCTGTTGCTTCTGATGCCTTAGAATTACATTTTCCT

CGCTGATTTAGTTTAGAAAAGAGAAAAGAGCTTCCATGACTAGTAGATTATCACTTTTGGGTTTGCTCTTGGA

AGTGACAAGATGCTAGGATCCCTCTTTGGAATGTAAAATTTATCTCTTATATAGAAAGGATATAAATGTAGCA

CCAGAGACTATAAAACTCTGATACTATCTACTGTACTGTATAGCTGAACGCCACAATGTGTCTGGTAATCTAT

TGACTATCATAAATGCTATTTCTACAGAAAAGTTAGGAGGTCCATATTTCGGGCAACCAATGTATAGCTGAAT

GCAGAACAGTCATAGTTGGGTACTAACCATATATATGATTTATCCATCAACAGGTGCATATGCTCAGAAATTC

TGTATCCATAAGAAATCAGACTACTTTCTTTTCCTTTTGCAAGTAAATTGAATTTAGCCTGAGAGGCTGAGGG

GAAATTTTCACATATAAGCCACGGTTTTGTGTTTTGTGTTTTGTTTTGTTTATAGATATAGTACTAACTGGAT

GGATGCGATAAAATTCATAGGTGGTACTAAGATACAATAGGATTTGTGAAATGGACAATTGTCTTGCATAAAT

AGCAAGTAAAAAATCAAGCCTGTCCTTCATAAAAATTTTATTCTGGGGTGTCTCTGGCTAACTAGAGAACCCA

CTGCTTACTGGCTTATCGAAATTAATACGACTCACTATAGGGAGACCCAAGCTGGCTAGCGCCACCATGAAGT

GGGTAACCTTTATTTCCCTTCTTTTTCTCTTTAGCTCGGCTTATTCCAGGGGTGTGTTTCGTCGAGACTACAA

AGACGATGACGACAAGAGCGCTGGCCTGAAGCCAAGCTGCGCCAAGGAGGTGAAGAGCTGCAAGGGCAGATGT

TTCGAACGGACCTTCGGCAACTGCAGATGCGACGCCGCCTGCGTGGAACTGGGAAACTGTTGTCTGGACTACC

AGGAGACATGTATCGAGCCTGAGCACATCTGGACATGCAACAAGTTCAGATGTGGCGAGAAAAGACTGACTCG

GAGTCTGTGCGCCTGTTCTGACGACTGCAAGGACAAGGGCGATTGCTGCATCAACTACAGCAGCGTGTGCCAG

GGCGAAAAGAGCTGGGTCGAGGAACCCTGCGAGAGCATCAACGAGCCCCAGTGCCCTGCCGGATTTGAGACAC

CTCCTACCCTGCTCTTCTCCCTGGATGGCTTCAGAGCTGAGTACCTGCATACATGGGGAGGACTGCTGCCTGT

GATCAGCAAGCTGAAGAAGTGCGGCACCTACACAAAGAACATGCGGCCTGTCTACCCTACCAAGACCTTCCCC

AACCACTACAGCATCGTGACCGGCCTGTACCCCGAGAGCCACGGCATCATCGACAACAAGATGTACGACCCCA

AAATGAACGCCAGCTTCAGCCTGAAATCTAAGGAAAAGTTCAACCCTGAGTGGTATAAGGGCGAGCCAATCTG

GGTGACAGCCAAGTACCAGGGCCTGAAGAGCGGCACCTTCTTCTGGCCTGGCAGCGACGTGGAGATCAACGGA

ATCTTCCCTGATATCTACAAGATGTATAACGGCTCCGTGCCTTTCGAGGAGCGGATCTTGGCTGTTCTTCAGT

GGCTGCAGCTGCCCAAGGACGAGAGACCCCACTTCTACACCCTGTACCTGGAAGAACCTGACAGCAGCGGCCA

-continued

CAGCTACGGCCCTGTGTCTAGCGAGGTGATCAAGGCCCTGCAAAGAGTGGATGGCATGGTGGGCATGCTGATG

GATGGACTGAAGGAACTGAACCTCCATCGTTGCCTGAACCTGATCCTGATCTCCGACCACGGCATGGAACAGG

GCAGCTGTAAAAAGTACATCTACCTGAACAAGTACCTGGGCGACGTGAAGAATATCAAGGTGATCTACGGGCC

GGCCGCCAGGCTGCGGCCTAGCGACGTGCCCGACAAGTATTACAGCTTCAACTACGAGGGCATCGCCAGAAAC

CTGTCTTGCAGAGAACCCAATCAACACTTCAAGCCTTACCTGAAGCACTTTCTGCCTAAGAGACTGCACTTCG

CCAAAAGCGACAGAATTGAACCCCTGACATTCTATCTGGACCCTCAGTGGCAGCTGGCCCTCAATCCTTCTGA

ACGCAAATACTGCGGTAGCGGATTTCACGGCTCTGATAACGTGTTTTCTAACATGCAGGCCCTGTTTGTGGGC

TACGGCCCTGGCTTCAAGCACGGAATCGAGGCTGACACCTTCGAGAACATCGAAGTTTACAATCTGATGTGCG

ACCTGCTGAATCTGACCCCAGCCCCTAACAACGGCACACACGGCTCTCTGAATCACCTGCTCAAGAACCCCGT

GTATACCCCCAAACACCCTAAAGAGGTCCATCCACTGGTGCAGTGCCCATTCACCAGAAACCCTCGGGACAAC

CTTGGCTGCAGCTGCAACCCTAGCATCCTCCCTATCGAAGATTTCCAGACCCAGTTTAACCTGACTGTCGCCG

AAGAGAAGATCATCAAGCACGAAACCCTGCCCTACGGGAGGCCCAGAGTGCTGCAGAAAGAAAACACAATCTG

TCTGCTGAGCCAGCACCAGTTTATGAGCGGCTACAGTCAGGACATCCTGATGCCTCTGTGGACCAGCTACACC

GTGGACCGGAATGACAGCTTCAGCACCGAGGACTTCAGCAACTGCCTGTATCAGGACTTCCGCATCCCTCTGT

CCCCTGTGCATAAGTGCAGCTTTTACAAGAACAACACCAAGGTGAGCTACGGGTTTCTGAGCCCACCACAACT

GAACAAAAATAGCTCTGGCATCTACTCTGAGGCGCTGCTGACCACCAACATCGTGCCAATGTACCAGAGCTTC

CAGGTGATCTGGCGGTACTTCCATGATACCCTGCTTCGGAAGTACGCCGAAGAACGGAACGGCGTGAACGTGG

TGTCCGGCCCAGTGTTCGACTTCGACTACGACGGCAGATGTGATTCCCTTGAGAATCTGAGACAGAAGCGGCG

GGTTATCAGAAACCAGGAGATCCTGATTCCTACCCACTTCTTCATCGTGCTGACATCTTGCAAGGATACCAGC

CAAACACCTCTGCACTGCGAGAACCTGGACACCCTGGCCTTCATCCTGCCTCACCGGACCGATAATAGCGAAT

CCTGTGTGCACGGCAAACACGACTCTAGCTGGGTGGAAGAGCTGCTGATGCTGCACAGAGCCCGGATCACAGA

TGTGGAACACATCACCGGCCTGTCCTTCTACCAACAGAGAAAGGAACCCGTGTCTGATATCCTGAAGCTGAAA

ACCCACCTGCCTACCTTCAGCCAGGAGGACCTGATCGTTAACGATGCACACAAGAGTGAGGTTGCTCATCGGT

TTAAAGATTTGGGAGAAGAAAATTTCAAAGCCTTGGTGTTGATTGCCTTTGCTCAGTATCTTCAGCAGTGTCC

ATTTGAAGATCATGTAAAATTAGTGAATGAAGTAACTGAATTTGCAAAAACATGTGTTGCTGATGAGTCAGCT

GAAAATTGTGACAAATCACTTCATACCCTTTTTGGAGACAAATTATGCACAGTTGCAACTCTTCGTGAAACCT

ATGGTGAAATGGCTGACTGCTGTGCAAAACAAGAACCTGAGAGAAATGAATGCTTCTTGCAACACAAAGATGA

CAACCCAAACCTCCCCCGATTGGTGAGACCAGAGGTTGATGTGATGTGCACTGCTTTTCATGACAATGAAGAG

ACATTTTTGAAAAAATACTTATATGAAATTGCCAGAAGACATCCTTACTTTTATGCCCCGGAACTCCTTTTCT

TTGCTAAAAGGTATAAAGCTGCTTTTACAGAATGTTGCCAAGCTGCTGATAAAGCTGCCTGCCTGTTGCCAAA

GCTCGATGAACTTCGGGATGAAGGGAAGGCTTCGTCTGCCAAACAGAGACTCAAGTGTGCCAGTCTCCAAAAA

TTTGGAGAAAGAGCTTTCAAAGCATGGGCAGTAGCTCGCCTGAGCCAGAGATTTCCCAAAGCTGAGTTTGCAG

AAGTTTCCAAGTTAGTGACAGATCTTACCAAAGTCCACACGGAATGCTGCCATGGAGATCTGCTTGAATGTGC

TGATGACAGGGCGGACCTTGCCAAGTATATCTGTGAAAATCAAGATTCGATCTCCAGTAAACTGAAGGAATGC

TGTGAAAAACCTCTGTTGGAAAAATCCCACTGCATTGCCGAAGTGGAAAATGATGAGATGCCTGCTGACTTGC

CTTCATTAGCTGCTGATTTTGTTGAAAGTAAGGATGTTTGCAAAAACTATGCTGAGGCAAAGGATGTCTTCCT

GGGCATGTTTTTGTATGAATATGCAAGAAGGCATCCTGATTACTCTGTCGTGCTGCTGCTGAGACTTGCCAAG

ACATATGAAACCACACTCGAGAAGTGCTGTGCCGCTGCAGATCCTCATGAATGCTATGCCAAAGTGTTCGATG

AATTTAAACCTCTTGTGGAAGAGCCTCAGAATTTAATCAAACAAAATTGTGAGCTTTTTGAGCAGCTTGGAGA

GTACAAATTCCAGAATGCGCTATTAGTTCGTTACACCAAGAAAGTACCCCAAGTGTCAACTCCAACTCTTGTA

-continued

GAGGTCTCAAGAAACCTAGGAAAAGTGGGCAGCAAATGTTGTAAACATCCTGAAGCAAAAAGAATGCCCTGTG

CAGAAGACTATCTATCCGTGGTCCTGAACCAGTTATGTGTGTTGCATGAGAAAACGCCAGTAAGTGACAGAGT

CACCAAATGCTGCACAGAATCCTTGGTGAACAGGCGACCATGCTTTTCAGCTCTGGAAGTCGATGAAACATAC

GTTCCCAAAGAGTTTAATGCTGAAACATTCACCTTCCATGCAGATATATGCACACTTTCTGAGAAGGAGAGAC

AAATCAAGAAACAAACTGCACTTGTTGAGCTCGTGAAACACAAGCCCAAGGCAACAAAAGAGCAACTGAAAGC

TGTTATGGATGATTTCGCAGCTTTTGTAGAGAAGTGCTGCAAGGCTGACGATAAGGAGACCTGCTTTGCCGAG

GAGGGTAAAAAACTTGTTGCTGCAAGTCAAGCTGCCTTAGGCTTATGAGGTACCGAGCTCGGATCCACTAGTC

CAGTGTGGTGGAATTCTGCAGATATCCAGCACAGTGGCGGCCGCTCGAGTCTAGAGGGCCCGTTTAAACCCGC

TGATCAGCCTCGACTGTGCCTTCTAGTTGCCAGCCATCTGTTGTTTGCCCCTCCCCCGTGCCTTCCTTGACCC

TGGAAGGTGCCACTCCCACTGTCCTTTCCTAATAAAATGAGGAAATTGCATCGCATTGTCTGAGTAGGTGTCA

TTCTATTCTGGGGGGTGGGGTGGGGCAGGACAGCAAGGGGGAGGATTGGGAAGACAATAGCAGGCATGCTGGG

GATGCGGTGGGCTCTATGGCTTCTGAGGCGGAAAGAACCAGCTGGGGCTCTAGGGGGTATCCCCACGCGCCCT

GTAGCGGCGCATTAAGCGCGGCGGGTGTGGTGGTTACGCGCAGCGTGACCGCTACACTTGCCAGCGCCCTAGC

GCCCGCTCCTTTCGCTTTCTTCCCTTCCTTTCTCGCCACGTTCGCCGGCTTTCCCCGTCAAGCTCTAAATCGG

GGGCTCCCTTTAGGGTTCCGATTTAGTGCTTTACGGCACCTCGACCCCAAAAAACTTGATTAGGGTGATGGTT

CACGTAGTGGGCCATCGCCCTGATAGACGGTTTTTCGCCCTTTGACGTTGGAGTCCACGTTCTTTAATAGTGG

ACTCTTGTTCCAAACTGGAACAACACTCAACCCTATCTCGGTCTATTCTTTTGATTTATAAGGGATTTTGCCG

ATTTCGGCCTATTGGTTAAAAAATGAGCTGATTTAACAAAAATTTAACGCGAATTAATTCTGTGGAATGTGTG

TCAGTTAGGGTGTGGAAAGTCCCCAGGCTCCCCAGCAGGCAGAAGTATGCAAAGCATGCATCTCAATTAGTCA

GCAACCAGGTGTGGAAAGTCCCCAGGCTCCCCAGCAGGCAGAAGTATGCAAAGCATGCATCTCAATTAGTCAG

CAACCATAGTCCCGCCCCTAACTCCGCCCATCCCGCCCCTAACTCCGCCCAGTTCCGCCCATTCTCCGCCCCA

TGGCTGACTAATTTTTTTTATTTATGCAGAGGCCGAGGCCGCCTCTGCCTCTGAGCTATTCCAGAAGTAGTGA

GGAGGCTTTTTTGGAGGCCTAGGCTTTTGCAAAAAGCTCCCGGGAGCTTGTATATCCATTTTCGGATCTGATC

AAGAGACAGGATGAGGATCGTTTCGCATGATTGAACAAGATGGATTGCACGCAGGTTCTCCGGCCGCTTGGGT

GGAGAGGCTATTCGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGCAGGACGAGGCAG

CGCGGCTATCGTGGCTGGCCACGACGGGCGTTCCTTGCGCAGCTGTGCTCGACGTTGTCACTGAAGCGGGAAG

GGACTGGCTGCTATTGGGCGAAGTGCCGGGGCAGGATCTCCTGTCATCTCACCTTGCTCCTGCCGAGAAAGTA

TCCATCATGGCTGATGCAATGCGGCGGCTGCATACGCTTGATCCGGCTACCTGCCCATTCGACCACCAAGCGA

AACATCGCATCGAGCGAGCACGTACTCGGATGGAAGCCGGTCTTGTCGATCAGGATGATCTGGACGAAGAGCA

TCAGGGGCTCGCGCCAGCCGAACTGTTCGCCAGGCTCAAGGCGCGCATGCCCGACGGCGAGGATCTCGTCGTG

ACCCATGGCGATGCCTGCTTGCCGAATATCATGGTGGAAAATGGCCGCTTTTCTGGATTCATCGACTGTGGCC

GGCTGGGTGTGGCGGACCGCTATCAGGACATAGCGTTGGCTACCCGTGATATTGCTGAAGAGCTTGGCGGCGA

ATGGGCTGACCGCTTCCTCGTGCTTTACGGTATCGCCGCTCCCGATTCGCAGCGCATCGCCTTCTATCGCCTT

CTTGACGAGTTCTTCTGAGCGGGACTCTGGGGTTCGAAATGACCGACCAAGCGACGCCCAACCTGCCATCACG

AGATTTCGATTCCACCGCCGCCTTCTATGAAAGGTTGGGCTTCGGAATCGTTTTCCGGGACGCCGGCTGGATG

ATCCTCCAGCGCGGGGATCTCATGCTGGAGTTCTTCGCCCACCCCAACTTGTTTATTGCAGCTTATAATGGTT

ACAAATAAAGCAATAGCATCACAAATTTCACAAATAAAGCATTTTTTTCACTGCATTCTAGTTGTGGTTTGTC

CAAACTCATCAATGTATCTTATCATGTCTGTATACCGTCGACCTCTAGCTAGAGCTTGGCGTAATCATGGTCA

-continued

TAGCTGTTTCCTGTGTGAAATTGTTATCCGCTCACAATTCCACACAACATACGAGCCGGAAGCATAAAGTGTA

AAGCCTGGGGTGCCTAATGAGTGAGCTAACTCACATTAATTGCGTTGCGCTCACTGCCCGCTTTCCAGTCGGG

AAACCTGTCGTGCCAGCTGCATTAATGAATCGGCCAACGCGCGGGGAGAGGCGGTTTGCGTATTGGGCGCTCT

TCCGCTTCCTCGCTCACTGACTCGCTGCGCTCGGTCGTTCGGCTGCGGCGAGCGGTATCAGCTCACTCAAAGG

CGGTAATACGGTTATCCACAGAATCAGGGGATAACGCAGGAAAGAACATGTGAGCAAAAGGCCAGCAAAAGGC

CAGGAACCGTAAAAAGGCCGCGTTGCTGGCGTTTTTCCATAGGCTCCGCCCCCCTGACGAGCATCACAAAAAT

CGACGCTCAAGTCAGAGGTGGCGAAACCCGACAGGACTATAAAGATACCAGGCGTTTCCCCCTGGAAGCTCCC

TCGTGCGCTCTCCTGTTCCGACCCTGCCGCTTACCGGATACCTGTCCGCCTTTCTCCCTTCGGGAAGCGTGGC

GCTTTCTCATAGCTCACGCTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATGTAGGCGGTGCTACAGAGTT

CTTGAAGTGGTGGCCTAACTACGGCTACACTAGAAGAACAGTATTTGGTATCTGCGCTCTGCTGAAGCCAGTT

ACCTTCGGAAAAAGAGTTGGTAGCTCTTGATCCGGCAAACAAACCACCGCTGGTAGCGGTGGTTTTTTTGTTT

GCAAGCAGCAGATTACGCGCAGAAAAAAAGGATCTCAAGAAGATCCTTTGATCTTTTCTACGGGGTCTGACGC

TCAGTGGAACGAAAACTCACGTTAAGGGATTTTGGTCATGAGATTATCAAAAAGGATCTTCACCTAGATCCTT

TTAAATTAAAAATGAAGTTTTAAATCAATCTAAAGTATATATGAGTAAACTTGGTCTGACAGTTACCAATGCT

TAATCAGTGAGGCACCTATCTCAGCGATCTGTCTATTTCGTTCATCCATAGTTGCCTGACTCCCCGTCGTGTA

GATAACTACGATACGGGAGGGCTTACCATCTGGCCCCAGTGCTGCAATGATACCGCGAGACCCACGCTCACCG

GCTCCAGATTTATCAGCAATAAACCAGCCAGCCGGAAGGGCCGAGCGCAGAAGTGGTCCTGCAACTTTATCCG

CCTCCATCCAGTCTATTAATTGTTGCCGGGAAGCTAGAGTAAGTAGTTCGCCAGTTAATAGTTTGCGCAACGT

TGTTGCCATTGCTACAGGCATCGTGGTGTCACGCTCGTCGTTTGGTATGGCTTCATTCAGCTCCGGTTCCCAA

CGATCAAGGCGAGTTACATGATCCCCCATGTTGTGCAAAAAAGCGGTTAGCTCCTTCGGTCCTCCGATCGTTG

TCAGAAGTAAGTTGGCCGCAGTGTTATCACTCATGGTTATGGCAGCACTGCATAATTCTCTTACTGTCATGCC

ATCCGTAAGATGCTTTTCTGTGACTGGTGAGTACTCAACCAAGTCATTCTGAGAATAGTGTATGCGGCGACCG

AGTTGCTCTTGCCCGGCGTCAATACGGGATAATACCGCGCCACATAGCAGAACTTTAAAAGTGCTCATCATTG

GAAAACGTTCTTCGGGGCGAAAACTCTCAAGGATCTTACCGCTGTTGAGATCCAGTTCGATGTAACCCACTCG

TGCACCCAACTGATCTTCAGCATCTTTTACTTTCACCAGCGTTTCTGGGTGAGCAAAAACAGGAAGGCAAAAT

GCCGCAAAAAAGGGAATAAGGGCGACACGGAAATGTTGAATACTCATACTCTTCCTTTTTCAATATTATTGAA

GCATTTATCAGGGTTATTGTCTCATGAGCGGATACATATTTGAATGTATTTAGAAAAATAAACAAATAGGGGT

TCCGCGCACATTTCCCCGAAAAGTGCCACCTGACGTC

CMV_kozak_hAlb_sig_FLAG_ENPPlopt_LINK_hAlb_STOP_pcDNA3.1 (+)
(CMV_srENPP1_Albumin)

pcDNA3.1+, CMV enhancer, CMV promoter, Kozak seq, h-albumin secretory seq, Flag tag, ENPP1 opt, Linker seq, h-albumin seq, Stop codon

(SEQ ID NO: 91)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGACATTGATTATTGACTAGTTATTAATAGTAATCAATTACGGGGTCATTAGTTCATAG

CCCATATATGGAGTTCCGCGTTACATAACTTACGGTAAATGGCCCGCCTGGCTGACCGCCCAACGACCCCCGC

-continued

CCATTGACGTCAATAATGACGTATGTTCCCATAGTAACGCCAATAGGGACTTTCCATTGACGTCAATGGGTGG

AGTATTTACGGTAAACTGCCCACTTGGCAGTACATCAAGTGTATCATATGCCAAGTACGCCCCCTATTGACGT

CAATGACGGTAAATGGCCCGCCTGGCATTATGCCCAGTACATGACCTTATGGGACTTTCCTACTTGGCAGTAC

ATCTACGTATTAGTCATCGCTATTACCATGGTGATGCGGTTTTGGCAGTACATCAATGGGCGTGGATAGCGGT

TTGACTCACGGGGATTTCCAAGTCTCCACCCCATTGACGTCAATGGGAGTTTGTTTTGGCACCAAAATCAACG

GGACTTTCCAAAATGTCGTAACAACTCCGCCCCATTGACGCAAATGGGCGGTAGGCGTGTACGGTGGGAGGTC

TATATAAGCAGAGCTCTCTGGCTAACTAGAGAACCCACTGCTTACTGGCTTATCGAAATTAATACGACTCACT

ATAGGGAGACCCAAGCTGGCTAGCGCCACCATGAAGTGGGTAACCTTTATTTCCCTTCTTTTTCTCTTTAGCT

CGGCTTATTCCAGGGGTGTGTTTCGTCGAGACTAACAAAGACGATGACGACAAGAGCGCTGGCCTGAAGCCAAG

CTGCGCCAAGGAGGTGAAGAGCTGCAAGGGCAGATGTTTCGAACGGACCTTCGGCAACTGCAGATGCGACGCC

GCCTGCGTGGAACTGGGAAACTGTTGTCTGGACTACCAGGAGACATGTATCGAGCCTGAGCACATCTGGACAT

GCAACAAGTTCAGATGTGGCGAGAAAAGACTGACTCGGAGTCTGTGCGCCTGTTCTGACGACTGCAAGGACAA

GGGCGATTGCTGCATCAACTACAGCAGCGTGTGCCAGGGCGAAAAGAGCTGGGTCGAGGAACCCTGCGAGAGC

ATCAACGAGCCCCAGTGCCCTGCCGGATTTGAGACACCTCCTACCCTGCTCTTCTCCCTGGATGGCTTCAGAG

CTGAGTACCTGCATACATGGGGAGGACTGCTGCCTGTGATCAGCAAGCTGAAGAAGTGCGGCACCTACACAAA

GAACATGCGGCCTGTCTACCCTACCAAGACCTTCCCCAACCACTACAGCATCGTGACCGGCCTGTACCCCGAG

AGCCACGGCATCATCGACAACAAGATGTACGACCCCAAAATGAACGCCAGCTTCAGCCTGAAATCTAAGGAAA

AGTTCAACCCTGAGTGGTATAAGGGCGAGCCAATCTGGGTGACAGCCAAGTACCAGGGCCTGAAGAGCGGCAC

CTTCTTCTGGCCTGGCAGCGACGTGGAGATCAACGGAATCTTCCCTGATATCTACAAGATGTATAACGGCTCC

GTGCCTTTCGAGGAGCGGATCTTGGCTGTTCTTCAGTGGCTGCAGCTGCCCAAGGACGAGAGACCCCACTTCT

ACACCCTGTACCTGGAAGAACCTGACAGCAGCGGCCACAGCTACGGCCCTGTGTCTAGCGAGGTGATCAAGGC

CCTGCAAAGAGTGGATGGCATGGTGGGCATGCTGATGGATGGACTGAAGGAACTGAACCTCCATCGTTGCCTG

AACCTGATCCTGATCTCCGACCACGGCATGGAACAGGGCAGCTGTAAAAAGTACATCTACCTGAACAAGTACC

TGGGCGACGTGAAGAATATCAAGGTGATCTACGGGCCGGCCGCCAGGCTGCGGCCTAGCGACGTGCCCGACAA

TAACGTGTTTTCTAACATGCAGGCCCTGTTTGTGGGCTACGGCCCTGGCTTCAAGCACGGAATCGAGGCTGAC

ACCTTCGAGAACATCGAAGTTTACAATCTGATGTGCGACCTGCTGAATCTGACCCCAGCCCCTAACAACGGCA

CACACGGCTCTCTGAATCACCTGCTCAAGAACCCCGTGTATACCCCCAAACACCCTAAAGAGGTCCATCCACT

GGTGCAGTGCCCATTCACCAGAAACCCTCGGGACAACCTTGGCTGCAGCTGCAACCCTAGCATCCTCCCTATC

GAAGATTTCCAGACCCAGTTTAACCTGACTGTCGCCGAAGAGAAGATCATCAAGCACGAAACCCTGCCCTACG

GGAGGCCCAGAGTGCTGCAGAAAGAAAACACAATCTGTCTGCTGAGCCAGCACCAGTTTATGAGCGGCTACAG

TCAGGACATCCTGATGCCTCTGTGGACCAGCTACACCGTGGACCGGAATGACAGCTTCAGCACCGAGGACTTC

AGCAACTGCCTGTATCAGGACTTCCGCATCCCTCTGTCCCCTGTGCATAAGTGCAGCTTTTACAAGAACAACA

CCAAGGTGAGCTACGGGTTTCTGAGCCCACCACAACTGAACAAAAATAGCTCTGGCATCTACTCTGAGGCGCT

GCTGACCACCAACATCGTGCCAATGTACCAGAGCTTCCAGGTGATCTGGCGGTACTTCCATGATACCCTGCTT

CGGAAGTACGCCGAAGAACGGAACGGCGTGAACGTGGTGTCCGGCCCAGTGTTCGACTTCGACTACGACGGCA

GATGTGATTCCCTTGAGAATCTGAGACAGAAGCGGCGGGTTATCAGAAACCAGGAGATCCTGATTCCTACCCA

CTTCTTCATCGTGCTGACATCTTGCAAGGATACCAGCCAAACACCTCTGCACTGCGAGAACCTGGACACCCTG

-continued

GCCTTCATCCTGCCTCACCGGACCGATAATAGCGAATCCTGTGTGCACGGCAAACACGACTCTAGCTGGGTGG

AAGAGCTGCTGATGCTGCACAGAGCCCGGATCACAGATGTGGAACACATCACCGGCCTGTCCTTCTACCAACA

GAGAAAGGAACCCGTGTCTGATATCCTGAAGCTGAAAACCCACCTGCCTACCTTCAGCCAGGAGGACCTGATC

GTTAACGATGCACACAAGAGTGAGGTTGCTCATCGGTTTAAAGATTTGGGAGAAGAAAATTTCAAAGCCTTGG

TGTTGATTGCCTTTGCTCAGTATCTTCAGCAGTGTCCATTTGAAGATCATGTAAAATTAGTGAATGAAGTAAC

TGAATTTGCAAAAACATGTGTTGCTGATGAGTCAGCTGAAAATTGTGACAAATCACTTCATACCCTTTTTGGA

GACAAATTATGCACAGTTGCAACTCTTCGTGAAACCTATGGTGAAATGGCTGACTGCTGTGCAAAACAAGAAC

CTGAGAGAAATGAATGCTTCTTGCAACACAAAGATGACAACCCAAACCTCCCCCGATTGGTGAGACCAGAGGT

TGATGTGATGTGCACTGCTTTTCATGACAATGAAGAGACATTTTTGAAAAAATACTTATATGAAATTGCCAGA

AGACATCCTTACTTTTATGCCCCGGAACTCCTTTTCTTTGCTAAAAGGTATAAAGCTGCTTTTACAGAATGTT

GCCAAGCTGCTGATAAAGCTGCCTGCCTGTTGCCAAAGCTCGATGAACTTCGGGATGAAGGGAAGGCTTCGTC

TGCCAAACAGAGACTCAAGTGTGCCAGTCTCCAAAAATTTGGAGAAAGAGCTTTCAAAGCATGGGCAGTAGCT

CGCCTGAGCCAGAGATTTCCCAAAGCTGAGTTTGCAGAAGTTTCCAAGTTAGTGACAGATCTTACCAAAGTCC

ACACGGAATGCTGCCATGGAGATCTGCTTGAATGTGCTGATGACAGGGCGGACCTTGCCAAGTATATCTGTGA

AAATCAAGATTCGATCTCCAGTAAACTGAAGGAATGCTGTGAAAAACCTCTGTTGGAAAAATCCCACTGCATT

GCCGAAGTGGAAAATGATGAGATGCCTGCTGACTTGCCTTCATTAGCTGCTGATTTTGTTGAAAGTAAGGATG

TTTGCAAAAACTATGCTGAGGCAAAGGATGTCTTCCTGGGCATGTTTTTGTATGAATATGCAAGAAGGCATCC

TGATTACTCTGTCGTGCTGCTGCTGAGACTTGCCAAGACATATGAAACCACACTCGAGAAGTGCTGTGCCGCT

GCAGATCCTCATGAATGCTATGCCAAAGTGTTCGATGAATTTAAACCTCTTGTGGAAGAGCCTCAGAATTTAA

TCAAACAAAATTGTGAGCTTTTTGAGCAGCTTGGAGAGTACAAATTCCAGAATGCGCTATTAGTTCGTTACAC

CAAGAAAGTACCCCAAGTGTCAACTCCAACTCTTGTAGAGGTCTCAAGAAACCTAGGAAAAGTGGGCAGCAAA

TGTTGTAAACATCCTGAAGCAAAAAGAATGCCCTGTGCAGAAGACTATCTATCCGTGGTCCTGAACCAGTTAT

GTGTGTTGCATGAGAAAACGCCAGTAAGTGACAGAGTCACCAAATGCTGCACAGAATCCTTGGTGAACAGGCG

ACCATGCTTTTCAGCTCTGGAAGTCGATGAAACATACGTTCCCAAAGAGTTTAATGCTGAAACATTCACCTTC

CATGCAGATATATGCACACTTTCTGAGAAGGAGAGACAAATCAAGAAACAAACTGCACTTGTTGAGCTCGTGA

AACACAAGCCCAAGGCAACAAAAGAGCAACTGAAAGCTGTTATGGATGATTTCGCAGCTTTTGTAGAGAAGTG

CTGCAAGGCTGACGATAAGGAGACCTGCTTTGCCGAGGAGGGTAAAAAACTTGTTGCTGCAAGTCAAGCTGCC

TTAGGCTTATGAGGTACCGAGCTCGGATCCACTAGTCCAGTGTGGTGGAATTCTGCAGATATCCAGCACAGTG

GCGGCCGCTCGAGTCTAGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTGTCCTTTCCTAATAAA

ATGAGGAAATTGCATCGCATTGTCTGAGTAGGTGTCATTCTATTCTGGGGGGTGGGGTGGGGCAGGACAGCAA

GGGGGAGGATTGGGAAGACAATAGCAGGCATGCTGGGGATGCGGTGGGCTCTATGGCTTCTGAGGCGGAAAGA

ACCAGCTGGGGCTCTAGGGGGTATCCCCACGCGCCCTGTAGCGGCGCATTAAGCGCGGCGGGTGTGGTGGTTA

CGCGCAGCGTGACCGCTACACTTGCCAGCGCCCTAGCGCCCGCTCCTTTCGCTTTCTTCCCTTCCTTTCTCGC

CACGTTCGCCGGCTTTCCCCGTCAAGCTCTAAATCGGGGGCTCCCTTTAGGGTTCCGATTTAGTGCTTTACGG

CACCTCGACCCCAAAAAACTTGATTAGGGTGATGGTTCACGTAGTGGGCCATCGCCCTGATAGACGGTTTTTC

GCCCTTTGACGTTGGAGTCCACGTTCTTTAATAGTGGACTCTTGTTCCAAACTGGAACAACACTCAACCCTAT

CTCGGTCTATTCTTTTGATTTATAAGGGATTTTGCCGATTTCGGCCTATTGGTTAAAAAATGAGCTGATTTAA

-continued

CAAAAATTTAACGCGAATTAATTCTGTGGAATGTGTGTCAGTTAGGGTGTGGAAAGTCCCCAGGCTCCCCAGC
AGGCAGAAGTATGCAAAGCATGCATCTCAATTAGTCAGCAACCAGGTGTGGAAAGTCCCCAGGCTCCCCAGCA
GGCAGAAGTATGCAAAGCATGCATCTCAATTAGTCAGCAACCATAGTCCCGCCCCTAACTCCGCCCATCCCGC
CCCTAACTCCGCCCAGTTCCGCCCATTCTCCGCCCCATGGCTGACTAATTTTTTTTATTTATGCAGAGGCCGA
GGCCGCCTCTGCCTCTGAGCTATTCCAGAAGTAGTGAGGAGGCTTTTTTGGAGGCCTAGGCTTTTGCAAAAAG
CTCCCGGGAGCTTGTATATCCATTTTCGGATCTGATCAAGAGACAGGATGAGGATCGTTTCGCATGATTGAAC
AAGATGGATTGCACGCAGGTTCTCCGGCCGCTTGGGTGGAGAGGCTATTCGGCTATGACTGGGCACAACAGAC
AATCGGCTGCTCTGATGCCGCCGTGTTCCGGCTGTCAGCGCAGGGGCGCCCGGTTCTTTTTGTCAAGACCGAC
CTGTCCGGTGCCCTGAATGAACTGCAGGACGAGGCAGCGCGGCTATCGTGGCTGGCCACGACGGGCGTTCCTT
GCGCAGCTGTGCTCGACGTTGTCACTGAAGCGGGAAGGGACTGGCTGCTATTGGGCGAAGTGCCGGGGCAGGA
TCTCCTGTCATCTCACCTTGCTCCTGCCGAGAAAGTATCCATCATGGCTGATGCAATGCGGCGGCTGCATACG
CTTGATCCGGCTACCTGCCCATTCGACCACCAAGCGAAACATCGCATCGAGCGAGCACGTACTCGGATGGAAG
CCGGTCTTGTCGATCAGGATGATCTGGACGAAGAGCATCAGGGGCTCGCGCCAGCCGAACTGTTCGCCAGGCT
CAAGGCGCGCATGCCCGACGGCGAGGATCTCGTCGTGACCCATGGCGATGCCTGCTTGCCGAATATCATGGTG
GAAAATGGCCGCTTTTCTGGATTCATCGACTGTGGCCGGCTGGGTGTGGCGGACCGCTATCAGGACATAGCGT
TGGCTACCCGTGATATTGCTGAAGAGCTTGGCGGCGAATGGGCTGACCGCTTCCTCGTGCTTTACGGTATCGC
CGCTCCCGATTCGCAGCGCATCGCCTTCTATCGCCTTCTTGACGAGTTCTTCTGAGCGGGACTCTGGGGTTCG
AAATGACCGACCAAGCGACGCCCAACCTGCCATCACGAGATTTCGATTCCACCGCCGCCTTCTATGAAAGGTT
GGGCTTCGGAATCGTTTTCCGGGACGCCGGCTGGATGATCCTCCAGCGCGGGGATCTCATGCTGGAGTTCTTC
GCCCACCCCAACTTGTTTATTGCAGCTTATAATGGTTACAAATAAAGCAATAGCATCACAAATTTCACAAATA
AAGCATTTTTTTCACTGCATTCTAGTTGTGGTTTGTCCAAACTCATCAATGTATCTTATCATGTCTGTATACC
GTCGACCTCTAGCTAGAGCTTGGCGTAATCATGGTCATAGCTGTTTCCTGTGTGAAATTGTTATCCGCTCACA
ATTCCACACAACATACGAGCCGGAAGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTGCCAGCTGCATTAATGAATCGGCCA
ACGCGCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAACG
CAGGAAAGAACATGTGAGCAAAAGGCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGCTCACGCTGTAGGTATCTCAGTTC
GGTGTAGGTCGTTCGCTCCAAGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTAACTACGGCTACACTAGAAG
AACAGTATTTGGTATCTGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATCAATCTAAAGT
ATATATGAGTAAACTTGGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATAAACCAGCCAGCCGGA

-continued

AGGGCCGAGCGCAGAAGTGGTCCTGCAACTTTATCCGCCTCCATCCAGTCTATTAATTGTTGCCGGGAAGCTA

GAGTAAGTAGTTCGCCAGTTAATAGTTTGCGCAACGTTGTTGCCATTGCTACAGGCATCGTGGTGTCACGCTC

GTCGTTTGGTATGGCTTCATTCAGCTCCGGTTCCCAACGATCAAGGCGAGTTACATGATCCCCCATGTTGTGC

AAAAAAGCGGTTAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACTGGTGAGTACTC

AACCAAGTCATTCTGAGAATAGTGTATGCGGCGACCGAGTTGCTCTTGCCCGGCGTCAATACGGGATAATACC

GCGCCACATAGCAGAACTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGGGAATAAGGGCGACACGGAAATGT

TGAATACTCATACTCTTCCTTTTTCAATATTATTGAAGCATTTATCAGGGTTATTGTCTCATGAGCGGATACA

TATTTGAATGTATTTAGAAAAATAAACAAATAGGGGTTCCGCGCACATTTCCCCGAAAAGTGCCACCTGACGT

C

CAG_Kozak_hAlb_sig_FLAG_ENPPlopt_LINK_hAlb_stop_pcDNA3.1 (+)

pcDNA3.1+, CAG promoter, Kozak seq, h-albumin secretory, Flag tag,

ENPP1 opt, Linker seq, h-albumin seq, Stop codon

(SEQ ID NO: 92)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGCGTTACATAACTTACGGTAAATGGCCCGCCTGGCTGACCGCCCAACGACCCCCGCCC

ATTGACGTCAATAATGACGTATGTTCCCATAGTAACGCCAATAGGGACTTTCCATTGACGTCAATGGGTGGAG

TATTTACGGTAAACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTTGGCAGTACAT

CTACGTATTAGTCATCGCTATTACCATGGTCGAGGTGAGCCCCACGTTCTGCTTCACTCTCCCCATCTCCCCC

CCCTCCCCACCCCCAATTTTGTATTTATTTATTTTTTAATTATTTTGTGCAGCGATGGGGGGGGGGGGGGGGG

GGGGGCGCGCGCCAGGCGGGGCGGGGCGGGGCGAGGGGCGGGGCGGGGCGAGGCGGAGAGGTGCGGCGGCAGC

CAATCAGAGCGGCGCGCTCCGAAAGTTTCCTTTTATGGCGAGGCGGCGGCGGCGGCGGCCCTATAAAAAGCGA

AGCGCGCGGCGGGCGCTCTGGCTAACTAGAGAACCCACTGCTTACTGGCTTATCGAAATTAATACGACTCACT

ATAGGGAGACCCAAGCTGGCTAGCGCCACCATGAAGTGGGTAACCTTTATTTCCCTTCTTTTTCTCTTTAGCT

CGGCTTATTCCAGGGGTGTGTTTCGTCGAGACTACAAAGACGATGACGACAAGAGCGCTGGCCTGAAGCCAAG

CTGCGCCAAGGAGGTGAAGAGCTGCAAGGGCAGATGTTTCGAACGGACCTTCGGCAACTGCAGATGCGACGCC

GCCTGCGTGGAACTGGGAAACTGTTGTCTGGACTACCAGGAGACATGTATCGAGCCTGAGCACATCTGGACAT

GCAACAAGTTCAGATGTGGCGAGAAAAGACTGACTCGGAGTCTGTGCGCCTGTTCTGACGACTGCAAGGACAA

GGGCGATTGCTGCATCAACTACAGCAGCGTGTGCCAGGGCGAAAAGAGCTGGGTCGAGGAACCCTGCGAGAGC

ATCAACGAGCCCCAGTGCCCTGCCGGATTTGAGACACCTCCTACCCTGCTCTTCTCCCTGGATGGCTTCAGAG

CTGAGTACCTGCATACATGGGGAGGACTGCTGCCTGTGATCAGCAAGCTGAAGAAGTGCGGCACCTACACAAA

GAACATGCGGCCTGTCTACCCTACCAAGACCTTCCCCAACCACTACAGCATCGTGACCGGCCTGTACCCCGAG

AGCCACGGCATCATCGACAACAAGATGTACGACCCCAAAATGAACGCCAGCTTCAGCCTGAAATCTAAGGAAA

AGTTCAACCCTGAGTGGTATAAGGGCGAGCCAATCTGGGTGACAGCCAAGTACCAGGGCCTGAAGAGCGGCAC

-continued

CTTCTTCTGGCCTGGCAGCGACGTGGAGATCAACGGAATCTTCCCTGATATCTACAAGATGTATAACGGCTCC

GTGCCTTTCGAGGAGCGGATCTTGGCTGTTCTTCAGTGGCTGCAGCTGCCCAAGGACGAGAGACCCCACTTCT

ACACCCTGTACCTGGAAGAACCTGACAGCAGCGGCCACAGCTACGGCCCTGTGTCTAGCGAGGTGATCAAGGC

CCTGCAAAGAGTGGATGGCATGGTGGGCATGCTGATGGATGGACTGAAGGAACTGAACCTCCATCGTTGCCTG

AACCTGATCCTGATCTCCGACCACGGCATGGAACAGGGCAGCTGTAAAAAGTACATCTACCTGAACAAGTACC

TGGGCGACGTGAAGAATATCAAGGTGATCTACGGGCCGGCCGCCAGGCTGCGGCCTAGCGACGTGCCCGACAA

GTATTACAGCTTCAACTACGAGGGCATCGCCAGAAACCTGTCTTGCAGAGAACCCAATCAACACTTCAAGCCT

TACCTGAAGCACTTTCTGCCTAAGAGACTGCACTTCGCCAAAAGCGACAGAATTGAACCCCTGACATTCTATC

TGGACCCTCAGTGGCAGCTGGCCCTCAATCCTTCTGAACGCAAATACTGCGGTAGCGGATTTCACGGCTCTGA

TAACGTGTTTTCTAACATGCAGGCCCTGTTTGTGGGCTACGGCCCTGGCTTCAAGCACGGAATCGAGGCTGAC

ACCTTCGAGAACATCGAAGTTTACAATCTGATGTGCGACCTGCTGAATCTGACCCCAGCCCCTAACAACGGCA

CACACGGCTCTCTGAATCACCTGCTCAAGAACCCCGTGTATACCCCCAAACACCCTAAAGAGGTCCATCCACT

GGTGCAGTGCCCATTCACCAGAAACCCTCGGGACAACCTTGGCTGCAGCTGCAACCCTAGCATCCTCCCTATC

GAAGATTTCCAGACCCAGTTTAACCTGACTGTCGCCGAAGAGAAGATCATCAAGCACGAAACCCTGCCCTACG

GGAGGCCCAGAGTGCTGCAGAAAGAAAACACAATCTGTCTGCTGAGCCAGCACCAGTTTATGAGCGGCTACAG

TCAGGACATCCTGATGCCTCTGTGGACCAGCTACACCGTGGACCGGAATGACAGCTTCAGCACCGAGGACTTC

AGCAACTGCCTGTATCAGGACTTCCGCATCCCTCTGTCCCCTGTGCATAAGTGCAGCTTTTACAAGAACAACA

CCAAGGTGAGCTACGGGTTTCTGAGCCCACCACAACTGAACAAAAATAGCTCTGGCATCTACTCTGAGGCGCT

GCTGACCACCAACATCGTGCCAATGTACCAGAGCTTCCAGGTGATCTGGCGGTACTTCCATGATACCCTGCTT

CGGAAGTACGCCGAAGAACGGAACGGCGTGAACGTGGTGTCCGGCCCAGTGTTCGACTTCGACTACGACGGCA

GATGTGATTCCCTTGAGAATCTGAGACAGAAGCGGCGGGTTATCAGAAACCAGGAGATCCTGATTCCTACCCA

CTTCTTCATCGTGCTGACATCTTGCAAGGATACCAGCCAAACACCTCTGCACTGCGAGAACCTGGACACCCTG

GCCTTCATCCTGCCTCACCGGACCGATAATAGCGAATCCTGTGTGCACGGCAAACACGACTCTAGCTGGGTGG

AAGAGCTGCTGATGCTGCACAGAGCCCGGATCACAGATGTGGAACACATCACCGGCCTGTCCTTCTACCAACA

GAGAAAGGAACCCGTGTCTGATATCCTGAAGCTGAAAACCCACCTGCCTACCTTCAGCCAGGAGGACCTGATC

GTTAACGATGCACACAAGAGTGAGGTTGCTCATCGGTTTAAAGATTTGGGAGAAGAAAATTTCAAAGCCTTGG

TGTTGATTGCCTTTGCTCAGTATCTTCAGCAGTGTCCATTTGAAGATCATGTAAAATTAGTGAATGAAGTAAC

TGAATTTGCAAAAACATGTGTTGCTGATGAGTCAGCTGAAAATTGTGACAAATCACTTCATACCCTTTTTGGA

GACAAATTATGCACAGTTGCAACTCTTCGTGAAACCTATGGTGAAATGGCTGACTGCTGTGCAAAACAAGAAC

CTGAGAGAAATGAATGCTTCTTGCAACACAAAGATGACAACCCAAACCTCCCCCGATTGGTGAGACCAGAGGT

TGATGTGATGTGCACTGCTTTTCATGACAATGAAGAGACATTTTTGAAAAAATACTTATATGAAATTGCCAGA

AGACATCCTTACTTTTATGCCCCGGAACTCCTTTTCTTTGCTAAAAGGTATAAAGCTGCTTTTACAGAATGTT

GCCAAGCTGCTGATAAAGCTGCCTGCCTGTTGCCAAAGCTCGATGAACTTCGGGATGAAGGGAAGGCTTCGTC

TGCCAAACAGAGACTCAAGTGTGCCAGTCTCCAAAAATTTGGAGAAAGAGCTTTCAAAGCATGGGCAGTAGCT

CGCCTGAGCCAGAGATTTCCCAAAGCTGAGTTTGCAGAAGTTTCCAAGTTAGTGACAGATCTTACCAAAGTCC

ACACGGAATGCTGCCATGGAGATCTGCTTGAATGTGCTGATGACAGGGCGGACCTTGCCAAGTATATCTGTGA

AAATCAAGATTCGATCTCCAGTAAACTGAAGGAATGCTGTGAAAAACCTCTGTTGGAAAAATCCCACTGCATT

GCCGAAGTGGAAAATGATGAGATGCCTGCTGACTTGCCTTCATTAGCTGCTGATTTTGTTGAAAGTAAGGATG

TTTGCAAAAACTATGCTGAGGCAAAGGATGTCTTCCTGGGCATGTTTTTGTATGAATATGCAAGAAGGCATCC

-continued

TGATTACTCTGTCGTGCTGCTGCTGAGACTTGCCAAGACATATGAAACCACACTCGAGAAGTGCTGTGCCGCT

GCAGATCCTCATGAATGCTATGCCAAAGTGTTCGATGAATTTAAACCTCTTGTGGAAGAGCCTCAGAATTTAA

TCAAACAAAATTGTGAGCTTTTTGAGCAGCTTGGAGAGTACAAATTCCAGAATGCGCTATTAGTTCGTTACAC

CAAGAAAGTACCCCAAGTGTCAACTCCAACTCTTGTAGAGGTCTCAAGAAACCTAGGAAAAGTGGGCAGCAAA

TGTTGTAAACATCCTGAAGCAAAAAGAATGCCCTGTGCAGAAGACTATCTATCCGTGGTCCTGAACCAGTTAT

GTGTGTTGCATGAGAAAACGCCAGTAAGTGACAGAGTCACCAAATGCTGCACAGAATCCTTGGTGAACAGGCG

ACCATGCTTTTCAGCTCTGGAAGTCGATGAAACATACGTTCCCAAAGAGTTTAATGCTGAAACATTCACCTTC

CATGCAGATATATGCACACTTTCTGAGAAGGAGAGACAAATCAAGAAACAAACTGCACTTGTTGAGCTCGTGA

AACACAAGCCCAAGGCAACAAAAGAGCAACTGAAAGCTGTTATGGATGATTTCGCAGCTTTTGTAGAGAAGTG

CTGCAAGGCTGACGATAAGGAGACCTGCTTTGCCGAGGAGGGTAAAAAACTTGTTGCTGCAAGTCAAGCTGCC

TTAGGCTTATGAGGTACCGAGCTCGGATCCACTAGTCCAGTGTGGTGGAATTCTGCAGATATCCAGCACAGTG

GCGGCCGCTCGAGTCTAGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTGTCCTTTCCTAATAAA

ATGAGGAAATTGCATCGCATTGTCTGAGTAGGTGTCATTCTATTCTGGGGGGTGGGGTGGGGCAGGACAGCAA

GGGGGAGGATTGGGAAGACAATAGCAGGCATGCTGGGGATGCGGTGGGCTCTATGGCTTCTGAGGCGGAAAGA

ACCAGCTGGGGCTCTAGGGGGTATCCCCACGCGCCCTGTAGCGGCGCATTAAGCGCGGCGGGTGTGGTGGTTA

CGCGCAGCGTGACCGCTACACTTGCCAGCGCCCTAGCGCCCGCTCCTTTCGCTTTCTTCCCTTCCTTTCTCGC

CACGTTCGCCGGCTTTCCCCGTCAAGCTCTAAATCGGGGGCTCCCTTTAGGGTTCCGATTTAGTGCTTTACGG

CACCTCGACCCCAAAAAACTTGATTAGGGTGATGGTTCACGTAGTGGGCCATCGCCCTGATAGACGGTTTTTC

GCCCTTTGACGTTGGAGTCCACGTTCTTTAATAGTGGACTCTTGTTCCAAACTGGAACAACACTCAACCCTAT

CTCGGTCTATTCTTTTGATTTATAAGGGATTTTGCCGATTTCGGCCTATTGGTTAAAAAATGAGCTGATTTAA

CAAAAATTTAACGCGAATTAATTCTGTGGAATGTGTGTCAGTTAGGGTGTGGAAAGTCCCCAGGCTCCCCAGC

AGGCAGAAGTATGCAAAGCATGCATCTCAATTAGTCAGCAACCAGGTGTGGAAAGTCCCCAGGCTCCCCAGCA

GGCAGAAGTATGCAAAGCATGCATCTCAATTAGTCAGCAACCATAGTCCCGCCCCTAACTCCGCCCATCCCGC

CCCTAACTCCGCCCAGTTCCGCCCATTCTCCGCCCCATGGCTGACTAATTTTTTTTATTTATGCAGAGGCCGA

GGCCGCCTCTGCCTCTGAGCTATTCCAGAAGTAGTGAGGAGGCTTTTTTGGAGGCCTAGGCTTTTGCAAAAAG

CTCCCGGGAGCTTGTATATCCATTTTCGGATCTGATCAAGAGACAGGATGAGGATCGTTTCGCATGATTGAAC

AAGATGGATTGCACGCAGGTTCTCCGGCCGCTTGGGTGGAGAGGCTATTCGGCTATGACTGGGCACAACAGAC

AATCGGCTGCTCTGATGCCGCCGTGTTCCGGCTGTCAGCGCAGGGGCGCCCGGTTCTTTTTGTCAAGACCGAC

CTGTCCGGTGCCCTGAATGAACTGCAGGACGAGGCAGCGCGGCTATCGTGGCTGGCCACGACGGGCGTTCCTT

GCGCAGCTGTGCTCGACGTTGTCACTGAAGCGGGAAGGGACTGGCTGCTATTGGGCGAAGTGCCGGGGCAGGA

TCTCCTGTCATCTCACCTTGCTCCTGCCGAGAAAGTATCCATCATGGCTGATGCAATGCGGCGGCTGCATACG

CTTGATCCGGCTACCTGCCCATTCGACCACCAAGCGAAACATCGCATCGAGCGAGCACGTACTCGGATGGAAG

CCGGTCTTGTCGATCAGGATGATCTGGACGAAGAGCATCAGGGGCTCGCGCCAGCCGAACTGTTCGCCAGGCT

CAAGGCGCGCATGCCCGACGGCGAGGATCTCGTCGTGACCCATGGCGATGCCTGCTTGCCGAATATCATGGTG

GAAAATGGCCGCTTTTCTGGATTCATCGACTGTGGCCGGCTGGGTGTGGCGGACCGCTATCAGGACATAGCGT

TGGCTACCCGTGATATTGCTGAAGAGCTTGGCGGCGAATGGGCTGACCGCTTCCTCGTGCTTTACGGTATCGC

CGCTCCCGATTCGCAGCGCATCGCCTTCTATCGCCTTCTTGACGAGTTCTTCTGAGCGGGACTCTGGGGTTCG

AAATGACCGACCAAGCGACGCCCAACCTGCCATCACGAGATTTCGATTCCACCGCCGCCTTCTATGAAAGGTT

-continued

GGGCTTCGGAATCGTTTTCCGGGACGCCGGCTGGATGATCCTCCAGCGCGGGGATCTCATGCTGGAGTTCTTC

GCCCACCCCAACTTGTTTATTGCAGCTTATAATGGTTACAAATAAAGCAATAGCATCACAAATTTCACAAATA

AAGCATTTTTTTCACTGCATTCTAGTTGTGGTTTGTCCAAACTCATCAATGTATCTTATCATGTCTGTATACC

GTCGACCTCTAGCTAGAGCTTGGCGTAATCATGGTCATAGCTGTTTCCTGTGTGAAATTGTTATCCGCTCACA

ATTCCACACAACATACGAGCCGGAAGCATAAAGTGTAAAGCCTGGGGTGCCTAATGAGTGAGCTAACTCACAT

TAATTGCGTTGCGCTCACTGCCCGCTTTCCAGTCGGGAAACCTGTCGTGCCAGCTGCATTAATGAATCGGCCA

ACGCGCGGGGAGAGGCGGTTTGCGTATTGGGCGCTCTTCCGCTTCCTCGCTCACTGACTCGCTGCGCTCGGTC

GTTCGGCTGCGGCGAGCGGTATCAGCTCACTCAAAGGCGGTAATACGGTTATCCACAGAATCAGGGGATAACG

CAGGAAAGAACATGTGAGCAAAAGGCCAGCAAAAGGCCAGGAACCGTAAAAAGGCCGCGTTGCTGGCGTTTTT

CCATAGGCTCCGCCCCCCTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACGCTGTAGGTATCTCAGTTC

GGTGTAGGTCGTTCGCTCCAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTAACTACGGCTACACTAGAAG

AACAGTATTTGGTATCTGCGCTCTGCTGAAGCCAGTTACCTTCGGAAAAAGAGTTGGTAGCTCTTGATCCGGC

AAACAAACCACCGCTGGTAGCGGTGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAAAACTCACGTTAAGGGATTTTGGT

CATGAGATTATCAAAAAGGATCTTCACCTAGATCCTTTTAAATTAAAAATGAAGTTTTAAATCAATCTAAAGT

ATATATGAGTAAACTTGGTCTGACAGTTACCAATGCTTAATCAGTGAGGCACCTATCTCAGCGATCTGTCTAT

TTCGTTCATCCATAGTTGCCTGACTCCCCGTCGTGTAGATAACTACGATACGGGAGGGCTTACCATCTGGCCC

CAGTGCTGCAATGATACCGCGAGACCCACGCTCACCGGCTCCAGATTTATCAGCAATAAACCAGCCAGCCGGA

AGGGCCGAGCGCAGAAGTGGTCCTGCAACTTTATCCGCCTCCATCCAGTCTATTAATTGTTGCCGGGAAGCTA

GAGTAAGTAGTTCGCCAGTTAATAGTTTGCGCAACGTTGTTGCCATTGCTACAGGCATCGTGGTGTCACGCTC

GTCGTTTGGTATGGCTTCATTCAGCTCCGGTTCCCAACGATCAAGGCGAGTTACATGATCCCCCATGTTGTGC

AAAAAAGCGGTTAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACTGGTGAGTACTC

AACCAAGTCATTCTGAGAATAGTGTATGCGGCGACCGAGTTGCTCTTGCCCGGCGTCAATACGGGATAATACC

GCGCCACATAGCAGAACTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGGGAATAAGGGCGACACGGAAATGT

TGAATACTCATACTCTTCCTTTTTCAATATTATTGAAGCATTTATCAGGGTTATTGTCTCATGAGCGGATACA

TATTTGAATGTATTTAGAAAAATAAACAAATAGGGGTTCCGCGCACATTTCCCCGAAAAGTGCCACCTGACGT

C hALB_kozak_hAlbsig_FLAG_ENPP1opt_LINK_hAlb_pcDNA3.1(+)

pcDNA3.1+, h-albumin promoter, Kozak seq, h-albumin secretory, Flag tag, ENPP1opt, Linker seq, h-albumin seq, Stop codon

(SEQ ID NO: 93)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

-continued

CAAGGCTTGACCGACAATTGCATGAAGAATCTGCTTAGGGTTAGGCGTTTTGCGCTGCTTCGCGATGTACGGG

CCAGATATACGCGTTAGTTCCAGATGGTAAATATACACAAGGGATTTAGTCAAACAATTTTTTGGCAAGAATA

TTATGAATTTTGTAATCGGTTGGCAGCCAATGAAATACAAAGATGAGTCTAGTTAATAATCTACAATTATTGG

TTAAAGAAGTATATTAGTGCTAATTTCCCTCCGTTTGTCCTAGCTTTTCTCTTCTGTCAACCCCACACGCCTT

TGGCACCTCTGGCTAACTAGAGAACCCACTGCTTACTGGCTTATCGAAATTAATACGACTCACTATAGGGAGA

CCCAAGCTGGCTAGCGCCACCATGAAGTGGGTAACCTTTATTTCCCTTCTTTTTCTCTTTAGCTCGGCTTATT per sme, get not needed, same data as get 70

GGAGGTGAAGAGCTGCAAGGGCAGATGTTTCGAACGGACCTTCGGCAACTGCAGATGCGACGCCGCCTGCGTG

GAACTGGGAAACTGTTGTCTGGACTACCAGGAGACATGTATCGAGCCTGAGCACATCTGGACATGCAACAAGT

TCAGATGTGGCGAGAAAAGACTGACTCGGAGTCTGTGCGCCTGTTCTGACGACTGCAAGGACAAGGGCGATTG

CTGCATCAACTACAGCAGCGTGTGCCAGGGCGAAAAGAGCTGGGTCGAGGAACCCTGCGAGAGCATCAACGAG

CCCCAGTGCCCTGCCGGATTTGAGACACCTCCTACCCTGCTCTTCTCCCTGGATGGCTTCAGAGCTGAGTACC

TGCATACATGGGGAGGACTGCTGCCTGTGATCAGCAAGCTGAAGAAGTGCGGCACCTACACAAAGAACATGCG

GCCTGGCAGCGACGTGGAGATCAACGGAATCTTCCCTGATATCTACAAGATGTATAACGGCTCCGTGCCTTTC

ATCATCGACAACAAGATGTACGACCCCAAAATGAACGCCAGCTTCAGCCTGAAATCTAAGGAAAAGTTCAACC

CTGAGTGGTATAAGGGCGAGCCAATCTGGGTGACAGCCAAGTACCAGGGCCTGAAGAGCGGCACCTTCTTCTG

GCCTGGCAGCGACGTGGAGATCAACGGAATCTTCCCTGATATCTACAAGATGTATAACGGCTCCGTGCCTTTC

GAGGAGCGGATCTTGGCTGTTCTTCAGTGGCTGCAGCTGCCCAAGGACGAGAGACCCCACTTCTACACCCTGT

ACCTGGAAGAACCTGACAGCAGCGGCCACAGCTACGGCCCTGTGTCTAGCGAGGTGATCAAGGCCCTGCAAAG

AGTGGATGGCATGGTGGGCATGCTGATGGATGGACTGAAGGAACTGAACCTCCATCGTTGCCTGAACCTGATC

CTGATCTCCGACCACGGCATGGAACAGGGCAGCTGTAAAAAGTACATCTACCTGAACAAGTACCTGGGCGACG

TGAAGAATATCAAGGTGATCTACGGGCCGGCCGCCAGGCTGCGGCCTAGCGACGTGCCCGACAAGTATTACAG

CTTCAACTACGAGGGCATCGCCAGAAACCTGTCTTGCAGAGAACCCAATCAACACTTCAAGCCTTACCTGAAG

CACTTTCTGCCTAAGAGACTGCACTTCGCCAAAAGCGACAGAATTGAACCCCTGACATTCTATCTGGACCCTC

AGTGGCAGCTGGCCCTCAATCCTTCTGAACGCAAATACTGCGGTAGCGGATTTCACGGCTCTGATAACGTGTT

TTCTAACATGCAGGCCCTGTTTGTGGGCTACGGCCCTGGCTTCAAGCACGGAATCGAGGCTGACACCTTCGAG

AACATCGAAGTTTACAATCTGATGTGCGACCTGCTGAATCTGACCCCAGCCCCTAACAACGGCACACACGGCT

CTCTGAATCACCTGCTCAAGAACCCCGTGTATACCCCCAAACACCCTAAAGAGGTCCATCCACTGGTGCAGTG

CCCATTCACCAGAAACCCTCGGGACAACCTTGGCTGCAGCTGCAACCCTAGCATCCTCCCTATCGAAGATTTC

CAGACCCAGTTTAACCTGACTGTCGCCGAAGAGAAGATCATCAAGCACGAAACCCTGCCCTACGGGAGGCCCA

GAGTGCTGCAGAAAGAAAACACAATCTGTCTGCTGAGCCAGCACCAGTTTATGAGCGGCTACAGTCAGGACAT

CCTGATGCCTCTGTGGACCAGCTACACCGTGGACCGGAATGACAGCTTCAGCACCGAGGACTTCAGCAACTGC

CTGTATCAGGACTTCCGCATCCCTCTGTCCCCTGTGCATAAGTGCAGCTTTTACAAGAACAACACCAAGGTGA

GCTACGGGTTTCTGAGCCCACCACAACTGAACAAAAATAGCTCTGGCATCTACTCTGAGGCGCTGCTGACCAC

CAACATCGTGCCAATGTACCAGAGCTTCCAGGTGATCTGGCGGTACTTCCATGATACCCTGCTTCGGAAGTAC

GCCGAAGAACGGAACGGCGTGAACGTGGTGTCCGGCCCAGTGTTCGACTTCGACTACGACGGCAGATGTGATT

CCCTTGAGAATCTGAGACAGAAGCGGCGGGTTATCAGAAACCAGGAGATCCTGATTCCTACCCACTTCTTCAT

CGTGCTGACATCTTGCAAGGATACCAGCCAAACACCTCTGCACTGCGAGAACCTGGACACCCTGGCCTTCATC

CTGCCTCACCGGACCGATAATAGCGAATCCTGTGTGCACGGCAAACACGACTCTAGCTGGGTGGAAGAGCTGC

-continued

TGATGCTGCACAGAGCCCGGATCACAGATGTGGAACACATCACCGGCCTGTCCTTCTACCAACAGAGAAAGGA

ACCCGTGTCTGATATCCTGAAGCTGAAAACCCACCTGCCTACCTTCAGCCAGGAGGACCTGATCGTTAACGAT

GCACACAAGAGTGAGGTTGCTCATCGGTTTAAAGATTTGGGAGAAGAAAATTTCAAAGCCTTGGTGTTGATTG

CCTTTGCTCAGTATCTTCAGCAGTGTCCATTTGAAGATCATGTAAAATTAGTGAATGAAGTAACTGAATTTGC

AAAAACATGTGTTGCTGATGAGTCAGCTGAAAATTGTGACAAATCACTTCATACCCTTTTTGGAGACAAATTA

TGCACAGTTGCAACTCTTCGTGAAACCTATGGTGAAATGGCTGACTGCTGTGCAAAACAAGAACCTGAGAGAA

ATGAATGCTTCTTGCAACACAAAGATGACAACCCAAACCTCCCCCGATTGGTGAGACCAGAGGTTGATGTGAT

GTGCACTGCTTTTCATGACAATGAAGAGACATTTTTGAAAAAATACTTATATGAAATTGCCAGAAGACATCCT

TACTTTTATGCCCCGGAACTCCTTTTCTTTGCTAAAAGGTATAAAGCTGCTTTTACAGAATGTTGCCAAGCTG

CTGATAAAGCTGCCTGCCTGTTGCCAAAGCTCGATGAACTTCGGGATGAAGGGAAGGCTTCGTCTGCCAAACA

GAGACTCAAGTGTGCCAGTCTCCAAAAATTTGGAGAAAGAGCTTTCAAAGCATGGGCAGTAGCTCGCCTGAGC

CAGAGATTTCCCAAAGCTGAGTTTGCAGAAGTTTCCAAGTTAGTGACAGATCTTACCAAAGTCCACACGGAAT

GCTGCCATGGAGATCTGCTTGAATGTGCTGATGACAGGGCGGACCTTGCCAAGTATATCTGTGAAAATCAAGA

TTCGATCTCCAGTAAACTGAAGGAATGCTGTGAAAAACCTCTGTTGGAAAAATCCCACTGCATTGCCGAAGTG

GAAAATGATGAGATGCCTGCTGACTTGCCTTCATTAGCTGCTGATTTTGTTGAAAGTAAGGATGTTTGCAAAA

ACTATGCTGAGGCAAAGGATGTCTTCCTGGGCATGTTTTTGTATGAATATGCAAGAAGGCATCCTGATTACTC

TGTCGTGCTGCTGCTGAGACTTGCCAAGACATATGAAACCACACTCGAGAAGTGCTGTGCCGCTGCAGATCCT

CATGAATGCTATGCCAAAGTGTTCGATGAATTTAAACCTCTTGTGGAAGAGCCTCAGAATTTAATCAAACAAA

ATTGTGAGCTTTTTGAGCAGCTTGGAGAGTACAAATTCCAGAATGCGCTATTAGTTCGTTACACCAAGAAAGT

ACCCCAAGTGTCAACTCCAACTCTTGTAGAGGTCTCAAGAAACCTAGGAAAAGTGGGCAGCAAATGTTGTAAA

CATCCTGAAGCAAAAAGAATGCCCTGTGCAGAAGACTATCTATCCGTGGTCCTGAACCAGTTATGTGTGTTGC

ATGAGAAAACGCCAGTAAGTGACAGAGTCACCAAATGCTGCACAGAATCCTTGGTGAACAGGCGACCATGCTT

TTCAGCTCTGGAAGTCGATGAAACATACGTTCCCAAAGAGTTTAATGCTGAAACATTCACCTTCCATGCAGAT

ATATGCACACTTTCTGAGAAGGAGAGACAAATCAAGAAACAAACTGCACTTGTTGAGCTCGTGAAACACAAGC

CCAAGGCAACAAAAGAGCAACTGAAAGCTGTTATGGATGATTTCGCAGCTTTTGTAGAGAAGTGCTGCAAGGC

TGACGATAAGGAGACCTGCTTTGCCGAGGAGGGTAAAAAACTTGTTGCTGCAAGTCAAGCTGCCTTAGGCTTA

TGAGGTACCGAGCTCGGATCCACTAGTCCAGTGTGGTGGAATTCTGCAGATATCCAGCACAGTGGCGGCCGCT

CGAGTCTAGAGGGCCCGTTTAAACCCGCTGATCAGCCTCGACTGTGCCTTCTAGTTGCCAGCCATCTGTTGTT

TGCCCCTCCCCCGTGCCTTCCTTGACCCTGGAAGGTGCCACTCCCACTGTCCTTTCCTAATAAAATGAGGAAA

TTGCATCGCATTGTCTGAGTAGGTGTCATTCTATTCTGGGGGGTGGGGTGGGGCAGGACAGCAAGGGGGAGGA

TTGGGAAGACAATAGCAGGCATGCTGGGGATGCGGTGGGCTCTATGGCTTCTGAGGCGGAAAGAACCAGCTGG

GGCTCTAGGGGGTATCCCCACGCGCCCTGTAGCGGCGCATTAAGCGCGGCGGGTGTGGTGGTTACGCGCAGCG

TGACCGCTACACTTGCCAGCGCCCTAGCGCCCGCTCCTTTCGCTTTCTTCCCTTCCTTTCTCGCCACGTTCGC

CGGCTTTCCCCGTCAAGCTCTAAATCGGGGGCTCCCTTTAGGGTTCCGATTTAGTGCTTTACGGCACCTCGAC

CCCAAAAAACTTGATTAGGGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACTCAACCCTATCTCGGTCTA

TTCTTTTGATTTATAAGGGATTTTGCCGATTTCGGCCTATTGGTTAAAAAATGAGCTGATTTAACAAAAATTT

AACGCGAATTAATTCTGTGGAATGTGTGTCAGTTAGGGTGTGGAAAGTCCCCAGGCTCCCCAGCAGGCAGAAG

TATGCAAAGCATGCATCTCAATTAGTCAGCAACCAGGTGTGGAAAGTCCCCAGGCTCCCCAGCAGGCAGAAGT

-continued

ATGCAAAGCATGCATCTCAATTAGTCAGCAACCATAGTCCCGCCCCTAACTCCGCCCATCCCGCCCCTAACTC

CGCCCAGTTCCGCCCATTCTCCGCCCCATGGCTGACTAATTTTTTTTATTTATGCAGAGGCCGAGGCCGCCTC

TGCCTCTGAGCTATTCCAGAAGTAGTGAGGAGGCTTTTTTGGAGGCCTAGGCTTTTGCAAAAAGCTCCCGGGA

GCTTGTATATCCATTTTCGGATCTGATCAAGAGACAGGATGAGGATCGTTTCGCATGATTGAACAAGATGGAT

TGCACGCAGGTTCTCCGGCCGCTTGGGTGGAGAGGCTATTCGGCTATGACTGGGCACAACAGACAATCGGCTG

CTCTGATGCCGCCGTGTTCCGGCTGTCAGCGCAGGGGCGCCCGGTTCTTTTTGTCAAGACCGACCTGTCCGGT

GCCCTGAATGAACTGCAGGACGAGGCAGCGCGGCTATCGTGGCTGGCCACGACGGGCGTTCCTTGCGCAGCTG

TGCTCGACGTTGTCACTGAAGCGGGAAGGGACTGGCTGCTATTGGGCGAAGTGCCGGGGCAGGATCTCCTGTC

ATCTCACCTTGCTCCTGCCGAGAAAGTATCCATCATGGCTGATGCAATGCGGCGGCTGCATACGCTTGATCCG

GCTACCTGCCCATTCGACCACCAAGCGAAACATCGCATCGAGCGAGCACGTACTCGGATGGAAGCCGGTCTTG

TCGATCAGGATGATCTGGACGAAGAGCATCAGGGGCTCGCGCCAGCCGAACTGTTCGCCAGGCTCAAGGCGCG

CATGCCCGACGGCGAGGATCTCGTCGTGACCCATGGCGATGCCTGCTTGCCGAATATCATGGTGGAAAATGGC

CGCTTTTCTGGATTCATCGACTGTGGCCGGCTGGGTGTGGCGGACCGCTATCAGGACATAGCGTTGGCTACCC

GTGATATTGCTGAAGAGCTTGGCGGCGAATGGGCTGACCGCTTCCTCGTGCTTTACGGTATCGCCGCTCCCGA

TTCGCAGCGCATCGCCTTCTATCGCCTTCTTGACGAGTTCTTCTGAGCGGGACTCTGGGGTTCGAAATGACCG

ACCAAGCGACGCCCAACCTGCCATCACGAGATTTCGATTCCACCGCCGCCTTCTATGAAAGGTTGGGCTTCGG

AATCGTTTTCCGGGACGCCGGCTGGATGATCCTCCAGCGCGGGGATCTCATGCTGGAGTTCTTCGCCCACCCC

AACTTGTTTATTGCAGCTTATAATGGTTACAAATAAAGCAATAGCATCACAAATTTCACAAATAAAGCATTTT

TTTCACTGCATTCTAGTTGTGGTTTGTCCAAACTCATCAATGTATCTTATCATGTCTGTATACCGTCGACCTC

TAGCTAGAGCTTGGCGTAATCATGGTCATAGCTGTTTCCTGTGTGAAATTGTTATCCGCTCACAATTCCACAC

AACATACGAGCCGGAAGCATAAAGTGTAAAGCCTGGGGTGCCTAATGAGTGAGCTAACTCACATTAATTGCGT

TGCGCTCACTGCCCGCTTTCCAGTCGGGAAACCTGTCGTGCCAGCTGCATTAATGAATCGGCCAACGCGCGGG

GAGAGGCGGTTTGCGTATTGGGCGCTCTTCCGCTTCCTCGCTCACTGACTCGCTGCGCTCGGTCGTTCGGCTG

CGGCGAGCGGTATCAGCTCACTCAAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCGTTGCTGGCGTTTTTCCATAGGCT

CCGCCCCCCTGACGAGCATCACAAAAATCGACGCTCAAGTCAGAGGTGGCGAAACCCGACAGGACTATAAAGA

TACCAGGCGTTTCCCCCTGGAAGCTCCCTCGTGCGCTCTCCTGTTCCGACCCTGCCGCTTACCGGATACCTGT

CCGCCTTTCTCCCTTCGGGAAGCGTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACACTAGAAGAACAGTATT

TGGTATCTGCGCTCTGCTGAAGCCAGTTACCTTCGGAAAAAGAGTTGGTAGCTCTTGATCCGGCAAACAAACC

ACCGCTGGTAGCGGTGGTTTTTTTGTTTGCAAGCAGCAGATTACGCGCAGAAAAAAAGGATCTCAAGAAGATC

CTTTGATCTTTTCTACGGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATCTGTCTATTTCGTTCAT

CCATAGTTGCCTGACTCCCCGTCGTGTAGATAACTACGATACGGGAGGGCTTACCATCTGGCCCCAGTGCTGC

AATGATACCGCGAGACCCACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGGGAAGCTAGAGTAAGTA

GTTCGCCAGTTAATAGTTTGCGCAACGTTGTTGCCATTGCTACAGGCATCGTGGTGTCACGCTCGTCGTTTGG

-continued

TATGGCTTCATTCAGCTCCGGTTCCCAACGATCAAGGCGAGTTACATGATCCCCCATGTTGTGCAAAAAAGCG

GTTAGCTCCTTCGGTCCTCCGATCGTTGTCAGAAGTAAGTTGGCCGCAGTGTTATCACTCATGGTTATGGCAG

CACTGCATAATTCTCTTACTGTCATGCCATCCGTAAGATGCTTTTCTGTGACTGGTGAGTACTCAACCAAGTC

ATTCTGAGAATAGTGTATGCGGCGACCGAGTTGCTCTTGCCCGGCGTCAATACGGGATAATACCGCGCCACAT

AGCAGAACTTTAAAAGTGCTCATCATTGGAAAACGTTCTTCGGGGCGAAAACTCTCAAGGATCTTACCGCTGT

TGAGATCCAGTTCGATGTAACCCACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGGCGACACGGAAATGTTGAATACTC

ATACTCTTCCTTTTTCAATATTATTGAAGCATTTATCAGGGTTATTGTCTCATGAGCGGATACATATTTGAAT

GTATTTAGAAAAATAAACAAATAGGGGTTCCGCGCACATTTCCCCGAAAAGTGCCACCTGACGTC

CMV_Kozak_hAlb sig_FLAG_ENPP1opt_LINK_hAlb_stop_mir155_pcDNA3.1(+)

pcDNA3.1+, CMV enhancer, CMV promoter, Kozak seq, h-alb secretory,

Flag tag, ENPP1 opt, Linker seq, h -alb seq, *stop codon*, mir155 target seq

(SEQ ID NO: 94)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGACATTGATTATTGACTAGTTATTAATAGTAATCAATTACGGGGTCATTAGTTCATAG

CCCATATATGGAGTTCCGCGTTACATAACTTACGGTAAATGGCCCGCCTGGCTGACCGCCCAACGACCCCCGC

CCATTGACGTCAATAATGACGTATGTTCCCATAGTAACGCCAATAGGGACTTTCCATTGACGTCAATGGGTGG

AGTATTTACGGTAAACTGCCCACTTGGCAGTACATCAAGTGTATCATATGCCAAGTACGCCCCCTATTGACGT

CAATGACGGTAAATGGCCCGCCTGGCATTATGCCCAGTACATGACCTTATGGGACTTTCCTACTTGGCAGTAC

ATCTACGTATTAGTCATCGCTATTACCATGGTGATGCGGTTTTGGCAGTACATCAATGGGCGTGGATAGCGGT

TTGACTCACGGGGATTTCCAAGTCTCCACCCCATTGACGTCAATGGGAGTTTGTTTTGGCACCAAAATCAACG

GGACTTTCCAAAATGTCGTAACAACTCCGCCCCATTGACGCAAATGGGCGGTAGGCGTGTACGGTGGGAGGTC

TATATAAGCAGAGCTCTCTGGCTAACTAGAGAACCCACTGCTTACTGGCTTATCGAAATTAATACGACTCACT

ATAGGGAGACCCAAGCTGGCTAGCGCCACCATGAAGTGGGTAACCTTTATTTCCCTTCTTTTTCTCTTTAGCT

CGGTTATTCCAGGGGTGTGTTTCGTCGAGACTACAAAGACGATGACGACAAGAGCGCTGGCCTGAAGCCAAG

CTGCGCCAAGGAGGTGAAGAGCTGCAAGGGCAGATGTTTCGAACGGACCTTCGGCAACTGCAGATGCGACGCC

GCCTGCGTGGAACTGGGAAACTGTTGTCTGGACTACCAGGAGACATGTATCGAGCCTGAGCACATCTGGACAT

GCAACAAGTTCAGATGTGGCGAGAAAAGACTGACTCGGAGTCTGTGCGCCTGTTCTGACGACTGCAAGGACAA

GGGCGATTGCTGCATCAACTACAGCAGCGTGTGCCAGGGCGAAAAGAGCTGGGTCGAGGAACCCTGCGAGAGC

ATCAACGAGCCCCAGTGCCCTGCCGGATTTGAGACACCTCCTACCCTGCTCTTCTCCCTGGATGGCTTCAGAG

CTGAGTACCTGCATACATGGGGAGGACTGCTGCCTGTGATCAGCAAGCTGAAGAAGTGCGGCACCTACACAAA

GAACATGCGGCCTGTCTACCCTACCAAGACCTTCCCCAACCACTACAGCATCGTGACCGGCCTGTACCCCGAG

AGCCACGGCATCATCGACAACAAGATGTACGACCCCAAAATGAACGCCAGCTTCAGCCTGAAATCTAAGGAAA

-continued

AGTTCAACCCTGAGTGGTATAAGGGCGAGCCAATCTGGGTGACAGCCAAGTACCAGGGCCTGAAGAGCGGCAC

CTTCTTCTGGCCTGGCAGCGACGTGGAGATCAACGGAATCTTCCCTGATATCTACAAGATGTATAACGGCTCC

GTGCCTTTCGAGGAGCGGATCTTGGCTGTTCTTCAGTGGCTGCAGCTGCCCAAGGACGAGAGACCCCACTTCT

ACACCCTGTACCTGGAAGAACCTGACAGCAGCGGCCACAGCTACGGCCCTGTGTCTAGCGAGGTGATCAAGGC

CCTGCAAAGAGTGGATGGCATGGTGGGCATGCTGATGGATGGACTGAAGGAACTGAACCTCCATCGTTGCCTG

AACCTGATCCTGATCTCCGACCACGGCATGGAACAGGGCAGCTGTAAAAAGTACATCTACCTGAACAAGTACC

TGGGCGACGTGAAGAATATCAAGGTGATCTACGGGCCGGCCGCCAGGCTGCGGCCTAGCGACGTGCCCGACAA

GTATTACAGCTTCAACTACGAGGGCATCGCCAGAAACCTGTCTTGCAGAGAACCCAATCAACACTTCAAGCCT

TACCTGAAGCACTTTCTGCCTAAGAGACTGCACTTCGCCAAAAGCGACAGAATTGAACCCCTGACATTCTATC

TGGACCCTCAGTGGCAGCTGGCCCTCAATCCTTCTGAACGCAAATACTGCGGTAGCGGATTTCACGGCTCTGA

TAACGTGTTTTCTAACATGCAGGCCCTGTTTGTGGGCTACGGCCCTGGCTTCAAGCACGGAATCGAGGCTGAC

ACCTTCGAGAACATCGAAGTTTACAATCTGATGTGCGACCTGCTGAATCTGACCCCAGCCCCTAACAACGGCA

CACACGGCTCTCTGAATCACCTGCTCAAGAACCCCGTGTATACCCCCAAACACCCTAAAGAGGTCCATCCACT

GGTGCAGTGCCCATTCACCAGAAACCCTCGGGACAACCTTGGCTGCAGCTGCAACCCTAGCATCCTCCCTATC

GAAGATTTCCAGACCCAGTTTAACCTGACTGTCGCCGAAGAGAAGATCATCAAGCACGAAACCCTGCCCTACG

GGAGGCCCAGAGTGCTGCAGAAAGAAAACACAATCTGTCTGCTGAGCCAGCACCAGTTTATGAGCGGCTACAG

TCAGGACATCCTGATGCCTCTGTGGACCAGCTACACCGTGGACCGGAATGACAGCTTCAGCACCGAGGACTTC

AGCAACTGCCTGTATCAGGACTTCCGCATCCCTCTGTCCCCTGTGCATAAGTGCAGCTTTTACAAGAACAACA

CCAAGGTGAGCTACGGGTTTCTGAGCCCACCACAACTGAACAAAAATAGCTCTGGCATCTACTCTGAGGCGCT

GCTGACCACCAACATCGTGCCAATGTACCAGAGCTTCCAGGTGATCTGGCGGTACTTCCATGATACCCTGCTT

CGGAAGTACGCCGAAGAACGGAACGGCGTGAACGTGGTGTCCGGCCCAGTGTTCGACTTCGACTACGACGGCA

GATGTGATTCCCTTGAGAATCTGAGACAGAAGCGGCGGGTTATCAGAAACCAGGAGATCCTGATTCCTACCCA

CTTCTTCATCGTGCTGACATCTTGCAAGGATACCAGCCAAACACCTCTGCACTGCGAGAACCTGGACACCCTG

GCCTTCATCCTGCCTCACCGGACCGATAATAGCGAATCCTGTGTGCACGGCAAACACGACTCTAGCTGGGTGG

AAGAGCTGCTGATGCTGCACAGAGCCCGGATCACAGATGTGGAACACATCACCGGCCTGTCCTTCTACCAACA

GAGAAAGGAACCCGTGTCTGATATCCTGAAGCTGAAAACCCACCTGCCTACCTTCAGCCAGGAGGACCTGATC

GTTAACGATGCACACAAGAGTGAGGTTGCTCATCGGTTTAAAGATTTGGGAGAAGAAAATTTCAAAGCCTTGG

TGTTGATTGCCTTTGCTCAGTATCTTCAGCAGTGTCCATTTGAAGATCATGTAAAATTAGTGAATGAAGTAAC

TGAATTTGCAAAAACATGTGTTGCTGATGAGTCAGCTGAAAATTGTGACAAATCACTTCATACCCTTTTTGGA

GACAAATTATGCACAGTTGCAACTCTTCGTGAAACCTATGGTGAAATGGCTGACTGCTGTGCAAAACAAGAAC

CTGAGAGAAATGAATGCTTCTTGCAACACAAAGATGACAACCCAAACCTCCCCCGATTGGTGAGACCAGAGGT

TGATGTGATGTGCACTGCTTTTCATGACAATGAAGAGACATTTTTGAAAAAATACTTATATGAAATTGCCAGA

AGACATCCTTACTTTTATGCCCCGGAACTCCTTTTCTTTGCTAAAAGGTATAAAGCTGCTTTTACAGAATGTT

GCCAAGCTGCTGATAAAGCTGCCTGCCTGTTGCCAAAGCTCGATGAACTTCGGGATGAAGGGAAGGCTTCGTC

TGCCAAACAGAGACTCAAGTGTGCCAGTCTCCAAAAATTTGGAGAAAGAGCTTTCAAAGCATGGGCAGTAGCT

CGCCTGAGCCAGAGATTTCCCAAAGCTGAGTTTGCAGAAGTTTCCAAGTTAGTGACAGATCTTACCAAAGTCC

ACACGGAATGCTGCCATGGAGATCTGCTTGAATGTGCTGATGACAGGGCGGACCTTGCCAAGTATATCTGTGA

AAATCAAGATTCGATCTCCAGTAAACTGAAGGAATGCTGTGAAAAACCTCTGTTGGAAAAATCCCACTGCATT

GCCGAAGTGGAAAATGATGAGATGCCTGCTGACTTGCCTTCATTAGCTGCTGATTTTGTTGAAAGTAAGGATG

-continued

TTTGCAAAAACTATGCTGAGGCAAAGGATGTCTTCCTGGGCATGTTTTTGTATGAATATGCAAGAAGGCATCC

TGATTACTCTGTCGTGCTGCTGCTGAGACTTGCCAAGACATATGAAACCACACTCGAGAAGTGCTGTGCCGCT

GCAGATCCTCATGAATGCTATGCCAAAGTGTTCGATGAATTTAAACCTCTTGTGGAAGAGCCTCAGAATTTAA

TCAAACAAAATTGTGAGCTTTTTGAGCAGCTTGGAGAGTACAAATTCCAGAATGCGCTATTAGTTCGTTACAC

CAAGAAAGTACCCCAAGTGTCAACTCCAACTCTTGTAGAGGTCTCAAGAAACCTAGGAAAAGTGGGCAGCAAA

TGTTGTAAACATCCTGAAGCAAAAAGAATGCCCTGTGCAGAAGACTATCTATCCGTGGTCCTGAACCAGTTAT

GTGTGTTGCATGAGAAAACGCCAGTAAGTGACAGAGTCACCAAATGCTGCACAGAATCCTTGGTGAACAGGCG

ACCATGCTTTTCAGCTCTGGAAGTCGATGAAACATACGTTCCCAAAGAGTTTAATGCTGAAACATTCACCTTC

CATGCAGATATATGCACACTTTCTGAGAAGGAGAGACAAATCAAGAAACAAACTGCACTTGTTGAGCTCGTGA

AACACAAGCCCAAGGCAACAAAAGAGCAACTGAAAGCTGTTATGGATGATTTCGCAGCTTTTGTAGAGAAGTG

CTGCAAGGCTGACGATAAGGAGACCTGCTTTGCCGAGGAGGGTAAAAAACTTGTTGCTGCAAGTCAAGCTGCC

TTAGGCTTA*TGA*CAATTACGATTAGCACTATCCAATTACGATTAGCACTATCCAATTACGATTAGCACTATCG

GTACCGAGCTCGGATCCACTAGTCCAGTGTGGTGGAATTCTGCAGATATCCAGCACAGTGGCGGCCGCTCGAG

TCTAGAGGGCCCGTTTAAACCCGCTGATCAGCCTCGACTGTGCCTTCTAGTTGCCAGCCATCTGTTGTTTGCC

CCTCCCCCGTGCCTTCCTTGACCCTGGAAGGTGCCACTCCCACTGTCCTTTCCTAATAAAATGAGGAAATTGC

ATCGCATTGTCTGAGTAGGTGTCATTCTATTCTGGGGGGTGGGGTGGGGCAGGACAGCAAGGGGGAGGATTGG

GAAGACAATAGCAGGCATGCTGGGGATGCGGTGGGCTCTATGGCTTCTGAGGCGGAAAGAACCAGCTGGGGCT

CTAGGGGGTATCCCCACGCGCCCTGTAGCGGCGCATTAAGCGCGGCGGGTGTGGTGGTTACGCGCAGCGTGAC

CGCTACACTTGCCAGCGCCCTAGCGCCCGCTCCTTTCGCTTTCTTCCCTTCCTTTCTCGCCACGTTCGCCGGC

TTTCCCCGTCAAGCTCTAAATCGGGGGCTCCCTTTAGGGTTCCGATTTAGTGCTTTACGGCACCTCGACCCCA

AAAAACTTGATTAGGGTGATGGTTCACGTAGTGGGCCATCGCCCTGATAGACGGTTTTTCGCCCTTTGACGTT

GGAGTCCACGTTCTTTAATAGTGGACTCTTGTTCCAAACTGGAACAACACTCAACCCTATCTCGGTCTATTCT

TTTGATTTATAAGGGATTTTGCCGATTTCGGCCTATTGGTTAAAAAATGAGCTGATTTAACAAAAATTTAACG

CGAATTAATTCTGTGGAATGTGTGTCAGTTAGGGTGTGGAAAGTCCCCAGGCTCCCCAGCAGGCAGAAGTATG

CAAAGCATGCATCTCAATTAGTCAGCAACCAGGTGTGGAAAGTCCCCAGGCTCCCCAGCAGGCAGAAGTATGC

AAAGCATGCATCTCAATTAGTCAGCAACCATAGTCCCGCCCCTAACTCCGCCCATCCCGCCCCTAACTCCGCC

CAGTTCCGCCCATTCTCCGCCCCATGGCTGACTAATTTTTTTTATTTATGCAGAGGCCGAGGCCGCCTCTGCC

TCTGAGCTATTCCAGAAGTAGTGAGGAGGCTTTTTTGGAGGCCTAGGCTTTTGCAAAAAGCTCCCGGGAGCTT

GTATATCCATTTTCGGATCTGATCAAGAGACAGGATGAGGATCGTTTCGCATGATTGAACAAGATGGATTGCA

CGCAGGTTCTCCGGCCGCTTGGGTGGAGAGGCTATTCGGCTATGACTGGGCACAACAGACAATCGGCTGCTCT

GATGCCGCCGTGTTCCGGCTGTCAGCGCAGGGGCGCCCGGTTCTTTTTGTCAAGACCGACCTGTCCGGTGCCC

TGAATGAACTGCAGGACGAGGCAGCGCGGCTATCGTGGCTGGCCACGACGGGCGTTCCTTGCGCAGCTGTGCT

CGACGTTGTCACTGAAGCGGGAAGGGACTGGCTGCTATTGGGCGAAGTGCCGGGGCAGGATCTCCTGTCATCT

CACCTTGCTCCTGCCGAGAAAGTATCCATCATGGCTGATGCAATGCGGCGGCTGCATACGCTTGATCCGGCTA

CCTGCCCATTCGACCACCAAGCGAAACATCGCATCGAGCGAGCACGTACTCGGATGGAAGCCGGTCTTGTCGA

TCAGGATGATCTGGACGAAGAGCATCAGGGGCTCGCGCCAGCCGAACTGTTCGCCAGGCTCAAGGCGCGCATG

-continued

CCCGACGGCGAGGATCTCGTCGTGACCCATGGCGATGCCTGCTTGCCGAATATCATGGTGGAAAATGGCCGCT

TTTCTGGATTCATCGACTGTGGCCGGCTGGGTGTGGCGGACCGCTATCAGGACATAGCGTTGGCTACCCGTGA

TATTGCTGAAGAGCTTGGCGGCGAATGGGCTGACCGCTTCCTCGTGCTTTACGGTATCGCCGCTCCCGATTCG

CAGCGCATCGCCTTCTATCGCCTTCTTGACGAGTTCTTCTGAGCGGGACTCTGGGGTTCGAAATGACCGACCA

AGCGACGCCCAACCTGCCATCACGAGATTTCGATTCCACCGCCGCCTTCTATGAAAGGTTGGGCTTCGGAATC

GTTTTCCGGGACGCCGGCTGGATGATCCTCCAGCGCGGGGATCTCATGCTGGAGTTCTTCGCCCACCCCAACT

TGTTTATTGCAGCTTATAATGGTTACAAATAAAGCAATAGCATCACAAATTTCACAAATAAAGCATTTTTTTC

ACTGCATTCTAGTTGTGGTTTGTCCAAACTCATCAATGTATCTTATCATGTCTGTATACCGTCGACCTCTAGC

TAGAGCTTGGCGTAATCATGGTCATAGCTGTTTCCTGTGTGAAATTGTTATCCGCTCACAATTCCACACAACA

TACGAGCCGGAAGCATAAAGTGTAAAGCCTGGGGTGCCTAATGAGTGAGCTAACTCACATTAATTGCGTTGCG

CTCACTGCCCGCTTTCCAGTCGGGAAACCTGTCGTGCCAGCTGCATTAATGAATCGGCCAACGCGCGGGGAGA

GGCGGTTTGCGTATTGGGCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGGATAACGCAGGAAAGAACAT

GTGAGCAAAAGGCCAGCAAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGACAGGACTATAAAGATACC

AGGCGTTTCCCCCTGGAAGCTCCCTCGTGCGCTCTCCTGTTCCGACCCTGCCGCTTACCGGATACCTGTCCGC

CTTTCTCCCTTCGGGAAGCGTGGCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGCGCCTTATCCGGTAACTATCGTC

TTGAGTCCAACCCGGTAAGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAGAAGAACAGTATTTGGT

ATCTGCGCTCTGCTGAAGCCAGTTACCTTCGGAAAAAGAGTTGGTAGCTCTTGATCCGGCAAACAAACCACCG

CTGGTAGCGGTGGTTTTTTTGTTTGCAAGCAGCAGATTACGCGCAGAAAAAAAGGATCTCAAGAAGATCCTTT

GATCTTTTCTACGGGGTCTGACGCTCAGTGGAACGAAAACTCACGTTAAGGGATTTTGGTCATGAGATTATCA

AAAAGGATCTTCACCTAGATCCTTTTAAATTAAAAATGAAGTTTTAAATCAATCTAAAGTATATATGAGTAAA

CTTGGTCTGACAGTTACCAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCTGGCCCCAGTGCTGCAATG

ATACCGCGAGACCCACGCTCACCGGCTCCAGATTTATCAGCAATAAACCAGCCAGCCGGAAGGGCCGAGCGCA

GAAGTGGTCCTGCAACTTTATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGTTGTGCAAAAAAGCGGTTA

GCTCCTTCGGTCCTCCGATCGTTGTCAGAAGTAAGTTGGCCGCAGTGTTATCACTCATGGTTATGGCAGCACT

GCATAATTCTCTTACTGTCATGCCATCCGTAAGATGCTTTTCTGTGACTGGTGAGTACTCAACCAAGTCATTC

TGAGAATAGTGTATGCGGCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGATCTTACCGCTGTTGAG

ATCCAGTTCGATGTAACCCACTCGTGCACCCAACTGATCTTCAGCATCTTTTACTTTCACCAGCGTTTCTGGG

-continued

TGAGCAAAAACAGGAAGGCAAAATGCCGCAAAAAAGGGAATAAGGGCGACACGGAAATGTTGAATACTCATAC

TCTTCCTTTTTCAATATTATTGAAGCATTTATCAGGGTTATTGTCTCATGAGCGGATACATATTTGAATGTAT

TTAGAAAAATAAACAAATAGGGGTTCCGCGCACATTTCCCCGAAAAGTGCCACCTGACGTC

MGP_Kozak_hAlb sig_FLAG_ENPPlopt_LINK_hAlb_stop_pcDNA3.1(+) (SEQ ID NO: 95)

pcDNA3.1+, MGP promoter, Kozak seq, h-albumin secretory, Flag tag,

ENPP1 opt, Linker seq, h-albumin seq, Stop codon

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTAAGATTATAGTTGTCATTTGAACTTGGGGATAAAGGAGACATCTATGACTTGGCTGGA

AAAGACAGAGCTAATGTACATTGCAAAGCACATATTTATAGCAGGAAAATGGGAAGATTTCTCTTTAATTCTG

GAGATGGAGTGGGGATGGGGAGAGTAGACTACTCATTTTAAGGGTGAAACATTGGAATTCAACTTGTTTGATG

TTATATTAATTGGTGGTTAATTACTAAGCTAAGTACGTATAAAACTTTTATCTATGGCTAGCTTGTCCCCCCA

AAGTCATGCAATATAGTGAACTGGCTTTCGCACTTTAAATTATTCATTGATCATGTAATGATTCAGATGATTC

ATCTTCCAAGATGGACACTGAAACTAACACTCATAGTAGGTTGTGGTTTAAAGAGTGGAACAACCGCCAGTCT

CATTAGTGGAAATTGTGATGGTTGAATTTATCAAGGATGAACATACACGGTCTTCTTTCTGAGATTTTCTTTA

AGATTTTCGCACAGATAATCTATTTCTTAGGTTTTGGAGAGAAAACTTGAATTTTATTGATCCCTCAGAACTC

AATCTTTCAGATTTCAAAGGAGCTATTTCTTTTAATGGGGACTCTGTTAATATTTATAAAAGCTCTTCACAGG

ATGGAGGGTGGGAGGGAAACTCCATCCCAACAAGACAAAAAGAATGAAGCATGAGGCTCCACCTAGTTCATCA

CTGCTCCTTGAAATACATCAGTATTGAAAGACACATCCACCCCACCCCCAACCCAGCCCTATTGCTGTTCCAG

CTCAAGAGTCAGAGGTCCCGAAGCTGTAGCTCTTCTACAATCTGCTGCTCTGTGACTTCAAGTCTGTTGTCTG

CAAAGAAAACTATTGGGTTCCCAAGCAAGAGAGGCACATCTGGTAGGACAGATTTTGTGATTGCAAAAGAAGG

GGGAAAAAAAGAAAGAAAGAAAAGACCTCTCTATACAAGATAACCAGAGGCATCAAACTGAAATCCTCCTGTG

GAAAATAAGCTAGTACTTCTGGGCCTGATGGTGTAGTGAAAACCTGTGCTTGAGGATACATTACAGTGAAAGA

GCAAAGTGAATAGTAAGTAGCTATTACTTACCTCCTTAGGGAGGTGTGTTGTTTGTCTGTACATCCCCCACAG

CACCTAGCACAGTACCTTGCATCTCACCTGCCACTCACTAAAAAGTCTATCAAGTTAGTTAATTATCGAGACA

ACGCCCTCAGAAATGAGAGAACAGTACCCTCTTATCCTTGCTGCACTTTCCAGCACTGATACGCTGCCTAAAA

GAGGACTAGGGCACAGGTTTGAATTAATGTCACAAAACTGGATGGGCAAGTTACAACGGTGTTGATTAAGGAA

ACAGAACTCATGGTGCACCGGATATCTCCATCCTGATGAACCCTTGGAAAAATGCCAAAGATGCATATCCCCA

GGCAAATGCCTGATTAGTCTGGGATTGATAGATTGGTCTAGGATTCAGCCCTACTGGGAAGATGTCTAAATTA

TAATCAGTGTAGAAAGCGAAGTTCTCCTAGAAGAAGAGGCAAAGGTTAAAAAGAAGAAAAGAAAAGAAAGTGA

AGTCCTTTCTCCCCCAAAACCTCTCATCAATCAATCAGGGTAACAAACAGAACACTAGGGCTCTGTCTGTGGA

CCAAACCCAAAAGCCCTGCGGTCAGGGCCAGGAGGGTAGATCATGTGTTTGTGGCAACTTCCTCTGTGGGCTT

TTGCCCAGGTCTGTCCCCAAGCATACGATGGCCAAAACTTCTGCACCAGAGCAGCATCCTGTGTAACACAGTC

AGGTCCAGCAGTTAGGGAAAACTGCCCACTCAGAGTAGATAATATCTGGAAGGAATGACTGTTTGGGAAAAGT

TCCAATGCTAGTTCAGTGCCAACCCTTCCCCACCTTCTCCAGCTCTCTCCCACTGGTTCCTCCCCTCTCAACT

GCTCTGGTTCTTATAAAAACCTCACAGCCTTCCACTAACATCCCGTAGGAGCCTCTCTCCCTACTGCTGCTAC

ACAAGACCCTGAGACTGACCTGCAGGACGAAACCCTCTGGCTAACTAGAGAACCCACTGCTTACTGGCTTATC

GAAATTAATACGACTCACTATAGGGAGACCCAAGCTGGCTAGCGCCACCATGAAGTGGGTAACCTTTATTTCC

-continued

CTTCTTTTTCTCTTTAGCTCGGCTTATTCCAGGGGTGTGTTTCGTCGAGACTACAAAGACGATGACGACAAGA

GCGCTGGCCTGAAGCCAAGCTGCGCCAAGGAGGTGAAGAGCTGCAAGGGCAGATGTTTCGAACGGACCTTCGG

CAACTGCAGATGCGACGCCGCCTGCGTGGAACTGGGAAACTGTTGTCTGGACTACCAGGAGACATGTATCGAG

CCTGAGCACATCTGGACATGCAACAAGTTCAGATGTGGCGAGAAAAGACTGACTCGGAGTCTGTGCGCCTGTT

CTGACGACTGCAAGGACAAGGGCGATTGCTGCATCAACTACAGCAGCGTGTGCCAGGGCGAAAAGAGCTGGGT

CGAGGAACCCTGCGAGAGCATCAACGAGCCCCAGTGCCCTGCCGGATTTGAGACACCTCCTACCCTGCTCTTC

TCCCTGGATGGCTTCAGAGCTGAGTACCTGCATACATGGGGAGGACTGCTGCCTGTGATCAGCAAGCTGAAGA

AGTGCGGCACCTACACAAAGAACATGCGGCCTGTCTACCCTACCAAGACCTTCCCCAACCACTACAGCATCGT

GACCGGCCTGTACCCCGAGAGCCACGGCATCATCGACAACAAGATGTACGACCCCAAAATGAACGCCAGCTTC

AGCCTGAAATCTAAGGAAAAGTTCAACCCTGAGTGGTATAAGGGCGAGCCAATCTGGGTGACAGCCAAGTACC

AGGGCCTGAAGAGCGGCACCTTCTTCTGGCCTGGCAGCGACGTGGAGATCAACGGAATCTTCCCTGATATCTA

CAAGATGTATAACGGCTCCGTGCCTTTCGAGGAGCGGATCTTGGCTGTTCTTCAGTGGCTGCAGCTGCCCAAG

GACGAGAGACCCCACTTCTACACCCTGTACCTGGAAGAACCTGACAGCAGCGGCCACAGCTACGGCCCTGTGT

CTAGCGAGGTGATCAAGGCCCTGCAAAGAGTGGATGGCATGGTGGGCATGCTGATGGATGGACTGAAGGAACT

GAACCTCCATCGTTGCCTGAACCTGATCCTGATCTCCGACCACGGCATGGAACAGGGCAGCTGTAAAAAGTAC

ATCTACCTGAACAAGTACCTGGGCGACGTGAAGAATATCAAGGTGATCTACGGGCCGGCCGCCAGGCTGCGGC

CTAGCGACGTGCCCGACAAGTATTACAGCTTCAACTACGAGGGCATCGCCAGAAACCTGTCTTGCAGAGAACC

CAATCAACACTTCAAGCCTTACCTGAAGCACTTTCTGCCTAAGAGACTGCACTTCGCCAAAAGCGACAGAATT

GAACCCCTGACATTCTATCTGGACCCTCAGTGGCAGCTGGCCCTCAATCCTTCTGAACGCAAATACTGCGGTA

GCGGATTTCACGGCTCTGATAACGTGTTTTCTAACATGCAGGCCCTGTTTGTGGGCTACGGCCCTGGCTTCAA

GCACGGAATCGAGGCTGACACCTTCGAGAACATCGAAGTTTACAATCTGATGTGCGACCTGCTGAATCTGACC

CCAGCCCCTAACAACGGCACACACGGCTCTCTGAATCACCTGCTCAAGAACCCCGTGTATACCCCCAAACACC

CTAAAGAGGTCCATCCACTGGTGCAGTGCCCATTCACCAGAAACCCTCGGGACAACCTTGGCTGCAGCTGCAA

CCCTAGCATCCTCCCTATCGAAGATTTCCAGACCCAGTTTAACCTGACTGTCGCCGAAGAGAAGATCATCAAG

CACGAAACCCTGCCCTACGGGAGGCCCAGAGTGCTGCAGAAAGAAAACACAATCTGTCTGCTGAGCCAGCACC

AGTTTATGAGCGGCTACAGTCAGGACATCCTGATGCCTCTGTGGACCAGCTACACCGTGGACCGGAATGACAG

CTTCAGCACCGAGGACTTCAGCAACTGCCTGTATCAGGACTTCCGCATCCCTCTGTCCCCTGTGCATAAGTGC

AGCTTTTACAAGAACAACACCAAGGTGAGCTACGGGTTTCTGAGCCCACCACAACTGAACAAAAATAGCTCTG

GCATCTACTCTGAGGCGCTGCTGACCACCAACATCGTGCCAATGTACCAGAGCTTCCAGGTGATCTGGCGGTA

CTTCCATGATACCCTGCTTCGGAAGTACGCCGAAGAACGGAACGGCGTGAACGTGGTGTCCGGCCCAGTGTTC

GACTTCGACTACGACGGCAGATGTGATTCCCTTGAGAATCTGAGACAGAAGCGGCGGGTTATCAGAAACCAGG

AGATCCTGATTCCTACCCACTTCTTCATCGTGCTGACATCTTGCAAGGATACCAGCCAAACACCTCTGCACTG

CGAGAACCTGGACACCCTGGCCTTCATCCTGCCTCACCGGACCGATAATAGCGAATCCTGTGTGCACGGCAAA

CACGACTCTAGCTGGGTGGAAGAGCTGCTGATGCTGCACAGAGCCCGGATCACAGATGTGGAACACATCACCG

GCCTGTCCTTCTACCAACAGAGAAAGGAACCCGTGTCTGATATCCTGAAGCTGAAAACCCACCTGCCTACCTT

CAGCCAGGAGGACCTGATCGTTAACGATGCACACAAGAGTGAGGTTGCTCATCGGTTTAAAGATTTGGGAGAA

GAAAATTTCAAAGCCTTGGTGTTGATTGCCTTTGCTCAGTATCTTCAGCAGTGTCCATTTGAAGATCATGTAA

AATTAGTGAATGAAGTAACTGAATTTGCAAAAACATGTGTTGCTGATGAGTCAGCTGAAAATTGTGACAAATC

ACTTCATACCCTTTTTGGAGACAAATTATGCACAGTTGCAACTCTTCGTGAAACCTATGGTGAAATGGCTGAC

-continued

TGCTGTGCAAAACAAGAACCTGAGAGAAATGAATGCTTCTTGCAACACAAAGATGACAACCCAAACCTCCCCC

GATTGGTGAGACCAGAGGTTGATGTGATGTGCACTGCTTTTCATGACAATGAAGAGACATTTTTGAAAAAATA

CTTATATGAAATTGCCAGAAGACATCCTTACTTTTATGCCCCGGAACTCCTTTTCTTTGCTAAAAGGTATAAA

GCTGCTTTTACAGAATGTTGCCAAGCTGCTGATAAAGCTGCCTGCCTGTTGCCAAAGCTCGATGAACTTCGGG

ATGAAGGGAAGGCTTCGTCTGCCAAACAGAGACTCAAGTGTGCCAGTCTCCAAAAATTTGGAGAAAGAGCTTT

CAAAGCATGGGCAGTAGCTCGCCTGAGCCAGAGATTTCCCAAAGCTGAGTTTGCAGAAGTTTCCAAGTTAGTG

ACAGATCTTACCAAAGTCCACACGGAATGCTGCCATGGAGATCTGCTTGAATGTGCTGATGACAGGGCGGACC

TTGCCAAGTATATCTGTGAAAATCAAGATTCGATCTCCAGTAAACTGAAGGAATGCTGTGAAAAACCTCTGTT

GGAAAAATCCCACTGCATTGCCGAAGTGGAAAATGATGAGATGCCTGCTGACTTGCCTTCATTAGCTGCTGAT

TTTGTTGAAAGTAAGGATGTTTGCAAAAACTATGCTGAGGCAAAGGATGTCTTCCTGGGCATGTTTTTGTATG

AATATGCAAGAAGGCATCCTGATTACTCTGTCGTGCTGCTGCTGAGACTTGCCAAGACATATGAAACCACACT

CGAGAAGTGCTGTGCCGCTGCAGATCCTCATGAATGCTATGCCAAAGTGTTCGATGAATTTAAACCTCTTGTG

GAAGAGCCTCAGAATTTAATCAAACAAAATTGTGAGCTTTTTGAGCAGCTTGGAGAGTACAAATTCCAGAATG

CGCTATTAGTTCGTTACACCAAGAAAGTACCCCAAGTGTCAACTCCAACTCTTGTAGAGGTCTCAAGAAACCT

AGGAAAAGTGGGCAGCAAATGTTGTAAACATCCTGAAGCAAAAAGAATGCCCTGTGCAGAAGACTATCTATCC

GTGGTCCTGAACCAGTTATGTGTGTTGCATGAGAAAACGCCAGTAAGTGACAGAGTCACCAAATGCTGCACAG

AATCCTTGGTGAACAGGCGACCATGCTTTTCAGCTCTGGAAGTCGATGAAACATACGTTCCCAAAGAGTTTAA

TGCTGCAAGTCAAGCTGCCTTAGGCTTATGAGGTACCGAGCTCGGATCCACTAGTCCAGTGTGGTGGAATTCT

GCACTTGTTGAGCTCGTGAAACACAAGCCCAAGGCAACAAAAGAGCAACTGAAAGCTGTTATGGATGATTTCG

CAGCTTTTGTAGAGAAGTGCTGCAAGGCTGACGATAAGGAGACCTGCTTTGCCGAGGAGGGTAAAAAACTTGT

TGCTGCAAGTCAAGCTGCCTTAGGCTTATGAGGTACCGAGCTCGGATCCACTAGTCCAGTGTGGTGGAATTCT

GCAGATATCCAGCACAGTGGCGGCCGCTCGAGTCTAGAGGGCCCGTTTAAACCCGCTGATCAGCCTCGACTGT

GCCTTCTAGTTGCCAGCCATCTGTTGTTTGCCCCTCCCCCGTGCCTTCCTTGACCCTGGAAGGTGCCACTCCC

ACTGTCCTTTCCTAATAAAATGAGGAAATTGCATCGCATTGTCTGAGTAGGTGTCATTCTATTCTGGGGGGTG

GGGTGGGGCAGGACAGCAAGGGGGAGGATTGGGAAGACAATAGCAGGCATGCTGGGGATGCGGTGGGCTCTAT

GGCTTCTGAGGCGGAAAGAACCAGCTGGGGCTCTAGGGGGTATCCCCACGCGCCCTGTAGCGGCGCATTAAGC

GCGGCGGGTGTGGTGGTTACGCGCAGCGTGACCGCTACACTTGCCAGCGCCCTAGCGCCCGCTCCTTTCGCTT

TCTTCCCTTCCTTTCTCGCCACGTTCGCCGGCTTTCCCCGTCAAGCTCTAAATCGGGGGCTCCCTTTAGGGTT

CCGATTTAGTGCTTTACGGCACCTCGACCCCAAAAAACTTGATTAGGGTGATGGTTCACGTAGTGGGCCATCG

CCCTGATAGACGGTTTTTCGCCCTTTGACGTTGGAGTCCACGTTCTTTAATAGTGGACTCTTGTTCCAAACTG

GAACAACACTCAACCCTATCTCGGTCTATTCTTTTGATTTATAAGGGATTTTGCCGATTTCGGCCTATTGGTT

AAAAAATGAGCTGATTTAACAAAAATTTAACGCGAATTAATTCTGTGGAATGTGTGTCAGTTAGGGTGTGGAA

AGTCCCCAGGCTCCCCAGCAGGCAGAAGTATGCAAAGCATGCATCTCAATTAGTCAGCAACCAGGTGTGGAAA

GTCCCCAGGCTCCCCAGCAGGCAGAAGTATGCAAAGCATGCATCTCAATTAGTCAGCAACCATAGTCCCGCCC

CTAACTCCGCCCATCCCGCCCCTAACTCCGCCCAGTTCCGCCCATTCTCCGCCCCATGGCTGACTAATTTTTT

TTATTTATGCAGAGGCCGAGGCCGCCTCTGCCTCTGAGCTATTCCAGAAGTAGTGAGGAGGCTTTTTTGGAGG

CCTAGGCTTTTGCAAAAAGCTCCCGGGAGCTTGTATATCCATTTTCGGATCTGATCAAGAGACAGGATGAGGA

TCGTTTCGCATGATTGAACAAGATGGATTGCACGCAGGTTCTCCGGCCGCTTGGGTGGAGAGGCTATTCGGCT

ATGACTGGGCACAACAGACAATCGGCTGCTCTGATGCCGCCGTGTTCCGGCTGTCAGCGCAGGGGCGCCCGGT

-continued

TCTTTTTGTCAAGACCGACCTGTCCGGTGCCCTGAATGAACTGCAGGACGAGGCAGCGCGGCTATCGTGGCTG

GCCACGACGGGCGTTCCTTGCGCAGCTGTGCTCGACGTTGTCACTGAAGCGGGAAGGGACTGGCTGCTATTGG

GCGAAGTGCCGGGGCAGGATCTCCTGTCATCTCACCTTGCTCCTGCCGAGAAAGTATCCATCATGGCTGATGC

AATGCGGCGGCTGCATACGCTTGATCCGGCTACCTGCCCATTCGACCACCAAGCGAAACATCGCATCGAGCGA

GCACGTACTCGGATGGAAGCCGGTCTTGTCGATCAGGATGATCTGGACGAAGAGCATCAGGGGCTCGCGCCAG

CCGAACTGTTCGCCAGGCTCAAGGCGCGCATGCCCGACGGCGAGGATCTCGTCGTGACCCATGGCGATGCCTG

CTTGCCGAATATCATGGTGGAAAATGGCCGCTTTTCTGGATTCATCGACTGTGGCCGGCTGGGTGTGGCGGAC

CGCTATCAGGACATAGCGTTGGCTACCCGTGATATTGCTGAAGAGCTTGGCGGCGAATGGGCTGACCGCTTCC

TCGTGCTTTACGGTATCGCCGCTCCCGATTCGCAGCGCATCGCCTTCTATCGCCTTCTTGACGAGTTCTTCTG

AGCGGGACTCTGGGGTTCGAAATGACCGACCAAGCGACGCCCAACCTGCCATCACGAGATTTCGATTCCACCG

CCGCCTTCTATGAAAGGTTGGGCTTCGGAATCGTTTTCCGGGACGCCGGCTGGATGATCCTCCAGCGCGGGGA

TCTCATGCTGGAGTTCTTCGCCCACCCCAACTTGTTTATTGCAGCTTATAATGGTTACAAATAAAGCAATAGC

ATCACAAATTTCACAAATAAAGCATTTTTTTCACTGCATTCTAGTTGTGGTTTGTCCAAACTCATCAATGTAT

CTTATCATGTCTGTATACCGTCGACCTCTAGCTAGAGCTTGGCGTAATCATGGTCATAGCTGTTTCCTGTGTG

AAATTGTTATCCGCTCACAATTCCACACAACATACGAGCCGGAAGCATAAAGTGTAAAGCCTGGGGTGCCTAA

TGAGTGAGCTAACTCACATTAATTGCGTTGCGCTCACTGCCCGCTTTCCAGTCGGGAAACCTGTCGTGCCAGC

TGCATTAATGAATCGGCCAACGCGCGGGGAGAGGCGGTTTGCGTATTGGGCGCTCTTCCGCTTCCTCGCTCAC

TGACTCGCTGCGCTCGGTCGTTCGGCTGCGGCGAGCGGTATCAGCTCACTCAAAGGCGGTAATACGGTTATCC

ACAGAATCAGGGGATAACGCAGGAAAGAACATGTGAGCAAAAGGCCAGCAAAAGGCCAGGAACCGTAAAAAGG

CCGCGTTGCTGGCGTTTTTCCATAGGCTCCGCCCCCCTGACGAGCATCACAAAAATCGACGCTCAAGTCAGAG

GTGGCGAAACCCGACAGGACTATAAAGATACCAGGCGTTTCCCCCTGGAAGCTCCCTCGTGCGCTCTCCTGTT

CCGACCCTGCCGCTTACCGGATACCTGTCCGCCTTTCTCCCTTCGGGAAGCGTGGCGCTTTCTCATAGCTCAC

GCTGTAGGTATCTCAGTTCGGTGTAGGTCGTTCGCTCCAAGCTGGGCTGTGTGCACGAACCCCCCGTTCAGCC

CGACCGCTGCGCCTTATCCGGTAACTATCGTCTTGAGTCCAACCCGGTAAGACACGACTTATCGCCACTGGCA

GCAGCCACTGGTAACAGGATTAGCAGAGCGAGGTATGTAGGCGGTGCTACAGAGTTCTTGAAGTGGTGGCCTA

ACTACGGCTACACTAGAAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTGCAAGCAGCAGATTACG

CGCAGAAAAAAAGGATCTCAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCTTTTAAATTAAAAATGAAG

TTTTAAATCAATCTAAAGTATATATGAGTAAACTTGGTCTGACAGTTACCAATGCTTAATCAGTGAGGCACCT

ATCTCAGCGATCTGTCTATTTCGTTCATCCATAGTTGCCTGACTCCCCGTCGTGTAGATAACTACGATACGGG

AGGGCTTACCATCTGGCCCCAGTGCTGCAATGATACCGCGAGACCCACGCTCACCGGCTCCAGATTTATCAGC

AATAAACCAGCCAGCCGGAAGGGCCGAGCGCAGAAGTGGTCCTGCAACTTTATCCGCCTCCATCCAGTCTATT

AATTGTTGCCGGGAAGCTAGAGTAAGTAGTTCGCCAGTTAATAGTTTGCGCAACGTTGTTGCCATTGCTACAG

GCATCGTGGTGTCACGCTCGTCGTTTGGTATGGCTTCATTCAGCTCCGGTTCCCAACGATCAAGGCGAGTTAC

ATGATCCCCCATGTTGTGCAAAAAAGCGGTTAGCTCCTTCGGTCCTCCGATCGTTGTCAGAAGTAAGTTGGCC

GCAGTGTTATCACTCATGGTTATGGCAGCACTGCATAATTCTCTTACTGTCATGCCATCCGTAAGATGCTTTT

CTGTGACTGGTGAGTACTCAACCAAGTCATTCTGAGAATAGTGTATGCGGCGACCGAGTTGCTCTTGCCCGGC

GTCAATACGGGATAATACCGCGCCACATAGCAGAACTTTAAAAGTGCTCATCATTGGAAAACGTTCTTCGGGG

CGAAAACTCTCAAGGATCTTACCGCTGTTGAGATCCAGTTCGATGTAACCCACTCGTGCACCCAACTGATCTT

-continued

CAGCATCTTTTACTTTCACCAGCGTTTCTGGGTGAGCAAAAACAGGAAGGCAAAATGCCGCAAAAAAGGGAAT

AAGGGCGACACGGAAATGTTGAATACTCATACTCTTCCTTTTTCAATATTATTGAAGCATTTATCAGGGTTAT

TGTCTCATGAGCGGATACATATTTGAATGTATTTAGAAAAATAAACAAATAGGGGTTCCGCGCACATTTCCCC

GAAAAGTGCCACCTGACGTC

Prom2 (1350 bp)_hALB_kozak_hAlb sig_FLAG_ENPP1opt_LINK_hAlb_pcDNA3.1(+)

pcDNA3.1+, HDAC9 promoter, Kozak seq, h-alb signal seq, Flag tag,

ENPP1opt, Linker seq, h-alb seq, Stop codon

(SEQ ID NO: 96)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTATAAATGTTTTGTAGAATAAAAAAAAAAAAAGTTCTTCAAAAGAAATCTCAAATCTCC

AAATGGAAACAGGTAAAAGTGGAGCTCCCCTGGTTCCACGGAGAACCTTTTTTGAGGAAACTTAGGCAACTCG

CAGGTACCTTATGTCATGAGACAGAGTTTGAAAACTACAATTGACTATCTCTAAATTTCCTCCCAGGTCTAAA

ATGTGATGATAGTTACTACTTCAGTACATCATCCTTAAGGAAAATTATTAGGTCCACACTGTTTCTATCCTTT

GAATTTTACACATAAATTTTGTAATCAAAAGTTTATTTGTAATATCAGATGGAATCAGATAATTGCTTTTTGT

TTTTTCCACTGACAGGAACATAAGATTTTGTTGTGTAGCTTAAGTCAAACGCAGTTTGGAATATATATTTTTT

AAAAATTGTAACTTACATATCCAAATACAATTTTTCAAGAAGTAGAGTATTCAGTAGAAATTAATCTGTGAAA

GAAGAGGAATTCAGCAGTGGCCTATTTGATGAATGATTTAACGTGCTTATTTCTTCCCTTTCATCAAAACTCT

GTGTCCCCTTGTTTGCCCCCTCTGACTTCATACTCTGGAGTTGACCAAGATCCCTCTTCCATCGGATTGTTCT

GGGAATTTTGAAATAATCTGCTTTTTCCTCTCTTTCCCCTGTTGCTTCTGATGCCTTAGAATTACATTTTCCT

CGCTGATTTAGTTTAGAAAAGAGAAAAGAGCTTCCATGACTAGTAGATTATCACTTTTGGGTTTGCTCTTGGA

AGTGACAAGATGCTAGGATCCCTCTTTGGAATGTAAAATTTATCTCTTATATAGAAAGGATATAAATGTAGCA

CCAGAGACTATAAAACTCTGATACTATCTACTGTACTGTATAGCTGAACGCCACAATGTGTCTGGTAATCTAT

TGACTATCATAAATGCTATTTCTACAGAAAAGTTAGGAGGTCCATATTTCGGGCAACCAATGTATAGCTGAAT

GCAGAACAGTCATAGTTGGGTACTAACCATATATATGATTTATCCATCAACAGGTGCATATGCTCAGAAATTC

TGTATCCATAAGAAATCAGACTACTTTCTTTTCCTTTTGCAAGTAAATTGAATTTAGCCTGAGAGGCTGAGGG

GAAATTTTCACATATAAGCCACGGTTTTGTGTTTTGTGTTTTGTTTTGTTTATAGATATAGTACTAACTGGAT

GGATGCGATAAAATTCATAGGTGGTACTAAGATACAATAGGATTTGTGAAATGGACAATTGTCTTGCATAAAT

AGCAAGTAAAAAATCAAGCCTGTCCTTCATAAAAATTTTATTCTGGGGTGTCTCTGGCTAACTAGAGAACCCA

CTGTTACTGGCTTATCGAAATTAATACGACTCACTATAGGGAGACCCAAGCTGGCTAGCGCCACCATGAAGT

GGGTAACCTTTATTTCCCTTCTTTTTCTCTTTAGCTCGGCTTATTCCAGGGGTGTGTTTCGTCGAGACTACAA

AGACGATGACGACAAGAGCGCTGGCCTGAAGCCAAGCTGCGCCAAGGAGGTGAAGAGCTGCAAGGGCAGATGT

TTCGAACGGACCTTCGGCAACTGCAGATGCGACGCCGCCTGCGTGGAACTGGGAAACTGTTGTCTGGACTACC

AGGAGACATGTATCGAGCCTGAGCACATCTGGACATGCAACAAGTTCAGATGTGGCGAGAAAAGACTGACTCG

GAGTCTGTGCGCCTGTTCTGACGACTGCAAGGACAAGGGCGATTGCTGCATCAACTACAGCAGCGTGTGCCAG

GGCGAAAAGAGCTGGGTCGAGGAACCCTGCGAGAGCATCAACGACCCCCAGTGCCCTGCCGGATTTGAGACAC

CTCCTACCCTGCTCTTCTCCCTGGATGGCTTCAGAGCTGAGTACCTGCATACATGGGGAGGACTGCTGCCTGT

-continued

GATCAGCAAGCTGAAGAAGTGCGGCACCTACACAAAGAACATGCGGCCTGTCTACCCTACCAAGACCTTCCCC

AACCACTACAGCATCGTGACCGGCCTGTACCCCGAGAGCCACGGCATCATCGACAACAAGATGTACGACCCCA

AAATGAACGCCAGCTTCAGCCTGAAATCTAAGGAAAAGTTCAACCCTGAGTGGTATAAGGGCGAGCCAATCTG

GGTGACAGCCAAGTACCAGGGCCTGAAGAGCGGCACCTTCTTCTGGCCTGGCAGCGACGTGGAGATCAACGGA

ATCTTCCCTGATATCTACAAGATGTATAACGGCTCCGTGCCTTTCGAGGAGCGGATCTTGGCTGTTCTTCAGT

GGCTGCAGCTGCCCAAGGACGAGAGACCCCACTTCTACACCCTGTACCTGGAAGAACCTGACAGCAGCGGCCA

CAGCTACGGCCCTGTGTCTAGCGAGGTGATCAAGGCCCTGCAAAGAGTGGATGGCATGGTGGGCATGCTGATG

GATGGACTGAAGGAACTGAACCTCCATCGTTGCCTGAACCTGATCCTGATCTCCGACCACGGCATGGAACAGG

GCAGCTGTAAAAAGTACATCTACCTGAACAAGTACCTGGGCGACGTGAAGAATATCAAGGTGATCTACGGGCC

GGCCGCCAGGCTGCGGCCTAGCGACGTGCCCGACAAGTATTACAGCTTCAACTACGAGGGCATCGCCAGAAAC

CTGTCTTGCAGAGAACCCAATCAACACTTCAAGCCTTACCTGAAGCACTTTCTGCCTAAGAGACTGCACTTCG

CCAAAAGCGACAGAATTGAACCCCTGACATTCTATCTGGACCCTCAGTGGCAGCTGGCCCTCAATCCTTCTGA

ACGCAAATACTGCGGTAGCGGATTTCACGGCTCTGATAACGTGTTTTCTAACATGCAGGCCCTGTTTGTGGGC

TACGGCCCTGGCTTCAAGCACGGAATCGAGGCTGACACCTTCGAGAACATCGAAGTTTACAATCTGATGTGCG

ACCTGCTGAATCTGACCCCAGCCCCTAACAACGGCACACACGGCTCTCTGAATCACCTGCTCAAGAACCCCGT

GTATACCCCCAAACACCCTAAAGAGGTCCATCCACTGGTGCAGTGCCCATTCACCAGAAACCCTCGGGACAAC

CTTGGCTGCAGCTGCAACCCTAGCATCCTCCCTATCGAAGATTTCCAGACCCAGTTTAACCTGACTGTCGCCG

AAGAGAAGATCATCAAGCACGAAACCCTGCCCTACGGGAGGCCCAGAGTGCTGCAGAAAGAAAACACAATCTG

TCTGCTGAGCCAGCACCAGTTTATGAGCGGCTACAGTCAGGACATCCTGATGCCTCTGTGGACCAGCTACACC

GTGGACCGGAATGACAGCTTCAGCACCGAGGACTTCAGCAACTGCCTGTATCAGGACTTCCGCATCCCTCTGT

CCCCTGTGCATAAGTGCAGCTTTTACAAGAACAACACCAAGGTGAGCTACGGGTTTCTGAGCCCACCACAACT

GAACAAAAATAGCTCTGGCATCTACTCTGAGGCGCTGCTGACCACCAACATCGTGCCAATGTACCAGAGCTTC

CAGGTGATCTGGCGGTACTTCCATGATACCCTGCTTCGGAAGTACGCCGAAGAACGGAACGGCGTGAACGTGG

TGTCCGGCCCAGTGTTCGACTTCGACTACGACGGCAGATGTGATTCCCTTGAGAATCTGAGACAGAAGCGGCG

GGTTATCAGAAACCAGGAGATCCTGATTCCTACCCACTTCTTCATCGTGCTGACATCTTGCAAGGATACCAGC

CAAACACCTCTGCACTGCGAGAACCTGGACACCCTGGCCTTCATCCTGCCTCACCGGACCGATAATAGCGAAT

CCTGTGTGCACGGCAAACACGACTCTAGCTGGGTGGAAGAGCTGCTGATGCTGCACAGAGCCCGGATCACAGA

TGTGGAACACATCACCGGCCTGTCCTTCTACCAACAGAGAAAGGAACCCGTGTCTGATATCCTGAAGCTGAAA

ACCCACCTGCCTACCTTCAGCCAGGAGGACCTGATCGTTAACGATGCACACAAGAGTGAGGTTGCTCATCGGT

TTAAAGATTTGGGAGAAGAAAATTTCAAAGCCTTGGTGTTGATTGCCTTTGCTCAGTATCTTCAGCAGTGTCC

ATTTGAAGATCATGTAAAATTAGTGAATGAAGTAACTGAATTTGCAAAAACATGTGTTGCTGATGAGTCAGCT

GAAAATTGTGACAAATCACTTCATACCCTTTTTGGAGACAAATTATGCACAGTTGCAACTCTTCGTGAAACCT

ATGGTGAAATGGCTGACTGCTGTGCAAAACAAGAACCTGAGAGAAATGAATGCTTCTTGCAACACAAAGATGA

CAACCCAAACCTCCCCCGATTGGTGAGACCAGAGGTTGATGTGATGTGCACTGCTTTTCATGACAATGAAGAG

ACATTTTTGAAAAAATACTTATATGAAATTGCCAGAAGACATCCTTACTTTTATGCCCCGGAACTCCTTTTCT

TTGCTAAAAGGTATAAAGCTGCTTTTACAGAATGTTGCCAAGCTGCTGATAAAGCTGCCTGCCTGTTGCCAAA

GCTCGATGAACTTCGGGATGAAGGGAAGGCTTCGTCTGCCAAACAGAGACTCAAGTGTGCCAGTCTCCAAAAA

TTTGGAGAAAGAGCTTTCAAAGCATGGGCAGTAGCTCGCCTGAGCCAGAGATTTCCCAAAGCTGAGTTTGCAG

AAGTTTCCAAGTTAGTGACAGATCTTACCAAAGTCCACACGGAATGCTGCCATGGAGATCTGCTTGAATGTGC

TGATGACAGGGCGGACCTTGCCAAGTATATCTGTGAAAATCAAGATTCGATCTCCAGTAAACTGAAGGAATGC

-continued

TGTGAAAAACCTCTGTTGGAAAAATCCCACTGCATTGCCGAAGTGGAAAATGATGAGATGCCTGCTGACTTGC

CTTCATTAGCTGCTGATTTTGTTGAAAGTAAGGATGTTTGCAAAAACTATGCTGAGGCAAAGGATGTCTTCCT

GGGCATGTTTTTGTATGAATATGCAAGAAGGCATCCTGATTACTCTGTCGTGCTGCTGCTGAGACTTGCCAAG

ACATATGAAACCACACTCGAGAAGTGCTGTGCCGCTGCAGATCCTCATGAATGCTATGCCAAAGTGTTCGATG

AATTTAAACCTCTTGTGGAAGAGCCTCAGAATTTAATCAAACAAAATTGTGAGCTTTTTGAGCAGCTTGGAGA

GTACAAATTCCAGAATGCGCTATTAGTTCGTTACACCAAGAAAGTACCCCAAGTGTCAACTCCAACTCTTGTA

GAGGTCTCAAGAAACCTAGGAAAAGTGGGCAGCAAATGTTGTAAACATCCTGAAGCAAAAAGAATGCCCTGTG

CAGAAGACTATCTATCCGTGGTCCTGAACCAGTTATGTGTGTTGCATGAGAAAACGCCAGTAAGTGACAGAGT

CACCAAATGCTGCACAGAATCCTTGGTGAACAGGCGACCATGCTTTTCAGCTCTGGAAGTCGATGAAACATAC

GTTCCCAAAGAGTTTAATGCTGAAACATTCACCTTCCATGCAGATATATGCACACTTTCTGAGAAGGAGAGAC

AAATCAAGAAACAAACTGCACTTGTTGAGCTCGTGAAACACAAGCCCAAGGCAACAAAAGAGCAACTGAAAGC

TGTTATGGATGATTTCGCAGCTTTTGTAGAGAAGTGCTGCAAGGCTGACGATAAGGAGACCTGCTTTGCCGAG

GAGGGTAAAAAACTTGTTGCTGCAAGTCAAGCTGCCTTAGGCTTATGAGGTACCGAGCTCGGATCCACTAGTC

CAGTGTGGTGGAATTCTGCAGATATCCAGCACAGTGGCGGCCGCTCGAGTCTAGAGGGCCCGTTTAAACCCGC

TGATCAGCCTCGACTGTGCCTTCTAGTTGCCAGCCATCTGTTGTTTGCCCCTCCCCCGTGCCTTCCTTGACCC

TGGAAGGTGCCACTCCCACTGTCCTTTCCTAATAAAATGAGGAAATTGCATCGCATTGTCTGAGTAGGTGTCA

TTCTATTCTGGGGGGTGGGGTGGGGCAGGACAGCAAGGGGGAGGATTGGGAAGACAATAGCAGGCATGCTGGG

GATGCGGTGGGCTCTATGGCTTCTGAGGCGGAAAGAACCAGCTGGGGCTCTAGGGGGTATCCCCACGCGCCCT

GTAGCGGCGCATTAAGCGCGGCGGGTGTGGTGGTTACGCGCAGCGTGACCGCTACACTTGCCAGCGCCCTAGC

GCCCGCTCCTTTCGCTTTCTTCCCTTCCTTTCTCGCCACGTTCGCCGGCTTTCCCCGTCAAGCTCTAAATCGG

GGGCTCCCTTTAGGGTTCCGATTTAGTGCTTTACGGCACCTCGACCCCAAAAAACTTGATTAGGGTGATGGTT

CACGTAGTGGGCCATCGCCCTGATAGACGGTTTTTCGCCCTTTGACGTTGGAGTCCACGTTCTTTAATAGTGG

ACTCTTGTTCCAAACTGGAACAACACTCAACCCTATCTCGGTCTATTCTTTTGATTTATAAGGGATTTTGCCG

ATTTCGGCCTATTGGTTAAAAAATGAGCTGATTTAACAAAAATTTAACGCGAATTAATTCTGTGGAATGTGTG

TCAGTTAGGGTGTGGAAAGTCCCCAGGCTCCCCAGCAGGCAGAAGTATGCAAAGCATGCATCTCAATTAGTCA

GCAACCAGGTGTGGAAAGTCCCCAGGCTCCCCAGCAGGCAGAAGTATGCAAAGCATGCATCTCAATTAGTCAG

CAACCATAGTCCCGCCCCTAACTCCGCCCATCCCGCCCCTAACTCCGCCCAGTTCCGCCCATTCTCCGCCCCA

TGGCTGACTAATTTTTTTTATTTATGCAGAGGCCGAGGCCGCCTCTGCCTCTGAGCTATTCCAGAAGTAGTGA

GGAGGCTTTTTTGGAGGCCTAGGCTTTTGCAAAAAGCTCCCGGGAGCTTGTATATCCATTTTCGGATCTGATC

AAGAGACAGGATGAGGATCGTTTCGCATGATTGAACAAGATGGATTGCACGCAGGTTCTCCGGCCGCTTGGGT

GGAGAGGCTATTCGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGCAGGACGAGGCAG

CGCGGCTATCGTGGCTGGCCACGACGGGCGTTCCTTGCGCAGCTGTGCTCGACGTTGTCACTGAAGCGGGAAG

GGACTGGCTGCTATTGGGCGAAGTGCCGGGGCAGGATCTCCTGTCATCTCACCTTGCTCCTGCCGAGAAAGTA

TCCATCATGGCTGATGCAATGCGGCGGCTGCATACGCTTGATCCGGCTACCTGCCCATTCGACCACCAAGCGA

-continued

AACATCGCATCGAGCGAGCACGTACTCGGATGGAAGCCGGTCTTGTCGATCAGGATGATCTGGACGAAGAGCA
TCAGGGGCTCGCGCCAGCCGAACTGTTCGCCAGGCTCAAGGCGCGCATGCCCGACGGCGAGGATCTCGTCGTG
ACCCATGGCGATGCCTGCTTGCCGAATATCATGGTGGAAAATGGCCGCTTTTCTGGATTCATCGACTGTGGCC
GGCTGGGTGTGGCGGACCGCTATCAGGACATAGCGTTGGCTACCCGTGATATTGCTGAAGAGCTTGGCGGCGA
ATGGGCTGACCGCTTCCTCGTGCTTTACGGTATCGCCGCTCCCGATTCGCAGCGCATCGCCTTCTATCGCCTT
CTTGACGAGTTCTTCTGAGCGGGACTCTGGGGTTCGAAATGACCGACCAAGCGACGCCCAACCTGCCATCACG
AGATTTCGATTCCACCGCCGCCTTCTATGAAAGGTTGGGCTTCGGAATCGTTTTCCGGGACGCCGGCTGGATG
ATCCTCCAGCGCGGGGATCTCATGCTGGAGTTCTTCGCCCACCCCAACTTGTTTATTGCAGCTTATAATGGTT
ACAAATAAAGCAATAGCATCACAAATTTCACAAATAAAGCATTTTTTTCACTGCATTCTAGTTGTGGTTTGTC
CAAACTCATCAATGTATCTTATCATGTCTGTATACCGTCGACCTCTAGCTAGAGCTTGGCGTAATCATGGTCA
TAGCTGTTTCCTGTGTGAAATTGTTATCCGCTCACAATTCCACACAACATACGAGCCGGAAGCATAAAGTGTA
AAGCCTGGGGTGCCTAATGAGTGAGCTAACTCACATTAATTGCGTTGCGCTCACTGCCCGCTTTCCAGTCGGG
AAACCTGTCGTGCCAGCTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGTATCAGCTCACTCAAAGG
CGGTAATACGGTTATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACAGAGTT
CTTGAAGTGGTGGCCTAACTACGGCTACACTAGAAGAACAGTATTTGGTATCTGCGCTCTGCTGAAGCCAGTT
ACCTTCGGAAAAAGAGTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGGTCTGACAGTTACCAATGCT
TAATCAGTGAGGCACCTATCTCAGCGATCTGTCTATTTCGTTCATCCATAGTTGCCTGACTCCCCGTCGTGTA
GATAACTACGATACGGGAGGGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTCGCCAGTTAATAGTTTGCGCAACGT
TGTTGCCATTGCTACAGGCATCGTGGTGTCACGCTCGTCGTTTGGTATGGCTTCATTCAGCTCCGGTTCCCAA
CGATCAAGGCGAGTTACATGATCCCCCATGTTGTGCAAAAAAGCGGTTAGCTCCTTCGGTCCTCCGATCGTTG
TCAGAAGTAAGTTGGCCGCAGTGTTATCACTCATGGTTATGGCAGCACTGCATAATTCTCTTACTGTCATGCC
ATCCGTAAGATGCTTTTCTGTGACTGGTGAGTACTCAACCAAGTCATTCTGAGAATAGTGTATGCGGCGACCG
AGTTGCTCTTGCCCGGCGTCAATACGGGATAATACCGCGCCACATAGCAGAACTTTAAAAGTGCTCATCATTG
GAAAACGTTCTTCGGGGCGAAAACTCTCAAGGATCTTACCGCTGTTGAGATCCAGTTCGATGTAACCCACTCG
TGCACCCAACTGATCTTCAGCATCTTTTACTTTCACCAGCGTTTCTGGGTGAGCAAAAACAGGAAGGCAAAAT
GCCGCAAAAAAGGGAATAAGGGCGACACGGAAATGTTGAATACTCATACTCTTCCTTTTTCAATATTATTGAA
GCATTTATCAGGGTTATTGTCTCATGAGCGGATACATATTTGAATGTATTTAGAAAAATAAACAAATAGGGGT
TCCGCGCACATTTCCCCGAAAAGTGCCACCTGACGTC

-continued

MGP_Kozak_hMGP sig_FLAG_ENPP1opt_LINK_hAlb_stop_pcDNA3.1(+)
(SEQ ID NO: 97)

pcDNA3.1+, MGP promoter, Kozak seq, h-MGP secretory seq, Flag tag, ENPP1 opt, Linker seq, h-albumin seq, Stop codon

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTAAGATTATAGTTGTCATTTGAACTTGGGGATAAAGGAGACATCTATGACTTGGCTGGA

AAAGACAGAGCTAATGTACATTGCAAAGCACATATTTATAGCAGGAAAATGGGAAGATTTCTCTTTAATTCTG

GAGATGGAGTGGGGATGGGGAGAGTAGACTACTCATTTTAAGGGTGAAACATTGGAATTCAACTTGTTTGATG

TTATATTAATTGGTGGTTAATTACTAAGCTAAGTACGTATAAAACTTTTATCTATGGCTAGCTTGTCCCCCCA

AAGTCATGCAATATAGTGAACTGGCTTTCGCACTTTAAATTATTCATTGATCATGTAATGATTCAGATGATTC

ATCTTCCAAGATGGACACTGAAACTAACACTCATAGTAGGTTGTGGTTTAAAGAGTGGAACAACCGCCAGTCT

CATTAGTGGAAATTGTGATGGTTGAATTTATCAAGGATGAACATACACGGTCTTCTTTCTGAGATTTTCTTTA

AGATTTTCGCACAGATAATCTATTTCTTAGGTTTTGGAGAGAAAACTTGAATTTTATTGATCCCTCAGAACTC

AATCTTTCAGATTTCAAAGGAGCTATTTCTTTTAATGGGGACTCTGTTAATATTTATAAAAGCTCTTCACAGG

ATGGAGGGTGGGAGGGAAACTCCATCCCAACAAGACAAAAAGAATGAAGCATGAGGCTCCACCTAGTTCATCA

CTGCTCCTTGAAATACATCAGTATTGAAAGACACATCCACCCCACCCCCAACCCAGCCCTATTGCTGTTCCAG

CTCAAGAGTCAGAGGTCCCGAAGCTGTAGCTCTTCTACAATCTGCTGCTCTGTGACTTCAAGTCTGTTGTCTG

CAAAGAAAACTATTGGGTTCCCAAGCAAGAGAGGCACATCTGGTAGGACAGATTTTGTGATTGCAAAAGAAGG

GGGAAAAAAAGAAAGAAAGAAAAGACCTCTCTATACAAGATAACCAGAGGCATCAAACTGAAATCCTCCTGTG

GAAAATAAGCTAGTACTTCTGGGCCTGATGGTGTAGTGAAAACCTGTGCTTGAGGATACATTACAGTGAAAGA

GCAAAGTGAATAGTAAGTAGCTATTACTTACCTCCTTAGGGAGGTGTGTTGTTTGTCTGTACATCCCCCACAG

CACCTAGCACAGTACCTTGCATCTCACCTGCCACTCACTAAAAAGTCTATCAAGTTAGTTAATTATCGAGACA

ACGCCCTCAGAAATGAGAGAACAGTACCCTCTTATCCTTGCTGCACTTTCCAGCACTGATACGCTGCCTAAAA

GAGGACTAGGGCACAGGTTTGAATTAATGTCACAAAACTGGATGGGCAAGTTACAACGGTGTTGATTAAGGAA

ACAGAACTCATGGTGCACCGGATATCTCCATCCTGATGAACCCTTGGAAAAATGCCAAAGATGCATATCCCCA

GGCAAATGCCTGATTAGTCTGGGATTGATAGATTGGTCTAGGATTCAGCCCTACTGGGAAGATGTCTAAATTA

TAATCAGTGTAGAAAGCGAAGTTCTCCTAGAAGAAGAGGCAAAGGTTAAAAAGAAGAAAAGAAAAGAAAGTGA

AGTCCTTTCTCCCCCAAAACCTCTCATCAATCAATCAGGGTAACAAACAGAACACTAGGGCTCTGTCTGTGGA

CCAAACCCAAAAGCCCTGCGGTCAGGGCCAGGAGGGTAGATCATGTGTTTGTGGCAACTTCCTCTGTGGGCTT

TTGCCCAGGTCTGTCCCCAAGCATACGATGGCCAAAACTTCTGCACCAGAGCAGCATCCTGTGTAACACAGTC

AGGTCCAGCAGTTAGGGAAAACTGCCCACTCAGAGTAGATAATATCTGGAAGGAATGACTGTTTGGGAAAAGT

TCCAATGCTAGTTCAGTGCCAACCCTTCCCCACCTTCTCCAGCTCTCTCCCACTGGTTCCTCCCCTCTCAACT

GCTCTGGTTCTTATAAAAACCTCACAGCCTTCCACTAACATCCCGTAGGAGCCTCTCTCCCTACTGCTGCTAC

ACAAGACCCTGAGACTGACCTGCAGGACGAAACCCTCTGGCTAACTAGAGAACCCACTGCTTACTGGCTTATC

GAAATTAATACGACTCACTATAGGGAGACCCAAGCTGGCTAGCGCCACCATGAAGAGCCTGATCCTTCTTGCC

ATCCTGGCCGCCTTAGCGGTAGTAACTTTGTGTGACTACAAAGACGATGACGACAAGAGCGCTGGCCTGAAGC

CAAGCTGCGCCAAGGAGGTGAAGAGCTGCAAGGGCAGATGTTTCGAACGGACCTTCGGCAACTGCAGATGCGA

-continued

CGCCGCCTGCGTGGAACTGGGAAACTGTTGTCTGGACTACCAGGAGACATGTATCGAGCCTGAGCACATCTGG

ACATGCAACAAGTTCAGATGTGGCGAGAAAAGACTGACTCGGAGTCTGTGCGCCTGTTCTGACGACTGCAAGG

ACAAGGGCGATTGCTGCATCAACTACAGCAGCGTGTGCCAGGGCGAAAAGAGCTGGGTCGAGGAACCCTGCGA

GAGCATCAACGAGCCCCAGTGCCCTGCCGGATTTGAGACACCTCCTACCCTGCTCTTCTCCCTGGATGGCTTC

AGAGCTGAGTACCTGCATACATGGGGAGGACTGCTGCCTGTGATCAGCAAGCTGAAGAAGTGCGGCACCTACA

CAAAGAACATGCGGCCTGTCTACCCTACCAAGACCTTCCCCAACCACTACAGCATCGTGACCGGCCTGTACCC

CGAGAGCCACGGCATCATCGACAACAAGATGTACGACCCCAAAATGAACGCCAGCTTCAGCCTGAAATCTAAG

GAAAAGTTCAACCCTGAGTGGTATAAGGGCGAGCCAATCTGGGTGACAGCCAAGTACCAGGGCCTGAAGAGCG

GCACCTTCTTCTGGCCTGGCAGCGACGTGGAGATCAACGGAATCTTCCCTGATATCTACAAGATGTATAACGG

CTCCGTGCCTTTCGAGGAGCGGATCTTGGCTGTTCTTCAGTGGCTGCAGCTGCCCAAGGACGAGAGACCCCAC

TTCTACACCCTGTACCTGGAAGAACCTGACAGCAGCGGCCACAGCTACGGCCCTGTGTCTAGCGAGGTGATCA

AGGCCCTGCAAAGAGTGGATGGCATGGTGGGCATGCTGATGGATGGACTGAAGGAACTGAACCTCCATCGTTG

CCTGAACCTGATCCTGATCTCCGACCACGGCATGGAACAGGGCAGCTGTAAAAAGTACATCTACCTGAACAAG

TACCTGGGCGACGTGAAGAATATCAAGGTGATCTACGGGCCGGCCGCCAGGCTGCGGCCTAGCGACGTGCCCG

ACAAGTATTACAGCTTCAACTACGAGGGCATCGCCAGAAACCTGTCTTGCAGAGAACCCAATCAACACTTCAA

GCCTTACCTGAAGCACTTTCTGCCTAAGAGACTGCACTTCGCCAAAAGCGACAGAATTGAACCCCTGACATTC

TATCTGGACCCTCAGTGGCAGCTGGCCCTCAATCCTTCTGAACGCAAATACTGCGGTAGCGGATTTCACGGCT

CTGATAACGTGTTTTCTAACATGCAGGCCCTGTTTGTGGGCTACGGCCCTGGCTTCAAGCACGGAATCGAGGC

TGACACCTTCGAGAACATCGAAGTTTACAATCTGATGTGCGACCTGCTGAATCTGACCCCAGCCCCTAACAAC

GGCACACACGGCTCTCTGAATCACCTGCTCAAGAACCCCGTGTATACCCCCAAACACCCTAAAGAGGTCCATC

CACTGGTGCAGTGCCCATTCACCAGAAACCCTCGGGACAACCTTGGCTGCAGCTGCAACCCTAGCATCCTCCC

TATCGAAGATTTCCAGACCCAGTTTAACCTGACTGTCGCCGAAGAGAAGATCATCAAGCACGAAACCCTGCCC

TACGGGAGGCCCAGAGTGCTGCAGAAAGAAAACACAATCTGTCTGCTGAGCCAGCACCAGTTTATGAGCGGCT

ACAGTCAGGACATCCTGATGCCTCTGTGGACCAGCTACACCGTGGACCGGAATGACAGCTTCAGCACCGAGGA

CTTCAGCAACTGCCTGTATCAGGACTTCCGCATCCCTCTGTCCCCTGTGCATAAGTGCAGCTTTTACAAGAAC

AACACCAAGGTGAGCTACGGGTTTCTGAGCCCACCACAACTGAACAAAAATAGCTCTGGCATCTACTCTGAGG

CGCTGCTGACCACCAACATCGTGCCAATGTACCAGAGCTTCCAGGTGATCTGGCGGTACTTCCATGATACCCT

GCTTCGGAAGTACGCCGAAGAACGGAACGGCGTGAACGTGGTGTCCGGCCCAGTGTTCGACTTCGACTACGAC

GGCAGATGTGATTCCCTTGAGAATCTGAGACAGAAGCGGCGGGTTATCAGAAACCAGGAGATCCTGATTCCTA

CCCACTTCTTCATCGTGCTGACATCTTGCAAGGATACCAGCCAAACACCTCTGCACTGCGAGAACCTGGACAC

CCTGGCCTTCATCCTGCCTCACCGGACCGATAATAGCGAATCCTGTGTGCACGGCAAACACGACTCTAGCTGG

GTGGAAGAGCTGCTGATGCTGCACAGAGCCCGGATCACAGATGTGGAACACATCACCGGCCTGTCCTTCTACC

AACAGAGAAAGGAACCCGTGTCTGATATCCTGAAGCTGAAAACCCACCTGCCTACCTTCAGCCAGGAGGACCT

GATCGTTAACGATGCACACAAGAGTGAGGTTGCTCATCGGTTTAAAGATTTGGGAGAAGAAAATTTCAAAGCC

TTGGTGTTGATTGCCTTTGCTCAGTATCTTCAGCAGTGTCCATTTGAAGATCATGTAAAATTAGTGAATGAAG

TAACTGAATTTGCAAAAACATGTGTTGCTGATGAGTCAGCTGAAAATTGTGACAAATCACTTCATACCCTTTT

TGGAGACAAATTATGCACAGTTGCAACTCTTCGTGAAACCTATGGTGAAATGGCTGACTGCTGTGCAAAACAA

GAACCTGAGAGAAATGAATGCTTCTTGCAACACAAAGATGACAACCCAAACCTCCCCCGATTGGTGAGACCAG

AGGTTGATGTGATGTGCACTGCTTTTCATGACAATGAAGAGACATTTTTGAAAAAATACTTATATGAAATTGC

-continued

CAGAAGACATCCTTACTTTTATGCCCCGGAACTCCTTTTCTTTGCTAAAAGGTATAAAGCTGCTTTTACAGAA

TGTTGCCAAGCTGCTGATAAAGCTGCCTGCCTGTTGCCAAAGCTCGATGAACTTCGGGATGAAGGGAAGGCTT

CGTCTGCCAAACAGAGACTCAAGTGTGCCAGTCTCCAAAAATTTGGAGAAAGAGCTTTCAAAGCATGGGCAGT

AGCTCGCCTGAGCCAGAGATTTCCCAAAGCTGAGTTTGCAGAAGTTTCCAAGTTAGTGACAGATCTTACCAAA

GTCCACACGGAATGCTGCCATGGAGATCTGCTTGAATGTGCTGATGACAGGGCGGACCTTGCCAAGTATATCT

GTGAAAATCAAGATTCGATCTCCAGTAAACTGAAGGAATGCTGTGAAAAACCTCTGTTGGAAAAATCCCACTG

CATTGCCGAAGTGGAAAATGATGAGATGCCTGCTGACTTGCCTTCATTAGCTGCTGATTTTGTTGAAAGTAAG

GATGTTTGCAAAAACTATGCTGAGGCAAAGGATGTCTTCCTGGGCATGTTTTTGTATGAATATGCAAGAAGGC

ATCCTGATTACTCTGTCGTGCTGCTGCTGAGACTTGCCAAGACATATGAAACCACACTCGAGAAGTGCTGTGC

CGCTGCAGATCCTCATGAATGCTATGCCAAAGTGTTCGATGAATTTAAACCTCTTGTGGAAGAGCCTCAGAAT

TTAATCAAACAAAATTGTGAGCTTTTTGAGCAGCTTGGAGAGTACAAATTCCAGAATGCGCTATTAGTTCGTT

ACACCAAGAAAGTACCCCAAGTGTCAACTCCAACTCTTGTAGAGGTCTCAAGAAACCTAGGAAAAGTGGGCAG

CAAATGTTGTAAACATCCTGAAGCAAAAAGAATGCCCTGTGCAGAAGACTATCTATCCGTGGTCCTGAACCAG

TTATGTGTGTTGCATGAGAAAACGCCAGTAAGTGACAGAGTCACCAAATGCTGCACAGAATCCTTGGTGAACA

GGCGACCATGCTTTTCAGCTCTGGAAGTCGATGAAACATACGTTCCCAAAGAGTTTAATGCTGAAACATTCAC

CTTCCATGCAGATATATGCACACTTTCTGAGAAGGAGAGACAAATCAAGAAACAAACTGCACTTGTTGAGCTC

GTGAAACACAAGCCCAAGGCAACAAAAGAGCAACTGAAAGCTGTTATGGATGATTTCGCAGCTTTTGTAGAGA

AGTGCTGCAAGGCTGACGATAAGGAGACCTGCTTTGCCGAGGAGGGTAAAAAACTTGTTGCTGCAAGTCAAGC

TGCCTTAGGCTTATGAGGTACCGAGCTCGGATCCACTAGTCCAGTGTGGTGGAATTCTGCAGATATCCAGCAC

AGTGGCGGCCGCTCGAGTCTAGAGGGCCCGTTTAAACCCGCTGATCAGCCTCGACTGTGCCTTCTAGTTGCCA

GCCATCTGTTGTTTGCCCCTCCCCCGTGCCTTCCTTGACCCTGGAAGGTGCCACTCCCACTGTCCTTTCCTAA

TAAAATGAGGAAATTGCATCGCATTGTCTGAGTAGGTGTCATTCTATTCTGGGGGGTGGGGTGGGGCAGGACA

GCAAGGGGGAGGATTGGGAAGACAATAGCAGGCATGCTGGGGATGCGGTGGGCTCTATGGCTTCTGAGGCGGA

AAGAACCAGCTGGGGCTCTAGGGGGTATCCCCACGCGCCCTGTAGCGGCGCATTAAGCGCGGCGGGTGTGGTG

GTTACGCGCAGCGTGACCGCTACACTTGCCAGCGCCCTAGCGCCCGCTCCTTTCGCTTTCTTCCCTTCCTTTC

TCGCCACGTTCGCCGGCTTTCCCCGTCAAGCTCTAAATCGGGGGCTCCCTTTAGGGTTCCGATTTAGTGCTTT

ACGGCACCTCGACCCCAAAAAACTTGATTAGGGTGATGGTTCACGTAGTGGGCCATCGCCCTGATAGACGGTT

TTTCGCCCTTTGACGTTGGAGTCCACGTTCTTTAATAGTGGACTCTTGTTCCAAACTGGAACAACACTCAACC

CTATCTCGGTCTATTCTTTTGATTTATAAGGGATTTTGCCGATTTCGGCCTATTGGTTAAAAAATGAGCTGAT

TTAACAAAAATTTAACGCGAATTAATTCTGTGGAATGTGTGTCAGTTAGGGTGTGGAAAGTCCCCAGGCTCCC

CAGCAGGCAGAAGTATGCAAAGCATGCATCTCAATTAGTCAGCAACCAGGTGTGGAAAGTCCCCAGGCTCCCC

AGCAGGCAGAAGTATGCAAAGCATGCATCTCAATTAGTCAGCAACCATAGTCCCGCCCCTAACTCCGCCCATC

CCGCCCCTAACTCCGCCCAGTTCCGCCCATTCTCCGCCCCATGGCTGACTAATTTTTTTTATTTATGCAGAGG

CCGAGGCCGCCTCTGCCTCTGAGCTATTCCAGAAGTAGTGAGGAGGCTTTTTTGGAGGCCTAGGCTTTTGCAA

AAAGCTCCCGGGAGCTTGTATATCCATTTTCGGATCTGATCAAGAGACAGGATGAGGATCGTTTCGCATGATT

GAACAAGATGGATTGCACGCAGGTTCTCCGGCCGCTTGGGTGGAGAGGCTATTCGGCTATGACTGGGCACAAC

AGACAATCGGCTGCTCTGATGCCGCCGTGTTCCGGCTGTCAGCGCAGGGGCGCCCGGTTCTTTTTGTCAAGAC

CGACCTGTCCGGTGCCCTGAATGAACTGCAGGACGAGGCAGCGCGGCTATCGTGGCTGGCCACGACGGGCGTT

CCTTGCGCAGCTGTGCTCGACGTTGTCACTGAAGCGGGAAGGGACTGGCTGCTATTGGGCGAAGTGCCGGGGC

-continued

AGGATCTCCTGTCATCTCACCTTGCTCCTGCCGAGAAAGTATCCATCATGGCTGATGCAATGCGGCGGCTGCA

TACGCTTGATCCGGCTACCTGCCCATTCGACCACCAAGCGAAACATCGCATCGAGCGAGCACGTACTCGGATG

GAAGCCGGTCTTGTCGATCAGGATGATCTGGACGAAGAGCATCAGGGGCTCGCGCCAGCCGAACTGTTCGCCA

GGCTCAAGGCGCGCATGCCCGACGGCGAGGATCTCGTCGTGACCCATGGCGATGCCTGCTTGCCGAATATCAT

GGTGGAAAATGGCCGCTTTTCTGGATTCATCGACTGTGGCCGGCTGGGTGTGGCGGACCGCTATCAGGACATA

GCGTTGGCTACCCGTGATATTGCTGAAGAGCTTGGCGGCGAATGGGCTGACCGCTTCCTCGTGCTTTACGGTA

TCGCCGCTCCCGATTCGCAGCGCATCGCCTTCTATCGCCTTCTTGACGAGTTCTTCTGAGCGGGACTCTGGGG

TTCGAAATGACCGACCAAGCGACGCCCAACCTGCCATCACGAGATTTCGATTCCACCGCCGCCTTCTATGAAA

GGTTGGGCTTCGGAATCGTTTTCCGGGACGCCGGCTGGATGATCCTCCAGCGCGGGGATCTCATGCTGGAGTT

CTTCGCCCACCCCAACTTGTTTATTGCAGCTTATAATGGTTACAAATAAAGCAATAGCATCACAAATTTCACA

AATAAAGCATTTTTTTCACTGCATTCTAGTTGTGGTTTGTCCAAACTCATCAATGTATCTTATCATGTCTGTA

TACCGTCGACCTCTAGCTAGAGCTTGGCGTAATCATGGTCATAGCTGTTTCCTGTGTGAAATTGTTATCCGCT

CACAATTCCACACAACATACGAGCCGGAAGCATAAAGTGTAAAGCCTGGGGTGCCTAATGAGTGAGCTAACTC

ACATTAATTGCGTTGCGCTCACTGCCCGCTTTCCAGTCGGGAAACCTGTCGTGCCAGCTGCATTAATGAATCG

GCCAACGCGCGGGGAGAGGCGGTTTGCGTATTGGGCGCTCTTCCGCTTCCTCGCTCACTGACTCGCTGCGCTC

GGTCGTTCGGCTGCGGCGAGCGGTATCAGCTCACTCAAAGGCGGTAATACGGTTATCCACAGAATCAGGGGAT

AACGCAGGAAAGAACATGTGAGCAAAAGGCCAGCAAAAGGCCAGGAACCGTAAAAAGGCCGCGTTGCTGGCGT

TTTTCCATAGGCTCCGCCCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGTTCCGACCCTGCCGCTT

ACCGGATACCTGTCCGCCTTTCTCCCTTCGGGAAGCGTGGCGCTTTCTCATAGCTCACGCTGTAGGTATCTCA

GTTCGGTGTAGGTCGTTCGCTCCAAGCTGGGCTGTGTGCACGAACCCCCCGTTCAGCCCGACCGCTGCGCCTT

ATCCGGTAACTATCGTCTTGAGTCCAACCCGGTAAGACACGACTTATCGCCACTGGCAGCAGCCACTGGTAAC

AGGATTAGCAGAGCGAGGTATGTAGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGAAAAAGAGTTGGTAGCTCTTGATC

CGGCAAACAAACCACCGCTGGTAGCGGTGGTTTTTTTGTTTGCAAGCAGCAGATTACGCGCAGAAAAAAAGGA

TCTCAAGAAGATCCTTTGATCTTTTCTACGGGGTCTGACGCTCAGTGGAACGAAAACTCACGTTAAGGGATTT

TGGTCATGAGATTATCAAAAAGGATCTTCACCTAGATCCTTTTAAATTAAAAATGAAGTTTTAAATCAATCTA

AAGTATATATGAGTAAACTTGGTCTGACAGTTACCAATGCTTAATCAGTGAGGCACCTATCTCAGCGATCTGT

CTATTTCGTTCATCCATAGTTGCCTGACTCCCCGTCGTGTAGATAACTACGATACGGGAGGGCTTACCATCTG

GCCCCAGTGCTGCAATGATACCGCGAGACCCACGCTCACCGGCTCCAGATTTATCAGCAATAAACCAGCCAGC

CGGAAGGGCCGAGCGCAGAAGTGGTCCTGCAACTTTATCCGCCTCCATCCAGTCTATTAATTGTTGCCGGGAA

GCTAGAGTAAGTAGTTCGCCAGTTAATAGTTTGCGCAACGTTGTTGCCATTGCTACAGGCATCGTGGTGTCAC

GCTCGTCGTTTGGTATGGCTTCATTCAGCTCCGGTTCCCAACGATCAAGGCGAGTTACATGATCCCCCATGTT

GTGCAAAAAAGCGGTTAGCTCCTTCGGTCCTCCGATCGTTGTCAGAAGTAAGTTGGCCGCAGTGTTATCACTC

ATGGTTATGGCAGCACTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGGCGTCAATACGGGATAA

TACCGCGCCACATAGCAGAACTTTAAAAGTGCTCATCATTGGAAAACGTTCTTCGGGGCGAAAACTCTCAAGG

ATCTTACCGCTGTTGAGATCCAGTTCGATGTAACCCACTCGTGCACCCAACTGATCTTCAGCATCTTTTACTT

TCACCAGCGTTTCTGGGTGAGCAAAAACAGGAAGGCAAAATGCCGCAAAAAAGGGAATAAGGGCGACACGGAA

ATGTTGAATACTCATACTCTTCCTTTTTCAATATTATTGAAGCATTTATCAGGGTTATTGTCTCATGAGCGGA

-continued

TACATATTTGAATGTATTTAGAAAAATAAACAAATAGGGGTTCCGCGCACATTTCCCCGAAAAGTGCCACCTG

ACGTC
CAG_Kozak_hAlb sig_FLAG_ENPPlopt_LINK_hAlb_stop_mir155_pcDNA3.1(+)

pcDNA3.1+, CAG promoter, Kozak seq, h-alb secretory seq, Flag tag, ENPP1 opt, Linker seq, h-alb seq, *stop codon,* mir155 target seq

(SEQ ID NO: 98)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGCGTTACATAACTTACGGTAAATGGCCCGCCTGGCTGACCGCCCAACGACCCCCGCCC

ATTGACGTCAATAATGACGTATGTTCCCATAGTAACGCCAATAGGGACTTTCCATTGACGTCAATGGGTGGAG

TATTTACGGTAAACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTTGGCAGTACAT

CTACGTATTAGTCATCGCTATTACCATGGTCGAGGTGAGCCCCACGTTCTGCTTCACTCTCCCCATCTCCCCC

CCCTCCCCACCCCCAATTTTGTATTTATTTATTTTTTAATTATTTTGTGCAGCGATGGGGGCGGGGGGGGGGG

GGGGGCGCGCGCCAGGCGGGGCGGGGCGGGGCGAGGGGCGGGGCGGGGCGAGGCGGAGAGGTGCGGCGGCAGC

CAATCAGAGCGGCGCGCTCCGAAAGTTTCCTTTTATGGCGAGGCGGCGGCGGCGGCGGCCCTATAAAAAGCGA

AGCGCGCGGCGGGCGCTCTGGCTAACTAGAGAACCCACTGCTTACTGGCTTATCGAAATTAATACGACTCACT

ATAGGGAGACCCAAGCTGGCTAGCGCCACCATGAAGTGGGTAACCTTTATTTCCCTTCTTTTTCTCTTTAGCT

CGGCTTATTCCAGGGGTGTGTTTCGTCGAGACTACAAAGACGATGACGACAAGAGCGCTGGCCTGAAGCCAAG

CTGCGCCAAGGAGGTGAAGAGCTGCAAGGGCAGATGTTTCGAACGGACCTTCGGCAACTGCAGATGCGACGCC

GCCTGCGTGGAACTGGGAAACTGTTGTCTGGACTACCAGGAGACATGTATCGAGCCTGAGCACATCTGGACAT

GCAACAAGTTCAGATGTGGCGAGAAAAGACTGACTCGGAGTCTGTGCGCCTGTTCTGACGACTGCAAGGACAA

GGGCGATTGCTGCATCAACTACAGCAGCGTGTGCCAGGGCGAAAAGAGCTGGGTCGAGGAACCCTGCGAGAGC

ATCAACGAGCCCCAGTGCCCTGCCGGATTTGAGACACCTCCTACCCTGCTCTTCTCCCTGGATGGCTTCAGAG

CTGAGTACCTGCATACATGGGGAGGACTGCTGCCTGTGATCAGCAAGCTGAAGAAGTGCGGCACCTACACAAA

GAACATGCGGCCTGTCTACCCTACCAAGACCTTCCCCAACCACTACAGCATCGTGACCGGCCTGTACCCCGAG

AGCCACGGCATCATCGACAACAAGATGTACGACCCCAAAATGAACGCCAGCTTCAGCCTGAAATCTAAGGAAA

AGTTCAACCCTGAGTGGTATAAGGGCGAGCCAATCTGGGTGACAGCCAAGTACCAGGGCCTGAAGAGCGGCAC

CTTCTTCTGGCCTGGCAGCGACGTGGAGATCAACGGAATCTTCCCTGATATCTACAAGATGTATAACGGCTCC

GTGCCTTTCGAGGAGCGGATCTTGGCTGTTCTTCAGTGGCTGCAGCTGCCCAAGGACGAGAGACCCCACTTCT

ACACCCTGTACCTGGAAGAACCTGACAGCAGCGGCCACAGCTACGGCCCTGTGTCTAGCGAGGTGATCAAGGC

CCTGCAAAGAGTGGATGGCATGGTGGGCATGCTGATGGATGGACTGAAGGAACTGAACCTCCATCGTTGCCTG

AACCTGATCCTGATCTCCGACCACGGCATGGAACAGGGCAGCTGTAAAAAGTACATCTACCTGAACAAGTACC

TGGGCGACGTGAAGAATATCAAGGTGATCTACGGGCCGGCCGCCAGGCTGCGGCCTAGCGACGTGCCCGACAA

GTATTACAGCTTCAACTACGAGGGCATCGCCAGAAACCTGTCTTGCAGAGAACCCAATCAACACTTCAAGCCT

TACCTGAAGCACTTTCTGCCTAAGAGACTGCACTTCGCCAAAAGCGACAGAATTGAACCCCTGACATTCTATC

-continued

TGGACCCTCAGTGGCAGCTGGCCCTCAATCCTTCTGAACGCAAATACTGCGGTAGCGGATTTCACGGCTCTGA

TAACGTGTTTTCTAACATGCAGGCCCTGTTTGTGGGCTACGGCCCTGGCTTCAAGCACGGAATCGAGGCTGAC

ACCTTCGAGAACATCGAAGTTTACAATCTGATGTGCGACCTGCTGAATCTGACCCCAGCCCCTAACAACGGCA

CACACGGCTCTCTGAATCACCTGCTCAAGAACCCCGTGTATACCCCCAAACACCCTAAAGAGGTCCATCCACT

GGTGCAGTGCCCATTCACCAGAAACCCTCGGGACAACCTTGGCTGCAGCTGCAACCCTAGCATCCTCCCTATC

GAAGATTTCCAGACCCAGTTTAACCTGACTGTCGCCGAAGAGAAGATCATCAAGCACGAAACCCTGCCCTACG

GGAGGCCCAGAGTGCTGCAGAAAGAAAACACAATCTGTCTGCTGAGCCAGCACCAGTTTATGAGCGGCTACAG

TCAGGACATCCTGATGCCTCTGTGGACCAGCTACACCGTGGACCGGAATGACAGCTTCAGCACCGAGGACTTC

AGCAACTGCCTGTATCAGGACTTCCGCATCCCTCTGTCCCCTGTGCATAAGTGCAGCTTTTACAAGAACAACA

CCAAGGTGAGCTACGGGTTTCTGAGCCCACCACAACTGAACAAAAATAGCTCTGGCATCTACTCTGAGGCGCT

GCTGACCACCAACATCGTGCCAATGTACCAGAGCTTCCAGGTGATCTGGCGGTACTTCCATGATACCCTGCTT

CGGAAGTACGCCGAAGAACGGAACGGCGTGAACGTGGTGTCCGGCCCAGTGTTCGACTTCGACTACGACGGCA

GATGTGATTCCCTTGAGAATCTGAGACAGAAGCGGCGGGTTATCAGAAACCAGGAGATCCTGATTCCTACCCA

CTTCTTCATCGTGCTGACATCTTGCAAGGATACCAGCCAAACACCTCTGCACTGCGAGAACCTGGACACCCTG

GCCTTCATCCTGCCTCACCGGACCGATAATAGCGAATCCTGTGTGCACGGCAAACACGACTCTAGCTGGGTGG

AAGAGCTGCTGATGCTGCACAGAGCCCGGATCACAGATGTGGAACACATCACCGGCCTGTCCTTCTACCAACA

GAGAAAGGAACCCGTGTCTGATATCCTGAAGCTGAAAACCCACCTGCCTACCTTCAGCCAGGAGGACCTGATC

GTTAACGATGCACACAAGAGTGAGGTTGCTCATCGGTTTAAAGATTTGGGAGAAGAAAATTTCAAAGCCTTGG

TGTTGATTGCCTTTGCTCAGTATCTTCAGCAGTGTCCATTTGAAGATCATGTAAAATTAGTGAATGAAGTAAC

TGAATTTGCAAAAACATGTGTTGCTGATGAGTCAGCTGAAAATTGTGACAAATCACTTCATACCCTTTTTGGA

GACAAATTATGCACAGTTGCAACTCTTCGTGAAACCTATGGTGAAATGGCTGACTGCTGTGCAAAACAAGAAC

CTGAGAGAAATGAATGCTTCTTGCAACACAAAGATGACAACCCAAACCTCCCCCGATTGGTGAGACCAGAGGT

TGATGTGATGTGCACTGCTTTTCATGACAATGAAGAGACATTTTTGAAAAAATACTTATATGAAATTGCCAGA

AGACATCCTTACTTTTATGCCCCGGAACTCCTTTTCTTTGCTAAAAGGTATAAAGCTGCTTTTACAGAATGTT

GCCAAGCTGCTGATAAAGCTGCCTGCCTGTTGCCAAAGCTCGATGAACTTCGGGATGAAGGGAAGGCTTCGTC

TGCCAAACAGAGACTCAAGTGTGCCAGTCTCCAAAAATTTGGAGAAAGAGCTTTCAAAGCATGGGCAGTAGCT

CGCCTGAGCCAGAGATTTCCCAAAGCTGAGTTTGCAGAAGTTTCCAAGTTAGTGACAGATCTTACCAAAGTCC

ACACGGAATGCTGCCATGGAGATCTGCTTGAATGTGCTGATGACAGGGCGGACCTTGCCAAGTATATCTGTGA

AAATCAAGATTCGATCTCCAGTAAACTGAAGGAATGCTGTGAAAAACCTCTGTTGGAAAAATCCCACTGCATT

GCCGAAGTGGAAAATGATGAGATGCCTGCTGACTTGCCTTCATTAGCTGCTGATTTTGTTGAAAGTAAGGATG

TTTGCAAAAACTATGCTGAGGCAAAGGATGTCTTCCTGGGCATGTTTTTGTATGAATATGCAAGAAGGCATCC

TGATTACTCTGTCGTGCTGCTGCTGAGACTTGCCAAGACATATGAAACCACACTCGAGAAGTGCTGTGCCGCT

GCAGATCCTCATGAATGCTATGCCAAAGTGTTCGATGAATTTAAACCTCTTGTGGAAGAGCCTCAGAATTTAA

TCAAACAAAATTGTGAGCTTTTTGAGCAGCTTGGAGAGTACAAATTCCAGAATGCGCTATTAGTTCGTTACAC

CAAGAAAGTACCCCAAGTGTCAACTCCAACTCTTGTAGAGGTCTCAAGAAACCTAGGAAAAGTGGGCAGCAAA

TGTTGTAAACATCCTGAAGCAAAAAGAATGCCCTGTGCAGAAGACTATCTATCCGTGGTCCTGAACCAGTTAT

GTGTGTTGCATGAGAAAACGCCAGTAAGTGACAGAGTCACCAAATGCTGCACAGAATCCTTGGTGAACAGGCG

ACCATGCTTTTCAGCTCTGGAAGTCGATGAAACATACGTTCCCAAAGAGTTTAATGCTGAAACATTCACCTTC

CATGCAGATATATGCACACTTTCTGAGAAGGAGAGACAAATCAAGAAACAAACTGCACTTGTTGAGCTCGTGA

-continued

AACACAAGCCCAAGGCAACAAAAGAGCAACTGAAAGCTGTTATGGATGATTTCGCAGCTTTTGTAGAGAAGTG

CTGCAAGGCTGACGATAAGGAGACCTGCTTTGCCGAGGAGGGTAAAAAACTTGTTGCTGCAAGTCAAGCTGCC

TTAGGCTTA*TGA*CAATTACGATTAGCACTATCCAATTACGATTAGCACTATCCAATTACGATTAGCACTATCG

GTACCGAGCTCGGATCCACTAGTCCAGTGTGGTGGAATTCTGCAGATATCCAGCACAGTGGCGGCCGCTCGAG

TCTAGAGGGCCCGTTTAAACCCGCTGATCAGCCTCGACTGTGCCTTCTAGTTGCCAGCCATCTGTTGTTTGCC

CCTCCCCCGTGCCTTCCTTGACCCTGGAAGGTGCCACTCCCACTGTCCTTTCCTAATAAAATGAGGAAATTGC

ATCGCATTGTCTGAGTAGGTGTCATTCTATTCTGGGGGGTGGGGTGGGGCAGGACAGCAAGGGGGAGGATTGG

GAAGACAATAGCAGGCATGCTGGGGATGCGGTGGGCTCTATGGCTTCTGAGGCGGAAAGAACCAGCTGGGGCT

CTAGGGGGTATCCCCACGCGCCCTGTAGCGGCGCATTAAGCGCGGCGGGTGTGGTGGTTACGCGCAGCGTGAC

CGCTACACTTGCCAGCGCCCTAGCGCCCGCTCCTTTCGCTTTCTTCCCTTCCTTTCTCGCCACGTTCGCCGGC

TTTCCCCGTCAAGCTCTAAATCGGGGGCTCCCTTTAGGGTTCCGATTTAGTGCTTTACGGCACCTCGACCCCA

AAAAACTTGATTAGGGTGATGGTTCACGTAGTGGGCCATCGCCCTGATAGACGGTTTTTCGCCCTTTGACGTT

GGAGTCCACGTTCTTTAATAGTGGACTCTTGTTCCAAACTGGAACAACACTCAACCCTATCTCGGTCTATTCT

TTTGATTTATAAGGGATTTTGCCGATTTCGGCCTATTGGTTAAAAAATGAGCTGATTTAACAAAAATTTAACG

CGAATTAATTCTGTGGAATGTGTGTCAGTTAGGGTGTGGAAAGTCCCCAGGCTCCCCAGCAGGCAGAAGTATG

CAAAGCATGCATCTCAATTAGTCAGCAACCAGGTGTGGAAAGTCCCCAGGCTCCCCAGCAGGCAGAAGTATGC

AAAGCATGCATCTCAATTAGTCAGCAACCATAGTCCCGCCCCTAACTCCGCCCATCCCGCCCCTAACTCCGCC

CAGTTCCGCCCATTCTCCGCCCCATGGCTGACTAATTTTTTTTATTTATGCAGAGGCCGAGGCCGCCTCTGCC

TCTGAGCTATTCCAGAAGTAGTGAGGAGGCTTTTTTGGAGGCCTAGGCTTTTGCAAAAAGCTCCCGGGAGCTT

GTATATCCATTTTCGGATCTGATCAAGAGACAGGATGAGGATCGTTTCGCATGATTGAACAAGATGGATTGCA

CGCAGGTTCTCCGGCCGCTTGGGTGGAGAGGCTATTCGGCTATGACTGGGCACAACAGACAATCGGCTGCTCT

GATGCCGCCGTGTTCCGGCTGTCAGCGCAGGGGCGCCCGGTTCTTTTTGTCAAGACCGACCTGTCCGGTGCCC

TGAATGAACTGCAGGACGAGGCAGCGCGGCTATCGTGGCTGGCCACGACGGGCGTTCCTTGCGCAGCTGTGCT

CGACGTTGTCACTGAAGCGGGAAGGGACTGGCTGCTATTGGGCGAAGTGCCGGGGCAGGATCTCCTGTCATCT

CACCTTGCTCCTGCCGAGAAAGTATCCATCATGGCTGATGCAATGCGGCGGCTGCATACGCTTGATCCGGCTA

CCTGCCCATTCGACCACCAAGCGAAACATCGCATCGAGCGAGCACGTACTCGGATGGAAGCCGGTCTTGTCGA

TCAGGATGATCTGGACGAAGAGCATCAGGGGCTCGCGCCAGCCGAACTGTTCGCCAGGCTCAAGGCGCGCATG

CCCGACGGCGAGGATCTCGTCGTGACCCATGGCGATGCCTGCTTGCCGAATATCATGGTGGAAAATGGCCGCT

TTTCTGGATTCATCGACTGTGGCCGGCTGGGTGTGGCGGACCGCTATCAGGACATAGCGTTGGCTACCCGTGA

TATTGCTGAAGAGCTTGGCGGCGAATGGGCTGACCGCTTCCTCGTGCTTTACGGTATCGCCGCTCCCGATTCG

CAGCGCATCGCCTTCTATCGCCTTCTTGACGAGTTCTTCTGAGCGGGACTCTGGGGTTCGAAATGACCGACCA

AGCGACGCCCAACCTGCCATCACGAGATTTCGATTCCACCGCCGCCTTCTATGAAAGGTTGGGCTTCGGAATC

GTTTTCCGGGACGCCGGCTGGATGATCCTCCAGCGCGGGGATCTCATGCTGGAGTTCTTCGCCCACCCCAACT

TGTTTATTGCAGCTTATAATGGTTACAAATAAAGCAATAGCATCACAAATTTCACAAATAAAGCATTTTTTTC

ACTGCATTCTAGTTGTGGTTTGTCCAAACTCATCAATGTATCTTATCATGTCTGTATACCGTCGACCTCTAGC

TAGAGCTTGGCGTAATCATGGTCATAGCTGTTTCCTGTGTGAAATTGTTATCCGCTCACAATTCCACACAACA

TACGAGCCGGAAGCATAAAGTGTAAAGCCTGGGGTGCCTAATGAGTGAGCTAACTCACATTAATTGCGTTGCG

CTCACTGCCCGCTTTCCAGTCGGGAAACCTGTCGTGCCAGCTGCATTAATGAATCGGCCAACGCGCGGGGAGA

GGCGGTTTGCGTATTGGGCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGGATAACGCAGGAAAGAACAT

-continued

GTGAGCAAAAGGCCAGCAAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGACAGGACTATAAAGATACC

AGGCGTTTCCCCCTGGAAGCTCCCTCGTGCGCTCTCCTGTTCCGACCCTGCCGCTTACCGGATACCTGTCCGC

CTTTCTCCCTTCGGGAAGCGTGGCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGCGCCTTATCCGGTAACTATCGTC

TTGAGTCCAACCCGGTAAGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAGAAGAACAGTATTTGGT

ATCTGCGCTCTGCTGAAGCCAGTTACCTTCGGAAAAAGAGTTGGTAGCTCTTGATCCGGCAAACAAACCACCG

CTGGTAGCGGTGGTTTTTTTGTTTGCAAGCAGCAGATTACGCGCAGAAAAAAAGGATCTCAAGAAGATCCTTT

GATCTTTTCTACGGGGTCTGACGCTCAGTGGAACGAAAACTCACGTTAAGGGATTTTGGTCATGAGATTATCA

AAAAGGATCTTCACCTAGATCCTTTTAAATTAAAAATGAAGTTTTAAATCAATCTAAAGTATATATGAGTAAA

CTTGGTCTGACAGTTACCAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCTGGCCCCAGTGCTGCAATG

ATACCGCGAGACCCACGCTCACCGGCTCCAGATTTATCAGCAATAAACCAGCCAGCCGGAAGGGCCGAGCGCA

GAAGTGGTCCTGCAACTTTATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGTTGTGCAAAAAAGCGGTTA

GCTCCTTCGGTCCTCCGATCGTTGTCAGAAGTAAGTTGGCCGCAGTGTTATCACTCATGGTTATGGCAGCACT

GCATAATTCTCTTACTGTCATGCCATCCGTAAGATGCTTTTCTGTGACTGGTGAGTACTCAACCAAGTCATTC

TGAGAATAGTGTATGCGGCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGATCTTACCGCTGTTGAG

ATCCAGTTCGATGTAACCCACTCGTGCACCCAACTGATCTTCAGCATCTTTTACTTTCACCAGCGTTTCTGGG

TGAGCAAAAACAGGAAGGCAAAATGCCGCAAAAAAGGGAATAAGGGCGACACGGAAATGTTGAATACTCATAC

TCTTCCTTTTTCAATATTATTGAAGCATTTATCAGGGTTATTGTCTCATGAGCGGATACATATTTGAATGTAT

TTAGAAAAATAAACAAATAGGGGTTCCGCGCACATTTCCCCGAAAAGTGCCACCTGACGTC

CBA_Spacer_hAlb sig_FLAG_ENPPlopt_LINK_hAlb_SV40pA_pcDNA3.1(+)

(SEQ ID NO: 99)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTCTAGATGTACACTCGAGGTGAGCCCCACGTTCTGCTTCACTCTCCCCATCTCCCCCCC

CTCCCCACCCCCAATTTTGTATTTATTTATTTTTTAATTATTTTGTGCAGCGATGGGGGCGGGGGGGGGGGGG

GGGGCGCGCGCCAGGCGGGGCGGGGCGGGGCGAGGGGCGGGGCGGGGCGAGGCGGAGAGGTGCGGCGGCAGCC

AATCAGAGCGGCGCGCTCCGAAAGTTTCCTTTTATGGCGAGGCGGCGGCGGCGGCGGCCCTATAAAAAGCGAA

GCGCGCGGCGGGCGGCCACCCCGCGGGCCCGTTAATTAAACCGGTCGCCACCATGAAGTGGGTAACCTTTATT

TCCCTTCTTTTTCTCTTTAGCTCGGCTTATTCCAGGGGTGTGTTTCGTCGAGACTACAAAGACGATGACGACA

AGAGCGCTGGCCTGAAGCCAAGCTGCGCCAAGGAGGTGAAGAGCTGCAAGGGCAGATGTTTCGAACGGACCTT

CGGCAACTGCAGATGCGACGCCGCCTGCGTGGAACTGGGAAACTGTTGTCTGGACTACCAGGAGACATGTATC

GAGCCTGAGCACATCTGGACATGCAACAAGTTCAGATGTGGCGAGAAAAGACTGACTCGGAGTCTGTGCGCCT

GTTCTGACGACTGCAAGGACAAGGGCGATTGCTGCATCAACTACAGCAGCGTGTGCCAGGGCGAAAAGAGCTG

GGTCGAGGAACCCTGCGAGAGCATCAACGAGCCCCAGTGCCCTGCCGGATTTGAGACACCTCCTACCCTGCTC

-continued

TTCTCCCTGGATGGCTTCAGAGCTGAGTACCTGCATACATGGGGAGGACTGCTGCCTGTGATCAGCAAGCTGA

AGAAGTGCGGCACCTACACAAAGAACATGCGGCCTGTCTACCCTACCAAGACCTTCCCCAACCACTACAGCAT

CGTGACCGGCCTGTACCCCGAGAGCCACGGCATCATCGACAACAAGATGTACGACCCCAAAATGAACGCCAGC

TTCAGCCTGAAATCTAAGGAAAAGTTCAACCCTGAGTGGTATAAGGGCGAGCCAATCTGGGTGACAGCCAAGT

ACCAGGGCCTGAAGAGCGGCACCTTCTTCTGGCCTGGCAGCGACGTGGAGATCAACGGAATCTTCCCTGATAT

CTACAAGATGTATAACGGCTCCGTGCCTTTCGAGGAGCGGATCTTGGCTGTTCTTCAGTGGCTGCAGCTGCCC

AAGGACGAGAGACCCCACTTCTACACCCTGTACCTGGAAGAACCTGACAGCAGCGGCCACAGCTACGGCCCTG

TGTCTAGCGAGGTGATCAAGGCCCTGCAAAGAGTGGATGGCATGGTGGGCATGCTGATGGATGGACTGAAGGA

ACTGAACCTCCATCGTTGCCTGAACCTGATCCTGATCTCCGACCACGGCATGGAACAGGGCAGCTGTAAAAAG

TACATCTACCTGAACAAGTACCTGGGCGACGTGAAGAATATCAAGGTGATCTACGGGCCGGCCGCCAGGCTGC

GGCCTAGCGACGTGCCCGACAAGTATTACAGCTTCAACTACGAGGGCATCGCCAGAAACCTGTCTTGCAGAGA

ACCCAATCAACACTTCAAGCCTTACCTGAAGCACTTTCTGCCTAAGAGACTGCACTTCGCCAAAAGCGACAGA

ATTGAACCCCTGACATTCTATCTGGACCCTCAGTGGCAGCTGGCCCTCAATCCTTCTGAACGCAAATACTGCG

GTAGCGGATTTCACGGCTCTGATAACGTGTTTTCTAACATGCAGGCCCTGTTTGTGGGCTACGGCCCTGGCTT

CAAGCACGGAATCGAGGCTGACACCTTCGAGAACATCGAAGTTTACAATCTGATGTGCGACCTGCTGAATCTG

ACCCCAGCCCCTAACAACGGCACACACGGCTCTCTGAATCACCTGCTCAAGAACCCCGTGTATACCCCCAAAC

ACCCTAAAGAGGTCCATCCACTGGTGCAGTGCCCATTCACCAGAAACCCTCGGGACAACCTTGGCTGCAGCTG

CAACCCTAGCATCCTCCCTATCGAAGATTTCCAGACCCAGTTTAACCTGACTGTCGCCGAAGAGAAGATCATC

AAGCACGAAACCCTGCCCTACGGGAGGCCCAGAGTGCTGCAGAAAGAAAACACAATCTGTCTGCTGAGCCAGC

ACCAGTTTATGAGCGGCTACAGTCAGGACATCCTGATGCCTCTGTGGACCAGCTACACCGTGGACCGGAATGA

CAGCTTCAGCACCGAGGACTTCAGCAACTGCCTGTATCAGGACTTCCGCATCCCTCTGTCCCCTGTGCATAAG

TGCAGCTTTTACAAGAACAACACCAAGGTGAGCTACGGGTTTCTGAGCCCACCACAACTGAACAAAAATAGCT

CTGGCATCTACTCTGAGGCGCTGCTGACCACCAACATCGTGCCAATGTACCAGAGCTTCCAGGTGATCTGGCG

GTACTTCCATGATACCCTGCTTCGGAAGTACGCCGAAGAACGGAACGGCGTGAACGTGGTGTCCGGCCCAGTG

TTCGACTTCGACTACGACGGCAGATGTGATTCCCTTGAGAATCTGAGACAGAAGCGGCGGGTTATCAGAAACC

AGGAGATCCTGATTCCTACCCACTTCTTCATCGTGCTGACATCTTGCAAGGATACCAGCCAAACACCTCTGCA

CTGCGAGAACCTGGACACCCTGGCCTTCATCCTGCCTCACCGGACCGATAATAGCGAATCCTGTGTGCACGGC

AAACACGACTCTAGCTGGGTGGAAGAGCTGCTGATGCTGCACAGAGCCCGGATCACAGATGTGGAACACATCA

CCGGCCTGTCCTTCTACCAACAGAGAAAGGAACCCGTGTCTGATATCCTGAAGCTGAAAACCCACCTGCCTAC

CTTCAGCCAGGAGGACCTGATCGTTAACGATGCACACAAGAGTGAGGTTGCTCATCGGTTTAAAGATTTGGGA

GAAGAAAATTTCAAAGCCTTGGTGTTGATTGCCTTTGCTCAGTATCTTCAGCAGTGTCCATTTGAAGATCATG

TAAAATTAGTGAATGAAGTAACTGAATTTGCAAAAACATGTGTTGCTGATGAGTCAGCTGAAAATTGTGACAA

ATCACTTCATACCCTTTTTGGAGACAAATTATGCACAGTTGCAACTCTTCGTGAAACCTATGGTGAAATGGCT

GACTGCTGTGCAAAACAAGAACCTGAGAGAAATGAATGCTTCTTGCAACACAAAGATGACAACCCAAACCTCC

CCCGATTGGTGAGACCAGAGGTTGATGTGATGTGCACTGCTTTTCATGACAATGAAGAGACATTTTTGAAAAA

ATACTTATATGAAATTGCCAGAAGACATCCTTACTTTTATGCCCCGGAACTCCTTTTCTTTGCTAAAAGGTAT

AAAGCTGCTTTTACAGAATGTTGCCAAGCTGCTGATAAAGCTGCCTGCCTGTTGCCAAAGCTCGATGAACTTC

GGGATGAAGGGAAGGCTTCGTCTGCCAAACAGAGACTCAAGTGTGCCAGTCTCCAAAAATTTGGAGAAAGAGC

TTTCAAAGCATGGGCAGTAGCTCGCCTGAGCCAGAGATTTCCCAAAGCTGAGTTTGCAGAAGTTTCCAAGTTA

-continued

GTGACAGATCTTACCAAAGTCCACACGGAATGCTGCCATGGAGATCTGCTTGAATGTGCTGATGACAGGGCGG

ACCTTGCCAAGTATATCTGTGAAAATCAAGATTCGATCTCCAGTAAACTGAAGGAATGCTGTGAAAAACCTCT

GTTGGAAAAATCCCACTGCATTGCCGAAGTGGAAAATGATGAGATGCCTGCTGACTTGCCTTCATTAGCTGCT

GATTTTGTTGAAAGTAAGGATGTTTGCAAAAACTATGCTGAGGCAAAGGATGTCTTCCTGGGCATGTTTTTGT

ATGAATATGCAAGAAGGCATCCTGATTACTCTGTCGTGCTGCTGCTGAGACTTGCCAAGACATATGAAACCAC

ACTCGAGAAGTGCTGTGCCGCTGCAGATCCTCATGAATGCTATGCCAAAGTGTTCGATGAATTTAAACCTCTT

GTGGAAGAGCCTCAGAATTTAATCAAACAAAATTGTGAGCTTTTTGAGCAGCTTGGAGAGTACAAATTCCAGA

ATGCGCTATTAGTTCGTTACACCAAGAAAGTACCCCAAGTGTCAACTCCAACTCTTGTAGAGGTCTCAAGAAA

CCTAGGAAAAGTGGGCAGCAAATGTTGTAAACATCCTGAAGCAAAAAGAATGCCCTGTGCAGAAGACTATCTA

TCCGTGGTCCTGAACCAGTTATGTGTGTTGCATGAGAAAACGCCAGTAAGTGACAGAGTCACCAAATGCTGCA

CAGAATCCTTGGTGAACAGGCGACCATGCTTTTCAGCTCTGGAAGTCGATGAAACATACGTTCCCAAAGAGTT

TAATGCTGAAACATTCACCTTCCATGCAGATATATGCACACTTTCTGAGAAGGAGAGACAAATCAAGAAACAA

ACTGCACTTGTTGAGCTCGTGAAACACAAGCCCAAGGCAACAAAAGAGCAACTGAAAGCTGTTATGGATGATT

TCGCAGCTTTTGTAGAGAAGTGCTGCAAGGCTGACGATAAGGAGACCTGCTTTGCCGAGGAGGGTAAAAAACT

TGTTGCTGCAAGTCAAGCTGCCTTAGGCTTATAAGGCGCGCCCACGTGTAAAACTTGTTTATTGCAGCTTATA

ATGGTTACAAATAAAGCAATAGCATCACAAATTTCACAAATAAAGCATTTTTTTCACTGCATTCTAGTTGTGG

TTTGTCCAAACTCATCAATGTATCTTATCATGTCTGGATCATCGATGCGGCCGCTCGAGTCTAGAGGGCCCGT

TTAAACCCGCTGATCAGCCTCGACTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGAGGAAATTGCATCGCATTGTCTGA

GTAGGTGTCATTCTATTCTGGGGGGTGGGGTGGGGCAGGACAGCAAGGGGGAGGATTGGGAAGACAATAGCAG

GCATGCTGGGGATGCGGTGGGCTCTATGGCTTCTGAGGCGGAAAGAACCAGCTGGGGCTCTAGGGGGTATCCC

CACGCGCCCTGTAGCGGCGCATTAAGCGCGGCGGGTGTGGTGGTTACGCGCAGCGTGACCGCTACACTTGCCA

GCGCCCTAGCGCCCGCTCCTTTCGCTTTCTTCCCTTCCTTTCTCGCCACGTTCGCCGGCTTTCCCCGTCAAGC

TCTAAATCGGGGGCTCCCTTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGCGAATTAATTCTGT

GGAATGTGTGTCAGTTAGGGTGTGGAAAGTCCCCAGGCTCCCCAGCAGGCAGAAGTATGCAAAGCATGCATCT

CAATTAGTCAGCAACCAGGTGTGGAAAGTCCCCAGGCTCCCCAGCAGGCAGAAGTATGCAAAGCATGCATCTC

AATTAGTCAGCAACCATAGTCCCGCCCCTAACTCCGCCCATCCCGCCCCTAACTCCGCCCAGTTCCGCCCATT

CTCCGCCCCATGGCTGACTAATTTTTTTTATTTATGCAGAGGCCGAGGCCGCCTCTGCCTCTGAGCTATTCCA

GAAGTAGTGAGGAGGCTTTTTTGGAGGCCTAGGCTTTTGCAAAAAGCTCCCGGGAGCTTGTATATCCATTTTC

GGATCTGATCAAGAGACAGGATGAGGATCGTTTCGCATGATTGAACAAGATGGATTGCACGCAGGTTCTCCGG

CCGCTTGGGTGGAGAGGCTATTCGGCTATGACTGGGCACAACAGACAATCGGCTGCTCTGATGCCGCCGTGTT

CCGGCTGTCAGCGCAGGGGCGCCCGGTTCTTTTTGTCAAGACCGACCTGTCCGGTGCCCTGAATGAACTGCAG

GACGAGGCAGCGCGGCTATCGTGGCTGGCCACGACGGGCGTTCCTTGCGCAGCTGTGCTCGACGTTGTCACTG

AAGCGGGAAGGGACTGGCTGCTATTGGGCGAAGTGCCGGGGCAGGATCTCCTGTCATCTCACCTTGCTCCTGC

CGAGAAAGTATCCATCATGGCTGATGCAATGCGGCGGCTGCATACGCTTGATCCGGCTACCTGCCCATTCGAC

CACCAAGCGAAACATCGCATCGAGCGAGCACGTACTCGGATGGAAGCCGGTCTTGTCGATCAGGATGATCTGG

ACGAAGAGCATCAGGGGCTCGCGCCAGCCGAACTGTTCGCCAGGCTCAAGGCGCGCATGCCCGACGGCGAGGA

-continued

TCTCGTCGTGACCCATGGCGATGCCTGCTTGCCGAATATCATGGTGGAAAATGGCCGCTTTTCTGGATTCATC

GACTGTGGCCGGCTGGGTGTGGCGGACCGCTATCAGGACATAGCGTTGGCTACCCGTGATATTGCTGAAGAGC

TTGGCGGCGAATGGGCTGACCGCTTCCTCGTGCTTTACGGTATCGCCGCTCCCGATTCGCAGCGCATCGCCTT

CTATCGCCTTCTTGACGAGTTCTTCTGAGCGGGACTCTGGGGTTCGAAATGACCGACCAAGCGACGCCCAACC

TGCCATCACGAGATTTCGATTCCACCGCCGCCTTCTATGAAAGGTTGGGCTTCGGAATCGTTTTCCGGGACGC

CGGCTGGATGATCCTCCAGCGCGGGGATCTCATGCTGGAGTTCTTCGCCCACCCCAACTTGTTTATTGCAGCT

TATAATGGTTACAAATAAAGCAATAGCATCACAAATTTCACAAATAAAGCATTTTTTTCACTGCATTCTAGTT

GTGGTTTGTCCAAACTCATCAATGTATCTTATCATGTCTGTATACCGTCGACCTCTAGCTAGAGCTTGGCGTA

ATCATGGTCATAGCTGTTTCCTGTGTGAAATTGTTATCCGCTCACAATTCCACACAACATACGAGCCGGAAGC

ATAAAGTGTAAAGCCTGGGGTGCCTAATGAGTGAGCTAACTCACATTAATTGCGTTGCGCTCACTGCCCGCTT

TCCAGTCGGGAAACCTGTCGTGCCAGCTGCATTAATGAATCGGCCAACGCGCGGGGAGAGGCGGTTTGCGTAT

TGGGCGCTCTTCCGCTTCCTCGCTCACTGACTCGCTGCGCTCGGTCGTTCGGCTGCGGCGAGCGGTATCAGCT

CACTCAAAGGCGGTAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCCCCCCTGACGAGCA

TCACAAAAATCGACGCTCAAGTCAGAGGTGGCGAAACCCGACAGGACTATAAAGATACCAGGCGTTTCCCCCT

GGAAGCTCCCTCGTGCGCTCTCCTGTTCCGACCCTGCCGCTTACCGGATACCTGTCCGCCTTTCTCCCTTCGG

GAAGCGTGGCGCTTTCTCATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGCGAGGTATGTAGGCGGTG

CTACAGAGTTCTTGAAGTGGTGGCCTAACTACGGCTACACTAGAAGAACAGTATTTGGTATCTGCGCTCTGCT

GAAGCCAGTTACCTTCGGAAAAAGAGTTGGTAGCTCTTGATCCGGCAAACAAACCACCGCTGGTAGCGGTGGT

TTTTTTGTTTGCAAGCAGCAGATTACGCGCAGAAAAAAAGGATCTCAAGAAGATCCTTTGATCTTTTCTACGG

GGTCTGACGCTCAGTGGAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTAAACTTGGTCTGACAGT

TACCAATGCTTAATCAGTGAGGCACCTATCTCAGCGATCTGTCTATTTCGTTCATCCATAGTTGCCTGACTCC

CCGTCGTGTAGATAACTACGATACGGGAGGGCTTACCATCTGGCCCCAGTGCTGCAATGATACCGCGAGACCC

ACGCTCACCGGCTCCAGATTTATCAGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAGTAAGTAGTTCGCCAGTTAATAGTT

TGCGCAACGTTGTTGCCATTGCTACAGGCATCGTGGTGTCACGCTCGTCGTTTGGTATGGCTTCATTCAGCTC

CGGTTCCCAACGATCAAGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCACTGCATAATTCTCTTA

CTGTCATGCCATCCGTAAGATGCTTTTCTGTGACTGGTGAGTACTCAACCAAGTCATTCTGAGAATAGTGTAT

GCGGCGACCGAGTTGCTCTTGCCCGGCGTCAATACGGGATAATACCGCGCCACATAGCAGAACTTTAAAAGTG

CTCATCATTGGAAAACGTTCTTCGGGGCGAAAACTCTCAAGGATCTTACCGCTGTTGAGATCCAGTTCGATGT

AACCCACTCGTGCACCCAACTGATCTTCAGCATCTTTTACTTTCACCAGCGTTTCTGGGTGAGCAAAAACAGG

-continued

AAGGCAAAATGCCGCAAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTATTTAGAAAAATAAAC

AAATAGGGGTTCCGCGCACATTTCCCCGAAAAGTGCCACCTGACGTC

MimiH9Prom_kozak_hAlb sig_FLAG_ENPPlopt_LINK_hAlb_pcDNA3.1(+)
(SEQ ID NO: 100)

GACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGG

CAAGGCTTGACCGACAATTGCATGAAGAATCTGCTTAGGGTTAGGCGTTTTGCGCTGCTTCGCGATGTACGGG

CCAGATATACGCGTTGAAAACTACAATTGACTATCTCTAAATTTTAAAATGTGATGATAGTTACTACTTCAGT

GGTCCACACTGTTTCTATCCTTTGGAACATAAGATTTTGTTGTGTAGCTTAAGGAAGAGGAATTCAGCAGTTG

ACTATCTCGATTGTTCTGGGAATTTTGGAGGCTGAGGGGAAATTTTCACATATAAGCGCTGGGTTTGCTGGGG

TATTGAGAGTGACCTCTGGCTAACTAGAGAACCCACTGCTTACTGGCTTATCGAAATTAATACGACTCACTAT

AGGGAGACCCAAGCTGGCTAGCGCCACCATGAAGTGGGTAACCTTTATTTCCCTTCTTTTTCTCTTTAGCTCG

GCTTATTCCAGGGGTGTGTTTCGTCGAGACTACAAAGACGATGACGACAAGAGCGCTGGCCTGAAGCCAAGCT

GCGCCAAGGAGGTGAAGAGCTGCAAGGGCAGATGTTTCGAACGGACCTTCGGCAACTGCAGATGCGACGCCGC

CTGCGTGGAACTGGGAAACTGTTGTCTGGACTACCAGGAGACATGTATCGAGCCTGAGCACATCTGGACATGC

AACAAGTTCAGATGTGGCGAGAAAAGACTGACTCGGAGTCTGTGCGCCTGTTCTGACGACTGCAAGGACAAGG

GCGATTGCTGCATCAACTACAGCAGCGTGTGCCAGGGCGAAAAGAGCTGGGTCGAGGAACCCTGCGAGAGCAT

CAACGAGCCCCAGTGCCCTGCCGGATTTGAGACACCTCCTACCCTGCTCTTCTCCCTGGATGGCTTCAGAGCT

GAGTACCTGCATACATGGGGAGGACTGCTGCCTGTGATCAGCAAGCTGAAGAAGTGCGGCACCTACACAAAGA

ACATGCGGCCTGTCTACCCTACCAAGACCTTCCCCAACCACTACAGCATCGTGACCGGCCTGTACCCCGAGAG

CCACGGCATCATCGACAACAAGATGTACGACCCCAAAATGAACGCCAGCTTCAGCCTGAAATCTAAGGAAAAG

TTCAACCCTGAGTGGTATAAGGGCGAGCCAATCTGGGTGACAGCCAAGTACCAGGGCCTGAAGAGCGGCACCT

TCTTCTGGCCTGGCAGCGACGTGGAGATCAACGGAATCTTCCCTGATATCTACAAGATGTATAACGGCTCCGT

GCCTTTCGAGGAGCGGATCTTGGCTGTTCTTCAGTGGCTGCAGCTGCCCAAGGACGAGAGACCCCACTTCTAC

ACCCTGTACCTGGAAGAACCTGACAGCAGCGGCCACAGCTACGGCCCTGTGTCTAGCGAGGTGATCAAGGCCC

TGCAAAGAGTGGATGGCATGGTGGGCATGCTGATGGATGGACTGAAGGAACTGAACCTCCATCGTTGCCTGAA

CCTGATCCTGATCTCCGACCACGGCATGGAACAGGGCAGCTGTAAAAAGTACATCTACCTGAACAAGTACCTG

GGCGACGTGAAGAATATCAAGGTGATCTACGGGCCGGCCGCCAGGCTGCGGCCTAGCGACGTGCCCGACAAGT

ATTACAGCTTCAACTACGAGGGCATCGCCAGAAACCTGTCTTGCAGAGAACCCAATCAACACTTCAAGCCTTA

CCTGAAGCACTTTCTGCCTAAGAGACTGCACTTCGCCAAAAGCGACAGAATTGAACCCCTGACATTCTATCTG

GACCCTCAGTGGCAGCTGGCCCTCAATCCTTCTGAACGCAAATACTGCGGTAGCGGATTTCACGGCTCTGATA

ACGTGTTTTCTAACATGCAGGCCCTGTTTGTGGGCTACGGCCCTGGCTTCAAGCACGGAATCGAGGCTGACAC

CTTCGAGAACATCGAAGTTTACAATCTGATGTGCGACCTGCTGAATCTGACCCCAGCCCCTAACAACGGCACA

CACGGCTCTCTGAATCACCTGCTCAAGAACCCCGTGTATACCCCCAAACACCCTAAAGAGGTCCATCCACTGG

TGCAGTGCCCATTCACCAGAAACCCTCGGGACAACCTTGGCTGCAGCTGCAACCCTAGCATCCTCCCTATCGA

AGATTTCCAGACCCAGTTTAACCTGACTGTCGCCGAAGAGAAGATCATCAAGCACGAAACCCTGCCCTACGGG

AGGCCCAGAGTGCTGCAGAAAGAAAACACAATCTGTCTGCTGAGCCAGCACCAGTTTATGAGCGGCTACAGTC

AGGACATCCTGATGCCTCTGTGGACCAGCTACACCGTGGACCGGAATGACAGCTTCAGCACCGAGGACTTCAG

CAACTGCCTGTATCAGGACTTCCGCATCCCTCTGTCCCCTGTGCATAAGTGCAGCTTTTACAAGAACAACACC

AAGGTGAGCTACGGGTTTCTGAGCCCACCACAACTGAACAAAAATAGCTCTGGCATCTACTCTGAGGCGCTGC

-continued

TGACCACCAACATCGTGCCAATGTACCAGAGCTTCCAGGTGATCTGGCGGTACTTCCATGATACCCTGCTTCG

GAAGTACGCCGAAGAACGGAACGGCGTGAACGTGGTGTCCGGCCCAGTGTTCGACTTCGACTACGACGGCAGA

TGTGATTCCCTTGAGAATCTGAGACAGAAGCGGCGGGTTATCAGAAACCAGGAGATCCTGATTCCTACCCACT

TCTTCATCGTGCTGACATCTTGCAAGGATACCAGCCAAACACCTCTGCACTGCGAGAACCTGGACACCCTGGC

CTTCATCCTGCCTCACCGGACCGATAATAGCGAATCCTGTGTGCACGGCAAACACGACTCTAGCTGGGTGGAA

GAGCTGCTGATGCTGCACAGAGCCCGGATCACAGATGTGGAACACATCACCGGCCTGTCCTTCTACCAACAGA

GAAAGGAACCCGTGTCTGATATCCTGAAGCTGAAAACCCACCTGCCTACCTTCAGCCAGGAGGACCTGATCGT

TAACGATGCACACAAGAGTGAGGTTGCTCATCGGTTTAAAGATTTGGGAGAAGAAAATTTCAAAGCCTTGGTG

TTGATTGCCTTTGCTCAGTATCTTCAGCAGTGTCCATTTGAAGATCATGTAAAATTAGTGAATGAAGTAACTG

AATTTGCAAAAACATGTGTTGCTGATGAGTCAGCTGAAAATTGTGACAAATCACTTCATACCCTTTTTGGAGA

CAAATTATGCACAGTTGCAACTCTTCGTGAAACCTATGGTGAAATGGCTGACTGCTGTGCAAAACAAGAACCT

GAGAGAAATGAATGCTTCTTGCAACACAAAGATGACAACCCAAACCTCCCCCGATTGGTGAGACCAGAGGTTG

ATGTGATGTGCACTGCTTTTCATGACAATGAAGAGACATTTTTGAAAAAATACTTATATGAAATTGCCAGAAG

ACATCCTTACTTTTATGCCCCGGAACTCCTTTTCTTTGCTAAAAGGTATAAAGCTGCTTTTACAGAATGTTGC

CAAGCTGCTGATAAAGCTGCCTGCCTGTTGCCAAAGCTCGATGAACTTCGGGATGAAGGGAAGGCTTCGTCTG

CCAAACAGAGACTCAAGTGTGCCAGTCTCCAAAAATTTGGAGAAAGAGCTTTCAAAGCATGGGCAGTAGCTCG

CCTGAGCCAGAGATTTCCCAAAGCTGAGTTTGCAGAAGTTTCCAAGTTAGTGACAGATCTTACCAAAGTCCAC

ACGGAATGCTGCCATGGAGATCTGCTTGAATGTGCTGATGACAGGGCGGACCTTGCCAAGTATATCTGTGAAA

ATCAAGATTCGATCTCCAGTAAACTGAAGGAATGCTGTGAAAAACCTCTGTTGGAAAAATCCCACTGCATTGC

CGAAGTGGAAAATGATGAGATGCCTGCTGACTTGCCTTCATTAGCTGCTGATTTTGTTGAAAGTAAGGATGTT

TGCAAAAACTATGCTGAGGCAAAGGATGTCTTCCTGGGCATGTTTTTGTATGAATATGCAAGAAGGCATCCTG

ATTACTCTGTCGTGCTGCTGCTGAGACTTGCCAAGACATATGAAACCACACTCGAGAAGTGCTGTGCCGCTGC

AGATCCTCATGAATGCTATGCCAAAGTGTTCGATGAATTTAAACCTCTTGTGGAAGAGCCTCAGAATTTAATC

AAACAAAATTGTGAGCTTTTTGAGCAGCTTGGAGAGTACAAATTCCAGAATGCGCTATTAGTTCGTTACACCA

AGAAAGTACCCCAAGTGTCAACTCCAACTCTTGTAGAGGTCTCAAGAAACCTAGGAAAAGTGGGCAGCAAATG

TTGTAAACATCCTGAAGCAAAAAGAATGCCCTGTGCAGAAGACTATCTATCCGTGGTCCTGAACCAGTTATGT

GTGTTGCATGAGAAAACGCCAGTAAGTGACAGAGTCACCAAATGCTGCACAGAATCCTTGGTGAACAGGCGAC

CATGCTTTTCAGCTCTGGAAGTCGATGAAACATACGTTCCCAAAGAGTTTAATGCTGAAACATTCACCTTCCA

TGCAGATATATGCACACTTTCTGAGAAGGAGAGACAAATCAAGAAACAAACTGCACTTGTTGAGCTCGTGAAA

CACAAGCCCAAGGCAACAAAAGAGCAACTGAAAGCTGTTATGGATGATTTCGCAGCTTTTGTAGAGAAGTGCT

GCAAGGCTGACGATAAGGAGACCTGCTTTGCCGAGGAGGGTAAAAAACTTGTTGCTGCAAGTCAAGCTGCCTT

AGGCTTATGAGGTACCGAGCTCGGATCCACTAGTCCAGTGTGGTGGAATTCTGCAGATATCCAGCACAGTGGC

GGCCGCTCGAGTCTAGAGGGCCCGTTTAAACCCGCTGATCAGCCTCGACTGTGCCTTCTAGTTGCCAGCCATC

TGTTGTTTGCCCCTCCCCCGTGCCTTCCTTGACCCTGGAAGGTGCCACTCCCACTGTCCTTTCCTAATAAAAT

GAGGAAATTGCATCGCATTGTCTGAGTAGGTGTCATTCTATTCTGGGGGGTGGGGTGGGGCAGGACAGCAAGG

GGGAGGATTGGGAAGACAATAGCAGGCATGCTGGGGATGCGGTGGGCTCTATGGCTTCTGAGGCGGAAAGAAC

CAGCTGGGGCTCTAGGGGGTATCCCCACGCGCCCTGTAGCGGCGCATTAAGCGCGGCGGGTGTGGTGGTTACG

CGCAGCGTGACCGCTACACTTGCCAGCGCCCTAGCGCCCGCTCCTTTCGCTTTCTTCCCTTCCTTTCTCGCCA

CGTTCGCCGGCTTTCCCCGTCAAGCTCTAAATCGGGGGCTCCCTTTAGGGTTCCGATTTAGTGCTTTACGGCA

CCTCGACCCCAAAAAACTTGATTAGGGTGATGGTTCACGTAGTGGGCCATCGCCCTGATAGACGGTTTTTCGC

-continued

CCTTTGACGTTGGAGTCCACGTTCTTTAATAGTGGACTCTTGTTCCAAACTGGAACAACACTCAACCCTATCT

CGGTCTATTCTTTTGATTTATAAGGGATTTTGCCGATTTCGGCCTATTGGTTAAAAAATGAGCTGATTTAACA

AAAATTTAACGCGAATTAATTCTGTGGAATGTGTGTCAGTTAGGGTGTGGAAAGTCCCCAGGCTCCCCAGCAG

GCAGAAGTATGCAAAGCATGCATCTCAATTAGTCAGCAACCAGGTGTGGAAAGTCCCCAGGCTCCCCAGCAGG

CAGAAGTATGCAAAGCATGCATCTCAATTAGTCAGCAACCATAGTCCCGCCCCTAACTCCGCCCATCCCGCCC

CTAACTCCGCCCAGTTCCGCCCATTCTCCGCCCCATGGCTGACTAATTTTTTTTATTTATGCAGAGGCCGAGG

CCGCCTCTGCCTCTGAGCTATTCCAGAAGTAGTGAGGAGGCTTTTTTGGAGGCCTAGGCTTTTGCAAAAAGCT

CCCGGGAGCTTGTATATCCATTTTCGGATCTGATCAAGAGACAGGATGAGGATCGTTTCGCATGATTGAACAA

GATGGATTGCACGCAGGTTCTCCGGCCGCTTGGGTGGAGAGGCTATTCGGCTATGACTGGGCACAACAGACAA

TCGGCTGCTCTGATGCCGCCGTGTTCCGGCTGTCAGCGCAGGGGCGCCCGGTTCTTTTTGTCAAGACCGACCT

GTCCGGTGCCCTGAATGAACTGCAGGACGAGGCAGCGCGGCTATCGTGGCTGGCCACGACGGGCGTTCCTTGC

GCAGCTGTGCTCGACGTTGTCACTGAAGCGGGAAGGGACTGGCTGCTATTGGGCGAAGTGCCGGGGCAGGATC

TCCTGTCATCTCACCTTGCTCCTGCCGAGAAAGTATCCATCATGGCTGATGCAATGCGGCGGCTGCATACGCT

TGATCCGGCTACCTGCCCATTCGACCACCAAGCGAAACATCGCATCGAGCGAGCACGTACTCGGATGGAAGCC

GGTCTTGTCGATCAGGATGATCTGGACGAAGAGCATCAGGGGCTCGCGCCAGCCGAACTGTTCGCCAGGCTCA

AGGCGCGCATGCCCGACGGCGAGGATCTCGTCGTGACCCATGGCGATGCCTGCTTGCCGAATATCATGGTGGA

AAATGGCCGCTTTTCTGGATTCATCGACTGTGGCCGGCTGGGTGTGGCGGACCGCTATCAGGACATAGCGTTG

GCTACCCGTGATATTGCTGAAGAGCTTGGCGGCGAATGGGCTGACCGCTTCCTCGTGCTTTACGGTATCGCCG

CTCCCGATTCGCAGCGCATCGCCTTCTATCGCCTTCTTGACGAGTTCTTCTGAGCGGGACTCTGGGGTTCGAA

ATGACCGACCAAGCGACGCCCAACCTGCCATCACGAGATTTCGATTCCACCGCCGCCTTCTATGAAAGGTTGG

GCTTCGGAATCGTTTTCCGGGACGCCGGCTGGATGATCCTCCAGCGCGGGGATCTCATGCTGGAGTTCTTCGC

CCACCCCAACTTGTTTATTGCAGCTTATAATGGTTACAAATAAAGCAATAGCATCACAAATTTCACAAATAAA

GCATTTTTTTCACTGCATTCTAGTTGTGGTTTGTCCAAACTCATCAATGTATCTTATCATGTCTGTATACCGT

CGACCTCTAGCTAGAGCTTGGCGTAATCATGGTCATAGCTGTTTCCTGTGTGAAATTGTTATCCGCTCACAAT

TCCACACAACATACGAGCCGGAAGCATAAAGTGTAAAGCCTGGGGTGCCTAATGAGTGAGCTAACTCACATTA

ATTGCGTTGCGCTCACTGCCCGCTTTCCAGTCGGGAAACCTGTCGTGCCAGCTGCATTAATGAATCGGCCAAC

GCGCGGGGAGAGGCGGTTTGCGTATTGGGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCACAGAATCAGGGGATAACGCA

GGAAAGAACATGTGAGCAAAAGGCCAGCAAAAGGCCAGGAACCGTAAAAAGGCCGCGTTGCTGGCGTTTTTCC

ATAGGCTCCGCCCCCCTGACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGACCCTGCCGCTTACCGGA

TACCTGTCCGCCTTTCTCCCTTCGGGAAGCGTGGCGCTTTCTCATAGCTCACGCTGTAGGTATCTCAGTTCGG

TGTAGGTCGTTCGCTCCAAGCTGGGCTGTGTGCACGAACCCCCCGTTCAGCCCGACCGCTGCGCCTTATCCGG

TAACTATCGTCTTGAGTCCAACCCGGTAAGACACGACTTATCGCCACTGGCAGCAGCCACTGGTAACAGGATT

AGCAGAGCGAGGTATGTAGGCGGTGCTACAGAGTTCTTGAAGTGGTGGCCTAACTACGGCTACACTAGAAGAA

CAGTATTTGGTATCTGCGCTCTGCTGAAGCCAGTTACCTTCGGAAAAAGAGTTGGTAGCTCTTGATCCGGCAA

ACAAACCACCGCTGGTAGCGGTGGTTTTTTTGTTTGCAAGCAGCAGATTACGCGCAGAAAAAAAGGATCTCAA

GAAGATCCTTTGATCTTTTCTACGGGGTCTGACGCTCAGTGGAACGAAAACTCACGTTAAGGGATTTTGGTCA

TGAGATTATCAAAAAGGATCTTCACCTAGATCCTTTTAAATTAAAAATGAAGTTTTAAATCAATCTAAAGTAT

-continued

ATATGAGTAAACTTGGTCTGACAGTTACCAATGCTTAATCAGTGAGGCACCTATCTCAGCGATCTGTCTATTT

CGTTCATCCATAGTTGCCTGACTCCCCGTCGTGTAGATAACTACGATACGGGAGGGCTTACCATCTGGCCCCA

GTGCTGCAATGATACCGCGAGACCCACGCTCACCGGCTCCAGATTTATCAGCAATAAACCAGCCAGCCGGAAG

GGCCGAGCGCAGAAGTGGTCCTGCAACTTTATCCGCCTCCATCCAGTCTATTAATTGTTGCCGGGAAGCTAGA

GTAAGTAGTTCGCCAGTTAATAGTTTGCGCAACGTTGTTGCCATTGCTACAGGCATCGTGGTGTCACGCTCGT

CGTTTGGTATGGCTTCATTCAGCTCCGGTTCCCAACGATCAAGGCGAGTTACATGATCCCCCATGTTGTGCAA

AAAAGCGGTTAGCTCCTTCGGTCCTCCGATCGTTGTCAGAAGTAAGTTGGCCGCAGTGTTATCACTCATGGTT

ATGGCAGCACTGCATAATTCTCTTACTGTCATGCCATCCGTAAGATGCTTTTCTGTGACTGGTGAGTACTCAA

CCAAGTCATTCTGAGAATAGTGTATGCGGCGACCGAGTTGCTCTTGCCCGGCGTCAATACGGGATAATACCGC

GCCACATAGCAGAACTTTAAAAGTGCTCATCATTGGAAAACGTTCTTCGGGGCGAAAACTCTCAAGGATCTTA

CCGCTGTTGAGATCCAGTTCGATGTAACCCACTCGTGCACCCAACTGATCTTCAGCATCTTTTACTTTCACCA

GCGTTTCTGGGTGAGCAAAAACAGGAAGGCAAAATGCCGCAAAAAAGGGAATAAGGGCGACACGGAAATGTTG

AATACTCATACTCTTCCTTTTTCAATATTATTGAAGCATTTATCAGGGTTATTGTCTCATGAGCGGATACATA

TTTGAATGTATTTAGAAAAATAAACAAATAGGGGTTCCGCGCACATTTCCCCGAAAAGTGCCACCTGACGTC pAAV-ENPP1 FL-miR122 3x BS (SEQ ID NO: 101)

CCAAGTCATTCTGAGAATAGTGTATGCGGCGACCGAGTTGCTCTTGCCCGGCGTCAATACGGGATAATACCGC

GCCACATAGCAGAACTTTAAAAGTGCTCATCATTGGAAAACGTTCTTCGGGGCGAAAACTCTCAAGGATCTTA

CCGCTGTTGAGATCCAGTTCGATGTAACCCACTCGTGCACCCAACTGATCTTCAGCATCTTTTACTTTCACCA

GCGTTTCTGGGTGAGCAAAAACAGGAAGGCAAAATGCCGCAAAAAAGGGAATAAGGGCGACACGGAAATGTTG

AATACTCATACTCTTCCTTTTTCAATATTATTGAAGCATTTATCAGGGTTATTGTCTCATGAGCGGATACATA

TTTGAATGTATTTAGAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTTCGTCTCGCGCGTTT

CGGTGATGACGGTGAAAACCTCTGACACATGCAGCTCCCGGAGACGGTCACAGCTTGTCTGTAAGCGGATGCC

GGGAGCAGACAAGCCCGTCAGGGCGCGTCAGCGGGTGTTGGCGGGTGTCGGGGCTGGCTTAACTATGCGGCAT

CAGAGCAGATTGTACTGAGAGTGCACCATATGCGGTGTGAAATACCGCACAGATGCGTAAGGAGAAAATACCG

CATCAGGAAATTGTAAGCGTTAATATTTTGTTAAAATTCGCGTTAAATTTTTGTTAAATCAGCTCATTTTTTA

ACCAATAGGCCGAAATCGGCAAAATCCCTTATAAATCAAAAGAATAGACCGAGATAGGGTTGAGTGTTGTTCC

AGTTTGGAACAAGAGTCCACTATTAAAGAACGTGGACTCCAACGTCAAAGGGCGAAAAACCGTCTATCAGGGC

GATGGCCCACTACGTGAACCATCACCCTAATCAAGTTTTTTGGGGTCGAGGTGCCGTAAAGCACTAAATCGGA

ACCCTAAAGGGAGCCCCCGATTTAGAGCTTGACGGGGAAAGCCGGCGAACGTGGCGAGAAAGGAAGGGAAGAA

AGCGAAAGGAGCGGGCGCTAGGGCGCTGGCAAGTGTAGCGGTCACGCTGCGCGTAACCACCACACCCGCCGCG

CTTAATGCGCCGCTACAGGGCGCGTCCATTCGCCATTCAGGCTGCGCAACTGTTGGGAAGGGCGATCGGTGCG

GGCCTCTTCGCTATTACGCCAGGCTGCAGGGGGGGGGGGGGGGGGGGCCACTCCCTCTCTGCGCGCTCGCTCGC

TCACTGAGGCCGCCCGGGCAAAGCCCGGGCGTCGGGCGACCTTTGGTCGCCCGGCCTCAGTGAGCGAGCGAGC

GCGCAGAGAGGGAGTGGCCAACTCCATCACTAGGGGTTCCTCAGATCTGAATTCGGTACCTAGTTATTAATAG

TAATCAATTACGGGGTCATTAGTTCATAGCCCATATATGGAGTTCCGCGTTACATAACTTACGGTAAATGGCC

CGCCTGGCTGACCGCCCAACGACCCCCGCCCATTGACGTCAATAATGACGTATGTTCCCATAGTAACGCCAAT

AGGGACTTTCCATTGACGTCAATGGGTGGAGTATTTACGGTAAACTGCCCACTTGGCAGTACATCAAGTGTAT

CATATGCCAAGTACGCCCCCTATTGACGTCAATGACGGTAAATGGCCCGCCTGGCATTATGCCCAGTACATGA

CCTTATGGGACTTTCCTACTTGGCAGTACATCTACGTATTAGTCATCGCTATTACCATGGTCGAGGTGAGCCC

-continued

CACGTTCTGCTTCACTCTCCCCATCTCCCCCCCCTCCCCACCCCCAATTTTGTATTTATTTATTTTTTAATTA

TTTTGTGCAGCGATGGGGGCGGGGGGGGGGGGGGGGCGCGCGCCAGGCGGGGGGGGCGGGGCGAGGGGGGGG

CGGGGCGAGGCGGAGAGGTGCGGCGGCAGCCAATCAGAGCGGCGCGCTCCGAAAGTTTCCTTTTATGGCGAGG

CGGCGGCGGCGGCGGCCCTATAAAAAGCGAAGCGCGCGGCGGGCGGGAGTCGCTGCGCGCTGCCTTCGCCCCG

TGCCCCGCTCCGCCGCCGCCTCGCGCCGCCCGCCCCGGCTCTGACTGACCGCGTTACTCCCACAGGTGAGCGG

GCGGGACGGCCCTTCTCCTCCGGGCTGTAATTAGCGCTTGGTTTAATGACGGCTTGTTTCTTTTCTGTGGCTG

CGTGAAAGCCTTGAGGGGCTCCGGGAGCTAGAGCCTCTGCTAACCATGTTCATGCCTTCTTCTTTTTCCTACA

GCTCCTGGGCAACGTGCTGGTTATTGTGCTGTCTCATCATTTTGGCAAAGAATTCCTCGAAGATCCGAAGGGG

TTCAAGCTTAGCGCCACCATGGAGCGCGACGGCTGCGCGGGGGGCGGGAGCCGCGGCGGCGAGGGGGGCGCG

CTCCCCGGGAGGGCCCGGCGGGGAACGGCCGCGATCGGGGCCGCAGCCACGCTGCCGAGGCGCCCGGGGACCC

GCAGGCCGCGGCGTCCTTGCTGGCCCCTATGGACGTGGGGGAGGAGCCGCTGGAGAAGGCGGCGCGCGCCCGC

ACTGCCAAGGACCCCAACACCTATAAAGTACTCTCGCTGGTATTGTCAGTATGTGTGTTAACAACAATACTTG

GTTGTATATTTGGGTTGAAACCAAGCTGTGCCAAAGAAGTTAAAAGTTGCAAAGGTCGCTGTTTCGAGAGAAC

ATTTGGGAACTGTCGCTGTGATGCTGCCTGTGTTGAGCTTGGAAACTGCTGTTTAGATTACCAGGAGACGTGC

ATAGAACCAGAACATATATGGACTTGCAACAAATTCAGGTGTGGTGAGAAAAGGTTGACCAGAAGCCTCTGTG

CCTGTTCAGATGACTGCAAGGACAAGGGCGACTGCTGCATCAACTACAGTTCTGTGTGTCAAGGTGAGAAAAG

TTGGGTAGAAGAACCATGTGAGAGCATTAATGAGCCACAGTGCCCAGCAGGGTTTGAAACGCCTCCTACCCTC

TTATTTTCTTTGGATGGATTCAGGGCAGAATATTTACACACTTGGGGTGGACTTCTTCCTGTTATTAGCAAAC

TAAAAAAATGTGGAACATATACTAAAAACATGAGACCGGTATATCCAACAAAAACTTTCCCCAATCACTACAG

CATTGTCACCGGATTGTATCCAGAATCTCATGGCATAATCGACAATAAAATGTATGATCCCAAAATGAATGCT

TCCTTTTCACTTAAAAGTAAAGAGAAATTTAATCCTGAGTGGTACAAAGGAGAACCAATTTGGGTCACAGCTA

AGTATCAAGGCCTCAAGTCTGGCACATTTTTCTGGCCAGGATCAGATGTGGAAATTAACGGAATTTTCCCAGA

CATCTATAAAATGTATAATGGTTCAGTACCATTTGAAGAAAGGATTTTAGCTGTTCTTCAGTGGCTACAGCTT

CCTAAAGATGAAAGACCACACTTTTACACTCTGTATTTAGAAGAACCAGATTCTTCAGGTCATTCATATGGAC

CAGTCAGCAGTGAAGTCATCAAAGCCTTGCAGAGGGTTGATGGTATGGTTGGTATGCTGATGGATGGTCTGAA

AGAGCTGAACTTGCACAGATGCCTGAACCTCATCCTTATTTCAGATCATGGCATGGAACAAGGCAGTTGTAAG

AAATACATATATCTGAATAAATATTTGGGGGATGTTAAAAATATTAAAGTTATCTATGGACCTGCAGCTCGAT

TGAGACCCTCTGATGTCCCAGATAAATACTATTCATTTAACTATGAAGGCATTGCCCGAAATCTTTCTTGCCG

GGAACCAAACCAGCACTTCAAACCTTACCTGAAACATTTCTTACCTAAGCGTTTGCACTTTGCTAAGAGTGAT

AGAATTGAGCCCTTGACATTCTATTTGGACCCTCAGTGGCAACTTGCATTGAATCCCTCAGAAAGGAAATATT

GTGGAAGTGGATTTCATGGCTCTGACAATGTATTTTCAAATATGCAAGCCCTCTTTGTTGGCTATGGACCTGG

ATTCAAGCATGGCATTGAGGCTGACACCTTTGAAAACATTGAAGTCTATAACTTAATGTGTGATTTACTGAAT

TTGACACCGGCTCCTAATAACGGAACTCATGGAAGTCTTAACCACCTTCTAAAGAATCCTGTTTATACGCCAA

AGCATCCCAAAGAAGTGCACCCCCTGGTACAGTGCCCCTTCACAAGAAACCCCAGAGATAACCTTGGCTGCTC

ATGTAACCCTTCGATTTTGCCGATTGAGGATTTTCAAACACAGTTCAATCTGACTGTGGCAGAAGAGAAGATT

ATTAAGCATGAAACTTTACCCTATGGAAGACCTAGAGTTCTCCAGAAGGAAAACACCATCTGTCTTCTTTCCC

AGCACCAGTTTATGAGTGGATACAGCCAAGACATCTTAATGCCCCTTTGGACATCCTATACCGTGGACAGAAA

TGACAGTTTCTCTACGGAAGACTTCTCCAACTGTCTGTACCAGGACTTTAGAATTCCTCTTAGTCCTGTCCAT

AAATGTTCATTTTATAAAAATAACACCAAAGTGAGTTACGGGTTCCTCTCCCCACCACAACTAAATAAAAATT

CAAGTGGAATATATTCTGAAGCTTTGCTTACTACAAATATAGTGCCAATGTACCAGAGTTTTCAAGTTATATG

-continued

GCGCTACTTTCATGACACCCTACTGCGAAAGTATGCTGAAGAAAGAAATGGTGTCAATGTCGTCAGTGGTCCT

GTGTTTGACTTTGATTATGATGGACGTTGTGATTCCTTAGAGAATCTGAGGCAAAAAAGAAGAGTCATCCGTA

ACCAAGAAATTTTGATTCCAACTCACTTCTTTATTGTGCTAACAAGCTGTAAAGATACATCTCAGACGCCTTT

GCACTGTGAAAACCTAGACACCTTAGCTTTCATTTTGCCTCACAGGACTGATAACAGCGAGAGCTGTGTGCAT

GGGAAGCATGACTCCTCATGGGTTGAAGAATTGTTAATGTTACACAGAGCACGGATCACAGATGTTGAGCACA

TCACTGGACTCAGCTTCTATCAACAAAGAAAAGAGCCAGTTTCAGACATTTTAAAGTTGAAAACACATTTGCC

AACCTTTAGCCAAGAAGACGACTACAAAGACGATGACGACAAGTGAGGTACCGAGCTCGGATCCAAACAAACA

CCATTGTCACACTCCAACAAACACCATTGTCACACTCCAACAAACACCATTGTCACACTCCATTCTCGAGTCT

AGAAAGAGATCCAGACATGATAAGATACATTGATGAGTTTGGACAAACCACAACTAGAATGCAGTGAAAAAAA

TGCTTTATTTGTGAAATTTGTGATGCTATTGCTTTATTTGTAACCATTATAAGCTGCAATAAACAAGTTAACA

ACAACAATTGCATTCATTTTATGTTTCAGGTTCAGGGGGAGGTGTGGGAGGTTTTTTAGTCGACTAGAGCTCG

CTGATCAGCCTCGACTGTGCCTTCTAGTTGCCAGCCATCTGTTGTTTGCCCCTCCCCCGTGCCTTCCTTGACC

CTGGAAGGTGCCACTCCCACTGTCCTTTCCTAATAAAATGAGGAAATTGCATCGCATTGTCTGAGTAGGTGTC

ATTCTATTCTGGGGGGTGGGGTGGGGCAGGACAGCAAGGGGGAGGATTGGGAAGACAATAGCAGGCATGCTGG

GGAGAGATCTGAGGAACCCCTAGTGATGGAGTTGGCCACTCCCTCTCTGCGCGCTCGCTCGCTCACTGAGGCC

GGGCGACCAAAGGTCGCCCGACGCCCGGGCTTTGCCCGGGCGGCCTCAGTGAGCGAGCGAGCGCGCAGAGAGG

GAGTGGCCCCCCCCCCCCCCCCCCCTGCAGCCTGCATTAATGAATCGGCCAACGCGCGGGGAGAGGCGGTTTG

CGTATTGGGCGCTCTTCCGCTTCCTCGCTCACTGACTCGCTGCGCTCGGTCGTTCGGCTGCGGCGAGCGGTAT

CAGCTCACTCAAAGGCGGTAATACGGTTATCCACAGAATCAGGGGATAACGCAGGAAAGAACATGTGAGCAAA

AGGCCAGCAAAAGGCCAGGAACCGTAAAAAGGCCGCGTTGCTGGCGTTTTTCCATAGGCTCCGCCCCCCTGAC

GAGCATCACAAAAATCGACGCTCAAGTCAGAGGTGGCGAAACCCGACAGGACTATAAAGATACCAGGCGTTTC

CCCCTGGAAGCTCCCTCGTGCGCTCTCCTGTTCCGACCCTGCCGCTTACCGGATACCTGTCCGCCTTTCTCCC

TTCGGGAAGCGTGGCGCTTTCTCATAGCTCACGCTGTAGGTATCTCAGTTCGGTGTAGGTCGTTCGCTCCAAG

CTGGGCTGTGTGCACGAACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGCAGAGCGAGGTATGTAGG

CGGTGCTACAGAGTTCTTGAAGTGGTGGCCTAACTACGGCTACACTAGAAGAACAGTATTTGGTATCTGCGCT

CTGCTGAAGCCAGTTACCTTCGGAAAAAGAGTTGGTAGCTCTTGATCCGGCAAACAAACCACCGCTGGTAGCG

GTGGTTTTTTTGTTTGCAAGCAGCAGATTACGCGCAGAAAAAAAGGATCTCAAGAAGATCCTTTGATCTTTTC

TACGGGGTCTGACGCTCAGTGGAACGAAAACTCACGTTAAGGGATTTTGGTCATGAGATTATCAAAAAGGATC

TTCACCTAGATCCTTTTAAATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCGTTCATCCATAGTTGCCTG

ACTCCCCGTCGTGTAGATAACTACGATACGGGAGGGCTTACCATCTGGCCCCAGTGCTGCAATGATACCGCGA

GACCCACGCTCACCGGCTCCAGATTTATCAGCAATAAACCAGCCAGCCGGAAGGGCCGAGCGCAGAAGTGGTC

CTGCAACTTTATCCGCCTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCGGTTAGCTCCTTCG

-continued

GTCCTCCGATCGTTGTCAGAAGTAAGTTGGCCGCAGTGTTATCACTCATGGTTATGGCAGCACTGCATAATTC

TCTTACTGTCATGCCATCCGTAAGATGCTTTTCTGTGACTGGTGAGTACTCAA pAAV-ENPP1-FL-miR155 3x BS (SEQ ID NO: 102)

CCAAGTCATTCTGAGAATAGTGTATGCGGCGACCGAGTTGCTCTTGCCCGGCGTCAATACGGGATAATACCGC

GCCACATAGCAGAACTTTAAAAGTGCTCATCATTGGAAAACGTTCTTCGGGGCGAAAACTCTCAAGGATCTTA

CCGCTGTTGAGATCCAGTTCGATGTAACCCACTCGTGCACCCAACTGATCTTCAGCATCTTTTACTTTCACCA

GCGTTTCTGGGTGAGCAAAAACAGGAAGGCAAAATGCCGCAAAAAAGGGAATAAGGGCGACACGGAAATGTTG

AATACTCATACTCTTCCTTTTTCAATATTATTGAAGCATTTATCAGGGTTATTGTCTCATGAGCGGATACATA

TTTGAATGTATTTAGAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTTCGTCTCGCGCGTTT

CGGTGATGACGGTGAAAACCTCTGACACATGCAGCTCCCGGAGACGGTCACAGCTTGTCTGTAAGCGGATGCC

GGGAGCAGACAAGCCCGTCAGGGCGCGTCAGCGGGTGTTGGCGGGTGTCGGGGCTGGCTTAACTATGCGGCAT

CAGAGCAGATTGTACTGAGAGTGCACCATATGCGGTGTGAAATACCGCACAGATGCGTAAGGAGAAAATACCG

CATCAGGAAATTGTAAGCGTTAATATTTTGTTAAAATTCGCGTTAAATTTTTGTTAAATCAGCTCATTTTTTA

ACCAATAGGCCGAAATCGGCAAAATCCCTTATAAATCAAAAGAATAGACCGAGATAGGGTTGAGTGTTGTTCC

AGTTTGGAACAAGAGTCCACTATTAAAGAACGTGGACTCCAACGTCAAAGGGCGAAAAACCGTCTATCAGGGC

GATGGCCCACTACGTGAACCATCACCCTAATCAAGTTTTTTGGGGTCGAGGTGCCGTAAAGCACTAAATCGGA

ACCCTAAAGGGAGCCCCCGATTTAGAGCTTGACGGGGAAAGCCGGCGAACGTGGCGAGAAAGGAAGGGAAGAA

AGCGAAAGGAGCGGGCGCTAGGGCGCTGGCAAGTGTAGCGGTCACGCTGCGCGTAACCACCACACCCGCCGCG

CTTAATGCGCCGCTACAGGGCGCGTCCATTCGCCATTCAGGCTGCGCAACTGTTGGGAAGGGCGATCGGTGCG

GGCCTCTTCGCTATTACGCCAGGCTGCAGGGGGGGGGGGGGGGGGGGCCACTCCCTCTCTGCGCGCTCGCTCGC

TCACTGAGGCCGCCCGGGCAAAGCCCGGGCGTCGGGCGACCTTTGGTCGCCCGGCCTCAGTGAGCGAGCGAGC

GCGCAGAGAGGGAGTGGCCAACTCCATCACTAGGGGTTCCTCAGATCTGAATTCGGTACCTAGTTATTAATAG

TAATCAATTACGGGGTCATTAGTTCATAGCCCATATATGGAGTTCCGCGTTACATAACTTACGGTAAATGGCC

CGCCTGGCTGACCGCCCAACGACCCCCGCCCATTGACGTCAATAATGACGTATGTTCCCATAGTAACGCCAAT

AGGGACTTTCCATTGACGTCAATGGGTGGAGTATTTACGGTAAACTGCCCACTTGGCAGTACATCAAGTGTAT

CATATGCCAAGTACGCCCCCTATTGACGTCAATGACGGTAAATGGCCCGCCTGGCATTATGCCCAGTACATGA

CCTTATGGGACTTTCCTACTTGGCAGTACATCTACGTATTAGTCATCGCTATTACCATGGTCGAGGTGAGCCC

CACGTTCTGCTTCACTCTCCCCATCTCCCCCCCCTCCCCACCCCCAATTTTGTATTTATTTATTTTTTAATTA

TTTTGTGCAGCGATGGGGGCGGGGGGGGGGGGGGGGCGCGCGCCAGGCGGGGCGGGGCGGGGCGAGGGGCGGGG

GCGGGGCGAGGCGGAGAGGTGCGGCGGCAGCCAATCAGAGCGGCGCGCTCCGAAAGTTTCCTTTTATGGCGAG

GCGGCGGCGGCGGCGGCCCTATAAAAAGCGAAGCGCGCGGCGGGCGGGAGTCGCTGCGCGCTGCCTTCGCCCC

GTGCCCCGCTCCGCCGCCGCCTCGCGCCGCCCGCCCCGGCTCTGACTGACCGCGTTACTCCCACAGGTGAGCG

GGCGGGACGGCCCTTCTCCTCCGGGCTGTAATTAGCGCTTGGTTTAATGACGGCTTGTTTCTTTTCTGTGGCT

GCGTGAAAGCCTTGAGGGGCTCCGGGAGCTAGAGCCTCTGCTAACCATGTTCATGCCTTCTTCTTTTTCCTAC

AGCTCCTGGGCAACGTGCTGGTTATTGTGCTGTCTCATCATTTTGGCAAAGAATTCCTCGAAGATCCGAAGGG

GTTCAAGCTTAGCGCCACCATGGAGCGCGACGGCTGCGCGGGGGGCGGGAGCCGCGGCGGCGAGGGCGGGCGC

GCTCCCCGGGAGGGCCCGGCGGGGAACGGCCGCGATCGGGGCCGCAGCCACGCTGCCGAGGCGCCCGGGGACC

CGCAGGCCGCGGCGTCCTTGCTGGCCCCTATGGACGTGGGGGAGGAGCCGCTGGAGAAGGCGGCGCGCGCCCG

CACTGCCAAGGACCCCAACACCTATAAAGTACTCTCGCTGGTATTGTCAGTATGTGTGTTAACAACAATACTT

-continued

GGTTGTATATTTGGGTTGAAACCAAGCTGTGCCAAAGAAGTTAAAAGTTGCAAAGGTCGCTGTTTCGAGAGAA

CATTTGGGAACTGTCGCTGTGATGCTGCCTGTGTTGAGCTTGGAAACTGCTGTTTAGATTACCAGGAGACGTG

CATAGAACCAGAACATATATGGACTTGCAACAAATTCAGGTGTGGTGAGAAAAGGTTGACCAGAAGCCTCTGT

GCCTGTTCAGATGACTGCAAGGACAAGGGCGACTGCTGCATCAACTACAGTTCTGTGTGTCAAGGTGAGAAAA

GTTGGGTAGAAGAACCATGTGAGAGCATTAATGAGCCACAGTGCCCAGCAGGGTTTGAAACGCCTCCTACCCT

CTTATTTTCTTTGGATGGATTCAGGGCAGAATATTTACACACTTGGGGTGGACTTCTTCCTGTTATTAGCAAA

CTAAAAAAATGTGGAACATATACTAAAAACATGAGACCGGTATATCCAACAAAAACTTTCCCCAATCACTACA

GCATTGTCACCGGATTGTATCCAGAATCTCATGGCATAATCGACAATAAAATGTATGATCCCAAAATGAATGC

TTCCTTTTCACTTAAAAGTAAAGAGAAATTTAATCCTGAGTGGTACAAAGGAGAACCAATTTGGGTCACAGCT

AAGTATCAAGGCCTCAAGTCTGGCACATTTTTCTGGCCAGGATCAGATGTGGAAATTAACGGAATTTTCCCAG

ACATCTATAAAATGTATAATGGTTCAGTACCATTTGAAGAAAGGATTTTAGCTGTTCTTCAGTGGCTACAGCT

TCCTAAAGATGAAAGACCACACTTTTACACTCTGTATTTAGAAGAACCAGATTCTTCAGGTCATTCATATGGA

CCAGTCAGCAGTGAAGTCATCAAAGCCTTGCAGAGGGTTGATGGTATGGTTGGTATGCTGATGGATGGTCTGA

AAGAGCTGAACTTGCACAGATGCCTGAACCTCATCCTTATTTCAGATCATGGCATGGAACAAGGCAGTTGTAA

GAAATACATATATCTGAATAAATATTTGGGGGATGTTAAAAATATTAAAGTTATCTATGGACCTGCAGCTCGA

TTGAGACCCTCTGATGTCCCAGATAAATACTATTCATTTAACTATGAAGGCATTGCCCGAAATCTTTCTTGCC

GGGAACCAAACCAGCACTTCAAACCTTACCTGAAACATTTCTTACCTAAGCGTTTGCACTTTGCTAAGAGTGA

TAGAATTGAGCCCTTGACATTCTATTTGGACCCTCAGTGGCAACTTGCATTGAATCCCTCAGAAAGGAAATAT

TGTGGAAGTGGATTTCATGGCTCTGACAATGTATTTTCAAATATGCAAGCCCTCTTTGTTGGCTATGGACCTG

GATTCAAGCATGGCATTGAGGCTGACACCTTTGAAAACATTGAAGTCTATAACTTAATGTGTGATTTACTGAA

TTTGACACCGGCTCCTAATAACGGAACTCATGGAAGTCTTAACCACCTTCTAAAGAATCCTGTTTATACGCCA

AAGCATCCCAAAGAAGTGCACCCCCTGGTACAGTGCCCCTTCACAAGAAACCCCAGAGATAACCTTGGCTGCT

CATGTAACCCTTCGATTTTGCCGATTGAGGATTTTCAAACACAGTTCAATCTGACTGTGGCAGAAGAGAAGAT

TATTAAGCATGAAACTTTACCCTATGGAAGACCTAGAGTTCTCCAGAAGGAAAACACCATCTGTCTTCTTTCC

CAGCACCAGTTTATGAGTGGATACAGCCAAGACATCTTAATGCCCCTTTGGACATCCTATACCGTGGACAGAA

ATGACAGTTTCTCTACGGAAGACTTCTCCAACTGTCTGTACCAGGACTTTAGAATTCCTCTTAGTCCTGTCCA

TAAATGTTCATTTTATAAAAATAACACCAAAGTGAGTTACGGGTTCCTCTCCCCACCACAACTAAATAAAAAT

TCAAGTGGAATATATTCTGAAGCTTTGCTTACTACAAATATAGTGCCAATGTACCAGAGTTTTCAAGTTATAT

GGCGCTACTTTCATGACACCCTACTGCGAAAGTATGCTGAAGAAAGAAATGGTGTCAATGTCGTCAGTGGTCC

TGTGTTTGACTTTGATTATGATGGACGTTGTGATTCCTTAGAGAATCTGAGGCAAAAAAGAAGAGTCATCCGT

AACCAAGAAATTTTGATTCCAACTCACTTCTTTATTGTGCTAACAAGCTGTAAAGATACATCTCAGACGCCTT

TGCACTGTGAAAACCTAGACACCTTAGCTTTCATTTTGCCTCACAGGACTGATAACAGCGAGAGCTGTGTGCA

TGGGAAGCATGACTCCTCATGGGTTGAAGAATTGTTAATGTTACACAGAGCACGGATCACAGATGTTGAGCAC

ATCACTGGACTCAGCTTCTATCAACAAAGAAAAGAGCCAGTTTCAGACATTTTAAAGTTGAAAACACATTTGC

CAACCTTTAGCCAAGAAGACGACTACAAAGACGATGACGACAAGTGAGGTACCGAGCTCGGATCCCAATTACG

ATTAGCACTATCCAATTACGATTAGCACTATCCAATTACGATTAGCACTATCCTCGAGTCTAGAAAGAGATCC

AGACATGATAAGATACATTGATGAGTTTGGACAAACCACAACTAGAATGCAGTGAAAAAAATGCTTTATTTGT

GAAATTTGTGATGCTATTGCTTTATTTGTAACCATTATAAGCTGCAATAAACAAGTTAACAACAACAATTGCA

TTCATTTTATGTTTCAGGTTCAGGGGGAGGTGTGGGAGGTTTTTTAGTCGACTAGAGCTCGCTGATCAGCCTC

GACTGTGCCTTCTAGTTGCCAGCCATCTGTTGTTTGCCCCTCCCCCGTGCCTTCCTTGACCCTGGAAGGTGCC

-continued

ACTCCCACTGTCCTTTCCTAATAAAATGAGGAAATTGCATCGCATTGTCTGAGTAGGTGTCATTCTATTCTGG

GGGGTGGGGTGGGGCAGGACAGCAAGGGGGAGGATTGGGAAGACAATAGCAGGCATGCTGGGGAGAGATCTGA

GGAACCCCTAGTGATGGAGTTGGCCACTCCCTCTCTGCGCGCTCGCTCGCTCACTGAGGCCGGGCGACCAAAG

GTCGCCCGACGCCCGGGCTTTGCCCGGGCGGCCTCAGTGAGCGAGCGAGCGCGCAGAGAGGGAGTGGCCCCCC

CCCCCCCCCCCCCCTGCAGCCTGCATTAATGAATCGGCCAACGCGCGGGGAGAGGCGGTTTGCGTATTGGGCGC

TCTTCCGCTTCCTCGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAAAAGGCCAGCAAAA

GGCCAGGAACCGTAAAAAGGCCGCGTTGCTGGCGTTTTTCCATAGGCTCCGCCCCCCTGACGAGCATCACAAA

AATCGACGCTCAAGTCAGAGGTGGCGAAACCCGACAGGACTATAAAGATACCAGGCGTTTCCCCCTGGAAGCT

CCCTCGTGCGCTCTCCTGTTCCGACCCTGCCGCTTACCGGATACCTGTCCGCCTTTCTCCCTTCGGGAAGCGT

GGCGCTTTCTCATAGCTCACGCTGTAGGTATCTCAGTTCGGTGTAGGTCGTTCGCTCCAAGCTGGGCTGTGTG

CACGAACCCCCCGTTCAGCCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGTATGTAGGCGGTGCTACAGA

GTTCTTGAAGTGGTGGCCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCTTTGATCTTTTCTACGGGGTCTGA

CGCTCAGTGGAACGAAAACTCACGTTAAGGGATTTTGGTCATGAGATTATCAAAAAGGATCTTCACCTAGATC

CTTTTAAATTAAAAATGAAGTTTTAAATCAATCTAAAGTATATATGAGTAAACTTGGTCTGACAGTTACCAAT

GCTTAATCAGTGAGGCACCTATCTCAGCGATCTGTCTATTTCGTTCATCCATAGTTGCCTGACTCCCCGTCGT

GTAGATAACTACGATACGGGAGGGCTTACCATCTGGCCCCAGTGCTGCAATGATACCGCGAGACCCACGCTCA

CCGGCTCCAGATTTATCAGCAATAAACCAGCCAGCCGGAAGGGCCGAGCGCAGAAGTGGTCCTGCAACTTTAT

CCGCCTCCATCCAGTCTATTAATTGTTGCCGGGAAGCTAGAGTAAGTAGTTCGCCAGTTAATAGTTTGCGCAA

CGTTGTTGCCATTGCTACAGGCATCGTGGTGTCACGCTCGTCGTTTGGTATGGCTTCATTCAGCTCCGGTTCC

CAACGATCAAGGCGAGTTACATGATCCCCCATGTTGTGCAAAAAAGCGGTTAGCTCCTTCGGTCCTCCGATCG

TTGTCAGAAGTAAGTTGGCCGCAGTGTTATCACTCATGGTTATGGCAGCACTGCATAATTCTCTTACTGTCAT

GCCATCCGTAAGATGCTTTTCTGTGACTGGTGAGTACTCAA pAAV-CAG-ENPP1 FL (SEQ ID NO: 103)

tcgactagagctcgctgatcagcctcgactgtgccttctagttgccagccatctgttgtttgcccctcccccg tgccttccttgaccctggaaggtgccactcccactgtcctttcctaataaaatgaggaaattgcatcgcattg tctgagtaggtgtcattctattctggggggtggggtggggcaggacagcaagggggaggattgggaagacaat agcaggcatgctggggagagatctgaggaacccctagtgatggagttggccactccctctctgcgcgctcgct cgctcactgaggccgggcgaccaaaggtcgcccgacgcccgggctttgcccgggcggcctcagtgagcgagcg agcgcgcagagagggagtggccccccccccccccctgcagcctgcattaatgaatcggccaacgcgcgggga gaggcggtttgcgtattgggcgctcttccgcttcctcgctcactgactcgctgcgctcggtcgttcggctgcg gcgagcggtatcagctcactcaaaggcggtaatacggttatccacagaatcaggggataacgcaggaaagaac atgtgagcaaaaggccagcaaaaggccaggaaccgtaaaaaggccgcgttgctggcgtttttccataggctcc gcccccctgacgagcatcacaaaaatcgacgctcaagtcagaggtggcgaaacccgacaggactataaagata ccaggcgtttccccctggaagctccctcgtgcgctctcctgttccgaccctgccgcttaccggatacctgtcc gcctttctcccttcgggaagcgtggcgctttctcatagctcacgctgtaggtatctcagttcggtgtaggtcg ttcgctccaagctgggctgtgtgcacgaaccccccgttcagcccgaccgctgcgccttatccggtaactatcg -continued tcttgagtccaacccggtaagacacgacttatcgccactggcagcagccactggtaacaggattagcagagcg aggtatgtaggcggtgctacagagttcttgaagtggtggcctaactacggctacactagaagaacagtatttg gtatctgcgctctgctgaagccagttaccttcggaaaaagagttggtagctcttgatccggcaaacaaaccac cgctggtagcggtggtttttttgtttgcaagcagcagattacgcgcagaaaaaaaggatctcaagaagatcct ttgatcttttctacggggtctgacgctcagtggaacgaaaactcacgttaagggattttggtcatgagattat caaaaaggatcttcacctagatccttttaaattaaaaatgaagttttaaatcaatctaaagtatatatgagta aacttggtctgacagttaccaatgcttaatcagtgaggcacctatctcagcgatctgtctatttcgttcatcc atagttgcctgactccccgtcgtgtagataactacgatacgggagggcttaccatctggccccagtgctgcaa tgataccgcgagacccacgctcaccggctccagatttatcagcaataaaccagccagccggaagggccgagcg cagaagtggtcctgcaactttatccgcctccatccagtctattaattgttgccgggaagctagagtaagtagt tcgccagttaatagtttgcgcaacgttgttgccattgctacaggcatcgtggtgtcacgctcgtcgtttggta tggcttcattcagctccggttcccaacgatcaaggcgagttacatgatcccccatgttgtgcaaaaaagcggt tagctccttcggtcctccgatcgttgtcagaagtaagttggccgcagtgttatcactcatggttatggcagca ctgcataattctcttactgtcatgccatccgtaagatgcttttctgtgactggtgagtactcaaccaagtcat tctgagaatagtgtatgcggcgaccgagttgctcttgcccggcgtcaatacgggataataccgcgccacatag cagaactttaaaagtgctcatcattggaaaacgttcttcggggcgaaaactctcaaggatcttaccgctgttg agatccagttcgatgtaacccactcgtgcacccaactgatcttcagcatcttttactttcaccagcgtttctg ggtgagcaaaaacaggaaggcaaaatgccgcaaaaaagggaataagggcgacacggaaatgttgaatactcat actcttcctttttcaatattattgaagcatttatcagggttattgtctcatgagcggatacatatttgaatgt atttagaaaaataaacaaataggggttccgcgcacatttccccgaaaagtgccacctgacgtctaagaaacca ttattatcatgacattaacctataaaaataggcgtatcacgaggccctttcgtctcgcgcgtttcggtgatga cggtgaaaacctctgacacatgcagctcccggagacggtcacagcttgtctgtaagcggatgccgggagcaga caagcccgtcagggcgcgtcagcgggtgttggcgggtgtcggggctggcttaactatgcggcatcagagcaga ttgtactgagagtgcaccatatgcggtgtgaaataccgcacagatgcgtaaggagaaaataccgcatcaggaa attgtaagcgttaatattttgttaaaattcgcgttaaatttttgttaaatcagctcattttttaaccaatagg ccgaaatcggcaaaatcccttataaatcaaaagaatagaccgagatagggttgagtgttgttccagtttggaa caagagtccactattaaagaacgtggactccaacgtcaaagggcgaaaaaccgtctatcagggcgatggccca ctacgtgaaccatcaccctaatcaagttttttggggtcgaggtgccgtaaagcactaaatcggaaccctaaag ggagcccccgatttagagcttgacggggaaagccggcgaacgtggcgagaaaggaagggaagaaagcgaaagg agcgggcgctagggcgctggcaagtgtagcggtcacgctgcgcgtaaccaccacacccgccgcgcttaatgcg ccgctacagggcgcgtccattcgccattcaggctgcgcaactgttgggaagggcgatcggtgcgggcctcttc gctattacgccaggctgcaggggggggggggggggggccactccctctctgcgcgctcgctcgctcactgaggcc gcccgggcaaagcccgggcgtcgggcgacctttggtcgcccggcctcagtgagcgagcgagcgcgcagagagg gagtggccaactccatcactaggggttcctcagatctgaattcggtacctagttattaatagtaatcaattac ggggtcattagttcatagcccatatatggagttccgcgttacataacttacggtaaatggcccgcctggctga ccgcccaacgacccccgcccattgacgtcaataatgacgtatgttcccatagtaacgccaatagggactttcc attgacgtcaatgggtggagtatttacggtaaactgcccacttggcagtacatcaagtgtatcatatgccaag tacgcccccctattgacgtcaatgacggtaaatggcccgcctggcattatgcccagtacatgaccttatgggac tttcctacttggcagtacatctacgtattagtcatcgctattaccatggtcgaggtgagccccacgttctgct -continued tcactctccccatctcccccccctccccacccccaattttgtatttatttatttttt aattattttgtgcagc gatgggggcgggggggggggggggcgcgcgccaggcggggcggggcggggcgaggggggggcggggcgagg cggagaggtgcggcggcagccaatcagagcggcgcgctccgaaagtttccttttatggcgaggcggcggcggc ggcggccctataaaaagcgaagcgcgcggcgggcgggagtcgctgcgcgctgccttcgccccgtgccccgctc cgccgccgcctcgcgccgcccgccccggctctgactgaccgcgttactcccacaggtgagcgggcgggacggc ccttctcctccgggctgtaattagcgcttggtttaatgacggcttgtttcttttctgtggctgcgtgaaagcc ttgaggggctccgggagctagagcctctgctaaccatgttcatgccttcttctttttcctacagctcctgggc aacgtgctggttattgtgctgtctcatcattttggcaaagaattcctcgaagatccgaaggggttcaagctCT

AGCGCCACCATGGAGCGCGACGGCTGCGCGGGGGGCGGGAGCCGCGGCGGCGAGGGCGGGCGCGCTCCCCGGG

AGGGCCCGGCGGGGAACGGCCGCGATCGGGGCCGCAGCCACGCTGCCGAGGCGCCCGGGGACCCGCAGGCCGC

GGCGTCCTTGCTGGCCCCTATGGACGTGGGGGAGGAGCCGCTGGAGAAGGCGGCGCGCGCCCGCACTGCCAAG

GACCCCAACACCTATAAAGTACTCTCGCTGGTATTGTCAGTATGTGTGTTAACAACAATACTTGGTTGTATAT

TTGGGTTGAAACCAAGCTGTGCCAAAGAAGTTAAAAGTTGCAAAGGTCGCTGTTTCGAGAGAACATTTGGGAA

CTGTCGCTGTGATGCTGCCTGTGTTGAGCTTGGAAACTGCTGTTTAGATTACCAGGAGACGTGCATAGAACCA

GAACATATATGGACTTGCAACAAATTCAGGTGTGGTGAGAAAAGGTTGACCAGAAGCCTCTGTGCCTGTTCAG

ATGACTGCAAGGACAAGGGCGACTGCTGCATCAACTACAGTTCTGTGTGTCAAGGTGAGAAAAGTTGGGTAGA

AGAACCATGTGAGAGCATTAATGAGCCACAGTGCCCAGCAGGGTTTGAAACGCCTCCTACCCTCTTATTTTCT

TTGGATGGATTCAGGGCAGAATATTTACACACTTGGGGTGGACTTCTTCCTGTTATTAGCAAACTAAAAAAAT

GTGGAACATATACTAAAAACATGAGACCGGTATATCCAACAAAAACTTTCCCCAATCACTACAGCATTGTCAC

CGGATTGTATCCAGAATCTCATGGCATAATCGACAATAAAATGTATGATCCCAAAATGAATGCTTCCTTTTCA

CTTAAAAGTAAAGAGAAATTTAATCCTGAGTGGTACAAAGGAGAACCAATTTGGGTCACAGCTAAGTATCAAG

GCCTCAAGTCTGGCACATTTTTCTGGCCAGGATCAGATGTGGAAATTAACGGAATTTTCCCAGACATCTATAA

AATGTATAATGGTTCAGTACCATTTGAAGAAAGGATTTTAGCTGTTCTTCAGTGGCTACAGCTTCCTAAAGAT

GAAAGACCACACTTTTACACTCTGTATTTAGAAGAACCAGATTCTTCAGGTCATTCATATGGACCAGTCAGCA

GTGAAGTCATCAAAGCCTTGCAGAGGGTTGATGGTATGGTTGGTATGCTGATGGATGGTCTGAAAGAGCTGAA

CTTGCACAGATGCCTGAACCTCATCCTTATTTCAGATCATGGCATGGAACAAGGCAGTTGTAAGAAATACATA

TATCTGAATAAATATTTGGGGGATGTTAAAAATATTAAAGTTATCTATGGACCTGCAGCTCGATTGAGACCCT

CTGATGTCCCAGATAAATACTATTCATTTAACTATGAAGGCATTGCCCGAAATCTTTCTTGCCGGGAACCAAA

CCAGCACTTCAAACCTTACCTGAAACATTTCTTACCTAAGCGTTTGCACTTTGCTAAGAGTGATAGAATTGAG

CCCTTGACATTCTATTTGGACCCTCAGTGGCAACTTGCATTGAATCCCTCAGAAAGGAAATATTGTGGAAGTG

GATTTCATGGCTCTGACAATGTATTTTCAAATATGCAAGCCCTCTTTGTTGGCTATGGACCTGGATTCAAGCA

TGGCATTGAGGCTGACACCTTTGAAAACATTGAAGTCTATAACTTAATGTGTGATTTACTGAATTTGACACCG

GCTCCTAATAACGGAACTCATGGAAGTCTTAACCACCTTCTAAAGAATCCTGTTTATACGCCAAAGCATCCCA

AAGAAGTGCACCCCCTGGTACAGTGCCCCTTCACAAGAAACCCCAGAGATAACCTTGGCTGCTCATGTAACCC

TTCGATTTTGCCGATTGAGGATTTTCAAACACAGTTCAATCTGACTGTGGCAGAAGAGAAGATTATTAAGCAT

GAAACTTTACCCTATGGAAGACCTAGAGTTCTCCAGAAGGAAAACACCATCTGTCTTCTTTCCCAGCACCAGT

TTATGAGTGGATACAGCCAAGACATCTTAATGCCCCTTTGGACATCCTATACCGTGGACAGAAATGACAGTTT

CTCTACGGAAGACTTCTCCAACTGTCTGTACCAGGACTTTAGAATTCCTCTTAGTCCTGTCCATAAATGTTCA

TTTTATAAAAATAACACCAAAGTGAGTTACGGGTTCCTCTCCCCACCACAACTAAATAAAAATTCAAGTGGAA

TATATTCTGAAGCTTTGCTTACTACAAATATAGTGCCAATGTACCAGAGTTTTCAAGTTATATGGCGCTACTT

-continued

```
TCATGACACCCTACTGCGAAAGTATGCTGAAGAAAGAAATGGTGTCAATGTCGTCAGTGGTCCTGTGTTTGAC

TTTGATTATGATGGACGTTGTGATTCCTTAGAGAATCTGAGGCAAAAAGAAGAGTCATCCGTAACCAAGAAA

TTTTGATTCCAACTCACTTCTTTATTGTGCTAACAAGCTGTAAAGATACATCTCAGACGCCTTTGCACTGTGA

AAACCTAGACACCTTAGCTTTCATTTTGCCTCACAGGACTGATAACAGCGAGAGCTGTGTGCATGGGAAGCAT

GACTCCTCATGGGTTGAAGAATTGTTAATGTTACACAGAGCACGGATCACAGATGTTGAGCACATCACTGGAC

TCAGCTTCTATCAACAAAGAAAAGAGCCAGTTTCAGACATTTTAAAGTTGAAAACACATTTGCCAACCTTTAG

CCAAGAAGACGACTACAAAGACGATGACGACAAGTGAGGTACCGAGCTCGGATCCACTAGTCCAGTGTGGTGG

AATTCTGCAGATATCCAGCACAGTGGCGGCCGCTCGAGTctagaaagagatccagacatgataagatacattg

atgagtttggacaaaccacaactagaatgcagtgaaaaaaatgctttatttgtgaaatttgtgatgctattgc

tttatttgtaaccattataagctgcaataaacaagttaacaacaacaattgcattcattttatgtttcaggtt

cagggggaggtgtgggaggttttttag
```

EXAMPLES

The invention is further described in the following examples, which do not limit the scope of the invention described in the claims.

Materials and Methods

The following materials and methods were used in the Examples below.

Chemicals and Antibodies

Chemicals used in the study were purchased either from Millipore Sigma, Invitrogen, or Thermofischer Scientific. Antibodies were purchased from Cell Signaling Technology (CST), Invitrogen or Abcam. A list of the antibodies used in the study is given below.

| Antibody | Catalog Number | Manufacturer |
|---|---|---|
| ENPP1 | 2061S | CST |
| DYKDDDDK tag (Flag) | 14793S, #ab205606 | CST, Abcam |
| F-Actin A-488 | #R37110 | Invitrogen |

Cell Cultures

HepG2 and HEK293T cells were maintained in Dulbecco's modified eagle medium supplemented with 10% FBS added with penicillin-streptomycin solution. Cells were grown in 75 $cm^2$ culture flasks in an incubator maintained at 37° C. supplied with 5% $CO_2$. Cells were trypsinized and passaged when they are 90% confluent.

Mouse Colony Management and Genotyping

C57BL/6J-Enpp1asj/GrsrJ (the ASJ mice) were ordered from the Jackson Laboratory. The heterozygous mice were breed together. The C57BL/6J-Enpp1asj/GrsrJ breeders are put on an acceleration diet (Envigo, TD.00442, 10 kg, pellet diet), all pups are maintained on the acceleration diet once they are weaned.

Plasmids and Transfections

DNA plasmids were designed at MGH and synthesized at Gene script. Transfection was performed in a 6 well plate when the cells were at 60% confluence. Cells were sat in Optimem 24 hrs. before transfection. Then 2 ug of DNA plasmid per mL was mixed with either LTX lipofectamine at 5 ul/mL or Fugene at 6 ul/ml in Optimem. Transfection mixture was incubated for 15 min at room temperature followed by incubation with cells for 36 hrs. Then the transfecting medium was replaced by normal growth media and cells were collected 72 hrs. post transfection.

Immunoprecipitation

Cell supernatant (media) added with protease and phosphatase inhibitor cocktail was incubated with anti-flag antibody overnight at 4° C. Protein A-agarose beads were blocked with 1% BSA in PBS for 1 hr at 4° C. followed by washings with PBS twice. Protein A-agarose beads were then added to cell supernatant solution and incubated for 1-3 hrs at 4° C. Beads were collected by centrifugation at 2500 rpm for 10 min at 4° C. Media was completely aspirated, and beads were resuspended in 20 ul of RIPA buffer added with protease and phosphatase inhibitor cocktail and heated at 95° C. by adding 2× NuPAGE LDS sample buffer. Samples were separated by SDS-PAGE and probed with either anti FLAG antibody or ENPP1 antibody.

SDS-Polyacrylamide Gel Electrophoresis and Western Blotting

Cells were lysed using RIPA cell lysis buffer added with protease and phosphatase inhibitor cocktail (Thermo Fischer Scientific Cat #78440). Lysates were sonicated (3 cycles of 2 sec pulse on-15 sec pulse off) briefly on ice and were cleared by centrifugation at 12.5K rpm for 10 min at 4° C. Protein concentration was estimated using Pierce BCA protein assay kit per the manufacturer's instructions. 30 ug of lysates were prepared by NuPAGE LDS sample buffer and the samples were heated at 95° C. by placing the Eppendorf tubes on a heat block for 3-5 min. Protein samples were separated by sodium dodecyl sulfate-polyacrylamide gel electrophoresis (SDS-PAGE) followed by dry electro transfer onto a PVDF membrane using iblot2 transfer apparatus. Membranes were blocked with 5% BSA in Tris buffered saline (TBS) solution for 1 hr at room temperature followed by incubation with primary antibodies overnight. Membranes were washed with TBS-Tween-20 (0.05%) solution 5 times with an interval of 5 min. Blots were incubated with horse radish peroxidase (HRP)-tagged 2° antibodies (1:10000) at room temperature for 90 min followed by above mentioned TBS-Tween-20 washings. Blots were added with chemiluminescence substrates, and the signals were captured on a Bio-Rad gel doc imaging system and processed in Microsoft PowerPoint for presentation.

ENPP1 Enzyme Activity Assay

Cells were seeded in 6-well plates and grown until confluent (10 days in DMEM follow by 5 days in αMEM). To measure ENPP1 enzyme activity, cells were lysed in 100 mM Tris-HCl (pH 9.0), 500 mM NaCl, 5 mM MgCl2, and 0.05% Triton X-100 and scraped into microcentrifuge tubes and kept on ice. Cell suspensions were spun at 12,000 g for 5 minutes. A 50 μl aliquot of the supernatant was added to a clear-bottom 96-well plate and the reaction with initiated upon adding 50 μl of 1 mM paranitrophenol-thymidine monophosphate (pNP-TMP; Sigma-Aldrich).

Mild Lysis Buffer [Store at 4° C.] pH 9.0 with 1 M NaOH

| | |
|---|---|
| 100 mM Tris-HCl | 20 mL of 1M Tris-HCl (pH 8.0) |
| 500 mM NaCl | 5.844 grams |
| 5 mM MgCl2 | 1 mL of 1M MgCl2 (4.76 gram in 50 mL diH2O) |
| 0.05% (v/v) Triton X-100 | 100 μl |
| diH2O | Fill up to 200 mL |

Assay Reagents 4 mM pNP-TMP (Sigma T4510-100 mg, MW=465.28)

0.0186 g pNP-TMP in 10 mL of Mild Lysis Buffer 10 mM pNP solution (Sigma N7660-100 ml)

Standard Curve

1. Make 1:10 dilution of 10 mM pNP to make final concentration of 1 mM 100 ul 10 mM pNP solution in 900 ul Mild Lysis Buffer
2. Prepare standard curve in duplicate (100 ul/well)

| [ ] | 0 nmol | 2 nmol | 4 nmol | 6 nmol | 8 nmol | 10 nmol | 20 nmol | 30 nmol | 40 nmol | 50 nmol |
|---|---|---|---|---|---|---|---|---|---|---|
| 1 mM standard | 0 ul | 8 ul | 16 ul | 24 ul | 32 ul | 40 ul | 80 ul | 120 ul | 160 ul | 200 ul |
| buffer | 400 ul | 392 ul | 384 ul | 376 ul | 368 ul | 360 ul | 320 ul | 280 ul | 240 ul | 200 ul |

For rENPP1 Activity Assay from Cell Lysates

1. Aspirate media from 6-well plates
2. Wash cells 2× with cold 1×PBS and aspirate wash solution
4. Lyse the cells (275 ul/well) with Mild Lysis Buffer
5. Scrape down cells with rubber policeman
6. Pipette into Eppendorf tubes and incubate on ice for 5 mins
7. Spin down cell debris at 12,000×g for 5 mins at 4° C.
8. Keep cell lysates on ice
9. Add 50 ul of sample/well (in triplicate) in 96-well plate
10. Initiate reaction by adding 50 ul of pNP-TMP substrate (with multi-channel pipette)
11. Incubate for 5, 10, 15, 20, 30 mins at 37° C. and read at 405 nm
12. Stop incubation when the absorbance of the samples reaches the range of the standards
13. Report data as nmol pNP produced/min/mg protein
14. Perform BCA to determine protein concentration during incubation; make BCA standards with Mild Lysis Buffer. Use 10 μl of standard or sample; 200 μl of WR reagent/well. A: 14 mL, B: 280 μl
15. Save remainder of protein lysate for Western blot (store at −80° C.)

For srENPP1 Activity Assay from Cell Supernatant (Media)

1. Collect media from 6 well plates.
2. Add 50 ul of sample/well (in triplicate) in 96-well plate.
3. Initiate reaction by adding 50 ul of pNP-TMP substrate (with multi-channel pipette)
4. Incubate for 5, 10, 15, 20, 30 mins at 37° C. and read at 405 nm.
5. Stop incubation when the absorbance of the samples reaches the range of the standards.
6. Report data as nmol pNP produced/min/mg protein.
7. Perform BCA to determine protein concentration during incubation; make BCA standards with Mild Lysis Buffer. Use 10 μl of standard or sample; 200 μl of WR reagent/well. A: 14 mL, B: 280 μl Retroorbital Injections The mouse was placed in a Plexiglas chamber and isoflurane was used for induction. Once adequate anesthesia was achieved, the mouse was placed in a left lateral position and gentle pressure is applied around the eye socket to partially protrude the eyeball. A 30 gauge, 0.5-in insulin needle was inserted bevel down into the retro-orbital sinus at the medial canthus and the solution was injected slowly. The needle was withdrawn smoothly, and the mouse was allowed to recover in its cage (JoVE Science Education Database. *Lab Animal Research—Compound Administration IV*. JoVE, Cambridge, MA, (2024)).

Mouse Tissue Harvest and Cryosectioning

Mice of the Asj+/+ genotype (or other genotypes) were subjected to treatment with nanoparticles containing plasmid at 3 days and then harvested for a biodistribution study at 10 days. Serum/Plasma were obtained via cardiac puncture from anesthetized mice. Various tissues, including brain, heart, lungs, spleen, liver, kidneys, large intestine, bladder, tail, aorta, small intestine, knee, foot, and vertebrae, were harvested after brief perfusion with cold PBS. These tissues were promptly placed in optimal cutting temperature (OCT) compound for frozen sectioning. Cryosectioning was performed in a Leica CM 1850 cryostat and tissue sections of 10 um were cut and collected on to slides for immunofluorescence staining.

Immunofluorescence

The tissue sections were washed with PBS twice to remove OCT and fixed with 4% paraformaldehyde (PFA) for 3 minutes at 4° C. followed by treatment with 0.1% Triton-X-100 for 5 min. The tissue slides were incubated in a 10% new donkey serum blocking solution. Primary antibodies used in the immunostaining included a recombinant Anti-DDDDK tag antibody (#ab205606, Abcam) and F-actin-A488 (#R37110, Invitrogen) was used for staining actin filaments. Alexa Fluor 594-conjugated secondary antibody was purchased from Jackson Immuno Research. Nuclei were stained with DAPI (#ab104139, Abcam). All the antibodies used in this study were validated for the species and applications by the indicated manufacturers. Confocal images were acquired using a Leica TCS SP8 X Laser Confocal Microscope (Leica). LAS X software (Leica) was used for acquisition and processing of images. Mean intensity was calculated using LAS X software and the values were plotted in Graph pad PRISM.

Lipid Nanoparticles—Formulation and Peptide Conjugation

LNPs were formulated by pipette mixing a stock of organic phase composed of a lipid mixture with an aqueous phase composed of mRNA dissolved in 10 mM sodium acetate buffer, pH 5.2 (Sigma, 567422) at a volume ratio of 1:3 organic to aqueous. DLin-MC3-DMA (MC3) (Eschelone Bioscience, N-1282) Ionizable lipid, 1,2-dioleoyl-sn-glycero-3-phosphoethanolamine (DOPE, Avanti Polar Lipids, 850725P), cholesterol (Sigma, C8667) and 1,2-dimyristoyl-rac-glycero-3-methoxypolyethylene glycol-2000 (DMG-PEG 2000, Avanti Polar Lipids, 880151P) were dissolved in ethanol and mixed at predetermined molar ratios (50:10.5:38:1.5) and a 40:1 total lipids to mRNA weight ratio. The assembled LNPs were dialyzed against PBS (pH 7.4) in dialysis tubes (3500 MW cutoff, Sigma, PURD35050) to remove the ethanol. In formulations where 1,2-dioleoyl-3-trimethylammonium-propane (chloride salt) (DOTAP) was incorporated, the percentage of DOTAP was considered as part of the total 100% while the ratios between the remaining lipids was kept (50:10.5:38:1.5). Peptide-conjugated LNPs were composed of 10% DOTAP and DSPE-PEG 2000 (1,2-distearoyl-sn-glycero-3-phosphoethanolamine-N-[maleimide(polyethylene glycol)-2000] (ammonium salt) in varying percentages (0.15%/0.3%/0.6%/0.9%/1.2%) as replacement for DMG-PEG 2000 (total lipid PEG ratio did not exceed 1.5%). In this study, the peptides under investigation were designed with dual objectives: firstly, to target the extracellular matrix of vascular smooth muscle cells (VSMCs) with a peptide targeting collagen 4 (Col-4; KLWVLPK-GGG-C(SEQ ID NO:48)), thereby enhancing the retention of LNPs around these cells; and secondly, to target surface receptors expressed on VSMCs to facilitate the internalization of LNPs. The sequences of the peptides targeting surface receptors were TL6R; C-GGG-LSLITRL (SEQ ID NO:49), Gal-3; C-GGG-ANTPCGPYTHDCPVKR (SEQ ID NO:51), and CD63; CRHSQMTVTSRL-GGG (SEQ ID NO:50).

For conjugating peptides to LNPs, the peptides were initially treated with tris(2-carboxyethyl)phosphine (TCEP) reducing agent (Thermo Scientific, 77712). Subsequently, the free peptides were incubated with Mal-functionalized LNPs for 1 hour at pH 7.4, with a peptide to Mal molar ratio of 2:1. The final product of peptide-conjugated LNPs was dialyzed against phosphate buffered saline (PBS) and concentrated using Amicon® tubes. To assess the efficiency of conjugation, a maleimide fluorometric detection kit (Sigma, MAK167) was utilized following the protocol of the manufacturer.

LNPs Characterization

The size (diameter) and surface charge (zeta potential) of the LNPs were determined via dynamic light scattering (DLS) using the Zetasizer® Nano ZS (633 nm, Malvern Instruments), with light collection at a scattering angle of 173°. Nucleic acid encapsulation efficiency was assessed employing the modified Quant-it™ RiboGreen® RNA assay (Invitrogen™). Initially, a nucleic acid standard curve was prepared in TE (Tris-EDTA) buffer. LNPs were subsequently diluted either in TE buffer or TE-Triton (TE supplemented with 2% Triton-X100) to match the nucleic acid concentration within the standard curve. Duplicates of LNPs and standard curve samples (100 μL each) were loaded into a black 96-well plate, followed by the addition of 100 μL of RiboGreen® reagent (diluted 1:200 in TE buffer). Fluorescence intensity originating from unencapsulated nucleic acid ($I_{free}$) was measured using a plate reader (Excitation: 485 nm, Emission: 528 nm, Infinite® M plex, TECAN®). Triton-treated LNP samples represented released nucleic acid from disrupted LNPs, while intact intensity of LNPs indicated unencapsulated nucleic acid. Encapsulation efficiency was computed as % EE=100×(1−($I_{intact}$/$I_{disrupted}$)).

Perfusion of Human Vessels

The perfusion bath for tubular organs (PBTO) system, peristaltic pump, and water bath containing sterile water at 37° C. were assembled inside a fume hood disinfected with 70% ethanol. The entire plumbing system was sterilized using 2% mucasol, followed by perfusion with 500 mL of physiological PBS for 1 hour to ensure sterility. Blood vessels were collected from the operating room (OR) in DMEM supplemented with 10% FBS and transferred under sterile conditions. Upon receipt, a ~6 cm vessel segment was cannulated into the PBTO system using a suture kit. The vessel was initially perfused with 10% FBS/DMEM for 15 minutes to assess potential leaks, which were sutured if detected. Next, 500 μL of AAVPR-GFP ($4.98\times10^{11}$ vg) or AAV9 ($5.3\times10^{11}$ vg) was injected into the vessel lumen and perfused through the system at a flow rate of 22 mL/min for 1 hour. Following perfusion, the vessel was decannulated and maintained in a $CO_2$ incubator for 7 days. At the end of the culture period, AAV-perfused vessels were sectioned for downstream analyses, with 5 mm segments allocated for immunofluorescence, 5 mm for tissue clearing and immunofluorescence, and 3 mm for PCR. See, e.g., Bianco et al., A Protocol for a Novel HumanEx VivoModel of Aneurysm, STRAR ptotocol, 1, 100108. doi.org/10.1016/j.xpro.2020.100108; Lipskaia er al., (2013) SERCA2a gene transfer prevents intimal proliferation in anorgan culture of human internal mammary artery. Gene Ther. 20(4): 396-406. doi:10.1038/gt.2012.50.

Histology of Human Vessels

Tissue sections were washed in PBS three times for 5 minutes each at room temperature to remove residual media and debris. Samples were then permeabilized using 0.3% PBTx for 2 hours at room temperature, followed by blocking in a solution containing 0.3% PBTx, 2.5% normal donkey serum (NDS), and 1% bovine serum albumin (BSA) for 45 minutes at room temperature to minimize nonspecific antibody binding. Unconjugated GFP primary antibody (Abcam) was diluted to 1:150 in blocking buffer, and slides were incubated with the primary antibody overnight at 4° C. The next day, slides were washed in PBS three times for 5 minutes each at room temperature before incubation with αSMA-Cy3 and a secondary antibody (Rb 647) diluted to 1:500 in blocking buffer for 1 hour at room temperature. Following secondary antibody incubation, slides were washed again in PBS three times for 5 minutes each and mounted using DAPI-containing mounting media. Images were acquired using an LSM Airyscan 800 confocal microscope.

Example 1. Constructs for Delivering Soluble Secreted Recombinant ENPP1

Figure 1A:
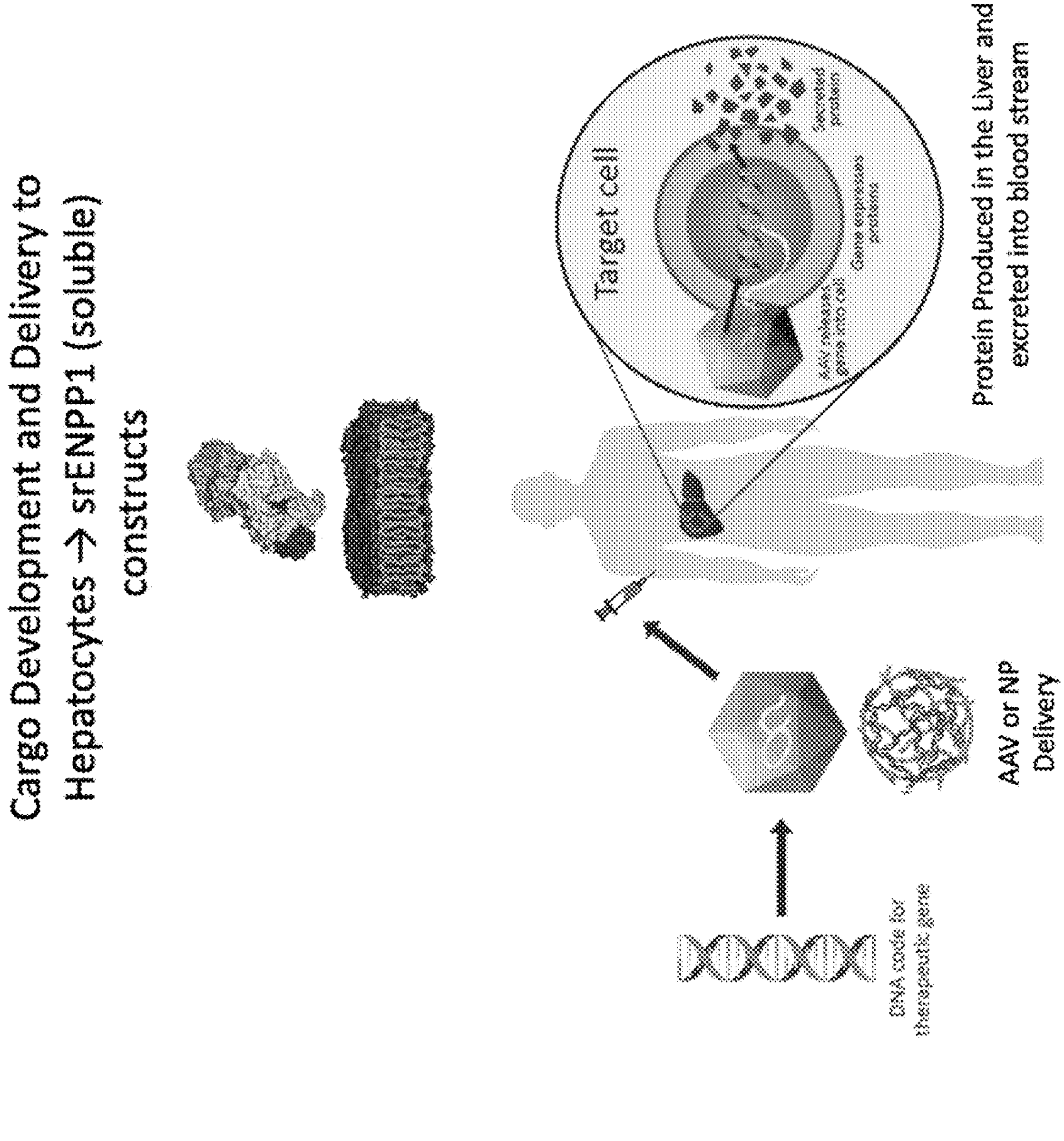
FIGS. 1A-B. Schematic illustrations of two general exemplary methods for delivery of ENPP1 gene therapy for systemic gene therapy, e.g., for infantile GACI, as described herein. 1A, Gene therapy using a construct encoding a soluble secreted recombinant ENPP1 (srENPP1) protein, delivered to hepatocytes; in this method, the protein is produced in the liver and secreted into the bloodstream. 1, Gene therapy using a construct encoding a transmembrane full-length recombinant ENPP1 (rENPP1), delivered to hepatocytes and vascular smooth muscle cells (VSMCs); in this method, the protein is produced locally in the vascular tissues as well as in the liver.
Figure 1B:
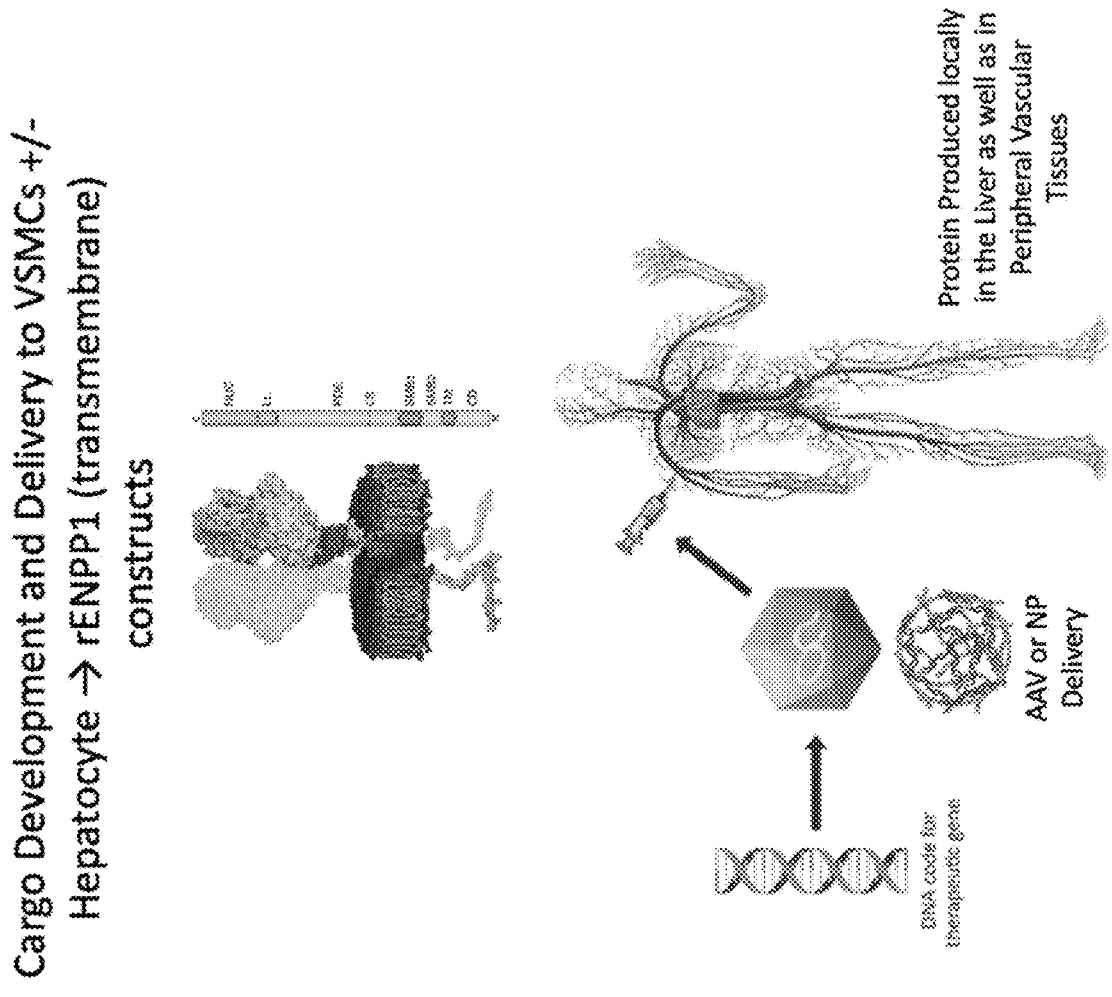
Figure 2:
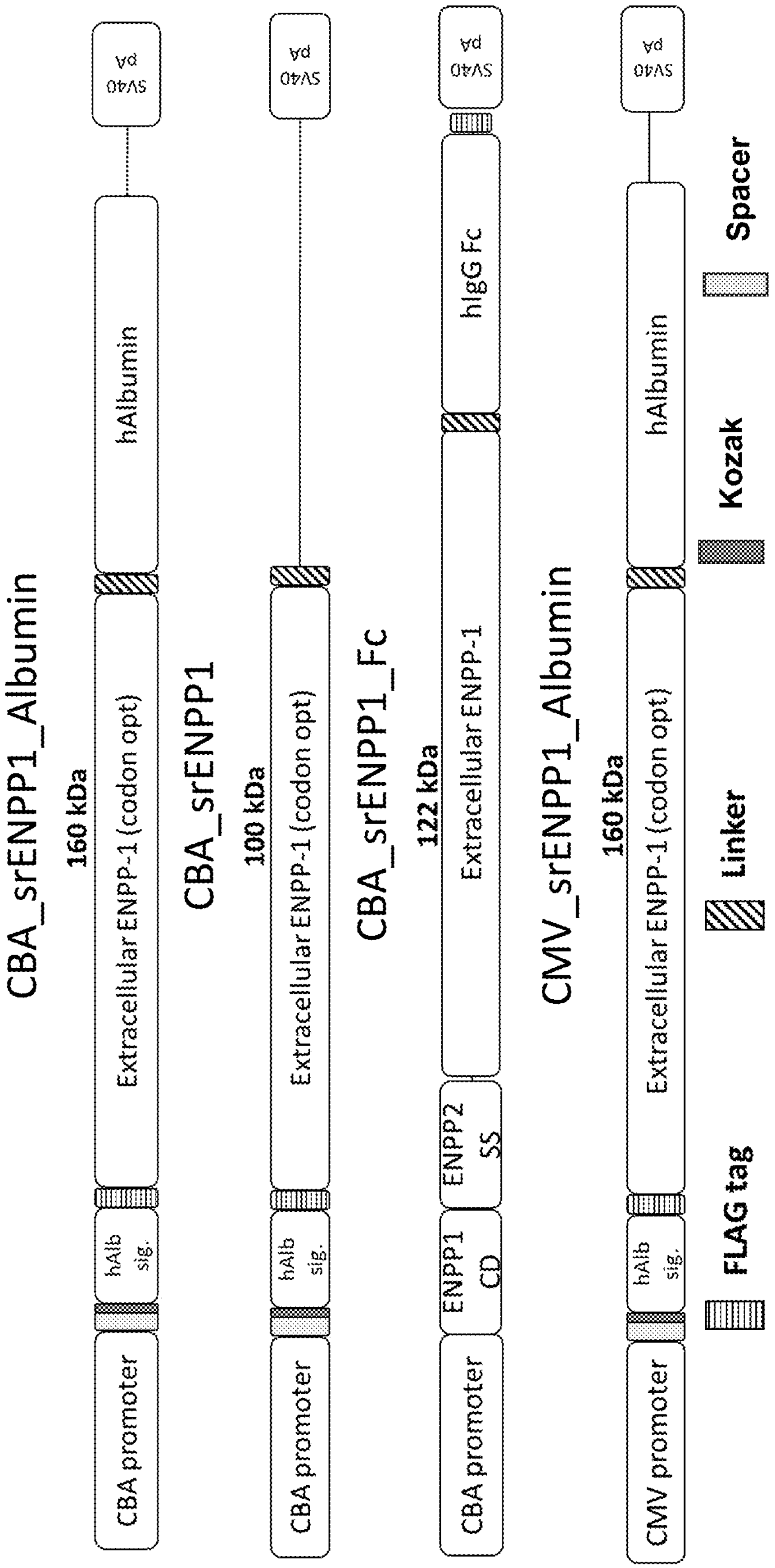
FIG. 2. Schematic illustration of four DNA constructs with the CBA or CMV promoter driving expression for delivering a soluble secreted recombinant srENPP1.

DNA constructs were designed with the aim of delivering soluble secreted recombinant ENPP1 (srENPP1). The constructs included human albumin (hAlb) or human IgG Fc domain (hIgG Fc) to improve protein half life, and once included the ENPP2-somatomedin like domain (SMD). As shown in FIG. 2, the constructs were: CBA_srENPP1_Albumin, which contained (1) albumin secretory signal (hAlb sig) to signal the protein for secretion from the cell and (2) hAlbumin to stabilize the protein and increase its half-life.

CBA_srENPP1, which contained the albumin secretory signal but not a stabilizing fusion protein.

CBA_srENPP1_Fc, which contained ENPP1 cytosolic domain (CD, amino acids 1-76), ENPP2 signal sequence (SS, amino acids 12-30), with the extracellular ENPP1 domain fused with the IgG Fc domain for stabilization (srENPP1_Fc construct).

CMV_srENPP1_Albumin, which contained (1) albumin secretory signal (hAlb sig) to signal the protein for secretion from the cell and (2) hAlbumin to stabilize the protein and increase its half-life.

These constructs were validated in vitro using CBA and CMV promoters. Western blot analysis was performed in total lysates of human HepG2 liver cells transfected with the constructs and assessed by ENPP1 or Flag-tag antibody immunoblot. The srENPP1 with hAlbumin constructs showed striking expression of soluble ENPP1 for both CBA and CMV promoters in cell lysates. As shown in FIG. 4, there was superior expression of ENPP1 transgene in cells transfected with the CMV_srENPP1_albumin construct as compared to the CBA_srENPP1_albumin. Additionally, there was increased expression of rENPP1 in HepG2 cells using the CMV promoter construct compared to CBA promoter. As shown in FIG. 5, similar results were seen in human HEK293T cells. Expected molecular weights: Soluble secreted rENPP1=160 kD rENPP1=130 kD. Additional experiments in HepG2 cells showed inconsistent expression of srENPP1 in cell lysates and supernatant with the CBA promoter, and no increase in ENPP1 activity was seen in cell lysates or supernatant, so the CMV promoter was chosen for further experiments.

Figure 6:
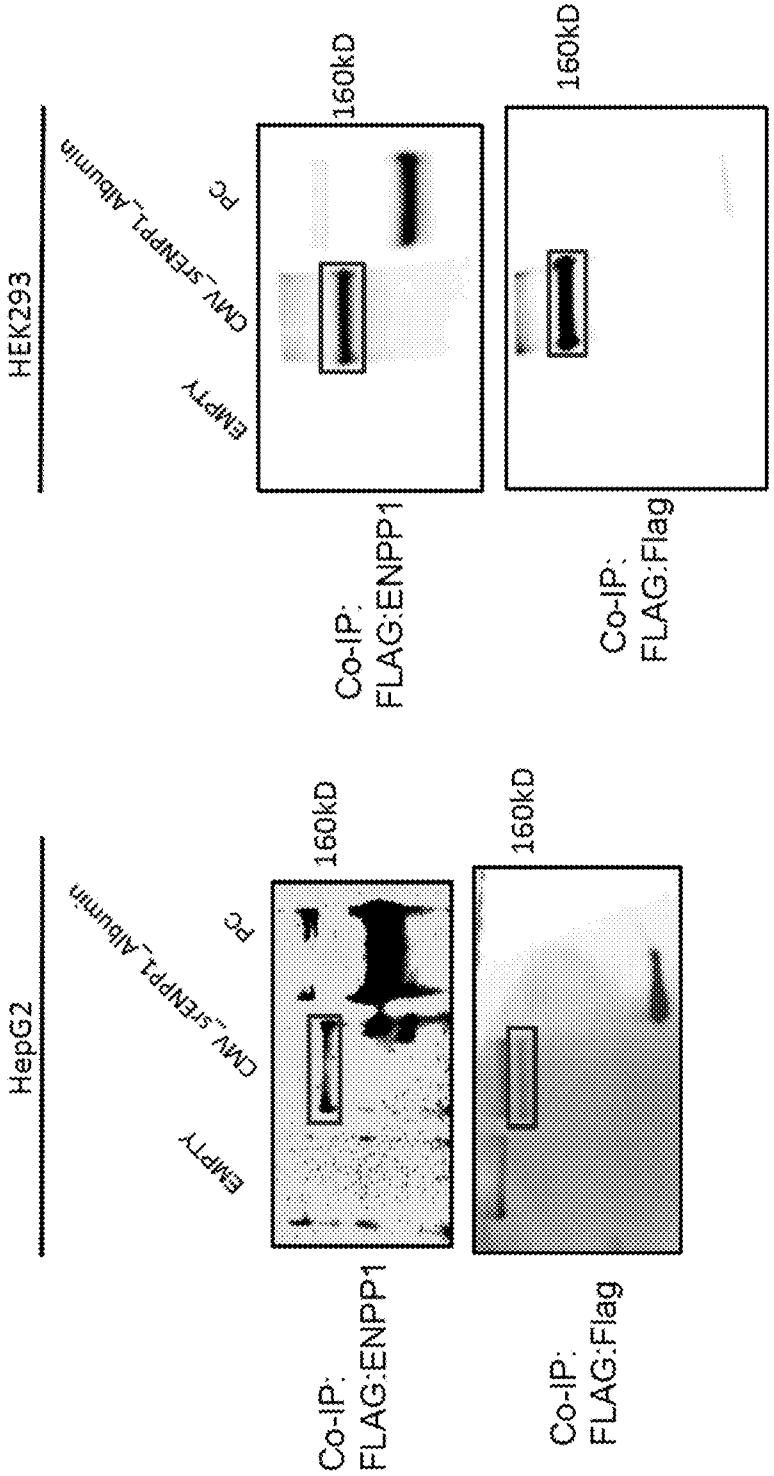

As shown in FIG. 6, the construct with srENPP1-hAlbumin and a CMV promoter showed expression of soluble, secreted srENPP1 in HepG2 (left) and HEK293 (right) cell supernatants, indicating proper secretion of srENPP1 into the extracellular space. The secreted protein was active; as shown in FIGS. 7A-B, the srENPP1-hAlbumin and CMV promoter construct showed significant ENPP1 activity in the supernatant of HepG2 and HEK293 cells indicating proper enzymatic function in addition to proper localization outside the cell. This was in contrast to the srENPP1_Fc construct for soluble recombinant ENPP1 Enzymatic activity of srENPP1_Fc ("plasmid #4") was measured from the cell lysates (FIG. 8A) and supernatants (FIG. 8B) of HepG2 cells transfected with srENPP1_Fc construct. A significant increase in the ENPP1 activity was observed compared to cell lysates from untransfected cells but no increase in activity was observed in the supernatant of transfected cells, that the srENPP1_Fc construct has some cellular activity but no activity in the supernatant likely indicates it was not well secreted.

Table 1 provides a protein expression summary of soluble, secreted recombinant ENPP1 (srENPP1) constructs in HepG2 cells and HEK293T cells, indicating that SrENPP1 with hAlbumin and CMV promoter (CMV_srENPP1_Albumin) had higher expression compared to the CBA promoter.

TABLE 1

| | Expression levels | | | | | |
|---|---|---|---|---|---|---|
| Construct | Cell-ENPP1 | Cell-Flag | Supernatant-ENPP1 | Supernatant-Flag | Cellular activity | Supernatant activity |
| CBA_srENPP1_Albumin #1 | low | low | ND* | ND* | ND* | ND* |
| CBA_srENPP1 #2 | ND | ND | ND* | ND* | ND* | ND* |
| CBA_srENPP1_Fc #4 | Medium | ND | ND* | ND* | Medium* | ND* |
| CMV-srENPP1-Alb (#5) | Medium | Medium | Medium | Medium | Low | high |

ND = not detected

Example 2. Constructs for Delivering Transmembrane Recombinant rENPP1

Two DNA constructs were designed with the aim of delivering transmembrane recombinant ENPP1, as shown in FIG. 2, with the CMV or CBA promoter driving expression of a FLAG-tagged full length human recombinant ENPP1 (rENPP1). These constructs were also validated in vitro. As shown in FIGS. 4 and 5, transmembrane rENPP1 expression via CMV promoter was more effective than with the CBA promoter.

Table 2 provides a protein expression summary of recombinant transmembrane ENPP1 (srENPP1) constructs, indicating that the CMV promoter (CBA_rENPP1) had higher expression compared to the CBA promoter.

TABLE 2

| plasmid# | Cell-ENPP1 | Cell-Flag | Supernatant-ENPP1 | Supernatant-Flag | Supernatant activity |
|---|---|---|---|---|---|
| CBA_rENPP1 | Medium | ND | NA | NA | NA |
| CMV-rENPP1 (#6) | Medium | Medium | NA | NA | NA |

ND = not detected,
NA = not applicable given that it is a transmembrane protein

Example 3. In Vitro Delivery of Soluble Recombinant ENPP1 Gene Construct Via Nanoparticle Packaging Delivery of the CMV_srENPP1_hAlbumin construct was performed using four versions of nanoparticles (LNP18, LNP30, CHK18, and CHK30) in human HepG2 cells, and protein expression evaluated by Western blotting. The results demonstrated srENPP1 expression after delivery using CHK18 and CHK30 nanoparticles in cell lysates (FIG. 9A) that was comparable to commercial LTX lipofectamine reagent using a Flag-directed antibody, and in supernatant ENPP1 expression was shown to be comparable to commercial LTX lipofectamine reagent using an ENPP1 antibody and Flag antibody. (FIG. 9B).

ENPP1 catalytic activity assay was performed on the supernatant and total lysates of human HepG2 cells transfected with CMV_srENPP1_albumin using nanoparticles. As shown in FIG. 10, transgene delivery and activity in CHK18 nanoparticles was comparable with LTX lipofectamine. As shown in FIG. 11, transgene delivery and activity with CHK18 nanoparticles was higher than with LTX lipofectamine.

In addition, newborn pups were injected on day 3 with srENPP1 or rENPP1 expression plasmid packed in various nanoparticle preparations through retroorbital route. Tissue/organs were harvested on day 6 post injection and placed on fresh OCT blocks followed by cryosectioning and immunohistochemistry to study the expression profile of srENPP1 in various tissues and organs. FIGS. 12A-B show expression of srENPP1 (12A) or rENPP1 (12B) in different tissues and organs injected with different plasmid concentrations and nanoparticle preparations compared to control un-injected. An increase in tissue expression of srENPP1 was observed with increase in CMV_srENPP1_Albumin concentration. Among the different nanoparticles used in the study, LNP1-DOPE with 0.3 ug of CMV_srENPP1_Albumin showed increased expression in the aorta and liver without causing appreciable toxicity.

Example 4. In Vivo Delivery of Soluble Recombinant ENPP1 Gene Construct Via Nanoparticle Packaging Delivery of the CMV_srENPP1_hAlbumin construct was performed in 10 day old mice using C6 RH-647 nanoparticles using retroorbital injection of 20 uL (5 ug NPs). 6 days later, mice were sacrificed and fresh tissue samples in optimal cutting temperature compound (OCT) were analyzed by immunofluorescence. The results showed nanoparticle autofluorescence in aortic and small intestinal tissue, but it was not detectable in heart, kidney, or liver. Expression of srENPP1 was seen in endothelial cells of the small intestine, heart, liver, and kidney, and in the medial layer of the aortic tissue that colocalized with F-actin, indicating that the ENPP1 transgene was expressed in smooth muscle cells.

Example 5. In Vitro rENPP1 Gene Delivery Via AAVPR Packaging

An in vitro assessment of AAVPR rENPP1 expression, activity, and inhibition of osteogenic VSMC phenotypic change was performed. As shown in FIG. 13A, AAVPR transduced human VSMCs more robustly than AAV9. As shown in FIG. 13B, juman aortic VSMCs treated with AAVPR rENPP1 at low and high doses demonstrated dose-dependent overexpression of ENPP1 at the protein level. As shown in FIG. 13C, increased rENPP1 activity was detected over time in VSMCs treated with AAVPR rENNP1 compared to untreated cells. In addition, AAVPR rENPP1 treatment decreased VSMC osteogenic phenotype switch: as shown in FIG. 13D, AAVPR rENPP1 treated cells demonstrated decreased calcification on Alizarin red staining compared to untreated cells after 21 days of culture in osteogenic media, and as shown in FIG. 13E) AAVPR treatment decreased migration of VSMCs compared to control-treated cells after 12 hours in osteogenic media. Finally, as shown in FIG. 13F, these phenotypic changes correlated with a reduction in RUNX2 protein levels with AAVPR rENPP1 treatment.

ENPP1 gene therapy was tested in vivo in $ASJ^{-/-}$ mice. Compared to vehicle-treated GACI mice, GACI mice treated with pBAE srENPP1 or LNP1-DOPE srENPP1 showed improved survival with log rank p=0.03 and p=0.008, respectively (FIG. 13G).

The reduction of human VSMC calcification, migration, and RUNX2 protein expression with AAVPR rENPP1 supports the use of AAVPR rENPP1 as a therapy for a multitude of vascular calcification disorders where VSMCs undergo osteogenic phenotype switch manifested by increased calcification, migration, and RUNX2 expression. These vascular calcification disorders include calciphylaxis and cardiovascular disease including diabetic vascular calcification, ESRD-associated vascular disease, calcific aortic valve disease (CAVD), coronary atherosclerosis, coronary artery bypass graft (CABG) stenosis, in-stent stenosis, peripheral vascular disease, or cerebral atherosclerosis.

Figure 15:
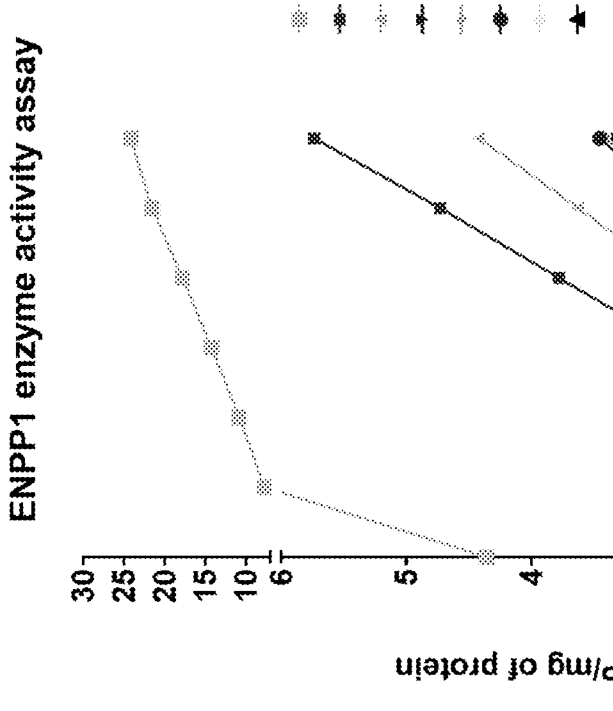

Example 6. Regulation of Expression of srENPP1 with miR155 and miR122 Reduced srENPP1 Expression in a Dose Dependent Manner To evaluate the ability of miR155 and miR122 to down regulate expression of an ENPP1 transgene, rENPP1 or srENPP1 was expressed from plasmid with constructs consisting of a CAG promoter upstream of rENPP1-FLAG; the constructs included miR155 or miR122 target sequences (three target sequences in tandem) were expressed in human aortic SMCs. The cells were transfected using LTX lipofectamine at 5 ul/ml with 1 ug/ml of the plasmid in normal media for three days. Expression of srENPP1 was evaluated by Western blot after being immunoprecipitated with an anti-FLAG antibody and run on a 4-12% gel with MOPS running buffer. The results, presented in FIGS. 14A-B, showed dose-dependent reductions in rENPP1 expression in the presence of miR122 or miR155, respectively (14A), and dose-dependent reductions in srENPP1 expression in the presence of miR155 (14B). As shown in FIG. 15, an activity assay showed decreased srENPP1 activity with an increase in miR155 that was consistent with the results of the Western blot.

Example 7: Particle Screening for Delivery of Constructs to Liver Hepatocytes to Produce a Soluble Protein The instant example describes screening of LNP composition(s) for efficient encapsulation of plasmid constructs. Screening was based on alteration of the cholesterol and DOPE lipid ratio while fixing the ionizable and DMG-PEG lipid amounts. Screening based on cholesterol and DOPE content was classified by high, medium, or low cholesterol amount as outlined in Table 3.

TABLE 3

| | Cholesterol Content | | |
|---|---|---|---|
| | High | Medium | Low |
| MC-3 | 50% | 50% | 50% |
| DOPE | 10% | 30% | 40% |

TABLE 3-continued

| | Cholesterol Content | | |
|---|---|---|---|
| | High | Medium | Low |
| PEG-DMG | 1.5% | 1.5% | 1.5% |
| Cholesterol | 38.5% | 18.5% | 8.5% |

The particles were screened for the delivery in liver hepatocytes (HepG2) cell line based on formulation composition varying in cholesterol and DOPE content illustrated in Table 3. It was found that a composition with high cholesterol was the most efficient in delivering a reporter plasmid expressing RFP, as well as delivering a plasmid encoding a soluble ENPP1 protein in liver hepatocyte cells in vitro (FIGS. 17A-C). FIG. 17A is a chart illustrating results of a flow cytometry experiment quantitating the percentage of RFP positive cells in the liver hepatocytes (HepG2) cell line. FIGS. 17B-C illustrate the detection of plasmid constructs expressing soluble ENPP1 and detection at cell lysates (FIG. 17B) and detection in cell media of ENPP1 protein expressed from constructs expressing the soluble protein.

The preferential delivery of an ENPP1 soluble construct in a mouse model for the generalized arterial calcification of infancy (GACI) disease (Asj mouse model (FIG. 18) was further demonstrated. This experiment demonstrated efficient soluble ENPP1 expression in the liver of Asj mouse models among other organs 6 days post injection. FIG. 18 provides histological images of liver of Asj mice injected with soluble ENPP1 plasmid (0.3 mg/kg) at day 3 (P3) express high levels of the enzyme (labeled red) in the liver, 6 days post injection, demonstrating in vivo expression of a construct delivered with the particles described in Table 3 to the liver.

Figure 19A:
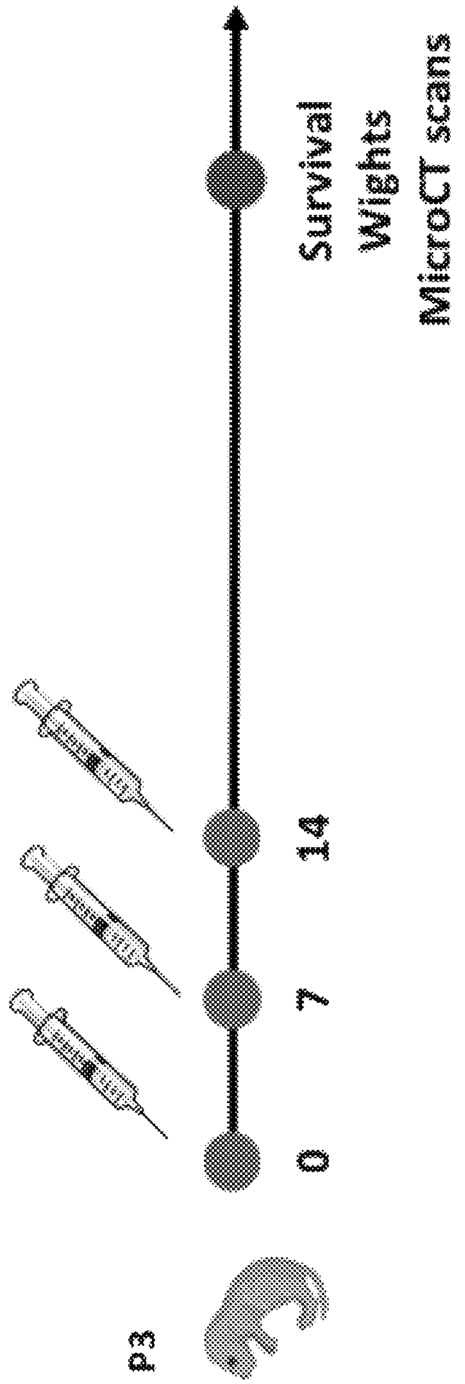
Figure 19B:
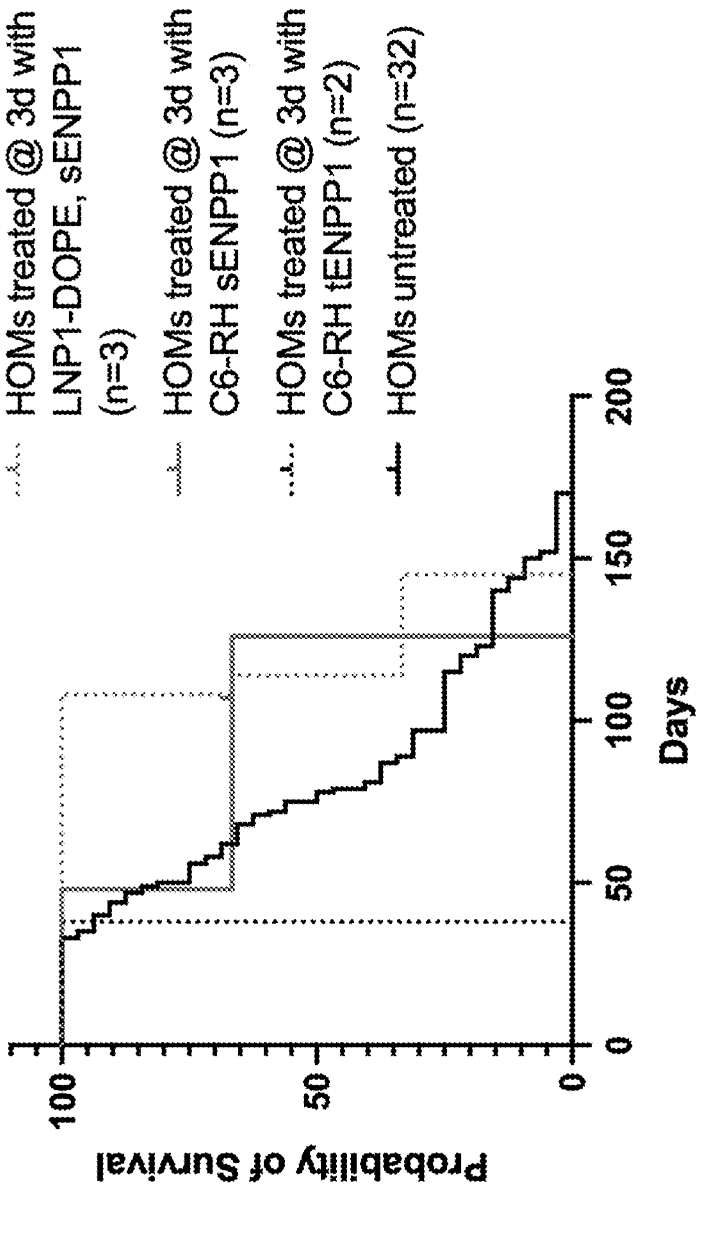
Figure 19C:
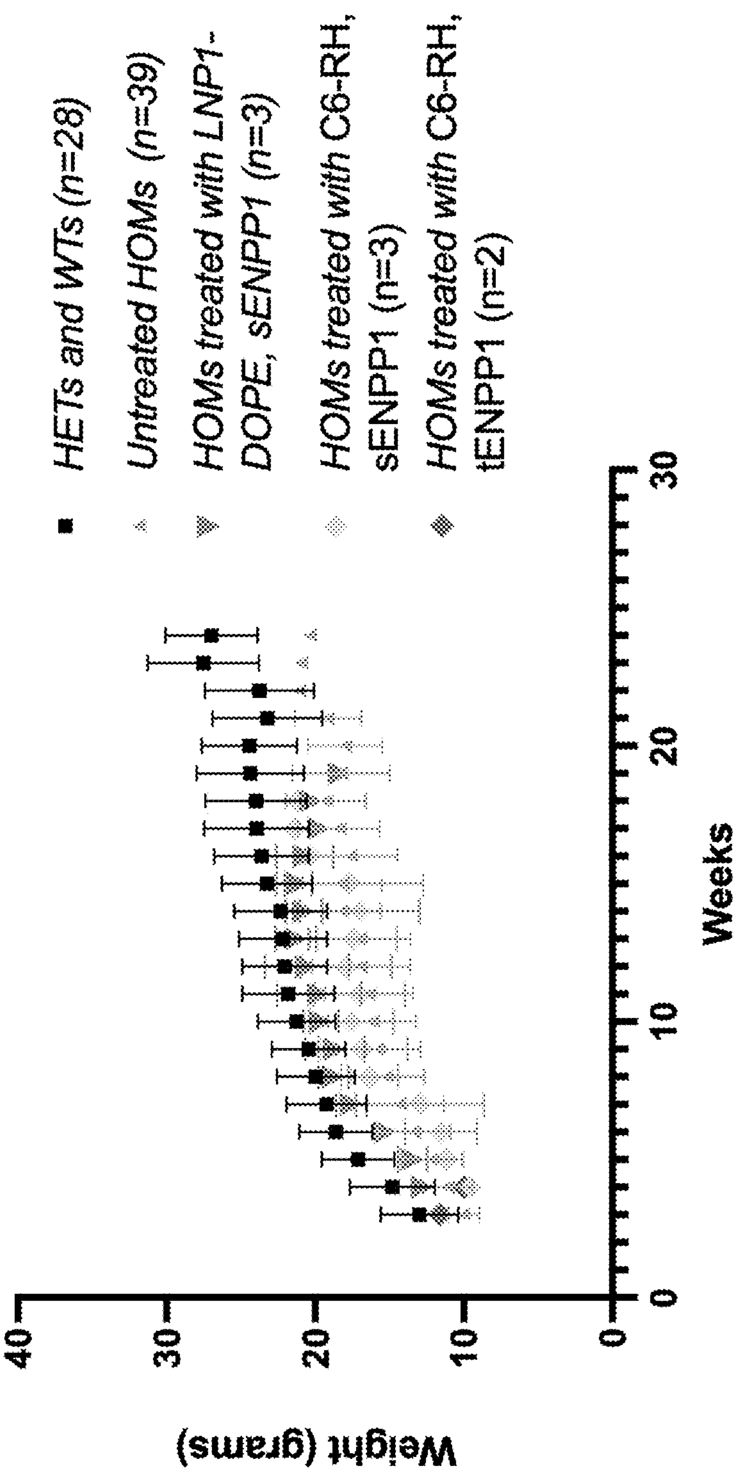
Figure 19D:
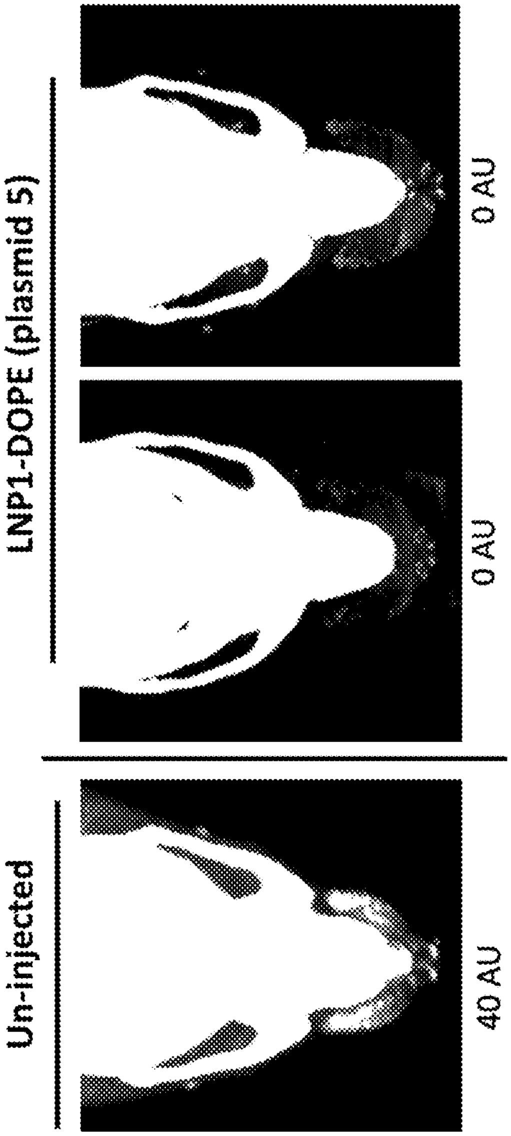

The outcome of treatment of soluble ENPP1 constructs delivered with LNPs with high cholesterol content (see Table 3) was further evaluated. The particles and compositions used in the delivery provided measurable survival benefits extending the life expectancy of treated animals from 80 days (untreated animals) to 114 days (treated animals) (n=3). In addition, microCT scans showed reduced calcification in the vibrissae of treated diseased animals in comparison with untreated group (FIGS. 19A-D). FIGS. 19A-D depict results of LNPs delivery efficacy studies using plasmids expressing soluble ENPP1. FIG. 19A is an illustration presenting the injection regimen. Briefly P3 mice were injected at day 0, day 7, and day 14. FIG. 19B shows survival curves of animals. FIG. 19C is a chart illustrating animal body weight. FIG. 19D is a set of MicroCT scans to detect early development of calcification in treated (LNPs encapsulating soluble ENPP1, 0.3 mg/kg) and untreated animals.

The experiment demonstrated (1) the efficacy of the particles in delivering the plasmid construct encoding the soluble ENPP1 construct in vivo; and (2) the effectiveness of the treatment as measured by increased survival, reversal of calcification, animal body weight.

Example 8: Particle Screening for Delivery of Therapeutic Cargos to Smooth Muscle Cells (SMCs)

Having established the therapeutic effect of a plasmid construct delivered with high cholesterol particles, particles that displayed select tropism to smooth muscle cells were screened in order to further improve delivery of the treatment.

To target nanoparticles to SMCs, a particle formulation based on the addition of a fifth component, DOTAP, a permanently cationic lipid (FIGS. 20A-B), was developed. It was reasoned that introducing DOTAP to the LNP composition at low percentage affects the chemical nature of the nanoparticles and increases the interactions with SMCs which is followed by cell internalization and construct expression. Importantly, a significant effect of the DOTAP with regards to particle size, size distribution, and zeta potential of the LNPs was not observed at the range that was screened (up to 10% DOTAP, FIGS. 20A-B).

Second, the transfection efficiency and expression of a model plasmid expressing RFP in mouse SMCs line (MOVAS) was evaluated. It was found that the presence of the permanently positive cationic lipid DOTAP, as well as the concentration of DOTAP, to be highly crucial for successful transfection of MOVAS cells. In contrast to the compositions incorporating DOTAP, the conventional four-component compositions of the art consisting only of ionizable lipids failed to demonstrate any expression. FIG. 21 is a pair of bar graphs depicting the results of the introduction of DOTAP lipid into the four-component formulation for screening its efficiency in delivering a plasmid cargo to MOVAS cells. As depicted in FIG. 21, the addition of as little as 1% DOTAP into the formulation drove an increase in cells expressing RFP (Left, the percentage of positive cells; right, the mean fluorescence intensity). In this experiment, MOVAS cells were incubated for 48 h with the reporter plasmid (2 μg/48 well plate) encoding RFP. Cellular expression was identified and measured using flow cytometry.

In addition to in vitro data, the role of DOTAP in the LNP formulation in the context of delivery of a plasmid nucleic acid encoding a therapeutic cargo to SMCs in vivo was confirmed. Using the Asj mouse model for the generalized arterial calcification of infancy (GACI) disease, successful delivery of plasmid DNA encoding the transmembrane ENPP1 expression at SMCs at the aorta (indicated by the white labeled SMC by F-actin) was demonstrated (FIG. 22, left column). Further, it was demonstrated that the conventional LNP formulations with four components do not demonstrate SMC expression in vivo (FIG. 22, middle column). The expression of the control LNPs of the art appear to be mainly localized at the adventitia. It was further confirmed that the described DOTAP formulations efficiently expressed a construct encoding a therapeutic gene, namely ENPP1 (FIG. 22, right column). In this experiment, the Asj mouse model at P3 was injected systemically with PBS (control), LNPs (conventional four-component formulation of the art), and DOTAP LNPs formulation (7% DOTAP) at 0.3 mg/kg plasmid dose. Histological images of the aorta show that ENPP1 expression (Flag-tag, top row) colocalized with SMCs marker expression (F-actin, bottom row).

Further, it was observed that the addition of a high percent of DOTAP (e.g. 50%) into the formulation increased tropism to the lung, which is undesired for smooth muscle cell delivery. In contrast, it was observed that the addition of DOTAP at relatively low percentages (<10%) enhanced uptake to SMCs without driving tropism to the lung (as our target in some cases is the liver). It was observed that the addition of DOTAP did not significantly affect the size of the formulated LNPs. However, the size distribution (PDI) increased with higher percentages of DOTAP, possibly due to the decreased proportions of the remaining lipids, which play a crucial structural role in particle formation. Furthermore, the zeta potential increased with higher DOTAP percentages, attributed to the substantial contribution of DOTAP quaternary amine head groups to the total surface charge of the nanoparticles. Despite varying percentages of DOTAP, encapsulation efficiency remained consistently above 90%, facilitating meaningful comparison between different formulations (FIG. 21).

The present disclosure provides the first demonstrated ability of this technology to deliver the claimed particles to smooth muscle cells, particularly to vascular smooth muscle cells (vSMCs).

Example 9: Delivery of Gene Therapy Cargos Using Particles Targeting Smooth Muscle Cells (SMCs)

Figure 24D:
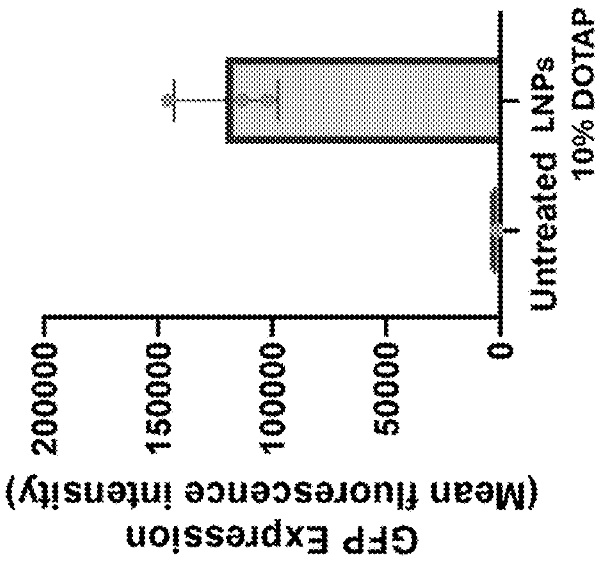

Further validation of the particles comprising the permanently cationic DOTAP component was sought by testing the delivery of different therapeutic cargos. In this experiment, an mRNA therapeutic cargo (as opposed to the plasmid therapeutic cargo of the aforementioned example) was first packaged into the DOTAP particles described above. As a threshold matter, it was determined that the nature of the nucleic acid therapeutic cargo (e.g., plasmid versus mRNA) appeared to have a minimum, insignificant effect on the size, size distribution, and zeta potential of the DOTAP LNPs encapsulating mRNA at the DOTAP ranges screened (up to 10%, FIGS. 23A-B). It was found that the DOTAP LNPs formulation increased the transfection of mRNA in VSMCs in vitro using the delivery of mRNA expressing GFP (FIGS. 24A-B). Moreover, in vitro studies using the MOVAS cell line demonstrated that increasing the content of DOTAP LNPs enhanced mRNA transfection efficiency in VSMCs, reaching an optimum at 10-20% DOTAP. Beyond this range, further increases in DOTAP content led to diminished mRNA delivery and reduced GFP expression (FIGS. 23A-B). Cell viability remained confirmed under experimental conditions, thus ruling out reduced expression due to cell death (FIG. 24C). 10% DOTAP LNPs also provided excellent delivery to primary human aortic cells cultured from an ACTA2 patient. (FIG. 24D).

Figure 25A:
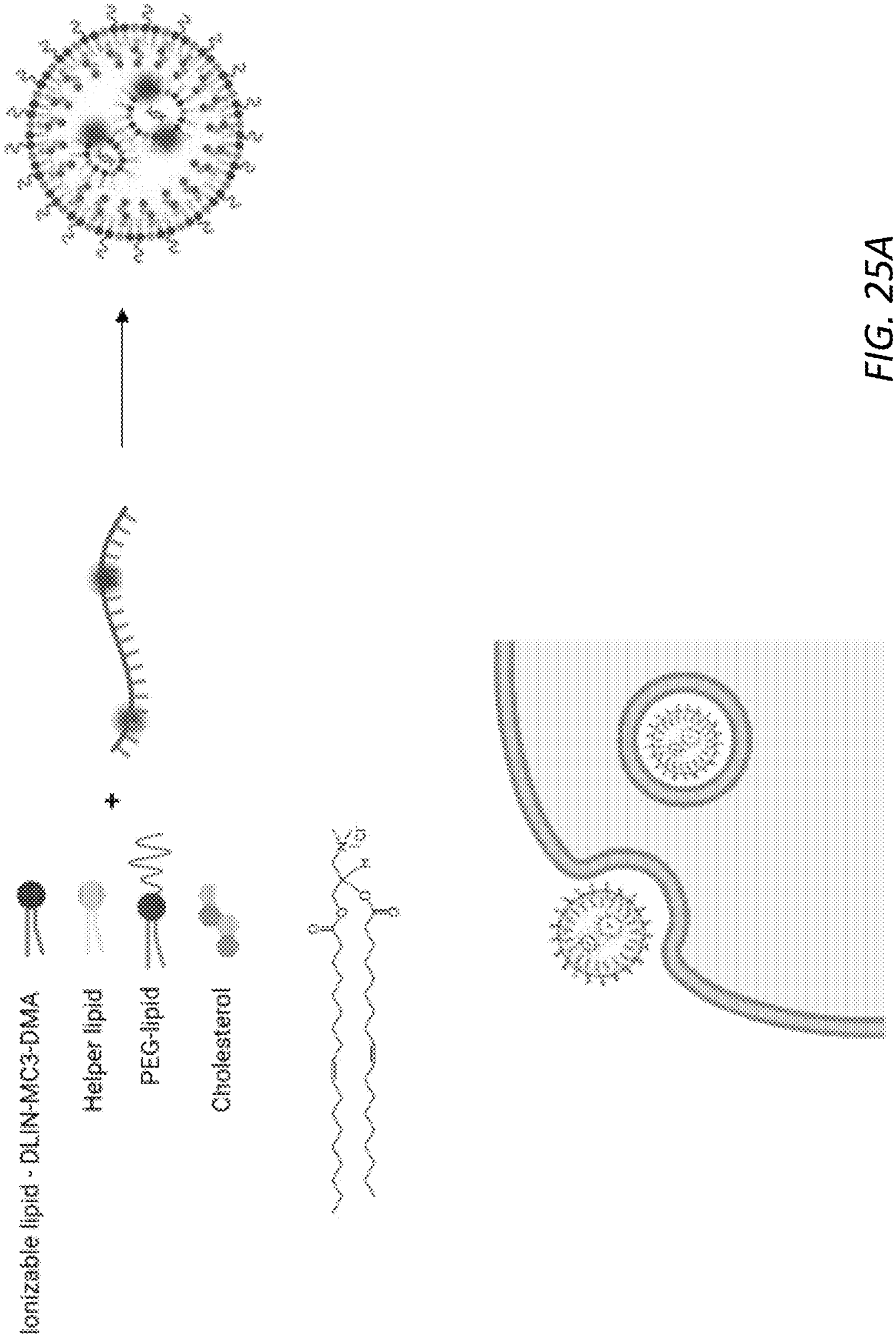

To investigate the underlying cause for the observed optimal mRNA delivery, cellular uptake studies were conducted based on the hypothesis that DOTAP may enhance LNPs uptake owing to its positively charged head groups. MOVAS cells were incubated with LNPs or DOTAP LNPs encapsulating Cy5-labeled mRNA for 4 and 24 hours (FIG. 25A). At each time point, cells were visualized using a fluorescent microscope to qualitatively assess mRNA internalization and were subsequently harvested and analyzed by flow cytometry for quantitative evaluation.

Figure 25B:
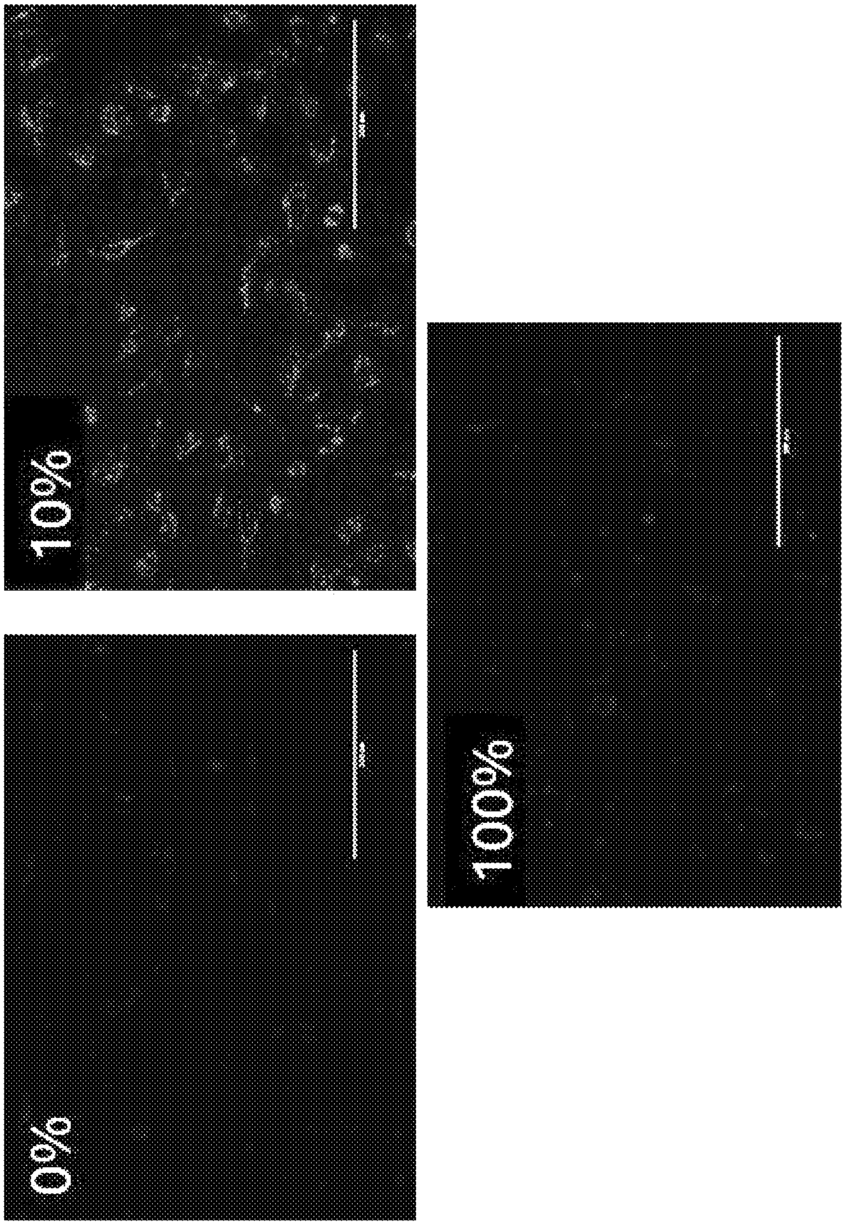
Figure 25C:
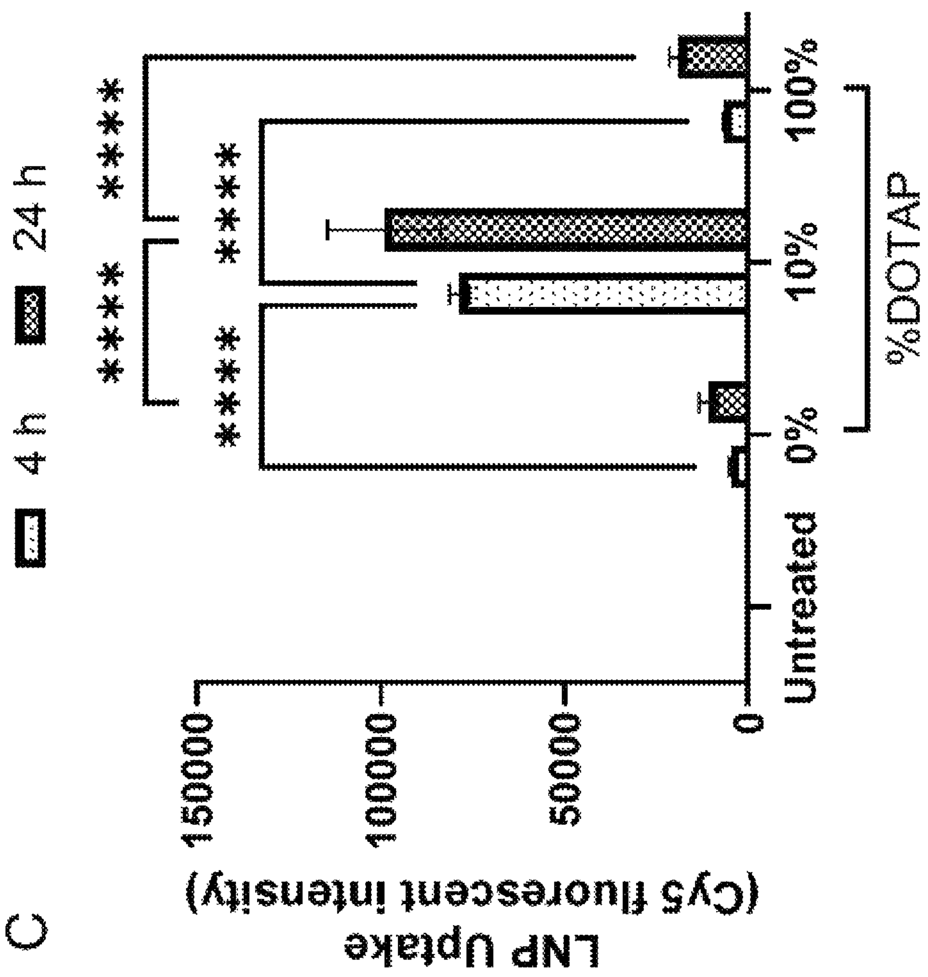
Figure 25D:
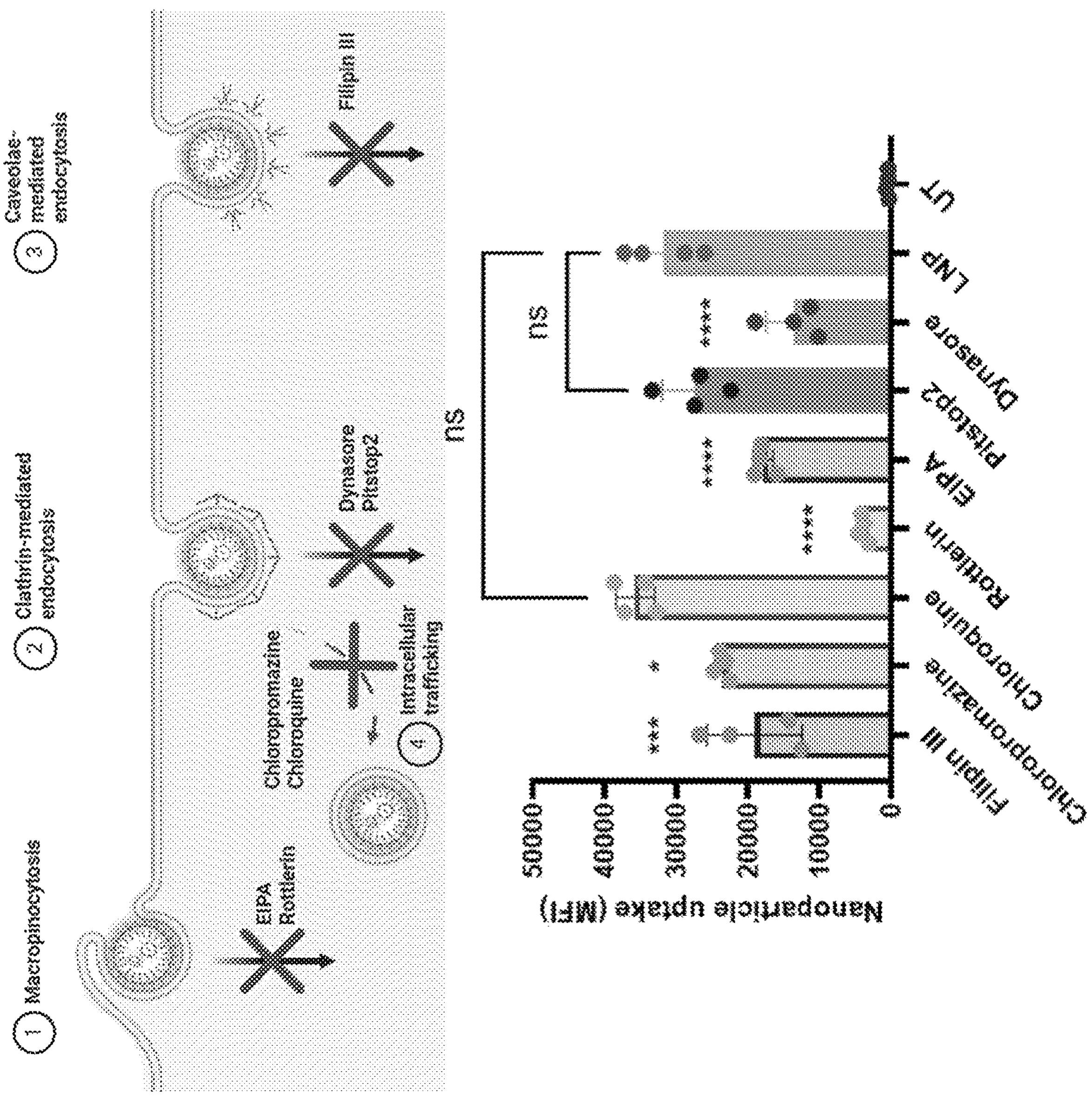
Figure 25E:
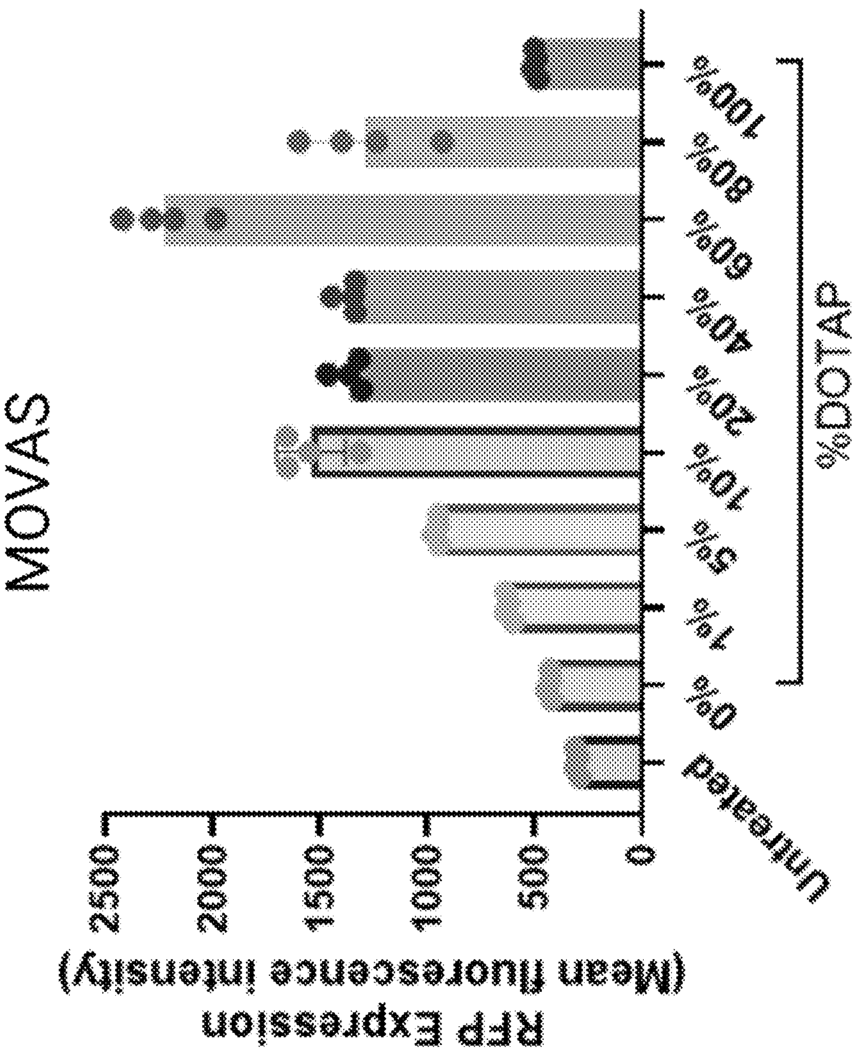

The results indicated that the efficient mRNA delivery facilitated by 10% DOTAP LNPs was attributed to enhanced cellular uptake, evidenced by an increased Cy5 intracellular signal (FIG. 25B). Specifically, a 20-fold increase in fluorescent intensity was observed when compared to 0% DOTAP, and a 10-fold increase when compared to 100% DOTAP at the 4-hour time point. Notably, a significant increase was also observed at the 24-hour incubation time point (FIG. 25C). A 10% DOTAP formulation was used to investigate uptake mechanism for LNP cellular internalization, using Cy5-fluorescently labeled LNPs (mRNA-Cy5) in the presence of various inhibitors including chlorpromazine, chloroquine, rottlerin, EIPA, pitstop2, and Dynasore. Uptake was quantified using flow cytometry. The results showed that LNPs appear to utilize caveolin and macropinocytosis-mediated uptake into SMCs (FIG. 25D). LNPs with 10% or more DOTAP also provided excellent delivery to of plasmid DNA encoding RFP to MOVAS cells (FIG. 25E).

In addition to in vitro data, the role of DOTAP in the LNP formulation in the context of delivery of an mRNA encoding a reporter gene to SMCs in vivo was confirmed. In this example, the effect of DOTAP as a fifth component added to LNPs and its ability to deliver mRNA to SMCs in vivo in a Marfan disease mouse model was studied. Using DOTAP particles with a 7% concentration, mRNA expressing a Cre recombinase enzyme was delivered. The Cre recombinase enzyme enables the expression of tdTom protein in this genetically engineered model. It was found that when comparing the LNPs of the art to the instant LNPs comprising DOTAP, the same extent of tdTom expression is achieved in certain organs.

Figure 26A:
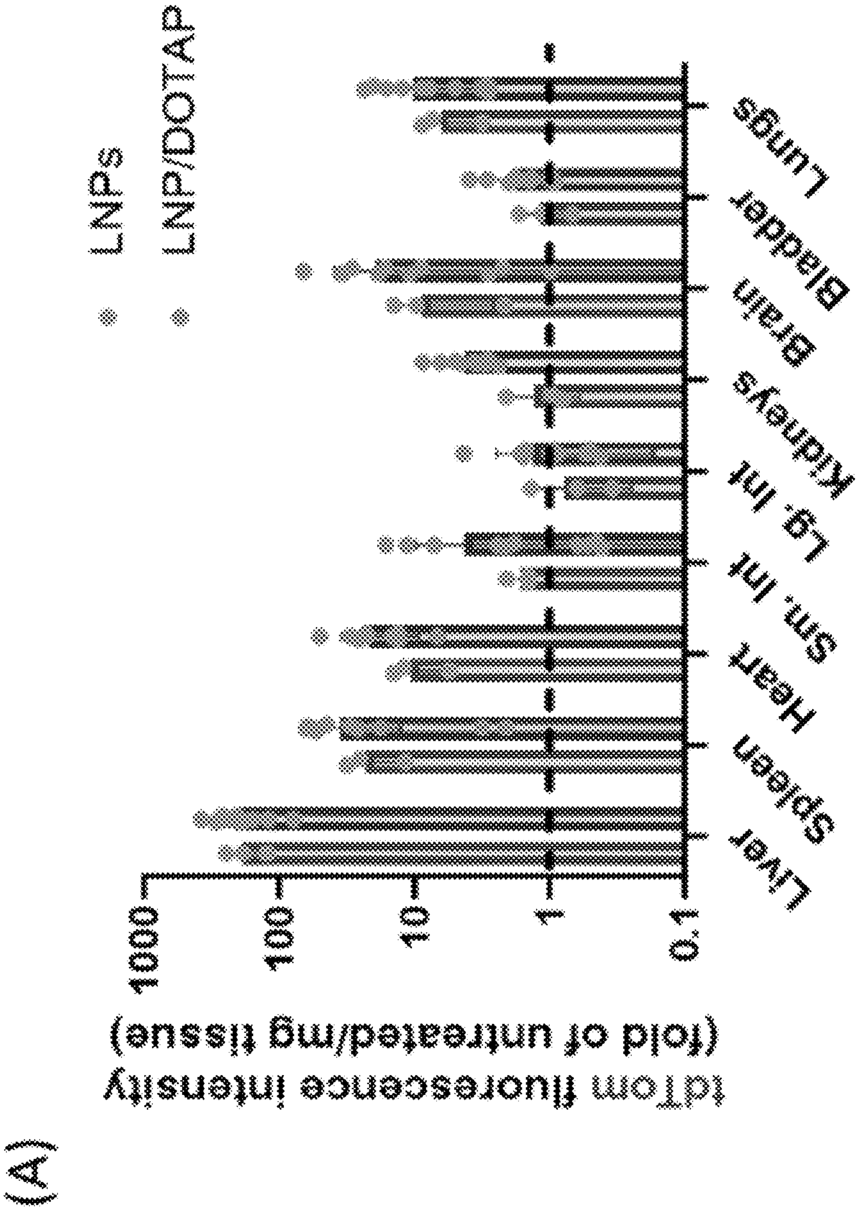
Figure 26B:
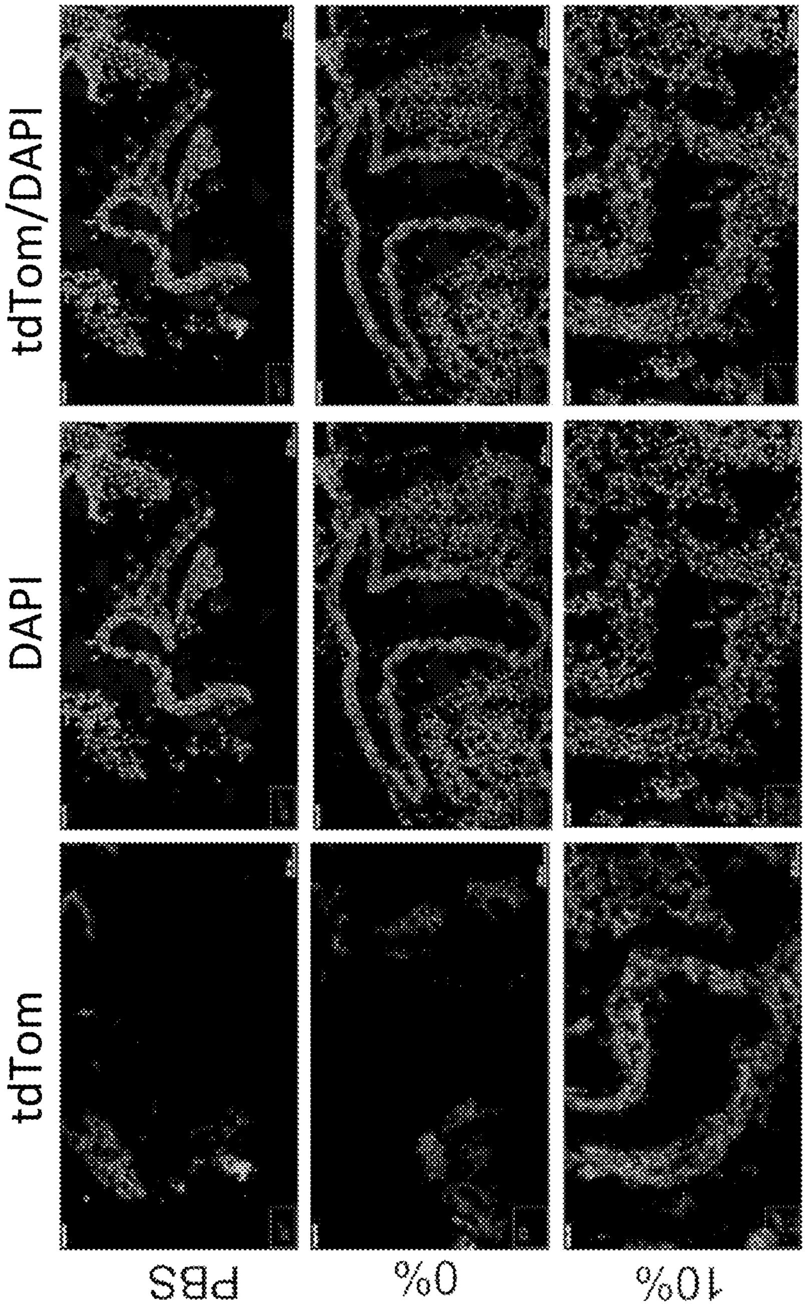

However, further histological analysis of the aorta revealed that the DOTAP formulation showed high expression in aorta SMCs, indicating SMC specificity in vivo (FIGS. 26A-B). FIGS. 26A-B illustrate the in vivo delivery of Cre-mRNA utilizing LNP and DOTAP LNP and expression of tdTom in the Marfan disease mouse model. Mice at P3 were injected with 1 mg/kg mRNA encapsulated in LNPs or DOTAP LNPs. FIG. 26A is a chart depicting expression of tdTom in different organs 6 days post injection. FIG. 26B comprises histology images of the aorta in which tdTom was expressed using DOTAP LNPs.

Figure 26C:
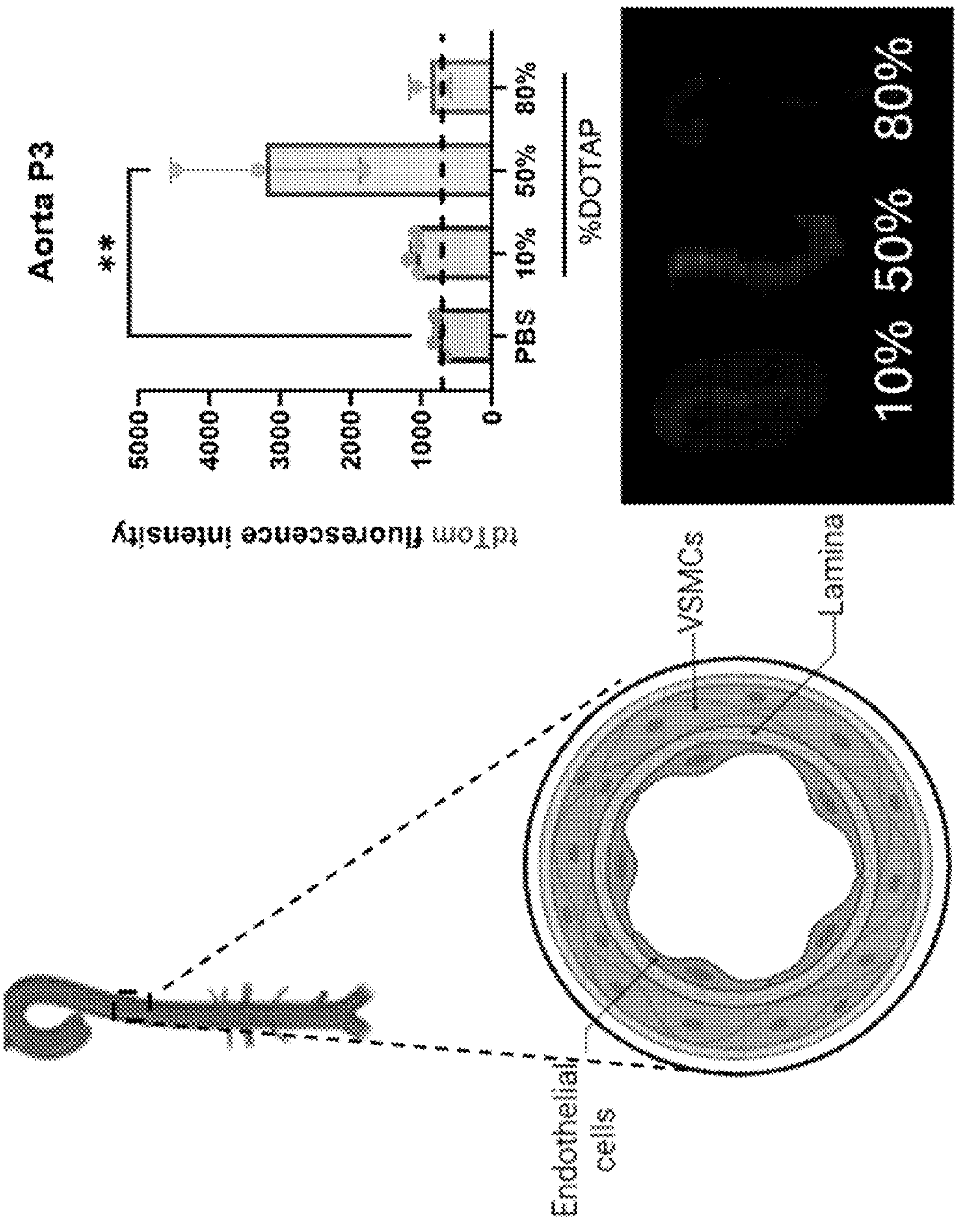
Figure 26D:
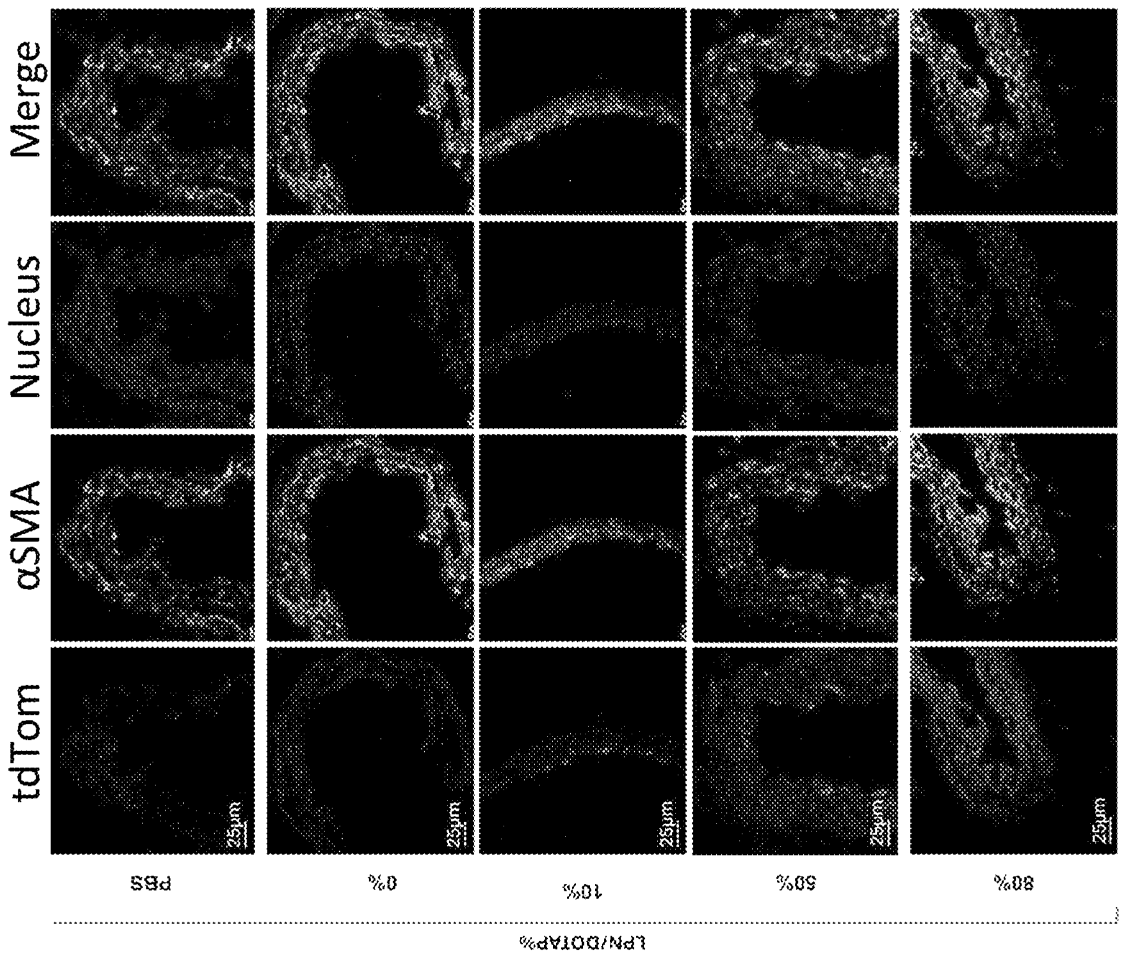

Increasing concentrations of DOTAP were also evaluated. FIGS. 26C-D show that increasing the % of DOTAP in LNP formulation increases SMC tdTom expression In vivo. In the experimental results shown in FIG. 26D, Cre-mRNA delivery utilizing LNPs with tested with increasing DOTAP content and expression of tdTom in a Marfan disease mouse model. Mice at P3 were injected with 1 mg/kg mRNA encapsulated in LNPs formulated with 0, 10, 50 and 80% DOTAP lipid. tdTom expression identified using immune fluorescence in histological sections of the aorta and localized to SMCs (indicated by α-SMA expression).

Thus, it was demonstrated that DOTAP (7%) comprising LNPs display preferential delivery towards smooth muscle cells in vivo, as compared to standard LNPs, in different mouse models and with two different cargos (plasmid and mRNA).

Example 10: Targeting LNPs to Mutant Smooth Muscle Cells Using Targeting Peptides In order to enhance the targeting, and potentially uptake, of the nanoparticles to specific tissue or cells DOTAP LNPs conjugated with peptides that can target smooth muscle cell tissue or cell surface receptors were developed. The targeting strategy was composed of two approaches. First, conjugating our DOTAP nanoparticles with peptides that target receptors highly expressed in diseased vasculature extracellular matrix (collagen IV) in order to increase the accumulation and the retention of the nanoparticles in diseased tissues. Second, conjugating our DOTAP nanoparticles with peptides that target receptors highly expressed on the surface of vSMCs (TL-6R, CD63, and GAL-3) increasing the uptake into these cells. A combination of the two approaches can potentially leverage both accumulation and retention at the target site and cell specificity. FIG. 27 is a schematic illustrating the aforementioned conjugation scheme. LNPs were conjugated with the desired peptide by swapping traditional PEG lipids typically present in standard LNP formulations with maleimide-terminally modified PEG lipid. Peptide conjugation was done in different densities controlled by the percentage of the maleimide-terminally modified PEG lipid in the LNP formulation, ranging from 0.15-1.2% (FIG. 27). Peptide sequences targeting extracellular matrix and cellular receptors are described in Table 4 below:

TABLE 4

| Peptide sequences targeting extracellular matrix and cellular receptors. | |
|---|---|
| Peptide receptor | Sequence |
| Col-4 | KLWVLPK-GGG-C; SEQ ID NO: 22 |
| IL6-R | C-GGG-LSLITRL; SEQ ID NO: 23 |
| CD63 | CRHSQMTVTSRL; SEQ ID NO: 24 |
| Gal-3 | C-GGG-ANTPCGPYTHDCPVKR; SEQ ID NO: 25 |

To evaluate this approach, LNPs conjugated with different peptides were first synthesized, their physical properties were characterized, and their functional activity in MOVAS cell line in vitro was examined.

Table 5 summarizes the physical properties of the assembled LNPs conjugated or non-conjugated with the listed peptides in changing surface densities controlled by the percentage of a linker lipid in the LNP formulation. Increasing linker percentages (0.15-1.2%) increases the conjugated peptides on LNPs surface which confirms the chemical conjugation to the surface of the LNPs. The physical properties highly affect the potential functionality of the LNPs therefore crucial to characterize. The physical properties of the LNPs post conjugation present a slight increase in size with no significant effect on PDI, however, not affected by the percent of conjugated peptide. On the other hand, zeta potential decreases while increasing the percentage of the conjugated peptide.

TABLE 5

Physical properties (size, PDI, and Zeta potential) of peptide-conjugated and non-conjugated LNPs by Col4/IL6R/CD63/Gal3 targeting peptides in varying densities.

| | Size (nm) | PDI | Zeta potential (mV) |
|---|---|---|---|
| LNP-DOTAP | 131.8 | 0.14 | −5.48 |
| 0.15% NC | 145.2 | 0.15 | −5.47 |
| 0.3% NC | 161.1 | 0.24 | −4.24 |
| 0.6% NC | 137.8 | 0.17 | −4.17 |
| 0.9% NC | 136.3 | 0.19 | −4.39 |
| 1.2% NC | 118.6 | 0.19 | −5.89 |
| 0.15% Col-4 | 188.33 | 0.17 | −6.79 |
| 0.3% Col-4 | 144.20 | 0.26 | −7.00 |
| 0.6% Col-4 | 165.63 | 0.14 | −11.87 |
| 0.9% Col-4 | 148.83 | 0.19 | −14.33 |
| 1.2% Col-4 | 139.43 | 0.15 | −17.30 |

TABLE 5-continued

Physical properties (size, PDI, and Zeta potential) of peptide-conjugated and non-conjugated LNPs by Col4/IL6R/CD63/Gal3 targeting peptides in varying densities.

| | Size (nm) | PDI | Zeta potential (mV) |
|---|---|---|---|
| 0.15% IL-6R | 131.97 | 0.25 | −7.66 |
| 0.3% IL-6R | 111.51 | 0.33 | −7.45 |
| 0.6% IL-6R | 60.24 | 0.57 | −9.78 |
| 0.9% IL-6R | 137.43 | 0.19 | −11.70 |
| 1.2% IL-6R | 140.30 | 0.07 | −13.90 |
| 0.15% CD-63 | 125.2 | 0.104 | 1.36 |
| 0.3% CD-63 | 120.2 | 0.047 | −3.67 |
| 0.6% CD-63 | 118.3 | 0.06 | −10.4 |
| 0.9% CD-63 | 195.1 | 0.24 | −13.5 |
| 1.2% CD-63 | 126.5 | 0.088 | −12.3 |
| 0.15% Gal-3 | 134.1 | 0.094 | −0.975 |
| 0.3% Gal-3 | 131.9 | 0.089 | −3.74 |
| 0.6% Gal-3 | 120.4 | 0.102 | −5.9 |
| 0.9% Gal-3 | 119.9 | 0.058 | −10.4 |
| 1.2% Gal-3 | 113 | 0.128 | −13.4 |

LNPs Decorated with Collagen IV (Col-JV)-Targeting Peptides

In addition, based on nanoparticle tracking analysis, the percentage of linker lipid was estimated and correlated to the concentration of conjugated peptide. Furthermore, the number of peptide units per LNP was plotted (FIG. 28) resulting in a range varying from about 194 peptides to about 1268 per LNP indicating the density of peptides per particle.

Following the synthesis and characterization, the efficiency of conjugated LNPs was first examined in functional assays in vitro. MOVAS cells were treated with peptide-conjugated LNPs encapsulating mRNA expressing GFP. GFP expression was analyzed by flow cytometry 24 h post treatment. The results in FIG. 29 demonstrate the extent of GFP expression as a function of conjugated peptide content and sequence. The efficiency of mRNA expression was highly affected by the peptide amount, demonstrating an optimum at 0.15-0.3% of conjugated peptide for in vitro application regardless of the peptide sequence. The addition of the lipid with the linker, even without the peptides, was also affected by the linker lipid content (non-conjugated), indicating that LNPs composed of high percentages of lipid linker affected their functional activity. It was then confirmed and a range was found for peptide conjugation that was not affected by the additional manipulations utilized for the purpose of peptide conjugation.

It was therefore optimized and confirmed that peptide-conjugated LNPs efficiently expressed GFP in vitro, suggesting that the conjugation did not moderate their functional activity, thereby encouraging the examination of the potential of targeting SMCs in vivo.

Following the in vitro validation of functional activity, we evaluated the ability of mRNA-loaded LNPs to selectively target VSMCs in vivo. The formulations shown in Table 6 were tested.

TABLE 6

LNP formulations.

| Formulation | MC-3 | DOPE | Cholesterol | DMG-PEG | DSPE-PEG-mal | DOTAP |
|---|---|---|---|---|---|---|
| 0.15% NC | 0.450 | 0.0945 | 0.3420 | 0.0120 | 0.0015 | 0.100 |
| 0.3%-Col-IV | 0.450 | 0.0945 | 0.3420 | 0.0105 | 0.0030 | 0.100 |
| 0.3% NC | 0.450 | 0.0945 | 0.3420 | 0.0105 | 0.0030 | 0.100 |
| 0.6%-Col-IV | 0.450 | 0.0945 | 0.3420 | 0.0075 | 0.0060 | 0.100 |
| 0.6% NC | 0.450 | 0.0945 | 0.3420 | 0.0075 | 0.0060 | 0.100 |

TABLE 6-continued

| LNP formulations. | | | | | | |
|---|---|---|---|---|---|---|
| Formulation | MC-3 | DOPE | Cholesterol | DMG-PEG | DSPE-PEG-mal | DOTAP |
| LNP/DOTAP/80% | 0.100 | 0.021 | 0.076 | 0.003 | 0.000 | 0.800 |
| 0.3%-Col-IV (80% DOTAP) | 0.100 | 0.0210 | 0.0760 | 0.0120 | 0.0030 | 0.7880 |
| 0.6%-Col-IV (80% DOTAP) | 0.100 | 0.0210 | 0.0760 | 0.0090 | 0.0060 | 0.7880 |
| 0.3%-IL-6R | 0.450 | 0.0945 | 0.3420 | 0.0105 | 0.0030 | 0.100 |
| 0.15%-Col-IV + 0.15%-IL-6R | 0.450 | 0.0945 | 0.3420 | 0.0105 | 0.0030 | 0.100 |

The LNPs were designed to encapsulate nucleic acids and were conjugated with peptides targeting extracellular matrix components or cell surface receptors. This technology demonstrates improved targeting and gene expression in vSMCs in mouse models of vascular diseases, in part by targeting receptors in vSMCs.

To achieve this, we encapsulated Cre-mRNA in LNPs that were subsequently conjugated with a Collagen IV-targeting peptide, leveraging its affinity for the extracellular matrix of VSMCs. We hypothesized that Col-IV peptide conjugation would enhance LNP retention within the VSMC extracellular matrix, thereby increasing bioavailability and uptake by SMCs. To test this, Marfan mice were injected at P3 with Col-IV-conjugated LNPs, and tdTom fluorescence expression was analyzed six days post-injection. Additionally, we sought to determine the optimal peptide density on the LNP surface for maximal retention and subsequent SMC uptake, leading to tdTom expression (Table 6). We evaluated three peptide densities, 0.15%, 0.3%, and 0.6% relative to the lipid component PEG-DSPE, into which the peptide was conjugated. Histological examination of mice aorta revealed that LNPs conjugated with Col-IV at 0.3% peptide density exhibited the most efficient SMC-specific tdTom expression. Moreover, this enhanced expression was significantly higher compared to non-conjugated LNPs, reinforcing the effectiveness of Col-IV peptide-mediated targeting.

In addition, we have explored potential synergy between the two examined elements, peptide-based targeting and the addition of DOTAP lipid to the formulation, in increasing the targeting efficiency for SMCs. We formulated Cre-mRNA in a formulation containing 80% DOTAP lipid which was then conjugated by Col-IV targeting peptide and tdTom expression was examined 6 days post injection. FIG. 15 presents histology sections of the aorta demonstrating that there was no increase in tdTom SMC expression for the combined Col-IV-DOTAP approach in comparison to the single approach where we either use the optimal formulation (80% DOTAP) to target SMCs or decorate the LNPs with Col-IV targeting peptide. Leveraging two approaches to target SMCs doesn't demonstrate an increase in SMC tdTom expression.

The incorporation of DSPE-PEG-maleimide (DSPE-PEG-mal) lipid into the formulation was helpful, as it appeared to play a role in stabilizing the outermost shell of the lipid nanoparticle (LNP) and maintaining the presentation of the conjugated peptide.

To explore the potential of targeting inflamed tissues in adult animals we conjugated LNPs with peptides targeting IL-6R, which is overexpressed in situations where inflammation is involved. In addition, we designed an LNP formulation where the two peptides were conjugated to the same LNP as a means to enhance tissue targeting and cellular targeting at the same delivery strategy. Therefore, IL-6R targeting peptide was conjugated in combination with Col-IV targeting peptide. To test this hypothesis, we encapsulated mRNA expressing GFP and examined expression using histology imaging and analysis and injected three-month-old (adult) wild type mice and mice engineered with a gain of function mutation in SMAD4 to model the human condition, Myhre syndrome both fed a high fat diet. We found increased GFP expression in examined organs (aorta, kidney, liver) with the LNPs that were conjugated with both peptides in comparison to a single IL-6R peptide conjugation. It is important to note that even the wildtype mice had elevated inflammation due to the high fat diet the mice are fed, causing this difference to appear in some cases mainly in the liver and kidney, but not the aorta.

We verified the results obtained in the Myhre mouse model in an LDLR knockout mouse model, which is used as a model for inflamed vascular disease indications. GFP mRNA was encapsulated in LNPs conjugated by IL-6R targeting peptide (0.3%). 12 h post intravenous injection we examined GFP expression in the aorta using histology analysis. While comparing conjugated to non-conjugated formulation, we identified a significant increase in GFP expression using the IL-6R targeting peptide formulation, showing that the peptide sequence on the surface of the LNPs increased delivery of the encapsulated mRNA in smooth muscle cells.

Example 11. Systemically-Delivered SMCs-Optimized LNPs Enable Efficient SMCs Gene Editing for ENPP1 Expression for GACI Gene Therapy $ENPP1^{asj/asj}$ mice were injected at P3 with SMC-optimized LNPs (10% DOTAP) carrying a plasmid encoding a FLAG-tagged wild type ENPP1, and aortic SMC ENPP1 expression was determined by detecting the FLAG-tag using TIC 7 days post injection. As shown in FIG. 30A, the 10% DOTAP LNPs provided robust expression. In addition, ENPP1 gene therapy was administered in $ENPP1^{asj/asj}$ mice in three doses of LNPs (10% DOTAP) encapsulating plasmid expressing ENPP, and therapeutic efficacy was identified by vibrissae calcification imaged by microCT. As shown in FIG. 30B, a significant reduction in calcification was seen.

Example 12: In Vivo rENPP1 Gene Delivery Via AAVPR Packaging

ENPP1 gene therapy was tested in vivo in $ASJ^{-/-}$ mice, the gold-standard mouse model of GACI (Li et al., Dis Model Mech. 2013 Jun. 20; 6(5):1227-1235). Pups were injected on postnatal day 3 with a CAG-rENPP1 expression construct packed in AAVPR through the retroorbital route or with NPs containing DNA plasmid cargo expressing rENPP1.

Tissues and organs were harvested on day 7 post injection and placed on fresh OCT blocks followed by cryosectioning and immunohistochemistry to study the expression profile of rENPP1 in various tissues and organs. In vivo biodistribution of NPs and AAVPR was determined based on localization of fluorescent signals of ENPP1 expression in the aorta, liver, brain, heart, small intestine, kidney, and bladder. FIG. 31 shows expression of rENPP1 in different tissues and organs injected with a construct expressing rENPP1 packed in AAVPR as compared to control un-injected, demonstrating the highest levels of expression were in the aorta.

Figure 32A:
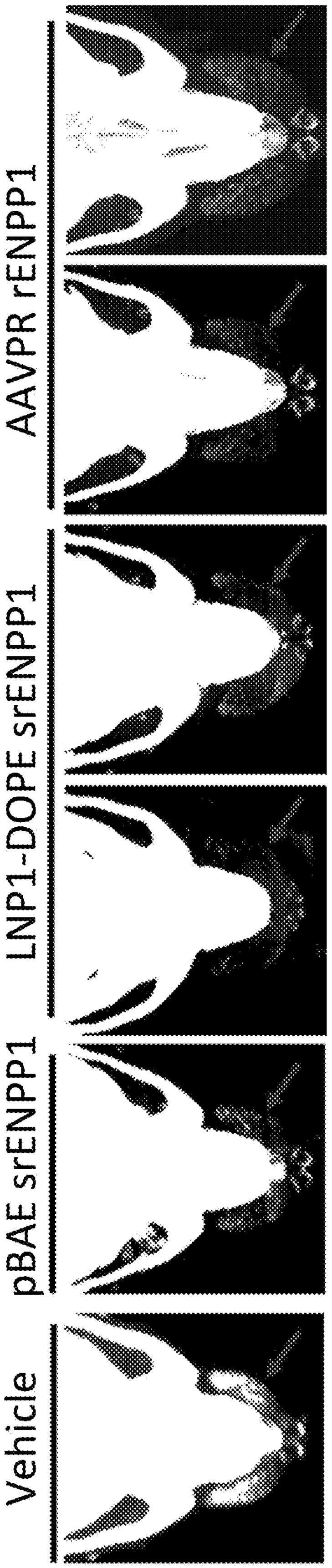
Figure 32B:
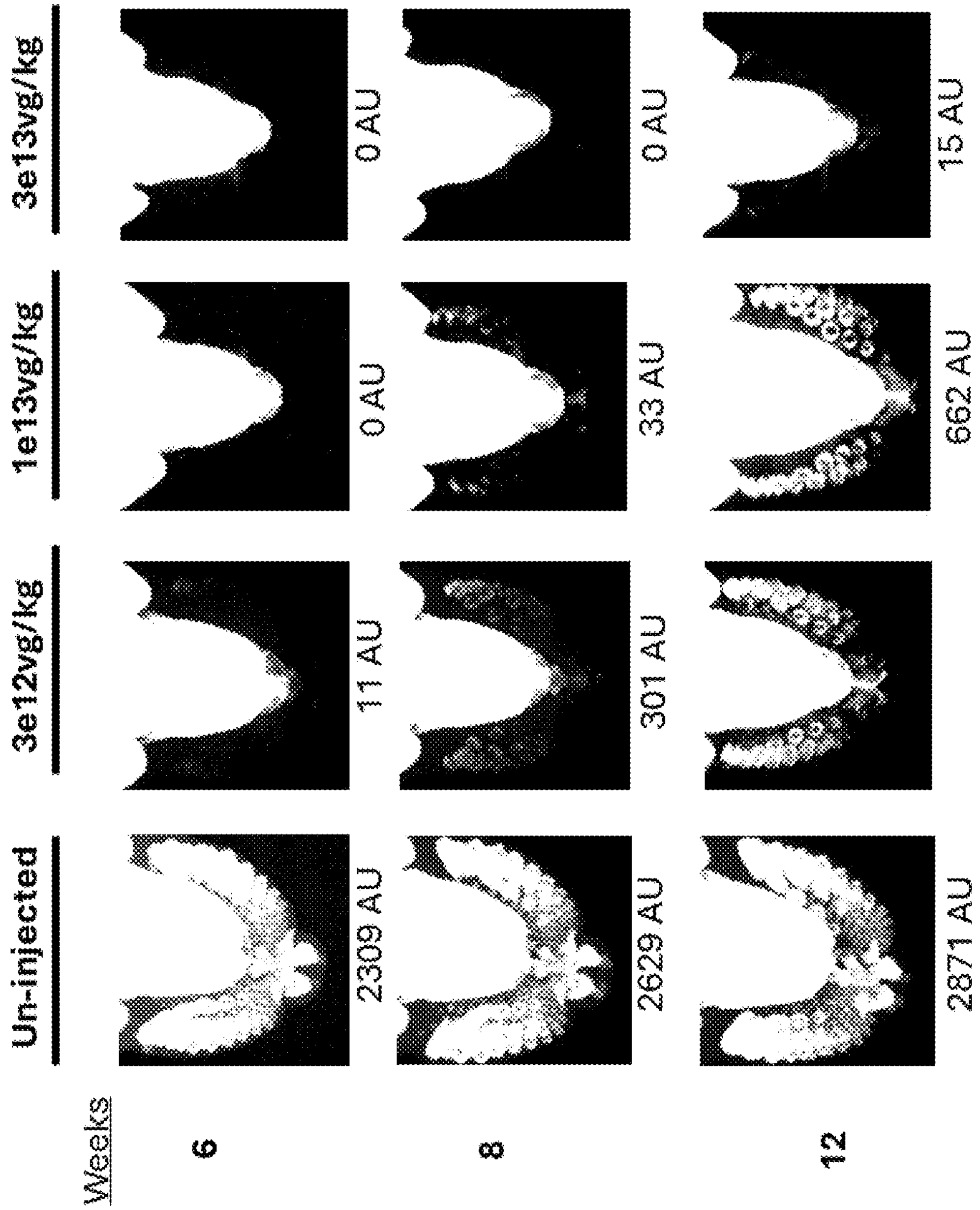
Figure 32C:
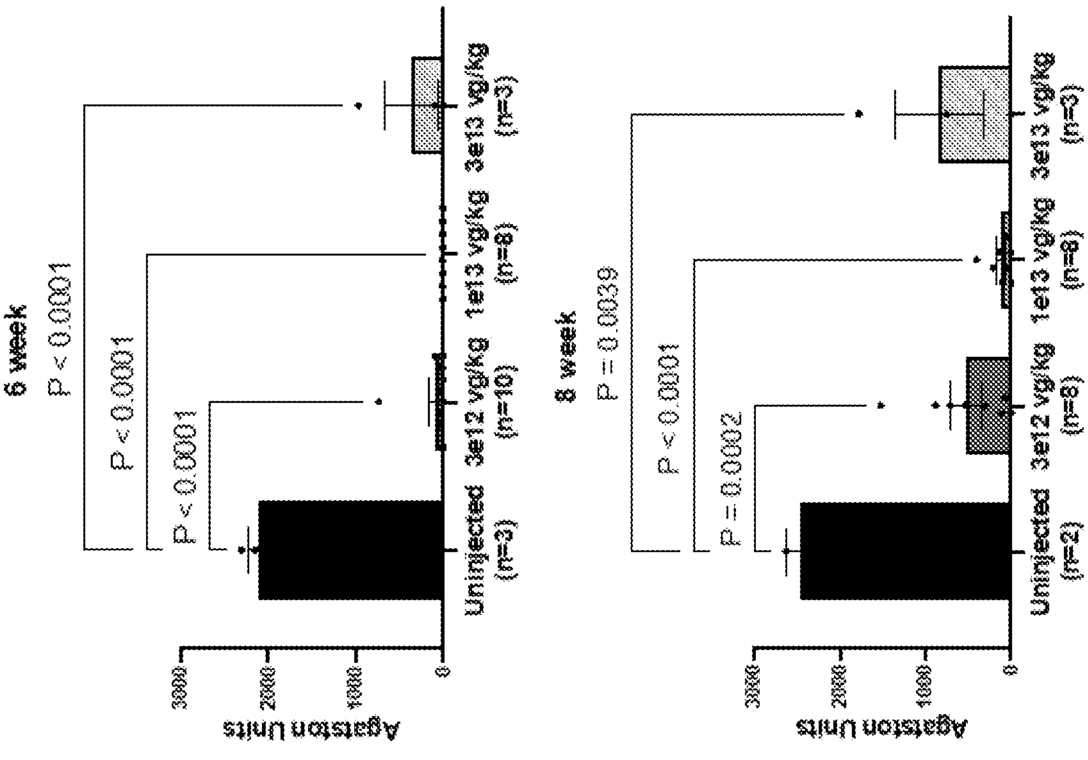
Figure 32D:
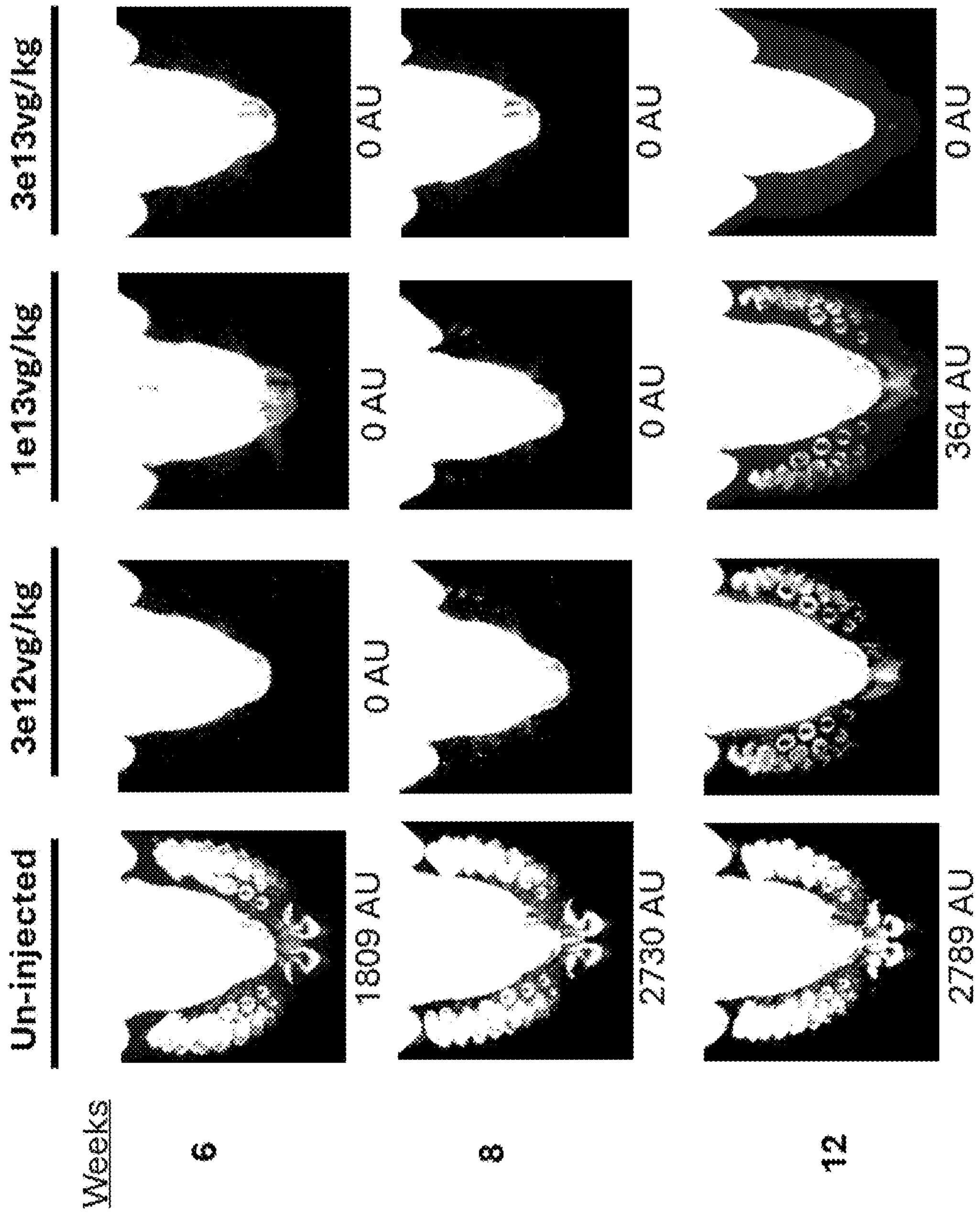
Figure 32E:
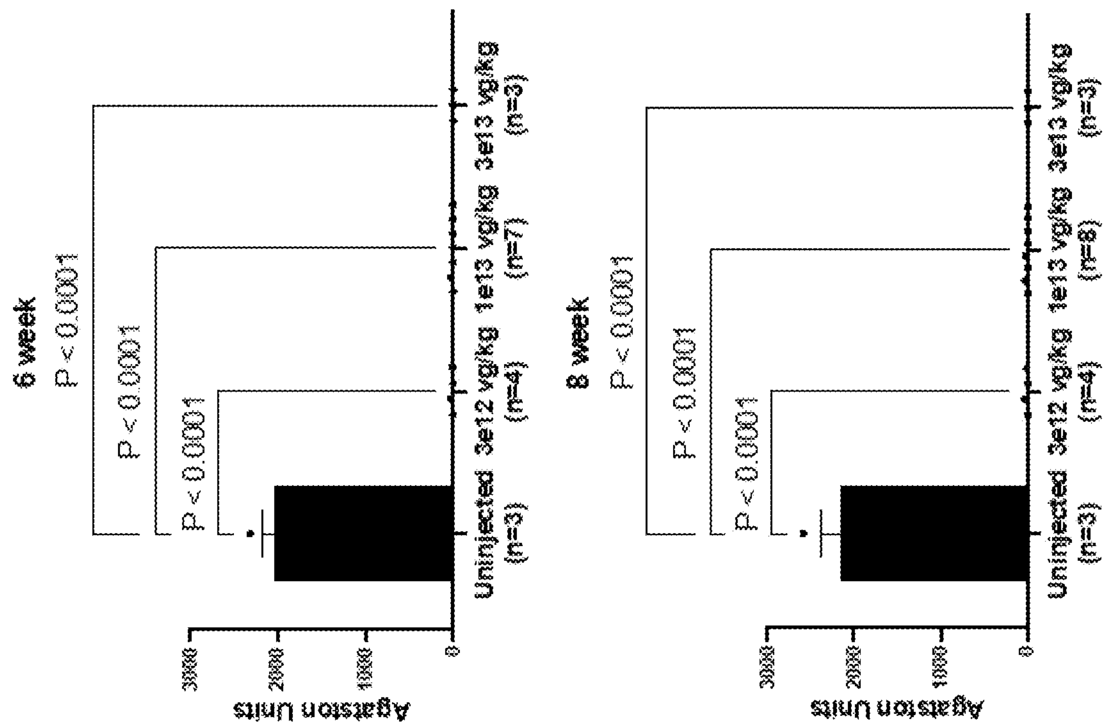

Micro-CT images were taken at 6, 8, and 12 weeks post-injection to evaluate levels of vibrissae calcification compared to untreated controls. As shown in FIG. 32A, ENPP1 gene therapy with either NP delivery of srENPP1 or AAVPR delivery of rENPP1 reduced vibrissae calcification on micro-CT. In addition, when post-natal day 3 $Asj^{-/-}$ mice were injected retro-orbitally with increasing doses of AAVPR-CAG-rENPP1 (3e12 vg/kg, 1e13 vg/kg, 3e13 vg/kg), statistically significant reductions in calcification ($P<0.004$) were observed in both male FIGS. 32B-C and female mice FIGS. 32D-E at 6, 8, and 12 weeks post-injection across all dosages administered.

The effect of ENPP1 gene therapy on plasma pyrophosphate (PPi) levels was evaluated in GACI mice treated with poly-beta amino ester nanoparticle (pBAE) carrying CMV-srENPP1 or AAVPR delivering CAG-rENPP1, delivered via retro-orbital systemic injections. As shown in FIG. 33A, serum PPi levels were normalized in the mice treated with pBAE-CMV-srENPP1 or AAVPR-CAG-rENPP1. In addition, PPi levels were evaluated in $ASJ^{-/-}$ mice that received 3 different doses of AAVPR-CAG-rENPP1 (low=3e12 vg/kg, intermediate=1e13 vg/kg, high=3e13 vg/kg). There was a dose-dependent increase in plasma PPi levels with AAVPR-CAG-rENPP1 treatment (FIG. 33B, trend ANOVA $p=0.0012$). Treatment with the intermediate and high dose AAVPR-CAG-rENPP1 restored plasma PPi levels to normal levels as measured in the untreated HET/WT group.

Survival of wild-type, heterozygous, and homozygous $ASJ^{-/-}$ mice was also evaluated. A significant improvement (>150 days compared to a median survival of ~79 days in the untreated group) in median survival of treated $ASJ^{-/-}$ mice, as compared to untreated mice, was observed. See FIG. 34A-B. FIG. 34A are Kaplan Meyer curves of $ASJ^{-/-}$ mice injected retro-orbitally at postnatal day 3 (P3) with 3 different doses of AAVPR-CAG-rENPP1 (low=3e12 vg/kg, intermediate=1e13 vg/kg, high=3e13 vg/kg) FIG. 34B $ASJ^{-/-}$ mice injected retro-orbitally at postnatal day 14 (P14) with a lower dose of AAVPR-CAG-rENPP1 FIG. 34B. In both instances, there was improvement in survival after treatment with AAVPR-CAG-rENPP1 compared to no treatment (FIG. 34A=Log-rank $p<0.001$ for all doses vs. untreated; FIG. 34B=Log-rank $p=0.012$). In addition, the effect of ENPP1 gene therapy with the AAVPR-CAG-rENPP1 construct was evaluated in $ASJ^{-/-}$ mice injected retro-orbitally with 3 different doses of AAVPR-CAG-ENPP1 (low=3e12 vg/kg, intermediate=1e13 vg/kg, high=3e13 vg/kg). Treatment with low dose of AAVPR-CAG-ENPP1 was associated with an improvement in weight compared to untreated mice, as shown in FIG. 35.

It was noted that survival of normal mice was not impacted by AAVPR-CAG-ENPP1 treatment at multiple doses or at a different age of injection, as depicted in the Kaplan Meier curves shown in FIG. 36A-B. Briefly, Wild-type (WT) and $ASJ^{+/-}$ (HETs) were injected retro-orbitally with 3 different doses of AAVPR-CAG-ENPP1 (low=3e12 vg/kg, intermediate=1e13 vg/kg, high=3e13 vg/kg) FIG. 36A. Survival was similar to what would be expected of untreated WT and HET mice. WT and ASJ HETs were injected retro-orbitally at postnatal day 3 (P3) versus postnatal day 14 (P14) with the low dose of AAVPR-CAG-ENPP1 FIG. 36B. Survival was similar to what would be expected of untreated WT and HET mice. The same was observed with weight; there was no significant difference in overall weights between treated and untreated mice.

Example 13: Treatment of Human Vascular Smooth Muscle Cells (VSMCs) with AAVPR-CAG-rENPP1

This example discloses a reduction in human vascular smooth muscle cell (VSMC) calcification after administering AAVPR-CAG-rENPP1. The method demonstrates a significant reduction in calcification, RUNX2 protein levels, and VSMC migration.

Briefly, human vascular smooth muscle cells (VSMCs) were treated with AAVPR-CAG-rENPP1 at doses of 8e9 vg/mL (low) and 1.6e10 vg/mL (high). The cells were cultured in osteogenic media for 21 days. Dose-dependent expression of the AVPR-CAG-rENPP1 construct was confirmed by Western blotting. See FIG. 37A. An enzyme assay as described above was used to measure ENPP1 activity in the treated human cells; AAVPR-CAG-rENPP1 treatment at both doses resulted in dose-dependent increase in ENPP1 activity compared to untreated cells. See FIG. 37B.

Figure 37A:
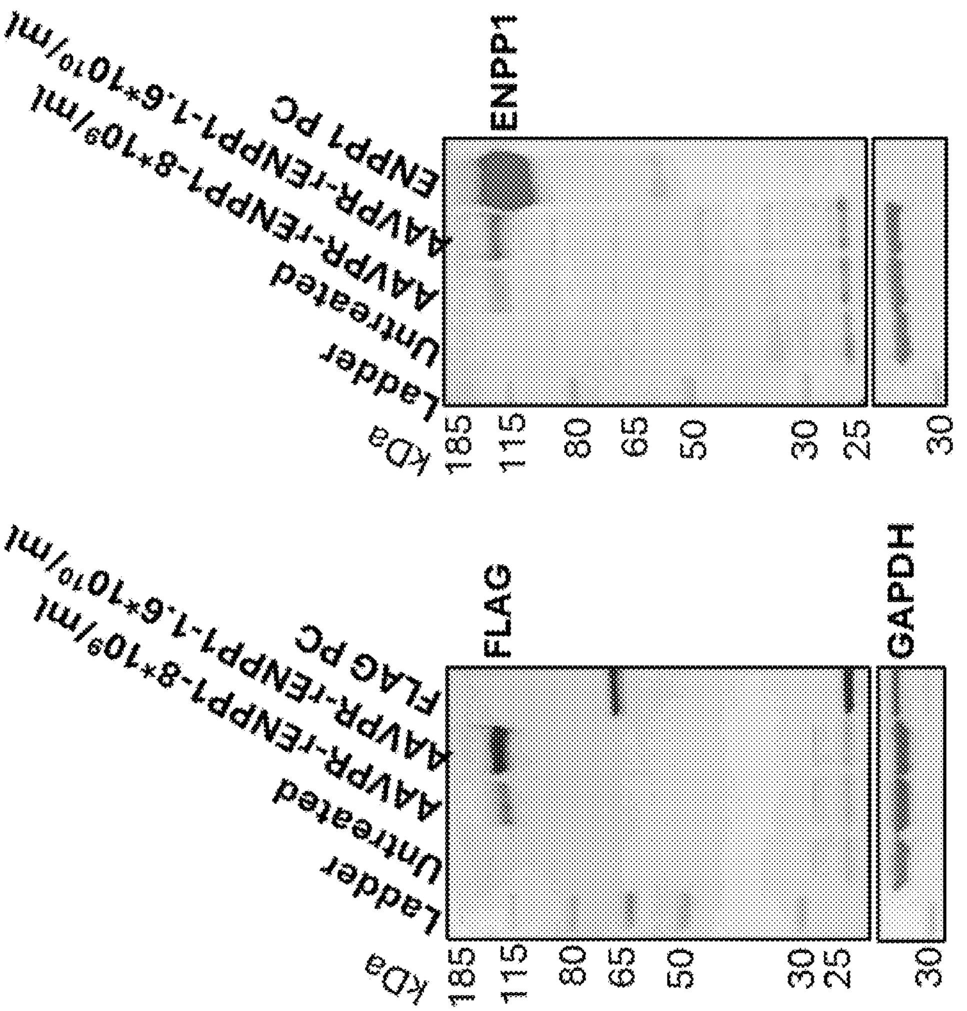
Figure 37B:
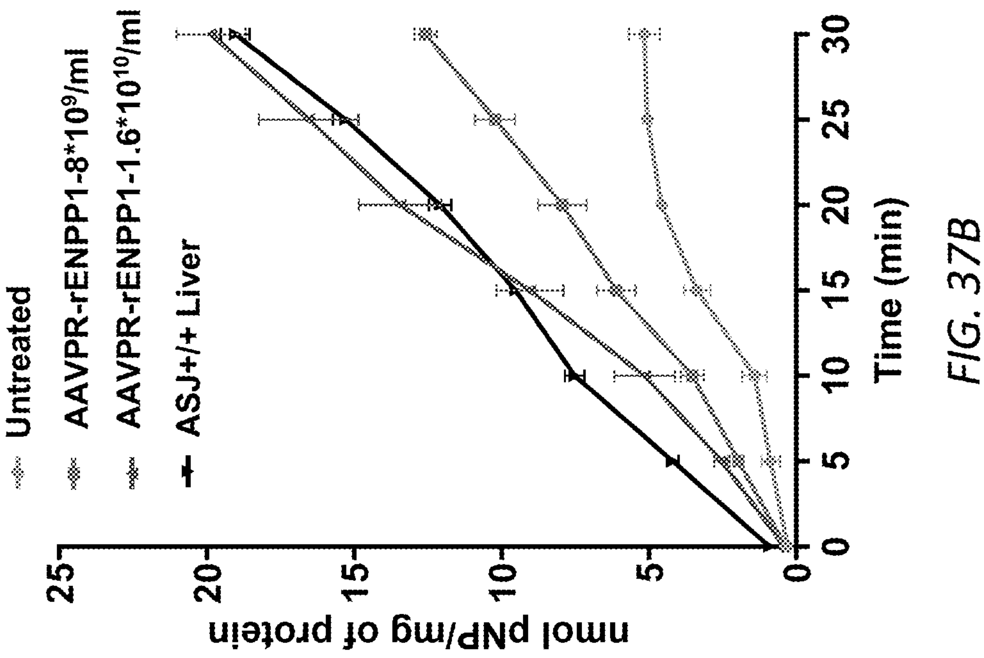
Figure 37C:
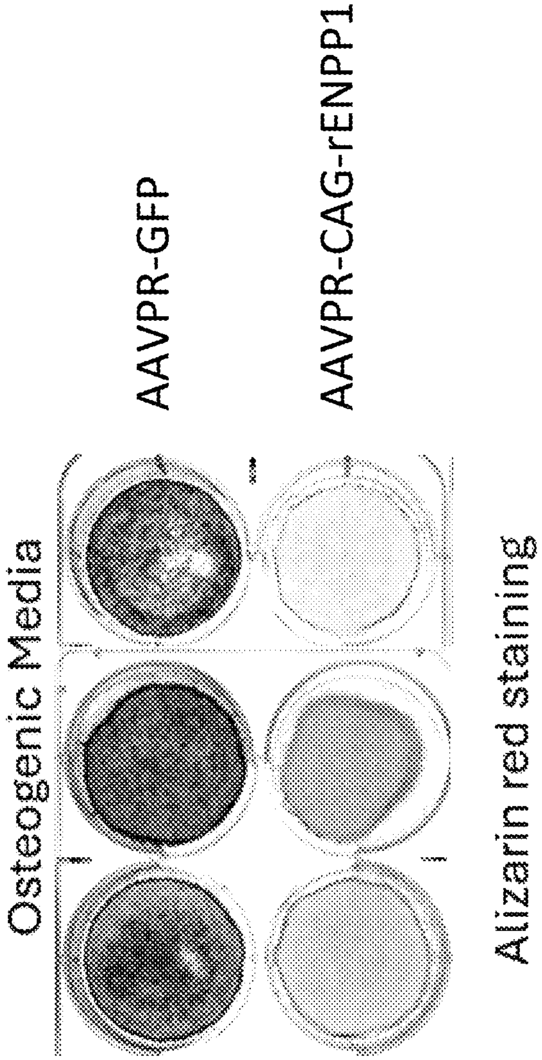
Figure 37D:
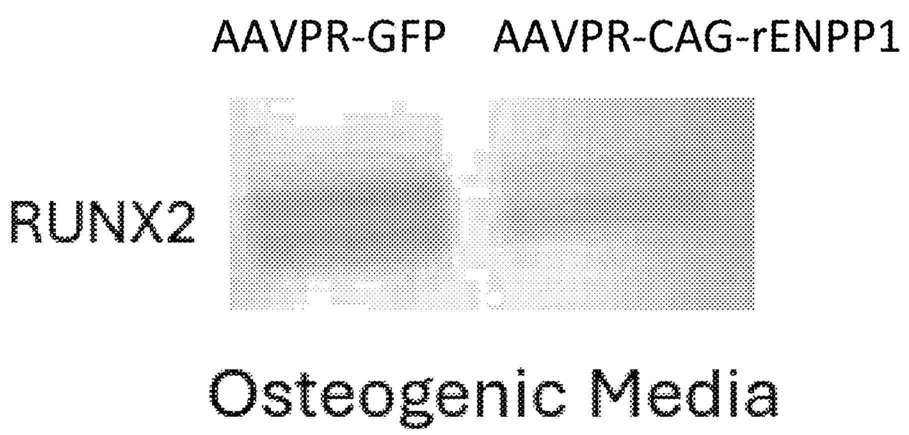
Figure 37E:
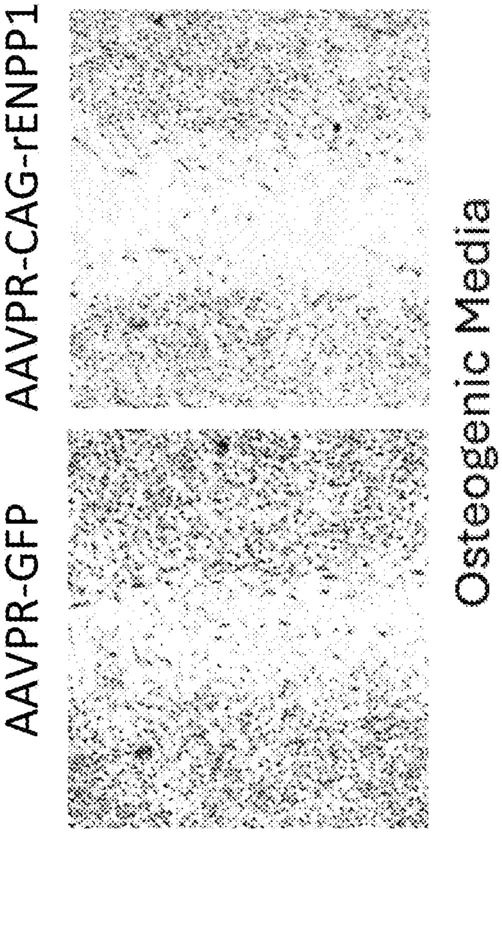

Alizarin red staining was used to assess calcification of human aortic SMCs, showing a significant reduction with AAVPR-CAG-rENPP1 treatment. FIG. 37C. Additionally, the physiological impact of the AAVPR-CAG-rENPP1 construct on calcification pathways was measured based on the activation of markers of the osteogenic phenotype. Briefly, RUNX2 is a master transcriptional regulator of the osteogenic phenotype switch of VSMCs that results in calcification across a whole host of disorders, including calciphylaxis, atherosclerosis, calcification related to chronic kidney disease and diabetes mellitus. RUNX2 protein levels and VSMC migration were reduced compared to controls treated with AAVPR-GFP. FIG. 37D. The osteogenic phenotype switch of VSMCs is associated with increased migration, which was reduced after treatment with AAVPR-CAG-rENPP1. FIG. 37E.

Example 14. Performance of AAVPR in Human Vessels Ex Vivo

To evaluate the performance of AAVPR in transducing human vessels ex vivo, vessels were harvested from human limbs after amputation (FIG. 38A), then transduced with either AAVPR-GFP or AAV9-GFP and maintained in a perfusion bioreactor (FIG. 38B) as described above. The results showed that AAVPR had high transduction efficiency in healthy human vessels (FIGS. 39A-B).

The AAVPR-transduced vessels exhibited significant GFP signal in the medial layer with co-localization with a-SMA indicating strong transduction of vascular smooth muscle cells (FIG. 40A). Ex vivo perfusion of diseased human vessels with AAVPR-CBA-GFP resulted in significantly higher viral copy numbers and GFP expression compared to AAV9-CBA-GFP, indicating a greater vascular tropism with AAVPR than AAV9 (FIG. 40B).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant adeno associated viral vector (AAV) encapsulating a construct encoding an ectonucleotide pyrophosphatase/phosphodiesterase 1 (ENPP1) enzyme, said vector comprising:

an expression cassette comprising:

a 5' ITR;

a promoter;

a nucleic acid encoding an ectonucleotide pyrophosphatase/phosphodiesterase 1 (ENPP1) enzyme, wherein said ENPP1 enzyme is a full-length transmembrane ENPP1 enzyme that comprises SEQ ID NO:1 or comprises a sequence that is at least 95% identical to SEQ ID NO:1; and a 3' ITR; and wherein the recombinant AAV vector comprises a capsid with a nucleic encoding peptide sequence PRPPSTH (SEQ ID NO:44) inserted therein.

2. The recombinant AAV vector of claim 1, wherein said promoter is a CMV immediate/early gene enhancer/CBA promoter (CAG).

3. The recombinant AAV vector of claim 1, wherein said expression cassette further comprises a regulatory sequence.

4. The recombinant AAV vector of claim 3, wherein said regulatory sequence comprises is a miRNA 155 (miR155) target sequence or a miR 122 target sequence.

5. The recombinant AAV vector of claim 3, wherein said regulatory sequence comprises one, two, or three repeats of SEQ ID NO: 2 or SEQ ID NO: 106.

6. The recombinant AAV vector of claim 1, wherein said recombinant AAV vector is an AAV9 vector.

7. The recombinant AAV vector of claim 1, wherein a nucleic acid sequence encoding the PRPPSTH sequence is inserted into the capsid of said AAV9 vector in a position corresponding to immediately following amino acid 588 of a VP1 protein in the AAV9 vector.

8. A host cell transduced with the recombinant AAV vector of claim 1.

9. The host cell of claim 8, for use in a method of reducing calcification in a vascular cell.

10. The host cell of claim 9, for use in a method of reducing calcification in a human vascular smooth muscle cell.

11. A nucleic acid construct for expression of an ectonucleotide pyrophosphatase/phosphodiesterase 1 (ENPP1) enzyme, said nucleic acid construct comprising:

a nucleic acid sequence encoding an AAV genome comprising:

a first inverted terminal repeats (ITR);

a nucleic acid encoding a replication (rep) sequence;

a nucleic acid encoding a capsid (cap) sequence, the nucleic acid encoding the cap sequence comprising a sequence encoding the peptide PRPPSTH inserted therein (SEQ ID NO:44);

a promoter;

a nucleic acid encoding an ectonucleotide pyrophosphatase/phosphodiesterase 1 (ENPP1) enzyme comprising a transmembrane domain, wherein said ENPP1 enzyme is a full-length transmembrane ENPP1 enzyme comprising SEQ ID NO:1 or comprises a sequence that is at least 95% identical to SEQ ID NO:1; and a second ITR.

12. The construct of claim 11, wherein said nucleic acid encoding the ENPP1 enzyme comprises the sequence of SEQ ID NO: 1.

13. The construct of claim 11, wherein said promoter is a CMV immediate/early gene enhancer/CBA promoter (CAG).

14. The construct of claim 11, wherein said nucleic acid comprises the sequence of SEQ ID NO: 75.

15. The construct of claim 11, wherein said expression cassette further comprises a regulatory sequence.

16. The construct of claim 15, wherein said regulatory sequence comprises one, two, or three repeats of SEQ ID NO: 2 or SEQ ID NO: 106.

17. The construct of claim 11, wherein said AAV genome is an AAV9 genome.

18. The construct of claim 17, wherein a nucleic acid sequence encoding a peptide having sequence PRPPSTH (SEQ ID NO:44) is inserted into the capsid of said AAV9 vector in a position corresponding to immediately following amino acid 588 of a VP1 protein in the AAV9 vector.

19. A particle comprising:

a) an amount of an ionizable lipid;
an amount of neutral lipid;
an amount of cholesterol;
an amount of one or more PEG-lipids; and
an amount of a DOTAP molecule;

b) a peptide conjugated to a linker in the particle; and c) a construct for expression of a full-length transmembrane ectonucleotide pyrophosphatase/phosphodiesterase 1 (ENPP1), comprising a sequence encoding a full-length ENPP1 transgene, wherein the ENPP1 is (i) full-length human transmembrane ENPP1, and a promoter that drives expression of the ENPP1 transgene.

20. The particle of claim 19, comprising:

a. about 78.8% of DOTAP;
b. about 10% of an MC3 ionizable lipid;
c. about 2.1% of a DOPE neutral lipid;
d. about 7.6% of cholesterol; and
e. about 1.5% of one or more PEG-lipids.

* * * * *

SEQUENCE LISTING

```
Sequence total quantity: 106
SEQ ID NO: 1            moltype = AA  length = 925
FEATURE                 Location/Qualifiers
source                  1..925
                        mol_type = protein
                        organism = Homo sapiens
SEQUENCE: 1
MERDGCAGGG SRGGEGGRAP REGPAGNGRD RGRSHAAEAP GDPQAAASLL APMDVGEEPL  60
EKAARARTAK DPNTYKVLSL VLSVCVLTTI LGCIFGLKPS CAKEVKSCKG RCFERTFGNC  120
RCDAACVELG NCCLDYQETC IEPEHIWTCN KFRCGEKRLT RSLCACSDDC KDKGDCCINY  180
SSVCQGEKSW VEEPCESINE PQCPAGFETP PTLLFSLDGF RAEYLHTWGG LLPVISKLKK  240
CGTYTKNMRP VYPTKTFPNH YSIVTGLYPE SHGIIDNKMY DPKMNASFSL KSKEKFNPEW  300
YKGEPIWVTA KYQGLKSGTF FWPGSDVEIN GIFPDIYKMY NGSVPFEERI LAVLQWLQLP  360
KDERPHFYTL YLEEPDSSGH SYGPVSSEVI KALQRVDGMV GMLMDGLKEL NLHRCLNLIL  420
ISDHGMEQGS CKKYIYLNKY LGDVKNIKVI YGPAARLRPS DVPDKYYSFN YEGIARNLSC  480
REPNQHFKPY LKHFLPKRLH FAKSDRIEPL TFYLDPQWQL ALNPSERKYC GSGFHGSDNV  540
FSNMQALFVG YGPGFKHGIE ADTFENIEVY NLMCDLLNLT PAPNNGTHGS LNHLLKNPVY  600
TPKHPKEVHP LVQCPFTRNP RDNLGCSCNP SILPIEDFQT QFNLTVAEEK IIKHETLPYG  660
RPRVLQKENT ICLLSQHQFM SGYSQDILMP LWTSYTVDRN DSFSTEDFSN CLYQDFRIPL  720
SPVHKCSFYK NNTKVSYGFL SPPQLNKNSS GIYSEALLTT NIVPMYQSFQ VIWRYFHDTL  780
LRKYAEERNG VNVVSGPVFD FDYDGRCDSL ENLRQKRRVI RNQEILIPTH FFIVLTSCKD  840
TSQTPLHCEN LDTLAFILPH RTDNSESCVH GKHDSSWVEE LLMLHRARIT DVEHITGLSF  900
YQQRKEPVSD ILKLKTHLPT FSQED                                       925

SEQ ID NO: 2            moltype = DNA  length = 20
FEATURE                 Location/Qualifiers
source                  1..20
                        mol_type = other DNA
                        organism = synthetic construct
SEQUENCE: 2
caattacgat tagcactatc                                             20

SEQ ID NO: 3            moltype = DNA  length = 60
FEATURE                 Location/Qualifiers
source                  1..60
                        mol_type = other DNA
                        organism = synthetic construct
SEQUENCE: 3
caattacgat tagcactatc caattacgat tagcactatc caattacgat tagcactatc  60

SEQ ID NO: 4            moltype = DNA  length = 82
FEATURE                 Location/Qualifiers
source                  1..82
                        mol_type = other DNA
                        organism = synthetic construct
SEQUENCE: 4
ctctggctaa ctagagaacc cactgcttac tggcttatcg aaattaatac gactcactat  60
agggagaccc aagctggcta gc                                          82

SEQ ID NO: 5            moltype = AA  length = 4
FEATURE                 Location/Qualifiers
source                  1..4
                        mol_type = protein
                        organism = synthetic construct
SEQUENCE: 5
GGGS                                                              4

SEQ ID NO: 6            moltype = AA  length = 5
FEATURE                 Location/Qualifiers
source                  1..5
                        mol_type = protein
                        organism = synthetic construct
SEQUENCE: 6
GGGGS                                                             5

SEQ ID NO: 7            moltype = DNA  length = 13
FEATURE                 Location/Qualifiers
source                  1..13
                        mol_type = other DNA
                        organism = synthetic construct
SEQUENCE: 7
```

-continued

```
gccgccacca tgg                                                    13

SEQ ID NO: 8            moltype = AA  length = 25
FEATURE                 Location/Qualifiers
source                  1..25
                        mol_type = protein
                        organism = synthetic construct
SEQUENCE: 8
MGVLLTQRTL LSLVLALLFP SMASM                                       25

SEQ ID NO: 9            moltype = AA  length = 19
FEATURE                 Location/Qualifiers
source                  1..19
                        mol_type = protein
                        organism = synthetic construct
SEQUENCE: 9
MGWSCIILFL VATATGVHS                                              19

SEQ ID NO: 10           moltype = AA  length = 21
FEATURE                 Location/Qualifiers
source                  1..21
                        mol_type = protein
                        organism = synthetic construct
SEQUENCE: 10
MWWRLWWLLL LLLLLWPMVW A                                           21

SEQ ID NO: 11           moltype = AA  length = 22
FEATURE                 Location/Qualifiers
source                  1..22
                        mol_type = protein
                        organism = synthetic construct
SEQUENCE: 11
MDMRVPAQLL GLLLLWLRGA RC                                          22

SEQ ID NO: 12           moltype = AA  length = 16
FEATURE                 Location/Qualifiers
source                  1..16
                        mol_type = protein
                        organism = synthetic construct
SEQUENCE: 12
MPLLLLLPLL WAGALA                                                 16

SEQ ID NO: 13           moltype = AA  length = 23
FEATURE                 Location/Qualifiers
source                  1..23
                        mol_type = protein
                        organism = synthetic construct
SEQUENCE: 13
MDAMKRGLCC VLLLCGAVFV SPS                                         23

SEQ ID NO: 14           moltype = AA  length = 18
FEATURE                 Location/Qualifiers
source                  1..18
                        mol_type = protein
                        organism = synthetic construct
SEQUENCE: 14
MAFLWLLSCW ALLGTTFG                                               18

SEQ ID NO: 15           moltype = AA  length = 15
FEATURE                 Location/Qualifiers
source                  1..15
                        mol_type = protein
                        organism = synthetic construct
SEQUENCE: 15
MNLLLILTFV AAAVA                                                  15

SEQ ID NO: 16           moltype = AA  length = 20
FEATURE                 Location/Qualifiers
source                  1..20
                        mol_type = protein
                        organism = synthetic construct
SEQUENCE: 16
MYRMQLLSCI ALSLALVTNS                                             20

SEQ ID NO: 17           moltype = AA  length = 16
FEATURE                 Location/Qualifiers
source                  1..16
                        mol_type = protein
                        organism = synthetic construct
```

```
SEQUENCE: 17
MKWVTFISLL FSSAYS                                                      16

SEQ ID NO: 18          moltype = AA  length = 20
FEATURE                Location/Qualifiers
source                 1..20
                       mol_type = protein
                       organism = synthetic construct
SEQUENCE: 18
MASHRLLLLC LAGLVFVSEA                                                  20

SEQ ID NO: 19          moltype = AA  length = 27
FEATURE                Location/Qualifiers
source                 1..27
                       mol_type = protein
                       organism = synthetic construct
SEQUENCE: 19
MARRSSFQSC QIISLFTFAV GVNICLG                                          27

SEQ ID NO: 20          moltype = AA  length = 24
FEATURE                Location/Qualifiers
source                 1..24
                       mol_type = protein
                       organism = synthetic construct
SEQUENCE: 20
MALWMRLLPL LALLALWGPD PAAA                                             24

SEQ ID NO: 21          moltype = AA  length = 24
FEATURE                Location/Qualifiers
source                 1..24
                       mol_type = protein
                       organism = synthetic construct
SEQUENCE: 21
MPSSVSWGIL LLAGLCCLVP VSLA                                             24

SEQ ID NO: 22          moltype = DNA  length = 24
FEATURE                Location/Qualifiers
source                 1..24
                       mol_type = other DNA
                       organism = synthetic construct
SEQUENCE: 22
aagaatttcc agagcagaag ccac                                             24

SEQ ID NO: 23          moltype = DNA  length = 24
FEATURE                Location/Qualifiers
source                 1..24
                       mol_type = other DNA
                       organism = synthetic construct
SEQUENCE: 23
aagagaagaa cccctgtgcg ggag                                             24

SEQ ID NO: 24          moltype = DNA  length = 24
FEATURE                Location/Qualifiers
source                 1..24
                       mol_type = other DNA
                       organism = synthetic construct
SEQUENCE: 24
aagacctacg cctctatgca gtgg                                             24

SEQ ID NO: 25          moltype = DNA  length = 24
FEATURE                Location/Qualifiers
source                 1..24
                       mol_type = other DNA
                       organism = synthetic construct
SEQUENCE: 25
gatgatgacg acgacgatga ctgc                                             24

SEQ ID NO: 26          moltype = DNA  length = 24
FEATURE                Location/Qualifiers
source                 1..24
                       mol_type = other DNA
                       organism = synthetic construct
SEQUENCE: 26
ttaatgctaa tcgtgatagg ggtt                                             24

SEQ ID NO: 27          moltype = DNA  length = 24
FEATURE                Location/Qualifiers
source                 1..24
                       mol_type = other DNA
```

-continued

```
                        organism = synthetic construct
SEQUENCE: 27
aattacgatt agcactatcc ccaa                                              24

SEQ ID NO: 28           moltype = DNA  length = 22
FEATURE                 Location/Qualifiers
source                  1..22
                        mol_type = other DNA
                        organism = synthetic construct
SEQUENCE: 28
tagcttatca gactgatgtt ga                                                22

SEQ ID NO: 29           moltype = DNA  length = 22
FEATURE                 Location/Qualifiers
source                  1..22
                        mol_type = other DNA
                        organism = synthetic construct
SEQUENCE: 29
atcgaatagt ctgactacaa ct                                                22

SEQ ID NO: 30           moltype = DNA  length = 22
FEATURE                 Location/Qualifiers
source                  1..22
                        mol_type = other DNA
                        organism = synthetic construct
SEQUENCE: 30
agcccctgcc caccgcacac tg                                                22

SEQ ID NO: 31           moltype = DNA  length = 22
FEATURE                 Location/Qualifiers
source                  1..22
                        mol_type = other DNA
                        organism = synthetic construct
SEQUENCE: 31
tcggggacgg gtggcgtgtg ac                                                22

SEQ ID NO: 32           moltype = DNA  length = 22
FEATURE                 Location/Qualifiers
source                  1..22
                        mol_type = other DNA
                        organism = synthetic construct
SEQUENCE: 32
tgtaaacatc ctacactcag ct                                                22

SEQ ID NO: 33           moltype = DNA  length = 22
FEATURE                 Location/Qualifiers
source                  1..22
                        mol_type = other DNA
                        organism = synthetic construct
SEQUENCE: 33
acatttgtag gatgtgagtc ga                                                22

SEQ ID NO: 34           moltype = DNA  length = 23
FEATURE                 Location/Qualifiers
source                  1..23
                        mol_type = other DNA
                        organism = synthetic construct
SEQUENCE: 34
tcatagccct gtacaatgct gct                                               23

SEQ ID NO: 35           moltype = DNA  length = 23
FEATURE                 Location/Qualifiers
source                  1..23
                        mol_type = other DNA
                        organism = synthetic construct
SEQUENCE: 35
agtatcggga catgttacga cga                                               23

SEQ ID NO: 36           moltype = DNA  length = 21
FEATURE                 Location/Qualifiers
source                  1..21
                        mol_type = other DNA
                        organism = synthetic construct
SEQUENCE: 36
gcaggaactt gtgagtctcc t                                                 21

SEQ ID NO: 37           moltype = DNA  length = 21
FEATURE                 Location/Qualifiers
source                  1..21
```

-continued

```
                       mol_type = other DNA
                       organism = synthetic construct
SEQUENCE: 37
cgtccttgaa cactcagagg a                                              21

SEQ ID NO: 38          moltype = DNA  length = 21
FEATURE                Location/Qualifiers
source                 1..21
                       mol_type = other DNA
                       organism = synthetic construct
SEQUENCE: 38
gtgttgaaac aatctctact g                                              21

SEQ ID NO: 39          moltype = DNA  length = 21
FEATURE                Location/Qualifiers
source                 1..21
                       mol_type = other DNA
                       organism = synthetic construct
SEQUENCE: 39
cacaactttg ttagagatga c                                              21

SEQ ID NO: 40          moltype = DNA  length = 18
FEATURE                Location/Qualifiers
source                 1..18
                       mol_type = other DNA
                       organism = synthetic construct
SEQUENCE: 40
tcgaggagct cacagtct                                                  18

SEQ ID NO: 41          moltype = DNA  length = 18
FEATURE                Location/Qualifiers
source                 1..18
                       mol_type = other DNA
                       organism = synthetic construct
SEQUENCE: 41
agctcctcga gtgtcaga                                                  18

SEQ ID NO: 42          moltype = DNA  length = 21
FEATURE                Location/Qualifiers
source                 1..21
                       mol_type = other DNA
                       organism = synthetic construct
SEQUENCE: 42
cattattact tttggtacgc g                                              21

SEQ ID NO: 43          moltype = DNA  length = 21
FEATURE                Location/Qualifiers
source                 1..21
                       mol_type = other DNA
                       organism = synthetic construct
SEQUENCE: 43
gtaataatga aaaccatgcg c                                              21

SEQ ID NO: 44          moltype = AA  length = 7
FEATURE                Location/Qualifiers
source                 1..7
                       mol_type = protein
                       organism = synthetic construct
SEQUENCE: 44
PRPPSTH                                                              7

SEQ ID NO: 45          moltype = AA  length = 7
FEATURE                Location/Qualifiers
source                 1..7
                       mol_type = protein
                       organism = synthetic construct
SEQUENCE: 45
MAEPGAR                                                              7

SEQ ID NO: 46          moltype = AA  length = 7
FEATURE                Location/Qualifiers
source                 1..7
                       mol_type = protein
                       organism = synthetic construct
SEQUENCE: 46
MLYADNT                                                              7

SEQ ID NO: 47          moltype = AA  length = 7
FEATURE                Location/Qualifiers
```

```
source                  1..7
                        mol_type = protein
                        organism = synthetic construct
SEQUENCE: 47
SQDPSTL                                                        7

SEQ ID NO: 48           moltype = AA  length = 11
FEATURE                 Location/Qualifiers
source                  1..11
                        mol_type = protein
                        organism = synthetic construct
SEQUENCE: 48
KLWVLPKGGG C                                                   11

SEQ ID NO: 49           moltype = AA  length = 11
FEATURE                 Location/Qualifiers
source                  1..11
                        mol_type = protein
                        organism = synthetic construct
SEQUENCE: 49
CGGGLSLITR L                                                   11

SEQ ID NO: 50           moltype = AA  length = 15
FEATURE                 Location/Qualifiers
source                  1..15
                        mol_type = protein
                        organism = synthetic construct
SEQUENCE: 50
CRHSQMTVTS RLGGG                                               15

SEQ ID NO: 51           moltype = AA  length = 20
FEATURE                 Location/Qualifiers
source                  1..20
                        mol_type = protein
                        organism = synthetic construct
SEQUENCE: 51
CGGGANTPCG PYTHDCPVKR                                          20

SEQ ID NO: 52           moltype = DNA  length = 72
FEATURE                 Location/Qualifiers
source                  1..72
                        mol_type = other DNA
                        organism = synthetic construct
SEQUENCE: 52
atgaagtggg taacctttat ttcccttctt tttctcttta gctcggctta ttccaggggt  60
gtgtttcgtc ga                                                  72

SEQ ID NO: 53           moltype = AA  length = 24
FEATURE                 Location/Qualifiers
source                  1..24
                        mol_type = protein
                        organism = synthetic construct
SEQUENCE: 53
MKWVTFISLL FLFSSAYSRG VFRR                                     24

SEQ ID NO: 54           moltype = DNA  length = 54
FEATURE                 Location/Qualifiers
source                  1..54
                        mol_type = other DNA
                        organism = synthetic construct
SEQUENCE: 54
atgaagtggg taacctttat ttcccttctt tttctcttta gctcggctta ttcc        54

SEQ ID NO: 55           moltype = AA  length = 18
FEATURE                 Location/Qualifiers
source                  1..18
                        mol_type = protein
                        organism = synthetic construct
SEQUENCE: 55
MKWVTFISLL FLFSSAYS                                            18

SEQ ID NO: 56           moltype = DNA  length = 81
FEATURE                 Location/Qualifiers
source                  1..81
                        mol_type = other DNA
                        organism = synthetic construct
SEQUENCE: 56
atggcaagga ggagctcgtt ccagtcgtgt cagataatat ccctgttcac ttttgccgtt  60
ggagtcaata tctgcttagg a                                        81
```

```
SEQ ID NO: 57          moltype = AA  length = 27
FEATURE                Location/Qualifiers
source                 1..27
                       mol_type = protein
                       organism = synthetic construct
SEQUENCE: 57
MARRSSFQSC QIISLFTFAV GVNICLG                                      27

SEQ ID NO: 58          moltype = DNA  length = 60
FEATURE                Location/Qualifiers
source                 1..60
                       mol_type = other DNA
                       organism = synthetic construct
SEQUENCE: 58
atggcttctc atcgtctgct cctcctctgc cttgctggac tggtatttgt gtctgaggct  60

SEQ ID NO: 59          moltype = AA  length = 20
FEATURE                Location/Qualifiers
source                 1..20
                       mol_type = protein
                       organism = synthetic construct
SEQUENCE: 59
MASHRLLLLC LAGLVFVSEA                                              20

SEQ ID NO: 60          moltype = DNA  length = 2541
FEATURE                Location/Qualifiers
source                 1..2541
                       mol_type = other DNA
                       organism = synthetic construct
SEQUENCE: 60
ataaatgttt tgtagaataa aaaaaaaaaa agttcttcaa aagaaatctc aaatctccaa  60
atggaaacag gtaaaagtgg agctcccctg gttccacgga gaaccttttt tgaggaaact  120
taggcaactc gcaggtacct tatgtcatga gacagagttt gaaaactaca attgactatc  180
tctaaatttc ctcccaggtc taaaatgtga tgatagttac tacttcagta catcatcctt  240
aaggaaaatt attaggtcca cactgtttct atcctttgaa ttttacacat aaattttgta  300
atcaaaagtt tatttgtaat atcagatgga atcagataat tgctttttgt tttttccact  360
gacaggaaca taagattttg ttgtgtagct taagtcaaac gcagtttgga atatatattt  420
tttaaaaatt gtaacttaca tatccaaata caatttttca agaagtagag tattcagtag  480
aaattaatct gtgaaagaag aggaattcag cagtggccta tttgatgaat gatttaacgt  540
gcttatttct tccctttcat caaaactctg tgtccccttg tttgccccct ctgacttcat  600
actctggagt tgaccaagat ccctcttcca tcggattgtt ctgggaattt tgaaataatc  660
tgctttttcc tctctttccc ctgttgcttc tgatgcctta gaattacatt ttcctcgctg  720
atttagttta gaaaagagaa aagagcttcc atgactagta gattatcact tttgggtttg  780
ctcttggaag tgacaagatg ctaggatccc tctttggaat gtaaaattta tctcttatat  840
agaaaggata taaatgtagc accagagact ataaaactct gatactatct actgtactgt  900
atagctgaac gccacaatgt gtctggtaat ctattgacta tcataaatgc tatttctaca  960
gaaaagttag gaggtccata tttcgggcaa ccaatgtata gctgaatgca gaacagtcat  1020
agttgggtac taaccatata tatgatttat ccatcaacag gtgcatatgc tcagaaattc  1080
tgtatccata agaaatcaga ctactttctt ttccttttgc aagtaaattg aatttagcct  1140
gagaggctga ggggaaattt tcacatataa gccacggttt tgtgttttgt gttttgtttt  1200
gtttatagat atagtactaa ctggatggat gcgataaaat tcataggtgg tactaagata  1260
caataggatt tgtgaaatgg acaattgtct tgcataaata gcaagtaaaa aatcaagcct  1320
gtccttcata aaaattttat tctggggtgt gcttgttttc caaaagtacc tctgctaaat  1380
ctcctgttag tcctgaaact agaaggcaga aaagcttcta gtgctacagc caactgcagt  1440
gtagcctgag aaacaggcaa caaaaataga acaccaggat tgctgtgcgt gggtgaggca  1500
gaaaccacat tatgagcaaa agcttccagt attattttag aaccaataca gagctctgta  1560
cttctctcct ctctcttcca aaaacacata ctacaaaaat aaaatgaaat gaaatgtatg  1620
tgcatttgcc ctcttagaat tatgattctt aatttttttt cttgccttcc tttctttgga  1680
agcgaatcgc cagtatggaa acacagtgtg taaagcaagc ttcgagagag gaaagagtta  1740
attggtttta aggccctgcg atagagaatt atggttggaa agatagaggc tggacagctg  1800
ggtttgctgg ggtattttta aatgcattaa tgcaggctcc aatcactcgg ccatgcttga  1860
cctatttttg gctcaggccg accattgttc tatttctgtg cctgtgggcc atgctgttgt  1920
tgattcatat gcaaatggat tatcactcgc tttagccaac ttgagctgag agagactgag  1980
aaagggggaa gagaggcaca gacacagata ggagaagggc accggctgga gccacttgca  2040
ggactgaggg tttttgcaac aaaaccctag cagcctgaag aactctaagc caggtttaat  2100
tggtttcttt ttctcgtggg tagacttaat aattttctac gtattctgac aaagaaataa  2160
ccccgaagca cgttcctatt tcccacctgc ttgtagtttc cgggataacc taaactccag  2220
agagctatag catccactct gtcctttctg ctttgcacac aggttggtaa catgggaaaa  2280
gtgtccaggt ctttttaaaa gtggatgccc atttgagcag aaaggaaatc attgtcgaag  2340
ttgatcctct gctgcttctc ctcagggagg agggagaacc agcgagggta gctcctgggg  2400
ccggtgcact gagcagtgat gaatgtttca tgtagctgaa gtaagagtga ctggaatatg  2460
ctgcagacaa tttacgagag tgactcctgt ttttcctcag atggggtggc tggacgagag  2520
cagctcttgg ctcagcaaag a                                            2541

SEQ ID NO: 61          moltype = DNA  length = 1350
FEATURE                Location/Qualifiers
source                 1..1350
                       mol_type = other DNA
```

-continued

```
                         organism = synthetic construct
SEQUENCE: 61
ataaatgttt tgtagaataa aaaaaaaaaa agttcttcaa aagaaatctc aaatctccaa  60
atggaaacag gtaaaagtgg agctcccctg gttccacgga gaaccttttt tgaggaaact  120
taggcaactc gcaggtacct tatgtcatga gacagagttt gaaaactaca attgactatc  180
tctaaatttc ctcccaggtc taaaatgtga tgatagttac tacttcagta catcatcctt  240
aaggaaaatt attaggtcca cactgtttct atcctttgaa ttttacacat aaattttgta  300
atcaaaagtt tatttgtaat atcagatgga atcagataat tgctttttgt tttttccact  360
gacaggaaca taagattttg ttgtgtagct taagtcaaac gcagtttgga atatatattt  420
tttaaaaatt gtaacttaca tatccaaata caatttttca agaagtagag tattcagtag  480
aaattaatct gtgaaagaag aggaattcag cagtggccta tttgatgaat gatttaacgt  540
gcttatttct tccctttcat caaaactctg tgtcccttg tttgcccccct ctgacttcat  600
actctggagt tgaccaagat ccctcttcca tcggattgtt ctgggaattt tgaaataatc  660
tgctttttcc tctctttccc ctgttgcttc tgatgcctta gaattacatt ttcctcgctg  720
atttagttta gaaaagagaa aagagcttcc atgactagta gattatcact tttgggtttg  780
ctcttggaag tgacaagatg ctaggatccc tctttggaat gtaaaattta tctcttatat  840
agaaaggata taaatgtagc accagagact ataaaactct gatactatct actgtactgt  900
atagctgaac gccacaatgt gtctggtaat ctattgacta tcataaatgc tatttctaca  960
gaaaagttag gaggtccata tttcgggcaa ccaatgtata gctgaatgca gaacagtcat  1020
agttgggtac taaccatata tatgatttat ccatcaacag gtgcatatgc tcagaaattc  1080
tgtatccata agaaatcaga ctactttctt ttccttttgc aagtaaattg aatttagcct  1140
gagaggctga ggggaaattt tcacatataa gccacggttt tgtgttttgt gttttgtttt  1200
gtttatagat atagtactaa ctggatggat gcgataaaat tcataggtgg tactaagata  1260
caataggatt tgtgaaatgg acaattgtct tgcataaata gcaagtaaaa aatcaagcct  1320
gtccttcata aaaattttat tctggggtgt                                 1350

SEQ ID NO: 62            moltype = DNA  length = 1191
FEATURE                  Location/Qualifiers
source                   1..1191
                         mol_type = other DNA
                         organism = synthetic construct
SEQUENCE: 62
gcttgtttc caaaagtacc tctgctaaat ctcctgttag tcctgaaact agaaggcaga  60
aaagcttcta gtgctacagc caactgcagt gtagcctgag aaacaggcaa caaaaataga  120
acaccaggat tgctgtgcgt gggtgaggca gaaaccacat tatgagcaaa agcttccagt  180
attattttag aaccaataca gagctctgta cttctctcct ctctcttcca aaaacacata  240
ctacaaaaat aaaatgaaat gaaatgtatg tgcatttgcc ctcttagaat tatgattctt  300
aatttttttt cttgccttcc tttctttgga agcgaatcgc cagtatggaa acacagtgtg  360
taaagcaagc ttcgagagag gaaagagtta attggtttta aggccctgcg atagagaatt  420
atggttggaa agatagaggc tggacagctg ggtttgctgg ggtattttta aatgcattaa  480
tgcaggctcc aatcactcgg ccatgcttga cctatttttg gctcaggccg accattgttc  540
tatttctgtg cctgtgggcc atgctgttgt tgattcatat gcaaatggat tatcactcgc  600
tttagccaac ttgagctgag agagactgag aaagggggaa gagaggcaca gacacagata  660
ggagaagggc accggctgga gccacttgca ggactgaggg tttttgcaac aaaaccctag  720
cagcctgaag aactctaagc caggtttaat tggtttcttt ttctcgtggg tagacttaat  780
aattttctac gtattctgac aaagaaataa ccccgaagca cgttcctatt tcccacctgc  840
ttgtagtttc cgggataacc taaactccag agagctatag catccactct gtcctttctg  900
ctttgcacac aggttggtaa catgggaaaa gtgtccaggt ctttttaaaa gtggatgccc  960
atttgagcag aaaggaaatc attgtcgaag ttgatcctct gctgcttctc ctcagggagg  1020
agggagaacc agcgagggta gctcctgggg ccggtgcact gagcagtgat gaatgtttca  1080
tgtagctgaa gtaagagtga ctggaatatg ctgcagacaa tttacgagag tgactcctgt  1140
ttttcctcag atggggtggc tggacgagag cagctcttgg ctcagcaaag a         1191

SEQ ID NO: 63            moltype = DNA  length = 434
FEATURE                  Location/Qualifiers
source                   1..434
                         mol_type = other DNA
                         organism = synthetic construct
SEQUENCE: 63
ataaatgttt tgtagaataa aaaaaaaaaa agttcttcaa aagaaatctc aaatctccaa  60
atggaaacag gtaaaagtgg agctcccctg gttccacgga gaaccttttt tgaggaaact  120
taggcaactc gcaggtacct tatgtcatga gacagagttt gaaaactaca attgactatc  180
tctaaatttc ctcccaggtc taaaatgtga tgatagttac tacttcagta catcatcctt  240
aaggaaaatt attaggtcca cactgtttct atcctttgaa ttttacacat aaattttgta  300
atcaaaagtt tatttgtaat atcagatgga atcagataat tgctttttgt tttttccact  360
gacaggaaca taagattttg ttgtgtagct taagtcaaac gcagtttgga atatatattt  420
tttaaaaatt gtaa                                                  434

SEQ ID NO: 64            moltype = DNA  length = 482
FEATURE                  Location/Qualifiers
source                   1..482
                         mol_type = other DNA
                         organism = synthetic construct
SEQUENCE: 64
cttacatatc caaatacaat ttttcaagaa gtagagtatt cagtagaaat taatctgtga  60
aagaagagga attcagcagt ggcctatttg atgaatgatt taacgtgctt atttcttccc  120
tttcatcaaa actctgtgtc cccttgtttg ccccctctga cttcatactc tggagttgac  180
caagatccct cttccatcgg attgttctgg gaattttgaa ataatctgct tttcctctc  240
tttcccctgt tgcttctgat gccttagaat tacattttcc tcgctgattt agtttagaaa  300
```

-continued

```
agagaaaaga gcttccatga ctagtagatt atcacttttg ggtttgctct tggaagtgac  360
aagatgctag gatccctctt tggaatgtaa aatttatctc ttatatagaa aggatataaa  420
tgtagcacca gagactataa aactctgata ctatctactg tactgtatag ctgaacgcca  480
ca                                                                482

SEQ ID NO: 65          moltype = DNA  length = 434
FEATURE                Location/Qualifiers
source                 1..434
                       mol_type = other DNA
                       organism = synthetic construct
SEQUENCE: 65
atgtgtctgg taatctattg actatcataa atgctatttc tacagaaaag ttaggaggtc  60
catatttcgg gcaaccaatg tatagctgaa tgcagaacag tcatagttgg gtactaacca  120
tatatatgat ttatccatca acaggtgcat atgctcagaa attctgtatc cataagaaat  180
cagactactt tcttttcctt ttgcaagtaa attgaattta gcctgagagg ctgaggggaa  240
attttcacat ataagccacg gttttgtgtt ttgtgttttg ttttgtttat agatatagta  300
ctaactggat ggatgcgata aaattcatag gtggtactaa gatacaatag gatttgtgaa  360
atggacaatt gtcttgcata aatagcaagt aaaaaatcaa gcctgtcctt cataaaaatt  420
ttattctggg gtgt                                                   434

SEQ ID NO: 66          moltype = DNA  length = 217
FEATURE                Location/Qualifiers
source                 1..217
                       mol_type = other DNA
                       organism = synthetic construct
SEQUENCE: 66
gaaaactaca attgactatc tctaaatttt aaaatgtgat gatagttact acttcagtgg  60
tccacactgt ttctatcctt tggaacataa gattttgttg tgtagcttaa ggaagaggaa  120
ttcagcagtt gactatctcg attgttctgg gaattttgga ggctgagggg aaattttcac  180
atataagcgc tgggtttgct ggggtattga gagtgac                          217

SEQ ID NO: 67          moltype = DNA  length = 2063
FEATURE                Location/Qualifiers
source                 1..2063
                       mol_type = other DNA
                       organism = synthetic construct
SEQUENCE: 67
aagattatag ttgtcatttg aacttgggga taaaggagac atctatgact tggctggaaa  60
agacagagct aatgtacatt gcaaagcaca tatttatagc aggaaaatgg gaagatttct  120
ctttaattct ggagatggag tggggatggg gagagtagac tactcatttt aagggtgaaa  180
cattggaatt caacttgttt gatgttatat taattggtgg ttaattacta agctaagtac  240
gtataaaact tttatctatg gctagcttgt ccccccaaag tcatgcaata tagtgaactg  300
gctttcgcac tttaaattat tcattgatca tgtaatgatt cagatgattc atcttccaag  360
atggacactg aaactaacac tcatagtagg ttgtggttta aagagtggaa caaccgccag  420
tctcattagt ggaaattgtg atggttgaat ttatcaagga tgaacataca cggtcttctt  480
tctgagattt tctttaagat tttcgcacag ataatctatt tcttaggttt tggagagaaa  540
acttgaattt tattgatccc tcagaactca atctttcaga tttcaaagga gctatttctt  600
ttaatgggga ctctgttaat atttataaaa gctcttcaca ggatggaggg tgggagggaa  660
actccatccc aacaagacaa aaagaatgaa gcatgaggct ccacctagtt catcactgct  720
ccttgaaata catcagtatt gaaagacaca tccaccccac ccccaaccca gccctattgc  780
tgttccagct caagagtcag aggtcccgaa gctgtagctc ttctacaatc tgctgctctg  840
tgacttcaag tctgttgtct gcaaagaaaa ctattgggtt cccaagcaag agaggcacat  900
ctggtaggac agattttgtg attgcaaaag aagggggaaa aaaagaaaga aagaaaagac  960
ctctctatac aagataacca gaggcatcaa actgaaatcc tcctgtggaa aataagctag  1020
tacttctggg cctgatggtg tagtgaaaac ctgtgcttga ggatacatta cagtgaaaga  1080
gcaaagtgaa tagtaagtag ctattactta cctccttagg gaggtgtgtt gtttgtctgt  1140
acatccccca cagcacctag cacagtacct tgcatctcac ctgccactca ctaaaaagtc  1200
tatcaagtta gttaattatc gagacaacgc cctcagaaat gagagaacag taccctctta  1260
tccttgctgc actttccagc actgatacgc tgcctaaaag aggactaggg cacaggtttg  1320
aattaatgtc acaaaactgg atgggcaagt tacaacggtg ttgattaagg aaacagaact  1380
catggtgcac cggatatctc catcctgatg aacccttgga aaaatgccaa agatgcatat  1440
ccccaggcaa atgcctgatt agtctgggat tgatagattg gtctaggatt cagccctact  1500
gggaagatgt ctaaattata atcagtgtag aaagcgaagt tctcctagaa gaagaggcaa  1560
aggttaaaaa gaagaaaaga aaagaaagtg aagtcctttc tcccccaaaa cctctcatca  1620
atcaatcagg gtaacaaaca gaacactagg gctctgtctg tggaccaaac ccaaaagccc  1680
tgcggtcagg gccaggaggg tagatcatgt gtttgtggca acttcctctg tgggcttttg  1740
cccaggtctg tccccaagca tacgatggcc aaaacttctg caccagagca gcatcctgtg  1800
taacacagtc aggtccagca gttagggaaa actgcccact cagagtagat aatatctgga  1860
aggaatgact gtttgggaaa agttccaatg ctagttcagt gccaaccctt ccccaccttc  1920
tccagctctc tcccactggt tcctcccctc tcaactgctc tggttcttat aaaaacctca  1980
cagccttcca ctaacatccc gtaggagcct ctctccctac tgctgctaca caagaccctg  2040
agactgacct gcaggacgaa acc                                         2063

SEQ ID NO: 68          moltype = DNA  length = 1675
FEATURE                Location/Qualifiers
source                 1..1675
                       mol_type = other DNA
                       organism = synthetic construct
SEQUENCE: 68
```

-continued

```
cgccggggag caggaaggcc actcggcacc atatttagtc agggggagcc ggcagcccag  60
agctggtatg cggcgctggg aattcctgca ggaaggagtc cgcgcctgcc ctttttgggt  120
tgtctcccgc ccgccgctcc cgccgctccc ggggaggggg accggcccgg cccggcccgg  180
cccgggaacc tcggaggagc tggtgccgcg cggggagcgg agcgcccggg ctgcccgcgg  240
gtccccggcc tggcgcgggg ccagcccacc gcctcgactt ccttttatgg cctgtgtgtg  300
cgtgcgtgga caggagcggg gagggaggga cggggagaag acggagagcc tggggaagag  360
agagagagaa agcgcagaga taggagtgag acacgcggga gagatggaga gcaagagaca  420
cagagaccag agacaaagtg agacaggagg gagagacaga tacatcgaca gatctagaga  480
agcgagaggg acagagacaa aagatagagc gagagacagc aatgatcaga gtgacagaca  540
tgcagagaca gtggcagaga cagagcgaga gagcctgtga tggagagaga cagggaatgc  600
aattttaggc gaggaatcct tggggaaggg aagttgttga agggaactcg cagactctgg  660
gggcacaccc actttctcct tggatcttga cacttgcatc ttgtaaataa cgtaattatc  720
accgccaccg ccttccccca ttttgtagct atggacacca agtctcagag aagtgaagtg  780
acttgcccaa ggtcacgcag ctggcgagtg gcgcacaggg gagggggaca gctgaaataa  840
tcacagtggg cttattttta atttttattt gtattttggt cgtggtgatg tgggtggagg  900
tggagatggc aagttgggaa aagtaaaaac ttccccttcc tgcacggttc ccagcaaggg  960
tgggggcctc ctgtcttgca ctttgcaaag ttcaagaaat cccctttccc tacccttcac  1020
gctgcacagc cggccctctt tccagacagt gcgatgccaa taaaatggga agtggggtgg  1080
gagatgtcaa gtcagatcca ccacagcccc gacacgggga ggaagaggtt aaagcctttg  1140
cggccggaac cgactcaggg aagacgttct caagcatccc gcacagacac tgcctgctcg  1200
accccctttc tctagggatc cggagcgtct gcgaccgcct ggggccgggg ctgagactcc  1260
cgtccctgtg cgcacctgtt ccgtgcgccc ttgtgcggtg cgcacctgtt ccgtgcaccc  1320
ttgtcccgag cgccccagct ccttgcgctc ccgccggggg tgcgccctgc agggggcgcg  1380
gcgagggggc cgcgagggac cctccccaac tccacccctt cggcctcctc ccctttccca  1440
gccgcgggca gctccgggtc tataaagaga ggcgtccgag gacgcgcagg gagatttgga  1500
cgctccggcc tgggaggtgc gtcagatccg agctcgccat ccagtttcct ctccactagt  1560
ccccccagtt ggagatctgt aagtagtagt tgtcattctg gggcagatt gcagggcagg  1620
ggggtgttaa aagtcctata gggtattcta taggggctgg ggtgcactta ggggt        1675
```

```
SEQ ID NO: 69          moltype = DNA  length = 2016
FEATURE                Location/Qualifiers
source                 1..2016
                       mol_type = other DNA
                       organism = synthetic construct
SEQUENCE: 69
ctctcataat attgaagtag ctttgttgtc tatggtgaca tccgaggttc ttggtctcac  60
ggccacaaag atcaaatatg tggacacaca caaagggtga ggtttggagc agaattttta  120
ataggcaaaa ggaggagaat agctctgcta cagagagggg tcccaaaaaa tgggttgcaa  180
tacgtggtga aatgcagggg tttttataga tgagctagtg gggaggcggt gtctgatcta  240
cataaggagg gaaaacccgg tttcgtgcat atggcatgaa aacccggtta ggaccaggtg  300
tgtcatctgc atagggctta agtgtctggc agccccggcc ccaatcttct actatatagg  360
caggtagcta ctccgtgttg cttatttcct tcttactgtg catgtggtaa aaaagagggg  420
aggtggaacc cccatggtgg acatgcctgg ccccagtagc cccttctgtc tgtgccgctg  480
ccggcatctc ccgtgcaagc ttccagtttc cttacctatg tttgcagccc aatcttccag  540
gttgctcttt gttagaaagg aagtgatttc ttgggctgct ttttgttaga aggtaagttc  600
tgccgagggc tcttttgctc atactatctg cctaaataat ttctatctcc tgtatcaata  660
tcctatgtgt gactctattc tgcatatatg acttaggttt taattatttt gtttacgagt  720
tggtcctacc cccccacccc cgcttccacc acacttaagg aaagatacat tttaattcat  780
tttttatatg gtatgcatag ttggaggcca aaagattgag ttgaaggatt cattacttga  840
tgaataaatg gatgggtgga tggatgagtc agtataaatg aagagcatcc caagttgact  900
attttaaagg gataacatgc attttatatt tgttaaacat tcattctcat ttgtaaacac  960
ttgtatatat tcatgtattc aaaatgtatt gaaaattaat tgttttcctt ggtacctgaa  1020
gtcagtcctg ggtattgcaa agtagttcga agtcactggt ttccctctgt ctcacttcac  1080
tacacactgg tgattttgct aagtgatgag ccagaaaatg tacaagttcc agaatcaaag  1140
gtaaaacaaa acccaccaag aatcagctca ctgttagcgt cctagttgaa aaataaggct  1200
tatcaaagta tttcagattg cattaacact tttgatatag ctaggtatca gtgtcaacct  1260
caggagaggg caacgccaac tcctgaaacc ttcaatacag aaagtctaga aaaataagca  1320
aatatacata caaacaatag cgagaagact ccagaaacca cataaaaccg tgggaatcga  1380
aatatccctt acgtgtgttc agtacatgta aacccacgta ttttaagtgg acgatttctc  1440
tctcagagta ccgtaggtag tgggggacgg ggcgcagagg gggagaaaca gaaagtcgcc  1500
ttcctccatg gttcatttgc atttccatcc agaaactcac aggtcgaccc caagactcca  1560
ctctctcccg cctttgagaa gccggaccgg catcggcggc tgcatccttc tcctcctccc  1620
cgctctattt tggggcccca tgatctcatg ccctctgcag accacacgct gcaattccag  1680
cccagcccgc gccgcgaggc cacgcagggc gattcctgca agtgtcggga gggtggccgg  1740
ggcgcgggga ggggacggct tgggggggaag tttaagacac gcccacgtaa gggacccaaa  1800
ataaccgaca cacagagtgc ccgaaatcag acaggaagcc aaataatccg gggcgttgag  1860
tcgctttgcc ctgactgcga gagccgggtg tagggcgggg agccaaggat ctgaccgcga  1920
ggggcgggcg cggcggggag gggcggggcg gggcgggcgg cgcggggcct attaaaggcg  1980
cggccgggca gcggggccgg agcggccggg gccacg                           2016
```

```
SEQ ID NO: 70          moltype = DNA  length = 2059
FEATURE                Location/Qualifiers
source                 1..2059
                       mol_type = other DNA
                       organism = synthetic construct
SEQUENCE: 70
gaggtggagg ctgcagtgag ccgagatcga gccattgcac tccagcctgg gcaacaagag  60
tgaaactcca tctcaaaata aacaaataaa caaacaaaaa caaaaaaaca aagaaatagt  120
ggctgaggtc aactcttttg gatattgggt aacaagcaga tcaacttggc tattacagct  180
```

-continued

```
tttcccccctg cccagctagt ctgcatataa gagaaaaata aatggatgat gttcagctcc  240
tgaaccctaa cttttttttcc aagggaaccc tcattgtctt ctagctaggt ttatacaatc  300
aaatatcaga caaagtcaaa agttgttaga ctctggcaag gcaaaagaag aggctgtttt  360
tgtttttaga acatttagag cactgtggca tataatgaaa taacaggatt gccttgatat  420
ttttctttgg ggtttattgt tttcctctat catgtctggc ttgtatcttg aaatttaaca  480
taaattatag gaaaatcttt catggagtta acatctttta taagccttgc taaataccct  540
actccaaatt tgttcagtat ggcatacaga caaaagcaag aggcttacat ataaaaatgt  600
ataagcctgt cctctttgca acagtgcaaa actaaaagga ttttagaaag gcaattaaca  660
gtttggcagt atgtgtattt tcttttttttc aattagatat tactagattc taagaatctg  720
taatgaaacc caggcctact gtacaacccc ctataaacaa gtttttgctt ttgtgctatc  780
atgttttatt tgagcagagc cactactctg ttactaattt gttgcatggt aagtctcgta  840
tttgtttacg cacgaacaca tgtgctgcgg aagaaaagat ggtcactgga cctgctgagg  900
aagaggccaa aaacaaatct ttttccctca tttgaatcct gaaggcatgt aatatttaaa  960
caactttcag atttagagcc cttgattttt tcttttgaaa gtgtgctggt tgccaaattg  1020
cttagtaaag aaactttagt acccacaata gcctcaaagg acacagtatt tggtggctac  1080
atttaaccaa gaaataacta gggaaacaat tcttgacatt tcaattcttg ctgccattga  1140
gatttccttc ctaaattcaa ttgctaataa agcttcccat gccatcccct tcccccaccc  1200
atctgcctct caaaaaccgc cccctcctcc gccccgcccg aaacaagctg acagtcttta  1260
cgggaagaag aggcagagac tgaagttatt ttgtccgtcc tcccagggca gaaggacttt  1320
atgctgcgtg gctggcattt ccagtatttt gataaaagtt acttctctaa acttgaacca  1380
cagcatgggg aaaataatgt tatcttttat gttagttaca attttgcgaa atttcatcat  1440
gagaaacttt caaggaggca gaagtagctg agaatgtgat actagggaca gggtcgctca  1500
aactgccagc aaaataaata gatgggaaag acaggaacgt tattaggttt ataaatgata  1560
aaactttcct tgcttaaaaa aataaagtgg tgaggttgac gccattgaat gactgcattg  1620
taaaccttaa aagcttaaag ctggtggaaa gcccttgcac agccctgttt tcatttttat  1680
cggatgaaat gcatttggtt tctttttgac aaaccatgtt tttgtgagga aaggaaaatg  1740
aacatgcact gttatgggcc acggcaatgt aacaaaccct cctgttgcca gaggatacca  1800
catgaaagtg tctgtgggtt aggggaggga cctgtaaggg ggcggggata agggggatga  1860
tagcttaagc ctcttaggct cagagctgcg atttgtgaac accctgtgat gtaatcaagc  1920
tctggacaaa tcagaggagt ctgtcaacct cccaggtggg attgcttata gttaatagac  1980
taaacccaga gcctcaaagc agtgcactcc gtgaaggcaa agagaacacg ctgcaaaagg  2040
ctttccaaga atcctcgac                                               2059
```

```
SEQ ID NO: 71          moltype = DNA  length = 2328
FEATURE                Location/Qualifiers
source                 1..2328
                       mol_type = other DNA
                       organism = synthetic construct
SEQUENCE: 71
gggaattacc tgtagattat tattaggaga aaaaaagtgc taattaatga acagtgtaca  60
tggtatatga tcatgctata aaagtgtttc tatatgcata aaatacttct agaagaaaac  120
ataacctgag gatattggct acagacagaa aaaataacag gtaagagaag agaaagagac  180
tagttattgg atccaccctt ttatacctgt gcattttgaa ccatataaat gtattaccta  240
ttagaaaaca actaaacaaa aaggttaaaa catgactgta ttggcattat atgatccatg  300
tctgagtggc aaatcttatc accagtggct gacacgcaaa cagttctcat ttccctacct  360
atagtgtacc atgagaaggt aaggcactac tgcaatgtga gctcttcgag gatgacacat  420
ttttgtcttt ttcacggata cattttctgg tagctgttct ttgttacttt tacagtttgt  480
ctcctcattt ttactataat attttcctat ccttattata gaatcttggt attcctattg  540
tagcatcttt gtatcaatgc tgtgccaatt cctttattta gcagaaaaat ggaatttgta  600
tccttgacaa gtaaagctta acatatctgt tttcaagtgt accaaataaa tccgaatagg  660
atgaaaatga tctcaattaa tctaacatag gggaggtttt ttttttttaaa catctcacac  720
tgtgcagtat caacttgact tctcaacaca ggttttccac tgaaatatac aaattaaaac  780
aaatggaagc cagaataaaa aatgataaca attttatttc tcccttctca ggaagatctt  840
aagagcagca tgaaagtaaa tgttaaaaga aaaaaaaaaa aaaaaagaag aggccaaaaa  900
tcatcagctg aatgtattaa aaatgaagcg ctcacctgag aaagaccacc ccaaaactgt  960
ctgaaggccc ccaaacagct aattagtttt gttttctcat cttcaggagt atccataaac  1020
atgctaaaaa aataaaaatt acattatttg tcattcgttt taaaaaggta attacacaca  1080
atcagaatag tggatcttat aaccttccaa cacgaaacta agtaaaatct gacagacaca  1140
atcacataaa aacacaaaac tctgccacgc atacactcac ccaggaaaag cctcttctat  1200
aacttccgtt ttctgtaaaa aaaaaaaaaa caaaatgtaa acaatgttaa ttttaaaaag  1260
gcgcctccct tagccaagta ttacaatgta acacagggca agtcacctta atcagctctg  1320
aaactatcaa tacctgtctg gcctgtcact gtatcgattt caaaggatac aatgaacttg  1380
acagcagttt gagaatcact aaacttcccc gcatacaacc tcggtgtcaa aacaagggaa  1440
taaaaaggga ggcgtgagag gaggttgccc aggccagttt ccttggtcgg ctgccccccgc  1500
gtctccccgt ccccaagccg tagtcctgga tggccggcag ctgcactcac caccacctct  1560
tcgaaaatgc tctgcagttg cgtctccatc tgtactatca cccccgcctt tccagggtgc  1620
ccggcaaggc ccggatcaga ctcgagctct gggaatatag gggcagaggg gcggagacct  1680
ctggaggaaa ccgtagctcc tcggcgtcgc ttcctccccc agcgctttac ctggagcgtt  1740
ccctcccgag cccagccaac agcaggaacc tgtacggaag acgggaaggg cccggtacgc  1800
gccgtttgca aaccccgcag aaaccagcgg cgccaccaga aggttccgtc tgtggagaag  1860
ggcggcccgc aagccggacg agagcgcccc caaacggaac cttgagccca aggacccccgg  1920
aggcatcgtc gaccgcaggc cgccacctcc cggctggaga aggagttgct tcctgttcgg  1980
ggctaacccg cttgcagact gagaaatgaa aagtttggaa cccagaagct gcagcctgcg  2040
gaaaatgctg gagccgcagc cgacaccaag ttgatgtctg tgagcagctg accttctgga  2100
cctccatcag cggcctgcag ccaggagctg aagccacaga gacggtgtct tctcagctat  2160
gataacctca gtgcaaatat tgcccaatca ctgaagagct gtgatcttcc taaacagtta  2220
aaagtcaggc acagctatgt aactcataca gtttctcttt gccagactag actaaagaag  2280
gagcactaat ttattctgat aaaacaggtc tatgcagcta ccaggaca              2328
```

```
SEQ ID NO: 72          moltype = DNA  length = 279
FEATURE                Location/Qualifiers
source                 1..279
                       mol_type = other DNA
                       organism = synthetic construct
SEQUENCE: 72
tcgaggtgag ccccacgttc tgcttcactc tccccatctc ccccccctcc ccaccccaa  60
ttttgtattt atttattttt taattatttt gtgcagcgat gggggcgggg gggggggggg  120
gggcgcgcgc caggcggggc ggggcggggc gaggggcggg gcggggcgag gcggagaggt  180
gcggcggcag ccaatcagag cggcgcgctc cgaaagtttc cttttatggc gaggcggcgg  240
cggcggcggc cctataaaaa gcgaagcgcg cggcgggcg                        279

SEQ ID NO: 73          moltype = DNA  length = 380
FEATURE                Location/Qualifiers
source                 1..380
                       mol_type = other DNA
                       organism = synthetic construct
SEQUENCE: 73
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg                                              380

SEQ ID NO: 74          moltype = DNA  length = 210
FEATURE                Location/Qualifiers
source                 1..210
                       mol_type = other DNA
                       organism = synthetic construct
SEQUENCE: 74
agttccagat ggtaaatata cacaagggat ttagtcaaac aattttttgg caagaatatt  60
atgaattttg taatcggttg gcagccaatg aaatacaaag atgagtctag ttaataatct  120
acaattattg gttaaagaag tatattagtg ctaatttccc tccgtttgtc ctagcttttc  180
tcttctgtca accccacacg cctttggcac                                   210

SEQ ID NO: 75          moltype = DNA  length = 584
FEATURE                Location/Qualifiers
source                 1..584
                       mol_type = other DNA
                       organism = synthetic construct
SEQUENCE: 75
gcgttacata acttacggta aatggcccgc ctggctgacc gcccaacgac ccccgcccat  60
tgacgtcaat aatgacgtat gttcccatag taacgccaat agggactttc cattgacgtc  120
aatgggtgga gtatttacgg taaactgccc acttggcagt acatcaagtg tatcatatgc  180
caagtacgcc ccctattgac gtcaatgacg gtaaatggcc cgcctggcat tatgcccagt  240
acatgacctt atgggacttt cctacttggc agtacatcta cgtattagtc atcgctatta  300
ccatggtcga ggtgagcccc acgttctgct tcactctccc catctccccc ccctccccac  360
ccccaatttt gtatttattt atttttaat tattttgtgc agcgatgggg gcgggggggg  420
gggggggcg cgcgccaggc ggggcggggc ggggcgaggg gcggggcggg gcgaggcgga  480
gaggtgcggc ggcagccaat cagagcggcg cgctccgaaa gtttcctttt atggcgaggc  540
ggcggcggcg gcggccctat aaaaagcgaa gcgcgcggcg ggcg                  584

SEQ ID NO: 76          moltype = DNA  length = 1000
FEATURE                Location/Qualifiers
source                 1..1000
                       mol_type = other DNA
                       organism = synthetic construct
SEQUENCE: 76
tgtgtgtgtg tgttttaatt ttctttatgg aaaaattgac aaaaaaaaaa tagagagaga  60
ggtatttaac tgcaataaac tggccccatg tggcccccgc cttgtctgct tgtgtgtttg  120
tccatctcag gagtggggag ggggcctggg gtctgcagag ctccacgagg catggttctg  180
ctgttgtgca catggctgtg catggtccct gccagctgca ccacccatta cccagtggtt  240
ggttggatgg atggaggaat taaggaatga atgtcccctt tgaggcccta gacgtgcatg  300
agggtgtggg gagctggggt caaggacatg tcccatgttg gaggagaggc aggggtctcc  360
gtgtcaacag ttcctgaaaa cacaaccagc ccctggccct gccctgctgg gccaaagccc  420
tcccctctgc accagccaat agtggggcct ggccttgagc cctcacccc cagggagggc  480
agatggccag ggcgccaagc ttggcccgtc agcctgtcgc cttgcaccaa ggctctggcg  540
cctgtgctgt gacccctgcc cctgctgatg atgaaacctg tcctcagctg agatgcagcg  600
atgcctggta gggctggggg ctgctcctgt gtctccccag gtgagcacac ccctattcac  660
tgggccctgc ttcagcctgc agcacccttc aactcccagg agctgggctt gccactctgc  720
tcaccttgtg gagctccatc tgcctttcct ccccaattcc cccactccct gcactcgtct  780
cttcccacaa gagccctgtc tccttttcct agctattccc atctgaggcc atctttattc  840
atttagtttt tagagacagg gtttcactct cacccaggct ggggtgcagt ggcacacaat  900
cacggctcac tgcagccttg accaactaca ggtgcgtagc accacagcca agtttttgta  960
tagatggggt ctcgctttgt tacccaggct gtgacaagag                        1000

SEQ ID NO: 77          moltype = DNA  length = 2075
```

-continued

```
FEATURE               Location/Qualifiers
source                1..2075
                      mol_type = other DNA
                      organism = synthetic construct
SEQUENCE: 77
agagcgtctc catgctatgg ttgcatttcc gttttctatg aatgaatttg cattcaataa  60
acaaccagac tcagttcttg ggcccttgt ttgcactccc tctgggtgga gctgttgagg  120
atgaggggag aggcggaggt cttccatttc cccattcttc aagccatggc cctactggga  180
actgcaattc cttgattctc ccgtttttcc tgtccctcca gcaacagcat taattcagta  240
aacatttacc ggggcactgt gctggacaga ggccagttcc tggaaaagcc tttcccacgc  300
catcccactg cagacatccc tccttacctc cccaggaaca gcagtctctg cccacctggc  360
cccgcccacc agactgaggc tcacttcacc tctgacctga gcggccccca gctcaccaag  420
ccacaggccc aagcagtgct ccctgatgcg gcgtttataa tccgctcagc gtgcaggccg  480
aggcaggagg gtgatgaaag ctgggcaggc tccaagagga gggagttttg atatgtccct  540
gaaagattca tttagacttc agtcggctaa ggaggacatg atttgggggc caaggaatct  600
gttgaattca gaacacaacc agaggtctgc agggtcaggg atggaggagt gggctttccc  660
ctcgccaggg cccactcctc ttcctgcttt tcctgcaggc gccactggga ggtgctatgg  720
ctgtgcctcc cctgggctct ggagcatgtc cagttgcagt gggcagaact gcggaggcgg  780
gcccctcctc tgccaggcct ggcagccccc tcctagggcc ttgtttggct aggggtggtg  840
ccgggtgtgg cagtgtgtgt gtagtggaga gtgttaggtc ttccctacca gatgcccttg  900
caggggagtg ccacagcagt cagtccaggg atcccactgt tagtctcacc tttttaacc  960
tcttatctct ccccaagatc cctgaagcca ggtacgagca agatgagagt gggttatctc  1020
tggagtgaca gaggctggtc tgttttccag gctggtaggg actgttccta aagggaggaa  1080
gggatgatac cagcctcctg agcctccttc tcctgcgtta gtgtctcagg ccctgccagg  1140
ccttatagac cctcttattg acactgccca ctggatgggg accggagttg gactcagctt  1200
ctgccgaacc ctcaaatccc agccccaact aaagcatata actcaagacc tacctgcact  1260
gaaagctctt ctcaacctga gcagggtggt ccaattgaaa gggtgggtct gaccacctct  1320
cctgcaccca tgcgggttgg cagaggtgtg caggatctgc cacttaccat tcaccatgtg  1380
gccttgagga agacgcactc ggggcctcag tttcctcatc tataaaatgg ggatgtaatt  1440
acaccctcac actgtagctg tgagtattca atgagagcac tgcaaagggc ctggtgtgga  1500
gtaggtcctc aggaaaggtt ggatcccatg tcccatcaga gctaaaagcc ccaggaggag  1560
agggtggctg gtttgtcccc acaaacccct gggattcccg gctccccagc cccttgcccc  1620
tctctccagc cagactctat tgaactcccc ctcttctcaa actcggggcc agagaacagt  1680
gaagtaggag cagccgtaag tccgggcagg gtcctgtcca taaaaggctt ttcccgggcc  1740
ggctccccgc cggcagcgtg ccccgccccg gcccgctcca tctccaaagc atgcagagaa  1800
tgtctcggca gccccggtag actgctccaa cttggtgtct ttccccaaat atggagcctg  1860
tgtggagtca ctgggggagc cgggggtggg gagcggagcc ggcttcctct agcagggagg  1920
gggccgagga gcgagccagt gggggaggct gacatcacca cggcggcagc cctttaaacc  1980
cctcacccag ccagcgcccc atcctgtctg tccgaaccca gacacaagtc ttcactcctt  2040
cctgcgagcc ctgaggaagc cttctttccc cagac                              2075

SEQ ID NO: 78         moltype = AA  length = 8
FEATURE               Location/Qualifiers
source                1..8
                      mol_type = protein
                      organism = synthetic construct
SEQUENCE: 78
KNFQSRSH                                                            8

SEQ ID NO: 79         moltype = AA  length = 8
FEATURE               Location/Qualifiers
source                1..8
                      mol_type = protein
                      organism = synthetic construct
SEQUENCE: 79
KRRTPVRE                                                            8

SEQ ID NO: 80         moltype = AA  length = 8
FEATURE               Location/Qualifiers
source                1..8
                      mol_type = protein
                      organism = synthetic construct
SEQUENCE: 80
KTYASMQW                                                            8

SEQ ID NO: 81         moltype = AA  length = 8
FEATURE               Location/Qualifiers
source                1..8
                      mol_type = protein
                      organism = synthetic construct
SEQUENCE: 81
DDDDDDDC                                                            8

SEQ ID NO: 82         moltype = DNA  length = 8223
FEATURE               Location/Qualifiers
source                1..8223
                      mol_type = other DNA
                      organism = synthetic construct
SEQUENCE: 82
```

-continued

```
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gccaccatgg agcgcgacgg ctgcgcgggg ggcgggagcc gcggcggcga gggcgggcgc  960
gctccccggg agggcccggc ggggaacggc cgcgatcggg gccgcagcca cgctgccgag  1020
gcgcccgggg acccgcaggc cgcggcgtcc ttgctggccc ctatggacgt gggggaggag  1080
ccgctggaga aggcggcgcg cgcccgcact gccaaggacc ccaacaccta taaagtactc  1140
tcgctggtat tgtcagtatg tgtgttaaca acaatacttg gttgtatatt tgggttgaaa  1200
ccaagctgtg ccaaagaagt taaaagttgc aaaggtcgct gtttcgagag aacatttggg  1260
aactgtcgct gtgatgctgc ctgtgttgag cttggaaact gctgtttaga ttaccaggag  1320
acgtgcatag aaccagaaca tatatggact tgcaacaaat tcaggtgtgg tgagaaaagg  1380
ttgaccagaa gcctctgtgc ctgttcagat gactgcaagg acaagggcga ctgctgcatc  1440
aactacagtt ctgtgtgtca aggtgagaaa agttgggtag aagaaccatg tgagagcatt  1500
aatgagccac agtgcccagc agggtttgaa acgcctccta ccctcttatt ttctttggat  1560
ggattcaggg cagaatattt acacacttgg ggtggacttc ttcctgttat tagcaaacta  1620
aaaaaatgtg gaacatatac taaaaacatg agaccggtat atccaacaaa aactttcccc  1680
aatcactaca gcattgtcac cggattgtat ccagaatctc atggcataat cgacaataaa  1740
atgtatgatc ccaaaatgaa tgcttccttt tcacttaaaa gtaaagagaa atttaatcct  1800
gagtggtaca aaggagaacc aatttgggtc acagctaagt atcaaggcct caagtctggc  1860
acatttttct ggccaggatc agatgtggaa attaacggaa ttttcccaga catctataaa  1920
atgtataatg gttcagtacc atttgaagaa aggattttag ctgttcttca gtggctacag  1980
cttcctaaag atgaaagacc acacttttac actctgtatt tagaagaacc agattcttca  2040
ggtcattcat atggaccagt cagcagtgaa gtcatcaaag ccttgcagag ggttgatggt  2100
atggttggta tgctgatgga tggtctgaaa gagctgaact tgcacagatg cctgaacctc  2160
atccttattt cagatcatgg catggaacaa ggcagttgta agaaatacat atatctgaat  2220
aaatatttgg gggatgttaa aaatattaaa gttatctatg gacctgcagc tcgattgaga  2280
ccctctgatg tcccagataa atactattca tttaactatg aaggcattgc ccgaaatctt  2340
tcttgccggg aaccaaacca gcacttcaaa ccttacctga aacatttctt acctaagcgt  2400
ttgcactttg ctaagagtga tagaattgag ccccttgacat tctatttgga ccctcagtgg  2460
caacttgcat tgaatccctc agaaaggaaa tattgtggaa gtggatttca tggctctgac  2520
aatgtatttt caaatatgca agccctcttt gttggctatg gacctggatt caagcatggc  2580
attgaggctg acacctttga aaacattgaa gtctataact taatgtgtga tttactgaat  2640
ttgacaccgg ctcctaataa cggaactcat ggaagtctta accaccttct aaagaatcct  2700
gtttatacgc caaagcatcc caaagaagtg cacccccctgg tacagtgccc cttcacaaga  2760
aaccccagag ataaccttgg ctgctcatgt aacccttcga ttttgccgat tgaggatttt  2820
caaacacagt tcaatctgac tgtggcagaa gagaagatta ttaagcatga aactttaccc  2880
tatggaagac ctagagttct ccagaaggaa aacaccatct gtcttctttc ccagcaccag  2940
tttatgagtg gatacagcca agacatctta atgccccttt ggacatccta taccgtggac  3000
agaaatgaca gtttctctac ggaagacttc tccaactgtc tgtaccagga ctttagaatt  3060
cctcttagtc ctgtccataa atgttcattt tataaaaata acaccaaagt gagttacggg  3120
ttcctctccc caccacaact aaataaaaat tcaagtggaa tatattctga agctttgctt  3180
actacaaata tagtgccaat gtaccagagt tttcaagtta tatggcgcta ctttcatgac  3240
accctactgc gaaagtatgc tgaagaaaga aatggtgtca atgtcgtcag tggtcctgtg  3300
tttgactttg attatgatgg acgttgtgat tccttagaga atctgaggca aaaaagaaga  3360
gtcatccgta accaagaaat tttgattcca actcacttct ttattgtgct aacaagctgt  3420
aaagatacat ctcagacgcc tttgcactgt gaaaacctag acaccttagc tttcattttg  3480
cctcacagga ctgataacag cgagagctgt gtgcatggga agcatgactc ctcatgggtt  3540
gaagaattgt taatgttaca cagagcacgg atcacagatg ttgagcacat cactggactc  3600
agcttctatc aacaaagaaa agagccagtt tcagacattt taaagttgaa aacacatttg  3660
ccaaccttta gccaagaaga cgactacaaa gacgatgacg acaagtgagg taccgagctc  3720
ggatccacta gtccagtgtg gtggaattct gcagatatcc agcacagtgg cggccgctcg  3780
agtctagagg gcccgtttaa acccgctgat cagcctcgac tgtgccttct agttgccagc  3840
catctgttgt ttgcccctcc cccgtgcctt ccttgaccct ggaaggtgcc actcccactg  3900
tcctttccta ataaaatgag gaaattgcat cgcattgtct gagtaggtgt cattctattc  3960
tggggggtgg ggtggggcag gacagcaagg gggaggattg ggaagacaat agcaggcatg  4020
ctggggatgc ggtgggctct atggcttctg aggcggaaag aaccagctgg ggctctaggg  4080
ggtatcccca cgcgccctgt agcggcgcat taagcgcggc gggtgtggtg gttacgcgca  4140
gcgtgaccgc tacacttgcc agcgccctag cgcccgctcc tttcgctttc ttcccttcct  4200
ttctcgccac gttcgccggc tttccccgtc aagctctaaa tcgggggctc cctttagggt  4260
tccgatttag tgctttacgg cacctcgacc ccaaaaaact tgattagggt gatggttcac  4320
gtagtgggcc atcgccctga tagacggttt ttcgcccttt gacgttggag tccacgttct  4380
ttaatagtgg actcttgttc caaactggaa caacactcaa ccctatctcg gtctattctt  4440
ttgatttata agggattttg ccgatttcgg cctattggtt aaaaaatgag ctgatttaac  4500
aaaaatttaa cgcgaattaa ttctgtggaa tgtgtgtcag ttagggtgtg gaaagtcccc  4560
aggctcccca gcaggcagaa gtatgcaaag catgcatctc aattagtcag caaccaggtg  4620
tggaaagtcc ccaggctccc cagcaggcag aagtatgcaa agcatgcatc tcaattagtc  4680
agcaaccata gtcccgcccc taactccgcc catcccgccc ctaactccgc ccagttccgc  4740
```

```
ccattctccg ccccatggct gactaatttt ttttatttat gcagaggccg aggccgcctc  4800
tgcctctgag ctattccaga agtagtgagg aggctttttt ggaggcctag gcttttgcaa  4860
aaagctcccg ggagcttgta tatccatttt cggatctgat caagagacag gatgaggatc  4920
gtttcgcatg attgaacaag atggattgca cgcaggttct ccggccgctt gggtggagag  4980
gctattcggc tatgactggg cacaacagac aatcggctgc tctgatgccg ccgtgttccg  5040
gctgtcagcg caggggcgcc cggttctttt tgtcaagacc gacctgtccg gtgccctgaa  5100
tgaactgcag gacgaggcag cgcggctatc gtggctggcc acgacgggcg ttccttgcgc  5160
agctgtgctc gacgttgtca ctgaagcggg aagggactgg ctgctattgg gcgaagtgcc  5220
ggggcaggat ctcctgtcat ctcaccttgc tcctgccgag aaagtatcca tcatggctga  5280
tgcaatgcgg cggctgcata cgcttgatcc ggctacctgc ccattcgacc accaagcgaa  5340
acatcgcatc gagcgagcac gtactcggat ggaagccggt cttgtcgatc aggatgatct  5400
ggacgaagag catcaggggc tcgcgccagc cgaactgttc gccaggctca aggcgcgcat  5460
gcccgacggc gaggatctcg tcgtgaccca tggcgatgcc tgcttgccga atatcatggt  5520
ggaaaatggc cgcttttctg gattcatcga ctgtggccgg ctgggtgtgg cggaccgcta  5580
tcaggacata gcgttggcta cccgtgatat tgctgaagag cttggcggcg aatgggctga  5640
ccgcttcctc gtgctttacg gtatcgccgc tcccgattcg cagcgcatcg ccttctatcg  5700
ccttcttgac gagttcttct gagcgggact ctggggttcg aaatgaccga ccaagcgacg  5760
cccaacctgc catcacgaga tttcgattcc accgccgcct tctatgaaag gttgggcttc  5820
ggaatcgttt tccgggacgc cggctggatg atcctccagc gcggggatct catgctggag  5880
ttcttcgccc accccaactt gtttattgca gcttataatg gttacaaata aagcaatagc  5940
atcacaaatt tcacaaataa agcatttttt tcactgcatt ctagttgtgg tttgtccaaa  6000
ctcatcaatg tatcttatca tgtctgtata ccgtcgacct ctagctagag cttggcgtaa  6060
tcatggtcat agctgtttcc tgtgtgaaat tgttatccgc tcacaattcc acacaacata  6120
cgagccggaa gcataaagtg taaagcctgg ggtgcctaat gagtgagcta actcacatta  6180
attgcgttgc gctcactgcc cgctttccag tcgggaaacc tgtcgtgcca gctgcattaa  6240
tgaatcggcc aacgcgcggg gagaggcggt ttgcgtattg ggcgctcttc cgcttcctcg  6300
ctcactgact cgctgcgctc ggtcgttcgg ctgcggcgag cggtatcagc tcactcaaag  6360
gcggtaatac ggttatccac agaatcaggg gataacgcag gaaagaacat gtgagcaaaa  6420
ggccagcaaa aggccaggaa ccgtaaaaag gccgcgttgc tggcgttttt ccataggctc  6480
cgcccccctg acgagcatca caaaaatcga cgctcaagtc agaggtggcg aaacccgaca  6540
ggactataaa gataccaggc gtttccccct ggaagctccc tcgtgcgctc tcctgttccg  6600
accctgccgc ttaccggata cctgtccgcc tttctccctt cgggaagcgt ggcgctttct  6660
catagctcac gctgtaggta tctcagttcg gtgtaggtcg ttcgctccaa gctgggctgt  6720
gtgcacgaac cccccgttca gcccgaccgc tgcgccttat ccggtaacta tcgtcttgag  6780
tccaacccgg taagacacga cttatcgcca ctggcagcag ccactggtaa caggattagc  6840
agagcgaggt atgtaggcgg tgctacagag ttcttgaagt ggtggcctaa ctacggctac  6900
actagaagaa cagtatttgg tatctgcgct ctgctgaagc cagttacctt cggaaaaaga  6960
gttggtagct cttgatccgg caaacaaacc accgctggta gcggtggttt ttttgtttgc  7020
aagcagcaga ttacgcgcag aaaaaaagga tctcaagaag atcctttgat cttttctacg  7080
gggtctgacg ctcagtggaa cgaaaactca cgttaaggga ttttggtcat gagattatca  7140
aaaaggatct tcacctagat ccttttaaat taaaaatgaa gttttaaatc aatctaaagt  7200
atatatgagt aaacttggtc tgacagttac caatgcttaa tcagtgaggc acctatctca  7260
gcgatctgtc tatttcgttc atccatagtt gcctgactcc ccgtcgtgta gataactacg  7320
atacgggagg gcttaccatc tggccccagt gctgcaatga taccgcgaga cccacgctca  7380
ccggctccag atttatcagc aataaaccag ccagccggaa gggccgagcg cagaagtggt  7440
cctgcaactt tatccgcctc catccagtct attaattgtt gccgggaagc tagagtaagt  7500
agttcgccag ttaatagttt gcgcaacgtt gttgccattg ctacaggcat cgtggtgtca  7560
cgctcgtcgt ttggtatggc ttcattcagc tccggttccc aacgatcaag gcgagttaca  7620
tgatccccca tgttgtgcaa aaaagcggtt agctccttcg gtcctccgat cgttgtcaga  7680
agtaagttgg ccgcagtgtt atcactcatg gttatggcag cactgcataa ttctcttact  7740
gtcatgccat ccgtaagatg cttttctgtg actggtgagt actcaaccaa gtcattctga  7800
gaatagtgta tgcggcgacc gagttgctct tgcccggcgt caatacggga taataccgcg  7860
ccacatagca gaactttaaa agtgctcatc attggaaaac gttcttcggg gcgaaaactc  7920
tcaaggatct taccgctgtt gagatccagt tcgatgtaac ccactcgtgc acccaactga  7980
tcttcagcat cttttacttt caccagcgtt tctgggtgag caaaaacagg aaggcaaaat  8040
gccgcaaaaa agggaataag ggcgacacgg aaatgttgaa tactcatact cttccttttt  8100
caatattatt gaagcattta tcagggttat tgtctcatga gcggatacat atttgaatgt  8160
atttagaaaa ataaacaaat aggggttccg cgcacatttc cccgaaaagt gccacctgac  8220
gtc                                                                8223
```

```
SEQ ID NO: 83          moltype = DNA  length = 8223
FEATURE                Location/Qualifiers
source                 1..8223
                       mol_type = other DNA
                       organism = synthetic construct
SEQUENCE: 83
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgcgtta  240
cataacttac ggtaaatggc ccgcctggct gaccgcccaa cgacccccgc ccattgacgt  300
caataatgac gtatgttccc atagtaacgc caatagggac tttccattga cgtcaatggg  360
tggagtattt acggtaaact gcccacttgg cagtacatca agtgtatcat atgccaagta  420
cgccccctat tgacgtcaat gacggtaaat ggcccgcctg gcattatgcc cagtacatga  480
ccttatggga ctttcctact tggcagtaca tctacgtatt agtcatcgct attaccatgg  540
tcgaggtgag ccccacgttc tgcttcactc tccccatctc ccccccctcc ccacccccaa  600
ttttgtattt atttattttt taattatttt gtgcagcgat gggggcgggg gggggggggg  660
ggcgcgcgcc aggcggggcg gggcggggcg aggggcgggg cggggcgagg cggagaggtg  720
cggcggcagc caatcagagc ggcgcgctcc gaaagtttcc ttttatggcg aggcggcggc  780
```

-continued

```
ggcggcggcc ctataaaaag cgaagcgcgc ggcgggcgct ctggctaact agagaaccca  840
ctgcttactg gcttatcgaa attaatacga ctcactatag ggagacccaa gctggctagc  900
gccaccatgg agcgcgacgg ctgcgcgggg ggcgggagcc gcggcggcga gggcgggcgc  960
gctccccggg agggcccggc ggggaacggc cgcgatcggg gccgcagcca cgctgccgag  1020
gcgcccgggg acccgcaggc cgcggcgtcc ttgctggccc ctatggacgt gggggaggag  1080
ccgctggaga aggcggcgcg cgcccgcact gccaaggacc ccaacaccta taaagtactc  1140
tcgctggtat tgtcagtatg tgtgttaaca acaatacttg gttgtatatt tgggttgaaa  1200
ccaagctgtg ccaaagaagt taaaagttgc aaaggtcgct gtttcgagag aacatttggg  1260
aactgtcgct gtgatgctgc ctgtgttgag cttggaaact gctgtttaga ttaccaggag  1320
acgtgcatag aaccagaaca tatatggact tgcaacaaat tcaggtgtgg tgagaaaagg  1380
ttgaccagaa gcctctgtgc ctgttcagat gactgcaagg acaagggcga ctgctgcatc  1440
aactacagtt ctgtgtgtca aggtgagaaa agttgggtag aagaaccatg tgagagcatt  1500
aatgagccac agtgcccagc agggtttgaa acgcctccta ccctcttatt ttctttggat  1560
ggattcaggg cagaatattt acacacttgg ggtggacttc ttcctgttat tagcaaacta  1620
aaaaaatgtg gaacatatac taaaaacatg agaccggtat atccaacaaa aactttcccc  1680
aatcactaca gcattgtcac cggattgtat ccagaatctc atggcataat cgacaataaa  1740
atgtatgatc ccaaaatgaa tgcttccttt tcacttaaaa gtaaagagaa atttaatcct  1800
gagtggtaca aaggagaacc aatttgggtc acagctaagt atcaaggcct caagtctggc  1860
acatttttct ggccaggatc agatgtggaa attaacggaa ttttcccaga catctataaa  1920
atgtataatg gttcagtacc atttgaagaa aggattttag ctgttcttca gtggctacag  1980
cttcctaaag atgaaagacc acacttttac actctgtatt tagaagaacc agattcttca  2040
ggtcattcat atggaccagt cagcagtgaa gtcatcaaag ccttgcagag ggttgatggt  2100
atggttggta tgctgatgga tggtctgaaa gagctgaact tgcacagatg cctgaacctc  2160
atccttattt cagatcatgg catggaacaa ggcagttgta agaaatacat atatctgaat  2220
aaatatttgg gggatgttaa aaatattaaa gttatctatg gacctgcagc tcgattgaga  2280
ccctctgatg tcccagataa atactattca tttaactatg aaggcattgc ccgaaatctt  2340
tcttgccggg aaccaaacca gcacttcaaa ccttacctga aacatttctt acctaagcgt  2400
ttgcactttg ctaagagtga tagaattgag cccttgacat tctatttgga ccctcagtgg  2460
caacttgcat tgaatccctc agaaaggaaa tattgtggaa gtggatttca tggctctgac  2520
aatgtatttt caaatatgca agccctcttt gttggctatg gacctggatt caagcatggc  2580
attgaggctg acacctttga aaacattgaa gtctataact taatgtgtga tttactgaat  2640
ttgacaccgg ctcctaataa cggaactcat ggaagtctta accaccttct aaagaatcct  2700
gtttatacgc caaagcatcc caaagaagtg caccccctgg tacagtgccc cttcacaaga  2760
aaccccagag ataaccttgg ctgctcatgt aacccttcga ttttgccgat tgaggatttt  2820
caaacacagt tcaatctgac tgtggcagaa gagaagatta ttaagcatga aactttaccc  2880
tatggaagac ctagagttct ccagaaggaa aacaccatct gtcttctttc ccagcaccag  2940
tttatgagtg gatacagcca agacatctta atgccccttt ggacatccta taccgtggac  3000
agaaatgaca gtttctctac ggaagacttc tccaactgtc tgtaccagga ctttagaatt  3060
cctcttagtc ctgtccataa atgttcattt tataaaaata acaccaaagt gagttacggg  3120
ttcctctccc caccacaact aaataaaaat tcaagtggaa tatattctga agctttgctt  3180
actacaaata tagtgccaat gtaccagagt tttcaagtta tatggcgcta ctttcatgac  3240
accctactgc gaaagtatgc tgaagaaaga aatggtgtca atgtcgtcag tggtcctgtg  3300
tttgactttg attatgatgg acgttgtgat tccttagaga atctgaggca aaaaagaaga  3360
gtcatccgta accaagaaat tttgattcca actcacttct ttattgtgct aacaagctgt  3420
aaagatacat ctcagacgcc tttgcactgt gaaaacctag acaccttagc tttcattttg  3480
cctcacagga ctgataacag cgagagctgt gtgcatggga agcatgactc ctcatgggtt  3540
gaagaattgt taatgttaca cagagcacgg atcacagatg ttgagcacat cactggactc  3600
agcttctatc aacaaagaaa agagccagtt tcagacattt taaagttgaa aacacatttg  3660
ccaaccttta gccaagaaga cgactacaaa gacgatgacg acaagtgagg taccgagctc  3720
ggatccacta gtccagtgtg gtggaattct gcagatatcc agcacagtgg cggccgctcg  3780
agtctagagg gcccgtttaa acccgctgat cagcctcgac tgtgccttct agttgccagc  3840
catctgttgt ttgcccctcc cccgtgcctt ccttgaccct ggaaggtgcc actcccactg  3900
tcctttccta ataaaatgag gaaattgcat cgcattgtct gagtaggtgt cattctattc  3960
tggggggtgg ggtggggcag gacagcaagg gggaggattg ggaagacaat agcaggcatg  4020
ctggggatgc ggtgggctct atggcttctg aggcggaaag aaccagctgg ggctctaggg  4080
ggtatcccca cgcgccctgt agcggcgcat taagcgcggc gggtgtggtg gttacgcgca  4140
gcgtgaccgc tacacttgcc agcgccctag cgcccgctcc tttcgctttc ttcccttcct  4200
ttctcgccac gttcgccggc tttccccgtc aagctctaaa tcgggggctc cctttagggt  4260
tccgatttag tgctttacgg cacctcgacc ccaaaaaact tgattagggt gatggttcac  4320
gtagtgggcc atcgccctga tagacggttt ttcgcccttt gacgttggag tccacgttct  4380
ttaatagtgg actcttgttc caaactggaa caacactcaa ccctatctcg gtctattctt  4440
ttgatttata agggattttg ccgatttcgg cctattggtt aaaaaatgag ctgatttaac  4500
aaaaatttaa cgcgaattaa ttctgtggaa tgtgtgtcag ttagggtgtg gaaagtcccc  4560
aggctcccca gcaggcagaa gtatgcaaag catgcatctc aattagtcag caaccaggtg  4620
tggaaagtcc ccaggctccc cagcaggcag aagtatgcaa agcatgcatc tcaattagtc  4680
agcaaccata gtcccgcccc taactccgcc catcccgccc ctaactccgc ccagttccgc  4740
ccattctccg ccccatggct gactaatttt ttttatttat gcagaggccg aggccgcctc  4800
tgcctctgag ctattccaga agtagtgagg aggctttttt ggaggcctag gcttttgcaa  4860
aaagctcccg ggagcttgta tatccatttt cggatctgat caagagacag gatgaggatc  4920
gtttcgcatg attgaacaag atggattgca cgcaggttct ccggccgctt gggtggagag  4980
gctattcggc tatgactggg cacaacagac aatcggctgc tctgatgccg ccgtgttccg  5040
gctgtcagcg caggggcgcc cggttctttt tgtcaagacc gacctgtccg gtgccctgaa  5100
tgaactgcag gacgaggcag cgcggctatc gtggctggcc acgacgggcg ttccttgcgc  5160
agctgtgctc gacgttgtca ctgaagcggg aagggactgg ctgctattgg gcgaagtgcc  5220
ggggcaggat ctcctgtcat ctcaccttgc tcctgccgag aaagtatcca tcatggctga  5280
tgcaatgcgg cggctgcata cgcttgatcc ggctacctgc ccattcgacc accaagcgaa  5340
acatcgcatc gagcgagcac gtactcggat ggaagccggt cttgtcgatc aggatgatct  5400
ggacgaagag catcaggggc tcgcgccagc cgaactgttc gccaggctca aggcgcgcat  5460
gcccgacggc gaggatctcg tcgtgaccca tggcgatgcc tgcttgccga atatcatggt  5520
```

```
ggaaaatggc cgcttttctg gattcatcga ctgtggccgg ctgggtgtgg cggaccgcta  5580
tcaggacata gcgttggcta cccgtgatat tgctgaagag cttggcggcg aatgggctga  5640
ccgcttcctc gtgctttacg gtatcgccgc tcccgattcg cagcgcatcg ccttctatcg  5700
ccttcttgac gagttcttct gagcgggact ctggggttcg aaatgaccga ccaagcgacg  5760
cccaacctgc catcacgaga tttcgattcc accgccgcct tctatgaaag gttgggcttc  5820
ggaatcgttt tccgggacgc cggctggatg atcctccagc gcggggatct catgctggag  5880
ttcttcgccc accccaactt gtttattgca gcttataatg gttacaaata aagcaatagc  5940
atcacaaatt tcacaaataa agcatttttt tcactgcatt ctagttgtgg tttgtccaaa  6000
ctcatcaatg tatcttatca tgtctgtata ccgtcgacct ctagctagag cttggcgtaa  6060
tcatggtcat agctgtttcc tgtgtgaaat tgttatccgc tcacaattcc acacaacata  6120
cgagccggaa gcataaagtg taaagcctgg ggtgcctaat gagtgagcta actcacatta  6180
attgcgttgc gctcactgcc cgctttccag tcgggaaacc tgtcgtgcca gctgcattaa  6240
tgaatcggcc aacgcgcggg gagaggcggt ttgcgtattg ggcgctcttc cgcttcctcg  6300
ctcactgact cgctgcgctc ggtcgttcgg ctgcggcgag cggtatcagc tcactcaaag  6360
gcggtaatac ggttatccac agaatcaggg gataacgcag gaaagaacat gtgagcaaaa  6420
ggccagcaaa aggccaggaa ccgtaaaaag gccgcgttgc tggcgttttt ccataggctc  6480
cgcccccctg acgagcatca caaaaatcga cgctcaagtc agaggtggcg aaacccgaca  6540
ggactataaa gataccaggc gtttccccct ggaagctccc tcgtgcgctc tcctgttccg  6600
accctgccgc ttaccggata cctgtccgcc tttctccctt cgggaagcgt ggcgctttct  6660
catagctcac gctgtaggta tctcagttcg gtgtaggtcg ttcgctccaa gctgggctgt  6720
gtgcacgaac cccccgttca gcccgaccgc tgcgccttat ccggtaacta tcgtcttgag  6780
tccaacccgg taagacacga cttatcgcca ctggcagcag ccactggtaa caggattagc  6840
agagcgaggt atgtaggcgg tgctacagag ttcttgaagt ggtggcctaa ctacggctac  6900
actagaagaa cagtatttgg tatctgcgct ctgctgaagc cagttacctt cggaaaaaga  6960
gttggtagct cttgatccgg caaacaaacc accgctggta gcggtggttt ttttgtttgc  7020
aagcagcaga ttacgcgcag aaaaaaagga tctcaagaag atcctttgat cttttctacg  7080
gggtctgacg ctcagtggaa cgaaaactca cgttaaggga ttttggtcat gagattatca  7140
aaaaggatct tcacctagat ccttttaaat taaaaatgaa gttttaaatc aatctaaagt  7200
atatatgagt aaacttggtc tgacagttac caatgcttaa tcagtgaggc acctatctca  7260
gcgatctgtc tatttcgttc atccatagtt gcctgactcc ccgtcgtgta gataactacg  7320
atacgggagg gcttaccatc tggccccagt gctgcaatga taccgcgaga cccacgctca  7380
ccggctccag atttatcagc aataaaccag ccagccggaa gggccgagcg cagaagtggt  7440
cctgcaactt tatccgcctc catccagtct attaattgtt gccgggaagc tagagtaagt  7500
agttcgccag ttaatagttt gcgcaacgtt gttgccattg ctacaggcat cgtggtgtca  7560
cgctcgtcgt ttggtatggc ttcattcagc tccggttccc aacgatcaag gcgagttaca  7620
tgatccccca tgttgtgcaa aaaagcggtt agctccttcg gtcctccgat cgttgtcaga  7680
agtaagttgg ccgcagtgtt atcactcatg gttatggcag cactgcataa ttctcttact  7740
gtcatgccat ccgtaagatg cttttctgtg actggtgagt actcaaccaa gtcattctga  7800
gaatagtgta tgcggcgacc gagttgctct tgcccggcgt caatacggga taataccgcg  7860
ccacatagca gaactttaaa agtgctcatc attggaaaac gttcttcggg gcgaaaactc  7920
tcaaggatct taccgctgtt gagatccagt tcgatgtaac ccactcgtgc acccaactga  7980
tcttcagcat cttttacttt caccagcgtt tctgggtgag caaaaacagg aaggcaaaat  8040
gccgcaaaaa agggaataag ggcgacacgg aaatgttgaa tactcatact cttccttttt  8100
caatattatt gaagcattta tcagggttat tgtctcatga gcggatacat atttgaatgt  8160
atttagaaaa ataaacaaat aggggttccg cgcacatttc cccgaaaagt gccacctgac  8220
gtc                                                                8223

SEQ ID NO: 84          moltype = DNA  length = 9314
FEATURE                Location/Qualifiers
source                 1..9314
                       mol_type = other DNA
                       organism = synthetic construct
SEQUENCE: 84
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttcgccgg  240
ggagcaggaa ggccactcgg caccatattt agtcaggggg agccggcagc ccagagctgg  300
tatgcggcgc tgggaattcc tgcaggaagg agtccgcgcc tgccctttttt gggttgtctc  360
ccgcccgccg ctcccgccgc tcccggggag ggggaccggc ccggcccggc ccggcccggg  420
aacctcggag gagctggtgc cgcgcgggga gcggagcgcc cgggctgccc gcgggtcccc  480
ggcctggcgc ggggccagcc caccgcctcg acttcctttt atggcctgtg tgtgcgtgcg  540
tggacaggag cggggaggga gggacgggga gaagacggag agcctgggga agagagagag  600
agaaagcgca gagataggag tgagacacgc gggagagatg gagagcaaga gacacagaga  660
ccagagacaa agtgagacag gagggagaga cagatacatc gacagatcta gagaagcgag  720
agggacagag acaaaagata gagcgagaga cagcaatgat cagagtgaca gacatgcaga  780
gacagtggca gagacagagc gagagagcct gtgatggaga gagacaggga atgcaatttt  840
aggcgaggaa tccttgggga agggaagttg ttgaagggaa ctcgcagact ctgggggcac  900
acccactttc tccttggatc ttgacacttg catcttgtaa ataacgtaat tatcaccgcc  960
accgccttcc cccattttgt agctatggac accaagtctc agagaagtga agtgacttgc  1020
ccaaggtcac gcagctggcg agtggcgcac aggggagggg gacagctgaa ataatcacag  1080
tgggcttatt tttaattttt atttgtattt tggtcgtggt gatgtgggtg gaggtggaga  1140
tggcaagttg ggaaaagtaa aaacttcccc ttcctgcacg gttcccagca agggtggggg  1200
cctcctgtct tgcactttgc aaagttcaag aaatcccctt tccctaccct tcacgctgca  1260
cagccggccc tctttccaga cagtgcgatg ccaataaaat gggaagtggg gtgggagatg  1320
tcaagtcaga tccaccacag ccccgacacg gggaggaaga ggttaaagcc tttgcggccg  1380
gaaccgactc agggaagacg ttctcaagca tcccgcacag acactgcctg ctcgaccccc  1440
tttctctagg gatccggagc gtctgcgacc gcctggggcc ggggctgaga ctcccgtccc  1500
tgtgcgcacc tgttccgtgc gcccttgtgc ggtgcgcacc tgttccgtgc acccttgtcc  1560
```

-continued

```
cgagcgcccc agctccttgc gctcccgccg ggggtgcgcc ctgcaggggg cgcggcgagg  1620
gggccgcgag ggaccctccc caactccacc ccttcggcct cctccccttt cccagccgcg  1680
ggcagctccg ggtctataaa gagaggcgtc cgaggacgcg cagggagatt tggacgctcc  1740
ggcctgggag gtgcgtcaga tccgagctcg ccatccagtt tcctctccac tagtccccccc  1800
agttggagat ctgtaagtag tagttgtcat tctgggggca gattgcaggg caggggggtg  1860
ttaaaagtcc tatagggtat tctatagggg ctggggtgca cttaggggtc tctggctaac  1920
tagagaaccc actgcttact ggcttatcga aattaatacg actcactata gggagaccca  1980
agctggctag cgccaccatg gagcgcgacg gctgcgcggg gggcgggagc cgcggcggcg  2040
agggcgggcg cgctccccgg gagggcccgg cggggaacgg ccgcgatcgg ggccgcagcc  2100
acgctgccga ggcgcccggg gacccgcagg ccgcggcgtc cttgctggcc cctatggacg  2160
tgggggagga gccgctggag aaggcggcgc gcgcccgcac tgccaaggac cccaacacct  2220
ataaagtact ctcgctggta ttgtcagtat gtgtgttaac aacaatactt ggttgtatat  2280
ttgggttgaa accaagctgt gccaaagaag ttaaaagttg caaaggtcgc tgtttcgaga  2340
gaacatttgg gaactgtcgc tgtgatgctg cctgtgttga gcttggaaac tgctgtttag  2400
attaccagga gacgtgcata gaaccagaac atatatggac ttgcaacaaa ttcaggtgtg  2460
gtgagaaaag gttgaccaga agcctctgtg cctgttcaga tgactgcaag gacaagggcg  2520
actgctgcat caactacagt tctgtgtgtc aaggtgagaa aagttgggta gaagaaccat  2580
gtgagagcat taatgagcca cagtgcccag cagggtttga aacgcctcct accctcttat  2640
tttctttgga tggattcagg gcagaatatt tacacacttg ggtgggactt cttcctgtta  2700
ttagcaaact aaaaaaatgt ggaacatata ctaaaaacat gagaccggta tatccaacaa  2760
aaactttccc caatcactac agcattgtca ccggattgta tccagaatct catggcataa  2820
tcgacaataa aatgtatgat cccaaaatga atgcttcctt ttcacttaaa agtaaagaga  2880
aatttaatcc tgagtggtac aaaggagaac caatttgggt cacagctaag tatcaaggcc  2940
tcaagtctgg cacatttttc tggccaggat cagatgtgga aattaacgga attttcccag  3000
acatctataa aatgtataat ggttcagtac catttgaaga aaggatttta gctgttcttc  3060
agtggctaca gcttcctaaa gatgaaagac cacactttta cactctgtat ttagaagaac  3120
cagattcttc aggtcattca tatggaccag tcagcagtga agtcatcaaa gccttgcaga  3180
gggttgatgg tatggttggt atgctgatgg atggtctgaa agagctgaac ttgcacagat  3240
gcctgaacct catccttatt tcagatcatg gcatggaaca aggcagttgt aagaaataca  3300
tatatctgaa taaatatttg gggatgtta aaaatattaa agttatctat ggacctgcag  3360
ctcgattgag accctctgat gtcccagata aatactattc atttaactat gaaggcattg  3420
cccgaaatct ttcttgccgg gaaccaaacc agcacttcaa accttacctg aaacatttct  3480
tacctaagcg tttgcacttt gctaagagtg atagaattga gcccttgaca ttctatttgg  3540
accctcagtg gcaacttgca ttgaatccct cagaaaggaa atattgtgga agtggatttc  3600
atggctctga caatgtattt tcaaatatgc aagccctctt tgttggctat ggacctggat  3660
tcaagcatgg cattgaggct gacacctttg aaaacattga agtctataac ttaatgtgtg  3720
atttactgaa tttgacaccg gctcctaata acggaactca tggaagtctt aaccaccttc  3780
taaagaatcc tgtttatacg ccaaagcatc ccaaagaagt gcacccccctg gtacagtgcc  3840
ccttcacaag aaaccccaga gataaccttg gctgctcatg taacccttcg attttgccga  3900
ttgaggattt tcaaacacag ttcaatctga ctgtggcaga agagaagatt attaagcatg  3960
aaactttacc ctatggaaga cctagagttc tccagaagga aaacaccatc tgtcttcttt  4020
cccagcacca gtttatgagt ggatacagcc aagacatctt aatgcccctt tggacatcct  4080
ataccgtgga cagaaatgac agtttctcta cggaagactt ctccaactgt ctgtaccagg  4140
actttagaat tcctcttagt cctgtccata aatgttcatt ttataaaaat aacaccaaag  4200
tgagttacgg gttcctctcc ccaccacaac taaataaaaa ttcaagtgga atatattctg  4260
aagctttgct tactacaaat atagtgccaa tgtaccagag ttttcaagtt atatggcgct  4320
actttcatga caccctactg cgaaagtatg ctgaagaaag aaatggtgtc aatgtcgtca  4380
gtggtcctgt gtttgacttt gattatgatg gacgttgtga ttccttagag aatctgaggc  4440
aaaaaagaag agtcatccgt aaccaagaaa ttttgattcc aactcacttc tttattgtgc  4500
taacaagctg taaagataca tctcagacgc ctttgcactg tgaaaaccta gacaccttag  4560
ctttcatttt gcctcacagg actgataaca gcgagagctg tgtgcatggg aagcatgact  4620
cctcatgggt tgaagaattg ttaatgttac acagagcacg gatcacagat gttgagcaca  4680
tcactggact cagcttctat caacaaagaa aagagccagt ttcagacatt ttaaagttga  4740
aaacacattt gccaaccttt agccaagaag acgactacaa agacgatgac gacaagtgag  4800
gtaccgagct cggatccact agtccagtgt ggtggaattc tgcagatatc cagcacagtg  4860
gcggccgctc gagtctagag ggcccgttta aacccgctga tcagcctcga ctgtgccttc  4920
tagttgccag ccatctgttg tttgcccctc ccccgtgcct tccttgaccc tggaaggtgc  4980
cactcccact gtcctttcct aataaaatga ggaaattgca tcgcattgtc tgagtaggtg  5040
tcattctatt ctggggggtg gggtggggca ggacagcaag ggggaggatt gggaagacaa  5100
tagcaggcat gctggggatg cggtgggctc tatggcttct gaggcggaaa gaaccagctg  5160
gggctctagg gggtatcccc acgcgccctg tagcggcgca ttaagcgcgg cgggtgtggt  5220
ggttacgcgc agcgtgaccg ctacacttgc cagcgcccta gcgcccgctc ctttcgcttt  5280
cttcccttcc tttctcgcca cgttcgccgg ctttccccgt caagctctaa atcgggggct  5340
ccctttaggg ttccgattta gtgctttacg gcacctcgac cccaaaaaac ttgattaggg  5400
tgatggttca cgtagtgggc catcgccctg atagacggtt tttcgccctt tgacgttgga  5460
gtccacgttc tttaatagtg gactcttgtt ccaaactgga acaacactca accctatctc  5520
ggtctattct tttgatttat aagggatttt gccgatttcg gcctattggt taaaaaatga  5580
gctgatttaa caaaaattta acgcgaatta attctgtgga atgtgtgtca gttagggtgt  5640
ggaaagtccc caggctcccc agcaggcaga agtatgcaaa gcatgcatct caattagtca  5700
gcaaccaggt gtggaaagtc cccaggctcc ccagcaggca gaagtatgca aagcatgcat  5760
ctcaattagt cagcaaccat agtcccgccc ctaactccgc ccatcccgcc cctaactccg  5820
cccagttccg cccattctcc gccccatggc tgactaattt tttttattta tgcagaggcc  5880
gaggccgcct ctgcctctga gctattccag aagtagtgag gaggcttttt tggaggccta  5940
ggcttttgca aaaagctccc gggagcttgt atatccattt tcggatctga tcaagagaca  6000
ggatgaggat cgtttcgcat gattgaacaa gatggattgc acgcaggttc tccggccgct  6060
tgggtggaga ggctattcgg ctatgactgg gcacaacaga caatcggctg ctctgatgcc  6120
gccgtgttcc ggctgtcagc gcaggggcgc ccggttcttt ttgtcaagac cgacctgtcc  6180
ggtgccctga atgaactgca ggacgaggca gcgcggctat cgtggctggc cacgacgggc  6240
gttccttgcg cagctgtgct cgacgttgtc actgaagcgg gaagggactg gctgctattg  6300
```

```
ggcgaagtgc cggggcagga tctcctgtca tctcaccttg ctcctgccga gaaagtatcc  6360
atcatggctg atgcaatgcg gcggctgcat acgcttgatc cggctacctg cccattcgac  6420
caccaagcga aacatcgcat cgagcgagca cgtactcgga tggaagccgg tcttgtcgat  6480
caggatgatc tggacgaaga gcatcagggg ctcgcgccag ccgaactgtt cgccaggctc  6540
aaggcgcgca tgcccgacgg cgaggatctc gtcgtgaccc atggcgatgc ctgcttgccg  6600
aatatcatgg tggaaaatgg ccgcttttct ggattcatcg actgtggccg gctgggtgtg  6660
gcggaccgct atcaggacat agcgttggct acccgtgata ttgctgaaga gcttggcggc  6720
gaatgggctg accgcttcct cgtgctttac ggtatcgccg ctcccgattc gcagcgcatc  6780
gccttctatc gccttcttga cgagttcttc tgagcgggac tctggggttc gaaatgaccg  6840
accaagcgac gcccaacctg ccatcacgag atttcgattc caccgccgcc ttctatgaaa  6900
ggttgggctt cggaatcgtt ttccgggacg ccggctggat gatcctccag cgcggggatc  6960
tcatgctgga gttcttcgcc caccccaact tgtttattgc agcttataat ggttacaaat  7020
aaagcaatag catcacaaat ttcacaaata aagcattttt ttcactgcat tctagttgtg  7080
gtttgtccaa actcatcaat gtatcttatc atgtctgtat accgtcgacc tctagctaga  7140
gcttggcgta atcatggtca tagctgtttc ctgtgtgaaa ttgttatccg ctcacaattc  7200
cacacaacat acgagccgga agcataaagt gtaaagcctg gggtgcctaa tgagtgagct  7260
aactcacatt aattgcgttg cgctcactgc ccgctttcca gtcgggaaac ctgtcgtgcc  7320
agctgcatta atgaatcggc caacgcgcgg ggagaggcgg tttgcgtatt gggcgctctt  7380
ccgcttcctc gctcactgac tcgctgcgct cggtcgttcg gctgcggcga gcggtatcag  7440
ctcactcaaa ggcggtaata cggttatcca cagaatcagg ggataacgca ggaaagaaca  7500
tgtgagcaaa aggccagcaa aaggccagga accgtaaaaa ggccgcgttg ctggcgtttt  7560
tccataggct ccgcccccct gacgagcatc acaaaaatcg acgctcaagt cagaggtggc  7620
gaaacccgac aggactataa agataccagg cgtttccccc tggaagctcc ctcgtgcgct  7680
ctcctgttcc gaccctgccg cttaccggat acctgtccgc ctttctccct tcgggaagcg  7740
tggcgctttc tcatagctca cgctgtaggt atctcagttc ggtgtaggtc gttcgctcca  7800
agctgggctg tgtgcacgaa ccccccgttc agcccgaccg ctgcgcctta tccggtaact  7860
atcgtcttga gtccaacccg gtaagacacg acttatcgcc actggcagca gccactggta  7920
acaggattag cagagcgagg tatgtaggcg gtgctacaga gttcttgaag tggtggccta  7980
actacggcta cactagaaga acagtatttg gtatctgcgc tctgctgaag ccagttacct  8040
tcggaaaaag agttggtagc tcttgatccg gcaaacaaac caccgctggt agcggtggtt  8100
tttttgtttg caagcagcag attacgcgca gaaaaaaagg atctcaagaa gatcctttga  8160
tcttttctac ggggtctgac gctcagtgga acgaaaactc acgttaaggg attttggtca  8220
tgagattatc aaaaaggatc ttcacctaga tccttttaaa ttaaaaatga agttttaaat  8280
caatctaaag tatatatgag taaacttggt ctgacagtta ccaatgctta atcagtgagg  8340
cacctatctc agcgatctgt ctatttcgtt catccatagt tgcctgactc cccgtcgtgt  8400
agataactac gatacgggag ggcttaccat ctggccccag tgctgcaatg ataccgcgag  8460
acccacgctc accggctcca gatttatcag caataaacca gccagccgga agggccgagc  8520
gcagaagtgg tcctgcaact ttatccgcct ccatccagtc tattaattgt tgccgggaag  8580
ctagagtaag tagttcgcca gttaatagtt tgcgcaacgt tgttgccatt gctacaggca  8640
tcgtggtgtc acgctcgtcg tttggtatgg cttcattcag ctccggttcc caacgatcaa  8700
ggcgagttac atgatccccc atgttgtgca aaaaagcggt tagctccttc ggtcctccga  8760
tcgttgtcag aagtaagttg gccgcagtgt tatcactcat ggttatggca gcactgcata  8820
attctcttac tgtcatgcca tccgtaagat gcttttctgt gactggtgag tactcaacca  8880
agtcattctg agaatagtgt atgcggcgac cgagttgctc ttgcccggcg tcaatacggg  8940
ataataccgc gccacatagc agaactttaa aagtgctcat cattggaaaa cgttcttcgg  9000
ggcgaaaact ctcaaggatc ttaccgctgt tgagatccag ttcgatgtaa cccactcgtg  9060
cacccaactg atcttcagca tcttttactt tcaccagcgt ttctgggtga gcaaaaacag  9120
gaaggcaaaa tgccgcaaaa aagggaataa gggcgacacg gaaatgttga atactcatac  9180
tcttcctttt tcaatattat tgaagcattt atcagggtta ttgtctcatg agcggataca  9240
tatttgaatg tatttagaaa aataaacaaa taggggttcc gcgcacattt ccccgaaaag  9300
tgccacctga cgtc                                                    9314

SEQ ID NO: 85           moltype = DNA  length = 9702
FEATURE                 Location/Qualifiers
source                  1..9702
                        mol_type = other DNA
                        organism = synthetic construct
SEQUENCE: 85
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttaagatt  240
atagttgtca tttgaacttg gggataaagg agacatctat gacttggctg gaaaagacag  300
agctaatgta cattgcaaag cacatattta tagcaggaaa atgggaagat ttctctttaa  360
ttctggagat ggagtgggga tggggagagt agactactca ttttaagggt gaaacattgg  420
aattcaactt gtttgatgtt atattaattg gtggttaatt actaagctaa gtacgtataa  480
aacttttatc tatggctagc ttgtcccccc aaagtcatgc aatatagtga actggctttc  540
gcactttaaa ttattcattg atcatgtaat gattcagatg attcatcttc caagatggac  600
actgaaacta acactcatag taggttgtgg tttaaagagt ggaacaaccg ccagtctcat  660
tagtggaaat tgtgatggtt gaatttatca aggatgaaca tacacggtct tctttctgag  720
attttcttta agattttcgc acagataatc tatttcttag gttttggaga gaaaacttga  780
attttattga tccctcagaa ctcaatcttt cagatttcaa aggagctatt tcttttaatg  840
gggactctgt taatatttat aaaagctctt cacaggatgg agggtgggag ggaaactcca  900
tcccaacaag acaaaaagaa tgaagcatga ggctccacct agttcatcac tgctccttga  960
aatacatcag tattgaaaga cacatccacc ccacccccaa cccagcccta ttgctgttcc  1020
agctcaagag tcagaggtcc cgaagctgta gctcttctac aatctgctgc tctgtgactt  1080
caagtctgtt gtctgcaaag aaaactattg ggttcccaag caagagaggc acatctggta  1140
ggacagattt tgtgattgca aaagaagggg gaaaaaaaga aagaaagaaa agacctctct  1200
atacaagata accagaggca tcaaactgaa atcctcctgt ggaaaataag ctagtacttc  1260
```

-continued

```
tgggcctgat ggtgtagtga aaacctgtgc ttgaggatac attacagtga aagagcaaag  1320
tgaatagtaa gtagctatta cttacctcct tagggaggtg tgttgtttgt ctgtacatcc  1380
cccacagcac ctagcacagt accttgcatc tcacctgcca ctcactaaaa agtctatcaa  1440
gttagttaat tatcgagaca acgccctcag aaatgagaga acagtaccct cttatccttg  1500
ctgcactttc cagcactgat acgctgccta aaagaggact agggcacagg tttgaattaa  1560
tgtcacaaaa ctggatgggc aagttacaac ggtgttgatt aaggaaacag aactcatggt  1620
gcaccggata tctccatcct gatgaaccct tggaaaaatg ccaaagatgc atatccccag  1680
gcaaatgcct gattagtctg ggattgatag attggtctag gattcagccc tactgggaag  1740
atgtctaaat tataatcagt gtagaaagcg aagttctcct agaagaagag gcaaaggtta  1800
aaaagaagaa aagaaaagaa agtgaagtcc tttctccccc aaaacctctc atcaatcaat  1860
cagggtaaca aacagaacac tagggctctg tctgtggacc aaacccaaaa gccctgcggt  1920
cagggccagg agggtagatc atgtgtttgt ggcaacttcc tctgtgggct tttgcccagg  1980
tctgtcccca agcatacgat ggccaaaact tctgcaccag agcagcatcc tgtgtaacac  2040
agtcaggtcc agcagttagg gaaaactgcc cactcagagt agataatatc tggaaggaat  2100
gactgtttgg gaaaagttcc aatgctagtt cagtgccaac ccttccccac cttctccagc  2160
tctctcccac tggttcctcc cctctcaact gctctggttc ttataaaaac ctcacagcct  2220
tccactaaca tcccgtagga gcctctctcc ctactgctgc tacacaagac cctgagactg  2280
acctgcagga cgaaaccctc tggctaacta gagaacccac tgcttactgg cttatcgaaa  2340
ttaatacgac tcactatagg gagacccaag ctggctagcg ccaccatgga gcgcgacggc  2400
tgcgcggggg gcgggagccg cggcggcgag ggcgggcgcg ctccccggga gggcccggcg  2460
gggaacggcc gcgatcgggg ccgcagccac gctgccgagg cgcccgggga cccgcaggcc  2520
gcggcgtcct tgctggcccc tatggacgtg ggggaggagc cgctggagaa ggcggcgcgc  2580
gcccgcactg ccaaggaccc caacacctat aaagtactct cgctggtatt gtcagtatgt  2640
gtgttaacaa caatacttgg ttgtatattt gggttgaaac caagctgtgc caaagaagtt  2700
aaaagttgca aaggtcgctg tttcgagaga acatttggga actgtcgctg tgatgctgcc  2760
tgtgttgagc ttggaaactg ctgtttagat taccaggaga cgtgcataga accagaacat  2820
atatggactt gcaacaaatt caggtgtggt gagaaaaggt tgaccagaag cctctgtgcc  2880
tgttcagatg actgcaagga caagggcgac tgctgcatca actacagttc tgtgtgtcaa  2940
ggtgagaaaa gttgggtaga agaaccatgt gagagcatta atgagccaca gtgcccagca  3000
gggtttgaaa cgcctcctac cctcttattt tctttggatg gattcagggc agaatattta  3060
cacacttggg gtggacttct tcctgttatt agcaaactaa aaaaatgtgg aacatatact  3120
aaaaacatga gaccggtata tccaacaaaa actttcccca atcactacag cattgtcacc  3180
ggattgtatc cagaatctca tggcataatc gacaataaaa tgtatgatcc caaaatgaat  3240
gcttcctttt cacttaaaag taaagagaaa tttaatcctg agtggtacaa aggagaacca  3300
atttgggtca cagctaagta tcaaggcctc aagtctggca catttttctg gccaggatca  3360
gatgtggaaa ttaacggaat ttcccagac atctataaaa tgtataatgg ttcagtacca  3420
tttgaagaaa ggattttagc tgttcttcag tggctacagc ttcctaaaga tgaaagacca  3480
cacttttaca ctctgtattt agaagaacca gattcttcag gtcattcata tggaccagtc  3540
agcagtgaag tcatcaaagc cttgcagagg gttgatggta tggttggtat gctgatggat  3600
ggtctgaaag agctgaactt gcacagatgc ctgaacctca tccttatttc agatcatggc  3660
atggaacaag gcagttgtaa gaaatacata tatctgaata aatatttggg ggatgttaaa  3720
aatattaaag ttatctatgg acctgcagct cgattgagac cctctgatgt cccagataaa  3780
tactattcat ttaactatga aggcattgcc cgaaatcttt cttgccggga accaaaccag  3840
cacttcaaac cttacctgaa acatttctta cctaagcgtt tgcactttgc taagagtgat  3900
agaattgagc ccttgacatt ctatttggac cctcagtggc aacttgcatt gaatccctca  3960
gaaaggaaat attgtggaag tggatttcat ggctctgaca atgtattttc aaatatgcaa  4020
gccctctttg ttggctatgg acctggattc aagcatggca ttgaggctga cacctttgaa  4080
aacattgaag tctataactt aatgtgtgat ttactgaatt tgacaccggc tcctaataac  4140
ggaactcatg gaagtcttaa ccaccttcta aagaatcctg tttatacgcc aaagcatccc  4200
aaagaagtgc accccctggt acagtgcccc ttcacaagaa accccagaga taaccttggc  4260
tgctcatgta acccttcgat tttgccgatt gaggattttc aaacacagtt caatctgact  4320
gtggcagaag agaagattat taagcatgaa actttaccct atggaagacc tagagttctc  4380
cagaaggaaa acaccatctg tcttctttcc cagcaccagt ttatgagtgg atacagccaa  4440
gacatcttaa tgccccttg gacatcctat accgtggaca gaaatgacag tttctctacg  4500
gaagacttct ccaactgtct gtaccaggac tttagaattc ctcttagtcc tgtccataaa  4560
tgttcatttt ataaaaataa caccaaagtg agttacgggt tcctctcccc accacaacta  4620
aataaaaatt caagtggaat atattctgaa gctttgctta ctacaaatat agtgccaatg  4680
taccagagtt ttcaagttat atggcgctac tttcatgaca ccctactgcg aaagtatgct  4740
gaagaaagaa atggtgtcaa tgtcgtcagt ggtcctgtgt ttgactttga ttatgatgga  4800
cgttgtgatt ccttagagaa tctgaggcaa aaaagaagag tcatccgtaa ccaagaaatt  4860
ttgattccaa ctcacttctt tattgtgcta acaagctgta aagatacatc tcagacgcct  4920
ttgcactgtg aaaacctaga caccttagct ttcattttgc ctcacaggac tgataacagc  4980
gagagctgtg tgcatgggaa gcatgactcc tcatgggttg aagaattgtt aatgttacac  5040
agagcacgga tcacagatgt tgagcacatc actggactca gcttctatca acaaagaaaa  5100
gagccagttt cagacatttt aaagttgaaa acacatttgc caacctttag ccaagaagac  5160
gactacaaag acgatgacga caagtgaggt accgagctcg gatccactag tccagtgtgg  5220
tggaattctg cagatatcca gcacagtggc ggccgctcga gtctagaggg cccgtttaaa  5280
cccgctgatc agcctcgact gtgccttcta gttgccagcc atctgttgtt tgcccctccc  5340
ccgtgccttc cttgaccctg gaaggtgcca ctcccactgt cctttcctaa taaaatgagg  5400
aaattgcatc gcattgtctg agtaggtgtc attctattct ggggggtggg gtggggcagg  5460
acagcaaggg ggaggattgg gaagacaata gcaggcatgc tggggatgcg gtgggctcta  5520
tggcttctga ggcggaaaga accagctggg gctctagggg gtatccccac gcgccctgta  5580
gcggcgcatt aagcgcggcg ggtgtggtgg ttacgcgcag cgtgaccgct acacttgcca  5640
gcgccctagc gcccgctcct ttcgctttct tcccttcctt tctcgccacg ttcgccggct  5700
ttccccgtca agctctaaat cgggggctcc ctttagggtt ccgatttagt gctttacggc  5760
acctcgaccc caaaaaactt gattagggtg atggttcacg tagtgggcca tcgccctgat  5820
agacggtttt tcgccctttg acgttggagt ccacgttctt taatagtgga ctcttgttcc  5880
aaactggaac aacactcaac cctatctcgg tctattcttt tgatttataa gggattttgc  5940
cgatttcggc ctattggtta aaaaatgagc tgatttaaca aaaatttaac gcgaattaat  6000
```

-continued

```
tctgtggaat gtgtgtcagt tagggtgtgg aaagtcccca ggctccccag caggcagaag  6060
tatgcaaagc atgcatctca attagtcagc aaccaggtgt ggaaagtccc caggctcccc  6120
agcaggcaga agtatgcaaa gcatgcatct caattagtca gcaaccatag tcccgcccct  6180
aactccgccc atcccgcccc taactccgcc cagttccgcc cattctccgc cccatggctg  6240
actaattttt tttatttatg cagaggccga ggccgcctct gcctctgagc tattccagaa  6300
gtagtgagga ggcttttttg gaggcctagg cttttgcaaa aagctcccgg gagcttgtat  6360
atccattttc ggatctgatc aagagacagg atgaggatcg tttcgcatga ttgaacaaga  6420
tggattgcac gcaggttctc cggccgcttg ggtggagagg ctattcggct atgactgggc  6480
acaacagaca atcggctgct ctgatgccgc cgtgttccgg ctgtcagcgc aggggcgccc  6540
ggttcttttt gtcaagaccg acctgtccgg tgccctgaat gaactgcagg acgaggcagc  6600
gcggctatcg tggctggcca cgacgggcgt tccttgcgca gctgtgctcg acgttgtcac  6660
tgaagcggga agggactggc tgctattggg cgaagtgccg gggcaggatc tcctgtcatc  6720
tcaccttgct cctgccgaga aagtatccat catggctgat gcaatgcggc ggctgcatac  6780
gcttgatccg gctacctgcc cattcgacca ccaagcgaaa catcgcatcg agcgagcacg  6840
tactcggatg gaagccggtc ttgtcgatca ggatgatctg gacgaagagc atcaggggct  6900
cgcgccagcc gaactgttcg ccaggctcaa ggcgcgcatg cccgacggcg aggatctcgt  6960
cgtgacccat ggcgatgcct gcttgccgaa tatcatggtg gaaaatggcc gcttttctgg  7020
attcatcgac tgtggccggc tgggtgtggc ggaccgctat caggacatag cgttggctac  7080
ccgtgatatt gctgaagagc ttggcggcga atgggctgac cgcttcctcg tgctttacgg  7140
tatcgccgct cccgattcgc agcgcatcgc cttctatcgc cttcttgacg agttcttctg  7200
agcgggactc tggggttcga aatgaccgac caagcgacgc ccaacctgcc atcacgagat  7260
ttcgattcca ccgccgcctt ctatgaaagg ttgggcttcg gaatcgtttt ccgggacgcc  7320
ggctggatga tcctccagcg cggggatctc atgctggagt tcttcgccca ccccaacttg  7380
tttattgcag cttataatgg ttacaaataa agcaatagca tcacaaattt cacaaataaa  7440
gcattttttt cactgcattc tagttgtggt ttgtccaaac tcatcaatgt atcttatcat  7500
gtctgtatac cgtcgacctc tagctagagc ttggcgtaat catggtcata gctgtttcct  7560
gtgtgaaatt gttatccgct cacaattcca cacaacatac gagccggaag cataaagtgt  7620
aaagcctggg gtgcctaatg agtgagctaa ctcacattaa ttgcgttgcg ctcactgccc  7680
gctttccagt cgggaaacct gtcgtgccag ctgcattaat gaatcggcca acgcgcgggg  7740
agaggcggtt tgcgtattgg gcgctcttcc gcttcctcgc tcactgactc gctgcgctcg  7800
gtcgttcggc tgcggcgagc ggtatcagct cactcaaagg cggtaatacg gttatccaca  7860
gaatcagggg ataacgcagg aaagaacatg tgagcaaaag gccagcaaaa ggccaggaac  7920
cgtaaaaagg ccgcgttgct ggcgtttttc cataggctcc gcccccctga cgagcatcac  7980
aaaaatcgac gctcaagtca gaggtggcga aacccgacag gactataaag ataccaggcg  8040
tttccccctg gaagctccct cgtgcgctct cctgttccga ccctgccgct taccggatac  8100
ctgtccgcct ttctcccttc gggaagcgtg gcgctttctc atagctcacg ctgtaggtat  8160
ctcagttcgg tgtaggtcgt tcgctccaag ctgggctgtg tgcacgaacc ccccgttcag  8220
cccgaccgct gcgccttatc cggtaactat cgtcttgagt ccaacccggt aagacacgac  8280
ttatcgccac tggcagcagc cactggtaac aggattagca gagcgaggta tgtaggcggt  8340
gctacagagt tcttgaagtg gtggcctaac tacggctaca ctagaagaac agtatttggt  8400
atctgcgctc tgctgaagcc agttaccttc ggaaaaagag ttggtagctc ttgatccggc  8460
aaacaaacca ccgctggtag cggtggtttt tttgtttgca agcagcagat tacgcgcaga  8520
aaaaaaggat ctcaagaaga tcctttgatc ttttctacgg ggtctgacgc tcagtggaac  8580
gaaaactcac gttaagggat tttggtcatg agattatcaa aaaggatctt cacctagatc  8640
cttttaaatt aaaaatgaag ttttaaatca atctaaagta tatatgagta aacttggtct  8700
gacagttacc aatgcttaat cagtgaggca cctatctcag cgatctgtct atttcgttca  8760
tccatagttg cctgactccc cgtcgtgtag ataactacga tacgggaggg cttaccatct  8820
ggccccagtg ctgcaatgat accgcgagac ccacgctcac cggctccaga tttatcagca  8880
ataaaccagc cagccggaag ggccgagcgc agaagtggtc ctgcaacttt atccgcctcc  8940
atccagtcta ttaattgttg ccgggaagct agagtaagta gttcgccagt taatagtttg  9000
cgcaacgttg ttgccattgc tacaggcatc gtggtgtcac gctcgtcgtt tggtatggct  9060
tcattcagct ccggttccca acgatcaagg cgagttacat gatcccccat gttgtgcaaa  9120
aaagcggtta gctccttcgg tcctccgatc gttgtcagaa gtaagttggc cgcagtgtta  9180
tcactcatgg ttatggcagc actgcataat tctcttactg tcatgccatc cgtaagatgc  9240
ttttctgtga ctggtgagta ctcaaccaag tcattctgag aatagtgtat gcggcgaccg  9300
agttgctctt gcccggcgtc aatacgggat aataccgcgc cacatagcag aactttaaaa  9360
gtgctcatca ttggaaaacg ttcttcgggg cgaaaactct caaggatctt accgctgttg  9420
agatccagtt cgatgtaacc cactcgtgca cccaactgat cttcagcatc ttttactttc  9480
accagcgttt ctgggtgagc aaaaacagga aggcaaaatg ccgcaaaaaa gggaataagg  9540
gcgacacgga aatgttgaat actcatactc ttcctttttc aatattattg aagcatttat  9600
cagggttatt gtctcatgag cggatacata tttgaatgta tttagaaaaa taaacaaata  9660
ggggttccgc gcacatttcc ccgaaaagtg ccacctgacg tc                    9702
```

```
SEQ ID NO: 86          moltype = DNA  length = 7856
FEATURE                Location/Qualifiers
source                 1..7856
                       mol_type = other DNA
                       organism = synthetic construct
SEQUENCE: 86
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgaaaac  240
tacaattgac tatctctaaa ttttaaaatg tgatgatagt tactacttca gtggtccaca  300
ctgtttctat cctttggaac ataagatttt gttgtgtagc ttaaggaaga ggaattcagc  360
agttgactat ctcgattgtt ctgggaattt tggaggctga ggggaaattt tcacatataa  420
gcgctgggtt tgctggggta ttgagagtga cctctggcta actagagaac ccactgctta  480
ctggcttatc gaaattaata cgactcacta tagggagacc caagctggct agcgccacca  540
tggagcgcga cggctgcgcg gggggcggga gccgcggcgg cgagggcggg cgcgctcccc  600
```

-continued gggagggccc ggcggggaac ggccgcgatc ggggccgcag ccacgctgcc gaggcgcccg 660
gggacccgca ggccgcggcg tccttgctgg cccctatgga cgtgggggag gagccgctgg 720
agaaggcggc gcgcgcccgc actgccaagg accccaacac ctataaagta ctctcgctgg 780
tattgtcagt atgtgtgtta acaacaatac ttggttgtat atttgggttg aaaccaagct 840
gtgccaaaga agttaaaagt tgcaaaggtc gctgtttcga gagaacattt gggaactgtc 900
gctgtgatgc tgcctgtgtt gagcttggaa actgctgttt agattaccag gagacgtgca 960
tagaaccaga acatatatgg acttgcaaca aattcaggtg tggtgagaaa aggttgacca 1020
gaagcctctg tgcctgttca gatgactgca aggacaaggg cgactgctgc atcaactaca 1080
gttctgtgtg tcaaggtgag aaaagttggg tagaagaacc atgtgagagc attaatgagc 1140
cacagtgccc agcagggttt gaaacgcctc ctaccctctt attttctttg gatggattca 1200
gggcagaata tttacacact tggggtggac ttcttcctgt tattagcaaa ctaaaaaaat 1260
gtggaacata tactaaaaac atgagaccgg tatatccaac aaaaactttc cccaatcact 1320
acagcattgt caccggattg tatccagaat ctcatggcat aatcgacaat aaaatgtatg 1380
atcccaaaat gaatgcttcc ttttcactta aaagtaaaga gaaatttaat cctgagtggt 1440
acaaaggaga accaatttgg gtcacagcta agtatcaagg cctcaagtct ggcacatttt 1500
tctggccagg atcagatgtg gaaattaacg gaattttccc agacatctat aaaatgtata 1560
atggttcagt accatttgaa gaaaggattt tagctgttct tcagtggcta cagcttccta 1620
aagatgaaag accacacttt tacactctgt atttagaaga accagattct tcaggtcatt 1680
catatggacc agtcagcagt gaagtcatca aagccttgca gagggttgat ggtatggttg 1740
gtatgctgat ggatggtctg aaagagctga acttgcacag atgcctgaac ctcatcctta 1800
tttcagatca tggcatggaa caaggcagtt gtaagaaata catatatctg aataaatatt 1860
tgggggatgt taaaaatatt aaagttatct atggacctgc agctcgattg agaccctctg 1920
atgtcccaga taaatactat tcatttaact atgaaggcat tgcccgaaat ctttcttgcc 1980
gggaaccaaa ccagcacttc aaaccttacc tgaaacattt cttacctaag cgtttgcact 2040
ttgctaagag tgatagaatt gagcccttga cattctattt ggaccctcag tggcaacttg 2100
cattgaatcc ctcagaaagg aaatattgtg gaagtggatt tcatggctct gacaatgtat 2160
tttcaaatat gcaagccctc tttgttggct atggacctgg attcaagcat ggcattgagg 2220
ctgacacctt tgaaaacatt gaagtctata acttaatgtg tgatttactg aatttgacac 2280
cggctcctaa taacggaact catggaagtc ttaaccacct tctaaagaat cctgtttata 2340
cgccaaagca tcccaaagaa gtgcaccccc tggtacagtg ccccttcaca agaaacccca 2400
gagataacct tggctgctca tgtaaccctt cgattttgcc gattgaggat tttcaaacac 2460
agttcaatct gactgtggca gaagagaaga ttattaagca tgaaacttta ccctatggaa 2520
gacctagagt tctccagaag gaaaacacca tctgtcttct ttcccagcac cagtttatga 2580
gtggatacag ccaagacatc ttaatgcccc tttggacatc ctataccgtg gacagaaatg 2640
acagtttctc tacggaagac ttctccaact gtctgtacca ggactttaga attcctctta 2700
gtcctgtcca taaatgttca ttttataaaa ataacaccaa agtgagttac gggttcctct 2760
ccccaccaca actaaataaa aattcaagtg gaatatattc tgaagctttg cttactacaa 2820
atatagtgcc aatgtaccag agttttcaag ttatatggcg ctactttcat gacaccctac 2880
tgcgaaagta tgctgaagaa agaaatggtg tcaatgtcgt cagtggtcct gtgtttgact 2940
ttgattatga tggacgttgt gattccttag agaatctgag gcaaaaaaga agagtcatcc 3000
gtaaccaaga aattttgatt ccaactcact tctttattgt gctaacaagc tgtaaagata 3060
catctcagac gcctttgcac tgtgaaaacc tagacacctt agctttcatt ttgcctcaca 3120
ggactgataa cagcgagagc tgtgtgcatg ggaagcatga ctcctcatgg gttgaagaat 3180
tgttaatgtt acacagagca cggatcacag atgttgagca catcactgga ctcagcttct 3240
atcaacaaag aaaagagcca gtttcagaca ttttaaagtt gaaaacacat ttgccaacct 3300
ttagccaaga agacgactac aaagacgatg acgacaagtg aggtaccgag ctcggatcca 3360
ctagtccagt gtggtggaat tctgcagata tccagcacag tggcggccgc tcgagtctag 3420
agggcccgtt taaacccgct gatcagcctc gactgtgcct tctagttgcc agccatctgt 3480
tgtttgcccc tcccccgtgc cttccttgac cctggaaggt gccactccca ctgtcctttc 3540
ctaataaaat gaggaaattg catcgcattg tctgagtagg tgtcattcta ttctgggggg 3600
tggggtgggg caggacagca agggggagga ttgggaagac aatagcaggc atgctgggga 3660
tgcggtgggc tctatggctt ctgaggcgga aagaaccagc tggggctcta gggggtatcc 3720
ccacgcgccc tgtagcggcg cattaagcgc ggcgggtgtg gtggttacgc gcagcgtgac 3780
cgctacactt gccagcgccc tagcgcccgc tcctttcgct ttcttccctt cctttctcgc 3840
cacgttcgcc ggctttcccc gtcaagctct aaatcggggg ctccctttag ggttccgatt 3900
tagtgcttta cggcacctcg accccaaaaa acttgattag ggtgatggtt cacgtagtgg 3960
gccatcgccc tgatagacgg tttttcgccc tttgacgttg gagtccacgt tctttaatag 4020
tggactcttg ttccaaactg gaacaacact caaccctatc tcggtctatt cttttgattt 4080
ataagggatt ttgccgattt cggcctattg gttaaaaaat gagctgattt aacaaaaatt 4140
taacgcgaat taattctgtg gaatgtgtgt cagttagggt gtggaaagtc cccaggctcc 4200
ccagcaggca gaagtatgca aagcatgcat ctcaattagt cagcaaccag gtgtggaaag 4260
tccccaggct ccccagcagg cagaagtatg caaagcatgc atctcaatta gtcagcaacc 4320
atagtcccgc ccctaactcc gcccatcccg cccctaactc cgcccagttc cgcccattct 4380
ccgccccatg gctgactaat tttttttatt tatgcagagg ccgaggccgc ctctgcctct 4440
gagctattcc agaagtagtg aggaggcttt tttggaggcc taggcttttg caaaaagctc 4500
ccgggagctt gtatatccat tttcggatct gatcaagaga caggatgagg atcgtttcgc 4560
atgattgaac aagatggatt gcacgcaggt tctccggccg cttgggtgga gaggctattc 4620
ggctatgact gggcacaaca gacaatcggc tgctctgatg ccgccgtgtt ccggctgtca 4680
gcgcaggggc gcccggttct ttttgtcaag accgacctgt ccggtgccct gaatgaactg 4740
caggacgagg cagcgcggct atcgtggctg gccacgacgg gcgttccttg cgcagctgtg 4800
ctcgacgttg tcactgaagc gggaagggac tggctgctat tgggcgaagt gccggggcag 4860
gatctcctgt catctcacct tgctcctgcc gagaaagtat ccatcatggc tgatgcaatg 4920
cggcggctgc atacgcttga tccggctacc tgcccattcg accaccaagc gaaacatcgc 4980
atcgagcgag cacgtactcg gatggaagcc ggtcttgtcg atcaggatga tctggacgaa 5040
gagcatcagg ggctcgcgcc agccgaactg ttcgccaggc tcaaggcgcg catgcccgac 5100
ggcgaggatc tcgtcgtgac ccatggcgat gcctgcttgc cgaatatcat ggtggaaaat 5160
ggccgctttt ctggattcat cgactgtggc cggctgggtg tggcggaccg ctatcaggac 5220
atagcgttgg ctacccgtga tattgctgaa gagcttggcg gcgaatgggc tgaccgcttc 5280
ctcgtgcttt acggtatcgc cgctcccgat tcgcagcgca tcgccttcta tcgccttctt 5340

```
gacgagttct tctgagcggg actctggggt tcgaaatgac cgaccaagcg acgcccaacc  5400
tgccatcacg agatttcgat tccaccgccg ccttctatga aaggttgggc ttcggaatcg  5460
ttttccggga cgccggctgg atgatcctcc agcgcgggga tctcatgctg gagttcttcg  5520
cccaccccaa cttgtttatt gcagcttata atggttacaa ataaagcaat agcatcacaa  5580
atttcacaaa taaagcattt ttttcactgc attctagttg tggtttgtcc aaactcatca  5640
atgtatctta tcatgtctgt ataccgtcga cctctagcta gagcttggcg taatcatggt  5700
catagctgtt tcctgtgtga aattgttatc cgctcacaat tccacacaac atacgagccg  5760
gaagcataaa gtgtaaagcc tggggtgcct aatgagtgag ctaactcaca ttaattgcgt  5820
tgcgctcact gcccgctttc cagtcgggaa acctgtcgtg ccagctgcat taatgaatcg  5880
gccaacgcgc ggggagaggc ggtttgcgta ttgggcgctc ttccgcttcc tcgctcactg  5940
actcgctgcg ctcggtcgtt cggctgcggc gagcggtatc agctcactca aaggcggtaa  6000
tacggttatc cacagaatca ggggataacg caggaaagaa catgtgagca aaaggccagc  6060
aaaaggccag gaaccgtaaa aaggccgcgt tgctggcgtt tttccatagg ctccgccccc  6120
ctgacgagca tcacaaaaat cgacgctcaa gtcagaggtg gcgaaacccg acaggactat  6180
aaagatacca ggcgtttccc cctggaagct ccctcgtgcg ctctcctgtt ccgaccctgc  6240
cgcttaccgg atacctgtcc gcctttctcc cttcgggaag cgtggcgctt tctcatagct  6300
cacgctgtag gtatctcagt tcggtgtagg tcgttcgctc caagctgggc tgtgtgcacg  6360
aaccccccgt tcagcccgac cgctgcgcct tatccggtaa ctatcgtctt gagtccaacc  6420
cggtaagaca cgacttatcg ccactggcag cagccactgg taacaggatt agcagagcga  6480
ggtatgtagg cggtgctaca gagttcttga agtggtggcc taactacggc tacactagaa  6540
gaacagtatt tggtatctgc gctctgctga agccagttac cttcggaaaa agagttggta  6600
gctcttgatc cggcaaacaa accaccgctg gtagcggtgg tttttttgtt tgcaagcagc  6660
agattacgcg cagaaaaaaa ggatctcaag aagatccttt gatcttttct acggggtctg  6720
acgctcagtg gaacgaaaac tcacgttaag ggattttggt catgagatta tcaaaaagga  6780
tcttcaccta gatcctttta aattaaaaat gaagttttaa atcaatctaa agtatatatg  6840
agtaaacttg gtctgacagt taccaatgct taatcagtga ggcacctatc tcagcgatct  6900
gtctatttcg ttcatccata gttgcctgac tccccgtcgt gtagataact acgatacggg  6960
agggcttacc atctggcccc agtgctgcaa tgataccgcg agacccacgc tcaccggctc  7020
cagatttatc agcaataaac cagccagccg gaagggccga gcgcagaagt ggtcctgcaa  7080
ctttatccgc ctccatccag tctattaatt gttgccggga agctagagta agtagttcgc  7140
cagttaatag tttgcgcaac gttgttgcca ttgctacagg catcgtggtg tcacgctcgt  7200
cgtttggtat ggcttcattc agctccggtt cccaacgatc aaggcgagtt acatgatccc  7260
ccatgttgtg caaaaaagcg gttagctcct tcggtcctcc gatcgttgtc agaagtaagt  7320
tggccgcagt gttatcactc atggttatgg cagcactgca taattctctt actgtcatgc  7380
catccgtaag atgcttttct gtgactggtg agtactcaac caagtcattc tgagaatagt  7440
gtatgcggcg accgagttgc tcttgcccgg cgtcaatacg ggataatacc gcgccacata  7500
gcagaacttt aaaagtgctc atcattggaa aacgttcttc ggggcgaaaa ctctcaagga  7560
tcttaccgct gttgagatcc agttcgatgt aacccactcg tgcacccaac tgatcttcag  7620
catcttttac tttcaccagc gtttctgggt gagcaaaaac aggaaggcaa aatgccgcaa  7680
aaaagggaat aagggcgaca cggaaatgtt gaatactcat actcttcctt tttcaatatt  7740
attgaagcat ttatcagggt tattgtctca tgagcggata catatttgaa tgtatttaga  7800
aaaataaaca aataggggtt ccgcgcacat ttccccgaaa agtgccacct gacgtc      7856

SEQ ID NO: 87          moltype = DNA  length = 8989
FEATURE                Location/Qualifiers
source                 1..8989
                       mol_type = other DNA
                       organism = synthetic construct
SEQUENCE: 87
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttataaat  240
gttttgtaga ataaaaaaaa aaaaagttct tcaaaagaaa tctcaaatct ccaaatggaa  300
acaggtaaaa gtggagctcc cctggttcca cggagaacct tttttgagga aacttaggca  360
actcgcaggt accttatgtc atgagacaga gtttgaaaac tacaattgac tatctctaaa  420
tttcctccca ggtctaaaat gtgatgatag ttactacttc agtacatcat ccttaaggaa  480
aattattagg tccacactgt ttctatcctt tgaattttac acataaattt tgtaatcaaa  540
agtttatttg taatatcaga tggaatcaga taattgcttt ttgtttttttc cactgacagg  600
aacataagat tttgttgtgt agcttaagtc aaacgcagtt tggaatatat attttttaaa  660
aattgtaact tacatatcca aatacaattt ttcaagaagt agagtattca gtagaaatta  720
atctgtgaaa gaagaggaat tcagcagtgg cctatttgat gaatgattta acgtgcttat  780
ttcttccctt tcatcaaaac tctgtgtccc cttgtttgcc ccctctgact tcatactctg  840
gagttgacca agatccctct tccatcggat tgttctggga attttgaaat aatctgcttt  900
ttcctctctt tcccctgttg cttctgatgc cttagaatta cattttcctc gctgatttag  960
tttagaaaag agaaaagagc ttccatgact agtagattat cacttttggg tttgctcttg  1020
gaagtgacaa gatgctagga tccctctttg gaatgtaaaa tttatctctt atatagaaag  1080
gatataaatg tagcaccaga gactataaaa ctctgatact atctactgta ctgtatagct  1140
gaacgccaca atgtgtctgg taatctattg actatcataa atgctatttc tacagaaaag  1200
ttaggaggtc catatttcgg gcaaccaatg tatagctgaa tgcagaacag tcatagttgg  1260
gtactaacca tatatatgat ttatccatca acaggtgcat atgctcagaa attctgtatc  1320
cataagaaat cagactactt tcttttcctt ttgcaagtaa attgaattta gcctgagagg  1380
ctgaggggaa attttcacat ataagccacg gttttgtgtt ttgtgttttg ttttgtttat  1440
agatatagta ctaactggat ggatgcgata aaattcatag gtggtactaa gatacaatag  1500
gatttgtgaa atggacaatt gtcttgcata aatagcaagt aaaaaatcaa gcctgtcctt  1560
cataaaaatt ttattctggg gtgtctctgg ctaactagag aacccactgc ttactggctt  1620
atcgaaatta atacgactca ctatagggag acccaagctg gctagcgcca ccatggagcg  1680
cgacggctgc gcgggggcg ggagccgcgg cggcgagggc gggcgcgctc cccgggaggg  1740
cccggcgggg aacggccgcg atcggggccg cagccacgct gccgaggcgc ccggggaccc  1800
```

-continued

```
gcaggccgcg gcgtccttgc tggcccctat ggacgtgggg gaggagccgc tggagaaggc  1860
ggcgcgcgcc cgcactgcca aggaccccaa cacctataaa gtactctcgc tggtattgtc  1920
agtatgtgtg ttaacaacaa tacttggttg tatatttggg ttgaaaccaa gctgtgccaa  1980
agaagttaaa agttgcaaag gtcgctgttt cgagagaaca tttgggaact gtcgctgtga  2040
tgctgcctgt gttgagcttg gaaactgctg tttagattac caggagacgt gcatagaacc  2100
agaacatata tggacttgca acaaattcag gtgtggtgag aaaaggttga ccagaagcct  2160
ctgtgcctgt tcagatgact gcaaggacaa gggcgactgc tgcatcaact acagttctgt  2220
gtgtcaaggt gagaaaagtt gggtagaaga accatgtgag agcattaatg agccacagtg  2280
cccagcaggg tttgaaacgc ctcctaccct cttattttct ttggatggat tcagggcaga  2340
atatttacac acttggggtg gacttcttcc tgttattagc aaactaaaaa aatgtggaac  2400
atatactaaa aacatgagac cggtatatcc aacaaaaact ttccccaatc actacagcat  2460
tgtcaccgga ttgtatccag aatctcatgg cataatcgac aataaaatgt atgatcccaa  2520
aatgaatgct tccttttcac ttaaaagtaa agagaaattt aatcctgagt ggtacaaagg  2580
agaaccaatt tgggtcacag ctaagtatca aggcctcaag tctggcacat ttttctggcc  2640
aggatcagat gtggaaatta acggaatttt cccagacatc tataaaatgt ataatggttc  2700
agtaccattt gaagaaagga ttttagctgt tcttcagtgg ctacagcttc ctaaagatga  2760
aagaccacac ttttacactc tgtatttaga agaaccagat tcttcaggtc attcatatgg  2820
accagtcagc agtgaagtca tcaaagcctt gcagagggtt gatggtatgg ttggtatgct  2880
gatggatggt ctgaaagagc tgaacttgca cagatgcctg aacctcatcc ttatttcaga  2940
tcatggcatg gaacaaggca gttgtaagaa atacatatat ctgaataaat atttgggga   3000
tgttaaaaat attaaagtta tctatggacc tgcagctcga ttgagaccct ctgatgtccc  3060
agataaatac tattcattta actatgaagg cattgcccga aatctttctt gccgggaacc  3120
aaaccagcac ttcaaacctt acctgaaaca tttcttacct aagcgtttgc actttgctaa  3180
gagtgataga attgagccct tgacattcta tttggaccct cagtggcaac ttgcattgaa  3240
tccctcagaa aggaaatatt gtggaagtgg atttcatggc tctgacaatg tattttcaaa  3300
tatgcaagcc ctctttgttg gctatggacc tggattcaag catggcattg aggctgacac  3360
ctttgaaaac attgaagtct ataacttaat gtgtgattta ctgaatttga caccggctcc  3420
taataacgga actcatggaa gtcttaacca ccttctaaag aatcctgttt atacgccaaa  3480
gcatcccaaa gaagtgcacc ccctggtaca gtgccccttc acaagaaacc ccagagataa  3540
ccttggctgc tcatgtaacc cttcgatttt gccgattgag gattttcaaa cacagttcaa  3600
tctgactgtg gcagaagaga agattattaa gcatgaaact ttaccctatg gaagacctag  3660
agttctccag aaggaaaaca ccatctgtct tctttcccag caccagttta tgagtggata  3720
cagccaagac atcttaatgc ccctttggac atcctatacc gtggacagaa atgacagttt  3780
ctctacggaa gacttctcca actgtctgta ccaggacttt agaattcctc ttagtcctgt  3840
ccataaatgt tcattttata aaaataacac caaagtgagt tacgggttcc tctccccacc  3900
acaactaaat aaaaattcaa gtggaatata ttctgaagct ttgcttacta caaatatagt  3960
gccaatgtac cagagttttc aagttatatg gcgctacttt catgacaccc tactgcgaaa  4020
gtatgctgaa gaaagaaatg gtgtcaatgt cgtcagtggt cctgtgtttg actttgatta  4080
tgatggacgt tgtgattcct tagagaatct gaggcaaaaa agaagagtca tccgtaacca  4140
agaaattttg attccaactc acttctttat tgtgctaaca agctgtaaag atacatctca  4200
gacgcctttg cactgtgaaa acctagacac cttagctttc attttgcctc acaggactga  4260
taacagcgag agctgtgtgc atgggaagca tgactcctca tgggttgaag aattgttaat  4320
gttacacaga gcacggatca cagatgttga gcacatcact ggactcagct tctatcaaca  4380
aagaaaagag ccagtttcag acattttaaa gttgaaaaca catttgccaa cctttagcca  4440
agaagacgac tacaaagacg atgacgacaa gtgaggtacc gagctcggat ccactagtcc  4500
agtgtggtgg aattctgcag atatccagca cagtggcggc cgctcgagtc tagagggccc  4560
gtttaaaccc gctgatcagc ctcgactgtg ccttctagtt gccagccatc tgttgtttgc  4620
ccctcccccg tgccttcctt gaccctggaa ggtgccactc ccactgtcct ttcctaataa  4680
aatgaggaaa ttgcatcgca ttgtctgagt aggtgtcatt ctattctggg gggtggggtg  4740
gggcaggaca gcaaggggga ggattgggaa gacaatagca ggcatgctgg ggatgcggtg  4800
ggctctatgg cttctgaggc ggaaagaacc agctggggct ctagggggta tccccacgcg  4860
ccctgtagcg gcgcattaag cgcggcgggt gtggtggtta cgcgcagcgt gaccgctaca  4920
cttgccagcg ccctagcgcc cgctcctttc gctttcttcc cttcctttct cgccacgttc  4980
gccggctttc cccgtcaagc tctaaatcgg gggctccctt tagggttccg atttagtgct  5040
ttacggcacc tcgaccccaa aaaacttgat tagggtgatg gttcacgtag tgggccatcg  5100
ccctgataga cggtttttcg ccctttgacg ttggagtcca cgttctttaa tagtggactc  5160
ttgttccaaa ctggaacaac actcaaccct atctcggtct attcttttga tttataaggg  5220
attttgccga tttcggccta ttggttaaaa aatgagctga tttaacaaaa atttaacgcg  5280
aattaattct gtggaatgtg tgtcagttag ggtgtggaaa gtccccaggc tccccagcag  5340
gcagaagtat gcaaagcatg catctcaatt agtcagcaac caggtgtgga aagtccccag  5400
gctccccagc aggcagaagt atgcaaagca tgcatctcaa ttagtcagca accatagtcc  5460
cgcccctaac tccgcccatc ccgcccctaa ctccgcccag ttccgcccat tctccgcccc  5520
atggctgact aatttttttt atttatgcag aggccgaggc cgcctctgcc tctgagctat  5580
tccagaagta gtgaggaggc ttttttggag gcctaggctt ttgcaaaaag ctcccgggag  5640
cttgtatatc cattttcgga tctgatcaag agacaggatg aggatcgttt cgcatgattg  5700
aacaagatgg attgcacgca ggttctccgg ccgcttgggt ggagaggcta ttcggctatg  5760
actgggcaca acagacaatc ggctgctctg atgccgccgt gttccggctg tcagcgcagg  5820
ggcgcccggt tctttttgtc aagaccgacc tgtccggtgc cctgaatgaa ctgcaggacg  5880
aggcagcgcg gctatcgtgg ctggccacga cgggcgttcc ttgcgcagct gtgctcgacg  5940
ttgtcactga agcgggaagg gactggctgc tattgggcga agtgccgggg caggatctcc  6000
tgtcatctca ccttgctcct gccgagaaag tatccatcat ggctgatgca atgcggcggc  6060
tgcatacgct tgatccggct acctgcccat tcgaccacca agcgaaacat cgcatcgagc  6120
gagcacgtac tcggatggaa gccggtcttg tcgatcagga tgatctggac gaagagcatc  6180
aggggctcgc gccagccgaa ctgttcgcca ggctcaaggc gcgcatgccc gacggcgagg  6240
atctcgtcgt gacccatggc gatgcctgct tgccgaatat catggtggaa aatggccgct  6300
tttctggatt catcgactgt ggccggctgg gtgtggcgga ccgctatcag gacatagcgt  6360
tggctacccg tgatattgct gaagagcttg gcggcgaatg ggctgaccgc ttcctcgtgc  6420
tttacggtat cgccgctccc gattcgcagc gcatcgcctt ctatcgcctt cttgacgagt  6480
tcttctgagc gggactctgg ggttcgaaat gaccgaccaa gcgacgccca acctgccatc  6540
```

```
acgagatttc gattccaccg ccgccttcta tgaaaggttg ggcttcggaa tcgttttccg  6600
ggacgccggc tggatgatcc tccagcgcgg ggatctcatg ctggagttct tcgcccaccc  6660
caacttgttt attgcagctt ataatggtta caaataaagc aatagcatca caaatttcac  6720
aaataaagca tttttttcac tgcattctag ttgtggtttg tccaaactca tcaatgtatc  6780
ttatcatgtc tgtataccgt cgacctctag ctagagcttg gcgtaatcat ggtcatagct  6840
gtttcctgtg tgaaattgtt atccgctcac aattccacac aacatacgag ccggaagcat  6900
aaagtgtaaa gcctggggtg cctaatgagt gagctaactc acattaattg cgttgcgctc  6960
actgcccgct ttccagtcgg gaaacctgtc gtgccagctg cattaatgaa tcggccaacg  7020
cgcggggaga ggcggtttgc gtattgggcg ctcttccgct tcctcgctca ctgactcgct  7080
gcgctcggtc gttcggctgc ggcgagcggt atcagctcac tcaaaggcgg taatacggtt  7140
atccacagaa tcaggggata acgcaggaaa gaacatgtga gcaaaaggcc agcaaaaggc  7200
caggaaccgt aaaaaggccg cgttgctggc gtttttccat aggctccgcc cccctgacga  7260
gcatcacaaa aatcgacgct caagtcagag gtggcgaaac ccgacaggac tataaagata  7320
ccaggcgttt ccccctggaa gctccctcgt gcgctctcct gttccgaccc tgccgcttac  7380
cggatacctg tccgcctttc tcccttcggg aagcgtggcg ctttctcata gctcacgctg  7440
taggtatctc agttcggtgt aggtcgttcg ctccaagctg ggctgtgtgc acgaaccccc  7500
cgttcagccc gaccgctgcg ccttatccgg taactatcgt cttgagtcca acccggtaag  7560
acacgactta tcgccactgg cagcagccac tggtaacagg attagcagag cgaggtatgt  7620
aggcggtgct acagagttct tgaagtggtg gcctaactac ggctacacta gaagaacagt  7680
atttggtatc tgcgctctgc tgaagccagt taccttcgga aaaagagttg gtagctcttg  7740
atccggcaaa caaaccaccg ctggtagcgg tggttttttt gtttgcaagc agcagattac  7800
gcgcagaaaa aaaggatctc aagaagatcc tttgatcttt tctacggggt ctgacgctca  7860
gtggaacgaa aactcacgtt aagggatttt ggtcatgaga ttatcaaaaa ggatcttcac  7920
ctagatcctt ttaaattaaa aatgaagttt taaatcaatc taaagtatat atgagtaaac  7980
ttggtctgac agttaccaat gcttaatcag tgaggcacct atctcagcga tctgtctatt  8040
tcgttcatcc atagttgcct gactccccgt cgtgtagata actacgatac gggagggctt  8100
accatctggc cccagtgctg caatgatacc gcgagaccca cgctcaccgg ctccagattt  8160
atcagcaata aaccagccag ccggaagggc cgagcgcaga agtggtcctg caactttatc  8220
cgcctccatc cagtctatta attgttgccg ggaagctaga gtaagtagtt cgccagttaa  8280
tagtttgcgc aacgttgttg ccattgctac aggcatcgtg gtgtcacgct cgtcgtttgg  8340
tatggcttca ttcagctccg gttcccaacg atcaaggcga gttacatgat cccccatgtt  8400
gtgcaaaaaa gcggttagct ccttcggtcc tccgatcgtt gtcagaagta agttggccgc  8460
agtgttatca ctcatggtta tggcagcact gcataattct cttactgtca tgccatccgt  8520
aagatgcttt tctgtgactg gtgagtactc aaccaagtca ttctgagaat agtgtatgcg  8580
gcgaccgagt tgctcttgcc cggcgtcaat acgggataat accgcgccac atagcagaac  8640
tttaaaagtg ctcatcattg gaaaacgttc ttcggggcga aaactctcaa ggatcttacc  8700
gctgttgaga tccagttcga tgtaacccac tcgtgcaccc aactgatctt cagcatcttt  8760
tactttcacc agcgtttctg ggtgagcaaa aacaggaagg caaaatgccg caaaaaaggg  8820
aataagggcg acacggaaat gttgaatact catactcttc ctttttcaat attattgaag  8880
catttatcag ggttattgtc tcatgagcgg atacatattt gaatgtattt agaaaaataa  8940
acaaataggg gttccgcgca catttccccg aaaagtgcca cctgacgtc             8989

SEQ ID NO: 88          moltype = DNA  length = 9409
FEATURE                Location/Qualifiers
source                 1..9409
                       mol_type = other DNA
                       organism = synthetic construct
SEQUENCE: 88
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttagttcc  240
agatggtaaa tatacacaag ggatttagtc aaacaatttt ttggcaagaa tattatgaat  300
tttgtaatcg gttggcagcc aatgaaatac aaagatgagt ctagttaata atctacaatt  360
attggttaaa gaagtatatt agtgctaatt tccctccgtt tgtcctagct tttctcttct  420
gtcaacccca cacgcctttg gcacctctgg ctaactagag aacccactgc ttactggctt  480
atcgaaatta atacgactca ctatagggag acccaagctg gctagcgcca ccatgaagtg  540
ggtaaccttt atttcccttc tttttctctt tagctcggct tattccaggg gtgtgtttcg  600
tcgagactac aaagacgatg acgacaagag cgctggcctg aagccaagct gcgccaagga  660
ggtgaagagc tgcaagggca gatgtttcga acggaccttc ggcaactgca gatgcgacgc  720
cgcctgcgtg gaactgggaa actgttgtct ggactaccag gagacatgta tcgagcctga  780
gcacatctgg acatgcaaca agttcagatg tggcgagaaa agactgactc ggagtctgtg  840
cgcctgttct gacgactgca aggacaaggg cgattgctgc atcaactaca gcagcgtgtg  900
ccagggcgaa aagagctggg tcgaggaacc ctgcgagagc atcaacgagc cccagtgccc  960
tgccggattt gagacacctc ctaccctgct cttctccctg gatggcttca gagctgagta  1020
cctgcataca tggggaggac tgctgcctgt gatcagcaag ctgaagaagt gcggcaccta  1080
cacaaagaac atgcggcctg tctaccctac caagaccttc cccaaccact acagcatcgt  1140
gaccggcctg taccccgaga gccacggcat catcgacaac aagatgtacg accccaaaat  1200
gaacgccagc ttcagcctga aatctaagga aaagttcaac cctgagtggt ataagggcga  1260
gccaatctgg gtgacagcca agtaccaggg cctgaagagc ggcaccttct tctggcctgg  1320
cagcgacgtg gagatcaacg gaatcttccc tgatatctac aagatgtata acggctccgt  1380
gcctttcgag gagcggatct tggctgttct tcagtggctg cagctgccca aggacgagag  1440
accccacttc tacaccctgt acctggaaga acctgacagc agcggccaca gctacggccc  1500
tgtgtctagc gaggtgatca aggccctgca aagagtggat ggcatggtgg gcatgctgat  1560
ggatggactg aaggaactga acctccatcg ttgcctgaac ctgatcctga tctccgacca  1620
cggcatggaa cagggcagct gtaaaaagta catctacctg aacaagtacc tgggcgacgt  1680
gaagaatatc aaggtgatct acgggccggc cgccaggctg cggcctagcg acgtgcccga  1740
caagtattac agcttcaact acgagggcat cgccagaaac ctgtcttgca gagaacccaa  1800
tcaacacttc aagccttacc tgaagcactt tctgcctaag agactgcact tcgccaaaag  1860
```

-continued

```
cgacagaatt gaacccctga cattctatct ggaccctcag tggcagctgg ccctcaatcc  1920
ttctgaacgc aaatactgcg gtagcggatt tcacggctct gataacgtgt tttctaacat  1980
gcaggccctg tttgtgggct acggccctgg cttcaagcac ggaatcgagg ctgacacctt  2040
cgagaacatc gaagtttaca atctgatgtg cgacctgctg aatctgaccc cagcccctaa  2100
caacggcaca cacggctctc tgaatcacct gctcaagaac cccgtgtata cccccaaaca  2160
ccctaaagag gtccatccac tggtgcagtg cccattcacc agaaaccctc gggacaacct  2220
tggctgcagc tgcaacccta gcatcctccc tatcgaagat ttccagaccc agtttaacct  2280
gactgtcgcc gaagagaaga tcatcaagca cgaaaccctg ccctacggga ggcccagagt  2340
gctgcagaaa gaaaacacaa tctgtctgct gagccagcac cagtttatga gcggctacag  2400
tcaggacatc ctgatgcctc tgtggaccag ctacaccgtg gaccggaatg acagcttcag  2460
caccgaggac ttcagcaact gcctgtatca ggacttccgc atccctctgt cccctgtgca  2520
taagtgcagc ttttacaaga acaacaccaa ggtgagctac gggtttctga gcccaccaca  2580
actgaacaaa aatagctctg gcatctactc tgaggcgctg ctgaccacca acatcgtgcc  2640
aatgtaccag agcttccagg tgatctggcg gtacttccat gataccctgc ttcggaagta  2700
cgccgaagaa cggaacggcg tgaacgtggt gtccggccca gtgttcgact tcgactacga  2760
cggcagatgt gattcccttg agaatctgag acagaagcgg cgggttatca gaaaccagga  2820
gatcctgatt cctacccact tcttcatcgt gctgacatct tgcaaggata ccagccaaac  2880
acctctgcac tgcgagaacc tggacaccct ggccttcatc ctgcctcacc ggaccgataa  2940
tagcgaatcc tgtgtgcacg gcaaacacga ctctagctgg gtggaagagc tgctgatgct  3000
gcacagagcc cggatcacag atgtggaaca catcaccggc ctgtccttct accaacagag  3060
aaaggaaccc gtgtctgata tcctgaagct gaaaacccac ctgcctacct tcagccagga  3120
ggacctgatc gttaacgatg cacacaagag tgaggttgct catcggttta aagatttggg  3180
agaagaaaat ttcaaagcct tggtgttgat tgcctttgct cagtatcttc agcagtgtcc  3240
atttgaagat catgtaaaat tagtgaatga agtaactgaa tttgcaaaaa catgtgttgc  3300
tgatgagtca gctgaaaatt gtgacaaatc acttcatacc ctttttggag acaaattatg  3360
cacagttgca actcttcgtg aaacctatgg tgaaatggct gactgctgtg caaaacaaga  3420
acctgagaga aatgaatgct tcttgcaaca caaagatgac aacccaaacc tcccccgatt  3480
ggtgagacca gaggttgatg tgatgtgcac tgcttttcat gacaatgaag agacattttt  3540
gaaaaaatac ttatatgaaa ttgccagaag acatccttac ttttatgccc cggaactcct  3600
tttctttgct aaaaggtata aagctgcttt tacagaatgt tgccaagctg ctgataaagc  3660
tgcctgcctg ttgccaaagc tcgatgaact tcgggatgaa gggaaggctt cgtctgccaa  3720
acagagactc aagtgtgcca gtctccaaaa atttggagaa agagctttca aagcatgggc  3780
agtagctcgc ctgagccaga gatttcccaa agctgagttt gcagaagttt ccaagttagt  3840
gacagatctt accaaagtcc acacggaatg ctgccatgga gatctgcttg aatgtgctga  3900
tgacagggcg gaccttgcca agtatatctg tgaaaatcaa gattcgatct ccagtaaact  3960
gaaggaatgc tgtgaaaaac ctctgttgga aaaatcccac tgcattgccg aagtggaaaa  4020
tgatgagatg cctgctgact tgccttcatt agctgctgat tttgttgaaa gtaaggatgt  4080
ttgcaaaaac tatgctgagg caaaggatgt cttcctgggc atgtttttgt atgaatatgc  4140
aagaaggcat cctgattact ctgtcgtgct gctgctgaga cttgccaaga catatgaaac  4200
cacactcgag aagtgctgtg ccgctgcaga tcctcatgaa tgctatgcca aagtgttcga  4260
tgaatttaaa cctcttgtgg aagagcctca gaatttaatc aaacaaaatt gtgagctttt  4320
tgagcagctt ggagagtaca aattccagaa tgcgctatta gttcgttaca ccaagaaagt  4380
accccaagtg tcaactccaa ctcttgtaga ggtctcaaga aacctaggaa aagtgggcag  4440
caaatgttgt aaacatcctg aagcaaaaag aatgccctgt gcagaagact atctatccgt  4500
ggtcctgaac cagttatgtg tgttgcatga gaaaacgcca gtaagtgaca gagtcaccaa  4560
atgctgcaca gaatccttgg tgaacaggcg accatgcttt tcagctctgg aagtcgatga  4620
aacatacgtt cccaaagagt ttaatgctga aacattcacc ttccatgcag atatatgcac  4680
actttctgag aaggagagac aaatcaagaa acaaactgca cttgttgagc tcgtgaaaca  4740
caagcccaag gcaacaaaag agcaactgaa agctgttatg gatgatttcg cagcttttgt  4800
agagaagtgc tgcaaggctg acgataagga gacctgcttt gccgaggagg gtaaaaaact  4860
tgttgctgca agtcaagctg ccttaggctt atgaggtacc gagctcggat ccactagtcc  4920
agtgtggtgg aattctgcag atatccagca cagtggcggc cgctcgagtc tagagggccc  4980
gtttaaaccc gctgatcagc ctcgactgtg ccttctagtt gccagccatc tgttgtttgc  5040
ccctcccccg tgccttcctt gaccctggaa ggtgccactc ccactgtcct ttcctaataa  5100
aatgaggaaa ttgcatcgca ttgtctgagt aggtgtcatt ctattctggg gggtggggtg  5160
gggcaggaca gcaaggggga ggattgggaa gacaatagca ggcatgctgg ggatgcggtg  5220
ggctctatgg cttctgaggc ggaaagaacc agctggggct ctagggggta tccccacgcg  5280
ccctgtagcg gcgcattaag cgcggcgggt gtggtggtta cgcgcagcgt gaccgctaca  5340
cttgccagcg ccctagcgcc cgctcctttc gctttcttcc cttcctttct cgccacgttc  5400
gccggctttc cccgtcaagc tctaaatcgg gggctccctt tagggttccg atttagtgct  5460
ttacggcacc tcgaccccaa aaaacttgat tagggtgatg gttcacgtag tgggccatcg  5520
ccctgataga cggtttttcg ccctttgacg ttggagtcca cgttctttaa tagtggactc  5580
ttgttccaaa ctggaacaac actcaaccct atctcggtct attcttttga tttataaggg  5640
attttgccga tttcggccta ttggttaaaa aatgagctga tttaacaaaa atttaacgcg  5700
aattaattct gtggaatgtg tgtcagttag ggtgtggaaa gtccccaggc tccccagcag  5760
gcagaagtat gcaaagcatg catctcaatt agtcagcaac caggtgtgga aagtccccag  5820
gctccccagc aggcagaagt atgcaaagca tgcatctcaa ttagtcagca accatagtcc  5880
cgcccctaac tccgcccatc ccgcccctaa ctccgcccag ttccgcccat tctccgcccc  5940
atggctgact aatttttttt atttatgcag aggccgaggc cgcctctgcc tctgagctat  6000
tccagaagta gtgaggaggc ttttttggag gcctaggctt ttgcaaaaag ctcccgggag  6060
cttgtatatc cattttcgga tctgatcaag agacaggatg aggatcgttt cgcatgattg  6120
aacaagatgg attgcacgca ggttctccgg ccgcttgggt ggagaggcta ttcggctatg  6180
actgggcaca acagacaatc ggctgctctg atgccgccgt gttccggctg tcagcgcagg  6240
ggcgcccggt tctttttgtc aagaccgacc tgtccggtgc cctgaatgaa ctgcaggacg  6300
aggcagcgcg gctatcgtgg ctggccacga cgggcgttcc ttgcgcagct gtgctcgacg  6360
ttgtcactga agcgggaagg gactggctgc tattgggcga agtgccgggg caggatctcc  6420
tgtcatctca ccttgctcct gccgagaaag tatccatcat ggctgatgca atgcggcggc  6480
tgcatacgct tgatccggct acctgcccat tcgaccacca agcgaaacat cgcatcgagc  6540
gagcacgtac tcggatggaa gccggtcttg tcgatcagga tgatctggac gaagagcatc  6600
```

```
aggggctcgc gccagccgaa ctgttcgcca ggctcaaggc gcgcatgccc gacggcgagg  6660
atctcgtcgt gacccatggc gatgcctgct tgccgaatat catggtggaa aatggccgct  6720
tttctggatt catcgactgt ggccggctgg gtgtggcgga ccgctatcag gacatagcgt  6780
tggctacccg tgatattgct gaagagcttg gcggcgaatg ggctgaccgc ttcctcgtgc  6840
tttacggtat cgccgctccc gattcgcagc gcatcgcctt ctatcgcctt cttgacgagt  6900
tcttctgagc gggactctgg ggttcgaaat gaccgaccaa gcgacgccca acctgccatc  6960
acgagatttc gattccaccg ccgccttcta tgaaaggttg ggcttcggaa tcgttttccg  7020
ggacgccggc tggatgatcc tccagcgcgg ggatctcatg ctggagttct tcgcccaccc  7080
caacttgttt attgcagctt ataatggtta caaataaagc aatagcatca caaatttcac  7140
aaataaagca tttttttcac tgcattctag ttgtggtttg tccaaactca tcaatgtatc  7200
ttatcatgtc tgtataccgt cgacctctag ctagagcttg gcgtaatcat ggtcatagct  7260
gtttcctgtg tgaaattgtt atccgctcac aattccacac aacatacgag ccggaagcat  7320
aaagtgtaaa gcctggggtg cctaatgagt gagctaactc acattaattg cgttgcgctc  7380
actgcccgct ttccagtcgg gaaacctgtc gtgccagctg cattaatgaa tcggccaacg  7440
cgcggggaga ggcggtttgc gtattgggcg ctcttccgct tcctcgctca ctgactcgct  7500
gcgctcggtc gttcggctgc ggcgagcggt atcagctcac tcaaaggcgg taatacggtt  7560
atccacagaa tcaggggata acgcaggaaa gaacatgtga gcaaaaggcc agcaaaaggc  7620
caggaaccgt aaaaaggccg cgttgctggc gtttttccat aggctccgcc cccctgacga  7680
gcatcacaaa aatcgacgct caagtcagag gtggcgaaac ccgacaggac tataaagata  7740
ccaggcgttt ccccctggaa gctccctcgt gcgctctcct gttccgaccc tgccgcttac  7800
cggatacctg tccgcctttc tcccttcggg aagcgtggcg ctttctcata gctcacgctg  7860
taggtatctc agttcggtgt aggtcgttcg ctccaagctg ggctgtgtgc acgaaccccc  7920
cgttcagccc gaccgctgcg ccttatccgg taactatcgt cttgagtcca acccggtaag  7980
acacgactta tcgccactgg cagcagccac tggtaacagg attagcagag cgaggtatgt  8040
aggcggtgct acagagttct tgaagtggtg gcctaactac ggctacacta gaagaacagt  8100
atttggtatc tgcgctctgc tgaagccagt taccttcgga aaaagagttg gtagctcttg  8160
atccggcaaa caaaccaccg ctggtagcgg tggttttttt gtttgcaagc agcagattac  8220
gcgcagaaaa aaaggatctc aagaagatcc tttgatcttt tctacggggt ctgacgctca  8280
gtggaacgaa aactcacgtt aagggatttt ggtcatgaga ttatcaaaaa ggatcttcac  8340
ctagatcctt ttaaattaaa aatgaagttt taaatcaatc taaagtatat atgagtaaac  8400
ttggtctgac agttaccaat gcttaatcag tgaggcacct atctcagcga tctgtctatt  8460
tcgttcatcc atagttgcct gactccccgt cgtgtagata actacgatac gggagggctt  8520
accatctggc cccagtgctg caatgatacc gcgagaccca cgctcaccgg ctccagattt  8580
atcagcaata aaccagccag ccggaagggc cgagcgcaga agtggtcctg caactttatc  8640
cgcctccatc cagtctatta attgttgccg ggaagctaga gtaagtagtt cgccagttaa  8700
tagtttgcgc aacgttgttg ccattgctac aggcatcgtg gtgtcacgct cgtcgtttgg  8760
tatggcttca ttcagctccg gttcccaacg atcaaggcga gttacatgat cccccatgtt  8820
gtgcaaaaaa gcggttagct ccttcggtcc tccgatcgtt gtcagaagta agttggccgc  8880
agtgttatca ctcatggtta tggcagcact gcataattct cttactgtca tgccatccgt  8940
aagatgcttt tctgtgactg gtgagtactc aaccaagtca ttctgagaat agtgtatgcg  9000
gcgaccgagt tgctcttgcc cggcgtcaat acgggataat accgcgccac atagcagaac  9060
tttaaaagtg ctcatcattg gaaaacgttc ttcggggcga aaactctcaa ggatcttacc  9120
gctgttgaga tccagttcga tgtaacccac tcgtgcaccc aactgatctt cagcatcttt  9180
tactttcacc agcgtttctg ggtgagcaaa aacaggaagg caaaatgccg caaaaaaggg  9240
aataagggcg acacggaaat gttgaatact catactcttc ctttttcaat attattgaag  9300
catttatcag ggttattgtc tcatgagcgg atacatattt gaatgtattt agaaaaataa  9360
acaaataggg gttccgcgca catttccccg aaaagtgcca cctgacgtc             9409
```

```
SEQ ID NO: 89           moltype = DNA  length = 9843
FEATURE                 Location/Qualifiers
source                  1..9843
                        mol_type = other DNA
                        organism = synthetic construct
SEQUENCE: 89
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gccaccatga agtgggtaac ctttatttcc cttctttttc tctttagctc ggcttattcc  960
aggggtgtgt ttcgtcgaga ctacaaagac gatgacgaca agagcgctgg cctgaagcca  1020
agctgcgcca aggaggtgaa gagctgcaag ggcagatgtt tcgaacggac cttcggcaac  1080
tgcagatgcg acgccgcctg cgtggaactg ggaaactgtt gtctggacta ccaggagaca  1140
tgtatcgagc ctgagcacat ctggacatgc aacaagttca gatgtggcga gaaaagactg  1200
actcggagtc tgtgcgcctg ttctgacgac tgcaaggaca agggcgattg ctgcatcaac  1260
tacagcagcg tgtgccaggg cgaaaagagc tgggtcgagg aaccctgcga gagcatcaac  1320
gagccccagt gccctgccgg atttgagaca cctcctaccc tgctcttctc cctggatggc  1380
ttcagagctg agtacctgca tacatgggga ggactgctgc ctgtgatcag caagctgaag  1440
aagtgcggca cctacacaaa gaacatgcgg cctgtctacc ctaccaagac cttccccaac  1500
```

-continued

```
cactacagca tcgtgaccgg cctgtacccc gagagccacg gcatcatcga caacaagatg  1560
tacgacccca aaatgaacgc cagcttcagc ctgaaatcta aggaaaagtt caaccctgag  1620
tggtataagg gcgagccaat ctgggtgaca gccaagtacc agggcctgaa gagcggcacc  1680
ttcttctggc ctggcagcga cgtggagatc aacggaatct tccctgatat ctacaagatg  1740
tataacggct ccgtgccttt cgaggagcgg atcttggctg ttcttcagtg gctgcagctg  1800
cccaaggacg agagacccca cttctacacc ctgtacctgg aagaacctga cagcagcggc  1860
cacagctacg gccctgtgtc tagcgaggtg atcaaggccc tgcaaagagt ggatggcatg  1920
gtgggcatgc tgatggatgg actgaaggaa ctgaacctcc atcgttgcct gaacctgatc  1980
ctgatctccg accacggcat ggaacagggc agctgtaaaa agtacatcta cctgaacaag  2040
tacctgggcg acgtgaagaa tatcaaggtg atctacgggc cggccgccag gctgcggcct  2100
agcgacgtgc ccgacaagta ttacagcttc aactacgagg gcatcgccag aaacctgtct  2160
tgcagagaac ccaatcaaca cttcaagcct tacctgaagc actttctgcc taagagactg  2220
cacttcgcca aaagcgacag aattgaaccc ctgacattct atctggaccc tcagtggcag  2280
ctggccctca atccttctga acgcaaatac tgcggtagcg gatttcacgg ctctgataac  2340
gtgttttcta acatgcaggc cctgtttgtg ggctacggcc ctggcttcaa gcacggaatc  2400
gaggctgaca ccttcgagaa catcgaagtt tacaatctga tgtgcgacct gctgaatctg  2460
accccagccc ctaacaacgg cacacacggc tctctgaatc acctgctcaa gaaccccgtg  2520
tatacccccca aacaccctaa agaggtccat ccactggtgc agtgcccatt caccagaaac  2580
cctcgggaca accttggctg cagctgcaac cctagcatcc tccctatcga agatttccag  2640
acccagttta acctgactgt cgccgaagag aagatcatca agcacgaaac cctgccctac  2700
gggaggccca gagtgctgca gaaagaaaac acaatctgtc tgctgagcca gcaccagttt  2760
atgagcggct acagtcagga catcctgatg cctctgtgga ccagctacac cgtggaccgg  2820
aatgacagct tcagcaccga ggacttcagc aactgcctgt atcaggactt ccgcatccct  2880
ctgtcccctg tgcataagtg cagcttttac aagaacaaca ccaaggtgag ctacgggttt  2940
ctgagcccac cacaactgaa caaaaatagc tctggcatct actctgaggc gctgctgacc  3000
accaacatcg tgccaatgta ccagagcttc caggtgatct ggcggtactt ccatgatacc  3060
ctgcttcgga agtacgccga agaacggaac ggcgtgaacg tggtgtccgg cccagtgttc  3120
gacttcgact acgacggcag atgtgattcc cttgagaatc tgagacagaa gcggcgggtt  3180
atcagaaacc aggagatcct gattcctacc cacttcttca tcgtgctgac atcttgcaag  3240
gataccagcc aaacacctct gcactgcgag aacctggaca ccctggcctt catcctgcct  3300
caccggaccg ataatagcga atcctgtgtg cacggcaaac acgactctag ctgggtggaa  3360
gagctgctga tgctgcacag agcccggatc acagatgtgg aacacatcac cggcctgtcc  3420
ttctaccaac agagaaagga acccgtgtct gatatcctga agctgaaaac ccacctgcct  3480
accttcagcc aggaggacct gatcgttaac gatgcacaca agagtgaggt tgctcatcgg  3540
tttaaagatt tgggagaaga aaatttcaaa gccttggtgt tgattgcctt tgctcagtat  3600
cttcagcagt gtccatttga agatcatgta aaattagtga atgaagtaac tgaatttgca  3660
aaaacatgtg ttgctgatga gtcagctgaa aattgtgaca aatcacttca taccctttttt  3720
ggagacaaat tatgcacagt tgcaactctt cgtgaaacct atggtgaaat ggctgactgc  3780
tgtgcaaaac aagaacctga gagaaatgaa tgcttcttgc aacacaaaga tgacaaccca  3840
aacctccccc gattggtgag accagaggtt gatgtgatgt gcactgcttt tcatgacaat  3900
gaagagacat ttttgaaaaa atacttatat gaaattgcca gaagacatcc ttacttttat  3960
gccccggaac tccttttctt tgctaaaagg tataaagctg cttttacaga atgttgccaa  4020
gctgctgata aagctgcctg cctgttgcca aagctcgatg aacttcggga tgaagggaag  4080
gcttcgtctg ccaaacagag actcaagtgt gccagtctcc aaaaatttgg agaaagagct  4140
ttcaaagcat gggcagtagc tcgcctgagc cagagatttc ccaaagctga gtttgcagaa  4200
gtttccaagt tagtgacaga tcttaccaaa gtccacacgg aatgctgcca tggagatctg  4260
cttgaatgtg ctgatgacag ggcggacctt gccaagtata tctgtgaaaa tcaagattcg  4320
atctccagta aactgaagga atgctgtgaa aaacctctgt tggaaaaatc ccactgcatt  4380
gccgaagtgg aaaatgatga gatgcctgct gacttgcctt cattagctgc tgattttgtt  4440
gaaagtaagg atgtttgcaa aaactatgct gaggcaaagg atgtcttcct gggcatgttt  4500
ttgtatgaat atgcaagaag gcatcctgat tactctgtcg tgctgctgct gagacttgcc  4560
aagacatatg aaaccacact cgagaagtgc tgtgccgctg cagatcctca tgaatgctat  4620
gccaaagtgt tcgatgaatt taaacctctt gtggaagagc ctcagaattt aatcaaacaa  4680
aattgtgagc tttttgagca gcttggagag tacaaattcc agaatgcgct attagttcgt  4740
tacaccaaga aagtacccca agtgtcaact ccaactcttg tagaggtctc aagaaaccta  4800
ggaaaagtgg gcagcaaatg ttgtaaacat cctgaagcaa aaagaatgcc ctgtgcagaa  4860
gactatctat ccgtggtcct gaaccagtta tgtgtgttgc atgagaaaac gccagtaagt  4920
gacagagtca ccaaatgctg cacagaatcc ttggtgaaca ggcgaccatg cttttcagct  4980
ctggaagtcg atgaaacata cgttcccaaa gagtttaatg ctgaaacatt caccttccat  5040
gcagatatat gcacactttc tgagaaggag agacaaatca agaaacaaac tgcacttgtt  5100
gagctcgtga aacacaagcc caaggcaaca aaagagcaac tgaaagctgt tatggatgat  5160
ttcgcagctt ttgtagagaa gtgctgcaag gctgacgata aggagacctg ctttgccgag  5220
gagggtaaaa aacttgttgc tgcaagtcaa gctgccttag gcttatgaca attacgatta  5280
gcactatcca attacgatta gcactatcca attacgatta gcactatcgg taccgagctc  5340
ggatccacta gtccagtgtg gtggaattct gcagatatcc agcacagtgg cggccgctcg  5400
agtctagagg gcccgtttaa acccgctgat cagcctcgac tgtgccttct agttgccagc  5460
catctgttgt ttgcccctcc cccgtgcctt ccttgaccct ggaaggtgcc actcccactg  5520
tcctttccta ataaaatgag gaaattgcat cgcattgtct gagtaggtgt cattctattc  5580
tggggggtgg ggtggggcag gacagcaagg gggaggattg ggaagacaat agcaggcatg  5640
ctggggatgc ggtgggctct atggcttctg aggcggaaag aaccagctgg ggctctaggg  5700
ggtatcccca cgcgccctgt agcggcgcat taagcgcggc gggtgtggtg gttacgcgca  5760
gcgtgaccgc tacacttgcc agcgccctag cgcccgctcc tttcgctttc ttcccttcct  5820
ttctcgccac gttcgccggc tttccccgtc aagctctaaa tcgggggctc cctttagggt  5880
tccgatttag tgctttacgg cacctcgacc ccaaaaaact tgattagggt gatggttcac  5940
gtagtgggcc atcgccctga tagacggttt ttcgcccttt gacgttggag tccacgttct  6000
ttaatagtgg actcttgttc caaactggaa caacactcaa ccctatctcg gtctattctt  6060
ttgatttata agggattttg ccgatttcgg cctattggtt aaaaaatgag ctgatttaac  6120
aaaaatttaa cgcgaattaa ttctgtggaa tgtgtgtcag ttagggtgtg gaaagtcccc  6180
aggctcccca gcaggcagaa gtatgcaaag catgcatctc aattagtcag caaccaggtg  6240
```

```
tggaaagtcc ccaggctccc cagcaggcag aagtatgcaa agcatgcatc tcaattagtc  6300
agcaaccata gtcccgcccc taactccgcc catcccgccc ctaactccgc ccagttccgc  6360
ccattctccg ccccatggct gactaatttt ttttatttat gcagaggccg aggccgcctc  6420
tgcctctgag ctattccaga agtagtgagg aggctttttt ggaggcctag gcttttgcaa  6480
aaagctcccg ggagcttgta tatccatttt cggatctgat caagagacag gatgaggatc  6540
gtttcgcatg attgaacaag atggattgca cgcaggttct ccggccgctt gggtggagag  6600
gctattcggc tatgactggg cacaacagac aatcggctgc tctgatgccg ccgtgttccg  6660
gctgtcagcg caggggcgcc cggttctttt tgtcaagacc gacctgtccg gtgccctgaa  6720
tgaactgcag gacgaggcag cgcggctatc gtggctggcc acgacgggcg ttccttgcgc  6780
agctgtgctc gacgttgtca ctgaagcggg aagggactgg ctgctattgg gcgaagtgcc  6840
ggggcaggat ctcctgtcat ctcaccttgc tcctgccgag aaagtatcca tcatggctga  6900
tgcaatgcgg cggctgcata cgcttgatcc ggctacctgc ccattcgacc accaagcgaa  6960
acatcgcatc gagcgagcac gtactcggat ggaagccggt cttgtcgatc aggatgatct  7020
ggacgaagag catcaggggc tcgcgccagc cgaactgttc gccaggctca aggcgcgcat  7080
gcccgacggc gaggatctcg tcgtgaccca tggcgatgcc tgcttgccga atatcatggt  7140
ggaaaatggc cgcttttctg gattcatcga ctgtggccgg ctgggtgtgg cggaccgcta  7200
tcaggacata gcgttggcta cccgtgatat tgctgaagag cttggcggcg aatgggctga  7260
ccgcttcctc gtgctttacg gtatcgccgc tcccgattcg cagcgcatcg ccttctatcg  7320
ccttcttgac gagttcttct gagcgggact ctggggttcg aaatgaccga ccaagcgacg  7380
cccaacctgc catcacgaga tttcgattcc accgccgcct tctatgaaag gttgggcttc  7440
ggaatcgttt tccgggacgc cggctggatg atcctccagc gcggggatct catgctggag  7500
ttcttcgccc accccaactt gtttattgca gcttataatg gttacaaata aagcaatagc  7560
atcacaaatt tcacaaataa agcatttttt tcactgcatt ctagttgtgg tttgtccaaa  7620
ctcatcaatg tatcttatca tgtctgtata ccgtcgacct ctagctagag cttggcgtaa  7680
tcatggtcat agctgtttcc tgtgtgaaat tgttatccgc tcacaattcc acacaacata  7740
cgagccggaa gcataaagtg taaagcctgg ggtgcctaat gagtgagcta actcacatta  7800
attgcgttgc gctcactgcc cgctttccag tcgggaaacc tgtcgtgcca gctgcattaa  7860
tgaatcggcc aacgcgcggg gagaggcggt ttgcgtattg ggcgctcttc cgcttcctcg  7920
ctcactgact cgctgcgctc ggtcgttcgg ctgcggcgag cggtatcagc tcactcaaag  7980
gcggtaatac ggttatccac agaatcaggg gataacgcag gaaagaacat gtgagcaaaa  8040
ggccagcaaa aggccaggaa ccgtaaaaag gccgcgttgc tggcgttttt ccataggctc  8100
cgcccccctg acgagcatca caaaaatcga cgctcaagtc agaggtggcg aaacccgaca  8160
ggactataaa gataccaggc gtttccccct ggaagctccc tcgtgcgctc tcctgttccg  8220
accctgccgc ttaccggata cctgtccgcc tttctccctt cgggaagcgt ggcgctttct  8280
catagctcac gctgtaggta tctcagttcg gtgtaggtcg ttcgctccaa gctgggctgt  8340
gtgcacgaac cccccgttca gcccgaccgc tgcgccttat ccggtaacta tcgtcttgag  8400
tccaacccgg taagacacga cttatcgcca ctggcagcag ccactggtaa caggattagc  8460
agagcgaggt atgtaggcgg tgctacagag ttcttgaagt ggtggcctaa ctacggctac  8520
actagaagaa cagtatttgg tatctgcgct ctgctgaagc cagttacctt cggaaaaaga  8580
gttggtagct cttgatccgg caaacaaacc accgctggta gcggtggttt ttttgtttgc  8640
aagcagcaga ttacgcgcag aaaaaaagga tctcaagaag atcctttgat cttttctacg  8700
gggtctgacg ctcagtggaa cgaaaactca cgttaaggga ttttggtcat gagattatca  8760
aaaaggatct tcacctagat ccttttaaat taaaaatgaa gttttaaatc aatctaaagt  8820
atatatgagt aaacttggtc tgacagttac caatgcttaa tcagtgaggc acctatctca  8880
gcgatctgtc tatttcgttc atccatagtt gcctgactcc ccgtcgtgta gataactacg  8940
atacgggagg gcttaccatc tggccccagt gctgcaatga taccgcgaga cccacgctca  9000
ccggctccag atttatcagc aataaaccag ccagccggaa gggccgagcg cagaagtggt  9060
cctgcaactt tatccgcctc catccagtct attaattgtt gccgggaagc tagagtaagt  9120
agttcgccag ttaatagttt gcgcaacgtt gttgccattg ctacaggcat cgtggtgtca  9180
cgctcgtcgt ttggtatggc ttcattcagc tccggttccc aacgatcaag gcgagttaca  9240
tgatccccca tgttgtgcaa aaaagcggtt agctccttcg gtcctccgat cgttgtcaga  9300
agtaagttgg ccgcagtgtt atcactcatg gttatggcag cactgcataa ttctcttact  9360
gtcatgccat ccgtaagatg cttttctgtg actggtgagt actcaaccaa gtcattctga  9420
gaatagtgta tgcggcgacc gagttgctct tgcccggcgt caatacggga taataccgcg  9480
ccacatagca gaactttaaa agtgctcatc attggaaaac gttcttcggg gcgaaaactc  9540
tcaaggatct taccgctgtt gagatccagt tcgatgtaac ccactcgtgc acccaactga  9600
tcttcagcat cttttacttt caccagcgtt tctgggtgag caaaaacagg aaggcaaaat  9660
gccgcaaaaa agggaataag ggcgacacgg aaatgttgaa tactcatact cttccttttt  9720
caatattatt gaagcattta tcagggttat tgtctcatga gcggatacat atttgaatgt  9780
atttagaaaa ataaacaaat aggggttccg cgcacatttc cccgaaaagt gccacctgac  9840
gtc                                                                9843
```

```
SEQ ID NO: 90          moltype = DNA  length = 10549
FEATURE                Location/Qualifiers
source                 1..10549
                       mol_type = other DNA
                       organism = synthetic construct
SEQUENCE: 90
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttataaat  240
gttttgtaga ataaaaaaaa aaaaagttct tcaaaagaaa tctcaaatct ccaaatggaa  300
acaggtaaaa gtggagctcc cctggttcca cggagaacct tttttgagga aacttaggca  360
actcgcaggt accttatgtc atgagacaga gtttgaaaac tacaattgac tatctctaaa  420
tttcctccca ggtctaaaat gtgatgatag ttactacttc agtacatcat ccttaaggaa  480
aattattagg tccacactgt ttctatcctt tgaattttac acataaattt tgtaatcaaa  540
agtttatttg taatatcaga tggaatcaga taattgcttt ttgtttttc cactgacagg  600
aacataagat tttgttgtgt agcttaagtc aaacgcagtt tggaatatat attttttaaa  660
```

-continued

```
aattgtaact tacatatcca aatacaattt ttcaagaagt agagtattca gtagaaatta  720
atctgtgaaa gaagaggaat tcagcagtgg cctatttgat gaatgattta acgtgcttat  780
ttcttccctt tcatcaaaac tctgtgtccc cttgtttgcc ccctctgact tcatactctg  840
gagttgacca agatccctct tccatcggat tgttctggga attttgaaat aatctgcttt  900
ttcctctctt tcccctgttg cttctgatgc cttagaatta cattttcctc gctgatttag  960
tttagaaaag agaaaagagc ttccatgact agtagattat cacttttggg tttgctcttg  1020
gaagtgacaa gatgctagga tccctctttg gaatgtaaaa tttatctctt atatagaaag  1080
gatataaatg tagcaccaga gactataaaa ctctgatact atctactgta ctgtatagct  1140
gaacgccaca atgtgtctgg taatctattg actatcataa atgctatttc tacagaaaag  1200
ttaggaggtc catatttcgg gcaaccaatg tatagctgaa tgcagaacag tcatagttgg  1260
gtactaacca tatatatgat ttatccatca acaggtgcat atgctcagaa attctgtatc  1320
cataagaaat cagactactt tcttttcctt ttgcaagtaa attgaattta gcctgagagg  1380
ctgaggggaa attttcacat ataagccacg gttttgtgtt ttgtgttttg ttttgtttat  1440
agatatagta ctaactggat ggatgcgata aaattcatag gtggtactaa gatacaatag  1500
gatttgtgaa atggacaatt gtcttgcata aatagcaagt aaaaaatcaa gcctgtcctt  1560
cataaaaatt ttattctggg gtgtctctgg ctaactagag aacccactgc ttactggctt  1620
atcgaaatta atacgactca ctatagggag acccaagctg gctagcgcca ccatgaagtg  1680
ggtaaccttt atttcccttc tttttctctt tagctcggct tattccaggg gtgtgtttcg  1740
tcgagactac aaagacgatg acgacaagag cgctggcctg aagccaagct gcgccaagga  1800
ggtgaagagc tgcaagggca gatgtttcga acggaccttc ggcaactgca gatgcgacgc  1860
cgcctgcgtg gaactgggaa actgttgtct ggactaccag gagacatgta tcgagcctga  1920
gcacatctgg acatgcaaca agttcagatg tggcgagaaa agactgactc ggagtctgtg  1980
cgcctgttct gacgactgca aggacaaggg cgattgctgc atcaactaca gcagcgtgtg  2040
ccagggcgaa aagagctggg tcgaggaacc ctgcgagagc atcaacgagc cccagtgccc  2100
tgccggattt gagacacctc ctaccctgct cttctccctg gatggcttca gagctgagta  2160
cctgcataca tggggaggac tgctgcctgt gatcagcaag ctgaagaagt gcggcaccta  2220
cacaaagaac atgcggcctg tctaccctac caagaccttc cccaaccact acagcatcgt  2280
gaccggcctg taccccgaga gccacggcat catcgacaac aagatgtacg accccaaaat  2340
gaacgccagc ttcagcctga aatctaagga aaagttcaac cctgagtggt ataagggcga  2400
gccaatctgg gtgacagcca agtaccaggg cctgaagagc ggcaccttct tctggcctgg  2460
cagcgacgtg gagatcaacg gaatcttccc tgatatctac aagatgtata acggctccgt  2520
gcctttcgag gagcggatct tggctgttct tcagtggctg cagctgccca aggacgagag  2580
accccacttc tacaccctgt acctggaaga acctgacagc agcggccaca gctacggccc  2640
tgtgtctagc gaggtgatca aggccctgca aagagtggat ggcatggtgg gcatgctgat  2700
ggatggactg aaggaactga acctccatcg ttgcctgaac ctgatcctga tctccgacca  2760
cggcatggaa cagggcagct gtaaaaagta catctacctg aacaagtacc tgggcgacgt  2820
gaagaatatc aaggtgatct acgggccggc cgccaggctg cggcctagcg acgtgcccga  2880
caagtattac agcttcaact acgagggcat cgccagaaac ctgtcttgca gagaacccaa  2940
tcaacacttc aagccttacc tgaagcactt tctgcctaag agactgcact tcgccaaaag  3000
cgacagaatt gaacccctga cattctatct ggaccctcag tggcagctgg ccctcaatcc  3060
ttctgaacgc aaatactgcg gtagcggatt tcacggctct gataacgtgt tttctaacat  3120
gcaggccctg tttgtgggct acggccctgg cttcaagcac ggaatcgagg ctgacacctt  3180
cgagaacatc gaagtttaca atctgatgtg cgacctgctg aatctgaccc cagcccctaa  3240
caacggcaca cacggctctc tgaatcacct gctcaagaac cccgtgtata cccccaaaca  3300
ccctaaagag gtccatccac tggtgcagtg cccattcacc agaaaccctc gggacaacct  3360
tggctgcagc tgcaacccta gcatcctccc tatcgaagat ttccagaccc agtttaacct  3420
gactgtcgcc gaagagaaga tcatcaagca cgaaaccctg ccctacggga ggcccagagt  3480
gctgcagaaa gaaaacacaa tctgtctgct gagccagcac cagtttatga gcggctacag  3540
tcaggacatc ctgatgcctc tgtggaccag ctacaccgtg gaccggaatg acagcttcag  3600
caccgaggac ttcagcaact gcctgtatca ggacttccgc atccctctgt cccctgtgca  3660
taagtgcagc ttttacaaga acaacaccaa ggtgagctac gggtttctga gcccaccaca  3720
actgaacaaa aatagctctg gcatctactc tgaggcgctg ctgaccacca acatcgtgcc  3780
aatgtaccag agcttccagg tgatctggcg gtacttccat gataccctgc ttcggaagta  3840
cgccgaagaa cggaacggcg tgaacgtggt gtccggccca gtgttcgact tcgactacga  3900
cggcagatgt gattcccttg agaatctgag acagaagcgg cgggttatca gaaaccagga  3960
gatcctgatt cctacccact tcttcatcgt gctgacatct tgcaaggata ccagccaaac  4020
acctctgcac tgcgagaacc tggacaccct ggccttcatc ctgcctcacc ggaccgataa  4080
tagcgaatcc tgtgtgcacg gcaaacacga ctctagctgg gtggaagagc tgctgatgct  4140
gcacagagcc cggatcacag atgtggaaca catcaccggc ctgtccttct accaacagag  4200
aaaggaaccc gtgtctgata tcctgaagct gaaaacccac ctgcctacct tcagccagga  4260
ggacctgatc gttaacgatg cacacaagag tgaggttgct catcggttta aagatttggg  4320
agaagaaaat ttcaaagcct tggtgttgat tgcctttgct cagtatcttc agcagtgtcc  4380
atttgaagat catgtaaaat tagtgaatga agtaactgaa tttgcaaaaa catgtgttgc  4440
tgatgagtca gctgaaaatt gtgacaaatc acttcatacc ctttttggag acaaattatg  4500
cacagttgca actcttcgtg aaacctatgg tgaaatggct gactgctgtg caaaacaaga  4560
acctgagaga aatgaatgct tcttgcaaca caaagatgac aacccaaacc tcccccgatt  4620
ggtgagacca gaggttgatg tgatgtgcac tgcttttcat gacaatgaag agacattttt  4680
gaaaaaatac ttatatgaaa ttgccagaag acatccttac ttttatgccc cggaactcct  4740
tttctttgct aaaaggtata aagctgcttt tacagaatgt tgccaagctg ctgataaagc  4800
tgcctgcctg ttgccaaagc tcgatgaact tcgggatgaa gggaaggctt cgtctgccaa  4860
acagagactc aagtgtgcca gtctccaaaa atttggagaa agagctttca aagcatgggc  4920
agtagctcgc ctgagccaga gatttcccaa agctgagttt gcagaagttt ccaagttagt  4980
gacagatctt accaaagtcc acacggaatg ctgccatgga gatctgcttg aatgtgctga  5040
tgacagggcg gaccttgcca agtatatctg tgaaaatcaa gattcgatct ccagtaaact  5100
gaaggaatgc tgtgaaaaac ctctgttgga aaaatcccac tgcattgccg aagtggaaaa  5160
tgatgagatg cctgctgact tgccttcatt agctgctgat tttgttgaaa gtaaggatgt  5220
ttgcaaaaac tatgctgagg caaaggatgt cttcctgggc atgtttttgt atgaatatgc  5280
aagaaggcat cctgattact ctgtcgtgct gctgctgaga cttgccaaga catatgaaac  5340
cacactcgag aagtgctgtg ccgctgcaga tcctcatgaa tgctatgcca aagtgttcga  5400
```

-continued

```
tgaatttaaa cctcttgtgg aagagcctca gaatttaatc aaacaaaatt gtgagctttt  5460
tgagcagctt ggagagtaca aattccagaa tgcgctatta gttcgttaca ccaagaaagt  5520
accccaagtg tcaactccaa ctcttgtaga ggtctcaaga aacctaggaa aagtgggcag  5580
caaatgttgt aaacatcctg aagcaaaaag aatgccctgt gcagaagact atctatccgt  5640
ggtcctgaac cagttatgtg tgttgcatga gaaaacgcca gtaagtgaca gagtcaccaa  5700
atgctgcaca gaatccttgg tgaacaggcg accatgcttt tcagctctgg aagtcgatga  5760
aacatacgtt cccaaagagt ttaatgctga aacattcacc ttccatgcag atatatgcac  5820
actttctgag aaggagagac aaatcaagaa acaaactgca cttgttgagc tcgtgaaaca  5880
caagcccaag gcaacaaaag agcaactgaa agctgttatg gatgatttcg cagcttttgt  5940
agagaagtgc tgcaaggctg acgataagga gacctgcttt gccgaggagg gtaaaaaact  6000
tgttgctgca agtcaagctg ccttaggctt atgaggtacc gagctcggat ccactagtcc  6060
agtgtggtgg aattctgcag atatccagca cagtggcggc cgctcgagtc tagagggccc  6120
gtttaaaccc gctgatcagc ctcgactgtg ccttctagtt gccagccatc tgttgtttgc  6180
ccctcccccg tgccttcctt gaccctggaa ggtgccactc ccactgtcct ttcctaataa  6240
aatgaggaaa ttgcatcgca ttgtctgagt aggtgtcatt ctattctggg gggtggggtg  6300
gggcaggaca gcaaggggga ggattgggaa gacaatagca ggcatgctgg ggatgcggtg  6360
ggctctatgg cttctgaggc ggaaagaacc agctggggct ctagggggta tccccacgcg  6420
ccctgtagcg gcgcattaag cgcggcgggt gtggtggtta cgcgcagcgt gaccgctaca  6480
cttgccagcg ccctagcgcc cgctcctttc gctttcttcc cttcctttct cgccacgttc  6540
gccggctttc cccgtcaagc tctaaatcgg gggctccctt tagggttccg atttagtgct  6600
ttacggcacc tcgaccccaa aaaacttgat tagggtgatg gttcacgtag tgggccatcg  6660
ccctgataga cggtttttcg ccctttgacg ttggagtcca cgttctttaa tagtggactc  6720
ttgttccaaa ctggaacaac actcaaccct atctcggtct attcttttga tttataaggg  6780
attttgccga tttcggccta ttggttaaaa aatgagctga tttaacaaaa atttaacgcg  6840
aattaattct gtggaatgtg tgtcagttag ggtgtggaaa gtccccaggc tccccagcag  6900
gcagaagtat gcaaagcatg catctcaatt agtcagcaac caggtgtgga aagtccccag  6960
gctccccagc aggcagaagt atgcaaagca tgcatctcaa ttagtcagca accatagtcc  7020
cgcccctaac tccgcccatc ccgcccctaa ctccgcccag ttccgcccat tctccgcccc  7080
atggctgact aatttttttt atttatgcag aggccgaggc cgcctctgcc tctgagctat  7140
tccagaagta gtgaggaggc ttttttggag gcctaggctt ttgcaaaaag ctcccgggag  7200
cttgtatatc cattttcgga tctgatcaag agacaggatg aggatcgttt cgcatgattg  7260
aacaagatgg attgcacgca ggttctccgg ccgcttgggt ggagaggcta ttcggctatg  7320
actgggcaca acagacaatc ggctgctctg atgccgccgt gttccggctg tcagcgcagg  7380
ggcgcccggt tctttttgtc aagaccgacc tgtccggtgc cctgaatgaa ctgcaggacg  7440
aggcagcgcg gctatcgtgg ctggccacga cgggcgttcc ttgcgcagct gtgctcgacg  7500
ttgtcactga agcgggaagg gactggctgc tattgggcga agtgccgggg caggatctcc  7560
tgtcatctca ccttgctcct gccgagaaag tatccatcat ggctgatgca atgcggcggc  7620
tgcatacgct tgatccggct acctgcccat tcgaccacca agcgaaacat cgcatcgagc  7680
gagcacgtac tcggatggaa gccggtcttg tcgatcagga tgatctggac gaagagcatc  7740
aggggctcgc gccagccgaa ctgttcgcca ggctcaaggc gcgcatgccc gacggcgagg  7800
atctcgtcgt gacccatggc gatgcctgct tgccgaatat catggtggaa aatggccgct  7860
tttctggatt catcgactgt ggccggctgg gtgtggcgga ccgctatcag gacatagcgt  7920
tggctacccg tgatattgct gaagagcttg gcggcgaatg ggctgaccgc ttcctcgtgc  7980
tttacggtat cgccgctccc gattcgcagc gcatcgcctt ctatcgcctt cttgacgagt  8040
tcttctgagc gggactctgg ggttcgaaat gaccgaccaa gcgacgccca acctgccatc  8100
acgagatttc gattccaccg ccgccttcta tgaaaggttg ggcttcggaa tcgttttccg  8160
ggacgccggc tggatgatcc tccagcgcgg ggatctcatg ctggagttct tcgcccaccc  8220
caacttgttt attgcagctt ataatggtta caaataaagc aatagcatca caaatttcac  8280
aaataaagca tttttttcac tgcattctag ttgtggtttg tccaaactca tcaatgtatc  8340
ttatcatgtc tgtataccgt cgacctctag ctagagcttg gcgtaatcat ggtcatagct  8400
gtttcctgtg tgaaattgtt atccgctcac aattccacac aacatacgag ccggaagcat  8460
aaagtgtaaa gcctggggtg cctaatgagt gagctaactc acattaattg cgttgcgctc  8520
actgcccgct ttccagtcgg gaaacctgtc gtgccagctg cattaatgaa tcggccaacg  8580
cgcggggaga ggcggtttgc gtattgggcg ctcttccgct tcctcgctca ctgactcgct  8640
gcgctcggtc gttcggctgc ggcgagcggt atcagctcac tcaaaggcgg taatacggtt  8700
atccacagaa tcaggggata acgcaggaaa gaacatgtga gcaaaaggcc agcaaaaggc  8760
caggaaccgt aaaaaggccg cgttgctggc gtttttccat aggctccgcc cccctgacga  8820
gcatcacaaa aatcgacgct caagtcagag gtggcgaaac ccgacaggac tataaagata  8880
ccaggcgttt ccccctggaa gctccctcgt gcgctctcct gttccgaccc tgccgcttac  8940
cggatacctg tccgcctttc tcccttcggg aagcgtggcg ctttctcata gctcacgctg  9000
taggtatctc agttcggtgt aggtcgttcg ctccaagctg ggctgtgtgc acgaaccccc  9060
cgttcagccc gaccgctgcg ccttatccgg taactatcgt cttgagtcca acccggtaag  9120
acacgactta tcgccactgg cagcagccac tggtaacagg attagcagag cgaggtatgt  9180
aggcggtgct acagagttct tgaagtggtg gcctaactac ggctacacta gaagaacagt  9240
atttggtatc tgcgctctgc tgaagccagt taccttcgga aaaagagttg gtagctcttg  9300
atccggcaaa caaaccaccg ctggtagcgg tggttttttt gtttgcaagc agcagattac  9360
gcgcagaaaa aaaggatctc aagaagatcc tttgatcttt tctacggggt ctgacgctca  9420
gtggaacgaa aactcacgtt aagggatttt ggtcatgaga ttatcaaaaa ggatcttcac  9480
ctagatcctt ttaaattaaa aatgaagttt taaatcaatc taaagtatat atgagtaaac  9540
ttggtctgac agttaccaat gcttaatcag tgaggcacct atctcagcga tctgtctatt  9600
tcgttcatcc atagttgcct gactccccgt cgtgtagata actacgatac gggagggctt  9660
accatctggc cccagtgctg caatgatacc gcgagaccca cgctcaccgg ctccagattt  9720
atcagcaata aaccagccag ccggaagggc cgagcgcaga agtggtcctg caactttatc  9780
cgcctccatc cagtctatta attgttgccg ggaagctaga gtaagtagtt cgccagttaa  9840
tagtttgcgc aacgttgttg ccattgctac aggcatcgtg gtgtcacgct cgtcgtttgg  9900
tatggcttca ttcagctccg gttcccaacg atcaaggcga gttacatgat cccccatgtt  9960
gtgcaaaaaa gcggttagct ccttcggtcc tccgatcgtt gtcagaagta agttggccgc  10020
agtgttatca ctcatggtta tggcagcact gcataattct cttactgtca tgccatccgt  10080
aagatgcttt tctgtgactg gtgagtactc aaccaagtca ttctgagaat agtgtatgcg  10140
```

```
gcgaccgagt tgctcttgcc cggcgtcaat acgggataat accgcgccac atagcagaac  10200
tttaaaagtg ctcatcattg gaaaacgttc ttcggggcga aaactctcaa ggatcttacc  10260
gctgttgaga tccagttcga tgtaacccac tcgtgcaccc aactgatctt cagcatcttt  10320
tactttcacc agcgtttctg ggtgagcaaa aacaggaagg caaaatgccg caaaaaaggg  10380
aataagggcg acacggaaat gttgaatact catactcttc ctttttcaat attattgaag  10440
catttatcag ggttattgtc tcatgagcgg atacatattt gaatgtattt agaaaaataa  10500
acaaataggg gttccgcgca catttccccg aaaagtgcca cctgacgtc             10549

SEQ ID NO: 91          moltype = DNA  length = 9783
FEATURE                Location/Qualifiers
source                 1..9783
                       mol_type = other DNA
                       organism = synthetic construct
SEQUENCE: 91
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gccaccatga agtgggtaac ctttatttcc cttcttttc tctttagctc ggcttattcc  960
aggggtgtgt ttcgtcgaga ctacaaagac gatgacgaca agagcgctgg cctgaagcca  1020
agctgcgcca aggaggtgaa gagctgcaag ggcagatgtt tcgaacggac cttcggcaac  1080
tgcagatgcg acgccgcctg cgtggaactg ggaaactgtt gtctggacta ccaggagaca  1140
tgtatcgagc ctgagcacat ctggacatgc aacaagttca gatgtggcga gaaaagactg  1200
actcggagtc tgtgcgcctg ttctgacgac tgcaaggaca agggcgattg ctgcatcaac  1260
tacagcagcg tgtgccaggg cgaaaagagc tgggtcgagg aaccctgcga gagcatcaac  1320
gagccccagt gccctgccgg atttgagaca cctcctaccc tgctcttctc cctggatggc  1380
ttcagagctg agtacctgca tacatgggga ggactgctgc ctgtgatcag caagctgaag  1440
aagtgcggca cctacacaaa gaacatgcgg cctgtctacc ctaccaagac cttccccaac  1500
cactacagca tcgtgaccgg cctgtacccc gagagccacg gcatcatcga caacaagatg  1560
tacgacccca aaatgaacgc cagcttcagc ctgaaatcta aggaaaagtt caaccctgag  1620
tggtataagg gcgagccaat ctgggtgaca gccaagtacc agggcctgaa gagcggcacc  1680
ttcttctggc ctggcagcga cgtggagatc aacggaatct tccctgatat ctacaagatg  1740
tataacggct ccgtgccttt cgaggagcgg atcttggctg ttcttcagtg gctgcagctg  1800
cccaaggacg agagacccca cttctacacc ctgtacctgg aagaacctga cagcagcggc  1860
cacagctacg gccctgtgtc tagcgaggtg atcaaggccc tgcaaaagagt ggatggcatg  1920
gtgggcatgc tgatggatgg actgaaggaa ctgaacctcc atcgttgcct gaacctgatc  1980
ctgatctccg accacggcat ggaacagggc agctgtaaaa agtacatcta cctgaacaag  2040
tacctgggcg acgtgaagaa tatcaaggtg atctacgggc cggccgccag gctgcggcct  2100
agcgacgtgc ccgacaagta ttacagcttc aactacgagg gcatcgccag aaacctgtct  2160
tgcagagaac ccaatcaaca cttcaagcct tacctgaagc actttctgcc taagagactg  2220
cacttcgcca aaagcgacag aattgaaccc ctgacattct atctggaccc tcagtggcag  2280
ctggccctca atccttctga acgcaaatac tgcggtagcg gatttcacgg ctctgataac  2340
gtgttttcta acatgcaggc cctgtttgtg ggctacggcc ctggcttcaa gcacggaatc  2400
gaggctgaca ccttcgagaa catcgaagtt tacaatctga tgtgcgacct gctgaatctg  2460
accccagccc ctaacaacgg cacacacggc tctctgaatc acctgctcaa gaaccccgtg  2520
tataccccca aacaccctaa agaggtccat ccactggtgc agtgcccatt caccagaaac  2580
cctcgggaca accttggctg cagctgcaac cctagcatcc tccctatcga agatttccag  2640
acccagttta acctgactgt cgccgaagag aagatcatca agcacgaaac cctgccctac  2700
gggaggccca gagtgctgca gaaagaaaac acaatctgtc tgctgagcca gcaccagttt  2760
atgagcggct acagtcagga catcctgatg cctctgtgga ccagctacac cgtggaccgg  2820
aatgacagct tcagcaccga ggacttcagc aactgcctgt atcaggactt ccgcatccct  2880
ctgtcccctg tgcataagtg cagcttttac aagaacaaca ccaaggtgag ctacgggttt  2940
ctgagcccac cacaactgaa caaaaatagc tctggcatct actctgaggc gctgctgacc  3000
accaacatcg tgccaatgta ccagagcttc caggtgatct ggcggtactt ccatgatacc  3060
ctgcttcgga agtacgccga agaacggaac ggcgtgaacg tggtgtccgg cccagtgttc  3120
gacttcgact acgacggcag atgtgattcc cttgagaatc tgagacagaa gcggcgggtt  3180
atcagaaacc aggagatcct gattcctacc cacttcttca tcgtgctgac atcttgcaag  3240
gataccagcc aaacacctct gcactgcgag aacctggaca ccctggcctt catcctgcct  3300
caccggaccg ataatagcga atcctgtgtg cacggcaaac acgactctag ctgggtggaa  3360
gagctgctga tgctgcacag agcccggatc acagatgtgg aacacatcac cggcctgtcc  3420
ttctaccaac agagaaagga acccgtgtct gatatcctga agctgaaaac ccacctgcct  3480
accttcagcc aggaggacct gatcgttaac gatgcacaca agagtgaggt tgctcatcgg  3540
tttaaagatt tgggagaaga aaatttcaaa gccttggtgt tgattgcctt tgctcagtat  3600
cttcagcagt gtccatttga agatcatgta aaattagtga atgaagtaac tgaatttgca  3660
aaaacatgtg ttgctgatga gtcagctgaa aattgtgaca aatcacttca taccctttttt  3720
ggagacaaat tatgcacagt tgcaactctt cgtgaaacct atggtgaaat ggctgactgc  3780
tgtgcaaaac aagaacctga gagaaatgaa tgcttcttgc aacacaaaga tgacaaccca  3840
aacctccccc gattggtgag accagaggtt gatgtgatgt gcactgcttt tcatgacaat  3900
```

```
gaagagacat ttttgaaaaa atacttatat gaaattgcca gaagacatcc ttacttttat  3960
gccccggaac tccttttctt tgctaaaagg tataaagctg cttttacaga atgttgccaa  4020
gctgctgata aagctgcctg cctgttgcca aagctcgatg aacttcggga tgaagggaag  4080
gcttcgtctg ccaaacagag actcaagtgt gccagtctcc aaaaatttgg agaaagagct  4140
ttcaaagcat gggcagtagc tcgcctgagc cagagatttc ccaaagctga gtttgcagaa  4200
gtttccaagt tagtgacaga tcttaccaaa gtccacacgg aatgctgcca tggagatctg  4260
cttgaatgtg ctgatgacag ggcggacctt gccaagtata tctgtgaaaa tcaagattcg  4320
atctccagta aactgaagga atgctgtgaa aaacctctgt tggaaaaatc ccactgcatt  4380
gccgaagtgg aaaatgatga gatgcctgct gacttgcctt cattagctgc tgattttgtt  4440
gaaagtaagg atgtttgcaa aaactatgct gaggcaaagg atgtcttcct gggcatgttt  4500
ttgtatgaat atgcaagaag gcatcctgat tactctgtcg tgctgctgct gagacttgcc  4560
aagacatatg aaaccacact cgagaagtgc tgtgccgctg cagatcctca tgaatgctat  4620
gccaaagtgt tcgatgaatt taaacctctt gtggaagagc ctcagaattt aatcaaacaa  4680
aattgtgagc tttttgagca gcttggagag tacaaattcc agaatgcgct attagttcgt  4740
tacaccaaga aagtacccca agtgtcaact ccaactcttg tagaggtctc aagaaaccta  4800
ggaaaagtgg gcagcaaatg ttgtaaacat cctgaagcaa aaagaatgcc ctgtgcagaa  4860
gactatctat ccgtggtcct gaaccagtta tgtgtgttgc atgagaaaac gccagtaagt  4920
gacagagtca ccaaatgctg cacagaatcc ttggtgaaca ggcgaccatg cttttcagct  4980
ctggaagtcg atgaaacata cgttcccaaa gagtttaatg ctgaaacatt caccttccat  5040
gcagatatat gcacactttc tgagaaggag agacaaatca agaaacaaac tgcacttgtt  5100
gagctcgtga aacacaagcc caaggcaaca aaagagcaac tgaaagctgt tatggatgat  5160
ttcgcagctt ttgtagagaa gtgctgcaag gctgacgata aggagacctg ctttgccgag  5220
gagggtaaaa aacttgttgc tgcaagtcaa gctgccttag gcttatgagg taccgagctc  5280
ggatccacta gtccagtgtg gtggaattct gcagatatcc agcacagtgg cggccgctcg  5340
agtctagagg gcccgtttaa acccgctgat cagcctcgac tgtgccttct agttgccagc  5400
catctgttgt ttgcccctcc cccgtgcctt ccttgaccct ggaaggtgcc actcccactg  5460
tcctttccta ataaaatgag gaaattgcat cgcattgtct gagtaggtgt cattctattc  5520
tggggggtgg ggtggggcag gacagcaagg gggaggattg ggaagacaat agcaggcatg  5580
ctggggatgc ggtgggctct atggcttctg aggcggaaag aaccagctgg ggctctaggg  5640
ggtatcccca cgcgccctgt agcggcgcat taagcgcggc gggtgtggtg gttacgcgca  5700
gcgtgaccgc tacacttgcc agcgccctag cgcccgctcc tttcgctttc ttcccttcct  5760
ttctcgccac gttcgccggc tttccccgtc aagctctaaa tcgggggctc cctttagggt  5820
tccgatttag tgctttacgg cacctcgacc ccaaaaaact tgattagggt gatggttcac  5880
gtagtgggcc atcgccctga tagacggttt ttcgcccttt gacgttggag tccacgttct  5940
ttaatagtgg actcttgttc caaactggaa caacactcaa ccctatctcg gtctattctt  6000
ttgatttata agggattttg ccgatttcgg cctattggtt aaaaaatgag ctgatttaac  6060
aaaaatttaa cgcgaattaa ttctgtggaa tgtgtgtcag ttagggtgtg gaaagtcccc  6120
aggctcccca gcaggcagaa gtatgcaaag catgcatctc aattagtcag caaccaggtg  6180
tggaaagtcc ccaggctccc cagcaggcag aagtatgcaa agcatgcatc tcaattagtc  6240
agcaaccata gtcccgcccc taactccgcc catcccgccc ctaactccgc ccagttccgc  6300
ccattctccg ccccatggct gactaatttt ttttatttat gcagaggccg aggccgcctc  6360
tgcctctgag ctattccaga agtagtgagg aggctttttt ggaggcctag gcttttgcaa  6420
aaagctcccg ggagcttgta tatccatttt cggatctgat caagagacag gatgaggatc  6480
gtttcgcatg attgaacaag atggattgca cgcaggttct ccggccgctt gggtggagag  6540
gctattcggc tatgactggg cacaacagac aatcggctgc tctgatgccg ccgtgttccg  6600
gctgtcagcg caggggcgcc cggttctttt tgtcaagacc gacctgtccg gtgccctgaa  6660
tgaactgcag gacgaggcag cgcggctatc gtggctggcc acgacgggcg ttccttgcgc  6720
agctgtgctc gacgttgtca ctgaagcggg aagggactgg ctgctattgg gcgaagtgcc  6780
ggggcaggat ctcctgtcat ctcaccttgc tcctgccgag aaagtatcca tcatggctga  6840
tgcaatgcgg cggctgcata cgcttgatcc ggctacctgc ccattcgacc accaagcgaa  6900
acatcgcatc gagcgagcac gtactcggat ggaagccggt cttgtcgatc aggatgatct  6960
ggacgaagag catcaggggc tcgcgccagc cgaactgttc gccaggctca aggcgcgcat  7020
gcccgacggc gaggatctcg tcgtgaccca tggcgatgcc tgcttgccga atatcatggt  7080
ggaaaatggc cgcttttctg gattcatcga ctgtggccgg ctgggtgtgg cggaccgcta  7140
tcaggacata gcgttggcta cccgtgatat tgctgaagag cttggcggcg aatgggctga  7200
ccgcttcctc gtgctttacg gtatcgccgc tcccgattcg cagcgcatcg ccttctatcg  7260
ccttcttgac gagttcttct gagcgggact ctggggttcg aaatgaccga ccaagcgacg  7320
cccaacctgc catcacgaga tttcgattcc accgccgcct tctatgaaag gttgggcttc  7380
ggaatcgttt tccgggacgc cggctggatg atcctccagc gcggggatct catgctggag  7440
ttcttcgccc accccaactt gtttattgca gcttataatg gttacaaata aagcaatagc  7500
atcacaaatt tcacaaataa agcatttttt tcactgcatt ctagttgtgg tttgtccaaa  7560
ctcatcaatg tatcttatca tgtctgtata ccgtcgacct ctagctagag cttggcgtaa  7620
tcatggtcat agctgtttcc tgtgtgaaat tgttatccgc tcacaattcc acacaacata  7680
cgagccggaa gcataaagtg taaagcctgg ggtgcctaat gagtgagcta actcacatta  7740
attgcgttgc gctcactgcc cgctttccag tcgggaaacc tgtcgtgcca gctgcattaa  7800
tgaatcggcc aacgcgcggg gagaggcggt ttgcgtattg ggcgctcttc cgcttcctcg  7860
ctcactgact cgctgcgctc ggtcgttcgg ctgcggcgag cggtatcagc tcactcaaag  7920
gcggtaatac ggttatccac agaatcaggg gataacgcag gaaagaacat gtgagcaaaa  7980
ggccagcaaa aggccaggaa ccgtaaaaag gccgcgttgc tggcgttttt ccataggctc  8040
cgcccccctg acgagcatca caaaaatcga cgctcaagtc agaggtggcg aaacccgaca  8100
ggactataaa gataccaggc gtttccccct ggaagctccc tcgtgcgctc tcctgttccg  8160
accctgccgc ttaccggata cctgtccgcc tttctccctt cgggaagcgt ggcgctttct  8220
catagctcac gctgtaggta tctcagttcg gtgtaggtcg ttcgctccaa gctgggctgt  8280
gtgcacgaac cccccgttca gcccgaccgc tgcgccttat ccggtaacta tcgtcttgag  8340
tccaacccgg taagacacga cttatcgcca ctggcagcag ccactggtaa caggattagc  8400
agagcgaggt atgtaggcgg tgctacagag ttcttgaagt ggtggcctaa ctacggctac  8460
actagaagaa cagtatttgg tatctgcgct ctgctgaagc cagttacctt cggaaaaaga  8520
gttggtagct cttgatccgg caaacaaacc accgctggta gcggtggttt ttttgtttgc  8580
aagcagcaga ttacgcgcag aaaaaaagga tctcaagaag atcctttgat cttttctacg  8640
```

```
gggtctgacg ctcagtggaa cgaaaactca cgttaaggga ttttggtcat gagattatca  8700
aaaaggatct tcacctagat ccttttaaat taaaaatgaa gttttaaatc aatctaaagt  8760
atatatgagt aaacttggtc tgacagttac caatgcttaa tcagtgaggc acctatctca  8820
gcgatctgtc tatttcgttc atccatagtt gcctgactcc ccgtcgtgta gataactacg  8880
atacgggagg gcttaccatc tggccccagt gctgcaatga taccgcgaga cccacgctca  8940
ccggctccag atttatcagc aataaaccag ccagccggaa gggccgagcg cagaagtggt  9000
cctgcaactt tatccgcctc catccagtct attaattgtt gccgggaagc tagagtaagt  9060
agttcgccag ttaatagttt gcgcaacgtt gttgccattg ctacaggcat cgtggtgtca  9120
cgctcgtcgt ttggtatggc ttcattcagc tccggttccc aacgatcaag gcgagttaca  9180
tgatccccca tgttgtgcaa aaaagcggtt agctccttcg gtcctccgat cgttgtcaga  9240
agtaagttgg ccgcagtgtt atcactcatg gttatggcag cactgcataa ttctcttact  9300
gtcatgccat ccgtaagatg cttttctgtg actggtgagt actcaaccaa gtcattctga  9360
gaatagtgta tgcggcgacc gagttgctct tgcccggcgt caatacggga taataccgcg  9420
ccacatagca gaactttaaa agtgctcatc attggaaaac gttcttcggg gcgaaaactc  9480
tcaaggatct taccgctgtt gagatccagt tcgatgtaac ccactcgtgc acccaactga  9540
tcttcagcat cttttacttt caccagcgtt tctgggtgag caaaaacagg aaggcaaaat  9600
gccgcaaaaa agggaataag ggcgacacgg aaatgttgaa tactcatact cttccttttt  9660
caatattatt gaagcattta tcagggttat tgtctcatga gcggatacat atttgaatgt  9720
atttagaaaa ataaacaaat aggggttccg cgcacatttc cccgaaaagt gccacctgac  9780
gtc                                                                9783
```

```
SEQ ID NO: 92          moltype = DNA  length = 9783
FEATURE                Location/Qualifiers
source                 1..9783
                       mol_type = other DNA
                       organism = synthetic construct
SEQUENCE: 92
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgcgtta  240
cataacttac ggtaaatggc ccgcctggct gaccgcccaa cgacccccgc ccattgacgt  300
caataatgac gtatgttccc atagtaacgc caatagggac tttccattga cgtcaatggg  360
tggagtattt acggtaaact gcccacttgg cagtacatca agtgtatcat atgccaagta  420
cgccccctat tgacgtcaat gacggtaaat ggcccgcctg gcattatgcc cagtacatga  480
ccttatggga ctttcctact tggcagtaca tctacgtatt agtcatcgct attaccatgg  540
tcgaggtgag ccccacgttc tgcttcactc tccccatctc ccccccctcc ccacccccaa  600
ttttgtattt atttattttt taattatttt gtgcagcgat gggggcgggg gggggggggg  660
ggcgcgcgcc aggcggggcg gggcggggcg aggggcgggg cggggcgagg cggagaggtg  720
cggcggcagc caatcagagc ggcgcgctcc gaaagtttcc ttttatggcg aggcggcggc  780
ggcggcggcc ctataaaaag cgaagcgcgc ggcgggcgct ctggctaact agagaaccca  840
ctgcttactg gcttatcgaa attaatacga ctcactatag ggagacccaa gctggctagc  900
gccaccatga agtgggtaac ctttatttcc cttcttttc tctttagctc ggcttattcc  960
aggggtgtgt ttcgtcgaga ctacaaagac gatgacgaca agagcgctgg cctgaagcca  1020
agctgcgcca aggaggtgaa gagctgcaag ggcagatgtt tcgaacggac cttcggcaac  1080
tgcagatgcg acgccgcctg cgtggaactg ggaaactgtt gtctggacta ccaggagaca  1140
tgtatcgagc ctgagcacat ctggacatgc aacaagttca gatgtggcga gaaaagactg  1200
actcggagtc tgtgcgcctg ttctgacgac tgcaaggaca agggcgattg ctgcatcaac  1260
tacagcagcg tgtgccaggg cgaaaagagc tgggtcgagg aaccctgcga gagcatcaac  1320
gagccccagt gccctgccgg atttgagaca cctcctaccc tgctcttctc cctggatggc  1380
ttcagagctg agtacctgca tacatgggga ggactgctgc ctgtgatcag caagctgaag  1440
aagtgcggca cctacacaaa gaacatgcgg cctgtctacc ctaccaagac cttccccaac  1500
cactacagca tcgtgaccgg cctgtacccc gagagccacg gcatcatcga caacaagatg  1560
tacgacccca aatgaacgc cagcttcagc ctgaaatcta aggaaaagtt caaccctgag  1620
tggtataagg gcgagccaat ctgggtgaca gccaagtacc agggcctgaa gagcggcacc  1680
ttcttctggc ctggcagcga cgtggagatc aacggaatct tccctgatat ctacaagatg  1740
tataacggct ccgtgccttt cgaggagcgg atcttggctg ttcttcagtg gctgcagctg  1800
cccaaggacg agagacccca cttctacacc ctgtacctgg aagaacctga cagcagcggc  1860
cacagctacg gccctgtgtc tagcgaggtg atcaaggccc tgcaaagagt ggatggcatg  1920
gtgggcatgc tgatggatgg actgaaggaa ctgaacctcc atcgttgcct gaacctgatc  1980
ctgatctccg accacggcat ggaacagggc agctgtaaaa agtacatcta cctgaacaag  2040
tacctgggcg acgtgaagaa tatcaaggtg atctacgggc cggccgccag gctgcggcct  2100
agcgacgtgc ccgacaagta ttacagcttc aactacgagg gcatcgccag aaacctgtct  2160
tgcagagaac ccaatcaaca cttcaagcct tacctgaagc actttctgcc taagagactg  2220
cacttcgcca aaagcgacag aattgaaccc ctgacattct atctggaccc tcagtggcag  2280
ctggccctca atccttctga acgcaaatac tgcggtagcg gatttcacgg ctctgataac  2340
gtgttttcta acatgcaggc cctgtttgtg ggctacggcc ctggcttcaa gcacggaatc  2400
gaggctgaca ccttcgagaa catcgaagtt tacaatctga tgtgcgacct gctgaatctg  2460
accccagccc ctaacaacgg cacacacggc tctctgaatc acctgctcaa gaaccccgtg  2520
tatacccccca aacaccctaa agaggtccat ccactggtgc agtgcccatt caccagaaac  2580
cctcgggaca accttggctg cagctgcaac cctagcatcc tccctatcga agatttccag  2640
acccagttta acctgactgt cgccgaagag aagatcatca agcacgaaac cctgccctac  2700
gggaggccca gagtgctgca gaaagaaaac acaatctgtc tgctgagcca gcaccagttt  2760
atgagcggct acagtcagga catcctgatg cctctgtgga ccagctacac cgtggaccgg  2820
aatgacagct tcagcaccga ggacttcagc aactgcctgt atcaggactt ccgcatccct  2880
ctgtcccctg tgcataagtg cagcttttac aagaacaaca ccaaggtgag ctacgggttt  2940
ctgagcccac cacaactgaa caaaaatagc tctggcatct actctgaggc gctgctgacc  3000
accaacatcg tgccaatgta ccagagcttc caggtgatct ggcggtactt ccatgatacc  3060
ctgcttcgga agtacgccga agaacggaac ggcgtgaacg tggtgtccgg cccagtgttc  3120
```

-continued

```
gacttcgact acgacggcag atgtgattcc cttgagaatc tgagacagaa gcggcgggtt  3180
atcagaaacc aggagatcct gattcctacc cacttcttca tcgtgctgac atcttgcaag  3240
gataccagcc aaacacctct gcactgcgag aacctggaca ccctggcctt catcctgcct  3300
caccggaccg ataatagcga atcctgtgtg cacggcaaac acgactctag ctgggtggaa  3360
gagctgctga tgctgcacag agcccggatc acagatgtgg aacacatcac cggcctgtcc  3420
ttctaccaac agagaaagga acccgtgtct gatatcctga agctgaaaac ccacctgcct  3480
accttcagcc aggaggacct gatcgttaac gatgcacaca agagtgaggt tgctcatcgg  3540
tttaaagatt tgggagaaga aaatttcaaa gccttggtgt tgattgcctt tgctcagtat  3600
cttcagcagt gtccatttga agatcatgta aaattagtga atgaagtaac tgaatttgca  3660
aaaacatgtg ttgctgatga gtcagctgaa aattgtgaca aatcacttca taccctttt  3720
ggagacaaat tatgcacagt tgcaactctt cgtgaaacct atggtgaaat ggctgactgc  3780
tgtgcaaaac aagaacctga gagaaatgaa tgcttcttgc aacacaaaga tgacaaccca  3840
aacctccccc gattggtgag accagaggtt gatgtgatgt gcactgcttt tcatgacaat  3900
gaagagacat ttttgaaaaa atacttatat gaaattgcca gaagacatcc ttacttttat  3960
gccccggaac tccttttctt tgctaaaagg tataaagctg cttttacaga atgttgccaa  4020
gctgctgata aagctgcctg cctgttgcca aagctcgatg aacttcggga tgaagggaag  4080
gcttcgtctg ccaaacagag actcaagtgt gccagtctcc aaaaatttgg agaaagagct  4140
ttcaaagcat gggcagtagc tcgcctgagc cagagatttc ccaaagctga gtttgcagaa  4200
gtttccaagt tagtgacaga tcttaccaaa gtccacacgg aatgctgcca tggagatctg  4260
cttgaatgtg ctgatgacag ggcggacctt gccaagtata tctgtgaaaa tcaagattcg  4320
atctccagta aactgaagga atgctgtgaa aaacctctgt tggaaaaatc ccactgcatt  4380
gccgaagtgg aaaatgatga gatgcctgct gacttgcctt cattagctgc tgattttgtt  4440
gaaagtaagg atgtttgcaa aaactatgct gaggcaaagg atgtcttcct gggcatgttt  4500
ttgtatgaat atgcaagaag gcatcctgat tactctgtcg tgctgctgct gagacttgcc  4560
aagacatatg aaaccacact cgagaagtgc tgtgccgctg cagatcctca tgaatgctat  4620
gccaaagtgt tcgatgaatt taaacctctt gtggaagagc ctcagaattt aatcaaacaa  4680
aattgtgagc tttttgagca gcttggagag tacaaattcc agaatgcgct attagttcgt  4740
tacaccaaga aagtacccca agtgtcaact ccaactcttg tagaggtctc aagaaaccta  4800
ggaaaagtgg gcagcaaatg ttgtaaacat cctgaagcaa aaagaatgcc ctgtgcagaa  4860
gactatctat ccgtggtcct gaaccagtta tgtgtgttgc atgagaaaac gccagtaagt  4920
gacagagtca ccaaatgctg cacagaatcc ttggtgaaca ggcgaccatg cttttcagct  4980
ctggaagtcg atgaaacata cgttcccaaa gagtttaatg ctgaaacatt caccttccat  5040
gcagatatat gcacactttc tgagaaggag agacaaatca agaaacaaac tgcacttgtt  5100
gagctcgtga aacacaagcc caaggcaaca aaagagcaac tgaaagctgt tatggatgat  5160
ttcgcagctt ttgtagagaa gtgctgcaag gctgacgata aggagacctg ctttgccgag  5220
gagggtaaaa aacttgttgc tgcaagtcaa gctgccttag gcttatgagg taccgagctc  5280
ggatccacta gtccagtgtg gtggaattct gcagatatcc agcacagtgg cggccgctcg  5340
agtctagagg gcccgtttaa acccgctgat cagcctcgac tgtgccttct agttgccagc  5400
catctgttgt ttgcccctcc cccgtgcctt ccttgaccct ggaaggtgcc actcccactg  5460
tcctttccta ataaaatgag gaaattgcat cgcattgtct gagtaggtgt cattctattc  5520
tggggggtgg ggtggggcag gacagcaagg gggaggattg ggaagacaat agcaggcatg  5580
ctggggatgc ggtgggctct atggcttctg aggcggaaag aaccagctgg ggctctaggg  5640
ggtatcccca cgcgccctgt agcggcgcat taagcgcggc gggtgtggtg gttacgcgca  5700
gcgtgaccgc tacacttgcc agcgccctag cgcccgctcc tttcgctttc ttcccttcct  5760
ttctcgccac gttcgccggc tttccccgtc aagctctaaa tcgggggctc cctttagggt  5820
tccgatttag tgctttacgg cacctcgacc ccaaaaaact tgattagggt gatggttcac  5880
gtagtgggcc atcgccctga tagacggttt ttcgcccttt gacgttggag tccacgttct  5940
ttaatagtgg actcttgttc caaactggaa caacactcaa ccctatctcg gtctattctt  6000
ttgatttata agggattttg ccgatttcgg cctattggtt aaaaaatgag ctgatttaac  6060
aaaaatttaa cgcgaattaa ttctgtggaa tgtgtgtcag ttagggtgtg gaaagtcccc  6120
aggctcccca gcaggcagaa gtatgcaaag catgcatctc aattagtcag caaccaggtg  6180
tggaaagtcc ccaggctccc cagcaggcag aagtatgcaa agcatgcatc tcaattagtc  6240
agcaaccata gtcccgcccc taactccgcc catcccgccc ctaactccgc ccagttccgc  6300
ccattctccg ccccatggct gactaatttt ttttatttat gcagaggccg aggccgcctc  6360
tgcctctgag ctattccaga agtagtgagg aggctttttt ggaggcctag gcttttgcaa  6420
aaagctcccg ggagcttgta tatccatttt cggatctgat caagagacag gatgaggatc  6480
gtttcgcatg attgaacaag atggattgca cgcaggttct ccggccgctt gggtggagag  6540
gctattcggc tatgactggg cacaacagac aatcggctgc tctgatgccg ccgtgttccg  6600
gctgtcagcg caggggcgcc cggttctttt tgtcaagacc gacctgtccg gtgccctgaa  6660
tgaactgcag gacgaggcag cgcggctatc gtggctggcc acgacgggcg ttccttgcgc  6720
agctgtgctc gacgttgtca ctgaagcggg aagggactgg ctgctattgg gcgaagtgcc  6780
ggggcaggat ctcctgtcat ctcaccttgc tcctgccgag aaagtatcca tcatggctga  6840
tgcaatgcgg cggctgcata cgcttgatcc ggctacctgc ccattcgacc accaagcgaa  6900
acatcgcatc gagcgagcac gtactcggat ggaagccggt cttgtcgatc aggatgatct  6960
ggacgaagag catcaggggc tcgcgccagc cgaactgttc gccaggctca aggcgcgcat  7020
gcccgacggc gaggatctcg tcgtgaccca tggcgatgcc tgcttgccga atatcatggt  7080
ggaaaatggc cgcttttctg gattcatcga ctgtggccgg ctgggtgtgg cggaccgcta  7140
tcaggacata gcgttggcta cccgtgatat tgctgaagag cttggcggcg aatgggctga  7200
ccgcttcctc gtgctttacg gtatcgccgc tcccgattcg cagcgcatcg ccttctatcg  7260
ccttcttgac gagttcttct gagcgggact ctggggttcg aaatgaccga ccaagcgacg  7320
cccaacctgc catcacgaga tttcgattcc accgccgcct tctatgaaag gttgggcttc  7380
ggaatcgttt tccgggacgc cggctggatg atcctccagc gcggggatct catgctggag  7440
ttcttcgccc accccaactt gtttattgca gcttataatg gttacaaata aagcaatagc  7500
atcacaaatt tcacaaataa agcatttttt tcactgcatt ctagttgtgg tttgtccaaa  7560
ctcatcaatg tatcttatca tgtctgtata ccgtcgacct ctagctagag cttggcgtaa  7620
tcatggtcat agctgtttcc tgtgtgaaat tgttatccgc tcacaattcc acacaacata  7680
cgagccggaa gcataaagtg taaagcctgg ggtgcctaat gagtgagcta actcacatta  7740
attgcgttgc gctcactgcc cgctttccag tcgggaaacc tgtcgtgcca gctgcattaa  7800
tgaatcggcc aacgcgcggg gagaggcggt ttgcgtattg gcgctcttc cgcttcctcg  7860
```

```
ctcactgact cgctgcgctc ggtcgttcgg ctgcggcgag cggtatcagc tcactcaaag  7920
gcggtaatac ggttatccac agaatcaggg gataacgcag gaaagaacat gtgagcaaaa  7980
ggccagcaaa aggccaggaa ccgtaaaaag gccgcgttgc tggcgttttt ccataggctc  8040
cgcccccctg acgagcatca caaaaatcga cgctcaagtc agaggtggcg aaacccgaca  8100
ggactataaa gataccaggc gtttccccct ggaagctccc tcgtgcgctc tcctgttccg  8160
accctgccgc ttaccggata cctgtccgcc tttctccctt cgggaagcgt ggcgctttct  8220
catagctcac gctgtaggta tctcagttcg gtgtaggtcg ttcgctccaa gctgggctgt  8280
gtgcacgaac cccccgttca gcccgaccgc tgcgccttat ccggtaacta tcgtcttgag  8340
tccaacccgg taagacacga cttatcgcca ctggcagcag ccactggtaa caggattagc  8400
agagcgaggt atgtaggcgg tgctacagag ttcttgaagt ggtggcctaa ctacggctac  8460
actagaagaa cagtatttgg tatctgcgct ctgctgaagc cagttacctt cggaaaaaga  8520
gttggtagct cttgatccgg caaacaaacc accgctggta gcggtggttt ttttgtttgc  8580
aagcagcaga ttacgcgcag aaaaaaagga tctcaagaag atcctttgat cttttctacg  8640
gggtctgacg ctcagtggaa cgaaaactca cgttaaggga ttttggtcat gagattatca  8700
aaaaggatct tcacctagat ccttttaaat taaaaatgaa gttttaaatc aatctaaagt  8760
atatatgagt aaacttggtc tgacagttac caatgcttaa tcagtgaggc acctatctca  8820
gcgatctgtc tatttcgttc atccatagtt gcctgactcc ccgtcgtgta gataactacg  8880
atacgggagg gcttaccatc tggccccagt gctgcaatga taccgcgaga cccacgctca  8940
ccggctccag atttatcagc aataaaccag ccagccggaa gggccgagcg cagaagtggt  9000
cctgcaactt tatccgcctc catccagtct attaattgtt gccgggaagc tagagtaagt  9060
agttcgccag ttaatagttt gcgcaacgtt gttgccattg ctacaggcat cgtggtgtca  9120
cgctcgtcgt ttggtatggc ttcattcagc tccggttccc aacgatcaag gcgagttaca  9180
tgatccccca tgttgtgcaa aaaagcggtt agctccttcg gtcctccgat cgttgtcaga  9240
agtaagttgg ccgcagtgtt atcactcatg gttatggcag cactgcataa ttctcttact  9300
gtcatgccat ccgtaagatg cttttctgtg actggtgagt actcaaccaa gtcattctga  9360
gaatagtgta tgcggcgacc gagttgctct tgcccggcgt caatacggga taataccgcg  9420
ccacatagca gaactttaaa agtgctcatc attggaaaac gttcttcggg gcgaaaactc  9480
tcaaggatct taccgctgtt gagatccagt tcgatgtaac ccactcgtgc acccaactga  9540
tcttcagcat cttttacttt caccagcgtt tctgggtgag caaaaacagg aaggcaaaat  9600
gccgcaaaaa agggaataag ggcgacacgg aaatgttgaa tactcatact cttccttttt  9660
caatattatt gaagcattta tcagggttat tgtctcatga gcggatacat atttgaatgt  9720
atttagaaaa ataaacaaat aggggttccg cgcacatttc cccgaaaagt gccacctgac  9780
gtc                                                                9783

SEQ ID NO: 93          moltype = DNA  length = 9409
FEATURE                Location/Qualifiers
source                 1..9409
                       mol_type = other DNA
                       organism = synthetic construct
SEQUENCE: 93
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttagttcc  240
agatggtaaa tatacacaag ggatttagtc aaacaatttt ttggcaagaa tattatgaat  300
tttgtaatcg gttggcagcc aatgaaatac aaagatgagt ctagttaata atctacaatt  360
attggttaaa gaagtatatt agtgctaatt tccctccgtt tgtcctagct tttctcttct  420
gtcaacccca cacgcctttg gcacctctgg ctaactagag aacccactgc ttactggctt  480
atcgaaatta atacgactca ctatagggag acccaagctg gctagcgcca ccatgaagtg  540
ggtaaccttt atttcccttc tttttctctt tagctcggct tattccaggg gtgtgtttcg  600
tcgagactac aaagacgatg acgacaagag cgctggcctg aagccaagct gcgccaagga  660
ggtgaagagc tgcaagggca gatgtttcga acggaccttc ggcaactgca gatgcgacgc  720
cgcctgcgtg gaactgggaa actgttgtct ggactaccag gagacatgta tcgagcctga  780
gcacatctgg acatgcaaca agttcagatg tggcgagaaa agactgactc ggagtctgtg  840
cgcctgttct gacgactgca aggacaaggg cgattgctgc atcaactaca gcagcgtgtg  900
ccagggcgaa aagagctggg tcgaggaacc ctgcgagagc atcaacgagc cccagtgccc  960
tgccggattt gagacacctc ctaccctgct cttctccctg gatggcttca gagctgagta  1020
cctgcataca tggggaggac tgctgcctgt gatcagcaag ctgaagaagt gcggcaccta  1080
cacaaagaac atgcggcctg tctaccctac caagaccttc cccaaccact acagcatcgt  1140
gaccggcctg taccccgaga gccacggcat catcgacaac aagatgtacg accccaaaat  1200
gaacgccagc ttcagcctga aatctaagga aaagttcaac cctgagtggt ataagggcga  1260
gccaatctgg gtgacagcca agtaccaggg cctgaagagc ggcaccttct tctggcctgg  1320
cagcgacgtg gagatcaacg gaatcttccc tgatatctac aagatgtata acggctccgt  1380
gcctttcgag gagcggatct tggctgttct tcagtggctg cagctgccca aggacgagag  1440
accccacttc tacaccctgt acctggaaga acctgacagc agcggccaca gctacggccc  1500
tgtgtctagc gaggtgatca aggccctgca aagagtggat ggcatggtgg gcatgctgat  1560
ggatggactg aaggaactga acctccatcg ttgcctgaac ctgatcctga tctccgacca  1620
cggcatggaa cagggcagct gtaaaaagta catctacctg aacaagtacc tgggcgacgt  1680
gaagaatatc aaggtgatct acgggccggc cgccaggctg cggcctagcg acgtgcccga  1740
caagtattac agcttcaact acgagggcat cgccagaaac ctgtcttgca gagaacccaa  1800
tcaacacttc aagccttacc tgaagcactt tctgcctaag agactgcact tcgccaaaag  1860
cgacagaatt gaacccctga cattctatct ggaccctcag tggcagctgg ccctcaatcc  1920
ttctgaacgc aaatactgcg gtagcggatt tcacggctct gataacgtgt tttctaacat  1980
gcaggccctg tttgtgggct acggccctgg cttcaagcac ggaatcgagg ctgacacctt  2040
cgagaacatc gaagtttaca atctgatgtg cgacctgctg aatctgaccc cagcccctaa  2100
caacggcaca cacggctctc tgaatcacct gctcaagaac cccgtgtata cccccaaaca  2160
ccctaaagag gtccatccac tggtgcagtg cccattcacc agaaaccctc gggacaacct  2220
tggctgcagc tgcaacccta gcatcctccc tatcgaagat ttccagaccc agtttaacct  2280
gactgtcgcc gaagagaaga tcatcaagca cgaaaccctg ccctacggga ggcccagagt  2340
```

-continued

```
gctgcagaaa gaaaacacaa tctgtctgct gagccagcac cagtttatga gcggctacag  2400
tcaggacatc ctgatgcctc tgtggaccag ctacaccgtg gaccggaatg acagcttcag  2460
caccgaggac ttcagcaact gcctgtatca ggacttccgc atccctctgt cccctgtgca  2520
taagtgcagc ttttacaaga acaacaccaa ggtgagctac gggtttctga gcccaccaca  2580
actgaacaaa aatagctctg gcatctactc tgaggcgctg ctgaccacca acatcgtgcc  2640
aatgtaccag agcttccagg tgatctggcg gtacttccat gataccctgc ttcggaagta  2700
cgccgaagaa cggaacggcg tgaacgtggt gtccggccca gtgttcgact tcgactacga  2760
cggcagatgt gattcccttg agaatctgag acagaagcgg cgggttatca gaaaccagga  2820
gatcctgatt cctacccact tcttcatcgt gctgacatct tgcaaggata ccagccaaac  2880
acctctgcac tgcgagaacc tggacaccct ggccttcatc ctgcctcacc ggaccgataa  2940
tagcgaatcc tgtgtgcacg gcaaacacga ctctagctgg gtggaagagc tgctgatgct  3000
gcacagagcc cggatcacag atgtggaaca catcaccggc ctgtccttct accaacagag  3060
aaaggaaccc gtgtctgata tcctgaagct gaaaacccac ctgcctacct tcagccagga  3120
ggacctgatc gttaacgatg cacacaagag tgaggttgct catcggttta aagatttggg  3180
agaagaaaat ttcaaagcct tggtgttgat tgcctttgct cagtatcttc agcagtgtcc  3240
atttgaagat catgtaaaat tagtgaatga agtaactgaa tttgcaaaaa catgtgttgc  3300
tgatgagtca gctgaaaatt gtgacaaatc acttcatacc ctttttggag acaaattatg  3360
cacagttgca actcttcgtg aaacctatgg tgaaatggct gactgctgtg caaaacaaga  3420
acctgagaga aatgaatgct tcttgcaaca caaagatgac aacccaaacc tcccccgatt  3480
ggtgagacca gaggttgatg tgatgtgcac tgcttttcat gacaatgaag agacattttt  3540
gaaaaaatac ttatatgaaa ttgccagaag acatccttac ttttatgccc cggaactcct  3600
tttctttgct aaaaggtata aagctgcttt tacagaatgt tgccaagctg ctgataaagc  3660
tgcctgcctg ttgccaaagc tcgatgaact tcgggatgaa gggaaggctt cgtctgccaa  3720
acagagactc aagtgtgcca gtctccaaaa atttggagaa agagctttca aagcatgggc  3780
agtagctcgc ctgagccaga gatttcccaa agctgagttt gcagaagttt ccaagttagt  3840
gacagatctt accaaagtcc acacggaatg ctgccatgga gatctgcttg aatgtgctga  3900
tgacagggcg gaccttgcca agtatatctg tgaaaatcaa gattcgatct ccagtaaact  3960
gaaggaatgc tgtgaaaaac ctctgttgga aaaatcccac tgcattgccg aagtggaaaa  4020
tgatgagatg cctgctgact tgccttcatt agctgctgat tttgttgaaa gtaaggatgt  4080
ttgcaaaaac tatgctgagg caaaggatgt cttcctgggc atgtttttgt atgaatatgc  4140
aagaaggcat cctgattact ctgtcgtgct gctgctgaga cttgccaaga catatgaaac  4200
cacactcgag aagtgctgtg ccgctgcaga tcctcatgaa tgctatgcca aagtgttcga  4260
tgaatttaaa cctcttgtgg aagagcctca gaatttaatc aaacaaaatt gtgagctttt  4320
tgagcagctt ggagagtaca aattccagaa tgcgctatta gttcgttaca ccaagaaagt  4380
accccaagtg tcaactccaa ctcttgtaga ggtctcaaga aacctaggaa aagtgggcag  4440
caaatgttgt aaacatcctg aagcaaaaag aatgccctgt gcagaagact atctatccgt  4500
ggtcctgaac cagttatgtg tgttgcatga gaaaacgcca gtaagtgaca gagtcaccaa  4560
atgctgcaca gaatccttgg tgaacaggcg accatgcttt tcagctctgg aagtcgatga  4620
aacatacgtt cccaaagagt ttaatgctga aacattcacc ttccatgcag atatatgcac  4680
actttctgag aaggagagac aaatcaagaa acaaactgca cttgttgagc tcgtgaaaca  4740
caagcccaag gcaacaaaag agcaactgaa agctgttatg gatgatttcg cagcttttgt  4800
agagaagtgc tgcaaggctg acgataagga gacctgcttt gccgaggagg gtaaaaaact  4860
tgttgctgca agtcaagctg ccttaggctt atgaggtacc gagctcggat ccactagtcc  4920
agtgtggtgg aattctgcag atatccagca cagtggcggc cgctcgagtc tagagggccc  4980
gtttaaaccc gctgatcagc ctcgactgtg ccttctagtt gccagccatc tgttgtttgc  5040
ccctcccccg tgccttcctt gaccctggaa ggtgccactc ccactgtcct ttcctaataa  5100
aatgaggaaa ttgcatcgca ttgtctgagt aggtgtcatt ctattctggg gggtggggtg  5160
gggcaggaca gcaaggggga ggattgggaa gacaatagca ggcatgctgg ggatgcggtg  5220
ggctctatgg cttctgaggc ggaaagaacc agctggggct ctagggggta tccccacgcg  5280
ccctgtagcg gcgcattaag cgcggcgggt gtggtggtta cgcgcagcgt gaccgctaca  5340
cttgccagcg ccctagcgcc cgctcctttc gctttcttcc cttcctttct cgccacgttc  5400
gccggctttc cccgtcaagc tctaaatcgg gggctccctt tagggttccg atttagtgct  5460
ttacggcacc tcgaccccaa aaaacttgat tagggtgatg gttcacgtag tgggccatcg  5520
ccctgataga cggtttttcg ccctttgacg ttggagtcca cgttctttaa tagtggactc  5580
ttgttccaaa ctggaacaac actcaaccct atctcggtct attcttttga tttataaggg  5640
attttgccga tttcggccta ttggttaaaa aatgagctga tttaacaaaa atttaacgcg  5700
aattaattct gtggaatgtg tgtcagttag ggtgtggaaa gtccccaggc tccccagcag  5760
gcagaagtat gcaaagcatg catctcaatt agtcagcaac caggtgtgga aagtccccag  5820
gctccccagc aggcagaagt atgcaaagca tgcatctcaa ttagtcagca accatagtcc  5880
cgcccctaac tccgcccatc ccgcccctaa ctccgcccag ttccgcccat tctccgcccc  5940
atggctgact aatttttttt atttatgcag aggccgaggc cgcctctgcc tctgagctat  6000
tccagaagta gtgaggaggc ttttttggag gcctaggctt ttgcaaaaag ctcccgggag  6060
cttgtatatc cattttcgga tctgatcaag agacaggatg aggatcgttt cgcatgattg  6120
aacaagatgg attgcacgca ggttctccgg ccgcttgggt ggagaggcta ttcggctatg  6180
actgggcaca acagacaatc ggctgctctg atgccgccgt gttccggctg tcagcgcagg  6240
ggcgcccggt tctttttgtc aagaccgacc tgtccggtgc cctgaatgaa ctgcaggacg  6300
aggcagcgcg gctatcgtgg ctggccacga cgggcgttcc ttgcgcagct gtgctcgacg  6360
ttgtcactga agcgggaagg gactggctgc tattgggcga agtgccgggg caggatctcc  6420
tgtcatctca ccttgctcct gccgagaaag tatccatcat ggctgatgca atgcggcggc  6480
tgcatacgct tgatccggct acctgcccat tcgaccacca agcgaaacat cgcatcgagc  6540
gagcacgtac tcggatggaa gccggtcttg tcgatcagga tgatctggac gaagagcatc  6600
aggggctcgc gccagccgaa ctgttcgcca ggctcaaggc gcgcatgccc gacggcgagg  6660
atctcgtcgt gacccatggc gatgcctgct tgccgaatat catggtggaa aatggccgct  6720
tttctggatt catcgactgt ggccggctgg gtgtggcgga ccgctatcag gacatagcgt  6780
tggctacccg tgatattgct gaagagcttg gcggcgaatg ggctgaccgc ttcctcgtgc  6840
tttacggtat cgccgctccc gattcgcagc gcatcgcctt ctatcgcctt cttgacgagt  6900
tcttctgagc gggactctgg ggttcgaaat gaccgaccaa gcgacgccca acctgccatc  6960
acgagatttc gattccaccg ccgccttcta tgaaaggttg ggcttcggaa tcgttttccg  7020
ggacgccggc tggatgatcc tccagcgcgg ggatctcatg ctggagttct tcgcccaccc  7080
```

-continued

```
caacttgttt attgcagctt ataatggtta caaataaagc aatagcatca caaatttcac  7140
aaataaagca tttttttcac tgcattctag ttgtggtttg tccaaactca tcaatgtatc  7200
ttatcatgtc tgtataccgt cgacctctag ctagagcttg gcgtaatcat ggtcatagct  7260
gtttcctgtg tgaaattgtt atccgctcac aattccacac aacatacgag ccggaagcat  7320
aaagtgtaaa gcctggggtg cctaatgagt gagctaactc acattaattg cgttgcgctc  7380
actgcccgct ttccagtcgg gaaacctgtc gtgccagctg cattaatgaa tcggccaacg  7440
cgcggggaga ggcggtttgc gtattgggcg ctcttccgct tcctcgctca ctgactcgct  7500
gcgctcggtc gttcggctgc ggcgagcggt atcagctcac tcaaaggcgg taatacggtt  7560
atccacagaa tcaggggata acgcaggaaa gaacatgtga gcaaaaggcc agcaaaaggc  7620
caggaaccgt aaaaaggccg cgttgctggc gtttttccat aggctccgcc cccctgacga  7680
gcatcacaaa aatcgacgct caagtcagag gtggcgaaac ccgacaggac tataaagata  7740
ccaggcgttt ccccctggaa gctccctcgt gcgctctcct gttccgaccc tgccgcttac  7800
cggatacctg tccgcctttc tcccttcggg aagcgtggcg ctttctcata gctcacgctg  7860
taggtatctc agttcggtgt aggtcgttcg ctccaagctg ggctgtgtgc acgaaccccc  7920
cgttcagccc gaccgctgcg ccttatccgg taactatcgt cttgagtcca acccggtaag  7980
acacgactta tcgccactgg cagcagccac tggtaacagg attagcagag cgaggtatgt  8040
aggcggtgct acagagttct tgaagtggtg gcctaactac ggctacacta gaagaacagt  8100
atttggtatc tgcgctctgc tgaagccagt taccttcgga aaaagagttg gtagctcttg  8160
atccggcaaa caaaccaccg ctggtagcgg tggttttttt gtttgcaagc agcagattac  8220
gcgcagaaaa aaaggatctc aagaagatcc tttgatcttt tctacggggt ctgacgctca  8280
gtggaacgaa aactcacgtt aagggatttt ggtcatgaga ttatcaaaaa ggatcttcac  8340
ctagatcctt ttaaattaaa aatgaagttt taaatcaatc taaagtatat atgagtaaac  8400
ttggtctgac agttaccaat gcttaatcag tgaggcacct atctcagcga tctgtctatt  8460
tcgttcatcc atagttgcct gactccccgt cgtgtagata actacgatac gggagggctt  8520
accatctggc cccagtgctg caatgatacc gcgagaccca cgctcaccgg ctccagattt  8580
atcagcaata aaccagccag ccggaagggc cgagcgcaga agtggtcctg caactttatc  8640
cgcctccatc cagtctatta attgttgccg ggaagctaga gtaagtagtt cgccagttaa  8700
tagtttgcgc aacgttgttg ccattgctac aggcatcgtg gtgtcacgct cgtcgtttgg  8760
tatggcttca ttcagctccg gttcccaacg atcaaggcga gttacatgat cccccatgtt  8820
gtgcaaaaaa gcggttagct ccttcggtcc tccgatcgtt gtcagaagta agttggccgc  8880
agtgttatca ctcatggtta tggcagcact gcataattct cttactgtca tgccatccgt  8940
aagatgcttt tctgtgactg gtgagtactc aaccaagtca ttctgagaat agtgtatgcg  9000
gcgaccgagt tgctcttgcc cggcgtcaat acgggataat accgcgccac atagcagaac  9060
tttaaaagtg ctcatcattg gaaaacgttc ttcggggcga aaactctcaa ggatcttacc  9120
gctgttgaga tccagttcga tgtaacccac tcgtgcaccc aactgatctt cagcatcttt  9180
tactttcacc agcgtttctg ggtgagcaaa aacaggaagg caaaatgccg caaaaaaggg  9240
aataagggcg acacggaaat gttgaatact catactcttc ctttttcaat attattgaag  9300
catttatcag ggttattgtc tcatgagcgg atacatattt gaatgtattt agaaaaataa  9360
acaaataggg gttccgcgca catttccccg aaaagtgcca cctgacgtc             9409

SEQ ID NO: 94          moltype = DNA  length = 9843
FEATURE                Location/Qualifiers
source                 1..9843
                       mol_type = other DNA
                       organism = synthetic construct
SEQUENCE: 94
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tggactttcc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gccaccatga agtgggtaac ctttatttcc cttcttttc tctttagctc ggcttattcc  960
aggggtgtgt ttcgtcgaga ctacaaagac gatgacgaca agagcgctgg cctgaagcca  1020
agctgcgcca aggaggtgaa gagctgcaag ggcagatgtt tcgaacggac cttcggcaac  1080
tgcagatgcg acgccgcctg cgtggaactg ggaaactgtt gtctggacta ccaggagaca  1140
tgtatcgagc ctgagcacat ctggacatgc aacaagttca gatgtggcga gaaaagactg  1200
actcggagtc tgtgcgcctg ttctgacgac tgcaaggaca agggcgattg ctgcatcaac  1260
tacagcagcg tgtgccaggg cgaaaagagc tgggtcgagg aaccctgcga gagcatcaac  1320
gagccccagt gccctgccgg atttgagaca cctcctaccc tgctcttctc cctggatggc  1380
ttcagagctg agtacctgca tacatgggga ggactgctgc ctgtgatcag caagctgaag  1440
aagtgcggca cctacacaaa gaacatgcgg cctgtctacc ctaccaagac cttcccaac  1500
cactacagca tcgtgaccgg cctgtacccc gagagccacg gcatcatcga caacaagatg  1560
tacgacccca aaatgaacgc cagcttcagc ctgaaatcta aggaaaagtt caaccctgag  1620
tggtataagg gcgagccaat ctgggtgaca gccaagtacc agggcctgaa gagcggcacc  1680
ttcttctggc ctggcagcga cgtggagatc aacggaatct tccctgatat ctacaagatg  1740
tataacggct ccgtgccttt cgaggagcgg atcttggctg ttcttcagtg gctgcagctg  1800
cccaaggacg agagacccca cttctacacc ctgtacctgg aagaacctga cagcagcggc  1860
cacagctacg gccctgtgtc tagcgaggtg atcaaggccc tgcaaagagt ggatggcatg  1920
gtgggcatgc tgatggatgg actgaaggaa ctgaacctcc atcgttgcct gaacctgatc  1980
```

```
ctgatctccg accacggcat ggaacagggc agctgtaaaa agtacatcta cctgaacaag  2040
tacctgggcg acgtgaagaa tatcaaggtg atctacgggc cggccgccag gctgcggcct  2100
agcgacgtgc ccgacaagta ttacagcttc aactacgagg gcatcgccag aaacctgtct  2160
tgcagagaac ccaatcaaca cttcaagcct tacctgaagc actttctgcc taagagactg  2220
cacttcgcca aaagcgacag aattgaaccc ctgacattct atctggaccc tcagtggcag  2280
ctggccctca atccttctga acgcaaatac tgcggtagcg gatttcacgg ctctgataac  2340
gtgttttcta acatgcaggc cctgtttgtg ggctacggcc ctggcttcaa gcacggaatc  2400
gaggctgaca ccttcgagaa catcgaagtt tacaatctga tgtgcgacct gctgaatctg  2460
accccagccc ctaacaacgg cacacacggc tctctgaatc acctgctcaa gaaccccgtg  2520
tataccccca aacaccctaa agaggtccat ccactggtgc agtgcccatt caccagaaac  2580
cctcgggaca accttggctg cagctgcaac cctagcatcc tccctatcga agatttccag  2640
acccagttta acctgactgt cgccgaagag aagatcatca agcacgaaac cctgccctac  2700
gggaggccca gagtgctgca gaaagaaaac acaatctgtc tgctgagcca gcaccagttt  2760
atgagcggct acagtcagga catcctgatg cctctgtgga ccagctacac cgtggaccgg  2820
aatgacagct tcagcaccga ggacttcagc aactgcctgt atcaggactt ccgcatccct  2880
ctgtcccctg tgcataagtg cagcttttac aagaacaaca ccaaggtgag ctacgggttt  2940
ctgagcccac cacaactgaa caaaaatagc tctggcatct actctgaggc gctgctgacc  3000
accaacatcg tgccaatgta ccagagcttc caggtgatct ggcggtactt ccatgatacc  3060
ctgcttcgga agtacgccga agaacggaac ggcgtgaacg tggtgtccgg cccagtgttc  3120
gacttcgact acgacggcag atgtgattcc cttgagaatc tgagacagaa gcggcgggtt  3180
atcagaaacc aggagatcct gattcctacc cacttcttca tcgtgctgac atcttgcaag  3240
gataccagcc aaacacctct gcactgcgag aacctggaca ccctggcctt catcctgcct  3300
caccggaccg ataatagcga atcctgtgtg cacggcaaac acgactctag ctgggtggaa  3360
gagctgctga tgctgcacag agcccggatc acagatgtgg aacacatcac cggcctgtcc  3420
ttctaccaac agagaaagga acccgtgtct gatatcctga agctgaaaac ccacctgcct  3480
accttcagcc aggaggacct gatcgttaac gatgcacaca agagtgaggt tgctcatcgg  3540
tttaaagatt tgggagaaga aaatttcaaa gccttggtgt tgattgcctt tgctcagtat  3600
cttcagcagt gtccatttga agatcatgta aaattagtga atgaagtaac tgaatttgca  3660
aaaacatgtg ttgctgatga gtcagctgaa aattgtgaca aatcacttca tacccttttt  3720
ggagacaaat tatgcacagt tgcaactctt cgtgaaacct atggtgaaat ggctgactgc  3780
tgtgcaaaac aagaacctga gagaaatgaa tgcttcttgc aacacaaaga tgacaaccca  3840
aacctccccc gattggtgag accagaggtt gatgtgatgt gcactgcttt tcatgacaat  3900
gaagagacat ttttgaaaaa atacttatat gaaattgcca gaagacatcc ttacttttat  3960
gccccggaac tccttttctt tgctaaaagg tataaagctg cttttacaga atgttgccaa  4020
gctgctgata aagctgcctg cctgttgcca aagctcgatg aacttcggga tgaagggaag  4080
gcttcgtctg ccaaacagag actcaagtgt gccagtctcc aaaaatttgg agaaagagct  4140
ttcaaagcat gggcagtagc tcgcctgagc cagagatttc ccaaagctga gtttgcagaa  4200
gtttccaagt tagtgacaga tcttaccaaa gtccacacgg aatgctgcca tggagatctg  4260
cttgaatgtg ctgatgacag ggcggacctt gccaagtata tctgtgaaaa tcaagattcg  4320
atctccagta aactgaagga atgctgtgaa aaacctctgt tggaaaaatc ccactgcatt  4380
gccgaagtgg aaaatgatga gatgcctgct gacttgcctt cattagctgc tgattttgtt  4440
gaaagtaagg atgtttgcaa aaactatgct gaggcaaagg atgtcttcct gggcatgttt  4500
ttgtatgaat atgcaagaag gcatcctgat tactctgtcg tgctgctgct gagacttgcc  4560
aagacatatg aaaccacact cgagaagtgc tgtgccgctg cagatcctca tgaatgctat  4620
gccaaagtgt tcgatgaatt taaacctctt gtggaagagc ctcagaattt aatcaaacaa  4680
aattgtgagc tttttgagca gcttggagag tacaaattcc agaatgcgct attagttcgt  4740
tacaccaaga aagtacccca agtgtcaact ccaactcttg tagaggtctc aagaaaccta  4800
ggaaaagtgg gcagcaaatg ttgtaaacat cctgaagcaa aaagaatgcc ctgtgcagaa  4860
gactatctat ccgtggtcct gaaccagtta tgtgtgttgc atgagaaaac gccagtaagt  4920
gacagagtca ccaaatgctg cacagaatcc ttggtgaaca ggcgaccatg cttttcagct  4980
ctggaagtcg atgaaacata cgttcccaaa gagtttaatg ctgaaacatt caccttccat  5040
gcagatatat gcacactttc tgagaaggag agacaaatca agaaacaaac tgcacttgtt  5100
gagctcgtga aacacaagcc caaggcaaca aaagagcaac tgaaagctgt tatggatgat  5160
ttcgcagctt ttgtagagaa gtgctgcaag gctgacgata aggagacctg ctttgccgag  5220
gagggtaaaa aacttgttgc tgcaagtcaa gctgccttag gcttatgaca attacgatta  5280
gcactatcca attacgatta gcactatcca attacgatta gcactatcgg taccgagctc  5340
ggatccacta gtccagtgtg gtggaattct gcagatatcc agcacagtgg cggccgctcg  5400
agtctagagg gcccgtttaa acccgctgat cagcctcgac tgtgccttct agttgccagc  5460
catctgttgt ttgcccctcc cccgtgcctt ccttgaccct ggaaggtgcc actcccactg  5520
tcctttccta ataaaatgag gaaattgcat cgcattgtct gagtaggtgt cattctattc  5580
tggggggtgg ggtggggcag gacagcaagg gggaggattg ggaagacaat agcaggcatg  5640
ctggggatgc ggtgggctct atggcttctg aggcggaaag aaccagctgg ggctctaggg  5700
ggtatcccca cgcgccctgt agcggcgcat taagcgcggc gggtgtggtg gttacgcgca  5760
gcgtgaccgc tacacttgcc agcgccctag cgcccgctcc tttcgctttc ttcccttcct  5820
ttctcgccac gttcgccggc tttccccgtc aagctctaaa tcgggggctc cctttagggt  5880
tccgatttag tgctttacgg cacctcgacc ccaaaaaact tgattagggt gatggttcac  5940
gtagtgggcc atcgccctga tagacggttt ttcgcccttt gacgttggag tccacgttct  6000
ttaatagtgg actcttgttc caaactggaa caacactcaa ccctatctcg gtctattctt  6060
ttgatttata agggattttg ccgatttcgg cctattggtt aaaaaatgag ctgatttaac  6120
aaaaatttaa cgcgaattaa ttctgtggaa tgtgtgtcag ttagggtgtg gaaagtcccc  6180
aggctcccca gcaggcagaa gtatgcaaag catgcatctc aattagtcag caaccaggtg  6240
tggaaagtcc ccaggctccc cagcaggcag aagtatgcaa agcatgcatc tcaattagtc  6300
agcaaccata gtcccgcccc taactccgcc catcccgccc ctaactccgc ccagttccgc  6360
ccattctccg ccccatggct gactaatttt ttttatttat gcagaggccg aggccgcctc  6420
tgcctctgag ctattccaga agtagtgagg aggctttttt ggaggcctag gcttttgcaa  6480
aaagctcccg ggagcttgta tatccatttt cggatctgat caagagacag gatgaggatc  6540
gtttcgcatg attgaacaag atggattgca cgcaggttct ccggccgctt gggtggagag  6600
gctattcggc tatgactggg cacaacagac aatcggctgc tctgatgccg ccgtgttccg  6660
gctgtcagcg caggggcgcc cggttctttt tgtcaagacc gacctgtccg gtgccctgaa  6720
```

```
tgaactgcag gacgaggcag cgcggctatc gtggctggcc acgacgggcg ttccttgcgc  6780
agctgtgctc gacgttgtca ctgaagcggg aagggactgg ctgctattgg gcgaagtgcc  6840
ggggcaggat ctcctgtcat ctcaccttgc tcctgccgag aaagtatcca tcatggctga  6900
tgcaatgcgg cggctgcata cgcttgatcc ggctacctgc ccattcgacc accaagcgaa  6960
acatcgcatc gagcgagcac gtactcggat ggaagccggt cttgtcgatc aggatgatct  7020
ggacgaagag catcaggggc tcgcgccagc cgaactgttc gccaggctca aggcgcgcat  7080
gcccgacggc gaggatctcg tcgtgaccca tggcgatgcc tgcttgccga atatcatggt  7140
ggaaaatggc cgcttttctg gattcatcga ctgtggccgg ctgggtgtgg cggaccgcta  7200
tcaggacata gcgttggcta cccgtgatat tgctgaagag cttggcggcg aatgggctga  7260
ccgcttcctc gtgctttacg gtatcgccgc tcccgattcg cagcgcatcg ccttctatcg  7320
ccttcttgac gagttcttct gagcgggact ctggggttcg aaatgaccga ccaagcgacg  7380
cccaacctgc catcacgaga tttcgattcc accgccgcct tctatgaaag gttgggcttc  7440
ggaatcgttt tccgggacgc cggctggatg atcctccagc gcggggatct catgctggag  7500
ttcttcgccc accccaactt gtttattgca gcttataatg gttacaaata aagcaatagc  7560
atcacaaatt tcacaaataa agcatttttt tcactgcatt ctagttgtgg tttgtccaaa  7620
ctcatcaatg tatcttatca tgtctgtata ccgtcgacct ctagctagag cttggcgtaa  7680
tcatggtcat agctgtttcc tgtgtgaaat tgttatccgc tcacaattcc acacaacata  7740
cgagccggaa gcataaagtg taaagcctgg ggtgcctaat gagtgagcta actcacatta  7800
attgcgttgc gctcactgcc cgctttccag tcgggaaacc tgtcgtgcca gctgcattaa  7860
tgaatcggcc aacgcgcggg gagaggcggt ttgcgtattg ggcgctcttc cgcttcctcg  7920
ctcactgact cgctgcgctc ggtcgttcgg ctgcggcgag cggtatcagc tcactcaaag  7980
gcggtaatac ggttatccac agaatcaggg gataacgcag gaaagaacat gtgagcaaaa  8040
ggccagcaaa aggccaggaa ccgtaaaaag gccgcgttgc tggcgttttt ccataggctc  8100
cgcccccctg acgagcatca caaaaatcga cgctcaagtc agaggtggcg aaacccgaca  8160
ggactataaa gataccaggc gtttccccct ggaagctccc tcgtgcgctc tcctgttccg  8220
accctgccgc ttaccggata cctgtccgcc tttctccctt cgggaagcgt ggcgctttct  8280
catagctcac gctgtaggta tctcagttcg gtgtaggtcg ttcgctccaa gctgggctgt  8340
gtgcacgaac cccccgttca gcccgaccgc tgcgccttat ccggtaacta tcgtcttgag  8400
tccaacccgg taagacacga cttatcgcca ctggcagcag ccactggtaa caggattagc  8460
agagcgaggt atgtaggcgg tgctacagag ttcttgaagt ggtggcctaa ctacggctac  8520
actagaagaa cagtatttgg tatctgcgct ctgctgaagc cagttacctt cggaaaaaga  8580
gttggtagct cttgatccgg caaacaaacc accgctggta gcggtggttt ttttgtttgc  8640
aagcagcaga ttacgcgcag aaaaaaagga tctcaagaag atcctttgat cttttctacg  8700
gggtctgacg ctcagtggaa cgaaaactca cgttaaggga ttttggtcat gagattatca  8760
aaaaggatct tcacctagat ccttttaaat taaaaatgaa gttttaaatc aatctaaagt  8820
atatatgagt aaacttggtc tgacagttac caatgcttaa tcagtgaggc acctatctca  8880
gcgatctgtc tatttcgttc atccatagtt gcctgactcc ccgtcgtgta gataactacg  8940
atacgggagg gcttaccatc tggccccagt gctgcaatga taccgcgaga cccacgctca  9000
ccggctccag atttatcagc aataaaccag ccagccggaa gggccgagcg cagaagtggt  9060
cctgcaactt tatccgcctc catccagtct attaattgtt gccgggaagc tagagtaagt  9120
agttcgccag ttaatagttt gcgcaacgtt gttgccattg ctacaggcat cgtggtgtca  9180
cgctcgtcgt ttggtatggc ttcattcagc tccggttccc aacgatcaag gcgagttaca  9240
tgatccccca tgttgtgcaa aaaagcggtt agctccttcg gtcctccgat cgttgtcaga  9300
agtaagttgg ccgcagtgtt atcactcatg gttatggcag cactgcataa ttctcttact  9360
gtcatgccat ccgtaagatg cttttctgtg actggtgagt actcaaccaa gtcattctga  9420
gaatagtgta tgcggcgacc gagttgctct tgcccggcgt caatacggga taataccgcg  9480
ccacatagca gaactttaaa agtgctcatc attggaaaac gttcttcggg gcgaaaactc  9540
tcaaggatct taccgctgtt gagatccagt tcgatgtaac ccactcgtgc acccaactga  9600
tcttcagcat cttttacttt caccagcgtt tctgggtgag caaaaacagg aaggcaaaat  9660
gccgcaaaaa agggaataag ggcgacacgg aaatgttgaa tactcatact cttccttttt  9720
caatattatt gaagcattta tcagggttat tgtctcatga gcggatacat atttgaatgt  9780
atttagaaaa ataaacaaat aggggttccg cgcacatttc cccgaaaagt gccacctgac  9840
gtc                                                                9843
```

```
SEQ ID NO: 95          moltype = DNA  length = 11262
FEATURE                Location/Qualifiers
source                 1..11262
                       mol_type = other DNA
                       organism = synthetic construct
SEQUENCE: 95
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttaagatt  240
atagttgtca tttgaacttg gggataaagg agacatctat gacttggctg gaaaagacag  300
agctaatgta cattgcaaag cacatattta tagcaggaaa atgggaagat ttctctttaa  360
ttctggagat ggagtgggga tggggagagt agactactca ttttaagggt gaaacattgg  420
aattcaactt gtttgatgtt atattaattg gtggttaatt actaagctaa gtacgtataa  480
aacttttatc tatggctagc ttgtcccccc aaagtcatgc aatatagtga actggctttc  540
gcactttaaa ttattcattg atcatgtaat gattcagatg attcatcttc caagatggac  600
actgaaacta acactcatag taggttgtgg tttaaagagt ggaacaaccg ccagtctcat  660
tagtggaaat tgtgatggtt gaatttatca aggatgaaca tacacggtct tctttctgag  720
atttcttta agattttcgc acagataatc tatttcttag gttttggaga gaaaacttga  780
attttattga tccctcagaa ctcaatcttt cagatttcaa aggagctatt tcttttaatg  840
gggactctgt taatatttat aaaagctctt cacaggatgg agggtgggag ggaaactcca  900
tcccaacaag acaaaaagaa tgaagcatga ggctccacct agttcatcac tgctccttga  960
aatacatcag tattgaaaga cacatccacc ccaccccaa cccagcccta ttgctgttcc  1020
agctcaagag tcagaggtcc cgaagctgta gctcttctac aatctgctgc tctgtgactt  1080
caagtctgtt gtctgcaaag aaaactattg ggttcccaag caagagaggc acatctggta  1140
```

-continued

```
ggacagattt tgtgattgca aaagaagggg gaaaaaaaga aagaaagaaa agacctctct  1200
atacaagata accagaggca tcaaactgaa atcctcctgt ggaaaataag ctagtacttc  1260
tgggcctgat ggtgtagtga aaacctgtgc ttgaggatac attacagtga aagagcaaag  1320
tgaatagtaa gtagctatta cttacctcct tagggaggtg tgttgtttgt ctgtacatcc  1380
cccacagcac ctagcacagt accttgcatc tcacctgcca ctcactaaaa agtctatcaa  1440
gttagttaat tatcgagaca acgccctcag aaatgagaga acagtaccct cttatccttg  1500
ctgcactttc cagcactgat acgctgccta aaagaggact agggcacagg tttgaattaa  1560
tgtcacaaaa ctggatgggc aagttacaac ggtgttgatt aaggaaacag aactcatggt  1620
gcaccggata tctccatcct gatgaaccct tggaaaaatg ccaaagatgc atatccccag  1680
gcaaatgcct gattagtctg ggattgatag attggtctag gattcagccc tactgggaag  1740
atgtctaaat tataatcagt gtagaaagcg aagttctcct agaagaagag gcaaaggtta  1800
aaaagaagaa aagaaaagaa agtgaagtcc tttctccccc aaaacctctc atcaatcaat  1860
cagggtaaca aacagaacac tagggctctg tctgtggacc aaacccaaaa gccctgcggt  1920
cagggccagg agggtagatc atgtgtttgt ggcaacttcc tctgtgggct tttgcccagg  1980
tctgtcccca agcatacgat ggccaaaact tctgcaccag agcagcatcc tgtgtaacac  2040
agtcaggtcc agcagttagg gaaaactgcc cactcagagt agataatatc tggaaggaat  2100
gactgtttgg gaaaagttcc aatgctagtt cagtgccaac ccttccccac cttctccagc  2160
tctctcccac tggttcctcc cctctcaact gctctggttc ttataaaaac ctcacagcct  2220
tccactaaca tcccgtagga gcctctctcc ctactgctgc tacacaagac cctgagactg  2280
acctgcagga cgaaaccctc tggctaacta gagaacccac tgcttactgg cttatcgaaa  2340
ttaatacgac tcactatagg gagacccaag ctggctagcg ccaccatgaa gtgggtaacc  2400
tttatttccc ttcttttttct ctttagctcg gcttattcca ggggtgtgtt tcgtcgagac  2460
tacaaagacg atgacgacaa gagcgctggc ctgaagccaa gctgcgccaa ggaggtgaag  2520
agctgcaagg gcagatgttt cgaacggacc ttcggcaact gcagatgcga cgccgcctgc  2580
gtggaactgg gaaactgttg tctggactac caggagacat gtatcgagcc tgagcacatc  2640
tggacatgca acaagttcag atgtggcgag aaaagactga ctcggagtct gtgcgcctgt  2700
tctgacgact gcaaggacaa gggcgattgc tgcatcaact acagcagcgt gtgccagggc  2760
gaaaagagct gggtcgagga accctgcgag agcatcaacg agccccagtg ccctgccgga  2820
tttgagacac ctcctaccct gctcttctcc ctggatggct tcagagctga gtacctgcat  2880
acatggggag gactgctgcc tgtgatcagc aagctgaaga agtgcggcac ctacacaaag  2940
aacatgcggc ctgtctaccc taccaagacc ttccccaacc actacagcat cgtgaccggc  3000
ctgtaccccg agagccacgg catcatcgac aacaagatgt acgaccccaa aatgaacgcc  3060
agcttcagcc tgaaatctaa ggaaaagttc aaccctgagt ggtataaggg cgagccaatc  3120
tgggtgacag ccaagtacca gggcctgaag agcggcacct tcttctggcc tggcagcgac  3180
gtggagatca acggaatctt ccctgatatc tacaagatgt ataacggctc cgtgcctttc  3240
gaggagcgga tcttggctgt tcttcagtgg ctgcagctgc ccaaggacga gagaccccac  3300
ttctacaccc tgtacctgga agaacctgac agcagcggcc acagctacgg ccctgtgtct  3360
agcgaggtga tcaaggccct gcaaagagtg gatggcatgg tgggcatgct gatggatgga  3420
ctgaaggaac tgaacctcca tcgttgcctg aacctgatcc tgatctccga ccacggcatg  3480
gaacagggca gctgtaaaaa gtacatctac ctgaacaagt acctgggcga cgtgaagaat  3540
atcaaggtga tctacgggcc ggccgccagg ctgcggccta gcgacgtgcc cgacaagtat  3600
tacagcttca actacgaggg catcgccaga aacctgtctt gcagagaacc caatcaacac  3660
ttcaagcctt acctgaagca ctttctgcct aagagactgc acttcgccaa aagcgacaga  3720
attgaacccc tgacattcta tctggaccct cagtggcagc tggccctcaa tccttctgaa  3780
cgcaaatact gcggtagcgg atttcacggc tctgataacg tgttttctaa catgcaggcc  3840
ctgtttgtgg gctacggccc tggcttcaag cacggaatcg aggctgacac cttcgagaac  3900
atcgaagttt acaatctgat gtgcgacctg ctgaatctga ccccagcccc taacaacggc  3960
acacacggct ctctgaatca cctgctcaag aaccccgtgt ataccccccaa acaccctaaa  4020
gaggtccatc cactggtgca gtgcccattc accagaaacc ctcgggacaa ccttggctgc  4080
agctgcaacc ctagcatcct ccctatcgaa gatttccaga cccagtttaa cctgactgtc  4140
gccgaagaga agatcatcaa gcacgaaacc ctgccctacg ggaggcccag agtgctgcag  4200
aaagaaaaca caatctgtct gctgagccag caccagttta tgagcggcta cagtcaggac  4260
atcctgatgc ctctgtggac cagctacacc gtggaccgga atgacagctt cagcaccgag  4320
gacttcagca actgcctgta tcaggacttc cgcatccctc tgtcccctgt gcataagtgc  4380
agcttttaca agaacaacac caaggtgagc tacgggtttc tgagcccacc acaactgaac  4440
aaaaatagct ctggcatcta ctctgaggcg ctgctgacca ccaacatcgt gccaatgtac  4500
cagagcttcc aggtgatctg gcggtacttc catgataccc tgcttcggaa gtacgccgaa  4560
gaacggaacg gcgtgaacgt ggtgtccggc ccagtgttcg acttcgacta cgacggcaga  4620
tgtgattccc ttgagaatct gagacagaag cggcgggtta tcagaaacca ggagatcctg  4680
attcctaccc acttcttcat cgtgctgaca tcttgcaagg ataccagcca aacacctctg  4740
cactgcgaga acctggacac cctggccttc atcctgcctc accggaccga taatagcgaa  4800
tcctgtgtgc acggcaaaca cgactctagc tgggtggaag agctgctgat gctgcacaga  4860
gcccggatca cagatgtgga acacatcacc ggcctgtcct tctaccaaca gagaaaggaa  4920
cccgtgtctg atatcctgaa gctgaaaacc cacctgccta ccttcagcca ggaggacctg  4980
atcgttaacg atgcacacaa gagtgaggtt gctcatcggt ttaaagattt gggagaagaa  5040
aatttcaaag ccttggtgtt gattgccttt gctcagtatc ttcagcagtg tccatttgaa  5100
gatcatgtaa aattagtgaa tgaagtaact gaatttgcaa aaacatgtgt tgctgatgag  5160
tcagctgaaa attgtgacaa atcacttcat acccttttttg gagacaaatt atgcacagtt  5220
gcaactcttc gtgaaaccta tggtgaaatg gctgactgct gtgcaaaaca agaacctgag  5280
agaaatgaat gcttcttgca acacaaagat gacaacccaa acctcccccg attggtgaga  5340
ccagaggttg atgtgatgtg cactgctttt catgacaatg aagagacatt tttgaaaaaa  5400
tacttatatg aaattgccag aagacatcct tacttttatg ccccggaact cctttttcttt  5460
gctaaaaggt ataaagctgc ttttacagaa tgttgccaag ctgctgataa agctgcctgc  5520
ctgttgccaa agctcgatga acttcgggat gaagggaagg cttcgtctgc caaacagaga  5580
ctcaagtgtg ccagtctcca aaaatttgga gaaagagctt tcaaagcatg ggcagtagct  5640
cgcctgagcc agagatttcc caaagctgag tttgcagaag tttccaagtt agtgacagat  5700
cttaccaaag tccacacgga atgctgccat ggagatctgc ttgaatgtgc tgatgacagg  5760
gcggaccttg ccaagtatat ctgtgaaaat caagattcga tctccagtaa actgaaggaa  5820
tgctgtgaaa aacctctgtt ggaaaaatcc cactgcattg ccgaagtgga aaatgatgag  5880
```

-continued

```
atgcctgctg acttgccttc attagctgct gattttgttg aaagtaagga tgtttgcaaa  5940
aactatgctg aggcaaagga tgtcttcctg ggcatgtttt tgtatgaata tgcaagaagg  6000
catcctgatt actctgtcgt gctgctgctg agacttgcca agacatatga aaccacactc  6060
gagaagtgct gtgccgctgc agatcctcat gaatgctatg ccaaagtgtt cgatgaattt  6120
aaacctcttg tggaagagcc tcagaattta atcaaacaaa attgtgagct tttgagcag  6180
cttggagagt acaaattcca gaatgcgcta ttagttcgtt acaccaagaa agtaccccaa  6240
gtgtcaactc caactcttgt agaggtctca agaaacctag gaaaagtggg cagcaaatgt  6300
tgtaaacatc ctgaagcaaa aagaatgccc tgtgcagaag actatctatc cgtggtcctg  6360
aaccagttat gtgtgttgca tgagaaaacg ccagtaagtg acagagtcac caaatgctgc  6420
acagaatcct tggtgaacag gcgaccatgc ttttcagctc tggaagtcga tgaaacatac  6480
gttcccaaag agtttaatgc tgaaacattc accttccatg cagatatatg cacactttct  6540
gagaaggaga gacaaatcaa gaaacaaact gcacttgttg agctcgtgaa acacaagccc  6600
aaggcaacaa aagagcaact gaaagctgtt atggatgatt tcgcagcttt tgtagagaag  6660
tgctgcaagg ctgacgataa ggagacctgc tttgccgagg agggtaaaaa acttgttgct  6720
gcaagtcaag ctgccttagg cttatgaggt accgagctcg gatccactag tccagtgtgg  6780
tggaattctg cagatatcca gcacagtggc ggccgctcga gtctagaggg cccgtttaaa  6840
cccgctgatc agcctcgact gtgccttcta gttgccagcc atctgttgtt tgcccctccc  6900
ccgtgccttc cttgaccctg gaaggtgcca ctcccactgt cctttcctaa taaaatgagg  6960
aaattgcatc gcattgtctg agtaggtgtc attctattct ggggggtggg gtggggcagg  7020
acagcaaggg ggaggattgg gaagacaata gcaggcatgc tggggatgcg gtgggctcta  7080
tggcttctga ggcggaaaga accagctggg gctctagggg gtatccccac gcgccctgta  7140
gcggcgcatt aagcgcggcg ggtgtggtgg ttacgcgcag cgtgaccgct acacttgcca  7200
gcgccctagc gcccgctcct ttcgctttct tcccttcctt tctcgccacg ttcgccggct  7260
ttccccgtca agctctaaat cggggggctcc ctttagggtt ccgatttagt gctttacggc  7320
acctcgaccc caaaaaactt gattagggtg atggttcacg tagtgggcca tcgccctgat  7380
agacggtttt tcgccctttg acgttggagt ccacgttctt taatagtgga ctcttgttcc  7440
aaactggaac aacactcaac cctatctcgg tctattcttt tgatttataa gggattttgc  7500
cgatttcggc ctattggtta aaaaatgagc tgatttaaca aaaatttaac gcgaattaat  7560
tctgtggaat gtgtgtcagt tagggtgtgg aaagtcccca ggctccccag caggcagaag  7620
tatgcaaagc atgcatctca attagtcagc aaccaggtgt ggaaagtccc caggctcccc  7680
agcaggcaga agtatgcaaa gcatgcatct caattagtca gcaaccatag tcccgcccct  7740
aactccgccc atcccgcccc taactccgcc cagttccgcc cattctccgc cccatggctg  7800
actaattttt tttatttatg cagaggccga ggccgcctct gcctctgagc tattccagaa  7860
gtagtgagga ggcttttttg gaggcctagg cttttgcaaa aagctcccgg gagcttgtat  7920
atccattttc ggatctgatc aagagacagg atgaggatcg tttcgcatga ttgaacaaga  7980
tggattgcac gcaggttctc cggccgcttg ggtggagagg ctattcggct atgactgggc  8040
acaacagaca atcggctgct ctgatgccgc cgtgttccgg ctgtcagcgc aggggcgccc  8100
ggttcttttt gtcaagaccg acctgtccgg tgccctgaat gaactgcagg acgaggcagc  8160
gcggctatcg tggctggcca cgacgggcgt tccttgcgca gctgtgctcg acgttgtcac  8220
tgaagcggga agggactggc tgctattggg cgaagtgccg gggcaggatc tcctgtcatc  8280
tcaccttgct cctgccgaga aagtatccat catggctgat gcaatgcggc ggctgcatac  8340
gcttgatccg gctacctgcc cattcgacca ccaagcgaaa catcgcatcg agcgagcacg  8400
tactcggatg gaagccggtc ttgtcgatca ggatgatctg gacgaagagc atcaggggct  8460
cgcgccagcc gaactgttcg ccaggctcaa ggcgcgcatg cccgacggcg aggatctcgt  8520
cgtgacccat ggcgatgcct gcttgccgaa tatcatggtg gaaaatggcc gcttttctgg  8580
attcatcgac tgtggccggc tgggtgtggc ggaccgctat caggacatag cgttggctac  8640
ccgtgatatt gctgaagagc ttggcggcga atgggctgac cgcttcctcg tgctttacgg  8700
tatcgccgct cccgattcgc agcgcatcgc cttctatcgc cttcttgacg agttcttctg  8760
agcgggactc tggggttcga aatgaccgac caagcgacgc ccaacctgcc atcacgagat  8820
ttcgattcca ccgccgcctt ctatgaaagg ttgggcttcg gaatcgtttt ccgggacgcc  8880
ggctggatga tcctccagcg cggggatctc atgctggagt tcttcgccca ccccaacttg  8940
tttattgcag cttataatgg ttacaaataa agcaatagca tcacaaattt cacaaataaa  9000
gcattttttt cactgcattc tagttgtggt ttgtccaaac tcatcaatgt atcttatcat  9060
gtctgtatac cgtcgacctc tagctagagc ttggcgtaat catggtcata gctgtttcct  9120
gtgtgaaatt gttatccgct cacaattcca cacaacatac gagccggaag cataaagtgt  9180
aaagcctggg gtgcctaatg agtgagctaa ctcacattaa ttgcgttgcg ctcactgccc  9240
gctttccagt cgggaaacct gtcgtgccag ctgcattaat gaatcggcca acgcgcgggg  9300
agaggcggtt tgcgtattgg gcgctcttcc gcttcctcgc tcactgactc gctgcgctcg  9360
gtcgttcggc tgcggcgagc ggtatcagct cactcaaagg cggtaatacg gttatccaca  9420
gaatcagggg ataacgcagg aaagaacatg tgagcaaaag gccagcaaaa ggccaggaac  9480
cgtaaaaagg ccgcgttgct ggcgtttttc cataggctcc gcccccctga cgagcatcac  9540
aaaaatcgac gctcaagtca gaggtggcga aacccgacag gactataaag ataccaggcg  9600
tttccccctg gaagctccct cgtgcgctct cctgttccga ccctgccgct taccggatac  9660
ctgtccgcct ttctcccttc gggaagcgtg gcgctttctc atagctcacg ctgtaggtat  9720
ctcagttcgg tgtaggtcgt tcgctccaag ctgggctgtg tgcacgaacc ccccgttcag  9780
cccgaccgct gcgccttatc cggtaactat cgtcttgagt ccaacccggt aagacacgac  9840
ttatcgccac tggcagcagc cactggtaac aggattagca gagcgaggta tgtaggcggt  9900
gctacagagt tcttgaagtg gtggcctaac tacggctaca ctagaagaac agtatttggt  9960
atctgcgctc tgctgaagcc agttaccttc ggaaaaagag ttggtagctc ttgatccggc  10020
aaacaaacca ccgctggtag cggtggtttt tttgtttgca agcagcagat tacgcgcaga  10080
aaaaaaggat ctcaagaaga tcctttgatc ttttctacgg ggtctgacgc tcagtggaac  10140
gaaaactcac gttaagggat tttggtcatg agattatcaa aaaggatctt cacctagatc  10200
cttttaaatt aaaaatgaag ttttaaatca atctaaagta tatatgagta aacttggtct  10260
gacagttacc aatgcttaat cagtgaggca cctatctcag cgatctgtct atttcgttca  10320
tccatagttg cctgactccc cgtcgtgtag ataactacga tacgggaggg cttaccatct  10380
ggccccagtg ctgcaatgat accgcgagac ccacgctcac cggctccaga tttatcagca  10440
ataaaccagc cagccggaag ggccgagcgc agaagtggtc ctgcaacttt atccgcctcc  10500
atccagtcta ttaattgttg ccgggaagct agagtaagta gttcgccagt taatagtttg  10560
cgcaacgttg ttgccattgc tacaggcatc gtggtgtcac gctcgtcgtt tggtatggct  10620
```

```
tcattcagct ccggttccca acgatcaagg cgagttacat gatcccccat gttgtgcaaa  10680
aaagcggtta gctccttcgg tcctccgatc gttgtcagaa gtaagttggc cgcagtgtta  10740
tcactcatgg ttatggcagc actgcataat tctcttactg tcatgccatc cgtaagatgc  10800
ttttctgtga ctggtgagta ctcaaccaag tcattctgag aatagtgtat gcggcgaccg  10860
agttgctctt gcccggcgtc aatacgggat aataccgcgc cacatagcag aactttaaaa  10920
gtgctcatca ttggaaaacg ttcttcgggg cgaaaactct caaggatctt accgctgttg  10980
agatccagtt cgatgtaacc cactcgtgca cccaactgat cttcagcatc ttttactttc  11040
accagcgttt ctgggtgagc aaaaacagga aggcaaaatg ccgcaaaaaa gggaataagg  11100
gcgacacgga aatgttgaat actcatactc ttcctttttc aatattattg aagcatttat  11160
cagggttatt gtctcatgag cggatacata tttgaatgta tttagaaaaa taaacaaata  11220
ggggttccgc gcacatttcc ccgaaaagtg ccacctgacg tc                    11262

SEQ ID NO: 96          moltype = DNA  length = 10549
FEATURE                Location/Qualifiers
source                 1..10549
                       mol_type = other DNA
                       organism = synthetic construct
SEQUENCE: 96
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttataaat  240
gttttgtaga ataaaaaaaa aaaaagttct tcaaaagaaa tctcaaatct ccaaatggaa  300
acaggtaaaa gtggagctcc cctggttcca cggagaacct tttttgagga aacttaggca  360
actcgcaggt accttatgtc atgagacaga gtttgaaaac tacaattgac tatctctaaa  420
tttcctccca ggtctaaaat gtgatgatag ttactacttc agtacatcat ccttaaggaa  480
aattattagg tccacactgt ttctatcctt tgaattttac acataaattt tgtaatcaaa  540
agtttatttg taatatcaga tggaatcaga taattgcttt ttgttttttc cactgacagg  600
aacataagat tttgttgtgt agcttaagtc aaacgcagtt tggaatatat atttttttaaa  660
aattgtaact tacatatcca aatacaattt ttcaagaagt agagtattca gtagaaatta  720
atctgtgaaa gaagaggaat tcagcagtgg cctatttgat gaatgattta acgtgcttat  780
ttcttccctt tcatcaaaac tctgtgtccc cttgtttgcc ccctctgact tcatactctg  840
gagttgacca agatccctct tccatcggat tgttctggga attttgaaat aatctgcttt  900
ttcctctctt tcccctgttg cttctgatgc cttagaatta cattttcctc gctgatttag  960
tttagaaaag agaaaagagc ttccatgact agtagattat cacttttggg tttgctcttg  1020
gaagtgacaa gatgctagga tccctctttg gaatgtaaaa tttatctctt atatagaaag  1080
gatataaatg tagcaccaga gactataaaa ctctgatact atctactgta ctgtatagct  1140
gaacgccaca atgtgtctgg taatctattg actatcataa atgctatttc tacagaaaag  1200
ttaggaggtc catatttcgg gcaaccaatg tatagctgaa tgcagaacag tcatagttgg  1260
gtactaacca tatatatgat ttatccatca acaggtgcat atgctcagaa attctgtatc  1320
cataagaaat cagactactt tcttttcctt ttgcaagtaa attgaattta gcctgagagg  1380
ctgaggggaa attttcacat ataagccacg gttttgtgtt ttgtgttttg ttttgtttat  1440
agatatagta ctaactggat ggatgcgata aaattcatag gtggtactaa gatacaatag  1500
gatttgtgaa atggacaatt gtcttgcata aatagcaagt aaaaaatcaa gcctgtcctt  1560
cataaaaatt ttattctggg gtgtctctgg ctaactagag aacccactgc ttactggctt  1620
atcgaaatta atacgactca ctatagggag acccaagctg gctagcgcca ccatgaagtg  1680
ggtaaccttt atttcccttc tttttctctt tagctcggct tattccaggg gtgtgtttcg  1740
tcgagactac aaagacgatg acgacaagag cgctggcctg aagccaagct gcgccaagga  1800
ggtgaagagc tgcaagggca gatgtttcga acggaccttc ggcaactgca gatgcgacgc  1860
cgcctgcgtg gaactgggaa actgttgtct ggactaccag gagacatgta tcgagcctga  1920
gcacatctgg acatgcaaca agttcagatg tggcgagaaa agactgactc ggagtctgtg  1980
cgcctgttct gacgactgca aggacaaggg cgattgctgc atcaactaca gcagcgtgtg  2040
ccagggcgaa aagagctggg tcgaggaacc ctgcgagagc atcaacgagc cccagtgccc  2100
tgccggattt gagacacctc ctaccctgct cttctccctg gatggcttca gagctgagta  2160
cctgcataca tggggaggac tgctgcctgt gatcagcaag ctgaagaagt gcggcaccta  2220
cacaaagaac atgcggcctg tctaccctac caagaccttc cccaaccact acagcatcgt  2280
gaccggcctg taccccgaga gccacggcat catcgacaac aagatgtacg accccaaaat  2340
gaacgccagc ttcagcctga aatctaagga aaagttcaac cctgagtggt ataagggcga  2400
gccaatctgg gtgacagcca agtaccaggg cctgaagagc ggcaccttct tctggcctgg  2460
cagcgacgtg gagatcaacg gaatcttccc tgatatctac aagatgtata acggctccgt  2520
gcctttcgag gagcggatct tggctgttct tcagtggctg cagctgccca aggacgagag  2580
accccacttc tacaccctgt acctggaaga acctgacagc agcggccaca gctacggccc  2640
tgtgtctagc gaggtgatca aggccctgca aagagtggat ggcatggtgg gcatgctgat  2700
ggatggactg aaggaactga acctccatcg ttgcctgaac ctgatcctga tctccgacca  2760
cggcatggaa cagggcagct gtaaaaagta catctacctg aacaagtacc tgggcgacgt  2820
gaagaatatc aaggtgatct acgggccggc cgccaggctg cggcctagcg acgtgcccga  2880
caagtattac agcttcaact acgagggcat cgccagaaac ctgtcttgca gagaacccaa  2940
tcaacacttc aagccttacc tgaagcactt tctgcctaag agactgcact tcgccaaaag  3000
cgacagaatt gaacccctga cattctatct ggaccctcag tggcagctgg ccctcaatcc  3060
ttctgaacgc aaatactgcg gtagcggatt tcacggctct gataacgtgt tttctaacat  3120
gcaggccctg tttgtgggct acggccctgg cttcaagcac ggaatcgagg ctgacacctt  3180
cgagaacatc gaagtttaca atctgatgtg cgacctgctg aatctgaccc cagcccctaa  3240
caacggcaca cacggctctc tgaatcacct gctcaagaac cccgtgtata cccccaaaca  3300
ccctaaagag gtccatccac tggtgcagtg cccattcacc agaaaccctc gggacaacct  3360
tggctgcagc tgcaacccta gcatcctccc tatcgaagat ttccagaccc agtttaacct  3420
gactgtcgcc gaagagaaga tcatcaagca cgaaaccctg ccctacggga ggcccagagt  3480
gctgcagaaa gaaaacacaa tctgtctgct gagccagcac cagtttatga gcggctacag  3540
tcaggacatc ctgatgcctc tgtggaccag ctacaccgtg gaccggaatg acagcttcag  3600
caccgaggac ttcagcaact gcctgtatca ggacttccgc atccctctgt cccctgtgca  3660
```

-continued

```
taagtgcagc ttttacaaga acaacaccaa ggtgagctac gggtttctga gcccaccaca  3720
actgaacaaa aatagctctg gcatctactc tgaggcgctg ctgaccacca acatcgtgcc  3780
aatgtaccag agcttccagg tgatctggcg gtacttccat gataccctgc ttcggaagta  3840
cgccgaagaa cggaacggcg tgaacgtggt gtccggccca gtgttcgact tcgactacga  3900
cggcagatgt gattcccttg agaatctgag acagaagcgg cgggttatca gaaaccagga  3960
gatcctgatt cctacccact tcttcatcgt gctgacatct tgcaaggata ccagccaaac  4020
acctctgcac tgcgagaacc tggacaccct ggccttcatc ctgcctcacc ggaccgataa  4080
tagcgaatcc tgtgtgcacg gcaaacacga ctctagctgg gtggaagagc tgctgatgct  4140
gcacagagcc cggatcacag atgtggaaca catcaccggc ctgtccttct accaacagag  4200
aaaggaaccc gtgtctgata tcctgaagct gaaaacccac ctgcctacct tcagccagga  4260
ggacctgatc gttaacgatg cacacaagag tgaggttgct catcggttta aagatttggg  4320
agaagaaaat ttcaaagcct tggtgttgat tgcctttgct cagtatcttc agcagtgtcc  4380
atttgaagat catgtaaaat tagtgaatga agtaactgaa tttgcaaaaa catgtgttgc  4440
tgatgagtca gctgaaaatt gtgacaaatc acttcatacc ctttttggag acaaattatg  4500
cacagttgca actcttcgtg aaacctatgg tgaaatggct gactgctgtg caaaacaaga  4560
acctgagaga aatgaatgct tcttgcaaca caaagatgac aacccaaacc tcccccgatt  4620
ggtgagacca gaggttgatg tgatgtgcac tgcttttcat gacaatgaag agacattttt  4680
gaaaaaatac ttatatgaaa ttgccagaag acatccttac ttttatgccc cggaactcct  4740
tttctttgct aaaaggtata aagctgcttt tacagaatgt tgccaagctg ctgataaagc  4800
tgcctgcctg ttgccaaagc tcgatgaact tcgggatgaa gggaaggctt cgtctgccaa  4860
acagagactc aagtgtgcca gtctccaaaa atttggagaa agagctttca aagcatgggc  4920
agtagctcgc ctgagccaga gatttcccaa agctgagttt gcagaagttt ccaagttagt  4980
gacagatctt accaaagtcc acacggaatg ctgccatgga gatctgcttg aatgtgctga  5040
tgacagggcg gaccttgcca agtatatctg tgaaaatcaa gattcgatct ccagtaaact  5100
gaaggaatgc tgtgaaaaac ctctgttgga aaaatcccac tgcattgccg aagtggaaaa  5160
tgatgagatg cctgctgact tgccttcatt agctgctgat tttgttgaaa gtaaggatgt  5220
ttgcaaaaac tatgctgagg caaaggatgt cttcctgggc atgtttttgt atgaatatgc  5280
aagaaggcat cctgattact ctgtcgtgct gctgctgaga cttgccaaga catatgaaac  5340
cacactcgag aagtgctgtg ccgctgcaga tcctcatgaa tgctatgcca aagtgttcga  5400
tgaatttaaa cctcttgtgg aagagcctca gaatttaatc aaacaaaatt gtgagctttt  5460
tgagcagctt ggagagtaca aattccagaa tgcgctatta gttcgttaca ccaagaaagt  5520
accccaagtg tcaactccaa ctcttgtaga ggtctcaaga aacctaggaa aagtgggcag  5580
caaatgttgt aaacatcctg aagcaaaaag aatgccctgt gcagaagact atctatccgt  5640
ggtcctgaac cagttatgtg tgttgcatga gaaaacgcca gtaagtgaca gagtcaccaa  5700
atgctgcaca gaatccttgg tgaacaggcg accatgcttt tcagctctgg aagtcgatga  5760
aacatacgtt cccaaagagt ttaatgctga aacattcacc ttccatgcag atatatgcac  5820
actttctgag aaggagagac aaatcaagaa acaaactgca cttgttgagc tcgtgaaaca  5880
caagcccaag gcaacaaaag agcaactgaa agctgttatg gatgatttcg cagcttttgt  5940
agagaagtgc tgcaaggctg acgataagga gacctgcttt gccgaggagg gtaaaaaact  6000
tgttgctgca agtcaagctg ccttaggctt atgaggtacc gagctcggat ccactagtcc  6060
agtgtggtgg aattctgcag atatccagca cagtggcggc cgctcgagtc tagagggccc  6120
gtttaaaccc gctgatcagc ctcgactgtg ccttctagtt gccagccatc tgttgtttgc  6180
ccctcccccg tgccttcctt gaccctggaa ggtgccactc ccactgtcct ttcctaataa  6240
aatgaggaaa ttgcatcgca ttgtctgagt aggtgtcatt ctattctggg gggtggggtg  6300
gggcaggaca gcaaggggga ggattgggaa gacaatagca ggcatgctgg ggatgcggtg  6360
ggctctatgg cttctgaggc ggaaagaacc agctggggct ctagggggta tccccacgcg  6420
ccctgtagcg gcgcattaag cgcggcgggt gtggtggtta cgcgcagcgt gaccgctaca  6480
cttgccagcg ccctagcgcc cgctcctttc gctttcttcc cttcctttct cgccacgttc  6540
gccggctttc cccgtcaagc tctaaatcgg gggctccctt tagggttccg atttagtgct  6600
ttacggcacc tcgaccccaa aaaacttgat tagggtgatg gttcacgtag tgggccatcg  6660
ccctgataga cggtttttcg ccctttgacg ttggagtcca cgttctttaa tagtggactc  6720
ttgttccaaa ctggaacaac actcaaccct atctcggtct attcttttga tttataaggg  6780
attttgccga tttcggccta ttggttaaaa aatgagctga tttaacaaaa atttaacgcg  6840
aattaattct gtggaatgtg tgtcagttag ggtgtggaaa gtccccaggc tccccagcag  6900
gcagaagtat gcaaagcatg catctcaatt agtcagcaac caggtgtgga aagtccccag  6960
gctccccagc aggcagaagt atgcaaagca tgcatctcaa ttagtcagca accatagtcc  7020
cgcccctaac tccgcccatc ccgcccctaa ctccgcccag ttccgcccat tctccgcccc  7080
atggctgact aatttttttt atttatgcag aggccgaggc cgcctctgcc tctgagctat  7140
tccagaagta gtgaggaggc ttttttggag gcctaggctt ttgcaaaaag ctcccgggag  7200
cttgtatatc cattttcgga tctgatcaag agacaggatg aggatcgttt cgcatgattg  7260
aacaagatgg attgcacgca ggttctccgg ccgcttgggt ggagaggcta ttcggctatg  7320
actgggcaca acagacaatc ggctgctctg atgccgccgt gttccggctg tcagcgcagg  7380
ggcgcccggt tctttttgtc aagaccgacc tgtccggtgc cctgaatgaa ctgcaggacg  7440
aggcagcgcg gctatcgtgg ctggccacga cgggcgttcc ttgcgcagct gtgctcgacg  7500
ttgtcactga agcgggaagg gactggctgc tattgggcga agtgccgggg caggatctcc  7560
tgtcatctca ccttgctcct gccgagaaag tatccatcat ggctgatgca atgcggcggc  7620
tgcatacgct tgatccggct acctgcccat tcgaccacca agcgaaacat cgcatcgagc  7680
gagcacgtac tcggatggaa gccggtcttg tcgatcagga tgatctggac gaagagcatc  7740
aggggctcgc gccagccgaa ctgttcgcca ggctcaaggc gcgcatgccc gacggcgagg  7800
atctcgtcgt gacccatggc gatgcctgct tgccgaatat catggtggaa aatggccgct  7860
tttctggatt catcgactgt ggccggctgg gtgtggcgga ccgctatcag gacatagcgt  7920
tggctacccg tgatattgct gaagagcttg gcggcgaatg ggctgaccgc ttcctcgtgc  7980
tttacggtat cgccgctccc gattcgcagc gcatcgcctt ctatcgcctt cttgacgagt  8040
tcttctgagc gggactctgg ggttcgaaat gaccgaccaa gcgacgccca acctgccatc  8100
acgagatttc gattccaccg ccgccttcta tgaaaggttg ggcttcggaa tcgttttccg  8160
ggacgccggc tggatgatcc tccagcgcgg ggatctcatg ctggagttct tcgcccaccc  8220
caacttgttt attgcagctt ataatggtta caaataaagc aatagcatca caaatttcac  8280
aaataaagca tttttttcac tgcattctag ttgtggtttg tccaaactca tcaatgtatc  8340
ttatcatgtc tgtataccgt cgacctctag ctagagcttg gcgtaatcat ggtcatagct  8400
```

```
gtttcctgtg tgaaattgtt atccgctcac aattccacac aacatacgag ccggaagcat  8460
aaagtgtaaa gcctggggtg cctaatgagt gagctaactc acattaattg cgttgcgctc  8520
actgcccgct ttccagtcgg gaaacctgtc gtgccagctg cattaatgaa tcggccaacg  8580
cgcggggaga ggcggtttgc gtattgggcg ctcttccgct tcctcgctca ctgactcgct  8640
gcgctcggtc gttcggctgc ggcgagcggt atcagctcac tcaaaggcgg taatacggtt  8700
atccacagaa tcaggggata acgcaggaaa gaacatgtga gcaaaaggcc agcaaaaggc  8760
caggaaccgt aaaaaggccg cgttgctggc gtttttccat aggctccgcc cccctgacga  8820
gcatcacaaa aatcgacgct caagtcagag gtggcgaaac ccgacaggac tataaagata  8880
ccaggcgttt ccccctggaa gctccctcgt gcgctctcct gttccgaccc tgccgcttac  8940
cggatacctg tccgcctttc tcccttcggg aagcgtggcg ctttctcata gctcacgctg  9000
taggtatctc agttcggtgt aggtcgttcg ctccaagctg ggctgtgtgc acgaaccccc  9060
cgttcagccc gaccgctgcg ccttatccgg taactatcgt cttgagtcca acccggtaag  9120
acacgactta tcgccactgg cagcagccac tggtaacagg attagcagag cgaggtatgt  9180
aggcggtgct acagagttct tgaagtggtg gcctaactac ggctacacta gaagaacagt  9240
atttggtatc tgcgctctgc tgaagccagt taccttcgga aaaagagttg gtagctcttg  9300
atccggcaaa caaaccaccg ctggtagcgg tggttttttt gtttgcaagc agcagattac  9360
gcgcagaaaa aaaggatctc aagaagatcc tttgatcttt tctacggggt ctgacgctca  9420
gtggaacgaa aactcacgtt aagggatttt ggtcatgaga ttatcaaaaa ggatcttcac  9480
ctagatcctt ttaaattaaa aatgaagttt taaatcaatc taaagtatat atgagtaaac  9540
ttggtctgac agttaccaat gcttaatcag tgaggcacct atctcagcga tctgtctatt  9600
tcgttcatcc atagttgcct gactccccgt cgtgtagata actacgatac gggagggctt  9660
accatctggc cccagtgctg caatgatacc gcgagaccca cgctcaccgg ctccagattt  9720
atcagcaata aaccagccag ccggaagggc cgagcgcaga agtggtcctg caactttatc  9780
cgcctccatc cagtctatta attgttgccg ggaagctaga gtaagtagtt cgccagttaa  9840
tagtttgcgc aacgttgttg ccattgctac aggcatcgtg gtgtcacgct cgtcgtttgg  9900
tatggcttca ttcagctccg gttcccaacg atcaaggcga gttacatgat cccccatgtt  9960
gtgcaaaaaa gcggttagct ccttcggtcc tccgatcgtt gtcagaagta agttggccgc  10020
agtgttatca ctcatggtta tggcagcact gcataattct cttactgtca tgccatccgt  10080
aagatgcttt tctgtgactg gtgagtactc aaccaagtca ttctgagaat agtgtatgcg  10140
gcgaccgagt tgctcttgcc cggcgtcaat acgggataat accgcgccac atagcagaac  10200
tttaaaagtg ctcatcattg gaaaacgttc ttcggggcga aaactctcaa ggatcttacc  10260
gctgttgaga tccagttcga tgtaacccac tcgtgcaccc aactgatctt cagcatcttt  10320
tactttcacc agcgtttctg ggtgagcaaa aacaggaagg caaaatgccg caaaaaaggg  10380
aataagggcg acacggaaat gttgaatact catactcttc ctttttcaat attattgaag  10440
catttatcag ggttattgtc tcatgagcgg atacatattt gaatgtattt agaaaaataa  10500
acaaataggg gttccgcgca catttccccg aaaagtgcca cctgacgtc             10549

SEQ ID NO: 97          moltype = DNA  length = 11247
FEATURE                Location/Qualifiers
source                 1..11247
                       mol_type = other DNA
                       organism = synthetic construct
SEQUENCE: 97
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttaagatt  240
atagttgtca tttgaacttg gggataaagg agacatctat gacttggctg gaaaagacag  300
agctaatgta cattgcaaag cacatattta tagcaggaaa atgggaagat ttctctttaa  360
ttctggagat ggagtgggga tggggagagt agactactca ttttaagggt gaaacattgg  420
aattcaactt gtttgatgtt atattaattg gtggttaatt actaagctaa gtacgtataa  480
aacttttatc tatggctagc ttgtcccccc aaagtcatgc aatatagtga actggctttc  540
gcactttaaa ttattcattg atcatgtaat gattcagatg attcatcttc caagatggac  600
actgaaacta acactcatag taggttgtgg tttaaagagt ggaacaaccg ccagtctcat  660
tagtggaaat tgtgatggtt gaatttatca aggatgaaca tacacggtct tctttctgag  720
attttcttta agattttcgc acagataatc tatttcttag gttttggaga gaaaacttga  780
attttattga tccctcagaa ctcaatcttt cagatttcaa aggagctatt tcttttaatg  840
gggactctgt taatatttat aaaagctctt cacaggatgg agggtgggag ggaaactcca  900
tcccaacaag acaaaaagaa tgaagcatga ggctccacct agttcatcac tgctccttga  960
aatacatcag tattgaaaga cacatccacc ccaccccaa cccagcccta ttgctgttcc  1020
agctcaagag tcagaggtcc cgaagctgta gctcttctac aatctgctgc tctgtgactt  1080
caagtctgtt gtctgcaaag aaaactattg ggttcccaag caagagaggc acatctggta  1140
ggacagattt tgtgattgca aaagaagggg gaaaaaaaga aagaaagaaa agacctctct  1200
atacaagata accagaggca tcaaactgaa atcctcctgt ggaaaataag ctagtacttc  1260
tgggcctgat ggtgtagtga aaacctgtgc ttgaggatac attacagtga aagagcaaag  1320
tgaatagtaa gtagctatta cttacctcct tagggaggtg tgttgtttgt ctgtacatcc  1380
cccacagcac ctagcacagt accttgcatc tcacctgcca ctcactaaaa agtctatcaa  1440
gttagttaat tatcgagaca acgccctcag aaatgagaga acagtaccct cttatccttg  1500
ctgcactttc cagcactgat acgctgccta aaagaggact agggcacagg tttgaattaa  1560
tgtcacaaaa ctggatgggc aagttacaac ggtgttgatt aaggaaacag aactcatggt  1620
gcaccggata tctccatcct gatgaaccct tggaaaaatg ccaaagatgc atatccccag  1680
gcaaatgcct gattagtctg ggattgatag attggtctag gattcagccc tactgggaag  1740
atgtctaaat tataatcagt gtagaaagcg aagttctcct agaagaagag gcaaaggtta  1800
aaaagaagaa aagaaaagaa agtgaagtcc tttctccccc aaaacctctc atcaatcaat  1860
cagggtaaca aacagaacac tagggctctg tctgtggacc aaacccaaaa gccctgcggt  1920
cagggccagg agggtagatc atgtgtttgt ggcaacttcc tctgtgggct tttgcccagg  1980
tctgtcccca agcatacgat ggccaaaact tctgcaccag agcagcatcc tgtgtaacac  2040
agtcaggtcc agcagttagg gaaaactgcc cactcagagt agataatatc tggaaggaat  2100
gactgtttgg gaaaagttcc aatgctagtt cagtgccaac ccttccccac cttctccagc  2160
```

-continued

```
tctctcccac tggttcctcc cctctcaact gctctggttc ttataaaaac ctcacagcct  2220
tccactaaca tcccgtagga gcctctctcc ctactgctgc tacacaagac cctgagactg  2280
acctgcagga cgaaaccctc tggctaacta gagaacccac tgcttactgg cttatcgaaa  2340
ttaatacgac tcactatagg gagacccaag ctggctagcg ccaccatgaa gagcctgatc  2400
cttcttgcca tcctggccgc cttagcggta gtaactttgt gtgactacaa agacgatgac  2460
gacaagagcg ctggcctgaa gccaagctgc gccaaggagg tgaagagctg caagggcaga  2520
tgtttcgaac ggaccttcgg caactgcaga tgcgacgccg cctgcgtgga actgggaaac  2580
tgttgtctgg actaccagga gacatgtatc gagcctgagc acatctggac atgcaacaag  2640
ttcagatgtg gcgagaaaag actgactcgg agtctgtgcg cctgttctga cgactgcaag  2700
gacaagggcg attgctgcat caactacagc agcgtgtgcc agggcgaaaa gagctgggtc  2760
gaggaaccct gcgagagcat caacgagccc cagtgccctg ccggatttga gacacctcct  2820
accctgctct tctccctgga tggcttcaga gctgagtacc tgcatacatg ggaggactg  2880
ctgcctgtga tcagcaagct gaagaagtgc ggcacctaca caaagaacat gcggcctgtc  2940
taccctacca agaccttccc caaccactac agcatcgtga ccggcctgta ccccgagagc  3000
cacggcatca tcgacaacaa gatgtacgac cccaaaatga acgccagctt cagcctgaaa  3060
tctaaggaaa agttcaaccc tgagtggtat aagggcgagc caatctgggt gacagccaag  3120
taccagggcc tgaagagcgg caccttcttc tggcctggca gcgacgtgga gatcaacgga  3180
atcttccctg atatctacaa gatgtataac ggctccgtgc ctttcgagga gcggatcttg  3240
gctgttcttc agtggctgca gctgcccaag gacgagagac cccacttcta caccctgtac  3300
ctggaagaac ctgacagcag cggccacagc tacggccctg tgtctagcga ggtgatcaag  3360
gccctgcaaa gagtggatgg catggtgggc atgctgatgg atggactgaa ggaactgaac  3420
ctccatcgtt gcctgaacct gatcctgatc tccgaccacg gcatggaaca gggcagctgt  3480
aaaaagtaca tctacctgaa caagtacctg ggcgacgtga agaatatcaa ggtgatctac  3540
gggccggccg ccaggctgcg gcctagcgac gtgcccgaca agtattacag cttcaactac  3600
gagggcatcg ccagaaacct gtcttgcaga gaacccaatc aacacttcaa gccttacctg  3660
aagcactttc tgcctaagag actgcacttc gccaaaagcg acagaattga acccctgaca  3720
ttctatctgg accctcagtg gcagctggcc ctcaatcctt ctgaacgcaa atactgcggt  3780
agcggatttc acggctctga taacgtgttt tctaacatgc aggccctgtt tgtgggctac  3840
ggccctggct tcaagcacgg aatcgaggct gacaccttcg agaacatcga agtttacaat  3900
ctgatgtgcg acctgctgaa tctgacccca gccccctaaca acggcacaca cggctctctg  3960
aatcacctgc tcaagaaccc cgtgtatacc cccaaacacc ctaaagaggt ccatccactg  4020
gtgcagtgcc cattcaccag aaaccctcgg gacaaccttg gctgcagctg caaccctagc  4080
atcctcccta tcgaagattt ccagacccag tttaacctga ctgtcgccga agagaagatc  4140
atcaagcacg aaaccctgcc ctacgggagg cccagagtgc tgcagaaaga aaacacaatc  4200
tgtctgctga gccagcacca gtttatgagc ggctacagtc aggacatcct gatgcctctg  4260
tggaccagct acaccgtgga ccggaatgac agcttcagca ccgaggactt cagcaactgc  4320
ctgtatcagg acttccgcat ccctctgtcc cctgtgcata agtgcagctt ttacaagaac  4380
aacaccaagg tgagctacgg gtttctgagc ccaccacaac tgaacaaaaa tagctctggc  4440
atctactctg aggcgctgct gaccaccaac atcgtgccaa tgtaccagag cttccaggtg  4500
atctggcggt acttccatga taccctgctt cggaagtacg ccgaagaacg gaacggcgtg  4560
aacgtggtgt ccggcccagt gttcgacttc gactacgacg gcagatgtga ttcccttgag  4620
aatctgagac agaagcggcg ggttatcaga aaccaggaga tcctgattcc tacccacttc  4680
ttcatcgtgc tgacatcttg caaggatacc agccaaacac ctctgcactg cgagaacctg  4740
gacaccctgg ccttcatcct gcctcaccgg accgataata gcgaatcctg tgtgcacggc  4800
aaacacgact ctagctgggt ggaagagctg ctgatgctgc acagagcccg gatcacagat  4860
gtggaacaca tcaccggcct gtccttctac caacagagaa aggaacccgt gtctgatatc  4920
ctgaagctga aaacccacct gcctaccttc agccaggagg acctgatcgt taacgatgca  4980
cacaagagtg aggttgctca tcggtttaaa gatttgggag aagaaaattt caaagccttg  5040
gtgttgattg cctttgctca gtatcttcag cagtgtccat ttgaagatca tgtaaaatta  5100
gtgaatgaag taactgaatt tgcaaaaaca tgtgttgctg atgagtcagc tgaaaattgt  5160
gacaaatcac ttcataccct ttttggagac aaattatgca cagttgcaac tcttcgtgaa  5220
acctatggtg aaatggctga ctgctgtgca aaacaagaac ctgagagaaa tgaatgcttc  5280
ttgcaacaca aagatgacaa cccaaacctc ccccgattgg tgagaccaga ggttgatgtg  5340
atgtgcactg cttttcatga caatgaagag acatttttga aaaaatactt atatgaaatt  5400
gccagaagac atccttactt ttatgccccg gaactccttt tctttgctaa aaggtataaa  5460
gctgctttta cagaatgttg ccaagctgct gataaagctg cctgcctgtt gccaaagctc  5520
gatgaacttc gggatgaagg gaaggcttcg tctgccaaac agagactcaa gtgtgccagt  5580
ctccaaaaat ttggagaaag agctttcaaa gcatgggcag tagctcgcct gagccagaga  5640
tttcccaaag ctgagtttgc agaagtttcc aagttagtga cagatcttac caaagtccac  5700
acggaatgct gccatggaga tctgcttgaa tgtgctgatg acagggcgga ccttgccaag  5760
tatatctgtg aaaatcaaga ttcgatctcc agtaaactga aggaatgctg tgaaaaacct  5820
ctgttggaaa aatcccactg cattgccgaa gtggaaaatg atgagatgcc tgctgacttg  5880
ccttcattag ctgctgattt tgttgaaagt aaggatgttt gcaaaaacta tgctgaggca  5940
aaggatgtct tcctgggcat gtttttgtat gaatatgcaa gaaggcatcc tgattactct  6000
gtcgtgctgc tgctgagact tgccaagaca tatgaaacca cactcgagaa gtgctgtgcc  6060
gctgcagatc ctcatgaatg ctatgccaaa gtgttcgatg aatttaaacc tcttgtggaa  6120
gagcctcaga atttaatcaa acaaaattgt gagctttttg agcagcttgg agagtacaaa  6180
ttccagaatg cgctattagt tcgttacacc aagaaagtac cccaagtgtc aactccaact  6240
cttgtagagg tctcaagaaa cctaggaaaa gtgggcagca aatgttgtaa acatcctgaa  6300
gcaaaaagaa tgccctgtgc agaagactat ctatccgtgg tcctgaacca gttatgtgtg  6360
ttgcatgaga aaacgccagt aagtgacaga gtcaccaaat gctgcacaga atccttggtg  6420
aacaggcgac catgcttttc agctctggaa gtcgatgaaa catacgttcc caaagagttt  6480
aatgctgaaa cattcacctt ccatgcagat atatgcacac tttctgagaa ggagagacaa  6540
atcaagaaac aaactgcact tgttgagctc gtgaaacaca agcccaaggc aacaaaagag  6600
caactgaaag ctgttatgga tgatttcgca gcttttgtag agaagtgctg caaggctgac  6660
gataaggaga cctgctttgc cgaggagggt aaaaaacttg ttgctgcaag tcaagctgcc  6720
ttaggcttat gaggtaccga gctcggatcc actagtccag tgtggtggaa ttctgcagat  6780
atccagcaca gtggcggccg ctcgagtcta gagggcccgt ttaaacccgc tgatcagcct  6840
cgactgtgcc ttctagttgc cagccatctg ttgtttgccc ctcccccgtg ccttccttga  6900
```

-continued

```
ccctggaagg tgccactccc actgtccttt cctaataaaa tgaggaaatt gcatcgcatt  6960
gtctgagtag gtgtcattct attctggggg gtggggtggg gcaggacagc aagggggagg  7020
attgggaaga caatagcagg catgctgggg atgcggtggg ctctatggct tctgaggcgg  7080
aaagaaccag ctggggctct agggggtatc cccacgcgcc ctgtagcggc gcattaagcg  7140
cggcgggtgt ggtggttacg cgcagcgtga ccgctacact tgccagcgcc ctagcgcccg  7200
ctcctttcgc tttcttccct tcctttctcg ccacgttcgc cggctttccc cgtcaagctc  7260
taaatcgggg gctcccttta gggttccgat ttagtgcttt acggcacctc gaccccaaaa  7320
aacttgatta gggtgatggt tcacgtagtg ggccatcgcc ctgatagacg gtttttcgcc  7380
ctttgacgtt ggagtccacg ttctttaata gtggactctt gttccaaact ggaacaacac  7440
tcaaccctat ctcggtctat tcttttgatt tataagggat tttgccgatt tcggcctatt  7500
ggttaaaaaa tgagctgatt taacaaaaat ttaacgcgaa ttaattctgt ggaatgtgtg  7560
tcagttaggg tgtggaaagt ccccaggctc cccagcaggc agaagtatgc aaagcatgca  7620
tctcaattag tcagcaacca ggtgtggaaa gtccccaggc tccccagcag gcagaagtat  7680
gcaaagcatg catctcaatt agtcagcaac catagtcccg cccctaactc cgcccatccc  7740
gcccctaact ccgcccagtt ccgcccattc tccgccccat ggctgactaa ttttttttat  7800
ttatgcagag gccgaggccg cctctgcctc tgagctattc cagaagtagt gaggaggctt  7860
ttttggaggc ctaggctttt gcaaaaagct cccgggagct tgtatatcca ttttcggatc  7920
tgatcaagag acaggatgag gatcgtttcg catgattgaa caagatggat tgcacgcagg  7980
ttctccggcc gcttgggtgg agaggctatt cggctatgac tgggcacaac agacaatcgg  8040
ctgctctgat gccgccgtgt tccggctgtc agcgcagggg cgcccggttc tttttgtcaa  8100
gaccgacctg tccggtgccc tgaatgaact gcaggacgag gcagcgcggc tatcgtggct  8160
ggccacgacg ggcgttcctt gcgcagctgt gctcgacgtt gtcactgaag cgggaaggga  8220
ctggctgcta ttgggcgaag tgccggggca ggatctcctg tcatctcacc ttgctcctgc  8280
cgagaaagta tccatcatgg ctgatgcaat gcggcggctg catacgcttg atccggctac  8340
ctgcccattc gaccaccaag cgaaacatcg catcgagcga gcacgtactc ggatggaagc  8400
cggtcttgtc gatcaggatg atctggacga agagcatcag gggctcgcgc cagccgaact  8460
gttcgccagg ctcaaggcgc gcatgcccga cggcgaggat ctcgtcgtga cccatggcga  8520
tgcctgcttg ccgaatatca tggtggaaaa tggccgcttt tctggattca tcgactgtgg  8580
ccggctgggt gtggcggacc gctatcagga catagcgttg gctacccgtg atattgctga  8640
agagcttggc ggcgaatggg ctgaccgctt cctcgtgctt tacggtatcg ccgctcccga  8700
ttcgcagcgc atcgccttct atcgccttct tgacgagttc ttctgagcgg gactctgggg  8760
ttcgaaatga ccgaccaagc gacgcccaac ctgccatcac gagatttcga ttccaccgcc  8820
gccttctatg aaaggttggg cttcggaatc gttttccggg acgccggctg gatgatcctc  8880
cagcgcgggg atctcatgct ggagttcttc gcccacccca acttgtttat tgcagcttat  8940
aatggttaca aataaagcaa tagcatcaca aatttcacaa ataaagcatt tttttcactg  9000
cattctagtt gtggtttgtc caaactcatc aatgtatctt atcatgtctg tataccgtcg  9060
acctctagct agagcttggc gtaatcatgg tcatagctgt ttcctgtgtg aaattgttat  9120
ccgctcacaa ttccacacaa catacgagcc ggaagcataa agtgtaaagc ctggggtgcc  9180
taatgagtga gctaactcac attaattgcg ttgcgctcac tgcccgcttt ccagtcggga  9240
aacctgtcgt gccagctgca ttaatgaatc ggccaacgcg cggggagagg cggtttgcgt  9300
attgggcgct cttccgcttc ctcgctcact gactcgctgc gctcggtcgt tcggctgcgg  9360
cgagcggtat cagctcactc aaaggcggta atacggttat ccacagaatc aggggataac  9420
gcaggaaaga acatgtgagc aaaaggccag caaaaggcca ggaaccgtaa aaaggccgcg  9480
ttgctggcgt ttttccatag gctccgcccc cctgacgagc atcacaaaaa tcgacgctca  9540
agtcagaggt ggcgaaaccc gacaggacta taaagatacc aggcgtttcc ccctggaagc  9600
tccctcgtgc gctctcctgt tccgaccctg ccgcttaccg gatacctgtc cgcctttctc  9660
ccttcgggaa gcgtggcgct ttctcatagc tcacgctgta ggtatctcag ttcggtgtag  9720
gtcgttcgct ccaagctggg ctgtgtgcac gaaccccccg ttcagcccga ccgctgcgcc  9780
ttatccggta actatcgtct tgagtccaac ccggtaagac acgacttatc gccactggca  9840
gcagccactg gtaacaggat tagcagagcg aggtatgtag gcggtgctac agagttcttg  9900
aagtggtggc ctaactacgg ctacactaga agaacagtat ttggtatctg cgctctgctg  9960
aagccagtta ccttcggaaa aagagttggt agctcttgat ccggcaaaca aaccaccgct  10020
ggtagcggtg gtttttttgt ttgcaagcag cagattacgc gcagaaaaaa aggatctcaa  10080
gaagatcctt tgatcttttc tacggggtct gacgctcagt ggaacgaaaa ctcacgttaa  10140
gggattttgg tcatgagatt atcaaaaagg atcttcacct agatcctttt aaattaaaaa  10200
tgaagtttta aatcaatcta aagtatatat gagtaaactt ggtctgacag ttaccaatgc  10260
ttaatcagtg aggcacctat ctcagcgatc tgtctatttc gttcatccat agttgcctga  10320
ctccccgtcg tgtagataac tacgatacgg gagggcttac catctggccc cagtgctgca  10380
atgataccgc gagacccacg ctcaccggct ccagatttat cagcaataaa ccagccagcc  10440
ggaagggccg agcgcagaag tggtcctgca actttatccg cctccatcca gtctattaat  10500
tgttgccggg aagctagagt aagtagttcg ccagttaata gtttgcgcaa cgttgttgcc  10560
attgctacag gcatcgtggt gtcacgctcg tcgtttggta tggcttcatt cagctccggt  10620
tcccaacgat caaggcgagt tacatgatcc cccatgttgt gcaaaaaagc ggttagctcc  10680
ttcggtcctc cgatcgttgt cagaagtaag ttggccgcag tgttatcact catggttatg  10740
gcagcactgc ataattctct tactgtcatg ccatccgtaa gatgcttttc tgtgactggt  10800
gagtactcaa ccaagtcatt ctgagaatag tgtatgcggc gaccgagttg ctcttgcccg  10860
gcgtcaatac gggataatac cgcgccacat agcagaactt taaaagtgct catcattgga  10920
aaacgttctt cggggcgaaa actctcaagg atcttaccgc tgttgagatc cagttcgatg  10980
taacccactc gtgcacccaa ctgatcttca gcatctttta ctttcaccag cgtttctggg  11040
tgagcaaaaa caggaaggca aaatgccgca aaaaagggaa taagggcgac acggaaatgt  11100
tgaatactca tactcttcct ttttcaatat tattgaagca tttatcaggg ttattgtctc  11160
atgagcggat acatatttga atgtatttag aaaaataaac aaataggggt tccgcgcaca  11220
tttccccgaa aagtgccacc tgacgtc                                     11247
```

```
SEQ ID NO: 98          moltype = DNA  length = 9843
FEATURE                Location/Qualifiers
source                 1..9843
                       mol_type = other DNA
                       organism = synthetic construct
```

SEQUENCE: 98
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgcgtta 240
cataacttac ggtaaatggc ccgcctggct gaccgcccaa cgacccccgc ccattgacgt 300
caataatgac gtatgttccc atagtaacgc caatagggac tttccattga cgtcaatggg 360
tggagtattt acggtaaact gcccacttgg cagtacatca agtgtatcat atgccaagta 420
cgccccctat tgacgtcaat gacggtaaat ggcccgcctg gcattatgcc cagtacatga 480
ccttatggga ctttcctact tggcagtaca tctacgtatt agtcatcgct attaccatgg 540
tcgaggtgag ccccacgttc tgcttcactc tccccatctc ccccccctcc ccacccccaa 600
ttttgtattt atttattttt taattatttt gtgcagcgat gggggcgggg gggggggggg 660
ggcgcgcgcc aggcggggcg gggcggggcg aggggcgggg cggggcgagg cggagaggtg 720
cggcggcagc caatcagagc ggcgcgctcc gaaagtttcc ttttatggcg aggcggcggc 780
ggcggcggcc ctataaaaag cgaagcgcgc ggcgggcgct ctggctaact agagaaccca 840
ctgcttactg gcttatcgaa attaatacga ctcactatag ggagacccaa gctggctagc 900
gccaccatga agtgggtaac ctttatttcc cttctttttc tctttagctc ggcttattcc 960
aggggtgtgt ttcgtcgaga ctacaaagac gatgacgaca agagcgctgg cctgaagcca 1020
agctgcgcca aggaggtgaa gagctgcaag ggcagatgtt tcgaacggac cttcggcaac 1080
tgcagatgcg acgccgcctg cgtggaactg ggaaactgtt gtctggacta ccaggagaca 1140
tgtatcgagc ctgagcacat ctggacatgc aacaagttca gatgtggcga gaaaagactg 1200
actcggagtc tgtgcgcctg ttctgacgac tgcaaggaca agggcgattg ctgcatcaac 1260
tacagcagcg tgtgccaggg cgaaaagagc tgggtcgagg aaccctgcga gagcatcaac 1320
gagccccagt gccctgccgg atttgagaca cctcctaccc tgctcttctc cctggatggc 1380
ttcagagctg agtacctgca tacatgggga ggactgctgc ctgtgatcag caagctgaag 1440
aagtgcggca cctacacaaa gaacatgcgg cctgtctacc ctaccaagac cttcccccaac 1500
cactacagca tcgtgaccgg cctgtacccc gagagccacg gcatcatcga caacaagatg 1560
tacgacccca aaatgaacgc cagcttcagc ctgaaatcta aggaaaagtt caaccctgag 1620
tggtataagg gcgagccaat ctgggtgaca gccaagtacc agggcctgaa gagcggcacc 1680
ttcttctggc ctggcagcga cgtggagatc aacggaatct tccctgatat ctacaagatg 1740
tataacggct ccgtgccttt cgaggagcgg atcttggctg ttcttcagtg gctgcagctg 1800
cccaaggacg agagacccca cttctacacc ctgtacctgg aagaacctga cagcagcggc 1860
cacagctacg gccctgtgtc tagcgaggtg atcaaggccc tgcaaagagt ggatggcatg 1920
gtgggcatgc tgatggatgg actgaaggaa ctgaacctcc atcgttgcct gaacctgatc 1980
ctgatctccg accacggcat ggaacagggc agctgtaaaa agtacatcta cctgaacaag 2040
tacctgggcg acgtgaagaa tatcaaggtg atctacgggc cggccgccag gctgcggcct 2100
agcgacgtgc ccgacaagta ttacagcttc aactacgagg gcatcgccag aaacctgtct 2160
tgcagagaac ccaatcaaca cttcaagcct tacctgaagc actttctgcc taagagactg 2220
cacttcgcca aaagcgacag aattgaaccc ctgacattct atctggaccc tcagtggcag 2280
ctggccctca atccttctga acgcaaatac tgcggtagcg gatttcacgg ctctgataac 2340
gtgttttcta acatgcaggc cctgtttgtg ggctacggcc ctggcttcaa gcacggaatc 2400
gaggctgaca ccttcgagaa catcgaagtt tacaatctga tgtgcgacct gctgaatctg 2460
accccagccc ctaacaacgg cacacacggc tctctgaatc acctgctcaa gaaccccgtg 2520
tataccccca aacaccctaa agaggtccat ccactggtgc agtgcccatt caccagaaac 2580
cctcgggaca accttggctg cagctgcaac cctagcatcc tccctatcga agatttccag 2640
acccagttta acctgactgt cgccgaagag aagatcatca agcacgaaac cctgccctac 2700
gggaggccca gagtgctgca gaaagaaaac acaatctgtc tgctgagcca gcaccagttt 2760
atgagcggct acagtcagga catcctgatg cctctgtgga ccagctacac cgtggaccgg 2820
aatgacagct tcagcaccga ggacttcagc aactgcctgt atcaggactt ccgcatccct 2880
ctgtcccctg tgcataagtg cagcttttac aagaacaaca ccaaggtgag ctacgggttt 2940
ctgagcccac cacaactgaa caaaaatagc tctggcatct actctgaggc gctgctgacc 3000
accaacatcg tgccaatgta ccagagcttc caggtgatct ggcggtactt ccatgatacc 3060
ctgcttcgga agtacgccga agaacggaac ggcgtgaacg tggtgtccgg cccagtgttc 3120
gacttcgact acgacggcag atgtgattcc cttgagaatc tgagacagaa gcggcgggtt 3180
atcagaaacc aggagatcct gattcctacc cacttcttca tcgtgctgac atcttgcaag 3240
gataccagcc aaacacctct gcactgcgag aacctggaca ccctggcctt catcctgcct 3300
caccggaccg ataatagcga atcctgtgtg cacggcaaac acgactctag ctgggtggaa 3360
gagctgctga tgctgcacag agcccggatc acagatgtgg aacacatcac cggcctgtcc 3420
ttctaccaac agagaaagga acccgtgtct gatatcctga agctgaaaac ccacctgcct 3480
accttcagcc aggaggacct gatcgttaac gatgcacaca agagtgaggt tgctcatcgg 3540
tttaaagatt tgggagaaga aaatttcaaa gccttggtgt tgattgcctt tgctcagtat 3600
cttcagcagt gtccatttga agatcatgta aaattagtga atgaagtaac tgaatttgca 3660
aaaacatgtg ttgctgatga gtcagctgaa aattgtgaca aatcacttca taccctttttt 3720
ggagacaaat tatgcacagt tgcaactctt cgtgaaacct atggtgaaat ggctgactgc 3780
tgtgcaaaac aagaacctga gagaaatgaa tgcttcttgc aacacaaaga tgacaaccca 3840
aacctccccc gattggtgag accagaggtt gatgtgatgt gcactgcttt tcatgacaat 3900
gaagagacat ttttgaaaaa atacttatat gaaattgcca gaagacatcc ttacttttat 3960
gccccggaac tccttttctt tgctaaaagg tataaagctg cttttacaga atgttgccaa 4020
gctgctgata aagctgcctg cctgttgcca aagctcgatg aacttcggga tgaagggaag 4080
gcttcgtctg ccaaacagag actcaagtgt gccagtctcc aaaaatttgg agaaagagct 4140
ttcaaagcat gggcagtagc tcgcctgagc cagagatttc ccaaagctga gtttgcagaa 4200
gtttccaagt tagtgacaga tcttaccaaa gtccacacgg aatgctgcca tggagatctg 4260
cttgaatgtg ctgatgacag ggcggacctt gccaagtata tctgtgaaaa tcaagattcg 4320
atctccagta aactgaagga atgctgtgaa aaacctctgt tggaaaaatc ccactgcatt 4380
gccgaagtgg aaaatgatga gatgcctgct gacttgcctt cattagctgc tgattttgtt 4440
gaaagtaagg atgtttgcaa aaactatgct gaggcaaagg atgtcttcct gggcatgttt 4500
ttgtatgaat atgcaagaag gcatcctgat tactctgtcg tgctgctgct gagacttgcc 4560
aagacatatg aaaccacact cgagaagtgc tgtgccgctg cagatcctca tgaatgctat 4620
gccaaagtgt tcgatgaatt taaacctctt gtggaagagc ctcagaattt aatcaaacaa 4680

-continued

```
aattgtgagc tttttgagca gcttggagag tacaaattcc agaatgcgct attagttcgt  4740
tacaccaaga aagtacccca agtgtcaact ccaactcttg tagaggtctc aagaaaccta  4800
ggaaaagtgg gcagcaaatg ttgtaaacat cctgaagcaa aaagaatgcc ctgtgcagaa  4860
gactatctat ccgtggtcct gaaccagtta tgtgtgttgc atgagaaaac gccagtaagt  4920
gacagagtca ccaaatgctg cacagaatcc ttggtgaaca ggcgaccatg cttttcagct  4980
ctggaagtcg atgaaacata cgttcccaaa gagtttaatg ctgaaacatt caccttccat  5040
gcagatatat gcacactttc tgagaaggag agacaaatca agaaacaaac tgcacttgtt  5100
gagctcgtga aacacaagcc caaggcaaca aaagagcaac tgaaagctgt tatggatgat  5160
ttcgcagctt ttgtagagaa gtgctgcaag gctgacgata aggagacctg ctttgccgag  5220
gagggtaaaa aacttgttgc tgcaagtcaa gctgccttag gcttatgaca attacgatta  5280
gcactatcca attacgatta gcactatcca attacgatta gcactatcgg taccgagctc  5340
ggatccacta gtccagtgtg gtggaattct gcagatatcc agcacagtgg cggccgctcg  5400
agtctagagg gcccgtttaa acccgctgat cagcctcgac tgtgccttct agttgccagc  5460
catctgttgt ttgcccctcc cccgtgcctt ccttgaccct ggaaggtgcc actcccactg  5520
tcctttccta ataaaatgag gaaattgcat cgcattgtct gagtaggtgt cattctattc  5580
tggggggtgg ggtggggcag gacagcaagg gggaggattg ggaagacaat agcaggcatg  5640
ctggggatgc ggtgggctct atggcttctg aggcggaaag aaccagctgg ggctctaggg  5700
ggtatcccca cgcgccctgt agcggcgcat taagcgcggc gggtgtggtg gttacgcgca  5760
gcgtgaccgc tacacttgcc agcgccctag cgcccgctcc tttcgctttc ttcccttcct  5820
ttctcgccac gttcgccggc tttccccgtc aagctctaaa tcgggggctc cctttagggt  5880
tccgatttag tgctttacgg cacctcgacc ccaaaaaact tgattagggt gatggttcac  5940
gtagtgggcc atcgccctga tagacggttt ttcgcccttt gacgttggag tccacgttct  6000
ttaatagtgg actcttgttc caaactggaa caacactcaa ccctatctcg gtctattctt  6060
ttgatttata agggattttg ccgatttcgg cctattggtt aaaaaatgag ctgatttaac  6120
aaaaatttaa cgcgaattaa ttctgtggaa tgtgtgtcag ttagggtgtg gaaagtcccc  6180
aggctcccca gcaggcagaa gtatgcaaag catgcatctc aattagtcag caaccaggtg  6240
tggaaagtcc ccaggctccc cagcaggcag aagtatgcaa agcatgcatc tcaattagtc  6300
agcaaccata gtcccgcccc taactccgcc catcccgccc ctaactccgc ccagttccgc  6360
ccattctccg ccccatggct gactaatttt ttttatttat gcagaggccg aggccgcctc  6420
tgcctctgag ctattccaga agtagtgagg aggctttttt ggaggcctag gcttttgcaa  6480
aaagctcccg ggagcttgta tatccatttt cggatctgat caagagacag gatgaggatc  6540
gtttcgcatg attgaacaag atggattgca cgcaggttct ccggccgctt gggtggagag  6600
gctattcggc tatgactggg cacaacagac aatcggctgc tctgatgccg ccgtgttccg  6660
gctgtcagcg caggggcgcc cggttctttt tgtcaagacc gacctgtccg gtgccctgaa  6720
tgaactgcag gacgaggcag cgcggctatc gtggctggcc acgacgggcg ttccttgcgc  6780
agctgtgctc gacgttgtca ctgaagcggg aagggactgg ctgctattgg gcgaagtgcc  6840
ggggcaggat ctcctgtcat ctcaccttgc tcctgccgag aaagtatcca tcatggctga  6900
tgcaatgcgg cggctgcata cgcttgatcc ggctacctgc ccattcgacc accaagcgaa  6960
acatcgcatc gagcgagcac gtactcggat ggaagccggt cttgtcgatc aggatgatct  7020
ggacgaagag catcaggggc tcgcgccagc cgaactgttc gccaggctca aggcgcgcat  7080
gcccgacggc gaggatctcg tcgtgaccca tggcgatgcc tgcttgccga atatcatggt  7140
ggaaaatggc cgcttttctg gattcatcga ctgtggccgg ctgggtgtgg cggaccgcta  7200
tcaggacata gcgttggcta cccgtgatat tgctgaagag cttggcggcg aatgggctga  7260
ccgcttcctc gtgctttacg gtatcgccgc tcccgattcg cagcgcatcg ccttctatcg  7320
ccttcttgac gagttcttct gagcgggact ctggggttcg aaatgaccga ccaagcgacg  7380
cccaacctgc catcacgaga tttcgattcc accgccgcct tctatgaaag gttgggcttc  7440
ggaatcgttt tccgggacgc cggctggatg atcctccagc gcggggatct catgctggag  7500
ttcttcgccc accccaactt gtttattgca gcttataatg gttacaaata aagcaatagc  7560
atcacaaatt tcacaaataa agcatttttt tcactgcatt ctagttgtgg tttgtccaaa  7620
ctcatcaatg tatcttatca tgtctgtata ccgtcgacct ctagctagag cttggcgtaa  7680
tcatggtcat agctgtttcc tgtgtgaaat tgttatccgc tcacaattcc acacaacata  7740
cgagccggaa gcataaagtg taaagcctgg ggtgcctaat gagtgagcta actcacatta  7800
attgcgttgc gctcactgcc cgctttccag tcgggaaacc tgtcgtgcca gctgcattaa  7860
tgaatcggcc aacgcgcggg gagaggcggt ttgcgtattg ggcgctcttc cgcttcctcg  7920
ctcactgact cgctgcgctc ggtcgttcgg ctgcggcgag cggtatcagc tcactcaaag  7980
gcggtaatac ggttatccac agaatcaggg gataacgcag gaaagaacat gtgagcaaaa  8040
ggccagcaaa aggccaggaa ccgtaaaaag gccgcgttgc tggcgttttt ccataggctc  8100
cgcccccctg acgagcatca caaaaatcga cgctcaagtc agaggtggcg aaacccgaca  8160
ggactataaa gataccaggc gtttccccct ggaagctccc tcgtgcgctc tcctgttccg  8220
accctgccgc ttaccggata cctgtccgcc tttctccctt cgggaagcgt ggcgctttct  8280
catagctcac gctgtaggta tctcagttcg gtgtaggtcg ttcgctccaa gctgggctgt  8340
gtgcacgaac cccccgttca gcccgaccgc tgcgccttat ccggtaacta tcgtcttgag  8400
tccaacccgg taagacacga cttatcgcca ctggcagcag ccactggtaa caggattagc  8460
agagcgaggt atgtaggcgg tgctacagag ttcttgaagt ggtggcctaa ctacggctac  8520
actagaagaa cagtatttgg tatctgcgct ctgctgaagc cagttacctt cggaaaaaga  8580
gttggtagct cttgatccgg caaacaaacc accgctggta gcggtggttt ttttgtttgc  8640
aagcagcaga ttacgcgcag aaaaaaagga tctcaagaag atcctttgat cttttctacg  8700
gggtctgacg ctcagtggaa cgaaaactca cgttaaggga ttttggtcat gagattatca  8760
aaaaggatct tcacctagat ccttttaaat taaaaatgaa gttttaaatc aatctaaagt  8820
atatatgagt aaacttggtc tgacagttac caatgcttaa tcagtgaggc acctatctca  8880
gcgatctgtc tatttcgttc atccatagtt gcctgactcc ccgtcgtgta gataactacg  8940
atacgggagg gcttaccatc tggccccagt gctgcaatga taccgcgaga cccacgctca  9000
ccggctccag atttatcagc aataaaccag ccagccggaa gggccgagcg cagaagtggt  9060
cctgcaactt tatccgcctc catccagtct attaattgtt gccgggaagc tagagtaagt  9120
agttcgccag ttaatagttt gcgcaacgtt gttgccattg ctacaggcat cgtggtgtca  9180
cgctcgtcgt ttggtatggc ttcattcagc tccggttccc aacgatcaag gcgagttaca  9240
tgatccccca tgttgtgcaa aaaagcggtt agctccttcg gtcctccgat cgttgtcaga  9300
agtaagttgg ccgcagtgtt atcactcatg gttatggcag cactgcataa ttctcttact  9360
gtcatgccat ccgtaagatg cttttctgtg actggtgagt actcaaccaa gtcattctga  9420
```

```
gaatagtgta tgcggcgacc gagttgctct tgcccggcgt caatacggga taataccgcg  9480
ccacatagca gaactttaaa agtgctcatc attggaaaac gttcttcggg gcgaaaactc  9540
tcaaggatct taccgctgtt gagatccagt tcgatgtaac ccactcgtgc acccaactga  9600
tcttcagcat cttttacttt caccagcgtt tctgggtgag caaaaacagg aaggcaaaat  9660
gccgcaaaaa agggaataag ggcgacacgg aaatgttgaa tactcatact cttccttttt  9720
caatattatt gaagcattta tcagggttat tgtctcatga gcggatacat atttgaatgt  9780
atttagaaaa ataaacaaat aggggttccg cgcacatttc cccgaaaagt gccacctgac  9840
gtc                                                                9843

SEQ ID NO: 99          moltype = DNA  length = 9537
FEATURE                Location/Qualifiers
source                 1..9537
                       mol_type = other DNA
                       organism = synthetic construct
SEQUENCE: 99
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttctagat  240
gtacactcga ggtgagcccc acgttctgct tcactctccc catctccccc ccctccccac  300
ccccaatttt gtatttattt atttttaat tattttgtgc agcgatgggg gcgggggggg  360
gggggggggc gcgcgccagg cggggcgggg cggggcgagg ggcggggcgg ggcgaggcgg  420
agaggtgcgg cggcagccaa tcagagcggc gcgctccgaa agtttccttt tatggcgagg  480
cggcggcggc ggcggcccta taaaaagcga agcgcgcggc gggcggccac cccgcgggcc  540
cgttaattaa accggtcgcc accatgaagt gggtaacctt tatttccctt ctttttctct  600
ttagctcggc ttattccagg ggtgtgtttc gtcgagacta caaagacgat gacgacaaga  660
gcgctggcct gaagccaagc tgcgccaagg aggtgaagag ctgcaagggc agatgtttcg  720
aacggacctt cggcaactgc agatgcgacg ccgcctgcgt ggaactggga aactgttgtc  780
tggactacca ggagacatgt atcgagcctg agcacatctg gacatgcaac aagttcagat  840
gtggcgagaa aagactgact cggagtctgt gcgcctgttc tgacgactgc aaggacaagg  900
gcgattgctg catcaactac agcagcgtgt gccagggcga aaagagctgg gtcgaggaac  960
cctgcgagag catcaacgag ccccagtgcc ctgccggatt tgagacacct cctaccctgc  1020
tcttctccct ggatggcttc agagctgagt acctgcatac atggggagga ctgctgcctg  1080
tgatcagcaa gctgaagaag tgcggcacct acacaaagaa catgcggcct gtctacccta  1140
ccaagacctt ccccaaccac tacagcatcg tgaccggcct gtaccccgag agccacggca  1200
tcatcgacaa caagatgtac gaccccaaaa tgaacgccag cttcagcctg aaatctaagg  1260
aaaagttcaa ccctgagtgg tataagggcg agccaatctg ggtgacagcc aagtaccagg  1320
gcctgaagag cggcaccttc ttctggcctg gcagcgacgt ggagatcaac ggaatcttcc  1380
ctgatatcta caagatgtat aacggctccg tgcctttcga ggagcggatc ttggctgttc  1440
ttcagtggct gcagctgccc aaggacgaga gaccccactt ctacaccctg tacctggaag  1500
aacctgacag cagcggccac agctacggcc ctgtgtctag cgaggtgatc aaggccctgc  1560
aaagagtgga tggcatggtg ggcatgctga tggatggact gaaggaactg aacctccatc  1620
gttgcctgaa cctgatcctg atctccgacc acggcatgga acagggcagc tgtaaaaagt  1680
acatctacct gaacaagtac ctgggcgacg tgaagaatat caaggtgatc tacgggccgg  1740
ccgccaggct gcggcctagc gacgtgcccg acaagtatta cagcttcaac tacgagggca  1800
tcgccagaaa cctgtcttgc agagaaccca atcaacactt caagccttac ctgaagcact  1860
ttctgcctaa gagactgcac ttcgccaaaa gcgacagaat tgaacccctg acattctatc  1920
tggaccctca gtggcagctg gccctcaatc cttctgaacg caaatactgc ggtagcggat  1980
ttcacggctc tgataacgtg ttttctaaca tgcaggccct gtttgtgggc tacggccctg  2040
gcttcaagca cggaatcgag gctgacacct tcgagaacat cgaagtttac aatctgatgt  2100
gcgacctgct gaatctgacc ccagccccta acaacggcac acacggctct ctgaatcacc  2160
tgctcaagaa ccccgtgtat accccccaaac accctaaaga ggtccatcca ctggtgcagt  2220
gcccattcac cagaaaccct cgggacaacc ttggctgcag ctgcaaccct agcatcctcc  2280
ctatcgaaga tttccagacc cagtttaacc tgactgtcgc cgaagagaag atcatcaagc  2340
acgaaaccct gccctacggg aggcccagag tgctgcagaa agaaaacaca atctgtctgc  2400
tgagccagca ccagtttatg agcggctaca gtcaggacat cctgatgcct ctgtggacca  2460
gctacaccgt ggaccggaat gacagcttca gcaccgagga cttcagcaac tgcctgtatc  2520
aggacttccg catccctctg tcccctgtgc ataagtgcag cttttacaag aacaacacca  2580
aggtgagcta cgggtttctg agcccaccac aactgaacaa aaatagctct ggcatctact  2640
ctgaggcgct gctgaccacc aacatcgtgc caatgtacca gagcttccag gtgatctggc  2700
ggtacttcca tgataccctg cttcggaagt acgccgaaga acggaacggc gtgaacgtgg  2760
tgtccggccc agtgttcgac ttcgactacg acggcagatg tgattccctt gagaatctga  2820
gacagaagcg gcgggttatc agaaaccagg agatcctgat tcctacccac ttcttcatcg  2880
tgctgacatc ttgcaaggat accagccaaa cacctctgca ctgcgagaac ctggacaccc  2940
tggccttcat cctgcctcac cggaccgata atagcgaatc ctgtgtgcac ggcaaacacg  3000
actctagctg ggtggaagag ctgctgatgc tgcacagagc ccggatcaca gatgtggaac  3060
acatcaccgg cctgtccttc taccaacaga gaaaggaacc cgtgtctgat atcctgaagc  3120
tgaaaaccca cctgcctacc ttcagccagg aggacctgat cgttaacgat gcacacaaga  3180
gtgaggttgc tcatcggttt aaagatttgg gagaagaaaa tttcaaagcc ttggtgttga  3240
ttgcctttgc tcagtatctt cagcagtgtc catttgaaga tcatgtaaaa ttagtgaatg  3300
aagtaactga atttgcaaaa acatgtgttg ctgatgagtc agctgaaaat tgtgacaaat  3360
cacttcatac cctttttgga gacaaattat gcacagttgc aactcttcgt gaaacctatg  3420
gtgaaatggc tgactgctgt gcaaaacaag aacctgagag aaatgaatgc ttcttgcaac  3480
acaaagatga caacccaaac ctcccccgat tggtgagacc agaggttgat gtgatgtgca  3540
ctgcttttca tgacaatgaa gagacatttt tgaaaaaata cttatatgaa attgccagaa  3600
gacatcctta cttttatgcc ccggaactcc ttttctttgc taaaaggtat aaagctgctt  3660
ttacagaatg ttgccaagct gctgataaag ctgcctgcct gttgccaaag ctcgatgaac  3720
ttcgggatga agggaaggct tcgtctgcca aacagagact caagtgtgcc agtctccaaa  3780
aatttggaga aagagctttc aaagcatggg cagtagctcg cctgagccag agatttccca  3840
```

-continued

```
aagctgagtt tgcagaagtt tccaagttag tgacagatct taccaaagtc cacacggaat  3900
gctgccatgg agatctgctt gaatgtgctg atgacagggc ggaccttgcc aagtatatct  3960
gtgaaaatca agattcgatc tccagtaaac tgaaggaatg ctgtgaaaaa cctctgttgg  4020
aaaaatccca ctgcattgcc gaagtggaaa atgatgagat gcctgctgac ttgccttcat  4080
tagctgctga ttttgttgaa agtaaggatg tttgcaaaaa ctatgctgag gcaaaggatg  4140
tcttcctggg catgtttttg tatgaatatg caagaaggca tcctgattac tctgtcgtgc  4200
tgctgctgag acttgccaag acatatgaaa ccacactcga gaagtgctgt gccgctgcag  4260
atcctcatga atgctatgcc aaagtgttcg atgaatttaa acctcttgtg gaagagcctc  4320
agaatttaat caaacaaaat tgtgagcttt ttgagcagct tggagagtac aaattccaga  4380
atgcgctatt agttcgttac accaagaaag taccccaagt gtcaactcca actcttgtag  4440
aggtctcaag aaacctagga aaagtgggca gcaaatgttg taaacatcct gaagcaaaaa  4500
gaatgccctg tgcagaagac tatctatccg tggtcctgaa ccagttatgt gtgttgcatg  4560
agaaaacgcc agtaagtgac agagtcacca aatgctgcac agaatccttg gtgaacaggc  4620
gaccatgctt ttcagctctg gaagtcgatg aaacatacgt tcccaaagag tttaatgctg  4680
aaacattcac cttccatgca gatatatgca cactttctga gaaggagaga caaatcaaga  4740
aacaaactgc acttgttgag ctcgtgaaac acaagcccaa ggcaacaaaa gagcaactga  4800
aagctgttat ggatgatttc gcagcttttg tagagaagtg ctgcaaggct gacgataagg  4860
agacctgctt tgccgaggag ggtaaaaaac ttgttgctgc aagtcaagct gccttaggct  4920
tataaggcgc gcccacgtgt aaaacttgtt tattgcagct tataatggtt acaaataaag  4980
caatagcatc acaaatttca caaataaagc atttttttca ctgcattcta gttgtggttt  5040
gtccaaactc atcaatgtat cttatcatgt ctggatcatc gatgcggccg ctcgagtcta  5100
gagggcccgt ttaaacccgc tgatcagcct cgactgtgcc ttctagttgc cagccatctg  5160
ttgtttgccc ctcccccgtg ccttccttga ccctggaagg tgccactccc actgtccttt  5220
cctaataaaa tgaggaaatt gcatcgcatt gtctgagtag gtgtcattct attctggggg  5280
gtggggtggg gcaggacagc aagggggagg attgggaaga caatagcagg catgctgggg  5340
atgcggtggg ctctatggct tctgaggcgg aaagaaccag ctggggctct agggggtatc  5400
cccacgcgcc ctgtagcggc gcattaagcg cggcgggtgt ggtggttacg cgcagcgtga  5460
ccgctacact tgccagcgcc ctagcgcccg ctcctttcgc tttcttccct tcctttctcg  5520
ccacgttcgc cggctttccc cgtcaagctc taaatcgggg gctcccttta gggttccgat  5580
ttagtgcttt acggcacctc gaccccaaaa aacttgatta gggtgatggt tcacgtagtg  5640
ggccatcgcc ctgatagacg gtttttcgcc ctttgacgtt ggagtccacg ttctttaata  5700
gtggactctt gttccaaact ggaacaacac tcaaccctat ctcggtctat tcttttgatt  5760
tataagggat tttgccgatt tcggcctatt ggttaaaaaa tgagctgatt taacaaaaat  5820
ttaacgcgaa ttaattctgt ggaatgtgtg tcagttaggg tgtggaaagt ccccaggctc  5880
cccagcaggc agaagtatgc aaagcatgca tctcaattag tcagcaacca ggtgtggaaa  5940
gtccccaggc tccccagcag gcagaagtat gcaaagcatg catctcaatt agtcagcaac  6000
catagtcccg cccctaactc cgcccatccc gcccctaact ccgcccagtt ccgcccattc  6060
tccgccccat ggctgactaa ttttttttat ttatgcagag gccgaggccg cctctgcctc  6120
tgagctattc cagaagtagt gaggaggctt ttttggaggc ctaggctttt gcaaaaagct  6180
cccgggagct tgtatatcca ttttcggatc tgatcaagag acaggatgag gatcgtttcg  6240
catgattgaa caagatggat tgcacgcagg ttctccggcc gcttgggtgg agaggctatt  6300
cggctatgac tgggcacaac agacaatcgg ctgctctgat gccgccgtgt tccggctgtc  6360
agcgcagggg cgcccggttc tttttgtcaa gaccgacctg tccggtgccc tgaatgaact  6420
gcaggacgag gcagcgcggc tatcgtggct ggccacgacg ggcgttcctt gcgcagctgt  6480
gctcgacgtt gtcactgaag cgggaaggga ctggctgcta ttgggcgaag tgccggggca  6540
ggatctcctg tcatctcacc ttgctcctgc cgagaaagta tccatcatgg ctgatgcaat  6600
gcggcggctg catacgcttg atccggctac ctgcccattc gaccaccaag cgaaacatcg  6660
catcgagcga gcacgtactc ggatggaagc cggtcttgtc gatcaggatg atctggacga  6720
agagcatcag gggctcgcgc cagccgaact gttcgccagg ctcaaggcgc gcatgcccga  6780
cggcgaggat ctcgtcgtga cccatggcga tgcctgcttg ccgaatatca tggtggaaaa  6840
tggccgcttt tctggattca tcgactgtgg ccggctgggt gtggcggacc gctatcagga  6900
catagcgttg gctacccgtg atattgctga agagcttggc ggcgaatggg ctgaccgctt  6960
cctcgtgctt tacggtatcg ccgctcccga ttcgcagcgc atcgccttct atcgccttct  7020
tgacgagttc ttctgagcgg gactctgggg ttcgaaatga ccgaccaagc gacgcccaac  7080
ctgccatcac gagatttcga ttccaccgcc gccttctatg aaaggttggg cttcggaatc  7140
gttttccggg acgccggctg gatgatcctc cagcgcgggg atctcatgct ggagttcttc  7200
gcccacccca acttgtttat tgcagcttat aatggttaca aataaagcaa tagcatcaca  7260
aatttcacaa ataaagcatt tttttcactg cattctagtt gtggtttgtc caaactcatc  7320
aatgtatctt atcatgtctg tataccgtcg acctctagct agagcttggc gtaatcatgg  7380
tcatagctgt ttcctgtgtg aaattgttat ccgctcacaa ttccacacaa catacgagcc  7440
ggaagcataa agtgtaaagc ctggggtgcc taatgagtga gctaactcac attaattgcg  7500
ttgcgctcac tgcccgcttt ccagtcggga aacctgtcgt gccagctgca ttaatgaatc  7560
ggccaacgcg cggggagagg cggtttgcgt attgggcgct cttccgcttc ctcgctcact  7620
gactcgctgc gctcggtcgt tcggctgcgg cgagcggtat cagctcactc aaaggcggta  7680
atacggttat ccacagaatc aggggataac gcaggaaaga acatgtgagc aaaaggccag  7740
caaaaggcca ggaaccgtaa aaaggccgcg ttgctggcgt ttttccatag gctccgcccc  7800
cctgacgagc atcacaaaaa tcgacgctca agtcagaggt ggcgaaaccc gacaggacta  7860
taaagatacc aggcgtttcc ccctggaagc tccctcgtgc gctctcctgt tccgaccctg  7920
ccgcttaccg gatacctgtc cgcctttctc ccttcgggaa gcgtggcgct ttctcatagc  7980
tcacgctgta ggtatctcag ttcggtgtag gtcgttcgct ccaagctggg ctgtgtgcac  8040
gaaccccccg ttcagcccga ccgctgcgcc ttatccggta actatcgtct tgagtccaac  8100
ccggtaagac acgacttatc gccactggca gcagccactg gtaacaggat tagcagagcg  8160
aggtatgtag gcggtgctac agagttcttg aagtggtggc ctaactacgg ctacactaga  8220
agaacagtat ttggtatctg cgctctgctg aagccagtta ccttcggaaa aagagttggt  8280
agctcttgat ccggcaaaca aaccaccgct ggtagcggtg gtttttttgt ttgcaagcag  8340
cagattacgc gcagaaaaaa aggatctcaa gaagatcctt tgatcttttc tacggggtct  8400
gacgctcagt ggaacgaaaa ctcacgttaa gggattttgg tcatgagatt atcaaaaagg  8460
atcttcacct agatcctttt aaattaaaaa tgaagtttta aatcaatcta aagtatatat  8520
gagtaaactt ggtctgacag ttaccaatgc ttaatcagtg aggcacctat ctcagcgatc  8580
```

-continued

```
tgtctatttc gttcatccat agttgcctga ctccccgtcg tgtagataac tacgatacgg  8640
gagggcttac catctggccc cagtgctgca atgataccgc gagacccacg ctcaccggct  8700
ccagatttat cagcaataaa ccagccagcc ggaagggccg agcgcagaag tggtcctgca  8760
actttatccg cctccatcca gtctattaat tgttgccggg aagctagagt aagtagttcg  8820
ccagttaata gtttgcgcaa cgttgttgcc attgctacag gcatcgtggt gtcacgctcg  8880
tcgtttggta tggcttcatt cagctccggt tcccaacgat caaggcgagt tacatgatcc  8940
cccatgttgt gcaaaaaagc ggttagctcc ttcggtcctc cgatcgttgt cagaagtaag  9000
ttggccgcag tgttatcact catggttatg gcagcactgc ataattctct tactgtcatg  9060
ccatccgtaa gatgcttttc tgtgactggt gagtactcaa ccaagtcatt ctgagaatag  9120
tgtatgcggc gaccgagttg ctcttgcccg gcgtcaatac gggataatac cgcgccacat  9180
agcagaactt taaaagtgct catcattgga aaacgttctt cggggcgaaa actctcaagg  9240
atcttaccgc tgttgagatc cagttcgatg taacccactc gtgcacccaa ctgatcttca  9300
gcatctttta ctttcaccag cgtttctggg tgagcaaaaa caggaaggca aaatgccgca  9360
aaaaagggaa taagggcgac acggaaatgt tgaatactca tactcttcct ttttcaatat  9420
tattgaagca tttatcaggg ttattgtctc atgagcggat acatatttga atgtatttag  9480
aaaaataaac aaataggggt tccgcgcaca tttccccgaa aagtgccacc tgacgtc     9537

SEQ ID NO: 100          moltype = DNA  length = 9416
FEATURE                 Location/Qualifiers
source                  1..9416
                        mol_type = other DNA
                        organism = synthetic construct
SEQUENCE: 100
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgaaaac  240
tacaattgac tatctctaaa ttttaaaatg tgatgatagt tactacttca gtggtccaca  300
ctgtttctat cctttggaac ataagatttt gttgtgtagc ttaaggaaga ggaattcagc  360
agttgactat ctcgattgtt ctgggaattt tggaggctga ggggaaattt tcacatataa  420
gcgctgggtt tgctggggta ttgagagtga cctctggcta actagagaac ccactgctta  480
ctggcttatc gaaattaata cgactcacta tagggagacc caagctggct agcgccacca  540
tgaagtgggt aacctttatt tcccttcttt ttctctttag ctcggcttat tccaggggtg  600
tgtttcgtcg agactacaaa gacgatgacg acaagagcgc tggcctgaag ccaagctgcg  660
ccaaggaggt gaagagctgc aagggcagat gtttcgaacg gaccttcggc aactgcagat  720
gcgacgccgc ctgcgtggaa ctgggaaact gttgtctgga ctaccaggag acatgtatcg  780
agcctgagca catctggaca tgcaacaagt tcagatgtgg cgagaaaaga ctgactcgga  840
gtctgtgcgc ctgttctgac gactgcaagg acaagggcga ttgctgcatc aactacagca  900
gcgtgtgcca gggcgaaaag agctgggtcg aggaaccctg cgagagcatc aacgagcccc  960
agtgccctgc cggatttgag acacctccta ccctgctctt ctccctggat ggcttcagag  1020
ctgagtacct gcatacatgg ggaggactgc tgcctgtgat cagcaagctg aagaagtgcg  1080
gcacctacac aaagaacatg cggcctgtct accctaccaa gaccttcccc aaccactaca  1140
gcatcgtgac cggcctgtac cccgagagcc acggcatcat cgacaacaag atgtacgacc  1200
ccaaaatgaa cgccagcttc agcctgaaat ctaaggaaaa gttcaaccct gagtggtata  1260
agggcgagcc aatctgggtg acagccaagt accagggcct gaagagcggc accttcttct  1320
ggcctggcag cgacgtggag atcaacggaa tcttccctga tatctacaag atgtataacg  1380
gctccgtgcc tttcgaggag cggatcttgg ctgttcttca gtggctgcag ctgcccaagg  1440
acgagagacc ccacttctac accctgtacc tggaagaacc tgacagcagc ggccacagct  1500
acggccctgt gtctagcgag gtgatcaagg ccctgcaaag agtggatggc atggtgggca  1560
tgctgatgga tggactgaag gaactgaacc tccatcgttg cctgaacctg atcctgatct  1620
ccgaccacgg catggaacag ggcagctgta aaaagtacat ctacctgaac aagtacctgg  1680
gcgacgtgaa gaatatcaag gtgatctacg ggccggccgc caggctgcgg cctagcgacg  1740
tgcccgacaa gtattacagc ttcaactacg agggcatcgc cagaaacctg tcttgcagag  1800
aacccaatca acacttcaag ccttacctga agcactttct gcctaagaga ctgcacttcg  1860
ccaaaagcga cagaattgaa cccctgacat tctatctgga ccctcagtgg cagctggccc  1920
tcaatccttc tgaacgcaaa tactgcggta gcggatttca cggctctgat aacgtgtttt  1980
ctaacatgca ggccctgttt gtgggctacg gccctggctt caagcacgga atcgaggctg  2040
acaccttcga gaacatcgaa gtttacaatc tgatgtgcga cctgctgaat ctgaccccag  2100
cccctaacaa cggcacacac ggctctctga atcacctgct caagaacccc gtgtataccc  2160
ccaaacaccc taaagaggtc catccactgg tgcagtgccc attcaccaga aaccctcggg  2220
acaaccttgg ctgcagctgc aaccctagca tcctccctat cgaagatttc cagacccagt  2280
ttaacctgac tgtcgccgaa gagaagatca tcaagcacga aaccctgccc tacgggaggc  2340
ccagagtgct gcagaaagaa aacacaatct gtctgctgag ccagcaccag tttatgagcg  2400
gctacagtca ggacatcctg atgcctctgt ggaccagcta caccgtggac cggaatgaca  2460
gcttcagcac cgaggacttc agcaactgcc tgtatcagga cttccgcatc cctctgtccc  2520
ctgtgcataa gtgcagcttt tacaagaaca acaccaaggt gagctacggg tttctgagcc  2580
caccacaact gaacaaaaat agctctggca tctactctga ggcgctgctg accaccaaca  2640
tcgtgccaat gtaccagagc ttccaggtga tctggcggta cttccatgat accctgcttc  2700
ggaagtacgc cgaagaacgg aacggcgtga acgtggtgtc cggcccagtg ttcgacttcg  2760
actacgacgg cagatgtgat tcccttgaga atctgagaca gaagcggcgg gttatcagaa  2820
accaggagat cctgattcct acccacttct tcatcgtgct gacatcttgc aaggatacca  2880
gccaaacacc tctgcactgc gagaacctgg acaccctggc cttcatcctg cctcaccgga  2940
ccgataatag cgaatcctgt gtgcacggca aacacgactc tagctgggtg gaagagctgc  3000
tgatgctgca cagagcccgg atcacagatg tggaacacat caccggcctg tccttctacc  3060
aacagagaaa ggaacccgtg tctgatatcc tgaagctgaa aacccacctg cctaccttca  3120
gccaggagga cctgatcgtt aacgatgcac acaagagtga ggttgctcat cggtttaaag  3180
atttgggaga agaaaatttc aaagccttgg tgttgattgc ctttgctcag tatcttcagc  3240
agtgtccatt tgaagatcat gtaaaattag tgaatgaagt aactgaattt gcaaaaacat  3300
gtgttgctga tgagtcagct gaaaattgtg acaaatcact tcataccctt tttggagaca  3360
```

-continued

```
aattatgcac agttgcaact cttcgtgaaa cctatggtga aatggctgac tgctgtgcaa  3420
aacaagaacc tgagagaaat gaatgcttct tgcaacacaa agatgacaac ccaaacctcc  3480
cccgattggt gagaccagag gttgatgtga tgtgcactgc ttttcatgac aatgaagaga  3540
catttttgaa aaaatactta tatgaaattg ccagaagaca tccttacttt tatgccccgg  3600
aactcctttt ctttgctaaa aggtataaag ctgcttttac agaatgttgc caagctgctg  3660
ataaagctgc ctgcctgttg ccaaagctcg atgaacttcg ggatgaaggg aaggcttcgt  3720
ctgccaaaca gagactcaag tgtgccagtc tccaaaaatt tggagaaaga gctttcaaag  3780
catgggcagt agctcgcctg agccagagat ttcccaaagc tgagtttgca gaagtttcca  3840
agttagtgac agatcttacc aaagtccaca cggaatgctg ccatggagat ctgcttgaat  3900
gtgctgatga cagggcggac cttgccaagt atatctgtga aaatcaagat tcgatctcca  3960
gtaaactgaa ggaatgctgt gaaaaacctc tgttggaaaa atcccactgc attgccgaag  4020
tggaaaatga tgagatgcct gctgacttgc cttcattagc tgctgatttt gttgaaagta  4080
aggatgtttg caaaaactat gctgaggcaa aggatgtctt cctgggcatg tttttgtatg  4140
aatatgcaag aaggcatcct gattactctg tcgtgctgct gctgagactt gccaagacat  4200
atgaaaccac actcgagaag tgctgtgccg ctgcagatcc tcatgaatgc tatgccaaag  4260
tgttcgatga atttaaacct cttgtggaag agcctcagaa tttaatcaaa caaaattgtg  4320
agctttttga gcagcttgga gagtacaaat tccagaatgc gctattagtt cgttacacca  4380
agaaagtacc ccaagtgtca actccaactc ttgtagaggt ctcaagaaac ctaggaaaag  4440
tgggcagcaa atgttgtaaa catcctgaag caaaaagaat gccctgtgca gaagactatc  4500
tatccgtggt cctgaaccag ttatgtgtgt tgcatgagaa aacgccagta agtgacagag  4560
tcaccaaatg ctgcacagaa tccttggtga acaggcgacc atgcttttca gctctggaag  4620
tcgatgaaac atacgttccc aaagagttta atgctgaaac attcaccttc catgcagata  4680
tatgcacact ttctgagaag gagagacaaa tcaagaaaca aactgcactt gttgagctcg  4740
tgaaacacaa gcccaaggca acaaaagagc aactgaaagc tgttatggat gatttcgcag  4800
cttttgtaga gaagtgctgc aaggctgacg ataaggagac ctgctttgcc gaggagggta  4860
aaaaacttgt tgctgcaagt caagctgcct taggcttatg aggtaccgag ctcggatcca  4920
ctagtccagt gtggtggaat tctgcagata tccagcacag tggcggccgc tcgagtctag  4980
agggcccgtt taaacccgct gatcagcctc gactgtgcct tctagttgcc agccatctgt  5040
tgtttgcccc tcccccgtgc cttccttgac cctggaaggt gccactccca ctgtcctttc  5100
ctaataaaat gaggaaattg catcgcattg tctgagtagg tgtcattcta ttctgggggg  5160
tggggtgggg caggacagca agggggagga ttgggaagac aatagcaggc atgctgggga  5220
tgcggtgggc tctatggctt ctgaggcgga aagaaccagc tggggctcta gggggtatcc  5280
ccacgcgccc tgtagcggcg cattaagcgc ggcgggtgtg gtggttacgc gcagcgtgac  5340
cgctacactt gccagcgccc tagcgcccgc tcctttcgct ttcttccctt cctttctcgc  5400
cacgttcgcc ggctttcccc gtcaagctct aaatcggggg ctccctttag ggttccgatt  5460
tagtgcttta cggcacctcg accccaaaaa acttgattag ggtgatggtt cacgtagtgg  5520
gccatcgccc tgatagacgg tttttcgccc tttgacgttg gagtccacgt tctttaatag  5580
tggactcttg ttccaaactg gaacaacact caaccctatc tcggtctatt cttttgattt  5640
ataagggatt ttgccgattt cggcctattg gttaaaaaat gagctgattt aacaaaaatt  5700
taacgcgaat taattctgtg gaatgtgtgt cagttagggt gtggaaagtc cccaggctcc  5760
ccagcaggca gaagtatgca aagcatgcat ctcaattagt cagcaaccag gtgtggaaag  5820
tccccaggct ccccagcagg cagaagtatg caaagcatgc atctcaatta gtcagcaacc  5880
atagtcccgc ccctaactcc gcccatcccg cccctaactc cgcccagttc cgcccattct  5940
ccgccccatg gctgactaat tttttttatt tatgcagagg ccgaggccgc ctctgcctct  6000
gagctattcc agaagtagtg aggaggcttt tttggaggcc taggcttttg caaaaagctc  6060
ccgggagctt gtatatccat tttcggatct gatcaagaga caggatgagg atcgtttcgc  6120
atgattgaac aagatggatt gcacgcaggt tctccggccg cttgggtgga gaggctattc  6180
ggctatgact gggcacaaca gacaatcggc tgctctgatg ccgccgtgtt ccggctgtca  6240
gcgcaggggc gcccggttct ttttgtcaag accgacctgt ccggtgccct gaatgaactg  6300
caggacgagg cagcgcggct atcgtggctg gccacgacgg gcgttccttg cgcagctgtg  6360
ctcgacgttg tcactgaagc gggaagggac tggctgctat tgggcgaagt gccggggcag  6420
gatctcctgt catctcacct tgctcctgcc gagaaagtat ccatcatggc tgatgcaatg  6480
cggcggctgc atacgcttga tccggctacc tgcccattcg accaccaagc gaaacatcgc  6540
atcgagcgag cacgtactcg gatggaagcc ggtcttgtcg atcaggatga tctggacgaa  6600
gagcatcagg ggctcgcgcc agccgaactg ttcgccaggc tcaaggcgcg catgcccgac  6660
ggcgaggatc tcgtcgtgac ccatggcgat gcctgcttgc cgaatatcat ggtggaaaat  6720
ggccgctttt ctggattcat cgactgtggc cggctgggtg tggcggaccg ctatcaggac  6780
atagcgttgg ctacccgtga tattgctgaa gagcttggcg gcgaatgggc tgaccgcttc  6840
ctcgtgcttt acggtatcgc cgctcccgat tcgcagcgca tcgccttcta tcgccttctt  6900
gacgagttct tctgagcggg actctggggt tcgaaatgac cgaccaagcg acgcccaacc  6960
tgccatcacg agatttcgat tccaccgccg ccttctatga aaggttgggc ttcggaatcg  7020
ttttccggga cgccggctgg atgatcctcc agcgcgggga tctcatgctg gagttcttcg  7080
cccaccccaa cttgtttatt gcagcttata atggttacaa ataaagcaat agcatcacaa  7140
atttcacaaa taaagcattt ttttcactgc attctagttg tggtttgtcc aaactcatca  7200
atgtatctta tcatgtctgt ataccgtcga cctctagcta gagcttggcg taatcatggt  7260
catagctgtt tcctgtgtga aattgttatc cgctcacaat tccacacaac atacgagccg  7320
gaagcataaa gtgtaaagcc tggggtgcct aatgagtgag ctaactcaca ttaattgcgt  7380
tgcgctcact gcccgctttc cagtcgggaa acctgtcgtg ccagctgcat taatgaatcg  7440
gccaacgcgc ggggagaggc ggtttgcgta ttgggcgctc ttccgcttcc tcgctcactg  7500
actcgctgcg ctcggtcgtt cggctgcggc gagcggtatc agctcactca aaggcggtaa  7560
tacggttatc cacagaatca ggggataacg caggaaagaa catgtgagca aaaggccagc  7620
aaaaggccag gaaccgtaaa aaggccgcgt tgctggcgtt tttccatagg ctccgccccc  7680
ctgacgagca tcacaaaaat cgacgctcaa gtcagaggtg gcgaaacccg acaggactat  7740
aaagatacca ggcgtttccc cctggaagct ccctcgtgcg ctctcctgtt ccgaccctgc  7800
cgcttaccgg atacctgtcc gcctttctcc cttcgggaag cgtggcgctt tctcatagct  7860
cacgctgtag gtatctcagt tcggtgtagg tcgttcgctc caagctgggc tgtgtgcacg  7920
aaccccccgt tcagcccgac cgctgcgcct tatccggtaa ctatcgtctt gagtccaacc  7980
cggtaagaca cgacttatcg ccactggcag cagccactgg taacaggatt agcagagcga  8040
ggtatgtagg cggtgctaca gagttcttga agtggtggcc taactacggc tacactagaa  8100
```

```
gaacagtatt tggtatctgc gctctgctga agccagttac cttcggaaaa agagttggta  8160
gctcttgatc cggcaaacaa accaccgctg gtagcggtgg tttttttgtt tgcaagcagc  8220
agattacgcg cagaaaaaaa ggatctcaag aagatccttt gatcttttct acggggtctg  8280
acgctcagtg gaacgaaaac tcacgttaag ggattttggt catgagatta tcaaaaagga  8340
tcttcaccta gatcctttta aattaaaaat gaagttttaa atcaatctaa agtatatatg  8400
agtaaacttg gtctgacagt taccaatgct taatcagtga ggcacctatc tcagcgatct  8460
gtctatttcg ttcatccata gttgcctgac tccccgtcgt gtagataact acgatacggg  8520
agggcttacc atctggcccc agtgctgcaa tgataccgcg agacccacgc tcaccggctc  8580
cagatttatc agcaataaac cagccagccg gaagggccga gcgcagaagt ggtcctgcaa  8640
ctttatccgc ctccatccag tctattaatt gttgccggga agctagagta agtagttcgc  8700
cagttaatag tttgcgcaac gttgttgcca ttgctacagg catcgtggtg tcacgctcgt  8760
cgtttggtat ggcttcattc agctccggtt cccaacgatc aaggcgagtt acatgatccc  8820
ccatgttgtg caaaaaagcg gttagctcct tcggtcctcc gatcgttgtc agaagtaagt  8880
tggccgcagt gttatcactc atggttatgg cagcactgca taattctctt actgtcatgc  8940
catccgtaag atgcttttct gtgactggtg agtactcaac caagtcattc tgagaatagt  9000
gtatgcggcg accgagttgc tcttgcccgg cgtcaatacg ggataatacc gcgccacata  9060
gcagaacttt aaaagtgctc atcattggaa aacgttcttc ggggcgaaaa ctctcaagga  9120
tcttaccgct gttgagatcc agttcgatgt aacccactcg tgcacccaac tgatcttcag  9180
catcttttac tttcaccagc gtttctgggt gagcaaaaac aggaaggcaa aatgccgcaa  9240
aaaagggaat aagggcgaca cggaaatgtt gaatactcat actcttcctt tttcaatatt  9300
attgaagcat ttatcagggt tattgtctca tgagcggata catatttgaa tgtatttaga  9360
aaaataaaca aataggggtt ccgcgcacat ttccccgaaa agtgccacct gacgtc      9416

SEQ ID NO: 101          moltype = DNA  length = 7499
FEATURE                 Location/Qualifiers
source                  1..7499
                        mol_type = other DNA
                        organism = synthetic construct
SEQUENCE: 101
ccaagtcatt ctgagaatag tgtatgcggc gaccgagttg ctcttgcccg gcgtcaatac  60
gggataatac cgcgccacat agcagaactt taaaagtgct catcattgga aaacgttctt  120
cggggcgaaa actctcaagg atcttaccgc tgttgagatc cagttcgatg taacccactc  180
gtgcacccaa ctgatcttca gcatctttta ctttcaccag cgtttctggg tgagcaaaaa  240
caggaaggca aaatgccgca aaaaagggaa taagggcgac acggaaatgt tgaatactca  300
tactcttcct ttttcaatat tattgaagca tttatcaggg ttattgtctc atgagcggat  360
acatatttga atgtatttag aaaaataaac aaataggggt tccgcgcaca tttccccgaa  420
aagtgccacc tgacgtctaa gaaaccatta ttatcatgac attaacctat aaaaataggc  480
gtatcacgag gccctttcgt ctcgcgcgtt tcggtgatga cggtgaaaac ctctgacaca  540
tgcagctccc ggagacggtc acagcttgtc tgtaagcgga tgccgggagc agacaagccc  600
gtcagggcgc gtcagcgggt gttggcgggt gtcggggctg gcttaactat gcggcatcag  660
agcagattgt actgagagtg caccatatgc ggtgtgaaat accgcacaga tgcgtaagga  720
gaaaataccg catcaggaaa ttgtaagcgt taatattttg ttaaaattcg cgttaaattt  780
ttgttaaatc agctcatttt ttaaccaata ggccgaaatc ggcaaaatcc cttataaatc  840
aaaagaatag accgagatag ggttgagtgt tgttccagtt tggaacaaga gtccactatt  900
aaagaacgtg gactccaacg tcaaagggcg aaaaaccgtc tatcagggcg atggcccact  960
acgtgaacca tcaccctaat caagtttttt ggggtcgagg tgccgtaaag cactaaatcg  1020
gaaccctaaa gggagccccc gatttagagc ttgacgggga aagccggcga acgtggcgag  1080
aaaggaaggg aagaaagcga aaggagcggg cgctagggcg ctggcaagtg tagcggtcac  1140
gctgcgcgta accaccacac ccgccgcgct taatgcgccg ctacagggcg cgtccattcg  1200
ccattcaggc tgcgcaactg ttgggaaggg cgatcggtgc gggcctcttc gctattacgc  1260
caggctgcag gggggggggg ggggggggca ctccctctct gcgcgctcgc tcgctcactg  1320
aggccgcccg ggcaaagccc gggcgtcggg cgacctttgg tcgcccggcc tcagtgagcg  1380
agcgagcgcg cagagaggga gtggccaact ccatcactag gggttcctca gatctgaatt  1440
cggtacctag ttattaatag taatcaatta cggggtcatt agttcatagc ccatatatgg  1500
agttccgcgt tacataactt acggtaaatg gcccgcctgg ctgaccgccc aacgaccccc  1560
gcccattgac gtcaataatg acgtatgttc ccatagtaac gccaataggg actttccatt  1620
gacgtcaatg ggtggagtat ttacggtaaa ctgcccactt ggcagtacat caagtgtatc  1680
atatgccaag tacgccccct attgacgtca atgacggtaa atggcccgcc tggcattatg  1740
cccagtacat gaccttatgg gactttccta cttggcagta catctacgta ttagtcatcg  1800
ctattaccat ggtcgaggtg agccccacgt tctgcttcac tctccccatc tcccccccct  1860
ccccaccccc aattttgtat ttatttattt tttaattatt ttgtgcagcg atgggggcgg  1920
gggggggggg gggcgcgcgc caggcggggc ggggcggggc gaggggcggg gcggggcgag  1980
gcggagaggt gcggcggcag ccaatcagag cggcgcgctc cgaaagtttc cttttatggc  2040
gaggcggcgg cggcggcggc cctataaaaa gcgaagcgcg cggcgggcgg gagtcgctgc  2100
gcgctgcctt cgccccgtgc cccgctccgc gccgcctcg  cgccgcccgc cccggctctg  2160
actgaccgcg ttactcccac aggtgagcgg gcgggacggc ccttctcctc cgggctgtaa  2220
ttagcgcttg gtttaatgac ggcttgtttc ttttctgtgg ctgcgtgaaa gccttgaggg  2280
gctccgggag ctagagcctc tgctaaccat gttcatgcct tcttcttttt cctacagctc  2340
ctgggcaacg tgctggttat tgtgctgtct catcattttg gcaaagaatt cctcgaagat  2400
ccgaaggggt tcaagcttag cgccaccatg gagcgcgacg gctgcgcggg gggcgggagc  2460
cgcggcggcg agggcgggcg cgctccccgg gagggcccgg cggggaacgg ccgcgatcgg  2520
ggccgcagcc acgctgccga ggcgcccggg gacccgcagg ccgcggcgtc cttgctggcc  2580
cctatggacg tgggggagga gccgctggag aaggcggcgc gcgcccgcac tgccaaggac  2640
cccaacacct ataaagtact ctcgctggta ttgtcagtat gtgtgttaac aacaatactt  2700
ggttgtatat ttgggttgaa accaagctgt gccaaagaag ttaaaagttg caaaggtcgc  2760
tgtttcgaga gaacatttgg gaactgtcgc tgtgatgctg cctgtgttga gcttggaaac  2820
tgctgtttag attaccagga gacgtgcata gaaccagaac atatatggac ttgcaacaaa  2880
ttcaggtgtg gtgagaaaag gttgaccaga agcctctgtg cctgttcaga tgactgcaag  2940
gacaagggcg actgctgcat caactacagt tctgtgtgtc aaggtgagaa aagttgggta  3000
```

-continued

```
gaagaaccat gtgagagcat taatgagcca cagtgcccag cagggtttga aacgcctcct  3060
accctcttat tttctttgga tggattcagg gcagaatatt tacacacttg gggtggactt  3120
cttcctgtta ttagcaaact aaaaaaatgt ggaacatata ctaaaaacat gagaccggta  3180
tatccaacaa aaactttccc caatcactac agcattgtca ccggattgta tccagaatct  3240
catggcataa tcgacaataa aatgtatgat cccaaaatga atgcttcctt ttcacttaaa  3300
agtaaagaga aatttaatcc tgagtggtac aaaggagaac caatttgggt cacagctaag  3360
tatcaaggcc tcaagtctgg cacatttttc tggccaggat cagatgtgga aattaacgga  3420
attttcccag acatctataa aatgtataat ggttcagtac catttgaaga aaggatttta  3480
gctgttcttc agtggctaca gcttcctaaa gatgaaagac cacactttta cactctgtat  3540
ttagaagaac cagattcttc aggtcattca tatggaccag tcagcagtga agtcatcaaa  3600
gccttgcaga gggttgatgg tatggttggt atgctgatgg atggtctgaa agagctgaac  3660
ttgcacagat gcctgaacct catccttatt tcagatcatg gcatggaaca aggcagttgt  3720
aagaaataca tatatctgaa taaatatttg gggatgtta aaaatattaa agttatctat   3780
ggacctgcag ctcgattgag accctctgat gtcccagata aatactattc atttaactat  3840
gaaggcattg cccgaaatct ttcttgccgg gaaccaaacc agcacttcaa accttacctg  3900
aaacatttct tacctaagcg tttgcacttt gctaagagtg atagaattga gcccttgaca  3960
ttctatttgg accctcagtg gcaacttgca ttgaatccct cagaaaggaa atattgtgga  4020
agtggatttc atggctctga caatgtattt tcaaatatgc aagccctctt tgttggctat  4080
ggacctggat tcaagcatgg cattgaggct gacacctttg aaaacattga agtctataac  4140
ttaatgtgtg atttactgaa tttgacaccg gctcctaata acggaactca tggaagtctt  4200
aaccaccttc taaagaatcc tgtttatacg ccaaagcatc ccaaagaagt gcaccccctg  4260
gtacagtgcc ccttcacaag aaaccccaga gataaccttg gctgctcatg taacccttcg  4320
attttgccga ttgaggattt tcaaacacag ttcaatctga ctgtggcaga agagaagatt  4380
attaagcatg aaactttacc ctatggaaga cctagagttc tccagaagga aaacaccatc  4440
tgtcttcttt cccagcacca gtttatgagt ggatacagcc aagacatctt aatgcccctt  4500
tggacatcct ataccgtgga cagaaatgac agtttctcta cggaagactt ctccaactgt  4560
ctgtaccagg actttagaat tcctcttagt cctgtccata aatgttcatt ttataaaaat  4620
aacaccaaag tgagttacgg gttcctctcc ccaccacaac taaataaaaa ttcaagtgga  4680
atatattctg aagctttgct tactacaaat atagtgccaa tgtaccagag ttttcaagtt  4740
atatggcgct actttcatga caccctactg cgaaagtatg ctgaagaaag aaatggtgtc  4800
aatgtcgtca gtggtcctgt gtttgacttt gattatgatg gacgttgtga ttccttagag  4860
aatctgaggc aaaaaagaag agtcatccgt aaccaagaaa ttttgattcc aactcacttc  4920
tttattgtgc taacaagctg taaagataca tctcagacgc ctttgcactg tgaaaaccta  4980
gacaccttag ctttcatttt gcctcacagg actgataaca gcgagagctg tgtgcatggg  5040
aagcatgact cctcatgggt tgaagaattg ttaatgttac acagagcacg gatcacagat  5100
gttgagcaca tcactggact cagcttctat caacaaagaa aagagccagt ttcagacatt  5160
ttaaagttga aaacacattt gccaaccttt agccaagaag acgactacaa agacgatgac  5220
gacaagtgag gtaccgagct cggatccaaa caaacaccat tgtcacactc caacaaacac  5280
cattgtcaca ctccaacaaa caccattgtc acactccatt ctcgagtcta gaaagagatc  5340
cagacatgat aagatacatt gatgagtttg gacaaaccac aactagaatg cagtgaaaaa  5400
aatgctttat ttgtgaaatt tgtgatgcta ttgctttatt tgtaaccatt ataagctgca  5460
ataaacaagt taacaacaac aattgcattc attttatgtt tcaggttcag ggggaggtgt  5520
gggaggtttt ttagtcgact agagctcgct gatcagcctc gactgtgcct tctagttgcc  5580
agccatctgt tgtttgcccc tcccccgtgc cttccttgac cctggaaggt gccactccca  5640
ctgtcctttc ctaataaaat gaggaaattg catcgcattg tctgagtagg tgtcattcta  5700
ttctgggggg tggggtgggg caggacagca agggggagga ttgggaagac aatagcaggc  5760
atgctgggga gagatctgag gaacccctag tgatggagtt ggccactccc tctctgcgcg  5820
ctcgctcgct cactgaggcc gggcgaccaa aggtcgcccg acgcccgggc tttgcccggg  5880
cggcctcagt gagcgagcga gcgcgcagag agggagtggc cccccccccc cccccccctg  5940
cagcctgcat taatgaatcg gccaacgcgc ggggagaggc ggtttgcgta ttgggcgctc  6000
ttccgcttcc tcgctcactg actcgctgcg ctcggtcgtt cggctgcggc gagcggtatc  6060
agctcactca aaggcggtaa tacggttatc cacagaatca ggggataacg caggaaagaa  6120
catgtgagca aaaggccagc aaaaggccag gaaccgtaaa aaggccgcgt tgctggcgtt  6180
tttccatagg ctccgccccc ctgacgagca tcacaaaaat cgacgctcaa gtcagaggtg  6240
gcgaaacccg acaggactat aaagatacca ggcgtttccc cctggaagct ccctcgtgcg  6300
ctctcctgtt ccgaccctgc cgcttaccgg atacctgtcc gcctttctcc cttcgggaag  6360
cgtggcgctt tctcatagct cacgctgtag gtatctcagt tcggtgtagg tcgttcgctc  6420
caagctgggc tgtgtgcacg aaccccccgt tcagcccgac cgctgcgcct tatccggtaa  6480
ctatcgtctt gagtccaacc cggtaagaca cgacttatcg ccactggcag cagccactgg  6540
taacaggatt agcagagcga ggtatgtagg cggtgctaca gagttcttga agtggtggcc  6600
taactacggc tacactagaa gaacagtatt tggtatctgc gctctgctga agccagttac  6660
cttcggaaaa agagttggta gctcttgatc cggcaaacaa accaccgctg gtagcggtgg  6720
tttttttgtt tgcaagcagc agattacgcg cagaaaaaaa ggatctcaag aagatccttt  6780
gatcttttct acggggtctg acgctcagtg gaacgaaaac tcacgttaag ggattttggt  6840
catgagatta tcaaaaagga tcttcaccta gatcctttta aattaaaaat gaagttttaa  6900
atcaatctaa agtatatatg agtaaacttg gtctgacagt taccaatgct taatcagtga  6960
ggcacctatc tcagcgatct gtctatttcg ttcatccata gttgcctgac tccccgtcgt  7020
gtagataact acgatacggg agggcttacc atctggcccc agtgctgcaa tgataccgcg  7080
agacccacgc tcaccggctc cagatttatc agcaataaac cagccagccg gaagggccga  7140
gcgcagaagt ggtcctgcaa ctttatccgc ctccatccag tctattaatt gttgccggga  7200
agctagagta agtagttcgc cagttaatag tttgcgcaac gttgttgcca ttgctacagg  7260
catcgtggtg tcacgctcgt cgtttggtat ggcttcattc agctccggtt cccaacgatc  7320
aaggcgagtt acatgatccc ccatgttgtg caaaaaagcg gttagctcct tcggtcctcc  7380
gatcgttgtc agaagtaagt tggccgcagt gttatcactc atggttatgg cagcactgca  7440
taattctctt actgtcatgc catccgtaag atgcttttct gtgactggtg agtactcaa   7499

SEQ ID NO: 102         moltype = DNA  length = 7487
FEATURE                Location/Qualifiers
source                 1..7487
```

-continued

```
                        mol_type = other DNA
                        organism = synthetic construct
SEQUENCE: 102
ccaagtcatt ctgagaatag tgtatgcggc gaccgagttg ctcttgcccg gcgtcaatac  60
gggataatac cgcgccacat agcagaactt taaaagtgct catcattgga aaacgttctt  120
cggggcgaaa actctcaagg atcttaccgc tgttgagatc cagttcgatg taacccactc  180
gtgcacccaa ctgatcttca gcatctttta ctttcaccag cgtttctggg tgagcaaaaa  240
caggaaggca aaatgccgca aaaaagggaa taagggcgac acggaaatgt tgaatactca  300
tactcttcct ttttcaatat tattgaagca tttatcaggg ttattgtctc atgagcggat  360
acatatttga atgtatttag aaaaataaac aaataggggt tccgcgcaca tttccccgaa  420
aagtgccacc tgacgtctaa gaaaccatta ttatcatgac attaacctat aaaaataggc  480
gtatcacgag gccctttcgt ctcgcgcgtt tcggtgatga cggtgaaaac ctctgacaca  540
tgcagctccc ggagacggtc acagcttgtc tgtaagcgga tgccgggagc agacaagccc  600
gtcagggcgc gtcagcgggt gttggcgggt gtcggggctg gcttaactat gcggcatcag  660
agcagattgt actgagagtg caccatatgc ggtgtgaaat accgcacaga tgcgtaagga  720
gaaaataccg catcaggaaa ttgtaagcgt taatattttg ttaaaattcg cgttaaattt  780
ttgttaaatc agctcatttt ttaaccaata ggccgaaatc ggcaaaatcc cttataaatc  840
aaaagaatag accgagatag ggttgagtgt tgttccagtt tggaacaaga gtccactatt  900
aaagaacgtg gactccaacg tcaaagggcg aaaaaccgtc tatcagggcg atggcccact  960
acgtgaacca tcaccctaat caagtttttt ggggtcgagg tgccgtaaag cactaaatcg  1020
gaaccctaaa gggagccccc gatttagagc ttgacgggga aagccggcga acgtggcgag  1080
aaaggaaggg aagaaagcga aaggagcggg cgctagggcg ctggcaagtg tagcggtcac  1140
gctgcgcgta accaccacac ccgccgcgct taatgcgccg ctacagggcg cgtccattcg  1200
ccattcaggc tgcgcaactg ttgggaaggg cgatcggtgc gggcctcttc gctattacgc  1260
caggctgcag gggggggggg ggggggggcca ctccctctct gcgcgctcgc tcgctcactg  1320
aggccgcccg ggcaaagccc gggcgtcggg cgacctttgg tcgcccggcc tcagtgagcg  1380
agcgagcgcg cagagaggga gtggccaact ccatcactag gggttcctca gatctgaatt  1440
cggtacctag ttattaatag taatcaatta cggggtcatt agttcatagc ccatatatgg  1500
agttccgcgt tacataactt acggtaaatg gcccgcctgg ctgaccgccc aacgaccccc  1560
gcccattgac gtcaataatg acgtatgttc ccatagtaac gccaataggg actttccatt  1620
gacgtcaatg ggtggagtat ttacggtaaa ctgcccactt ggcagtacat caagtgtatc  1680
atatgccaag tacgccccct attgacgtca atgacggtaa atggcccgcc tggcattatg  1740
cccagtacat gaccttatgg gactttccta cttggcagta catctacgta ttagtcatcg  1800
ctattaccat ggtcgaggtg agccccacgt tctgcttcac tctccccatc tcccccccct  1860
ccccaccccc aattttgtat ttatttattt tttaattatt ttgtgcagcg atgggggcgg  1920
gggggggggg ggggcgcgcg ccaggcgggg cggggcgggg cgaggggcgg ggcggggcga  1980
ggcggagagg tgcggcggca gccaatcaga gcggcgcgct ccgaaagttt ccttttatgg  2040
cgaggcggcg gcggcggcgg ccctataaaa agcgaagcgc gcggcgggcg ggagtcgctg  2100
cgcgctgcct tcgccccgtg ccccgctccg ccgccgcctc gcgccgcccg ccccggctct  2160
gactgaccgc gttactccca caggtgagcg ggcgggacgg cccttctcct ccgggctgta  2220
attagcgctt ggtttaatga cggcttgttt cttttctgtg gctgcgtgaa agccttgagg  2280
ggctccggga gctagagcct ctgctaacca tgttcatgcc ttcttctttt tcctacagct  2340
cctgggcaac gtgctggtta ttgtgctgtc tcatcatttt ggcaaagaat tcctcgaaga  2400
tccgaagggg ttcaagctta gcgccaccat ggagcgcgac ggctgcgcgg ggggcgggag  2460
ccgcggcggc gagggcgggc gcgctccccg ggagggcccg gcggggaacg gccgcgatcg  2520
gggccgcagc cacgctgccg aggcgcccgg ggacccgcag gccgcggcgt ccttgctggc  2580
ccctatggac gtgggggagg agccgctgga gaaggcggcg cgcgcccgca ctgccaagga  2640
ccccaacacc tataaagtac tctcgctggt attgtcagta tgtgtgttaa caacaatact  2700
tggttgtata tttgggttga aaccaagctg tgccaaagaa gttaaaagtt gcaaaggtcg  2760
ctgtttcgag agaacatttg ggaactgtcg ctgtgatgct gcctgtgttg agcttggaaa  2820
ctgctgttta gattaccagg agacgtgcat agaaccagaa catatatgga cttgcaacaa  2880
attcaggtgt ggtgagaaaa ggttgaccag aagcctctgt gcctgttcag atgactgcaa  2940
ggacaagggc gactgctgca tcaactacag ttctgtgtgt caaggtgaga aaagttgggt  3000
agaagaacca tgtgagagca ttaatgagcc acagtgccca gcagggtttg aaacgcctcc  3060
taccctctta ttttctttgg atggattcag ggcagaatat ttacacactt ggggtggact  3120
tcttcctgtt attagcaaac taaaaaaatg tggaacatat actaaaaaca tgagaccggt  3180
atatccaaca aaaactttcc ccaatcacta cagcattgtc accggattgt atccagaatc  3240
tcatggcata atcgacaata aaatgtatga tcccaaaatg aatgcttcct tttcacttaa  3300
aagtaaagag aaatttaatc ctgagtggta caaaggagaa ccaatttggg tcacagctaa  3360
gtatcaaggc ctcaagtctg gcacattttt ctggccagga tcagatgtgg aaattaacgg  3420
aattttccca gacatctata aaatgtataa tggttcagta ccatttgaag aaaggatttt  3480
agctgttctt cagtggctac agcttcctaa agatgaaaga ccacactttt acactctgta  3540
tttagaagaa ccagattctt caggtcattc atatggacca gtcagcagtg aagtcatcaa  3600
agccttgcag agggttgatg gtatggttgg tatgctgatg gatggtctga aagagctgaa  3660
cttgcacaga tgcctgaacc tcatccttat ttcagatcat ggcatggaac aaggcagttg  3720
taagaaatac atatatctga ataaatattt gggggatgtt aaaaatatta aagttatcta  3780
tggacctgca gctcgattga gaccctctga tgtcccagat aaatactatt catttaacta  3840
tgaaggcatt gcccgaaatc tttcttgccg ggaaccaaac cagcacttca aaccttacct  3900
gaaacatttc ttacctaagc gtttgcactt tgctaagagt gatagaattg agcccttgac  3960
attctatttg gaccctcagt ggcaacttgc attgaatccc tcagaaagga aatattgtgg  4020
aagtggattt catggctctg acaatgtatt ttcaaatatg caagccctct ttgttggcta  4080
tggacctgga ttcaagcatg gcattgaggc tgacaccttt gaaaacattg aagtctataa  4140
cttaatgtgt gatttactga atttgacacc ggctcctaat aacggaactc atggaagtct  4200
taaccacctt ctaaagaatc ctgtttatac gccaaagcat cccaaagaag tgcacccccct  4260
ggtacagtgc cccttcacaa gaaaccccag agataacctt ggctgctcat gtaacccttc  4320
gattttgccg attgaggatt ttcaaacaca gttcaatctg actgtggcag aagagaagat  4380
tattaagcat gaaactttac cctatggaag acctagagtt ctccagaagg aaaacaccat  4440
ctgtcttctt tcccagcacc agtttatgag tggatacagc caagacatct taatgcccct  4500
ttggacatcc tataccgtgg acagaaatga cagtttctct acggaagact tctccaactg  4560
```

```
tctgtaccag gactttagaa ttcctcttag tcctgtccat aaatgttcat tttataaaaa  4620
taacaccaaa gtgagttacg ggttcctctc cccaccacaa ctaaataaaa attcaagtgg  4680
aatatattct gaagctttgc ttactacaaa tatagtgcca atgtaccaga gttttcaagt  4740
tatatggcgc tactttcatg acaccctact gcgaaagtat gctgaagaaa gaaatggtgt  4800
caatgtcgtc agtggtcctg tgtttgactt tgattatgat ggacgttgtg attccttaga  4860
gaatctgagg caaaaaagaa gagtcatccg taaccaagaa attttgattc caactcactt  4920
ctttattgtg ctaacaagct gtaaagatac atctcagacg cctttgcact gtgaaaacct  4980
agacacctta gctttcattt tgcctcacag gactgataac agcgagagct gtgtgcatgg  5040
gaagcatgac tcctcatggg ttgaagaatt gttaatgtta cacagagcac ggatcacaga  5100
tgttgagcac atcactggac tcagcttcta tcaacaaaga aaagagccag tttcagacat  5160
tttaaagttg aaaacacatt tgccaacctt tagccaagaa gacgactaca aagacgatga  5220
cgacaagtga ggtaccgagc tcggatccca attacgatta gcactatcca attacgatta  5280
gcactatcca attacgatta gcactatcct cgagtctaga aagagatcca gacatgataa  5340
gatacattga tgagtttgga caaaccacaa ctagaatgca gtgaaaaaaa tgctttattt  5400
gtgaaatttg tgatgctatt gctttatttg taaccattat aagctgcaat aaacaagtta  5460
acaacaacaa ttgcattcat tttatgtttc aggttcaggg ggaggtgtgg gaggtttttt  5520
agtcgactag agctcgctga tcagcctcga ctgtgccttc tagttgccag ccatctgttg  5580
tttgcccctc ccccgtgcct tccttgaccc tggaaggtgc cactcccact gtcctttcct  5640
aataaaatga ggaaattgca tcgcattgtc tgagtaggtg tcattctatt ctggggggtg  5700
gggtggggca ggacagcaag ggggaggatt gggaagacaa tagcaggcat gctggggaga  5760
gatctgagga acccctagtg atggagttgg ccactccctc tctgcgcgct cgctcgctca  5820
ctgaggccgg gcgaccaaag gtcgcccgac gcccgggctt tgcccgggcg gcctcagtga  5880
gcgagcgagc gcgcagagag ggagtggccc cccccccccc ccccctgca gcctgcatta  5940
atgaatcggc caacgcgcgg ggagaggcgg tttgcgtatt gggcgctctt ccgcttcctc  6000
gctcactgac tcgctgcgct cggtcgttcg gctgcggcga gcggtatcag ctcactcaaa  6060
ggcggtaata cggttatcca cagaatcagg ggataacgca ggaaagaaca tgtgagcaaa  6120
aggccagcaa aaggccagga accgtaaaaa ggccgcgttg ctggcgtttt tccataggct  6180
ccgcccccct gacgagcatc acaaaaatcg acgctcaagt cagaggtggc gaaacccgac  6240
aggactataa agataccagg cgtttccccc tggaagctcc ctcgtgcgct ctcctgttcc  6300
gaccctgccg cttaccggat acctgtccgc ctttctccct tcgggaagcg tggcgctttc  6360
tcatagctca cgctgtaggt atctcagttc ggtgtaggtc gttcgctcca agctgggctg  6420
tgtgcacgaa ccccccgttc agcccgaccg ctgcgcctta tccggtaact atcgtcttga  6480
gtccaacccg gtaagacacg acttatcgcc actggcagca gccactggta acaggattag  6540
cagagcgagg tatgtaggcg gtgctacaga gttcttgaag tggtggccta actacggcta  6600
cactagaaga acagtatttg gtatctgcgc tctgctgaag ccagttacct tcggaaaaag  6660
agttggtagc tcttgatccg gcaaacaaac caccgctggt agcggtggtt tttttgtttg  6720
caagcagcag attacgcgca gaaaaaaagg atctcaagaa gatcctttga tcttttctac  6780
ggggtctgac gctcagtgga acgaaaactc acgttaaggg attttggtca tgagattatc  6840
aaaaaggatc ttcacctaga tccttttaaa ttaaaaatga agttttaaat caatctaaag  6900
tatatatgag taaacttggt ctgacagtta ccaatgctta atcagtgagg cacctatctc  6960
agcgatctgt ctatttcgtt catccatagt tgcctgactc cccgtcgtgt agataactac  7020
gatacgggag ggcttaccat ctggccccag tgctgcaatg ataccgcgag acccacgctc  7080
accggctcca gatttatcag caataaacca gccagccgga agggccgagc gcagaagtgg  7140
tcctgcaact ttatccgcct ccatccagtc tattaattgt tgccgggaag ctagagtaag  7200
tagttcgcca gttaatagtt tgcgcaacgt tgttgccatt gctacaggca tcgtggtgtc  7260
acgctcgtcg tttggtatgg cttcattcag ctccggttcc caacgatcaa ggcgagttac  7320
atgatccccc atgttgtgca aaaaagcggt tagctccttc ggtcctccga tcgttgtcag  7380
aagtaagttg gccgcagtgt tatcactcat ggttatggca gcactgcata attctcttac  7440
tgtcatgcca tccgtaagat gcttttctgt gactggtgag tactcaa                7487

SEQ ID NO: 103          moltype = DNA  length = 7473
FEATURE                 Location/Qualifiers
source                  1..7473
                        mol_type = other DNA
                        organism = synthetic construct
SEQUENCE: 103
tcgactagag ctcgctgatc agcctcgact gtgccttcta gttgccagcc atctgttgtt  60
tgcccctccc ccgtgccttc cttgaccctg gaaggtgcca ctcccactgt cctttcctaa  120
taaaatgagg aaattgcatc gcattgtctg agtaggtgtc attctattct ggggggtggg  180
gtggggcagg acagcaaggg ggaggattgg gaagacaata gcaggcatgc tggggagaga  240
tctgaggaac ccctagtgat ggagttggcc actccctctc tgcgcgctcg ctcgctcact  300
gaggccgggc gaccaaaggt cgcccgacgc ccgggctttg cccgggcggc ctcagtgagc  360
gagcgagcgc gcagagaggg agtggccccc cccccccccc ctgcagcctg cattaatgaa  420
tcggccaacg cgcggggaga ggcggtttgc gtattgggcg ctcttccgct tcctcgctca  480
ctgactcgct gcgctcggtc gttcggctgc ggcgagcggt atcagctcac tcaaaggcgg  540
taatacggtt atccacagaa tcaggggata acgcaggaaa gaacatgtga gcaaaaggcc  600
agcaaaaggc caggaaccgt aaaaaggccg cgttgctggc gtttttccat aggctccgcc  660
cccctgacga gcatcacaaa aatcgacgct caagtcagag gtggcgaaac ccgacaggac  720
tataaagata ccaggcgttt ccccctggaa gctccctcgt gcgctctcct gttccgaccc  780
tgccgcttac cggatacctg tccgcctttc tcccttcggg aagcgtggcg ctttctcata  840
gctcacgctg taggtatctc agttcggtgt aggtcgttcg ctccaagctg ggctgtgtgc  900
acgaaccccc cgttcagccc gaccgctgcg ccttatccgg taactatcgt cttgagtcca  960
acccggtaag acacgactta tcgccactgg cagcagccac tggtaacagg attagcagag  1020
cgaggtatgt aggcggtgct acagagttct tgaagtggtg gcctaactac ggctacacta  1080
gaagaacagt atttggtatc tgcgctctgc tgaagccagt taccttcgga aaaagagttg  1140
gtagctcttg atccggcaaa caaaccaccg ctggtagcgg tggttttttt gtttgcaagc  1200
agcagattac gcgcagaaaa aaaggatctc aagaagatcc tttgatcttt tctacggggt  1260
ctgacgctca gtggaacgaa aactcacgtt aagggatttt ggtcatgaga ttatcaaaaa  1320
ggatcttcac ctagatcctt ttaaattaaa aatgaagttt taaatcaatc taaagtatat  1380
```

-continued

```
atgagtaaac ttggtctgac agttaccaat gcttaatcag tgaggcacct atctcagcga  1440
tctgtctatt tcgttcatcc atagttgcct gactccccgt cgtgtagata actacgatac  1500
gggagggctt accatctggc cccagtgctg caatgatacc gcgagaccca cgctcaccgg  1560
ctccagattt atcagcaata aaccagccag ccggaagggc cgagcgcaga agtggtcctg  1620
caactttatc cgcctccatc cagtctatta attgttgccg ggaagctaga gtaagtagtt  1680
cgccagttaa tagtttgcgc aacgttgttg ccattgctac aggcatcgtg gtgtcacgct  1740
cgtcgtttgg tatggcttca ttcagctccg gttcccaacg atcaaggcga gttacatgat  1800
cccccatgtt gtgcaaaaaa gcggttagct ccttcggtcc tccgatcgtt gtcagaagta  1860
agttggccgc agtgttatca ctcatggtta tggcagcact gcataattct cttactgtca  1920
tgccatccgt aagatgcttt tctgtgactg gtgagtactc aaccaagtca ttctgagaat  1980
agtgtatgcg gcgaccgagt tgctcttgcc cggcgtcaat acgggataat accgcgccac  2040
atagcagaac tttaaaagtg ctcatcattg gaaaacgttc ttcggggcga aaactctcaa  2100
ggatcttacc gctgttgaga tccagttcga tgtaacccac tcgtgcaccc aactgatctt  2160
cagcatcttt tactttcacc agcgtttctg ggtgagcaaa aacaggaagg caaaatgccg  2220
caaaaaaggg aataagggcg acacggaaat gttgaatact catactcttc ctttttcaat  2280
attattgaag catttatcag ggttattgtc tcatgagcgg atacatattt gaatgtattt  2340
agaaaaataa acaaataggg gttccgcgca catttccccg aaaagtgcca cctgacgtct  2400
aagaaaccat tattatcatg acattaacct ataaaaatag gcgtatcacg aggccctttc  2460
gtctcgcgcg tttcggtgat gacggtgaaa acctctgaca catgcagctc ccggagacgg  2520
tcacagcttg tctgtaagcg gatgccggga gcagacaagc ccgtcagggc gcgtcagcgg  2580
gtgttggcgg gtgtcggggc tggcttaact atgcggcatc agagcagatt gtactgagag  2640
tgcaccatat gcggtgtgaa ataccgcaca gatgcgtaag gagaaaatac cgcatcagga  2700
aattgtaagc gttaatattt tgttaaaatt cgcgttaaat ttttgttaaa tcagctcatt  2760
ttttaaccaa taggccgaaa tcggcaaaat cccttataaa tcaaaagaat agaccgagat  2820
agggttgagt gttgttccag tttggaacaa gagtccacta ttaaagaacg tggactccaa  2880
cgtcaaaggg cgaaaaaccg tctatcaggg cgatggccca ctacgtgaac catcacccta  2940
atcaagtttt ttggggtcga ggtgccgtaa agcactaaat cggaacccta aagggagccc  3000
ccgatttaga gcttgacggg gaaagccggc gaacgtggcg agaaaggaag ggaagaaagc  3060
gaaaggagcg ggcgctaggg cgctggcaag tgtagcggtc acgctgcgcg taaccaccac  3120
acccgccgcg cttaatgcgc cgctacaggg cgcgtccatt cgccattcag gctgcgcaac  3180
tgttgggaag ggcgatcggt gcgggcctct tcgctattac gccaggctgc aggggggggg  3240
ggggggcca ctccctctct gcgcgctcgc tcgctcactg aggccgcccg ggcaaagccc  3300
gggcgtcggg cgacctttgg tcgcccggcc tcagtgagcg agcgagcgcg cagagaggga  3360
gtggccaact ccatcactag gggttcctca gatctgaatt cggtacctag ttattaatag  3420
taatcaatta cggggtcatt agttcatagc ccatatatgg agttccgcgt tacataactt  3480
acggtaaatg gcccgcctgg ctgaccgccc aacgaccccc gcccattgac gtcaataatg  3540
acgtatgttc ccatagtaac gccaataggg actttccatt gacgtcaatg ggtggagtat  3600
ttacggtaaa ctgcccactt ggcagtacat caagtgtatc atatgccaag tacgccccct  3660
attgacgtca atgacggtaa atggcccgcc tggcattatg cccagtacat gaccttatgg  3720
gactttccta cttggcagta catctacgta ttagtcatcg ctattaccat ggtcgaggtg  3780
agccccacgt tctgcttcac tctccccatc tcccccccct ccccaccccc aattttgtat  3840
ttatttattt tttaattatt ttgtgcagcg atgggggcgg gggggggggg ggggcgcgcg  3900
ccaggcgggg cggggcgggg cgaggggcgg ggcggggcga ggcggagagg tgcggcggca  3960
gccaatcaga gcggcgcgct ccgaaagttt ccttttatgg cgaggcggcg gcggcggcgg  4020
ccctataaaa agcgaagcgc gcggcgggcg ggagtcgctg cgcgctgcct tcgccccgtg  4080
ccccgctccg ccgccgcctc gcgccgcccg ccccggctct gactgaccgc gttactccca  4140
caggtgagcg ggcgggacgg cccttctcct ccgggctgta attagcgctt ggtttaatga  4200
cggcttgttt cttttctgtg gctgcgtgaa agccttgagg ggctccggga gctagagcct  4260
ctgctaacca tgttcatgcc ttcttctttt tcctacagct cctgggcaac gtgctggtta  4320
ttgtgctgtc tcatcatttt ggcaaagaat tcctcgaaga tccgaagggg ttcaagctct  4380
agcgccacca tggagcgcga cggctgcgcg gggggcggga gccgcggcgg cgagggcggg  4440
cgcgctcccc gggagggccc ggcggggaac ggccgcgatc ggggccgcag ccacgctgcc  4500
gaggcgcccg gggacccgca ggccgcggcg tccttgctgg cccctatgga cgtgggggag  4560
gagccgctgg agaaggcggc gcgcgcccgc actgccaagg accccaacac ctataaagta  4620
ctctcgctgg tattgtcagt atgtgtgtta acaacaatac ttggttgtat atttgggttg  4680
aaaccaagct gtgccaaaga agttaaaagt tgcaaaggtc gctgtttcga gagaacattt  4740
gggaactgtc gctgtgatgc tgcctgtgtt gagcttggaa actgctgttt agattaccag  4800
gagacgtgca tagaaccaga acatatatgg acttgcaaca aattcaggtg tggtgagaaa  4860
aggttgacca gaagcctctg tgcctgttca gatgactgca aggacaaggg cgactgctgc  4920
atcaactaca gttctgtgtg tcaaggtgag aaaagttggg tagaagaacc atgtgagagc  4980
attaatgagc cacagtgccc agcagggttt gaaacgcctc ctaccctctt attttctttg  5040
gatggattca gggcagaata tttacacact tggggtggac ttcttcctgt tattagcaaa  5100
ctaaaaaaat gtggaacata tactaaaaac atgagaccgg tatatccaac aaaaactttc  5160
cccaatcact acagcattgt caccggattg tatccagaat ctcatggcat aatcgacaat  5220
aaaatgtatg atcccaaaat gaatgcttcc ttttcactta aaagtaaaga gaaatttaat  5280
cctgagtggt acaaaggaga accaatttgg gtcacagcta agtatcaagg cctcaagtct  5340
ggcacatttt tctggccagg atcagatgtg gaaattaacg gaattttccc agacatctat  5400
aaaatgtata atggttcagt accatttgaa gaaaggattt tagctgttct tcagtggcta  5460
cagcttccta aagatgaaag accacacttt tacactctgt atttagaaga accagattct  5520
tcaggtcatt catatggacc agtcagcagt gaagtcatca aagccttgca gagggttgat  5580
ggtatggttg gtatgctgat ggatggtctg aaagagctga acttgcacag atgcctgaac  5640
ctcatcctta tttcagatca tggcatggaa caaggcagtt gtaagaaata catatatctg  5700
aataaatatt tgggggatgt taaaaatatt aaagttatct atggacctgc agctcgattg  5760
agaccctctg atgtcccaga taaatactat tcatttaact atgaaggcat tgcccgaaat  5820
ctttcttgcc gggaaccaaa ccagcacttc aaaccttacc tgaaacattt cttacctaag  5880
cgtttgcact ttgctaagag tgatagaatt gagcccttga cattctattt ggaccctcag  5940
tggcaacttg cattgaatcc ctcagaaagg aaatattgtg gaagtggatt tcatggctct  6000
gacaatgtat tttcaaatat gcaagccctc tttgttggct atggacctgg attcaagcat  6060
ggcattgagg ctgacacctt tgaaaacatt gaagtctata acttaatgtg tgatttactg  6120
```

-continued

```
aatttgacac cggctcctaa taacggaact catggaagtc ttaaccacct tctaaagaat  6180
cctgtttata cgccaaagca tcccaaagaa gtgcaccccc tggtacagtg ccccttcaca  6240
agaaacccca gagataacct tggctgctca tgtaaccctt cgattttgcc gattgaggat  6300
tttcaaacac agttcaatct gactgtggca gaagagaaga ttattaagca tgaaacttta  6360
ccctatggaa gacctagagt tctccagaag gaaaacacca tctgtcttct ttcccagcac  6420
cagtttatga gtggatacag ccaagacatc ttaatgcccc tttggacatc ctataccgtg  6480
gacagaaatg acagtttctc tacggaagac ttctccaact gtctgtacca ggactttaga  6540
attcctctta gtcctgtcca taaatgttca ttttataaaa ataacaccaa agtgagttac  6600
gggttcctct ccccaccaca actaaataaa aattcaagtg gaatatattc tgaagctttg  6660
cttactacaa atatagtgcc aatgtaccag agttttcaag ttatatggcg ctactttcat  6720
gacaccctac tgcgaaagta tgctgaagaa agaaatggtg tcaatgtcgt cagtggtcct  6780
gtgtttgact ttgattatga tggacgttgt gattccttag agaatctgag gcaaaaaaga  6840
agagtcatcc gtaaccaaga aattttgatt ccaactcact tctttattgt gctaacaagc  6900
tgtaaagata catctcagac gcctttgcac tgtgaaaacc tagacacctt agctttcatt  6960
ttgcctcaca ggactgataa cagcgagagc tgtgtgcatg ggaagcatga ctcctcatgg  7020
gttgaagaat tgttaatgtt acacagagca cggatcacag atgttgagca catcactgga  7080
ctcagcttct atcaacaaag aaaagagcca gtttcagaca ttttaaagtt gaaaacacat  7140
ttgccaacct ttagccaaga agacgactac aaagacgatg acgacaagtg aggtaccgag  7200
ctcggatcca ctagtccagt gtggtggaat tctgcagata tccagcacag tggcggccgc  7260
tcgagtctag aaagagatcc agacatgata agatacattg atgagtttgg acaaaccaca  7320
actagaatgc agtgaaaaaa atgctttatt tgtgaaattt gtgatgctat tgctttattt  7380
gtaaccatta taagctgcaa taaacaagtt aacaacaaca attgcattca ttttatgttt  7440
caggttcagg gggaggtgtg ggaggttttt tag                                 7473

SEQ ID NO: 104         moltype = DNA  length = 12
FEATURE                Location/Qualifiers
source                 1..12
                       mol_type = other DNA
                       organism = synthetic construct
SEQUENCE: 104
ctgatcgtta ac                                                        12

SEQ ID NO: 105         moltype = DNA  length = 23
FEATURE                Location/Qualifiers
source                 1..23
                       mol_type = other DNA
                       organism = synthetic construct
SEQUENCE: 105
tgtttgtggt aacagtgtga ggt                                            23

SEQ ID NO: 106         moltype = DNA  length = 23
FEATURE                Location/Qualifiers
source                 1..23
                       mol_type = other DNA
                       organism = synthetic construct
SEQUENCE: 106
acaaacacca ttgtcacact cca                                            23
```